US007550456B2

(12) United States Patent
Trybulski et al.

(10) Patent No.: US 7,550,456 B2
(45) Date of Patent: Jun. 23, 2009

(54) SUBSTITUTED ARYL CYCLOALKANOYL DERIVATIVES AND METHODS OF THEIR USE

(75) Inventors: Eugene John Trybulski, Huntingdon Valley, PA (US); Joseph Peter Sabatucci, Collegeville, PA (US); An Thien Vu, Pottstown, PA (US); Stephen Todd Cohn, Spring, TX (US); Arthur Attilio Santilli, Havertown, PA (US); Lori Krim Gavrin, Philadelphia, PA (US); Fei Ye, Audubon, PA (US); Paige Erin Mahaney, Pottstown, PA (US)

(73) Assignee: Wyeth, Madison, NJ (US)

(*) Notice: Subject to any disclaimer, the term of this patent is extended or adjusted under 35 U.S.C. 154(b) by 0 days.

(21) Appl. No.: 12/031,187

(22) Filed: Feb. 14, 2008

(65) Prior Publication Data

US 2008/0153826 A1 Jun. 26, 2008

Related U.S. Application Data

(62) Division of application No. 10/963,111, filed on Oct. 12, 2004, now Pat. No. 7,365,076.

(60) Provisional application No. 60/510,943, filed on Oct. 14, 2003, provisional application No. 60/561,301, filed on Apr. 12, 2004, provisional application No. 60/569,996, filed on May 11, 2004.

(51) Int. Cl.
*A01N 43/62* (2006.01)
*C07D 243/08* (2006.01)

(52) U.S. Cl. ............................... 514/218; 540/575

(58) Field of Classification Search ............ 514/218; 540/575
See application file for complete search history.

(56) References Cited

U.S. PATENT DOCUMENTS

| 3,454,554 | A | 7/1969 | Biel et al. ............... 260/239 |
| 4,221,919 | A | 9/1980 | Grimova et al. ........... 562/465 |
| 4,229,449 | A | 10/1980 | Melloni et al. .......... 514/239.2 |
| 4,310,524 | A | 1/1982 | Wiech et al. .............. 514/217 |
| 4,535,186 | A | 8/1985 | Husbands et al. .......... 564/336 |
| 4,826,844 | A | 5/1989 | Husbands et al. .......... 514/252 |
| 5,502,047 | A | 3/1996 | Kavey ..................... 514/183 |
| 6,703,389 | B2 | 3/2004 | Wong et al. ............ 514/239.2 |
| 2002/0107249 | A1 | 8/2002 | Wong et al. ............. 514/238.5 |
| 2004/0019101 | A1 | 1/2004 | Karlstadt et al. .......... 514/464 |
| 2004/0143008 | A1 | 7/2004 | Deecher et al. ............ 514/521 |
| 2004/0152710 | A1 | 8/2004 | Deecher et al. ........ 514/255.04 |
| 2004/0180879 | A1 | 9/2004 | Deecher et al. ........... 514/225.8 |

FOREIGN PATENT DOCUMENTS

| DE | 2556474 | C2 | 8/2004 |
| EP | 0 065 757 | B1 | 1/1985 |
| EP | 0 310 268 | * | 4/1989 |
| EP | 0 310 268 | A2 | 4/1989 |
| EP | 0 208 235 | B1 | 1/1990 |
| EP | 0 303 961 | B1 | 4/1994 |
| EP | 1 266 659 | A1 | 12/2002 |
| JP | 2005336172 | A1 | 12/2005 |
| WO | WO 91/18602 | A1 | 12/1991 |
| WO | WO 97/35586 | A1 | 10/1997 |
| WO | WO 99/44601 | A1 | 9/1999 |
| WO | WO 00/59851 | A1 | 10/2000 |
| WO | WO 01/01973 | A2 | 1/2001 |
| WO | WO 02/064543 | A2 | 8/2002 |
| WO | WO 02/064543 | A3 | 8/2002 |
| WO | WO 02/078691 | A1 | 10/2002 |
| WO | WO 03/037334 | A1 | 5/2003 |
| WO | WO 03/053426 | A1 | 7/2003 |
| WO | WO 03/077897 | A1 | 9/2003 |
| WO | WO 03/106443 | A1 | 12/2003 |
| WO | WO 03/106444 | A1 | 12/2003 |
| WO | WO 2004/016272 | A1 | 2/2004 |
| WO | WO 2004/035036 | A1 | 4/2004 |
| WO | WO 2004/035058 | A1 | 4/2004 |
| WO | WO 2006/055854 | A2 | 5/2006 |

OTHER PUBLICATIONS

U.S. Appl. No. 60/557,651, filed Mar. 30, 2004, Kim et al.
U.S. Appl. No. 60/557,831, filed Mar. 30, 2004, Kim et al.
U.S. Appl. No. 60/569,863, filed May 11, 2004, Kim et al.
U.S. Appl. No. 60/569,861, filed May 11, 2004, Vu.
U.S. Appl. No. 10/963,458, filed Oct. 12, 2004, Mahaney et al.
U.S. Appl. No. 10/962,881, filed Oct. 12, 2004, Mahaney.

(Continued)

*Primary Examiner*—James O Wilson
*Assistant Examiner*—Erich A Leeser
(74) *Attorney, Agent, or Firm*—Thomas C. McKenzie; A. David Joran

(57) ABSTRACT

The present invention is directed to substituted aryl cycloalkanoyl derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

12 Claims, 2 Drawing Sheets

OTHER PUBLICATIONS

U.S. Appl. No. 10/963,064, filed Oct. 12, 2004, Trybulski et al.
U.S. Appl. No. 10/962,897, filed Oct. 12, 2004, Deecher et al.
U.S. Appl. No. 10/962,880, filed Oct. 12, 2004, Trybulski et al.
U.S. Appl. No. 10/962,971, filed Oct. 12, 2004, Mahaney et al.
U.S. Appl. No. 10/962,899, filed Oct. 12, 2004, Mahaney et al.
Clinical Trial: "Phase III Randomized Study of Medroxyprogesterone Versus Venlafaxine in Women With Symptomatic Hot Flashes", www.clinicaltrials.gov sponsored by the National Institutes of Health, Study ID Nos. CDR0000069217; NCCTG-N99C7; NCI-P02-0204, 2003, 6 pages.
Acs, N. et al., "Estrogen improves impaired musculocutaneous vascular adrenergic reactivity in pharmacologically ovariectomized rats: a potential peripheral mechanism for hot flashes?", *Endocrinology*, 2001 15: 68-73.
Barlow, D. H., "Venlafaxine for hot flushes," *Lancet*, Dec. 16, 2000, 356(9247): 2025-2026.
Barton, D. et al., "Hot Flashes—Actiology and Management," *Drugs and Aging*, 2001, 18(8): 597-606.
Berendsen, H. H. G., "Hot Flushes and serotonin," *Journal of the British Menopause Society*, Mar. 2002, 8(1): 30-34.
Berendsen, H. H. G., "Effect of tibolone and raloxifene on the tail temperature of oestrogen-deficient rats," *European Journal of Pharmacology*, 2001, 419(1): 47-54.
Berendsen, H. H. G., "The role of serotonin in hot flushes," *Maturitas*, 2000, 36(3): 155-164.
Bundgaard, H., "Means to enhance penetration; Prodrugs as a means to improve the delivery of peptide drugs," *Advanced Drug Deliver Reviews*, 1992, 8, 1-38.
Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.
Casper, R. F. et al., "Neuroendocrinology of menopausal flushes: an hypothesis of flush mechanism," *Clinical Endocrinology*, 1985, 22: 293-312.
Fink, G. et al., "Oestrogen and mental state," *Nature*, 1996, 383(6598): 306.
Freedman, R. R. et al., "Clonidine raises the sweating threshold in symptomatic but not asymptomatic postmenopausal women," *Fertility & Sterility*, 2000, 74(1): 20-3.
Freedman, R. R., "Physiology of hot flashes," *American Journal of Human Biology*, 2001, 13: 453-464.
French, N., "$\alpha_2$-Adrenoceptors and $I_2$ sites in the mammalian central nervous system," *Pharmacol. Ther.*, 1995, 68(2):175-208.
Janowsky, D. S. et al., "Desipramine: an overview," *Journal of Clinical Psychiatry*, 1984, 45(10 Pt 2): 3-9.
Katovich, M. J. et al., "Mechanisms Mediating the Thermal Response to Morphine Withdrawal in Rats," *Proceedings of the Society for Experimental Biology & Medicine*, 1990, 193(2): 129-35.
Katovich, M. J. et al., "Alpha-adrenergic mediation of the tail skin temperature response to naloxone in morphine-dependent rats," *Brain Research*, 1987, 426: 55-61.
Krämer et al., In: Murphy et al., *3rd Int'l Symposium on Recent Advances in Urological Cancer Diagnosis and Treatment-Proceedings*, Paris, France: SCI: 3-7 1992.
Krogsgaard-Larsen, et al., (ed). *Design and Application of Prodrugs, Textbook of Drug Design and Development*, Chapter 5, 113-191, 1991.
Kronenberg, F. et al., "Thermoregulatory Physiology of Menopausal Hot Flashes: A Review," *Can. J. Physiol. Pharmacol.*, 1987, 65:1312-1324.
Loprinzi, C.L. et al., "Venlafaxine in management of hot flashes in survivors of breast cancer: a randomized controlled trial," *Lancet*, Dec. 16, 2000, 356(9247): 2059-2063.
Loprinizi, C. L. et al. "Pilot Evaluation of Venlafaxine Hydrochloride for the Therapy of Hot Flashes in Cancer Survivors," *Journal of Clinical Oncology*, Jul. 1998, 16(7): 2377-2381.
Mackinnon et al., "$\alpha_2$-Adrenoceptors: more subtypes but fewer functional differences," *TIPS*, 1994, 15: 119-123.
Merchenthaler et al., "The effect of estrogens and antiestrogens in a rat model for hot flush," *Maturitas*, 1998, 30(3): 307-316.
Morin, S. M., "Atomoxetine Selectively Induces Fos Expression in the Rat Prefrontal Cortex," Presented at Society for Neuroscience Annual Meeting (SFN); Nov. 2-7, 2002, Orlando, FL.
Pacholczyk, T. et al., "Expression cloning of a cocaine-and antidepressant-sensitive human noradrenaline transporter," *Nature*, 1991, 350(6316): 350-4.
Panek, D.U. et al., "Effect of continuous intraventricular estrogen or catechol estrogen treatment on catecholamine turnover in various brain regions," *J. Pharmacol. Exp. Ther.*, 1986, 236(3), 646-652.
Prasad, P.D., et al., "Functional expression of the plasma membrane serotonin transporter but not the vesicular monoamine transporter in human placental trophoblasts and choriocarcinoma cells," *Placenta*, 1996, 17(4): 201-7.
Quella, S. K. et al., "Pilot evaluation of Venlafaxine for the treatment of hot flashes in men undergoing androgen ablation therapy for prostate cancer," *The Journal of Urology*, Jul. 1999, 162: 98-102.
Reneric, J-Ph. et al., "Idazoxan and 8-OH-DPAT modify the behavioral effects induced by either NA, or 5-HT, or dual NA/5-HT reuptake inhibition in the rat forced swimming test," *Nueropsychopharmacology*, Apr. 2001, 24(4): 379-390.
Rosenberg, J. et al., "Hypothesis: pathogenesis of postmenopausal hot flush," *Medical Hypotheses*, 1991, 35: 349-350.
Shaw, C. R., "The perimenopausal hot flash: epidemiology, physiology, and treatment," *Nurse Practitioner*, Mar. 1997, 22: 55-56, 61-66.
Stearns, V. et al., "Hot flushes," *Lancet*, Dec. 7, 2002, 360(9348): 1851-1861.
Stearns, V. et al., "Paroxetine controlled release in the treatment of menopausal hot flashes," *JAMA*, 2003, 289:2827-2834.
Stearns, V. et al., "A pilot trial assessing the efficacy of paroxetine hydrochloride (Paxil) in controlling hot flashes in breast cancer survivors," *Ann Oncol.*, 2000, 11:17-22.
Waldinger et al., "Treatment of hot flushes with mirtazapine: four case reports," *Maturitas*, 2000, 36(3): 165-168.
Wilen, S.H. *Tables of Resolving Agents and Optical Resolutions*, pp. 268-298, E.L. Eliel, Ed., University of Notre Dame Press, Notre Dame, IN 1972.
Wilen, S.H., et al., "Strategies in optical resolutions," *Tetrahedron*, 33:2725-2736, 1977.
Zhang, W. et al., "Synergistic Effects of Olanzapine and Other Antipsychotic Agents in Combination with Fluoxetine on Norepinephrine and Dopamine Release in Rat Prefrontal Cortex," *Neuropsychopharmacology*, 2000, 23(3): 250-262.
Bundgaard (ed.), Design of Prodrugs, Elsevier (1985), Ch. 1 (pp. 1-92), Ch. 4 (pp. 157-176), Ch. 5 (pp. 177-198), and Ch. 6 (pp. 199-241).
Widder, et al. (ed.), *Methods in Enzymology*, vol. 112, Academic Press (1985), pp. 309-396.
Higuchi and Stella (eds.), *Prodrugs as Novel Drug Delivery Systems*, American Chemical Society (1975), pp. 1-115 and 196-223.
Freedman, R. R. et al., "$\alpha 2$-Adrenergic mechanism in menopausal hot flushes," *Obstet Gynecol*, 1990, 76:573-578.
Brück, K. et al., "Adaptive changes in thermoregulation and their neuropharmacological basis" In: Schönbaum E. et al. (eds.). *Thermoregulation: Physiology and Biochemistry*, New York, Pergamon Press, (1991) pp. 255-307.
Ahmar, M. et al., "Enzymatic resolution of methyl 2-alkyl-2-arylacetates" *Tetrahedron Lett.*, 1989, 30(50): 7053-7056.
Campaigne, E. et al., "Benzo[*b*]thiophene Derivatives. XXVII. 5-Methoxy-6-halo-3-b-acetamidoethylbenzo[*b*]thiophenes, Blocked Analogs of Melatonin," *J. Heterocyclic Chem.* 1983, 20, 1697-1703.
Harrison, I. et al., "Nonsteroidal antiinflammatory agents. I. 6-substituted 2-naphthylacetic acids," *J. Med. Chem.* 1970, 13(2), 203-5.
Moon, S. et al., "An Efficient Conversion of Chiral $\alpha$-Amino Acids to Enantiomerically Pure 3-Amino Cyclic Amines," *Synth. Commun.* 1998, 28(21), 3919-3926.
Baker, W. et al., "Nonpeptide renin inhibitors employing a novel 3-aza(or oxa)-2,4-dialkyl glutaric acid moiety as a P2/P3 amide bond replacement," *J. Med. Chem.* 1992, 35 (10), 1722-1734.
Ley, S.V. et al., "Use of polymer supported reagents for clean multistep organic synthesis: preparation of amines and amine derivatives from alcohols for use in compound library generation," *J. Chem. Soc. Perkin Trans. 1*; 15; 1998; 2239-2242.

Manov et al., "Solid-Phase Synthesis of Polyamine Spider Toxins and Correlation with the Natural Products by HPLC-MS/MS," *Helvetica Chimica Acta*, 2002, 85(9):2827-2846.

Monguzzi, R. et al., "Synthesis of new α-hydrazinoarylacetic acids and derivatives," *Farmaco, Edizione Scientifica* , 1976, 31(8), 549-60.

*Remington's Pharmaceutical Sciences*, 17th edition, ed. Alfonso R. Gennaro, Mack Publishing Company, Easton, PA, 1985.

Eliel, E.L. *Stereochemistry of Carbon Compounds*, McGraw-Hill, NY, 1962.

Jacques, et al., *Enantiomers, Racemates and Resolutions*, Wiley Interscience, New York, 1981.

Greene, T.W. and Wuts, P.G.M., *Protective Groups in Organic Synthesis* 2d. Ed., Wiley & Sons, 1991.

* cited by examiner

SUBSTITUTED ARYL CYCLOALKANOYL DERIVATIVES AND METHODS OF THEIR USE

CROSS REFERENCE TO RELATED APPLICATIONS

This application is a divisional of application Ser. No. 10/963,111 filed Oct. 12, 2004, which claims the benefit of U.S. Application Nos. 60/510,943 filed Oct. 14, 2003, 60/561,301 filed Apr. 12, 2004, and 60/569,996 filed May 11, 2004, the entire disclosures of which are herein incorporated by reference.

FIELD OF THE INVENTION

The present invention relates to substituted aryl cycloalkanoyl derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

BACKGROUND OF THE INVENTION

Vasomotor symptoms (VMS), referred to as hot flushes and night sweats, are the most common symptoms associated with menopause, occurring in 60% to 80% of all women following natural or surgically-induced menopause. VMS are likely to be an adaptive response of the central nervous system (CNS) to declining sex steroids. To date, the most effective therapies for VMS are hormone-based treatments, including estrogens and/or some progestins. Hormonal treatments are very effective at alleviating VMS, but they are not appropriate for all women. It is well recognized that VMS are caused by fluctuations of sex steroid levels and can be disruptive and disabling in both males and females. A hot flush can last up to thirty minutes and vary in their frequency from several times a week to multiple occurrences per day. The patient experiences a hot flash as a sudden feeling of heat that spreads quickly from the face to the chest and back and then over the rest of the body. It is usually accompanied by outbreaks of profuse sweating. It may sometimes occur several times an hour, and it often occurs at night. Hot flushes and outbreaks of sweats occurring during the night can cause sleep deprivation. Psychological and emotional symptoms observed, such as nervousness, fatigue, irritability, insomnia, depression, memory loss, headache, anxiety, nervousness or inability to concentrate are considered to be caused by the sleep deprivation following hot flush and night sweats (Kramer et al., In: Murphy et al., $3^{rd}$ Int'l Symposium on Recent Advances in Urological Cancer Diagnosis and Treatment-Proceedings, Paris, France: SCI: 3-7 (1992)).

Hot flushes may be even more severe in women treated for breast cancer for several reasons: 1) many survivors of breast cancer are given tamoxifen, the most prevalent side effect of which is hot flush, 2) many women treated for breast cancer undergo premature menopause from chemotherapy, 3) women with a history of breast cancer have generally been denied estrogen therapy because of concerns about potential recurrence of breast cancer (Loprinzi, et al., Lancet, 2000, 356(9247): 2059-2063).

Men also experience hot flushes following steroid hormone (androgen) withdrawal. This is true in cases of age-associated androgen decline (Katovich, et al., Proceedings of the Society for Experimental Biology & Medicine, 1990, 193 (2): 129-35) as well as in extreme cases of hormone deprivation associated with treatments for prostate cancer (Berendsen, et al., European Journal of Pharmacology, 2001, 419(1): 47-54. As many as one-third of these patients will experience persistent and frequent symptoms severe enough to cause significant discomfort and inconvenience.

The precise mechanism of these symptoms is unknown but generally is thought to represent disturbances to normal homeostatic mechanisms controlling thermoregulation and vasomotor activity (Kronenberg et al., "Thermoregulatory Physiology of Menopausal Hot Flashes: A Review," Can. J. Physiol. Pharmacol., 1987, 65:1312-1324).

The fact that estrogen treatment (e.g. estrogen replacement therapy) relieves the symptoms establishes the link between these symptoms and an estrogen deficiency. For example, the menopausal stage of life is associated with a wide range of other acute symptoms as described above and these symptoms are generally estrogen responsive.

It has been suggested that estrogens may stimulate the activity of both the norepinephrine (NE) and/or serotonin (5-HT) systems (J. Pharmacology & Experimental Therapeutics, 1986, 236(3) 646-652). It is hypothesized that estrogens modulate NE and 5-HT levels providing homeostasis in the thermoregulatory center of the hypothalamus. The descending pathways from the hypothalamus via brainstem/spinal cord and the adrenals to the skin are involved in maintaining normal skin temperature. The action of NE and 5-HT reuptake inhibitors is known to impinge on both the CNS and peripheral nervous system (PNS). The pathophysiology of VMS is mediated by both central and peripheral mechanisms and, therefore, the interplay between the CNS and PNS may account for the efficacy of dual acting SRI/NRIs in the treatment of thermoregulatory dysfunction. In fact, the physiological aspects and the CNS/PNS involvement in VMS may account for the lower doses proposed to treat VMS (Loprinzi, et al. Lancet, 2000, 356:2059-2063; Stearns et al., JAMA, 2003, 289:2827-2834) compared to doses used to treat the behavioral aspects of depression. The interplay of the CNS/PNS in the pathophysiology of VMS and the presented data within this document were used to support the claims that the norepinephrine system could be targeted to treat VMS.

Although VMS are most commonly treated by hormone therapy (orally, transdermally, or via an implant), some patients cannot tolerate estrogen treatment (Berendsen, Maturitas, 2000, 36(3): 155-164, Fink et al., Nature, 1996, 383(6598): 306). In addition, hormone replacement therapy is usually not recommended for women or men with or at risk for hormonally sensitive cancers (e.g. breast or prostate cancer). Thus, non-hormonal therapies (e.g. fluoxetine, paroxetine [SRIs] and clonidine) are being evaluated clinically. WO9944601 discloses a method for decreasing hot flushes in a human female by administering fluoxetine. Other options have been studied for the treatment of hot flashes, including steroids, alpha-adrenergic agonists, and beta-blockers, with varying degree of success (Waldinger et al., Maturitas, 2000, 36(3): 165-168).

It has been reported that $\alpha_2$-adrenergic receptors play a role in thermoregulatory dysfunctions (Freedman et al., Fertility & Sterility, 2000, 74(1): 20-3). These receptors are located both pre- and post-synaptically and mediate an inhibitory role in the central and peripheral nervous system. There are four distinct subtypes of the adrenergic$_{\alpha 2}$ receptors, i.e., are $\alpha_{2A}$, $\alpha_{2B}$, $\alpha_{2C}$ and $\alpha_{2D}$ (Mackinnon et al., TIPS, 1994, 15: 119;

French, *Pharmacol. Ther.*, 1995, 68: 175). It has been reported that a non-select $\alpha_2$-adrenoceptor antagonist, yohimbine, induces a flush and an $\alpha_2$-adrenergic receptor agonist, clonidine, alleviates the yohimbine effect (Katovich, et al., *Proceedings of the Society for Experimental Biology & Medicine*, 1990, 193(2): 129-35, Freedman et al., *Fertility & Sterility*, 2000, 74(1): 20-3). Clonidine has been used to treat hot flush. However, using such treatment is associated with a number of undesired side effects caused by high doses necessary to abate hot flash described herein and known in the related arts.

Given the complex multifaceted nature of thermoregulation and the interplay between the CNS and PNS in maintaining thermoregulatory homeostasis, multiple therapies and approaches can be developed to target vasomotor symptoms. The present invention focuses on novel compounds and compositions containing these compounds directed to these and other important uses.

SUMMARY OF THE INVENTION

The present invention is directed to substituted aryl cycloalkanoyl derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In one embodiment, the present invention is directed to compounds of formula I:

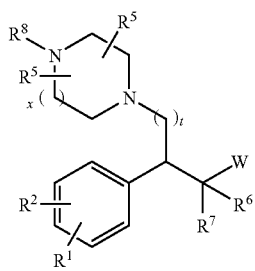

I or a pharmaceutical salt thereof;
wherein:
W is H or $OR^9$;
$R^1$ is phenyl, naphthyl, heteroaryl, benzyloxy, phenoxy, naphthyloxy, phenylethoxy, phenoxyethoxy, naphthylmethoxy, naphthylethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino;
where said phenyl, naphthyl, heteroaryl, benzyloxy, phenoxy, naphthyloxy, phenylethoxy, phenoxyethoxy, naphthylmethoxy, naphthylethoxy, phenylcarbonylamino, and phenylaminocarbonyl are optionally substituted with one or more $R^2$;
$R^2$ is H, or one or two substituents, the same or different selected from OH, alkyl, alkoxy, halo, trifluoromethyl, alkanoyloxy, methylenedioxy, trifluoromethoxy, nitrile, nitro, alkenyl, alkynyl, sulfonyl, or sulfonamido;

$R^5$ is H, ($C_1$-$C_6$)alkyl, or trifluoromethyl;
$R^6$ and $R^7$ are, independently, ($C_1$-$C_6$)alkyl or ($C_3$-$C_6$)cycloalkyl;
or $R^6$ and $R^7$ can together form a ring of 4 to 8 carbon atoms;
where any carbon atom of said $R^6$ and $R^7$ may be optionally replaced with N, S, or O;
where $R^6$ and $R^7$ may be optionally substituted with $R^5$ or OH;
where $R^6$ and $R^7$ can form a ring with 4 to 8 carbons fused onto a cycloalkyl ring of 4 to 6 carbon atoms;
$R^8$ is H, ($C_1$-$C_6$)alkyl, hydroxy($C_1$-$C_6$)alkyl, benzyl (optionally substituted with benzyloxy or phenyloxy), naphthylmethyl (optionally substituted with one or more $R^1$), phenyl ($C_2$-$C_6$)alkyl (optionally substituted with one or more $R^1$), heteroarylmethyl (optionally substituted with $R^1$), cycloalkyl, cycloalkenyl, cycloalkylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy), cycloalkenylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy);
or $R^5$ and $R^8$, together with the nitrogen atom to which $R^8$ is attached, form a ring optionally substituted with $R^5$;
$R^9$ is H, ($C_1$-$C_4$)alkyl, or ($C_1$-$C_4$)alkyl-C(=O);
t is 1, 2, or 3; and
x is 0, 1, or 2.

In yet other embodiments, the present invention is directed to compositions, comprising:

a. at least one compound of formula I; and b. at least one pharmaceutically acceptable carrier.

In another embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

In another embodiment, the present invention is directed to methods for treating or preventing vasomotor symptoms in a subject in need thereof, comprising the step of:

administering to said subject an effective amount of at least one compound of formula I or pharmaceutically acceptable salt thereof.

In yet another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of a compound of formula I or pharmaceutically acceptable salt thereof.

BRIEF DESCRIPTION OF THE DRAWINGS

The invention can be more fully understood from the following detailed description and the accompanying drawings that form a part of this application.

DETAILED DESCRIPTION OF THE INVENTION

Figure 1:
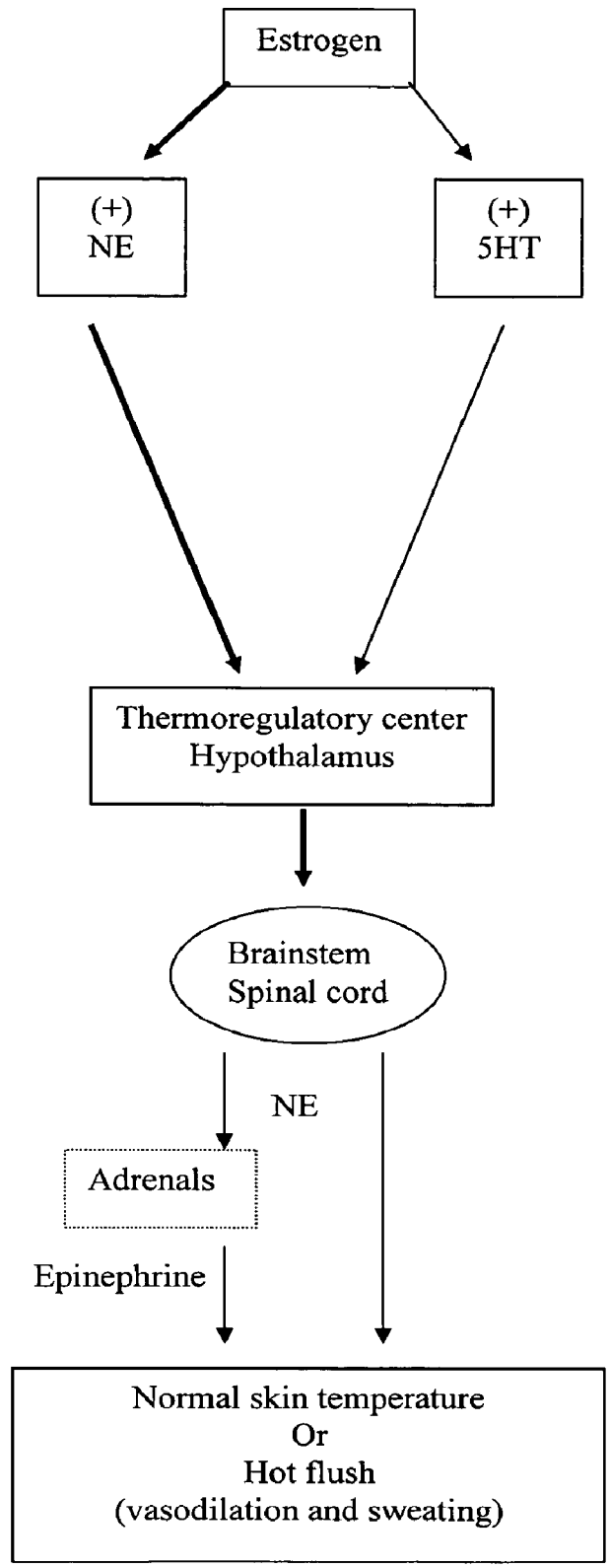
FIG. 1 is an overview of estrogen action on norepinephrine/serotonin mediated thermoregulation.

The present invention is directed to substituted aryl cycloalkanoyl derivatives, compositions containing these derivatives, and methods of their use for the prevention and treatment of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

The following definitions are provided for the full understanding of terms and abbreviations used in this specification.

As used herein and in the appended claims, the singular forms "a," "an," and "the" include the plural reference unless the context clearly indicates otherwise. Thus, for example, a reference to "an antagonist" includes a plurality of such antagonists, and a reference to "a compound" is a reference to one or more compounds and equivalents thereof known to those skilled in the art, and so forth.

The abbreviations in the specification correspond to units of measure, techniques, properties, or compounds as follows: "min" means minutes, "h" means hour(s), "µL" means microliter(s), "mL" means milliliter(s), "mM" means millimolar, "M" means molar, "mmole" means millimole(s), "cm" means centimeters, "SEM" means standard error of the mean and "IU" means International Units. "Δ° C." and Δ "ED$_{50}$ value" means dose which results in 50% alleviation of the observed condition or effect (50% mean maximum endpoint).

"Norepinephrine transporter" is abbreviated NET.
"Human norepinephrine transporter" is abbreviated hNET.
"Serotonin transporter" is abbreviated SERT.
"Human serotonin transporter" is abbreviated hSERT.
"Norepinephrine reuptake inhibitor" is abbreviated NRI.
"Selective norepinephrine reuptake inhibitor" is abbreviated SNRI.
"Serotonin reuptake inhibitor" is abbreviated SRI.
"Selective serotonin reuptake inhibitor" is abbreviated SSRI.
"Norepinephrine" is abbreviated NE.
"Serotonin is abbreviated 5-HT.
"Subcutaneous" is abbreviated sc.
"Intraperitoneal" is abbreviated ip.
"Oral" is abbreviated po.

In the context of this disclosure, a number of terms shall be utilized. The term "treatment" as used herein includes preventative (e.g., prophylactic), curative or palliative treatment and "treating" as used herein also includes preventative, curative and palliative treatment.

The term "effective amount," as used herein, refers to an amount effective, at dosages, and for periods of time necessary, to achieve the desired result with respect to prevention or treatment of vasomotor symptoms, depression disorders, sexual dysfunction, or pain. In particular with respect to vasomotor symptoms, "effective amount" refers to the amount of compound or composition of compounds that would increase norepinephrine levels to compensate in part or total for the lack of steroid availability in subjects subject afflicted with a vasomotor symptom. Varying hormone levels will influence the amount of compound required in the present invention. For example, the pre-menopausal state may require a lower level of compound due to higher hormone levels than the peri-menopausal state.

It will be appreciated that the effective amount of components of the present invention will vary from patient to patient not only with the particular compound, component or composition selected, the route of administration, and the ability of the components (alone or in combination with one or more combination drugs) to elicit a desired response in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage ultimately being at the discretion of the attendant physician. Dosage regimens may be adjusted to provide the improved therapeutic response. An effective amount is also one in which any toxic or detrimental effects of the components are outweighed by the therapeutically beneficial effects.

Preferably, the compounds of the present invention are administered at a dosage and for a time such that the number of hot flushes is reduced as compared to the number of hot flushes prior to the start of treatment. Such treatment can also be beneficial to reduce the overall severity or intensity distribution of any hot flushes still experienced, as compared to the severity of hot flushes prior to the start of the treatment. With respect to depression disorders, sexual dysfunction, and pain, the compounds of the present invention are administered at a dosage and for a time such that there is the prevention, alleviation, or elimination of the symptom or condition.

For example, for an afflicted patient, compounds of formula I may be administered, preferably, at a dosage of from about 0.1 mg/day to about 200 mg/day, more preferably from about 1 mg/day to about 100 mg/day and most preferably from about 1 mg/day to 50 mg/day for a time sufficient to reduce and/or substantially eliminate the number and/or severity of hot flushes or symptom or condition of the depression disorder, sexual dysfunction, or pain.

The terms "component," "composition of compounds," "compound," "drug," or "pharmacologically active agent" or "active agent" or "medicament" are used interchangeably herein to refer to a compound or compounds or composition of matter which, when administered to a subject (human or animal) induces a desired pharmacological and/or physiologic effect by local and/or systemic action.

The terms "component", "drug" or "pharmacologically active agent" or "active agent" or "medicament" are used interchangeably herein to refer to a compound or compounds or composition of matter which, when administered to an organism (human or animal) induces a desired pharmacologic and/or physiologic effect by local and/or systemic action.

The term "modulation" refers to the capacity to either enhance or inhibit a functional property of a biological activity or process, for example, receptor binding or signaling activity. Such enhancement or inhibition may be contingent on the occurrence of a specific event, such as activation of a signal transduction pathway and/or may be manifest only in particular cell types. The modulator is intended to comprise any compound, e.g., antibody, small molecule, peptide, oligopeptide, polypeptide, or protein, preferably small molecule, or peptide.

As used herein, the term "inhibitor" refers to any agent that inhibits, suppresses, represses, or decreases a specific activity, such as serotonin reuptake activity or the norepinephrine reuptake activity.

The term "inhibitor" is intended to comprise any compound, e.g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

Within the present invention, the compounds of formula I may be prepared in the form of pharmaceutically acceptable salts. As used herein, the term "pharmaceutically acceptable salts" refers to salts prepared from pharmaceutically acceptable non-toxic acids, including inorganic salts, and organic salts. Suitable non-organic salts include inorganic and organic acids such as acetic, benzenesulfonic, benzoic, camphorsulfonic, citric, ethenesulfonic, fumaric, gluconic, glutamic, hydrobromic, hydrochloric, isethionic, lactic, malic, maleic, mandelic, methanesulfonic, mucic, nitric, pamoic, pantothenic, phosphoric, succinic, sulfuric, tartaric acid, p-toluenesulfonic and the like. Particularly preferred are hydrochloric, hydrobromic, phosphoric, and sulfuric acids, and most preferably is the hydrochloride salt.

"Administering," as used herein, means either directly administering a compound or composition of the present invention, or administering a prodrug, derivative or analog which will form an equivalent amount of the active compound or substance within the body.

The term "subject" or "patient" refers to an animal including the human species that is treatable with the compositions, and/or methods of the present invention. The term "subject" or "subjects" is intended to refer to both the male and female gender unless one gender is specifically indicated. Accordingly, the term "patient" comprises any mammal which may benefit from treatment or prevention of vasomotor symptoms, depression disorders, sexual dysfunction, or pain, such as a human, especially if the mammal is female, either in the pre-menopausal, peri-menopausal, or post-menopausal period. Furthermore, the term patient includes female animals including humans and, among humans, not only women of advanced age who have passed through menopause but also women who have undergone hysterectomy or for some other reason have suppressed estrogen production, such as those who have undergone long-term administration of corticosteroids, suffer from Cushing's syndrome or have gonadal dysgenesis. However, the term "patient" is not intended to be limited to a woman.

The terms "premature menopause" or "artificial menopause" refer to ovarian failure of unknown cause that may occur before age 40. It may be associated with smoking, living at high altitude, or poor nutritional status. Artificial menopause may result from oophorectomy, chemotherapy, radiation of the pelvis, or any process that impairs ovarian blood supply.

The term "pre-menopausal" means before the menopause, the term "peri-menopausal" means during the menopause and the term "post-menopausal" means after the menopause. "Ovariectomy" means removal of an ovary or ovaries and can be effected according to Merchenthaler et al., *Maturitas*, 1998, 30(3): 307-316.

"Side effect" refers to a consequence other than the one(s) for which an agent or measure is used, as the adverse effects produced by a drug, especially on a tissue or organ system other then the one sought to be benefited by its administration. In the case, for example, of high doses of NRIs or NRI/SRI compounds alone, the term "side effect" may refer to such conditions as, for example, vomiting, nausea, sweating, and flushes (Janowsky, et al., *Journal of Clinical Psychiatry*, 1984, 45(10 Pt 2): 3-9).

"Alkyl," as used herein, refers to an aliphatic hydrocarbon chain of 1 to about 20 carbon atoms, preferably 1 to 10 carbon atoms, more preferably, 1 to 6 carbon atoms, and even more preferably, 1 to 4 carbon atoms and includes straight and branched chains such as methyl, ethyl, n-propyl, isopropyl, n-butyl, isobutyl, sec-butyl, t-butyl, n-pentyl, isopentyl, neopentyl, n-hexyl, and isohexyl. Lower alkyl refers to alkyl having 1 to 4 carbon atoms.

"Alkoxy," as used herein, refers to the group R—O— where R is an alkyl group of 1 to 6 carbon atoms.

"Alkoxycarbonyl," as used herein, refers to the group R—O—C(=O)— where R is an alkyl group of 1 to 6 carbon atoms.

"Alkanoyl," as used herein, refers to the group R—C(=O)— where R is an alkyl group of 1 to 6 carbon atoms.

"Alkanoyloxy," as used herein, refers to the group R—C(=O)—O— where R is an alkyl group of 1 to 6 carbon atoms.

"Alkylaminocarbonyl," as used herein, refers to the group R—NH—C(=O)—where R is an alkyl group of 1 to 6 carbon atoms.

"Alkylcarbonylamino," as used herein, refers to the group R—C(=O)—NH where R is an alkyl group of 1 to 6 carbon atoms.

"Alkenyl" or "olefinic," as used herein, refers to an alkyl group of at least two carbon atoms having one or more double bonds, wherein alkyl is as defined herein. Alkenyl groups can be optionally substituted.

"Alkynyl," as used herein, refers to an alkyl group of at least two carbon atoms having one or more triple bonds, wherein alkyl is as defined herein. Alkynyl groups can be optionally substituted.

"Aryl" as used herein, refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

"Heteroaryl," as used herein, refers to an optionally substituted, mono-, di-, tri-, or other multicyclic aromatic ring system that includes at least one, and preferably from 1 to about 4 sulfur, oxygen, or nitrogen heteroatom ring members. Heteroaryl groups can have, for example, from about 3 to about 50 carbon atoms (and all combinations and subcombinations of ranges and specific numbers of carbon atoms therein), with from about 4 to about 10 carbons being preferred. Non-limiting examples of heteroaryl groups include, for example, pyrryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl.

"Heterocyclic ring," as used herein, refers to a stable 5- to 7-membered monocyclic or bicyclic or 7- to 10-membered bicyclic heterocyclic ring that is saturated, partially unsaturated or unsaturated (aromatic), and which contains carbon atoms and from 1 to 4 heteroatoms independently selected from the group consisting of N, O and S and including any bicyclic group in which any of the above defined heterocyclic rings is fused to a benzene ring. The nitrogen and sulfur heteroatoms may optionally be oxidized. The heterocyclic ring may be attached to its pendant group at any heteroatom or carbon atom that results in a stable structure. The heterocyclic rings described herein may be substituted on carbon or on a nitrogen atom if the resulting compound is stable. If specifically noted, a nitrogen atom in the heterocycle may optionally be quaternized. It is preferred that when the total number of S and O atoms in the heterocycle exceeds one, then these heteroatoms are not adjacent to one another. It is preferred that the total number of S and O atoms in the heterocycle is not more than one. Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolonyl, carbazolyl, 4H-carbazolyl, α-, β-, or γ-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylpyrimidinyl, phenanthridinyl, phenanthrolinyl, phenoxazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred heterocycles include, but are not limited to, pyridinyl, furanyl, thienyl, pyrrolyl, pyrazolyl, imidazolyl, indolyl, benzimidazolyl, 1H-indazolyl, oxazolidinyl, benzotriazolyl, benzisoxazolyl, oxindolyl, benzoxazolinyl, or isatinoyl. Also included are fused ring and spiro compounds containing, for example, the above heterocycles.

"Heteroarylmethyl," as used herein, refers to the group R—CH$_2$— where R is a heteroaryl group, as defined herein.

"Heteroarylmethyloxy," as used herein, refers to the group R—CH$_2$—O— where R is a heteroaryl group, as defined herein.

"Heteroaryloxy," as used herein, refers to the group R—O— where R is a heteroaryl group, as defined herein.

"Heteroarylmethyloxy," as used herein, refers to the group R—CH$_2$—O— where R is a heteroaryl group, as defined herein.

"Cycloalkyl," as used herein, refers to an optionally substituted, alkyl group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropyl, cyclobutyl, cyclopentyl, cyclohexyl, cyclooctyl, 2-[4-isopropyl-1-methyl-7-oxa-bicyclo[2.2.1] heptanyl], 2-[1,2,3,4-tetrahydro-naphthalenyl], and adamantyl.

"Cycloalkylmethyl," as used herein, refers to the group R—CH$_2$— where R is a cycloalkyl group, as defined herein.

"Cycloalkenyl," as used herein, refers to an optionally substituted, alkene group having one or more rings in their structures having from 3 to about 20 carbon atoms (and all combinations and subcombinations of ranges and specific numbers of carbon atoms therein), with from 3 to about 10 carbon atoms being preferred. Multi-ring structures may be bridged or fused ring structures. Groups include, but are not limited to, cyclopropenyl, cyclobutenyl, cyclopentenyl, cyclohexenyl, cyclooctenyl.

"Cycloalkenylmethyl," as used herein, refers to the group R—CH$_2$— where R is a cycloalkenyl group, as defined herein.

"Sulfoxide," as used herein, refers to a compound or moiety containing the group —S(=O)—.

"Sulfonamido," as used herein, refers to a moiety containing the group —S(O)$_2$—NH—.

"Sulfonyl," as used herein, refers to a moiety containing the group —S(O)$_2$—.

"Halo" or "halogen," as used herein, refers to chloro, bromo, fluoro, and iodo.

In one embodiment, the present invention is directed to compounds of formula I:

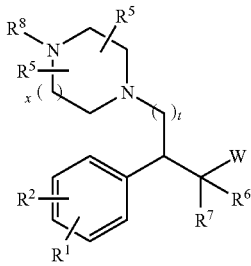

or a pharmaceutical salt thereof;
wherein:
W is H or $OR^9$;
$R^1$ is phenyl, naphthyl, heteroaryl, benzyloxy, phenoxy, naphthyloxy, phenylethoxy, phenoxyethoxy, naphthylmethoxy, naphthylethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino;
where said phenyl, naphthyl, heteroaryl, benzyloxy, phenoxy, naphthyloxy, phenylethoxy, phenoxyethoxy, naphthylmethoxy, naphthylethoxy, phenylcarbonylamino, and phenylaminocarbonyl are optionally substituted with one or more $R^2$;
$R^2$ is H, or one or two substituents, the same or different selected from OH, alkyl, alkoxy, halo, trifluoromethyl, alkanoyloxy, methylenedioxy, trifluoromethoxy, nitrile, nitro, alkenyl, alkynyl, sulfonyl, or sulfonamido;
$R^5$ is H, $(C_1-C_6)$alkyl, or trifluoromethyl;
$R^6$ and $R^7$ are, independently, $(C_1-C_6)$alkyl or $(C_3-C_6)$cycloalkyl;
or $R^6$ and $R^7$ can together form a ring of 4 to 8 carbon atoms;
where any carbon atom of said $R^6$ and $R^7$ may be optionally replaced with N, S, or O;
where $R^6$ and $R^7$ may be optionally substituted with $R^5$ or OH;
where $R^6$ and $R^7$ can form a ring with 4 to 8 carbons fused onto a cycloalkyl ring of 4 to 6 carbon atoms;
$R^8$ is H, $(C_1-C_6)$alkyl, hydroxy$(C_1-C_6)$alkyl, benzyl (optionally substituted with benzyloxy or phenyloxy), naphthylmethyl (optionally substituted with one or more $R^1$), phenyl $(C_2-C_6)$alkyl (optionally substituted with one or more $R^1$), heteroarylmethyl (optionally substituted with $R^1$), cycloalkyl, cycloalkenyl, cycloalkylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy), cycloalkenylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy);
or $R^5$ and $R^8$, together with the nitrogen atom to which $R^8$ is attached, form a ring optionally substituted with $R^5$;
$R^9$ is H, $(C_1-C_4)$alkyl, or $(C_1-C_4)$alkyl-C(=O);
t is 1, 2, or 3; and
x is 0, 1, or 2.
In certain preferred embodiments,
W is H or $OR^9$;
$R^1$ is phenyl, naphthyl, heteroaryl, benzyloxy, phenoxy, naphthyloxy, phenylethoxy, phenoxyethoxy, naphthylmethoxy, naphthylethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino;
where said phenyl, naphthyl, heteroaryl, benzyloxy, phenoxy, naphthyloxy, phenylethoxy, phenoxyethoxy, naphthylmethoxy, naphthylethoxy, phenylcarbonylamino, and phenylaminocarbonyl are optionally substituted with one or more $R^2$;
$R^2$ is $R^1$, H, OH, alkyl, alkoxy, halo, trifluoromethyl, alkanoyloxy, methylenedioxy, trifluoromethoxy, nitrile, nitro, alkenyl, alkynyl, sulfonyl, or sulfonamido;
$R^5$ is H, $(C_1-C_6)$alkyl or trifluoromethyl;
$R^6$ and $R^7$ together form a ring of 4 to 8 carbon atoms;
$R^8$ is H, $(C_1-C_6)$alkyl, hydroxy$(C_1-C_6)$alkyl, benzyl (optionally substituted with benzyloxy or phenyloxy), naphthylmethyl (optionally substituted with one or more $R^1$), phenyl $(C_2-C_6)$alkyl (optionally substituted with one or more $R^1$), heteroarylmethyl (optionally substituted with $R^1$), cycloalkyl, cycloalkenyl, cycloalkylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy), cycloalkenylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy);
or $R^5$ and $R^8$, together with the nitrogen atom to which $R^8$ is attached, form a ring optionally substituted with $R^5$;
$R^9$ is H;
t is 1, or 2; and
x is 1 or 2.
In certain preferred embodiments,
W is $OR^9$;
$R^1$ is phenyl, naphthyl, heteroaryl, benzyloxy, phenoxy, naphthyloxy, phenylethoxy, phenoxyethoxy, naphthylmethoxy, or naphthylethoxy;
where said phenyl, naphthyl, heteroaryl, benzyloxy, phenoxy, naphthyloxy, phenylethoxy, phenoxyethoxy, naphthylmethoxy, and naphthylethoxy are optionally substituted with one or more $R^2$;
$R^2$ is $R^1$, H, OH, alkyl, alkoxy, halo, trifluoromethyl, alkanoyloxy, methylenedioxy, trifluoromethoxy, nitrile, nitro, alkenyl, alkynyl, sulfonyl, or sulfonamido;
$R^5$ is H, $(C_1-C_6)$alkyl or trifluoromethyl;
$R^6$ and $R^7$ together form a ring of 4 to 8 carbon atoms;
$R^8$ is H, $(C_1-C_6)$alkyl, hydroxy$(C_1-C_6)$alkyl, benzyl (optionally substituted with benzyloxy or phenyloxy), naphthylmethyl (optionally substituted with one or more $R^1$), phenyl $(C_2-C_6)$alkyl (optionally substituted with one or more $R^1$), heteroarylmethyl (optionally substituted with $R^1$), cycloalkyl, cycloalkenyl, cycloalkylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy), cycloalkenylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy);
$R^9$ is H,
t is 1; and
x is 1.
In certain preferred embodiments,
W is $OR^9$;
$R^1$ is trifluoromethoxy, nitrile, alkenyl, or alkynyl;
$R^2$ is $R^1$, H, OH, alkyl, alkoxy, halo, or trifluoromethyl;
$R^5$ is H, $(C_1-C_6)$alkyl or trifluoromethyl;
$R^6$ and $R^7$ together form a ring of 4 to 8 carbon atoms;

$R^8$ is H, $(C_1-C_6)$alkyl, hydroxy$(C_1-C_6)$alkyl, benzyl (optionally substituted with benzyloxy or phenyloxy), naphthylmethyl (optionally substituted with one or more $R^1$), phenyl $(C_2-C_6)$alkyl (optionally substituted with one or more $R^1$), heteroarylmethyl (optionally substituted with $R^1$), cycloalkyl, cycloalkenyl, cycloalkylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy), cycloalkenylmethyl (where any carbon atom can be optionally replaced with N, S, or O and where said cycloalkylmethyl can be optionally substituted with OH, $CF_3$, halo, alkoxy, alkyl, benzyloxy, or alkanoyloxy);

or $R^5$ and $R^8$, together with the nitrogen atom to which $R^8$ is attached, form a ring optionally substituted with $R^5$;

$R^9$ is H;

t is 1; and x is 1.

In certain preferred embodiments,

W is $OR^9$;

$R^1$ is trifluoromethoxy, nitrile, alkenyl, or alkynyl;

$R^2$ is $R^1$, H, OH, alkyl, alkoxy, halo, or trifluoromethyl;

$R^5$ is $(C_1-C_6)$alkyl or trifluoromethyl;

$R^6$ and $R^7$ together form a ring of 4 to 8 carbon atoms;

$R^8$ is H or $(C_1-C_6)$alkyl;

$R^9$ is H;

t is 1; and x is 1.

In certain preferred embodiments, $R^1$ is phenyl, naphthyl, heteroaryl, benzyloxy, phenoxy, naphthyloxy, phenylethoxy, phenoxyethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino.

In certain preferred embodiments, $R^2$ is H, OH, alkyl (especially methyl, ethyl, propyl, and butyl), alkoxy (especially methoxy and ethoxy), halo (especially chloro, fluoro, and bromo).

In certain preferred embodiments, $R^5$ is H, $(C_1-C_6)$alkyl (especially methyl, ethyl, propyl, and butyl), halo (especially chloro, fluoro, and bromo).

In certain preferred embodiments, $R^6$ and $R^7$ are, independently, $(C_1-C_6)$alkyl (especially methyl, ethyl, propyl, and butyl) or $(C_3-C_6)$cycloalkyl (especially cyclopropyl, cyclobutyl, and cyclohexyl).

In certain preferred embodiments, $R^6$ and $R^7$ can together form a ring of 4 to 8 carbon atoms.

In certain preferred embodiments, $R^8$ is H, $(C_1-C_6)$alkyl (especially methyl, ethyl, propyl, and butyl), hydroxybutyl, benzyl, naphthylmethyl, phenyl$(C_2-C_6)$alkyl, heteroarylmethyl, cycloalkyl (especially cyclopropyl, cyclobutyl, and cyclohexyl), cycloalkenyl, cycloalkylmethyl, cycloalkenylmethyl.

In certain preferred embodiments, $R^5$ and $R^8$, together with the nitrogen atom to which $R^8$ is attached, form a ring optionally substituted with $R^5$.

In certain preferred embodiments, $R^9$ is H or $(C_1-C_4)$alkyl (especially methyl and ethyl).

In certain preferred embodiments, t is 1. In certain other preferred embodiments, t is 2. In yet certain other embodiments, t is 3.

In certain preferred embodiments, x is 0. In certain other preferred embodiments, x is 1. In yet certain other preferred embodiments, x is 2.

Examples of $R^6$ and $R^7$ together with the carbon to which they are attached include 4, 5 or 6 carbon rings, e.g. a cyclohexyl ring.

Examples of $R^1$ include trifluoromethoxy; thienyl; phenoxy; phenylethoxy; naphthyloxy; naphthylmethoxy; naphthylethoxy; alkenyl of 2 to 6 carbon atoms; alkynyl of 2 to 6 carbon atoms; phenyl optionally substituted by one, two or three substituents selected from halo, methylenedioxy, nitrile, nitro, alkoxy of 1 to 6 carbon atoms, alkyl of 1 to 6 carbon atoms, alkenyl of 2 to 6 carbon atoms, alkynyl of 2 to 6 carbon atoms trifluoromethoxy and trifluoromethyl; and benzyloxy optionally substituted by one or two substituents selected from halo, alkoxy of 1 to 6 carbon atoms, alkyl of 1 to 6 carbon atoms and trifluoromethyl.

Examples of $R^2$ are hydrogen, halo, alkoxy of 1 to 6 carbon atoms and hydroxy.

$R^8$ may be for example H, alkyl of 1 to 6 carbon atoms, hydroxy$(C_1-C_6)$alkyl, benzyl, phenyl$(C_2-C_6)$alkyl and cycloalkylmethyl.

W is for example OH. An example of x is 1. An example of t is 1.

Each $R^5$ is for example selected independently from H and alkyl of 1 to 6 carbon atoms.

Preferred compounds of formula I include:

1-{2-piperazin-1-yl-1-[3-(trifluoromethoxy)phenyl]ethyl}cyclohexanol dihydrochloride;

1-{2-(4-methylpiperazin-1-yl)-1-[3-(trifluoromethoxy)phenyl]ethyl}cyclohexanol dihydrochloride;

1-{1-[4-(benzyloxy)phenyl]-2-piperazin-1-ylethyl}cyclohexanol dihydrochloride;

1-{2-piperazin-1-yl-1-[4-(trifluoromethoxy)phenyl]ethyl}cyclohexanol dihydrochloride;

1-{2-piperazin-1-yl-1-[3-(trifluoromethoxy)phenyl]ethyl}cyclobutanol dihydrochloride;

1-{1-[4-(benzyloxy)phenyl]-2-piperazin-1-ylethyl}cyclobutanol dihydrochloride;

1-[1-[4-(benzyloxy)phenyl]-2-(4-methylpiperazin-1-yl)ethyl]cyclobutanol dihydrochloride;

1-{2-(4-methylpiperazin-1-yl)-1-[3-(trifluoromethoxy)phenyl]ethyl}cyclobutanol dihydrochloride;

1-{1-[3-(benzyloxy)phenyl]-2-piperazin-1-ylethyl}cyclohexanol dihydrochloride;

1-[1-[3-(benzyloxy)phenyl]-2-(4-methylpiperazin-1-yl)ethyl]cyclohexanol dihydrochloride;

1-{1-[3-(benzyloxy)phenyl]-2-piperazin-1-ylethyl}cyclobutanol dihydrochloride;

1-{1-[3-(benzyloxy)phenyl]-2-piperazin-1-ylethyl}cyclobutanol dihydrochloride;

1-[1-(3',4'-dichloro-1,1'-biphenyl-3-yl)-2-piperazin-1-ylethyl]cyclohexanol dihydrochloride;

1-[1-(3',4'-dichloro-1,1'-biphenyl-3-yl)-2-piperazin-1-ylethyl]cyclohexanol dihydrochloride;

1-[1-(1,1'-biphenyl-3-yl)-2-piperazin-1-ylethyl]cyclohexanol dihydrochloride;

1-[1-(4'-chloro-1,1'-biphenyl-3-yl)-2-piperazin-1-ylethyl]cyclohexanol dihydrochloride;

1-[1-(4'-chloro-1,1'-biphenyl-3-yl)-2-piperazin-1-ylethyl]cyclohexanol dihydrochloride;

1-[1-(3'-chloro-1,1'-biphenyl-3-yl)-2-piperazin-1-ylethyl]cyclohexanol dihydrochloride;

1-[1-(2'-fluoro-1,1'-biphenyl-3-yl)-2-piperazin-1-ylethyl]cyclohexanol maleate;

1-[1-(3',4'-difluoro-1,1'-biphenyl-3-yl)-2-piperazin-1-ylethyl]cyclohexanol dihydrochloride;

1-[1-(3',4'-dichloro-1,1'-biphenyl-2-yl)-2-piperazin-1-ylethyl]cyclohexanol dihydrochloride;

1-[1-(1,1'-biphenyl-2-yl)-2-piperazin-1-ylethyl]cyclohexanol dihydrochloride;

1-[1-(3'-chloro-1,1'-biphenyl-2-yl)-2-piperazin-1-ylethyl]cyclohexanol dihydrochloride;

1-{1-[2-(1,3-benzodioxol-5-yl)phenyl]-2-piperazin-1-ylethyl}cyclohexanol dihydrochloride;
1-[2-(4-aminopiperidin-1-yl)-1-(3',4'-dichloro-1,1'-biphenyl-3-yl)ethyl]cyclohexanol dihydrochloride;
1-[1-(3',4'-dichloro-1,1'-biphenyl-3-yl)-2-piperazin-1-ylethyl]cyclobutanol dihydrochloride;
1-[1-(3',4'-dichloro-1,1'-biphenyl-3-yl)-2-piperazin-1-ylethyl]cyclobutanol dihydrochloride;
1-[1-(1,1'-biphenyl-4-yl)-2-(4-methylpiperazin-1-ylethyl]cyclohexanol dihydrochloride;
1-[1-(3-cyanophenyl)-2-piperazin-1-ylethyl]cyclohexanol dihydrochloride;
1-[1-(3-cyanophenyl)-2-(4-methylpiperazin-1-yl)ethyl]cyclohexanol dihydrochloride;
1-[2-piperazin-1-yl-1-(3-vinylphenyl)ethyl]cyclohexanol dihydrochloride;
1-[2-piperazin-1-yl-1-(4-vinylphenyl)ethyl]cyclohexanol dihydrochloride;
1-[2-piperazin-1-yl-1-(4-prop-1-ynylphenyl)ethyl]cyclohexanol dihydrochloride;
1-[1-(2'-chloro-1,1'-biphenyl-4-yl)-2-piperazin-1-ylethyl]cyclohexanol dihydrochloride;
1-[1-(3'-fluoro-1,1'-biphenyl-4-yl)-2-piperazin-1-ylethyl]cyclohexanol dihydrochloride;
1-[1-(3'-chloro-1,1'-biphenyl-4-yl)-2-piperazin-1-ylethyl]cyclohexanol dihydrochloride;
1-[1-(3'-cyano-1,1'-biphenyl-4-yl)-2-piperazin-1-ylethyl]cyclohexanol dihydrochloride;
1-[1-(3'-nitro-1,1'-biphenyl-4-yl)-2-piperazin-1-ylethyl]cyclohexanol dihydrochloride;
1-[1-(3'-methoxy-1,1'-biphenyl-4-yl)-2-piperazin-1-ylethyl]cyclohexanol dihydrochloride;
1-{2-piperazin-1-yl-1-[3'-(trifluoromethoxy)-1,1'-biphenyl-4-yl]ethyl}cyclohexanol dihydrochloride;
1-[1-(4'-chloro-1,1'-biphenyl-4-yl)-2-piperazin-1-ylethyl]cyclohexanol dihydrochloride;
1-[1-(3',4'-dichloro-1,1'-biphenyl-4-yl)-2-piperazin-1-ylethyl]cyclohexanol dihydrochloride;
1-[2-piperazin-1-yl-1-(4-thien-3-ylphenyl)ethyl]cyclohexanol dihydrochloride;
1-[1-(2'-chloro-1,1'-biphenyl-4-yl)-2-(4-methyl piperazin-1-yl)ethyl]cyclohexanol dihydrochloride;
1-[1-(3'-chloro-1,1'-biphenyl-4-yl)-2-(4-methylpiperazin-1-yl)ethyl]cyclohexanol dihydrochloride;
1-[1-(3'-cyano-1,1'-biphenyl-4-yl)-2-(4-methylpiperazin-1-yl)ethyl]cyclohexanol dihydrochloride;
1-[2-(4-methylpiperazin-1-yl)-1-(3'-nitro-1,1'-biphenyl-4-yl)ethyl]cyclohexanol dihydrochloride;
1-[1-(3'-methoxy-1,1'-biphenyl-4-yl)-2-(4-methylpiperazin-1-yl)ethyl]cyclohexanol dihydrochloride;
1-[1-(4'-fluoro-1,1'-biphenyl-4-yl)-2-(4-methylpiperazin-1-yl)ethyl]cyclohexanol dihydrochloride;
1-[1-(4'-methyl-1,1'-biphenyl-4-yl)-2-(4-methylpiperazin-1-yl)ethyl]cyclohexanol dihydrochloride;
1-[1-(3'-chloro-1,1'-biphenyl-4-yl)-2-piperazin-1-ylethyl]cyclobutanol dihydrochloride;
1-{2-piperazin-1-yl-1-[3'-(trifluoromethoxy)-1,1'-biphenyl-4-yl]ethyl}cyclobutanol dihydrochloride;
1-[1-(3',4'-dichloro-1,1'-biphenyl-4-yl)-2-piperazin-1-ylethyl]cyclobutanol dihydrochloride;
1-[1-(3',5'-dichloro-1,1'-biphenyl-4-yl)-2-piperazin-1-ylethyl]cyclobutanol dihydrochloride;
1-{(1S)-2-piperazin-1-yl-1-[3-(trifluoromethoxy)phenyl]ethyl}cyclohexanol dihydrochloride;
1-{(1R)-2-piperazin-1-yl-1-[3-(trifluoromethoxy)phenyl]ethyl}cyclohexanol dihydrochloride;
1-{(1S)-2-(4-methylpiperazin-1-yl)-1-[3-(trifluoromethoxy)phenyl]ethyl}cyclohexanol dihydrochloride;
1-{(1R)-2-(4-methylpiperazin-1-yl)-1-[3-(trifluoromethoxy)phenyl]ethyl}cyclohexanol dihydrochloride;
1-[1-(3',4'-dichloro-1,1'-biphenyl-3-yl)-2-(4-methylpiperazin-1-yl)ethyl]cyclohexanol dihydrochloride;
1-{2-piperazin-1-yl-1-[3'-(trifluoromethoxy)-1,1'-biphenyl-3-yl]ethyl}cyclohexanol dihydrochloride;
1-{2-piperazin-1-yl-1-[4'-(trifluoromethyl)-1,1'-biphenyl-3-yl]ethyl}cyclohexanol dihydrochloride;
1-[1-(3',4'-dimethoxy-1,1'-biphenyl-3-yl)-2-piperazin-1-ylethyl]cyclohexanol dihydrochloride;
1-{1-[6-methoxy-3'-(trifluoromethoxy)-1,1'-biphenyl-3-yl]-2-piperazin-1-ylethyl}cyclohexanol dihydrochloride;
1-[1-(3',4'-dichloro-6-methoxy-1,1'-biphenyl-3-yl)-2-piperazin-1-ylethyl]cyclohexanol dihydrochloride;
1-{1-[6-methoxy-4'-(trifluoromethyl)-1,1'-biphenyl-3-yl]-2-piperazin-1-ylethyl}cyclohexanol dihydrochloride;
1-[1-(6-methoxy-1,1'-biphenyl-3-yl)-2-piperazin-1-ylethyl]cyclohexanol dihydrochloride;
1-[1-(3',4'-dichloro-6-methoxy-1,1'-biphenyl-3-yl)-2-(4-methylpiperazin-1-yl)ethyl]cyclohexanol dihydrochloride;
1-[1-[6-methoxy-3'-(trifluoromethoxy)-1,1'-biphenyl-3-yl]-2-(4-methylpiperazin-1-yl)ethyl]cyclohexanol dihydrochloride;
1-[1-[6-methoxy-4'-(trifluoromethyl)-1,1'-biphenyl-3-yl]-2-(4-methylpiperazin-1-yl)ethyl]cyclohexanol dihydrochloride;
1-{1-[4-(benzyloxy)-3-(trifluoromethyl)phenyl]-2-piperazin-1-ylethyl}cyclohexanol dihydrochloride;
1-[1-[4-(benzyloxy)-3-(trifluoromethyl)phenyl]-2-(4-methylpiperazin-1-yl)ethyl]cyclohexanol dihydrochloride;
1-[1-[4-(benzyloxy)-3-bromophenyl]-2-(4-methylpiperazin-1-yl)ethyl]cyclohexanol dihydrochloride;
2-(benzyloxy)-5-[1-(1-hydroxycyclohexyl)-2-piperazin-1-ylethyl]benzonitrile dihydrochloride;
2-(benzyloxy)-5-[1-(1-hydroxycyclohexyl)-2-(4-methylpiperazin-1-yl)ethyl]benzonitrile dihydrochloride;
1-{1-[4-(benzyloxy)-3-(trifluoromethoxy)phenyl]-2-piperazin-1-ylethyl}cyclohexanol dihydrochloride;
1-{2-(4-methylpiperazin-1-yl)-1-[4-(trifluoromethoxy)phenyl]ethyl}cyclohexanol dihydrochloride;
1-{2-[4-(1,3-benzoioxol-5-ylmethyl)piperazin-1-yl]-1-[4-(trifluoromethoxy)phenyl]ethyl}cyclohexanol dihydrochloride;
1-{2-[4-(cyclohexylmethyl)piperazin-1-yl]-1-[4-(trifluoromethoxy)phenyl]ethyl}cyclohexanol dihydrochloride;
1-{2-(4-ethylpiperazin-1-yl)-1-[4-(trifluoromethoxy)phenyl]ethyl}cyclohexanol dihydrochloride;
1-{2-[cis-3,5-dimethylpiperazin-1-yl]-1-[4-(trifluoromethoxy)phenyl]ethyl}cyclohexanol dihydrochloride;
1-[1-(2'-fluoro-1,1'-biphenyl-4-yl)-2-piperazin-1-ylethyl]cyclohexanol dihydrochloride;
4'-[1-(1-hydroxycyclohexyl)-2-piperazin-1-ylethyl]-1,1'-biphenyl-2-carbonitrile dihydrochloride;
1-[1-(2',5'-dichloro-1,1'-biphenyl-4-yl)-2-piperazin-1-ylethyl]cyclohexanol dihydrochloride;
1-{1-[4-(benzyloxy)-3-chlorophenyl]-2-piperazin-1-ylethyl}cyclohexanol dihydrochloride;
1-[1-[4-(benzyloxy)-3-chlorophenyl]-2-(4-methylpiperazin-1-yl)ethyl]cyclohexanol dihydrochloride;
1-[1-(3'-chloro-1,1'-biphenyl-4-yl)-2-(4-methylpiperazin-1-yl)ethyl]cyclobutanol dihydrochloride;
1-{2-(4-methylpiperazin-1-yl)-1-[3'-(trifluoromethoxy)-1,1'-biphenyl-4-yl]ethyl}cyclobutanol dihydrochloride;

1-[1-(3',4'-dichloro-1,1'-biphenyl-4-yl)-2-(4-methylpiperazin-1-yl)ethyl]cyclobutanol dihydrochloride;
1-[1-(3',5'-dichloro-1,1'-biphenyl-4-yl)-2-(4-methylpiperazin-1-yl)ethyl]cyclobutanol dihydrochloride;
1-[1-(3-ethynylphenyl)-2-piperazin-1-ylethyl]cyclohexanol dihydrochloride;
1-[1-(3-ethynylphenyl)-2-(4-methylpiperazin-1-yl)ethyl]cyclohexanol dihydrochloride;
1-[2-piperazin-1-yl-1-(3-prop-1-ynylphenyl)ethyl]cyclohexanol dihydrochloride;
1-[2-(4-methylpiperazin-1-yl)-1-(3-prop-1-ynylphenyl)ethyl]cyclohexanol dihydrochloride;
1-{2-(4-benzyl-1,4-diazepan-1-yl)-1-[4-(trifluoromethoxy)phenyl]ethyl}cyclohexanol dihydrochloride;
1-{2-piperazin-1-yl-1-[4-(trifluoromethoxy)phenyl]ethyl}cyclobutanol dihydrochloride;
1-{2-(4-methyl-1,4-diazepan-1-yl)-1-[4-(trifluoromethoxy)phenyl]ethyl)cyclobutanol dihydrochloride;
1-[1-(4-phenoxyphenyl)-2-piperazin-1-ylethyl]cyclohexanol dihydrochloride
1-[2-(4-methylpiperazin-1-yl)-1-(4-phenoxyphenyl)ethy]cyclohexanol dihydrochloride;
1-[2-[4-(cyclohexylmethyl)piperazin-1-yl]-1-(4-phenoxyphenyl)ethyl]cyclohexanol dihydrochloride;
1-[1-(3-phenoxyphenyl)-2-piperazin-1-ylethyl]cyclohexanol dihydrochloride;
1-[2-(4-methylpiperazin-1-yl)-1-(3-phenoxyphenyl)ethy]cyclohexanol dihydrochloride;
1-[2-[4-(cyclohexylmethyl)piperazin-1-yl]-1-(3-phenoxyphenyl)ethyl]cyclohexanol dihydrochloride;
1-[2-(4-methyl-1-piperazinyl)-1-[4-phenylmethoxy)phenyl]ethyl]cyclohexanol dihydrochloride;
1-{(1R)-1-[4-(benzyloxy)-3-chlorophenyl]-2-piperazin-1-ylethyl}cyclohexanol dihydrochloride;
1-{(1S)-1-[4-(benzyloxy)-3-chlorophenyl]-2-piperazin-1-ylethyl}cyclohexanol dihydrochloride;
1-[(1R)-1-[4-(benzyloxy)-3-chlorophenyl]-2-(4-methylpiperazin-1-yl)ethyl]cyclohexanol dihydrochloride;
1-[(1S)-1-[4-(benzyloxy)-3-chlorophenyl]-2-(4-methylpiperazin-1-yl)ethyl]cyclohexanol dihydrochloride;
1-{(1S)-2-[4-(3-phenylbutyl)piperazin-1-yl]-1-[3-(trifluoromethoxy)phenyl]ethyl}cyclohexanol;
1-{(1S)-2-[(3S)-3-methylpiperazin-1-yl]-1-[3-(trifluoromethoxy)phenyl]ethyl}cyclohexanol;
1-{(1S)-2-[(3S)-3,4-dimethylpiperazin-1-yl]-1-[3-(trifluoromethoxy)phenyl]ethyl}cyclohexanol;
1-{(1S)-2-(3-ethylpiperazin-1-yl)-1-[3-(trifluoromethoxy)phenyl]ethyl}cyclohexanol;
1-{(1S)-2-[(3S)-3-ethyl-4-methylpiperazin-1-yl]-1-[3-(trifluoromethoxy)phenyl]ethyl}cyclohexanol;
1-{(1S)-2-[(3R)-3-ethyl-4-methylpiperazin-1-yl]-1-[3-(trifluoromethoxy)phenyl]ethyl}cyclohexanol;
1-[(1S)-1-(3-phenoxyphenyl)-2-piperazin-1-ylethyl]cyclohexanol;
1-[(1R)-1-(3-phenoxyphenyl)-2-piperazin-1-ylethyl]cyclohexanol;
1-{2-(4-isopropylpiperazin-1-yl)-1-[3-(trifluoromethoxy)phenyl]ethyl}cyclohexanol;
1-{(1S)-2-{4-[(1S)-1-phenylethyl]piperazin-1-yl}-1-[3-(trifluoromethoxy)phenyl]ethyl}cyclohexanol;
1-{(1S)-2-{4-[(1R)-1-phenylethyl]piperazin-1-yl}-1-[3-(trifluoromethoxy)phenyl]ethyl}cyclohexanol;
1-{(1S)-2-[(3R,5S)-3,5-dimethylpiperazin-1-yl]-1-[3-(trifluoromethoxy)phenyl]ethyl}cyclohexanol;
1-{(1S)-1-[3-(trifluoromethoxy)phenyl]-2-[(3R,5S)-3,4,5-trimethylpiperazin-1-yl]ethyl}cyclohexanol;
1-{(1S)-2-[(3R)-3-methylpiperazin-1-yl]-1-[3-(trifluoromethoxy)phenyl]ethyl}cyclohexanol;
1-{(1S)-2-[(3R)-3,4-dimethylpiperazin-1-yl]-1-[3-(trifluoromethoxy)phenyl]ethyl}cyclohexanol;
1-{(1S)-2-(octahydro-2H-pyrido[1,2-a]pyrazin-2-yl)-1-[3-(trifluoromethoxy)phenyl]ethyl}cyclohexanol;
1-{2-[4-(2-hydroxy-2-methylpropyl)piperazin-1-yl]-1-[3-(trifluoromethoxy)phenyl]ethyl}cyclohexanol;
1-{2-[4-(2-hydroxy-1,1-dimethylethyl)piperazin-1-yl]-1-[3-(trifluoromethoxy)phenyl]ethyl}cyclohexanol;
1-{1-[4-(1-naphthyloxy)phenyl]-2-piperazin-1-ylethyl}cyclohexanol;
1-{1-[4-(benzyloxy)-3-bromo-5-methoxyphenyl]-2-piperazin-1-ylethyl}cyclohexanol;
1-[1-[4-(benzyloxy)-3-bromo-5-methoxyphenyl]-2-(4-methylpiperazin-1-yl)ethyl]cyclohexanol;
1-{1-[4-(benzyloxy)-3,5-dibromophenyl]-2-piperazin-1-ylethyl}cyclohexanol;
1-[1-[4-(benzyloxy)-3,5-dibromophenyl]-2-(4-methylpiperazin-1-yl)ethyl]cyclohexanol;
(3R)-3-methyl-1-{2-piperazin-1-yl-1-[3-(trifluoromethoxy)phenyl]ethyl}cyclopentanol;
(3R)-3-methyl-1-{2-(4-methylpiperazin-1-yl)-1-[3-(trifluoromethoxy)phenyl]ethyl}cyclopentanol;
2,2-dimethyl-1-{2-piperazin-1-yl-1-[3-(trifluoromethoxy)phenyl]ethyl}cyclopentanol;
2,2-dimethyl-1-{2-(4-methylpiperazin-1-yl)-1-[3-(trifluoromethoxy)phenyl]ethyl}cyclopentanol;
1-{2-(4-methylpiperazin-1-yl)-1-[4-(1-naphthyloxy)phenyl]ethyl}cyclohexanol;
4-[1-(1-hydroxycyclohexyl)-2-piperazin-1-ylethyl]-2-(trifluoro methoxy)phenol;
4-[1-(1-hydroxycyclohexyl)-2-(4-methylpiperazin-1-yl)ethyl]-2-(trifluoromethoxy)phenol;
1-{1-[4-methoxy-3-(trifluoromethoxy)phenyl]-2-piperazin-1-ylethyl}cyclohexanol;
1-[1-[4-methoxy-3-(trifluoromethoxy)phenyl]-2-(4-methylpiperazin-1-yl)ethyl]cyclohexanol;
1-{1-[4-ethoxy-3-(trifluoromethoxy)phenyl]-2-piperazin-1-ylethyl}cyclohexanol;
1-[1-[4-ethoxy-3-(trifluoromethoxy)phenyl]-2-(4-methylpiperazin-1-yl)ethyl]cyclohexanol;
1-{1-[4-isobutoxy-3-(trifluoromethoxy)phenyl]-2-piperazin-1-ylethyl}cyclohexanol;
1-[1-[4-isobutoxy-3-(trifluoromethoxy)phenyl]-2-(4-methylpiperazin-1-yl)ethyl]cyclohexanol;
1-[1-[4-(benzyloxy)-3-(trifluoromethoxy)phenyl]-2-(4-methylpiperazin-1-yl)ethyl]cyclohexanol;
1-{1-[4-(2-phenylethyl)phenyl]-2-piperazin-1-ylethyl}cyclohexanol;
1-{2-(4-methylpiperazin-1-yl)-1-[4-(2-phenylethyl)phenyl]ethyl}cyclohexanol;
1-[(1S)-1-[4-(benzyloxy)phenyl]-2-(4-methylpiperazin-1-yl)ethyl]cyclohexanol;
1-[(1R)-1-[4-(benzyloxy)phenyl]-2-(4-methylpiperazin-1-yl)ethyl]cyclohexanol;
1-{1-[4-(benzyloxy)-3-fluorophenyl]-2-piperazin-1-ylethyl}cyclohexanol;
1-[1-[4-(benzyloxy)-3-fluorophenyl]-2-(4-methylpiperazin-1-yl)ethyl]cyclohexanol;
1-[1-(3-fluoro-4-{[4-(trifluoromethyl)benzyl]oxy}phenyl)-2-piperazin-1-ylethyl]cyclohexanol;
1-[1-(3-fluoro-4-{[4-(trifluoromethyl)benzyl]oxy}phenyl)-2-(4-methylpiperazin-1-yl)ethyl]cyclohexanol;
1-(1-{3-fluoro-4-[(4-methylbenzyl)oxy]phenyl}-2-piperazin-1-ylethyl)cyclohexanol;

1-[1-{3-fluoro-4-[(4-methylbenzyl)oxy]phenyl}-2-(4-methylpiperazin-1-yl)ethyl]cyclohexanol;
1-[1-(3-chloro-4-{[4-(trifluoromethyl)benzyl]oxy}phenyl)-2-piperazin-1-ylethyl]cyclohexanol;
1-[1-(3-chloro-4-{[4-(trifluoromethyl)benzyl]oxy}phenyl)-2-(4-methylpiperazin-1-yl)ethyl]cyclohexanol;
1-[1-(3-chloro-4-{[2-(trifluoromethyl)benzyl]oxy}phenyl)-2-piperazin-1-ylethyl]cyclohexanol;
1-[1-(3-chloro-4-{[2-(trifluoromethyl)benzyl]oxy}phenyl)-2-(4-methylpiperazin-1-yl)ethyl]cyclohexanol;
1-[1-(3-chloro-4-{[3-(trifluoromethyl)benzyl]oxy}phenyl)-2-piperazin-1-ylethyl]cyclohexanol;
1-[1-(3-chloro-4-{[3-(trifluoromethyl)benzyl]oxy}phenyl)-2-(4-methylpiperazin-1-yl)ethyl]cyclohexanol;
1-(1-{4-[(4-bromo-2-fluorobenzyl)oxy]-3-chlorophenyl}-2-piperazin-1-ylethyl)cyclohexanol;
1-[1-{4-[(4-bromo-2-fluorobenzyl)oxy]-3-chlorophenyl}-2-(4-methylpiperazin-1-yl)ethyl]cyclohexanol;
1-{1-[3-chloro-4-(2-naphthylmethoxy)phenyl]-2-piperazin-1-ylethyl}cyclohexanol;
1-{1-[4-(2-naphthylmethoxy)phenyl]-2-piperazin-1-ylethyl}cyclohexanol;
1-{2-(4-methylpiperazin-1-yl)-1-[4-(2-naphthylmethoxy)phenyl]ethyl}cyclohexanol;
1-(1-{4-[(4-bromo-2-fluorobenzyl)oxy]phenyl}-2-piperazin-1-ylethyl)cyclohexanol;
1-[1-{4-[(4-bromo-2-fluorobenzyl)oxy]phenyl}-2-(4-methylpiperazin-1-yl)ethyl]cyclohexanol;
1-[2-piperazin-1-yl-1-(4-{[4-(trifluoromethyl)benzyl]oxy}phenyl)ethyl]cyclohexanol;
1-[2-(4-methylpiperazin-1-yl)-1-(4-{[4-(trifluoromethyl)benzyl]oxy}phenyl)ethyl]cyclohexanol;
1-[2-piperazin-1-yl-1-(4-{[3-(trifluoromethyl)benzyl]oxy}phenyl)ethyl]cyclohexanol;
1-[2-(4-methylpiperazin-1-yl)-1-(4-{[3-(trifluoromethyl)benzyl]oxy}phenyl)ethyl]cyclohexanol;
1-[2-piperazin-1-yl-1-(4-{[2-(trifluoromethyl)benzyl]oxy}phenyl)ethyl]cyclohexanol;
1-[2-(4-methylpiperazin-1-yl)-1-(4-{[2-(trifluoromethyl)benzyl]oxy}phenyl)ethyl]cyclohexanol;
1-{1-[4-(benzyloxy)-3-methoxyphenyl]-2-piperazin-1-ylethyl}cyclohexanol;
1-[1-[4-(benzyloxy)-3-methoxyphenyl]-2-(4-methylpiperazin-1-yl)ethyl]cyclohexanol;
1-{1-[3-methoxy-4-(2-naphthylmethoxy)phenyl]-2-piperazin-1-ylethyl}cyclohexanol;
1-[1-[3-methoxy-4-(2-naphthylmethoxy)phenyl]-2-(4-methylpiperazin-1-yl)ethyl]cyclohexanol;
1-(1-{4-[(4-bromo-2-fluorobenzyl)oxy]-3-methoxyphenyl}-2-piperazin-1-ylethyl)cyclohexanol;
1-[1-{4-[(4-bromo-2-fluorobenzyl)oxy]-3-methoxyphenyl}-2-(4-methylpiperazin-1-yl)ethyl]cyclohexanol;
1-[1-(3-methoxy-4-{[4-(trifluoromethyl)benzyl]oxy}phenyl)-2-piperazin-1-ylethyl]cyclohexanol;
1-[1-(3-methoxy-4-{[4-(trifluoromethyl)benzyl]oxy}phenyl)-2-(4-methylpiperazin-1-yl)ethyl]cyclohexanol;
1-{1-[3-chloro-4-(2-phenylethoxy)phenyl]-2-piperazin-1-ylethyl}cyclohexanol;
1-[1-[3-chloro-4-(2-phenylethoxy)phenyl]-2-(4-methylpiperazin-1-yl)ethyl]cyclohexanol;
1-(1-{3-chloro-4-[(3-methoxybenzyl)oxy]phenyl}-2-piperazin-1-ylethyl)cyclohexanol;
1-[1-{3-chloro-4-[(3-methoxybenzyl)oxy]phenyl}-2-(4-methylpiperazin-1-yl)ethyl]cyclohexanol;
1-(1-{3-chloro-4-[(2-methoxybenzyl)oxy]phenyl}-2-piperazin-1-ylethyl)cyclohexanol;
1-[1-{3-chloro-4-[(2-methoxybenzyl)oxy]phenyl}-2-(4-methylpiperazin-1-yl)ethyl]cyclohexanol;
1-{1-[4-(2-phenylethoxy)phenyl]-2-piperazin-1-ylethyl}cyclohexanol;
1-{2-(4-methylpiperazin-1-yl)-1-[4-(2-phenylethoxy)phenyl]ethyl}cyclohexanol;
1-(1-{4-[2-(4-fluorophenyl)ethoxy]phenyl}-2-piperazin-1-ylethyl)cyclohexanol;
1-[1-{4-[2-(4-fluorophenyl)ethoxy]phenyl}-2-(4-methylpiperazin-1-yl)ethyl]cyclohexanol;
1-(1-{4-[2-(1-naphthyl)ethoxy]phenyl}-2-piperazin-1-ylethyl)cyclohexanol;
1-(2-(4-methylpiperazin-1-yl)-1-{4-[2-(1-naphthyl)ethoxy]phenyl}ethyl)cyclohexanol;
1-[1-{4-[2-(4-methoxyphenyl)ethoxy]phenyl}-2-(4-methylpiperazin-1-yl)ethyl]cyclohexanol;
1-[1-[4-(cyclohexylmethoxy)phenyl]-2-(4-methylpiperazin-1-yl)ethyl]cyclohexanol;
1-(2-(4-methylpiperazin-1-yl)-1-{4-[(1R)-1-phenylethoxy]phenyl}ethyl)cyclohexanol;
1-(2-(4-methylpiperazin-1-yl)-1-{4-[(1S)-1-phenylethoxy]phenyl}ethyl)cyclohexanol;
and
pharmaceutically acceptable salts thereof.

Some of the compounds of the present invention may contain chiral centers and such compounds may exist in the form of stereoisomers (i.e. enantiomers). The present invention includes all such stereoisomers and any mixtures thereof including racemic mixtures. Racemic mixtures of the stereoisomers as well as the substantially pure stereoisomers are within the scope of the invention. The term "substantially pure," as used herein, refers to at least about 90 mole %, more preferably at least about 95 mole %, and most preferably at least about 98 mole % of the desired stereoisomer is present relative to other possible stereoisomers. Preferred enantiomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron,* 33:2725 (1977); Eliel, E. L. *Stereochemistry of Carbon Compounds*, (McGraw-Hill, NY, 1962); Wilen, S. H. *Tables of Resolving Agents and Optical Resolutions*, p. 268 (E. L. Eliel, Ed., University of Notre Dame Press, Notre Dame, Ind. 1972).

The present invention includes prodrugs of the compounds of formula I. "Prodrug," as used herein, means a compound which is convertible in vivo by metabolic means (e.g. by hydrolysis) to a compound of formula I. Various forms of prodrugs are known in the art, for example, as discussed in Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "Design and Application of Prodrugs," *Textbook of Drug Design and Development*, Chapter 5, 113-191 (1991), Bundgaard, et al., *Journal of Drug Deliver Reviews,* 1992, 8:1-38, Bundgaard, *J. of Pharmaceutical Sciences,* 1988, 77:285 et seq.; and Higuchi and Stella (eds.) *Prodrugs as Novel Drug Delivery Systems*, American Chemical Society (1975).

Further, the compounds of formula I may exist in unsolvated as well as in solvated forms with pharmaceutically acceptable solvents such as water, ethanol, and the like. In general, the solvated forms are considered equivalent to the unsolvated forms for the purpose of the present invention.

This invention also provides process for preparing a compound of formula I which includes one of the following:

a) reducing a compound of formula

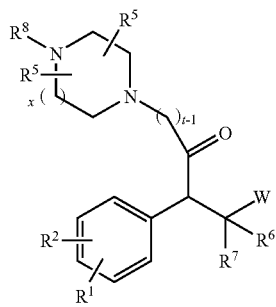

wherein $R^1$, $R^2$, $R^{5-8}$, x, t and W are as defined herein to give a compound of formula I; if necessary any reactive groups or sites being protected during the reaction by protecting group(s) and removed thereafter;

or b) alkylating a compound of formula I wherein $R^8$ is hydrogen with an alkylating agent to give a compound of formula I wherein $R^8$ is as defined herein excepting hydrogen;

or c) converting a compound of formula I having a reactive substituent group to a compound of formula I having a different substituent group;

or d) converting a basic compound of formula I to a pharmaceutically acceptable salt or vice versa.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Protecting groups that may be employed in accordance with the present invention may be described in Greene, T. W. and Wuts, P. G. M., *Protective Groups in Organic Synthesis* 2d. Ed., Wiley & Sons, 1991.

Compounds of the present invention are suitably prepared in accordance with the following general description and specific examples. Variables used are as defined for Formula I, unless otherwise noted. The reagents used in the preparation of the compounds of this invention can be either commercially obtained or can be prepared by standard procedures described in the literature. The reagents used in the preparation of the compounds of this invention can be either commercially obtained or can be prepared by standard procedures described in the literature. In accordance with this invention, compounds of formula I are produced by the following reaction schemes (Scheme 1-5).

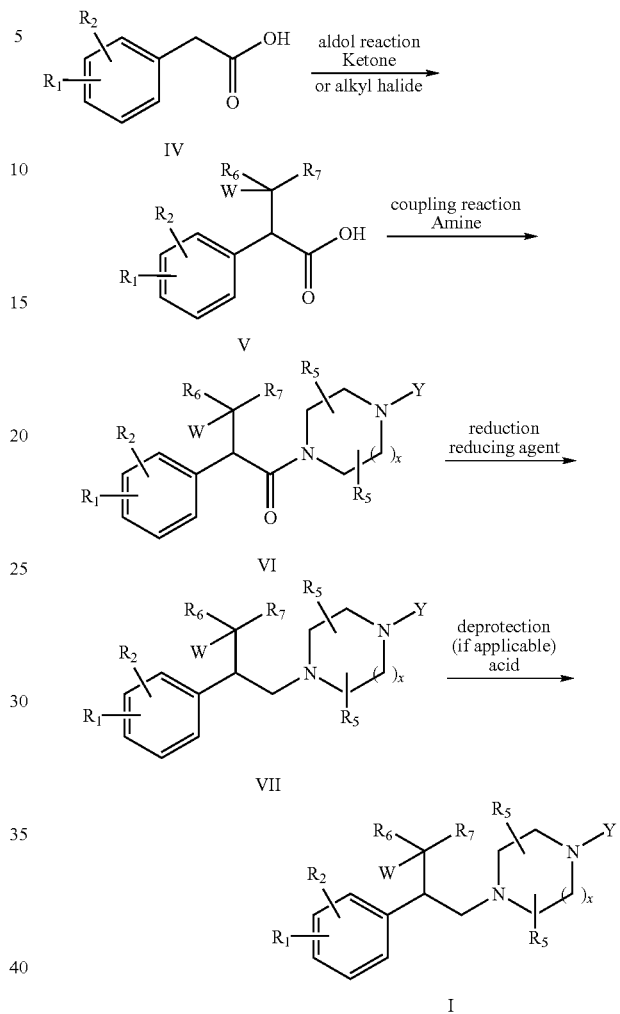

where
Y=H, $R_8$, or P;
P is an amine protecting group, preferably but not limited to tert-butoxycarbonyl; and
$R^1$, $R^2$, $R^3$, $R^4$, $R^5$, $R^6$, $R^7$, $R^8$, W and x are as previously described.

Compounds of formula I can be prepared from compounds of formula VI via reduction followed by deprotection, where Y=P; otherwise the deprotection step is omitted. Where P=tert-butoxycarbonyl, any conventional method for the deprotection of a carbamate can be utilized for this conversion. In accordance with the preferred embodiment of this invention, deprotection is carried out using a protic acid, i.e., hydrochloric acid. Reduction is performed using any conventional method of reducing an amide to an amine. In accordance with the preferred embodiment of this invention, the compounds of formula VI are treated with a solution of borane in tetrahydrofuran and heated at 70-80° C.

Compounds of formula VI can be prepared via the coupling of compounds of formula V with an appropriately substituted secondary or primary amine. The reaction is carried out by any conventional method for the activation of a carboxylic acid to form an amide. In the preferred embodiment of this invention, the carboxylic acid is treated with benzotriazol-1- yloxytris(dimethylamino)phosphonium hexafluoro phosphate in the presence of an appropriately substituted secondary or primary amine and triethylamine.

Compounds of formula V are prepared by reacting an appropriately substituted ketone with a phenylacetic acid of formula IV via an aldol reaction. The phenylacetic acids of formula IV can be either commercially obtained or are known compounds that can be prepared by standard procedures described in the literature. Compounds of formula IV represent an organic acid having an alpha carbon atom, so reaction with a ketone occurs at the alpha carbon atom of this carboxylic acid. This reaction is carried out by any conventional means of reacting the alpha carbon atom of a carboxylic acid with a ketone. Generally, in these aldol reactions, a ketone is reacted with the dianion of the acetic acid. The anion can be generated with a strong organic base such as lithium diisopropylamide, as well as other organic lithium bases. This reaction is performed in low boiling point solvents such as tetrahydrofuran at low temperatures from −80° C. to about −50° C. being preferred.

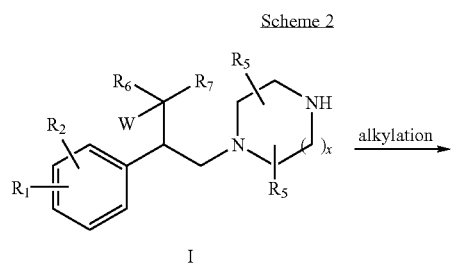

If it is desired to produce compounds of formula VIII, they can be formed from compounds of formula I, where Y=H, via an alkylation with an alkyl halide or via a reductive amination with an aldehyde or ketone. Any conventional method of alkylating a secondary amine with an alkyl halide can be utilized. In addition, any conventional method of performing a reductive amination can be utilized. In accordance with the preferred embodiment of this invention, when it is desired to form compounds of formula VIII where $R_8$=methyl, a mixture of the amine and formaldehyde in formic acid is heated at 60° C.-80° C. If is desired to form compounds of formula VIII where $R_8$=lower alkyl other than methyl, a mixture of the amine and an appropriately substituted aldehyde or ketone in methylene chloride is treated with trisacetoxyborohydride.

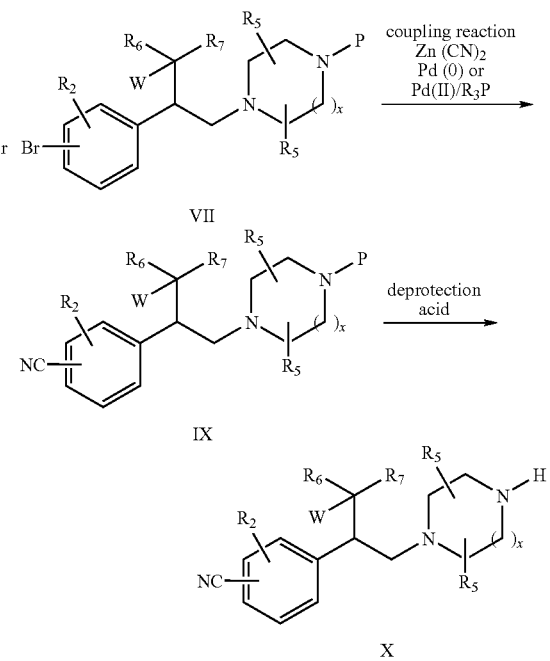

If it is desired to produce compounds of formula X where R1=nitrile, they can be formed from compounds of formula IX, where P=an amine protecting group, preferably but not limited to tert-butoxycarbonyl. In the case where P=tert-butoxycarbonyl, any conventional method for the deprotection of a carbamate can be utilized for this conversion. In accordance with the preferred embodiment of this invention, deprotection is carried out using a protic acid, i.e., hydrochloric acid.

Compounds of formula IX can be formed from compounds of formula VII where $R_1$=iodine or bromine, and Y=P (See Scheme 1). Any conventional method for converting an aryl iodide or aryl bromide to an aryl nitrile can be utilized for this conversion. According to the preferred embodiment of this invention, the aryl bromide of formula VII is treated with zinc cyanide, 1,1'-bis(diphenylphosphino)ferrocine, zinc dust, and catalytic tris(dibenzylideneacetone)dipalladium. This reaction is performed in high boiling point solvents such as N,N-dimethylformamide, under nitrogen, at elevated temperatures from 100° C. to about 150° C. being preferred. Compounds of formula VII are prepared in Scheme 1. If it is desired to form compounds of formula VIII from compounds of formula X, the procedure outlined in Scheme 2 can be followed.

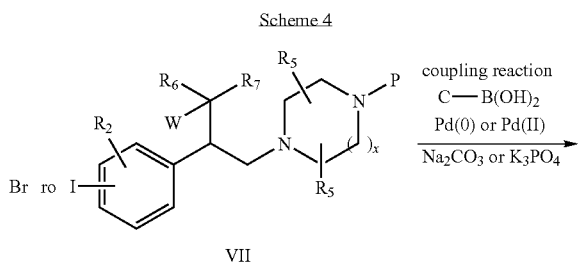

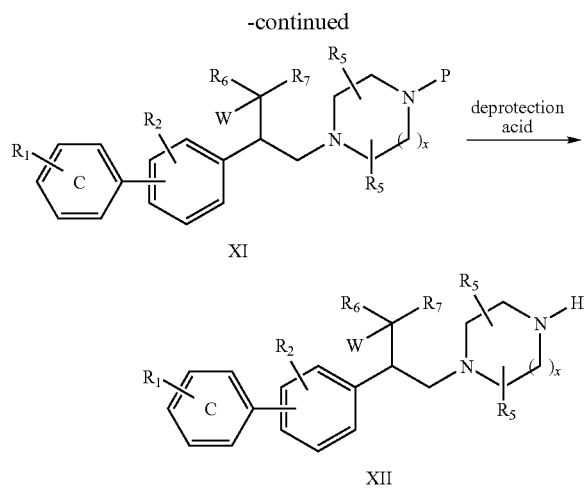

XI

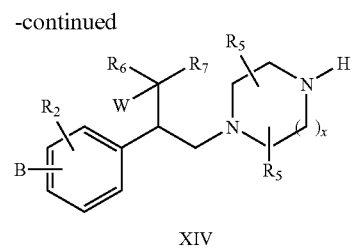

XIV where B = alkenyl or alkynyl.

Compounds of formula VII, where $R_1$=bromine or iodine and where Y=P (see Scheme 1), can also be used to form compounds of formula XII, where C=phenyl, substituted phenyl, heteroaryl, or substituted heteroaryl, if it is desired. Compounds of formula XII can be formed from compounds of formula VII where $R_1$=bromine or iodine via a cross-coupling reaction with either an aryl boronic acid or an aryl stannane. Any conventional method for the cross coupling of an aryl iodide or aryl bromide with an aryl boronic acid or aryl stannane can be employed. In accordance with the preferred embodiment of this invention, the aryl iodide or aryl bromide of formula VII is treated with an appropriately substituted aryl boronic acid, a base, i.e., sodium carbonate or potassium phosphate, and catalytic tetrakis(triphenylphosphine)palladium (0) or [1,4-bis-(diphenylphosphine)butane]palladium (II) dichloride. This reaction is performed in a high boiling point solvent such as N,N-dimethylformamide, 1,4-dioxane, or 1,2-dimethoxyethane in the presence of water, under nitrogen, at elevated temperatures from 70° C. to about 100° C. being preferred. If it is desired to form compounds of formula VIII from compounds of formula XII, the procedure outlined in Scheme 2 can be followed.

Scheme 5

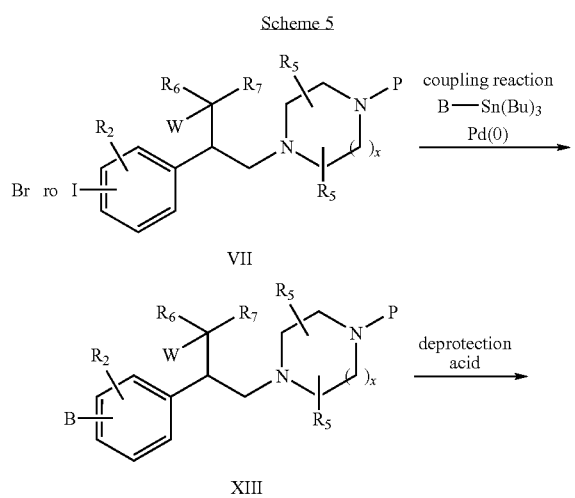

If it is desired to produce compounds of formula XIV, where B=alkynyl or alkenyl, they can be formed from compounds of formula VII, where $R_1$=bromine or iodine and where Y=P (See Scheme 1). Compounds of formula XIII can be formed from compounds of formula VII where $R_1$=bromine or iodine via a cross-coupling reaction with either an appropriately substituted alkenyl or alkynyl stannane. Any conventional method for the cross coupling of an aryl iodide or aryl bromide with an alkenyl or alkynyl stannane can be employed. In accordance with the preferred embodiment of this invention, the aryl iodide or aryl bromide of formula VII is treated with an appropriately substituted alkenyl or alkynyl stannane and catalytic tetrakis(triphenylphosphine)palladium (0). This reaction is performed in high boiling point solvents such as N,N-dimethylformamide or toluene, under nitrogen, at elevated temperatures from 90° C. to about 120° C. being preferred. Compounds of formula XIV are formed from compounds of formula XIV as described in Scheme 1. If it is desired to form compounds of formula VIII from compounds of formula XIV, the procedure outlined in Scheme 2 can be followed.

The compounds of formula I have an asymmetric carbon atom. In accordance with this invention the preferred stereoconfiguration is S. If it is desired to produce the R or the S isomer of the compounds of formula I, these compounds can be isolated as the desired isomer by any conventional method. Among the preferred means is to separate the isomers of either the amide of formula VI or formula VII, where Y=P, or the amine of formula I or formula VIII via either High Performance Liquid Chromatography (HPLC) or via Supercritical Fluid Chromatography.

The separation of R and S isomers can also be achieved by forming a lower alkyl ester of phenylacetic acids of formula V. Any conventional method for the formation of an ester from a carboxylic acid can be utilized. Separation is performed using an enzymatic ester hydrolysis of any lower alkyl esters corresponding to the compound of formula V (See, for example, Ahmar, M.; Girard, C.; Bloch, R. *Tetrahedron Lett*, 1989, 7053), which results in the formation of corresponding chiral acid and chiral ester. The ester and the acid can be separated by any conventional method of separating an acid from an ester.

In other embodiments, the invention is directed to pharmaceutical compositions, comprising:
a. at least compound of formula I or pharmaceutically acceptable salt thereof; and
b. at least one pharmaceutically acceptable carrier.

Generally, the compound of formula I or a pharmaceutically acceptable salt thereof will be present at a level of from about 0.1%, by weight, to about 90% by weight, based on the total weight of the pharmaceutical composition, based on the total weight of the pharmaceutical composition. Preferably, the compound of formula I or a pharmaceutically acceptable salt thereof will be present at a level of at least about 1%, by weight, based on the total weight of the pharmaceutical composition. More preferably, the compound of formula I or a pharmaceutically acceptable salt thereof will be present at a level of at least about 5%, by weight, based on the total weight of the pharmaceutical composition. Even more preferably, the norepinephrine reuptake inhibitor or a pharmaceutically acceptable salt thereof will be present at a level of at least about 10%, by weight, based on the total weight of the pharmaceutical composition. Yet even more preferably, the compound of formula I or a pharmaceutically acceptable salt thereof will be present at a level of at least about 25%, by weight, based on the total weight of the pharmaceutical composition.

Such compositions are prepared in accordance with acceptable pharmaceutical procedures, such as described in *Remington's Pharmaceutical Sciences,* 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances that may also act as flavoring agents, lubricants, solubilizers, suspending agents, fillers, glidants, compression aids, binders or tablet-disintegrating agents or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups, and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions, which are sterile solutions or suspensions, can be administered by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

In another embodiment of the present invention, the compounds useful in the present invention may be administered to a mammal with one or more other pharmaceutical active agents such as those agents being used to treat any other medical condition present in the mammal. Examples of such pharmaceutical active agents include pain relieving agents, anti-angiogenic agents, anti-neoplastic agents, anti-diabetic agents, anti-infective agents, or gastrointestinal agents, or combinations thereof.

The one or more other pharmaceutical active agents may be administered in a therapeutically effective amount simultaneously (such as individually at the same time, or together in a pharmaceutical composition), and/or successively with one or more compounds of the present invention.

The term "combination therapy" refers to the administration of two or more therapeutic agents or compounds to treat a therapeutic condition or disorder described in the present disclosure, for example hot flush, sweating, thermoregulatory-related condition or disorder, or other. Such administration includes use of each type of therapeutic agent in a concurrent manner. In either case, the treatment regimen will provide beneficial effects of the drug combination in treating the conditions or disorders described herein.

The route of administration may be any route, which effectively transports the active compound of formula I to the appropriate or desired site of action, such as oral, nasal, pulmonary, transdermal, such as passive or iontophoretic delivery, or parenteral, e.g. rectal, depot, subcutaneous, intravenous, intraurethral, intramuscular, intranasal, ophthalmic solution or an ointment. Furthermore, the administration of compound of formula I with other active ingredients may be concurrent or simultaneous.

It is believed that the present invention described presents a substantial breakthrough in the field of treatment, alleviation, inhibition, and/or prevention of conditions ameliorated by monoamine reuptake including, inter alia, vasomotor symptoms (VMS), sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

Accordingly, in one embodiment, the present invention is directed to methods for treating or preventing a condition ameliorated by monoamine reuptake in a subject in need thereof, comprising the step of:

administering to said subject an effective amount of a compound of formula I or pharmaceutically acceptable salt thereof.

The conditions ameliorated by monoamine reuptake include those selected from the group consisting of vasomotor symptoms, sexual dysfunction, gastrointestinal and genitourinary disorders, chronic fatigue syndrome, fibromyalgia syndrome, nervous system disorders, and combinations thereof, particularly those conditions selected from the group consisting of major depressive disorder, vasomotor symptoms, stress and urge urinary incontinence, fibromyalgia, pain, diabetic neuropathy, and combinations thereof.

"Vasomotor symptoms," "vasomotor instability symptoms" and "vasomotor disturbances" include, but are not limited to, hot flushes (flashes), insomnia, sleep disturbances, mood disorders, irritability, excessive perspiration, night sweats, fatigue, and the like, caused by, inter alia, thermoregulatory dysfunction.

The term "hot flush" is an art-recognized term that refers to an episodic disturbance in body temperature typically consisting of a sudden skin flushing, usually accompanied by perspiration in a subject.

The term "sexual dysfunction" includes, but is not limited to, condition relating to desire and/or arousal.

As used herein, "gastrointestinal and genitourinary disorders" includes irritable bowel syndrome, symptomatic GERD, hypersensitive esophagus, nonulcer dyspepsia, noncardiac chest pain, biliary dyskinesia, sphincter of Oddi dysfunction, incontinence (i.e., urge incontinence, stress incontinence, genuine stress incontinence, and mixed incontinence)(including the involuntary voiding of feces or urine, and dribbling or leakage or feces or urine which may be due to one or more causes including but not limited to pathology altering sphincter control, loss of cognitive function, overdistention of the bladder, hyperreflexia and/or involuntary urethral relaxation, weakness of the muscles associated with the bladder or neurologic abnormalities), interstitial cystitis (irritable bladder), and chronic pelvic pain (including, but not limited to vulvodynia, prostatodynia, and proctalgia).

As used herein, "chronic fatigue syndrome" (CFS) is a condition characterized by physiological symptoms selected from weakness, muscle aches and pains, excessive sleep, malaise, fever, sore throat, tender lymph nodes, impaired memory and/or mental concentration, insomnia, disordered sleep, localized tenderness, diffuse pain and fatigue, and combinations thereof.

As used herein, "fibromyalgia syndrome" (FMS) includes FMS and other somatoform disorders, including FMS associated with depression, somatization disorder, conversion disorder, pain disorder, hypochondriasis, body dysmorphic disorder, undifferentiated somatoform disorder, and somatoform NOS. FMS and other somatoform disorders are accompanied by physiological symptoms selected from a generalized heightened perception of sensory stimuli, abnormalities in pain perception in the form of allodynia (pain with innocuous stimulation), abnormalities in pain perception in the form of hyperalgesia (increased sensitivity to painful stimuli), and combinations thereof.

As used herein, "nervous system disorders," includes addictive disorders (including those due to alcohol, nicotine, and other psychoactive substances) and withdrawal syndrome, age-associated learning and mental disorders (including Alzheimer's disease), anorexia nervosa, bulimia nervosa, attention-deficit disorder with or without hyperactivity disorder bipolar disorder, pain (including chronic pain selected from the group consisting of lower back pain, atypical chest pain, headache such as cluster headache, migraine, herpes neuralgia, phantom limb pain, pelvic pain, myofascial face pain, abdominal pain, neck pain, central pain, dental pain, opioid resistant pain, visceral pain, surgical pain, bone injury pain, pain during labor and delivery, pain resulting from burns, post partum pain, angina pain, neuropathic pain such as peripheral neuropathy and diabetic neuropathy, post-operative pain, and pain which is co-morbid with nervous system disorders described herein), cyclothymic disorder, depression disorder (including major depressive disorder, refractory depression adolescent depression and minor depression), dysthymic disorder, generalized anxiety disorder (GAD), obesity (i.e., reducing the weight of obese or overweight patients), obsessive compulsive disorders and related spectrum disorders, oppositional defiant disorder, panic disorder, post-traumatic stress disorder, premenstrual dysphoric disorder (i.e., premenstrual syndrome and late luteal phase dysphoric disorder), psychotic disorders (including schizophrenia, schizoaffective and schizophreniform disorders), seasonal affective disorder, sleep disorders (such as narcolepsy and enuresis), social phobia (including social anxiety disorder), selective serotonin reuptake inhibition (SSRI) "poop out" syndrome (i.e., wherein a patient who fails to maintain a satisfactory response to SSRI therapy after an initial period of satisfactory response).

In one embodiment, the present invention is directed to methods for treating or preventing vasomotor symptoms in a subject in need thereof, comprising the step of:

administering to said subject an effective amount of at least one compound of formula I or pharmaceutically acceptable salt thereof.

When estrogen levels are low or estrogen is absent, the normal levels between NE and 5-HT is altered and this altered change in neurotransmitter levels may result in changes in the sensitivity of the thermoregulatory center. The altered chemical levels may be translated in the thermoregulatory center as heat sensation and as a response, the hypothalamus may activate the descending autonomic pathways and result in heat dissipation via vasodilation and sweating (hot flush) (FIG. 1). Accordingly, the estrogen deprivation may result in altered norepinephrine activity.

Figure 2:
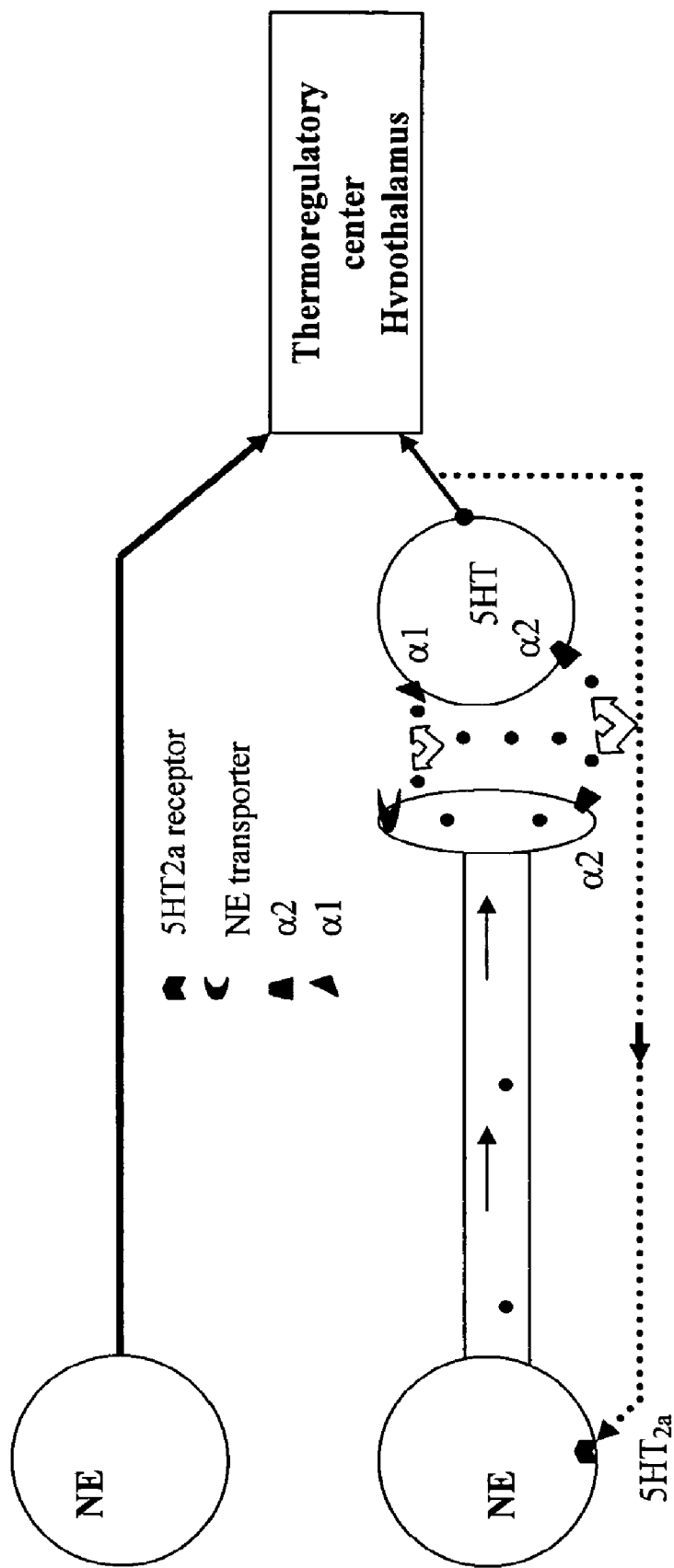
FIG. 2 is a schematic representation of the interactions of norepinephrine and serotonin and their respective receptors (5-HT$_{2a}$, $\alpha_1$ and $\alpha_2$-adrenergic).

Norepinephrine synthesized in perikarya of the brainstem is released at the nerve terminals in the hypothalamus and brainstem. In the hypothalamus, NE regulates the activity of neurons residing in the thermoregulatory center. In the brainstem, NE innervates serotoninergic neurons (5HT), and acting via adrenergic$_{\alpha1}$ and adrenergic$_{\alpha2}$ postsynaptic receptors, it stimulates the activity of the serotoninergic system. In response, 5-HT neurons also modulate the activity the thermoregulatory center and feedback to NE neurons. Via this feedback connection, 5-HT, acting via 5-HT$_{2a}$ receptors, inhibit the activity of NE neurons. Norepinephrine in the synaptic cleft is also taken up by NE transporter (NET) located in NE neurons. The transporter recycles NE and makes it available for multiple neurotransmission (FIG. 2).

The present invention provides a treatment for vasomotor symptoms by methods of recovering the reduced activity of norepinephrine. Norepinephrine activity in the hypothalamus or in the brainstem can be elevated by (i) blocking the activity of the NE transporter, (ii) blocking the activity of the presynaptic adrenergic$_{\alpha2}$ receptor with an antagonist, or (iii) blocking the activity of 5-HT on NE neurons with a 5-HT$_{2a}$ antagonist.

In another embodiment, the present invention is directed to methods for treating or preventing a depression disorder in a subject in need thereof, comprising the step of:

administering to said subject an effective amount of at least one compound of formula I or pharmaceutically acceptable salt thereof.

In yet other embodiments, the present invention is directed to methods for treating or preventing sexual dysfunction in a subject in need thereof, comprising the step of:

administering to said subject an effective amount of at least one compound of formula I or pharmaceutically acceptable salt thereof.

In another embodiment, the present invention is directed to methods for treating or preventing gastrointestinal or genitourinary disorder, particularly stress incontinence or urge urinary incontinence, in a subject in need thereof, comprising the step of:

administering to said subject an effective amount of a compound of formula I or pharmaceutically acceptable salt thereof.

In another embodiment, the present invention is directed to methods for treating or preventing chronic fatigue syndrome in a subject in need thereof, comprising the step of:

administering to said subject an effective amount of a compound of formula I or pharmaceutically acceptable salt thereof.

In another embodiment, the present invention is directed to methods for treating or preventing fibromyalgia syndrome in a subject in need thereof, comprising the step of:

administering to said subject an effective amount of a compound of formula I or pharmaceutically acceptable salt thereof.

In further embodiments, the present invention is directed to methods for treating or preventing pain in a subject in need thereof, comprising the step of:

administering to said subject an effective amount of at least one compound of formula I or pharmaceutically acceptable salt thereof.

The pain may be, for example, acute pain (short duration) or chronic pain (regularly reoccurring or persistent). The pain may also be centralized or peripheral.

Examples of pain that can be acute or chronic and that can be treated in accordance with the methods of the present invention include inflammatory pain, musculoskeletal pain, bony pain, lumbosacral pain, neck or upper back pain, visceral pain, somatic pain, neuropathic pain, cancer pain, pain caused by injury or surgery such as burn pain or dental pain, or headaches such as migraines or tension headaches, or combinations of these pains. One skilled in the art will recognize that these pains may overlap one another. For example, a pain caused by inflammation may also be visceral or musculoskeletal in nature.

In a preferred embodiment of the present invention the compounds useful in the present invention are administered in mammals to treat chronic pain such as neuropathic pain associated for example with damage to or pathological changes in the peripheral or central nervous systems; cancer pain; visceral pain associated with for example the abdominal, pelvic, and/or perineal regions or pancreatitis; musculoskeletal pain associated with for example the lower or upper back, spine, fibromyalgia, temporomandibular joint, or myofascial pain syndrome; bony pain associated with for example bone or joint degenerating disorders such as osteoarthritis, rheumatoid arthritis, or spinal stenosis; headaches such migraine or tension headaches; or pain associated with infections such as HIV, sickle cell, anemia, autoimmune disorders, multiple sclerosis, or inflammation such as osteoarthritis or rheumatoid arthritis.

In a more preferred embodiment, the compounds useful in this invention are used to treat chronic pain that is neuropathic pain, visceral pain, musculoskeletal pain, bony pain, cancer pain or inflammatory pain or combinations thereof, in accordance with the methods described herein. Inflammatory pain can be associated with a variety of medical conditions such as osteoarthritis, rheumatoid arthritis, surgery, or injury. Neuropathic pain may be associated with for example diabetic neuropathy, peripheral neuropathy, post-herpetic neuralgia, trigeminal neuralgia, lumbar or cervical radiculopathies, fibromyalgia, glossopharyngeal neuralgia, reflex sympathetic dystrophy, casualgia, thalamic syndrome, nerve root avulsion, or nerve damage cause by injury resulting in peripheral and/or central sensitization such as phantom limb pain, reflex sympathetic dystrophy or postthoracotomy pain, cancer, chemical injury, toxins, nutritional deficiencies, or viral or bacterial infections such as shingles or HIV, or combinations thereof. The methods of use for compounds of this invention further include treatments in which the neuropathic pain is a condition secondary to metastatic infiltration, adiposis dolorosa, burns, or central pain conditions related to thalamic conditions.

As mentioned previously, the methods of the present invention may be used to treat pain that is somatic and/or visceral in nature. For example, somatic pain that can be treated in accordance with the methods of the present invention include pains associated with structural or soft tissue injury experienced during surgery, dental procedures, burns, or traumatic body injuries. Examples of visceral pain that can be treated in accordance with the methods of the present invention include those types of pain associated with or resulting from maladies of the internal organs such as ulcerative colitis, irritable bowel syndrome, irritable bladder, Crohn's disease, rheumatologic (arthralgias), tumors, gastritis, pancreatitis, infections of the organs, or biliary tract disorders, or combinations thereof. One skilled in the art will also recognize that the pain treated according to the methods of the present invention may also be related to conditions of hyperalgesia, allodynia, or both. Additionally, the chronic pain may be with or without peripheral or central sensitization.

The compounds useful in this invention may also be used to treat acute and/or chronic pains associated with female conditions, which may also be referred to as female-specific pain. Such groups of pain include those that are encountered solely or predominately by females, including pain associated with menstruation, ovulation, pregnancy or childbirth, miscarriage, ectopic pregnancy, retrograde menstruation, rupture of a follicular or corpus luteum cyst, irritation of the pelvic viscera, uterine fibroids, adenomyosis, endometriosis, infection and inflammation, pelvic organ ischemia, obstruction, intra-abdominal adhesions, anatomic distortion of the pelvic viscera, ovarian abscess, loss of pelvic support, tumors, pelvic congestion or referred pain from non-gynecological causes.

EXAMPLES

The present invention is further defined in the following Examples, in which all parts and percentages are by weight and degrees are Celsius, unless otherwise stated. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various usages and conditions.

Reference Example 1-a

Aldol Reaction: Preparation of Acid Intermediates

A solution of diisopropylamine (7.87 mL, 56.2 mmol) in dry tetrahydrofuran (50 mL) under nitrogen was cooled to −78° C. and treated dropwise with a solution of n-butyllithium (2.5 M in hexanes, 22 mL, 55.0 mmol). The resulting solution was warmed to 0° C. and stirred for 15 min. The solution was re-cooled to −78° C. and treated, via cannula, with a solution of 3-chlorophenylacetic acid (4.0 g, 23.4 mmol) in tetrahydrofuran (20 mL). The reaction was then allowed to warm to 25° C. where it was stirred for 45 minutes and was then re-cooled to −78° C. A solution of cyclohexanone (3.65 mL, 35.3 mL) in tetrahydrofuran (10 mL) was then added via cannula, and the resulting mixture was stirred at −78° C. for 1.5 h. The reaction was then quenched by the addition of a saturated aqueous solution of ammonium chloride, and the tetrahydrofuran was removed in vacuo. The resulting residue was dissolved in a 2N aqueous solution of sodium hydroxide (30 mL) and washed with ethyl acetate (1×30 mL). The aqueous layer was then acidified to pH=1 with the addition of a 2 N aqueous solution of hydrochloric acid. The product was extracted with ethyl acetate (3×30 mL), and the combined organic extracts were dried over magnesium sulfate and concentrated in vacuo to yield 6.05 g (96%) of pure (3-chlorophenyl)(1-hydroxycyclohexyl)acetic acid as a white solid. HRMS: calcd for $C_{14}H_{17}ClO_3$, 268.0866; found (ESI_FT), 291.0748.

b) In an analogous manner, (3-bromophenyl)(1-hydroxycyclohexyl)acetic acid was prepared from 3-bromophenylacetic acid and cyclohexanone. HRMS: calcd for $C_{14}H_{17}BrO_3$, 312.0361; found (ESI_FT), 350.99924.

c) In an analogous manner, (1-hydroxycyclobutyl)(2-naphthyl)acetic acid was prepared from 2-napthylacetic acid and cyclobutanone. HRMS: calcd for $C_{16}H_{16}O_3$, 256.1099; found (ESI_FT), 279.09927.

d) In an analogous manner, 3,4-dichloro-alpha-(1-hydroxycyclohexyl)benzeneacetic acid was prepared from 3,4-dichlorophenylacetic acid and cyclohexanone. MS (ESI) m/z 301/303/305 ([M−H]⁻); Anal. Calcd for $C_{14}H_{16}Cl_2O_3$: C, 55.46; H, 5.32; N, 0.00. Found: C, 55.42; H, 5.30; N, 0.00.

e) In an analogous manner, (1-hydroxycyclohexyl)(1-naphthyl)acetic acid was prepared from 1-napthylacetic acid and cyclohexanone. MS (ESI) m/z 283 ([M−H]⁻); HRMS: calcd for $C_{18}H_{20}O_3$, 284.1412; found (ESI_FT), 307.13001.

f) In an analogous manner, (1-hydroxycyclohexyl)[3-(trifluoromethoxy)phenyl]acetic acid was prepared from 3-trifluoromethoxyphenylacetic acid and cyclohexanone. HRMS: calcd for $C_{15}H_{17}F_3O_4$, 318.1079; found (ESI), 317.1013.

g) In an analogous manner, (1-hydroxycyclohexyl)[4-(trifluoromethoxy)phenyl]acetic acid was prepared from 4-trifluoromethoxyphenylacetic acid and cyclohexanone. MS (ESI) m/z 317 ([M−H]⁻).

h) In an analogous manner, (4-bromophenyl)(1-hydroxycyclohexyl)acetic acid was prepared from 4-bromophenylacetic acid and cyclohexanone. MS (ESI) m/z 313/315 ([M+H]⁺); Anal. Calcd for $C_{14}H_{17}BrO_3$: C, 53.69; H, 5.47; N, 0.00. Found: C, 53.87; H, 5.42; N, 0.00.

i) In an analogous manner, (3,4-dichlorophenyl)(4-hydroxy-1-methylpiperidin-4-yl)acetic acid was prepared from 3,4-dichlorophenylacetic acid and 1-methyl-4-piperidone. HRMS: calcd for $C_{14}H_{17}Cl_2NO_3HCl$, 353.0352; found (ESI_FT), 318.0653.

j) In an analogous manner, (3-bromophenyl)(1-hydroxycyclobutyl)acetic acid was prepared from 3-bromophenylacetic acid and cyclobutanone. HRMS: calcd for $C_{12}H_{13}BrO_3$, 284.0048; found (ESI_FT), 306.99337.

k) In an analogous manner, (1-hydroxycyclobutyl)[3-(trifluoromethoxy)phenyl]acetic acid was prepared from 3-trifluoromethoxyphenylacetic acid and cyclobutanone. HRMS: calcd for $C_{13}H_{13}F_3O_4$, 290.0766; found (ESI), 289.0686.

l) In an analogous manner, (3-bromo-4-methoxyphenyl)(1-hydroxycyclohexyl)acetic acid was prepared from 3-bromo-4-methoxyphenylacetic acid and cyclohexanone. MS (ESI) m/z 341/343 ([M−H]⁻); HRMS: calcd for $C_{15}H_{19}BrO_4$, 342.0467; found (ESI_FT), 341.03897.

m) In an analogous manner, (1-hydroxycyclohexyl)[3-(trifluoromethyl)phenyl]acetic acid was prepared from 3-trifluoromethylphenylacetic acid and cyclohexanone. MS (ESI) m/z 301 ([M−H]⁻); HRMS: calcd for $C_{15}H_{17}F_3O_3$, 302.1130; found (ESI_FT), 325.1024.

n) In an analogous manner, (4-benzyloxyphenyl)(1-hydroxycyclohexyl)acetic acid was prepared from 4-benzyloxyphenylacetic acid and cyclohexanone.

o) In an analogous manner, (1-hydroxycyclobutyl)(1-naphthyl)acetic acid was prepared from 1-napthylacetic acid and cyclobutanone.

p) In an analogous manner, (3,4-dichlorophenyl)(1-hydroxycyclobutyl)acetic acid was prepared from 3,4-dichlorophenylacetic acid and cyclobutanone. HRMS: calcd for $C_{12}H_{12}Cl_2O_3$, 274.0163; found (ESI_FT), 273.00881.

q) In an analogous manner, (1-hydroxycyclohexyl)(2-naphthyl)acetic acid was prepared from 2-napthylacetic acid and cyclohexanone. HRMS: calcd for $C_{18}H_{20}O_3$, 284.1412; found (ESI_FT), 323.10414.

r) In an analogous manner, (3-bromophenyl)(4-hydroxy-1-methylpiperidin-4-yl)acetic acid was prepared from 3-bromophenylacetic acid and 1-methyl-4-piperidone. HRMS: calcd for $C_{14}H_{18}BrNO_3HCl$, 363.0237; found (ESI_FT), 328.05356.

s) In an analogous manner, (1-hydroxycyclopentyl)(1-naphthyl)acetic acid was prepared from 1-napthylacetic acid and cyclopentanone. MS (ESI) m/z 269 ([M−H]⁻); HRMS: calcd for $C_{17}H_{18}O_3$, 270.1256; found (ESI_FT), 293.11485.

t) In an analogous manner, 2-(3-bromophenyl)-3-ethyl-3-hydroxypentanoic acid was prepared from 3-bromophenylacetic acid and 3-pentanone. MS (ESI) m/z 299/301 ([M−H]⁻); HRMS: calcd for $C_{13}H_{17}BrO_3$, 300.0361; found (ESI_FT), 323.02505.

u) In an analogous manner, 2-(3-chlorophenyl)-3-hydroxy-3-propylhexanoic acid was prepared from 3-bromophenylacetic acid and 4-heptanone. MS (ESI) m/z 283/285 ([M+H]⁺); HRMS: calcd for $C_{15}H_{21}ClO_3$, 284.1179; found (ESI_FT), 307.1074.

v) In an analogous manner, 2-(3-chlorophenyl)-3-ethyl-3-hydroxypentanoic acid was prepared from 3-chlorophenylacetic acid and 3-pentanone. MS (ESI) m/z 255/257 ([M+H]⁺).

w) In an analogous manner, 3-ethyl-3-hydroxy-2-(1-naphthyl)pentanoic acid was prepared from 1-napthylacetic acid and 3-pentanone. MS (ESI) m/z 271 ([M−H]⁻).

x) In an analogous manner, (4-hydroxy-1-methylpiperidin-4-yl)(2-naphthyl)acetic acid was prepared from 2-napthylacetic acid and 1-methyl-4-piperidone. HRMS: calcd for $C_{18}H_{21}NO_3$, 299.1521; found (ESI_FT), 300.15911.

y) In an analogous manner, 2-(3-bromo-4-methoxyphenyl)-3-ethyl-3-hydroxypentanoic acid was prepared from 3-bromo-4-methoxyphenylacetic acid and 3-pentanone. MS (ESI) m/z 329/331 ([M+H]⁺).

z) In an analogous manner, (4-benzyloxyphenyl)(1-hydroxycyclobutyl)acetic acid was prepared from 4-benzyloxyphenylacetic acid and cyclobutanone.

aa) In an analogous manner, (3-chlorophenyl)(1-hydroxydecahydronapthyl)acetic acid was prepared from 3-chlorophenylacetic acid and decahydronapthlene-1-one. MS (ESI) m/z 321/323 ([M−H]⁻).

bb) In an analogous manner, (3-bromo-4-methoxyphenyl)(4-tert-butyl-1-hydroxycyclohexyl)acetic acid was prepared from 3-bromo-4-methoxyphenylacetic acid and 4-tert-butylcyclohexanone. MS (ESI) m/z 397/399 ([M−H]⁻); HRMS: calcd for $C_{19}H_{27}BrO_4$, 398.1093; found (ESI_FT), 421.09875.

cc) In an analogous manner, (3-chlorophenyl)(2-hydroxydecahydronapthyl)acetic acid was prepared from 3-chlorophenylacetic acid and decahydronapthlene-2-one. MS (ESI) m/z 321/323 ([M−H]−).

dd) In an analogous manner, (4-tert-butyl-1-hydroxycyclohexyl)(1-naphthyl)acetic acid was prepared from 1-napthylacetic acid and 4-tert-butylcyclohexanone. MS (ESI) m/z 339 ([M−H]−); HRMS: calcd for $C_{22}H_{28}O_3$, 340.2038; found (ESI_FT), 363.19309.

ee) In an analogous manner, (3-chlorophenyl)(4-hydroxytetrahydro-2H-pyran-4-yl)acetic acid was prepared from 3-chlorophenylacetic acid and tetrahydro-2H-pyran-4-one. MS (ESI) m/z 269 ([M−H]−); HRMS: calcd for $C_{13}H_{15}ClO_4$, 270.0659; found (ESI_FT), 293.05499.

ff) In an analogous manner, (3-bromophenyl)(4-tert-butyl-1-hydroxycyclohexyl)acetic acid was prepared from 3-bromophenylacetic acid and 4-tert-butylcyclohexanone. MS (ESI) m/z 367/369 ([M−H]−); HRMS: calcd for $C_{18}H_{25}BrO_3$, 368.0987; found (ESI_FT), 391.0878.

gg) In an analogous manner, 2-(3-bromophenyl)-3-hydroxy-3-propylhexanoic acid was prepared from 3-bromophenylacetic acid and 4-heptanone. MS (ESI) m/z 327/329 ([M+H]+).

hh) In an analogous manner, 2-(3-chlorophenyl)-3,3-dicyclopropyl-3-hydroxypropanoic acid was prepared from 3-chlorophenylacetic acid and dicyclopropyl ketone. MS (ESI) m/z 279.0801 ([M−H]−); HRMS: calcd for $C_{15}H_{17}ClO_3$, 280.0866; found (ESI), 279.0801; Anal. Calcd for $C_{15}H_{17}ClO_3$: C, 64.17; H, 6.10; N, 0.00. Found: C, 64.05; H, 6.31; N, 0.00.

ii) In an analogous manner, (3-bromophenyl)(1-hydroxy-3,3,5,5-tetramethylcyclohexyl)acetic acid was prepared from 3-bromophenylacetic acid and 3,3,5,5-tetramethylcyclohexanone. MS (ESI) m/z 367/369 ([M−H]−).

jj) In an analogous manner, (4-ethyl-1-hydroxycyclohexyl)-(1-naphthyl)acetic acid was prepared from 1-napthylacetic acid and 4-ethylcyclohexanone. MS (ESI) m/z 311 ([M−H]−).

kk) In an analogous manner, (3-chlorophenyl)(4-tert-butyl-1-hydroxycyclohexyl)acetic acid was prepared from 3-chlorophenylacetic acid and 4-tert-butylcyclohexanone.

ll) In an analogous manner, (4-methyl-1-hydroxycyclohexyl)-(1-naphthyl)acetic acid was prepared from 1-napthylacetic acid and 4-methylcyclohexanone. MS (ESI) m/z 297 ([M−H]−).

mm) In an analogous manner, (3-bromophenyl)(4-hydroxytetrahydro-2H-pyran-4-yl)acetic acid was prepared from 3-bromophenylacetic acid and tetrahydro-2H-pyran-4-one. MS (ESI) m/z 313/315 ([M+H]+); HRMS: calcd for $C_{13}H_{15}BrO_4$, 314.0154; found (ESI_FT), 315.02244.

nn) In an analogous manner, (3-benzyloxyphenyl)(1-hydroxycyclohexyl)acetic acid was prepared from 3-benzyloxyphenylacetic acid and cyclohexanone.

oo) In an analogous manner, (3-bromophenyl)(2-hydroxy-2-adamantyl)acetic acid was prepared from 3-bromophenylacetic acid and adamantanone. MS (ESI) m/z 363/365 ([M−H]−).

pp) In an analogous manner, (3-bromo-4-methoxyphenyl)(4-hydroxytetrahydro-2H-pyran-4-yl)acetic acid was prepared from 3-bromo-4-methoxyphenylacetic acid and tetrahydro-2H-pyran-4-one. MS (ESI) m/z 343/345 ([M−H]−); HRMS: calcd for $C_{14}H_{17}BrO_5$, 344.0259; found (ESI_FT), 367.01582.

qq) In an analogous manner, (3-benzyloxyphenyl)(1-hydroxycyclobutyl)acetic acid was prepared from 3-benzyloxyphenylacetic acid and cyclobutanone.

rr) In an analogous manner, (5-chlorothien-2-yl)(1-hydroxycyclohexyl)acetic acid was prepared from 5-chloro-2-thiophene-3-acetic acid (Example 142) and cyclohexanone. MS (ESI) m/z 273/275 ([M−H]−).

ss) In an analogous manner, (5-bromothien-2-yl)(1-hydroxycyclohexyl)acetic acid was prepared from 5-bromo-2-thiophene acetic acid (Example 143) and cyclohexanone. MS (ESI) m/z 317/319 ([M+H]+)

tt) In an analogous manner, 1-benzothien-3-yl(1-hydroxycyclohexyl)acetic acid was prepared from 1-benzothien-3-yl acetic acid and cyclohexanol. MS (ESI) m/z 289 ([M−H]−)

uu) In an analogous manner, (2-bromophenyl)(1-hydroxycyclohexyl)acetic acid was prepared from 2-bromophenylacetic acid and cyclohexanol. MS (ESI) m/z 311/313 ([M−H]−)

vv) In an analogous manner, (4-bromophenyl)(1-hydroxycyclohexyl)acetic acid was prepared from 4-bromophenylacetic acid and cyclohexanone. MS (ESI) m/z 313/315 ([M+H]+); Anal. Calcd for $C_{14}H_{17}BrO_3$: C, 53.69; H, 5.47; N, 0.00. Found: C, 53.87; H, 5.42; N, 0.00.

ww) In an analogous manner, (4-bromophenyl)(1-hydroxycyclobutyl)acetic acid was prepared from 4-bromophenylacetic acid and cyclobutanone.

xx) In an analogous manner, (1-methyl-1H-indol-3-yl)(1-hydroxycyclohexyl)acetic acid was prepared from N-Methyl-3-indole acetic acid and cyclohexanone.

yy) In an analogous manner, (1-(tert-butyl-dimethyl-silanyl)-1H-indol-3-yl)(1-hydroxycyclohexyl)acetic acid was prepared from [1-(tert-butyl-dimethyl-silanyl)-1H-indol-3-yl]-acetic acid[1] and cyclohexanone.

[1] Solid-phase synthesis of polyamine spider toxins and correlation with the natural products by HPLC-MS/MS. Manov, Nikolay; Tzouros, Manuel; Chesnov, Sergiy; Bigler, Laurent; Bienz, Stefan. Institute of Organic Chemistry, University of Zurich, Zurich, Switz. Helvetica Chimica Acta (2002), 85(9), 2827-2846 zz) In an analogous manner, (1-hydroxycyclohexyl)(1,1′-biphenyl-4-yl)acetic acid was prepared from 4-biphenylacetic acid and cyclohexanone. MS (ESI) m/z 309 ([M−H]−)

aaa) In an analogous manner (1-hydroxycyclobutyl)[4-trifluoromethoxy)phenyl]acetic acid was prepared from 4-trifluoromethoxyphenyl acetic acid and cyclobutanone. MS (ESI) m/z 289 ([M−H]−).

bbb) In an analogous manner (1-hydroxycyclohexyl)[4-phenoxyphenyl]acetic acid was prepared from 4-phenoxyphenylacetic acid and cyclohexanone. MS (ESI) m/z 325 ([M−H]−).

ccc) In an analogous manner (1-hydroxycyclohexyl)[3-phenoxyphenyl]acetic acid was prepared from 3-phenoxyphenylacetic acid and cyclohexanone. MS (ESI) m/z 325 ([M−H]−). Anal. Calcd for $C_{20}H_{22}O_4 \cdot 0.1H_2O$: C, 73.19; H, 6.82. Found: C, 73.04; H, 6.88.

ddd) In an analogous manner, (1-naphthyl)(1-hydroxycyclooctyl)acetic acid was prepared from 1-naphthyl acetic acid and cyclooctanone.

eee) In an analogous manner, [4-(benzyloxy)-3-chlorophenyl](1-hydroxycyclohexyl)acetic acid was prepared from [4-(benzyloxy)-3-chlorophenyl]acetic acid (DE 2556474, 1976, M. Kucher; B. Brunova; J. Grimova; N. Oldrich) and cyclohexanone. MS (ESI) m/z 373;

fff) In an analogous manner, (1-naphthyl)(1-hydroxycycloheptyl)acetic acid was prepared from 1-napthylacetic acid and cycloheptanone.

ggg) In an analogous manner, 2-(3-chlorophenyl)-3-hydroxy-3-methylbutanoic acid was prepared from 3-chlorophenylacetic acid and acetone. MS (ES) m/z 226.9.

hhh) In an analogous manner, (3-chlorophenyl)(1-hydroxy-3,3,5,5-tetramethylcyclohexyl)acetic acid was prepared from 3-chlorophenylacetic acid and 3,3,5,5-tetramethylcyclohexanone. MS (ES) m/z 323.2.

iii) In an analogous manner, (1-hydroxy-cyclohexyl)-(5-methoxy-benzo[b]thiophen-3-yl)-acetic acid was prepared from 5-methoxy benzo[b]thiophene acetic acid (Campaigne, E.; Kim, C. S.; Pinza, M.; Pifferi, G. J. Heterocyclic Chem. 1983, 20, 1697-1703) and cyclohexanone. HRMS: calcd for $C_{15}H_{17}F_3O_4$, 318.1079; found (ESI), 317.1013.

jjj) In an analogous manner, (2-hydroxydecahydronapthyl)(1-napthyl)acetic acid was prepared from 1-napthylacetic acid and decahydronapthlene-2-one. MS (ESI) m/z 337 ([M−H]−).

kkk) In an analogous manner, (3-chlorophenyl)(4-methyl-1-hydroxycyclohexyl)acetic acid was prepared from 3-chlorophenylacetic acid and 4-methylcyclohexanone. MS (ESI) m/z 281/283 ([M−H]−).

lll) Step 1: A mixture of 4-(chloromethyl)dibenzyl (0.92 g, 4 mmol) and potassium cyanide (0.039 g, 6 mmol) in N,N'-dimethylformamide (20 mL) was heated at 80° C. for 16 hours. At the end of this time the solution was poured into water and extracted 2 times with ethyl acetate. The extracts were combined and filtered through a plug of silica gel. The filtrate was concentrated to yield 4-(phenethylphenyl)acetonitrile as an oil which was used in the next step without further purification.

Step 2: 4-(Phenethylphenyl)acetonitrile from the above reaction was treated with a 6 N aqueous solution of hydrochloric acid (10 mL) and heated at 95° C. for 4 h. The reaction was cooled to 0° C. and solid potassium hydroxide was added until pH 14 was achieved. The solution was washed twice with diethyl ether and the resulting aqueous layer was then acidified to pH 1 with concentrated hydrochloric acid. The product was extracted with diethyl ether (2×50 mL) and the combined ethereal extracts were dried over magnesium sulfate and concentrated. Trituration with hexane and filtration of the resulting solid afforded 0.64 g of [4-(2-phenylethyl)phenyl]acetic acid as an off white solid. MS (ESI) m/z 239.

Step 3: In an analogous manner (as Reference Example I-a), (1-hydroxycyclohexyl)[4-(2-phenylethyl)phenyl]acetic acid was prepared from [4-(2-phenylethyl)phenyl]acetic acid and cyclohexanone. MS (ESI) m/z 337.

mmm) Step 1: 3-Fluoro-4-hydroxyphenylacetic acid (0.85 g, 3.62 mmol) and of benzyl bromide (1.30 g, 7.60 mmol) were added to a flask containing N,N'-dimethylformamide (20 mL). Potassium carbonate (1.25 g, 9.00 mmol) was then added, and the solution was heated at 50° C. for 4 hours. A 2 N aqueous solution of sodium hydroxide (10 mL) was added and heating was maintained for an additional 16 hours. At the end of this time the solution was poured into water and washed twice with diethyl ether. The ethereal extracts were discarded and the aqueous layer was acidified with concentrated hydrochloric acid until pH 1 was achieved. The product was then extracted with diethyl ether (2×50 mL). The combined ethereal layers were dried over magnesium sulfate and concentrated to afford 0.95 g of 4-benzyloxy-3-fluorophenylacetic acid which was used as such in the next step. MS (ESI) m/z 325.

Step 2: In an analogous manner (as Reference Example I-a), [4-(benzyloxy)-3-fluorophenyl](1-hydroxycyclohexyl)acetic acid was prepared from [4-(benzyloxy)-3-fluorophenyl]acetic acid and cyclohexanone. MS (ESI) m/z 357.

nnn) In an analogous manner, [4-(benzyloxy)-3-methoxyphenyl](1-hydroxycyclohexyl)acetic acid was prepared from [4-(benzyloxy)-3-methoxyphenyl]acetic acid and cyclohexanone. MS (ES) m/z 369.0.

ooo) Step 1: In an analogous manner to Reference Example I-mmm, step 1 {3-chloro-4-[(3-methoxybenzyl)oxy]phenyl}acetic acid was prepared from {3-chloro-4-hydroxy-phenyl)acetic acid and 3-methoxybenzyl chloride.

Step 2: In an analogous manner (as Reference Example I-a), [3-chloro-4-(3-methoxy-benzyloxy)-phenyl](1-hydroxy-cyclohexyl)acetic acid was from {3-chloro-4-[(3-methoxybenzyl)oxy]phenyl}acetic acid and cyclohexanone.

ppp) Step 1: In an analogous manner to Reference Example I-mmm, step 1 {3-chloro-4-[(2-methoxybenzyl)oxy]phenyl}acetic acid was prepared from {3-chloro-4-hydroxy-phenyl)acetic acid and 2-methoxybenzyl chloride MS (ES) m/z 304.9.

Step 2: In an analogous manner (as Reference Example I-a), [3-chloro-4-(2-methoxy-benzyloxy)-phenyl]-(1-hydroxy-cyclohexyl)-acetic acid was from {3-chloro-4-[(2-methoxybenzyl)oxy]phenyl}acetic acid and cyclohexanone.

qqq) In an analogous manner, [(3R)-1-hydroxy-3-methylcyclopentyl][3-(trifluoromethoxy)phenyl]acetic acid was prepared from (3-trifluoromethoxy-phenyl)-acetic acid and 3(R)-methyl-cyclopentanone.

rrr) In an analogous manner, (1-hydroxy-2,2-dimethyl-cyclopentyl)-(3-trifluoromethoxy-phenyl)-acetic acid was prepared from (3-trifluoromethoxy-phenyl)-acetic acid and 2,2-dimethyl-cyclopentanone.

sss) In an analogous manner, (1-hydroxycyclohexyl)(6-methoxy-2-naphthyl)acetic acid was prepared from (6-methoxy-2-naphthyl)acetic acid (Harrison, Ian Thomas; Lewis, Brian; Nelson, Peter; Rooks, Wendell; Roszkowski, Adolph; Tomolonis, Albert; Fried, John H. *J. Med. Chem.* 1970, 13, 203-5) and cyclohexanone. MS (ES) m/z 313.0; HRMS: calcd for $C_{19}H_{22}O_4$,H+, 315.15909; found (ESI, [M+H]+), 315.159.

ttt) In an analogous manner, (3-chloro-4-methoxyphenyl)-1(1-hydroxycyclohexyl)acetic acid was prepared from (3-chloro-4-methoxyphenyl)acetic acid and cyclohexanone. MS (ESI) m/z 297 ([M−H]−).

uuu) In an analogous manner, (1-hydroxycyclohexyl)-(4-phenethyloxyphenyl)acetic acid was prepared from (4-phenethyloxyphenyl)acetic acid and cyclohexanone. MS (ESI) m/z 353 ([M−H]−).

vvv) Step 1: In an analogous manner to Reference Example I-mmm, step 1 {4-[2-(4-fluoro-phenyl)-ethoxy]-phenyl}-acetic acid was prepared from (4-hydroxyphenyl)acetic acid and 2-(4-fluorophenyl)ethyl bromide. MS (ESI) m/z 273 ([M−H]−).

Step 2: In an analogous manner (as Reference Example I-a), {4-[2-(4-fluoro-phenyl)-ethoxy]-phenyl}-(1-hydroxy-cyclohexyl)-acetic acid was prepared from {4-[2-(4-fluoro-phenyl)-ethoxy]-phenyl}-acetic acid and cyclohexanone. MS (ESI) m/z 371 ([M−H]−)

www) Step 1: In an analogous manner to Reference Example I-mmm, step 1 [4-(2-naphthalen-1-yl-ethoxy)-phenyl]-acetic acid was prepared from (4-hydroxyphenyl)acetic acid and 1-(2-bromoethyl)napthalene. MS (ESI) m/z 305 ([M−H]−).

Step 2: In an analogous manner (as Reference Example I-a), (1-hydroxy-cyclohexyl)-[4-(2-naphthalen-1-yl-ethoxy)-phenyl]-acetic acid was prepared from [4-(2-naphthalen-1-yl-ethoxy)-phenyl]-acetic acid and cyclohexanone. MS (ESI) m/z 403 ([M−H]−)

xxx) Step 1: In an analogous manner to Reference Example I-mmm, step 1 {4-[2-(4-methoxy-phenyl)-ethoxy]-phenyl}-acetic acid was prepared from (4-hydroxyphenyl)acetic acid and 4-(2-chloroethyl)anisole. MS (ESI) m/z 273 ([M−H]−).

Step 2: In an analogous manner (as Reference Example I-a), (1-hydroxy-cyclohexyl)-{4-[2-(4-methoxy-phenyl)-ethoxy]-phenyl}-acetic acid was prepared from {4-[2-(4-methoxy-phenyl)-ethoxy]-phenyl}-acetic acid and cyclohexanone. MS (ESI) m/z 383 ([M−H]−)

yyy) Step 1: In an analogous manner to Reference Example I-mmm, step 1 (4-cyclohexylmethoxy-phenyl)-acetic acid was prepared from (4-hydroxyphenyl)acetic acid and cyclomethyl bromide. MS (ESI) m/z 247 ([M−H]−).

Step 2: In an analogous manner (as Reference Example I-a), (4-cyclohexylmethoxy-phenyl)-(1-hydroxy-cyclohexyl)-acetic acid was prepared from (4-cyclohexylmethoxy-phenyl)-acetic acid and cyclohexanone. MS (ESI) m/z 345 ([M−H]−)

zzz) Step 1: To a stirred solution of (4-hydroxyphenyl)acetic acid methyl ester (0.33 g, 0.002 mole), S-(−)-sec-phenethyl alcohol (0.24 g, 0.002 mole) and triphenylphosphine (0.52 g, 0.002 mole) in anhydrous tetrahydrofuran (6 mL) was added dropwise over 15 minutes diisopropyl azodicarboxylate (0.40 g, 0.002 mole) in tetrahydrofuran (16 mL). The reaction solution was stirred for 1 h at room temperature and was then evaporated to dryness in vacuo. To the residue was added methanol (12 mL) and sodium hydroxide (0.44 g, 0.011 mole), and the reaction solution was stirred under reflux for 1 h. The methanol was then removed in vacuo, and to the residue was added 12 mL of water. After stirring for 1 h, the precipitated triphenylphosphine oxide was removed by suction filtration. The aqueous filtrate was extracted with 25 mL of ethyl acetate. The ethyl acetate phase was discarded and the aqueous phase was acidified with concentrated hydrochloric acid giving the solid product 4-((1R)-1-phenylethoxyphenyl)acetic acid. MS (ESI) m/z 253 ([M−H]−).

Step 2: In an analogous manner (as Reference Example I-a), (1-hydroxycyclohexyl)-4-((1R)-1-phenylethoxyphenyl)acetic acid was prepared from 4-((1R)-1-phenylethoxyphenyl)acetic acid and cyclohexanone. MS (ESI) m/z 353 ([M−H]−)

aaaa) Step 1: In an analogous manner to Reference Example I-zzz, step 1 (1S)-1-phenylethoxyphenyl)acetic acid was prepared from (4-hydroxyphenyl)acetic acid and R-(+)-sec-phenethyl alcohol. MS (ESI) m/z 253 ([M−H]−).

Step 2: In an analogous manner (as Reference Example I-a), (1-hydroxycyclohexyl)-4-((1S)-1-phenylethoxyphenyl)acetic acid was prepared from 4-((1S)-1-phenylethoxyphenyl)acetic acid and cyclohexanone. MS (ESI) m/z 353 ([M−H]−)

Example 1

1-[1-(3-chlorophenyl-2-piperazin-1-ylethyl]cyclohexanol dihydrochloride

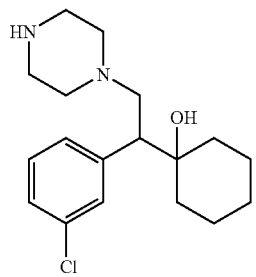

Step 1: A solution of (3-chlorophenyl)(1-hydroxycyclohexyl)acetic acid (Reference Example 1-a) (5.4 g, 20.1 mmol), benzotriazol-1-yloxytris(dimethylamino)phosphonium hexafluorophosphate (14.22 g, 32.15 mmol), and tert-butyl 1-piperazinecarboxylate (5.99 g, 32.15 mmol) in methylene chloride (20 mL) was treated with triethylamine (8.4 mL, 60.3 mmol). The reaction was stirred at 25° C. for 16 h, after which time the solvent was removed in vacuo and the product was purified via Biotage Horizon (FLASH 40 M, silica, gradient from 0% EtOAc/hexane to 30% EtOAc/hexane) to yield 7.10 g (81%) tert-butyl 4-[(3-chlorophenyl)(1-hydroxycyclohexyl)acetyl]piperazine-1-carboxylate as a white foam. HRMS: calcd for $C_{23}H_{33}ClN_2O_4$, 436.2129; found (ESI_FT), 437.21996.

Step 2: A solution of 4-[(3-chlorophenyl)(1-hydroxycyclohexyl)acetyl]piperazine-1-carboxylate (200 mg, 0.46 mmol) in dry tetrahydrofuran (3 mL) under nitrogen was treated dropwise with a solution of borane (1.0 M in tetrahydrofuran, 1.60 mL, 1.60 mmol). The resulting solution was heated at 70° C. for 2 h, after which time the reaction was cooled in an ice bath and was treated dropwise with a 2N aqueous solution of hydrochloric acid (1 mL). The reaction was again heated at 70° C. for 1 h, and was then cooled and treated with methanol (1 mL). After the solvent was removed in vacuo, the resulting residue was dissolved in water (5 mL) and was washed with ethyl acetate (1×4 mL). The aqueous layer was basified with the addition of a 2 N aqueous solution of sodium hydroxide until the pH=10. The product was extracted with ethyl acetate (4×5 mL) and the combined organic extracts were dried over magnesium sulfate and concentrated in vacuo to yield 146 mg (99%) 1-[1-(3-chlorophenyl)-2-piperazin-1-ylethyl]cyclohexanol as a colorless oil. HRMS: calcd for $C_{18}H_{27}ClN_2O$, 322.1812; found (ESI_FT), 323.18977. 1-[1-(3-Chlorophenyl)-2-piperazin-1-ylethyl]cyclohexanol (146 mg) was dissolved in methanol (0.5 mL) and treated with a saturated methanolic solution of hydrochloric acid (0.5 mL) followed by diethyl ether. After crystallizing in the refrigerator for 16 h, the resulting solid was collected, washed with diethyl ether and dried in vacuo to yield 110 mg (60%) 1-[1-(3-chlorophenyl)-2-piperazin-1-ylethyl]cyclohexanol dihydrochloride as a white solid. MS (ESI) m/z 323/325 ([M+H]+); HRMS: calcd for $C_{18}H_{27}ClN_2O$.2.00 HCl, 394.1345; found (ESI_FT), 323.18831.

Example 2

1-[2-(1,4'-bipiperidin-1'-yl)-1-(3-chlorophenyl)ethyl]cyclohexanol dihydrochloride

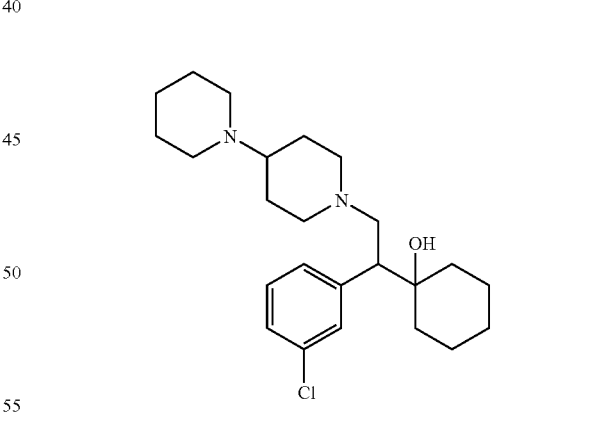

In an analogous manner to Example 1, step 1 1-[2-(1,4'-bipiperidin-1'-yl)-1-(3-chlorophenyl)-2-oxoethyl]cyclohexanol was prepared from (3-chlorophenyl)(1-hydroxycyclohexyl)acetic acid (Reference Example 1-a) and N-(4-piperidine)piperidine. MS (ESI) m/z 419/421 ([M+H]+); HRMS: calcd for $C_{24}H_{35}ClN_2O_2$, 418.2387; found (ESI), 419.2451.

In an analogous manner to Example 1, step 2 1-[2-(1,4'-bipiperidin-1'-yl)-1-(3-chlorophenyl)ethyl]cyclohexanol dihydrochloride was prepared from 1-[2-(1,4'-bipiperidin-1'-yl)-1-(3-chlorophenyl)-2-oxoethyl]cyclohexanol. MS (ESI)

m/z 405/407 ([M+H]⁺); HRMS: calcd for $C_{24}H_{37}ClN_2O\cdot 2.00$ HCl, 476.2128; found (ESI), 405.2664.

Example 3

1-[1-(3-chlorophenyl)-2-(4-pyrrolidin-1-ylpiperidin-1-yl)ethyl]cyclohexanol dihydrochloride

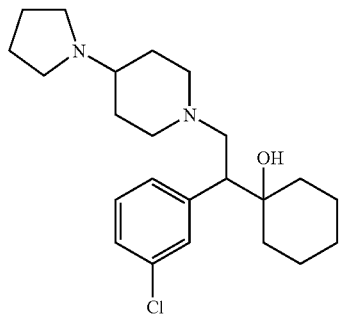

In an analogous manner to Example 1, step 1 1-[1-(3-chlorophenyl)-2-(4-pyrrolidin-1-ylpiperidin-1-yl)-2-oxoethyl]cyclohexanol was prepared from (3-chlorophenyl)(1-hydroxycyclohexyl)acetic acid (Reference Example 1-a) and 4-(1-pyrrolidinyl)piperidine.

In an analogous manner to Example 1, step 2 1-[1-(3-chlorophenyl)-2-(4-pyrrolidin-1-ylpiperidin-1-yl)ethyl]cyclohexanoldihydrochloride was prepared from 1-[1-(3-chlorophenyl)-2-(4-pyrrolidin-1-ylpiperidin-1-yl)-2-oxoethyl]cyclohexanol. MS (ESI) m/z 391/393 ([M+H]⁺); HRMS: calcd for $C_{23}H_{35}ClN_2O\cdot 2.00$ HCl, 462.1971; found (ESI), 391.2497.

Example 4

1-[2-(1,4'-bipiperidin-1'-yl)-1-(3-bromophenyl)ethyl]cyclohexanol dihydrochloride

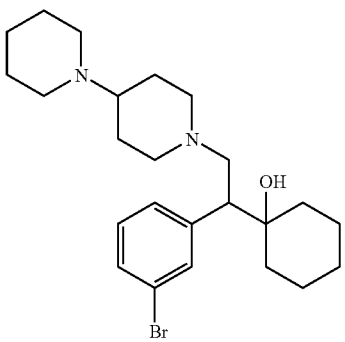

In an analogous manner to Example 1, step 1 1-[2-(1,4'-bipiperidin-1'-yl)-1-(3-bromophenyl)-2-oxoethyl]cyclohexanol was prepared from (3-bromophenyl)(1-hydroxycyclohexyl)acetic acid (Reference Example 1-b) and N-(4-piperidine)piperidine. MS (ESI) m/z 463 ([M+H]⁺); HRMS: calcd for $C_{24}H_{35}BrN_2O_2$, 462.1882; found (ESI), 463.1975.

In an analogous manner to Example 1, step 2 1-[2-(1,4'-bipiperidin-1'-yl)-1-(3-bromophenyl)ethyl]cyclohexanol dihydrochloride was prepared from 1-[2-(1,4'-bipiperidin-1'-yl)-1-(3-bromophenyl)-2-oxoethyl]cyclohexanol. MS m/z 449/451 ([M+H]⁺); HRMS: calcd for $C_{24}H_{37}BrN_2O\cdot 2.00$ HCl, 520.1623; found (ESI), 449.2149.

Example 5

1-[1-(2-naphthyl)-2-piperazin-1-ylethyl]cyclobutanol dihydrochloride

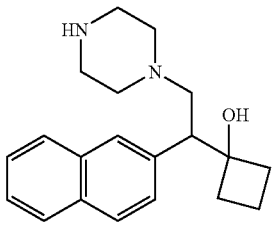

In an analogous manner to Example 1, step 1 tert-butyl 4-[(1-hydroxycyclobutyl)(2-naphthyl)acetyl]piperazine-1-carboxylate was prepared from (1-hydroxycyclobutyl)(2-naphthyl)acetic acid (Reference Example 1-c) and tert-butyl 1-piperazinecarboxylate. HRMS: calcd for $C_{25}H_{32}N_2O_4$, 424.2362; found (ESI_FT), 425.24337.

In an analogous manner to Example 1, step 2 1-[1-(2-naphthyl)-2-piperazin-1-ylethyl]cyclobutanol dihydrochloride was prepared from tert-butyl 4-[(1-hydroxycyclobutyl)(2-naphthyl)acetyl]piperazine-1-carboxylate. HRMS: calcd for $C_{20}H_{26}N_2O\cdot 2.00$ HCl, 382.1579; found (ESI_FT), 311.21184.

Example 6

1-[2-(1,4'-bipiperidin-1'-yl)-1-(3,4-dichlorophenyl)ethyl]cyclohexanol dihydrochloride

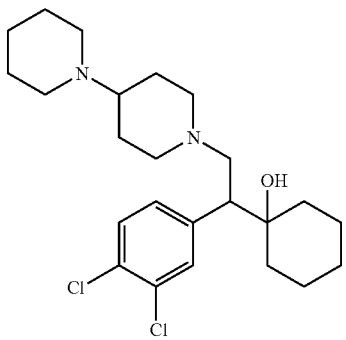

In an analogous manner to Example 1, step 1 1-[2-(1,4'-bipiperidin-1'-yl)-1-(3,4-dichlorophenyl)-2-oxoethyl]cyclohexanol was prepared from 3,4-dichloro-alpha-(1-hydroxycyclohexyl)benzeneacetic acid (Reference Example 1-d) and N-(4-piperidine)piperidine.

In an analogous manner to Example 1, step 2 1-[2-(1,4'-bipiperidin-1'-yl)-1-(3,4-dichlorophenyl)ethyl]cyclohexanol dihydrochloride was prepared from 1-[2-(1,4'-bipiperidin-1'-yl)-1-(3,4-dichlorophenyl)-2-oxoethyl]cyclohexanol. MS m/z 439/441/443 ([M+H]$^+$); HRMS: calcd for C$_{24}$H$_{36}$Cl$_2$N$_2$O.2.00 HCl, 510.1738; found (ESI), 439.2267.

Example 7

1-[1-(3-bromophenyl)-2-(4-pyrrolidin-1-ylpiperidin-1-yl)ethyl]cyclohexanol dihydrochloride

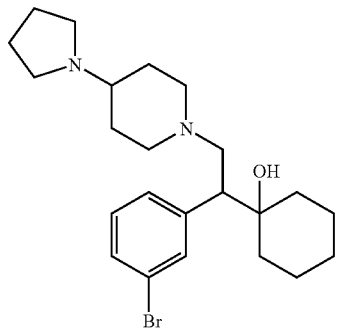

In an analogous manner to Example 1, step 1 1-[1-(3-bromophenyl)-2-oxo-2-(4-pyrrolidin-1-ylpiperidin-1-yl)ethyl]cyclohexanol was prepared from (3-bromophenyl)(1-hydroxycyclohexyl)acetic acid (Reference Example 1-b) and 4-(1-pyrrolidinyl)piperidine. MS (ESI) m/z 449 ([M+H]$^+$); HRMS: calcd for C$_{23}$H$_{33}$BrN$_2$O$_2$, 448.1725; found (ESI), 449.1789.

In an analogous manner to Example 1, step 2 1-[1-(3-bromophenyl)-2-(4-pyrrolidin-1-ylpiperidin-1-yl)ethyl]cyclohexanol dihydrochloride was prepared from 1-[1-(3-bromophenyl)-2-oxo-2-(4-pyrrolidin-1-ylpiperidin-1-yl)ethyl]cyclohexanol. MS m/z 435/437 ([M+H]$^+$); HRMS: calcd for C$_{23}$H$_{35}$BrN$_2$O.2.00 HCl, 506.1466; found (ESI), 435.2021.

Example 8

1-[2-(1,4'-bipiperidin-1'-yl)-1-(3-bromo-4-methoxyphenyl)ethyl]cyclohexanol dihydrochloride

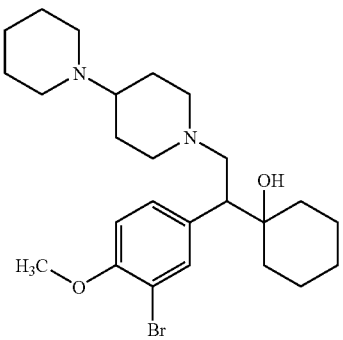

In an analogous manner to Example 1, step 1 1-[2-(1,4'-bipiperidin-1'-yl)-1-(3-bromo-4-methoxyphenyl)-2-oxoethyl]cyclohexanol was prepared from (3-bromo-4-methoxyphenyl)(1-hydroxycyclohexyl)acetic acid (Reference Example 1-l) and N-(4-piperidine)piperidine.

In an analogous manner to Example 1, step 2 1-[2-(1,4'-bipiperidin-1'-yl)-1-(3-bromo-4-methoxyphenyl)ethyl]cyclohexanol dihydrochloride was prepared from 1-[2-(1,4'-bipiperidin-1'-yl)-1-(3,4-dichlorophenyl)-2-oxoethyl]cyclohexanol. MS m/z 479/481 ([M+H]$^+$); HRMS: calcd for C$_{25}$H$_{39}$BrN$_2$O$_2$.2.00 HCl, 550.1728; found (ESI), 479.2269.

Example 9

1-[1-(3-bromo-4-methoxyphenyl)-2-(4-pyrrolidin-1-ylpiperidin-1-yl)ethyl]cyclohexanol dihydrochloride

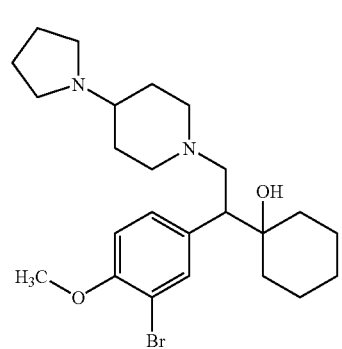

In an analogous manner to Example 1, step 1 1-[1-(3-bromo-4-methoxyphenyl)-2-(4-pyrrolidin-1-ylpiperidin-1-yl)-2-oxoethyl]cyclohexanol was prepared from (3-bromo-4-methoxyphenyl)(1-hydroxycyclohexyl)acetic acid (Reference Example 1-l) and 4-(1-pyrrolidinyl)piperidine.

In an analogous manner to Example 1, step 2 1-[1-(3-bromo-4-methoxyphenyl)-2-(4-pyrrolidin-1-ylpiperidin-1-yl)ethyl]cyclohexanol dihydrochloride was prepared from 1-[1-(3-bromo-4-methoxyphenyl)-2-(4-pyrrolidin-1-ylpiperidin-1-yl)-2-oxoethyl]cyclohexanol. MS m/z 465/467 ([M+H]$^+$); HRMS: calcd for C$_{24}$H$_{37}$BrN$_2$O$_2$.2.00 HCl, 536.1572; found (ESI), 465.2096.

Example 10

1-[2-(benzylamino)-1-(3,4-dichlorophenyl)ethyl]cyclobutanol hydrochloride

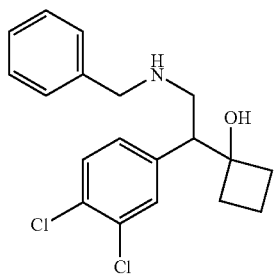

In an analogous manner to Example 1, step 1 N-benzyl-2-(3,4-dichlorophenyl)-2-(1-hydroxycyclobutyl)acetamide was prepared from (3,4-dichlorophenyl)(1-hydroxycyclobutyl)acetic acid (Reference Example 1-p) and benzylamine. HRMS: calcd for C$_{19}$H$_{19}$Cl$_2$NO$_2$, 363.0793; found (ESI_FT), 364.08658.

In an analogous manner to Example 1, step 2 1-[2-(benzylamino)-1-(3,4-dichlorophenyl)ethyl]cyclobutanol hydrochloride was prepared from N-benzyl-2-(3,4-dichlorophenyl)-2-(1-hydroxycyclobutyl)acetamide. HRMS: calcd for C$_{19}$H$_{21}$Cl$_2$NO.HCl, 385.0767; found (ESI_FT), 350.10832.

Example 11

1-[1-(3,4-dichlorophenyl)-2-(4-pyrrolidin-1-ylpiperidin-1-yl)ethyl]cyclohexanol dihydrochloride

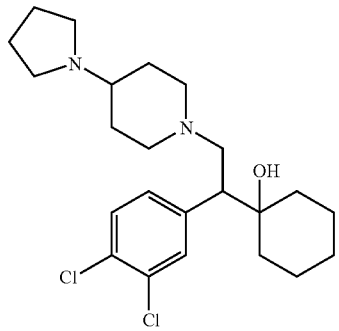

In an analogous manner to Example 1, step 1 1-[1-(3,4-dichlorophenyl)-2-(4-pyrrolidin-1-ylpiperidin-1-yl)-2-oxo-ethyl]cyclohexanol was prepared from 3,4-dichloro-alpha-(1-hydroxycyclohexyl)benzeneacetic acid (Reference Example 1-d) and 4-(1-pyrrolidinyl)piperidine.

In an analogous manner to Example 1, step 2 1-[1-(3,4-dichlorophenyl)-2-(4-pyrrolidin-1-ylpiperidin-1-yl)ethyl]cyclohexanol dihydrochloride was prepared from 1-[1-(3,4-dichlorophenyl)-2-(4-pyrrolidin-1-ylpiperidin-1-yl)-2-oxoethyl]cyclohexanol. MS m/z 425/427/429 ([M+H]$^+$); HRMS: calcd for $C_{23}H_{34}Cl_2N_2O \cdot 2.00$ HCl, 496.1582; found (ESI), 425.2129.

Example 12

1-[2-(benzylamino)-1-(2-naphthyl)ethyl]cyclobutanol hydrochloride

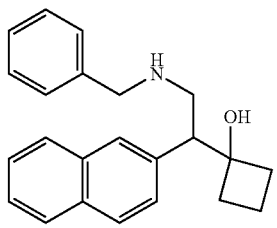

In an analogous manner to Example 1, step 1 N-benzyl-2-(1-hydroxycyclobutyl)-2-(2-naphthyl)acetamide was prepared from (1-hydroxycyclobutyl) (2-naphthyl)acetic acid (Reference Example 1-c) and benzylamine. HRMS: calcd for $C_{23}H_{23}NO_2$, 345.1729; found (ESI_FT), 346.17885.

In an analogous manner to Example 1, step 2 1-[2-(benzylamino)-1-(2-naphthyl)ethyl]cyclobutanol hydrochloride was prepared from N-benzyl-2-(1-hydroxycyclobutyl)-2-(2-naphthyl)acetamide. HRMS: calcd for $C_{23}H_{25}NO \cdot HCl$, 367.1703; found (ESI_FT), 332.20146.

Example 13

1-{1-(3,4-dichlorophenyl)-2-[4-(methylamino)piperidin-1-yl]ethyl}cyclohexanol dihydrochloride

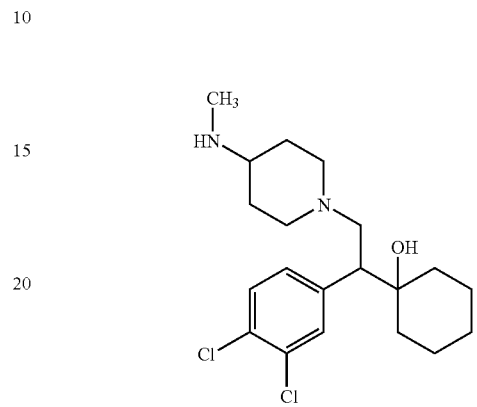

Step 1: In an analogous manner to Example 1, step 1 tert-butyl {1-[(3,4-dichlorophenyl)(1-hydroxycyclohexyl)acetyl]piperidin-4-yl}carbamate was prepared from 3,4-dichloro-alpha-(1-hydroxycyclohexyl)benzeneacetic acid (Reference Example 1-d) and 4-N-boc-aminopiperidine. MS (ES) m/z 485.2 ([M+H]$^+$); HRMS: calcd for $C_{24}H_{34}Cl_2N_2O_4$, 484.1896; found (ESI), 485.1987.

Step 2: A solution of tert-butyl {1-[(3,4-dichlorophenyl)(1-hydroxycyclohexyl)acetyl]piperidin-4-yl}carbamate (364 mg, 0.75 mmol) in dry tetrahydrofuran (1 mL), under nitrogen, was treated with a solution of borane (1.0 M in tetrahydrofuran, 2.62 mL, 2.62 mmol). The reaction was heated at 74° C. for 2 h, after which time the reaction was cooled and quenched by the addition of methanol (4 mL). The solvents were removed in vacuo, and the products were purified via Biotage Horizon (FLASH 25 M, silica, gradient from 10% EtOAc/hexane to 90% EtOAc/hexane) to yield 187 mg (53%) tert-butyl {1-[2-(3,4-dichlorophenyl)-2-(1-hydroxycyclohexyl)ethyl]piperidin-4-yl}carbamate as a white foam which eluted first and 88 mg (31%) 1-{1-(3,4-dichlorophenyl)-2-[4-(methylamino)piperidin-1-yl]ethyl}cyclohexanol as a colorless oil which eluted second. tert-butyl {1-[2-(3,4-dichlorophenyl)-2-(1-hydroxycyclohexyl)ethyl]piperidin-4-yl}carbamate: MS (ES) m/z 471.3 ([M+H]$^+$); HRMS: calcd for $C_{24}H_{36}Cl_2N_2O_3$, 470.2103; found (ESI), 471.2165. 1-{1-(3,4-dichlorophenyl)-2-[4-(methylamino)piperidin-1-yl]ethyl}cyclohexanol: MS m/z 385/387/389 ([M+H]$^+$). 1-{1-(3,4-dichlorophenyl)-2-[4-(methylamino)piperidin-1-yl]ethyl}cyclohexanol was converted to the dihydrochloride salt with a methanolic solution of hydrochloric acid and diethyl ether to yield 45 mg (41%) 1-{1-(3,4-dichlorophenyl)-2-[4-(methylamino)piperidin-1-yl]ethyl}cyclohexanol dihydrochloride as a white solid. HRMS: calcd for $C_{20}H_{30}Cl_2N_2O \cdot 2.00$ HCl, 456.1269; found (ESI), 385.183.

Example 14

1-[2-(4-aminopiperidin-1-yl)-1-(3,4-dichlorophenyl)ethyl]cyclohexanol dihydrochloride

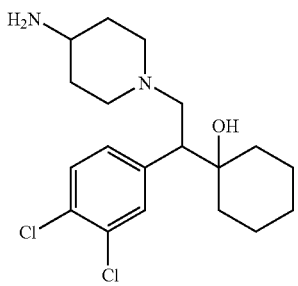

A solution of tert-butyl {1-[2-(3,4-dichlorophenyl)-2-(1-hydroxycyclohexyl)ethyl]piperidin-4-yl}carbamate (130 mg, 0.28 mmol) (Example 13), in diethyl ether (2 mL) was treated with a 4 N solution of hydrogen chloride in dioxane (1 mL). The resulting solution was stored at 25° C. for 16 h, during which time crystals began to form. The mixture was transferred to the refrigerator where it was stored for an additional 16 h. The resulting crystals were collected, washed with diethyl ether, and dried in vacuo to yield 101 mg (82%) 1-[2-(4-aminopiperidin-1-yl)-1-(3,4-dichlorophenyl)ethyl]cyclohexanol dihydrochloride as a white solid. MS m/z 371/373/375 ([M+H]$^+$); HRMS: calcd for $C_{19}H_{28}Cl_2N_2O.2.00$ HCl, 442.1112; found (ESI), 371.1642.

Example 15

4-[2-(benzylamino)-1-(3,4-dichlorophenyl)ethyl]-1-methylpiperidin-4-ol dihydrochloride

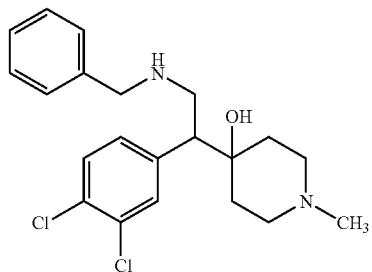

In an analogous manner to Example 1, step 1 N-benzyl-2-(3,4-dichlorophenyl)-2-(4-hydroxy-1-methylpiperidin-4-yl)acetamide was prepared from (3,4-dichlorophenyl)(4-hydroxy-1-methylpiperidin-4-yl)acetic acid (Reference Example 1-i) and benzylamine. HRMS: calcd for $C_{21}H_{24}Cl_2N_2O_2$, 406.1215; found (ESI_FT), 407.12885.

In an analogous manner to Example 1, step 2 4-[2-(benzylamino)-1-(3,4-dichlorophenyl)ethyl]-1-methylpiperidin-4-ol dihydrochloride was prepared from N-benzyl-2-(3,4-dichlorophenyl)-2-(4-hydroxy-1-methylpiperidin-4-yl)acetamide. HRMS: calcd for $C_{21}H_{26}Cl_2N_2O.2.00$ HCl, 464.0956; found (ESI_FT), 393.14924.

Example 16

1-[2-[(3S)-3-aminopyrrolidin-1-yl]-1-(3-chlorophenyl)ethyl]cyclohexanol dihydrochloride

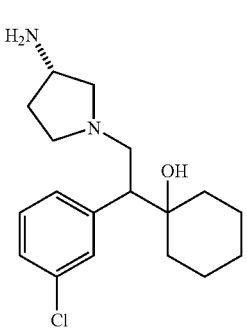

In an analogous manner to Example 1, step 1 {(S)-1-[2-(3-Chloro-phenyl)-2-(1-hydroxy-cyclohexyl)-acetyl]-pyrrolidin-3-yl}-carbamic acid tert-butyl ester was prepared from (3-chlorophenyl)(1-hydroxycyclohexyl)acetic acid (Reference Example 1-a) and (3S)-(−)-3-(tert-butoxycarbonylamino)pyrrolodine.

In an analogous manner to Example 1, step 2 1-[2-[(3S)-3-aminopyrrolidin-1-yl]-1-(3-chlorophenyl)ethyl]cyclohexanol dihydrochloride was prepared from {(S)-1-[2-(3-Chloro-phenyl)-2-(1-hydroxy-cyclohexyl)-acetyl]-pyrrolidin-3-yl}-carbamic acid tert-butyl ester. HRMS: calcd for $C_{18}H_{27}ClN_2O.2.00$ HCl, 394.1345; found (ESI), 323.1884.

Example 17

1-{1-(3-chlorophenyl)-2-[4-(methylamino)piperidin-1-yl]ethyl}cyclohexanol dihydrochloride

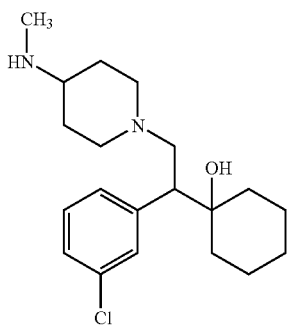

In an analogous manner to Example 1, step 1 tert-butyl {1-[(3-chlorophenyl)(1-hydroxycyclohexyl)acetyl]piperidin-4-yl}carbamate was prepared from (3-chlorophenyl)(1-hydroxycyclohexyl)acetic acid (Reference Example 1-a) and 4-N-boc-aminopiperidine. MS m/z 451/453 ([M+H]$^+$); HRMS: calcd for $C_{24}H_{35}ClN_2O_4$, 450.2285; found (ESI), 451.2353.

In an analogous manner to Example 13, step 2 1-{1-(3-chlorophenyl)-2-[4-(methylamino)piperidin-1-yl]

ethyl}cyclohexanol dihydrochloride was prepared from tert-butyl {1-[(3-chlorophenyl)(1-hydroxycyclohexyl)acetyl]piperidin-4-yl}carbamate. MS m/z 351/353 ([M+H]$^+$); HRMS: calcd for C$_{20}$H$_{31}$ClN$_2$O.2.00 HCl, 422.1658; found (ESI), 351.2208.

Example 18

1-[2-(4-aminopiperidin-1-yl)-1-(3-bromophenyl) ethyl]cyclohexanol dihydrochloride

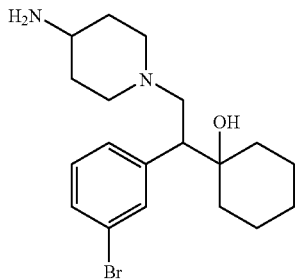

In an analogous manner to Example 1, step 1 tert-butyl {1-[(3-bromophenyl)(1-hydroxycyclohexyl)acetyl]piperidin-4-yl}carbamate was prepared from (3-bromophenyl)(1-hydroxycyclohexyl)acetic acid (Reference Example 1-b) and 4-N-boc-aminopiperidine. MS (ES) m/z 495.2 ([M+H]$^+$); HRMS: calcd for C$_{24}$H$_{35}$BrN$_2$O$_4$, 494.1780; found (ESI), 495.1864.

In an analogous manner to Example 13, step 2 tert-butyl {1-[2-(3-bromophenyl)-2-(1-hydroxycyclohexyl)ethyl]piperidin-4-yl}carbamate was prepared from tert-butyl {1-[(3-bromophenylphenyl)(1-hydroxycyclohexyl)acetyl]piperidin-4-yl}carbamate. MS (ES) m/z 481.3 ([M+H]$^+$); HRMS: calcd for C$_{24}$H$_{37}$BrN$_2$O$_3$, 480.1988; found (ESI), 481.2081.

In an analogous manner to Example 14, 1-[2-(4-aminopiperidin-1-yl)-1-(3-bromophenyl)ethyl]cyclohexanol dihydrochloride was prepared from tert-butyl {1-[2-(3-bromophenyl)-2-(1-hydroxycyclohexyl)ethyl]piperidin-4-yl}carbamate. HRMS: calcd for C$_{19}$H$_{29}$BrN$_2$O.2.00 HCl, 452.0997; found (ESI), 381.1525.

Example 19

1-{1-(3-bromophenyl)-2-[4-(methylamino)piperidin-1-yl]ethyl}cyclohexanol dihydrochloride

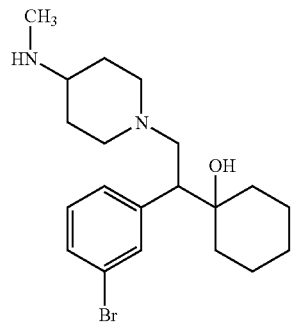

In an analogous manner to Example 1, step 1 tert-butyl {1-[(3-bromophenyl)(1-hydroxycyclohexyl)acetyl]piperidin-4-yl}carbamate was prepared from (3-bromophenyl)(1-hydroxycyclohexyl)acetic acid (Reference Example 1-b) and 4-N-boc-aminopiperidine. MS (ES) m/z 495.2 ([M+H]$^+$); HRMS: calcd for C$_{24}$H$_{35}$BrN$_2$O$_4$, 494.1780; found (ESI), 495.1864.

In an analogous manner to Example 13, step 2 1-{1-(3-bromophenyl)-2-[4-(methylamino)piperidin-1-yl]ethyl}cyclohexanol dihydrochloride was prepared from tert-butyl {1-[(3-bromophenylphenyl)(1-hydroxycyclohexyl)acetyl]piperidin-4-yl}carbamate. MS (ESI) m/z 395 ([M+H]$^+$); HRMS: calcd for C$_{20}$H$_{31}$BrN$_2$O' 2.00 HCl, 466.1153; found (ESI), 395.1708.

Example 20

1-{2-(1,4'-bipiperidin-1'-yl)-1-[3-(trifluoromethyl)phenyl]ethyl}cyclohexanol dihydrochloride

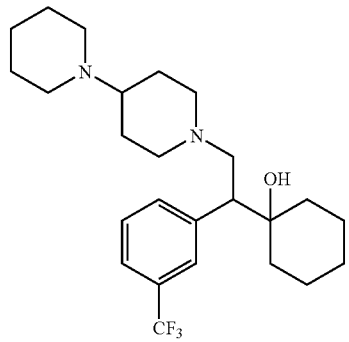

In an analogous manner to Example 1, step 1 1-[2-(1,4'-bipiperidin-1'-yl)-1-[3-(trifluoromethyl)phenyl]-2-oxoethyl]cyclohexanol was prepared from (1-hydroxycyclohexyl)[3-(trifluoromethoxy)phenyl]acetic acid (Reference Example 1-f) and N-(4-piperidine)piperidine.

In an analogous manner to Example 1, step 2 1-{2-(1,4'-bipiperidin-1'-yl)-1-[3-(trifluoromethyl)phenyl]ethyl}cyclohexanol dihydrochloride was prepared from (1-hydroxycyclohexyl)[3-(trifluoromethoxy)phenyl]acetic acid. m/z 439 ([M+H]$^+$); HRMS: calcd for C$_{25}$H$_{37}$F$_3$N$_2$O.2.00 HCl, 510.2392; found (ESI), 439.2928.

Example 21

1-[1-(1-naphthyl)-2-piperazin-1-ylethyl]cyclohexanol dihydrochloride

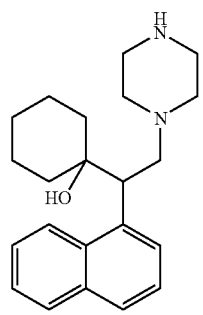

In an analogous manner to Example 1, step 1 tert-butyl 4-[(1-hydroxycyclohexyl)(1-naphthyl)acetyl]piperazine-1-carboxylate was prepared from (1-hydroxycyclohexyl)(1-naphthyl)acetic acid (Reference Example 1-e) and tert-butyl 1-piperazinecarboxylate. MS (ESI) m/z 453 ([M+H]$^+$); HRMS: calcd for $C_{27}H_{36}N_2O_4$, 452.2675; found (ES_FT), 453.27518.

In an analogous manner to Example 1, step 2 1-[1-(1-naphthyl)-2-piperazin-1-ylethyl]cyclohexanol dihydrochloride was prepared from tert-butyl 4-[(1-hydroxycyclohexyl)(1-naphthyl)acetyl]piperazine-1-carboxylate. MS (ESI) m/z 339 ([M+H]$^+$); HRMS: calcd for $C_{22}H_{30}N_2O$, HCl, 374.2125; found (ESI_FT), 339.24268.

Example 22

1-[2-(1,4'-bipiperidin-1'-yl)-1-(2-naphthyl)ethyl]cyclohexanol dihydrochloride

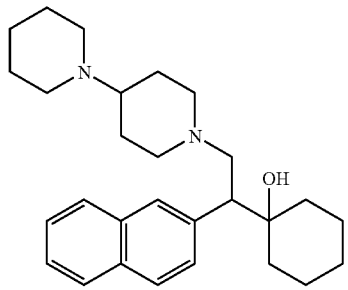

In an analogous manner to Example 1, step 1 1-[2-(1,4'-bipiperidin-1'-yl)-1-(2-naphthyl)-2-oxoethyl]cyclohexanol was prepared from (1-hydroxycyclohexyl)(2-naphthyl)acetic acid (Reference Example 1-q) and N-(4-piperidine)piperidine.

In an analogous manner to Example 1, step 2 1-[2-(1,4'-bipiperidin-1'-yl)-1-(2-naphthyl)ethyl]cyclohexanol dihydrochloride was prepared from 1-[2-(1,4'-bipiperidin-1'-yl)-1-(2-naphthyl)-2-oxoethyl]cyclohexanol. MS m/z 421 ([M+H]$^+$); HRMS: calcd for $C_{28}H_{40}N_2O.2.00$ HCl, 492.2674; found (ESI), 421.3224.

Example 23

1-{2-piperazin-1-yl-1-[3-(trifluoromethoxy)phenyl]ethyl}cyclohexanol dihydrochloride

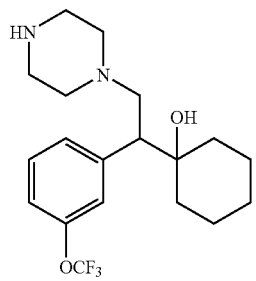

In an analogous manner to Example 1, step 1 tert-butyl 4-{(1-hydroxycyclohexyl)[3-(trifluoromethoxy)phenyl]acetyl}piperazine-1-carboxylate was prepared from (1-hydroxycyclohexyl)[3-(trifluoromethoxy)phenyl]acetic acid (Reference Example 1-f) and tert-butyl 1-piperazinecarboxylate. HRMS: calcd for $C_{24}H_{33}F_3N_2O_5$, 486.2342; found (ESI), 487.2398.

In an analogous manner to Example 1, step 2 1-{2-piperazin-1-yl-1-[3-(trifluoromethoxy)phenyl]ethyl}cyclohexanol dihydrochloride was prepared from tert-butyl 4-{(1-hydroxycyclohexyl)[3-(trifluoromethoxy)phenyl]acetyl}piperazine-1-carboxylate. HRMS: calcd for $C_{19}H_{27}F_3N_2O_2.2.00$ HCl, 444.1558; found (ESI), 373.2095.

Example 24

1-{2-(4-methylpiperazin-1-yl)-1-[3-(trifluoromethoxy)phenyl]ethyl}cyclohexanol dihydrochloride

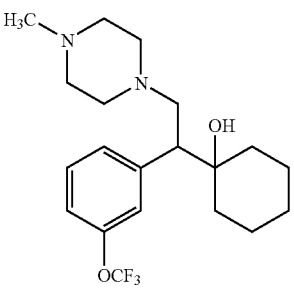

A solution of 1-{2-piperazin-1-yl-1-[3-(trifluoromethoxy)phenyl]ethyl}cyclohexanol (590 mg, 1.59 mmol) (see Example 23), in formic acid (3.1 mL) at 50° C., was treated with an aqueous solution of formaldehyde (37% in water, 1.3 mL, 1.94 mmol). The reaction was heated at 70° C. for 1.5 h, after which time the reaction was poured into water (50 mL) and basified to pH=10 with the addition of a 2 N aqueous solution of sodium hydroxide. The product was then extracted with ethyl acetate (3×20 mL), and the combined organic extracts were dried over magnesium sulfate and concentrated to yield 442 mg (72%) 1-{2-(4-methylpiperazin-1-yl)-1-[3-(trifluoromethoxy)phenyl]ethyl}cyclohexanol as a colorless oil. The product was dissolved in methanol (0.5 mL) and the resulting solution was treated with a saturated methanolic solution of hydrochloric acid (0.5 mL) followed by diethyl ether (2 mL). The solution was stored in the refrigerator for 16 h. The resulting precipitate was filtered and washed with diethyl ether to yield 299 mg (57%) 1-{2-(4-methylpiperazin-1-yl)-1-[3-(trifluoromethoxy)phenyl]ethyl}cyclohexanol dihydrochloride as a white solid. HRMS: calcd for $C_{20}H_{29}F_3N_2O_2.2.00$ HCl, 458.1715; found (ESI), 387.2263.

Example 25

1-[2-(4-aminopiperidin-1-yl)-1-(3-bromo-4-methoxyphenyl)ethyl]cyclohexanol dihydrochloride

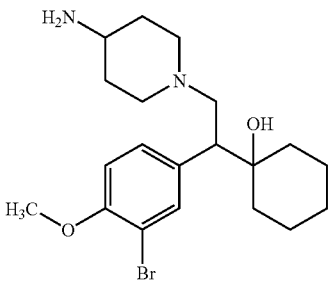

In an analogous manner to Example 1, step 1 tert-butyl {1-[(3-bromo-4-methoxyphenyl)(1-hydroxycyclohexyl)acetyl]piperidin-4-yl}carbamate was prepared from (3-bromo-4-methoxyphenyl)(1-hydroxycyclohexyl)acetic acid (Reference Example 1-l) and 4-N-boc-aminopiperidine. MS (ES) m/z 525.2 ([M+H]$^+$); HRMS: calcd for $C_{25}H_{37}BrN_2O_5$, 524.1886; found (ESI), 525.1971.

In an analogous manner to Example 13, step 2 tert-butyl {1-[2-(3-bromo-4-methoxyphenyl)-2-(1-hydroxycyclohexyl)ethyl]piperidin-4-yl}carbamate was prepared from tert-butyl {1-[(3-bromo-4-methoxyphenyl)(1-hydroxycyclohexyl)acetyl]piperidin-4-yl}carbamate. MS (ES) m/z 511.4 ([M+H]$^+$); HRMS: calcd for $C_{25}H_{39}BrN_2O_4$, 510.2093; found (ESI), 511.2147.

In an analogous manner to Example 14, 1-[2-(4-aminopiperidin-1-yl)-1-(3-bromo-4-methoxyphenyl)ethyl]cyclohexanol dihydrochloride was prepared from tert-butyl {1-[2-(3-bromophenyl)-2-(1-hydroxycyclohexyl)ethyl]piperidin-4-yl}carbamate. MS m/z 411/413 ([M+H]$^+$); HRMS: calcd for $C_{20}H_{31}BrN_2O_2 \cdot 2.00$ HCl, 482.1102; found (ESI), 411.1656.

Example 26

1-{2-(4-pyrrolidin-1-ylpiperidin-1-yl)-1-[3-(trifluoromethyl)phenyl]ethyl}cyclohexanol dihydrochloride

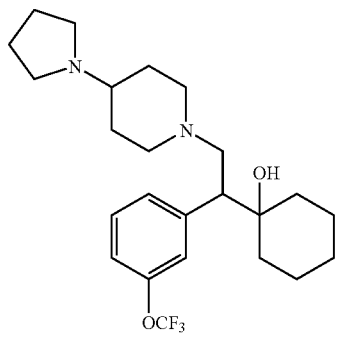

In an analogous manner to Example 1, step 1 1-[2-(4-pyrrolidin-1-ylpiperidin-1-yl)-1-[3-(trifluoromethyl)phenyl]-2-oxoethyl]cyclohexanol was prepared from (1-hydroxycyclohexyl)[3-(trifluoromethyl)phenyl]acetic acid (Reference Example 1-m) and 4-(1-pyrrolidinyl)piperidine.

In an analogous manner to Example 1, step 2 1-{2-(4-pyrrolidin-1-ylpiperidin-1-yl)-1-[3-(trifluoromethyl)phenyl]ethyl}cyclohexanol dihydrochloride was prepared from 1-{2-(4-pyrrolidin-1-ylpiperidin-1-yl)-1-[3-(trifluoromethyl)phenyl]-2-oxoethyl}cyclohexanol. MS m/z 425 ([M+H]$^+$); HRMS: calcd for $C_{24}H_{35}F_3N_2O \cdot 2.00$ HCl, 496.2235; found (ESI), 425.2789.

Example 27

1-{1-[4-(benzyloxy)phenyl]-2-piperazin-1-ylethyl}cyclohexanol dihydrochloride

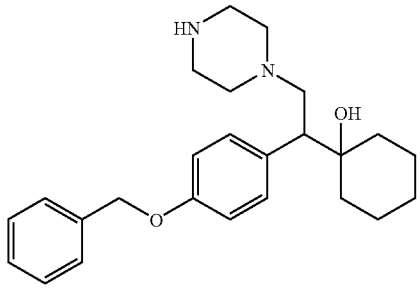

In an analogous manner to Example 1, step 1 tert-butyl 4-[[4-(benzyloxy)phenyl](1-hydroxycyclohexyl)acetyl]piperazine-1-carboxylate was prepared from (4-benzyloxyphenyl)(1-hydroxycyclohexyl)acetic acid (Reference Example 1-n) and tert-butyl 1-piperazinecarboxylate. MS (ESI) m/z 509 ([M+H]$^+$); HRMS: calcd for $C_{30}H_{40}N_2O_5$, 508.2937; found (ESI), 509.3027.

In an analogous manner to Example 1, step 1-{1-[4-(benzyloxy)phenyl]-2-piperazin-1-ylethyl}cyclohexanol dihydrochloride was prepared from tert-butyl 4-[[4-(benzyloxy)phenyl](1-hydroxycyclohexyl)acetyl]piperazine-1-carboxylate. HRMS: calcd for $C_{25}H_{34}N_2O_2 \cdot 2.00$ HCl, 466.2154; found (ESI), 395.2683.

Example 28

1-{2-piperazin-1-yl-1-[4-(trifluoromethoxy)phenyl]ethyl}cyclohexanol dihydrochloride

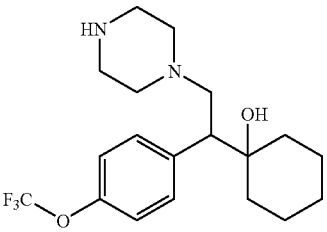

In an analogous manner to Example 1, step 1 tert-butyl 4-{(1-hydroxycyclohexyl)[4-(trifluoromethoxy)phenyl]acetyl}piperazine-1-carboxylate was prepared from (1-hydroxycyclohexyl)[4-(trifluoromethoxy)phenyl]acetic acid (Reference Example 1-g) and tert-butyl 1-piperazinecarboxylate. MS (ESI) m/z 487 ([M+H]$^+$).

In an analogous manner to Example 1, step 2 1-{2-piperazin-1-yl-1-[4-(trifluoromethoxy)phenyl]

ethyl}cyclohexanol dihydrochloride was prepared from tert-butyl 4-{(1-hydroxycyclohexyl)[4-(trifluoromethoxy)phenyl]acetyl}piperazine-1-carboxylate. MS m/z 373 ([M+H]⁺); Anal. Calcd for $C_{19}H_{27}F_3N_2O_2.2.00$ HCl.$2.10H_2O$: C, 47.23; H, 6.93; N, 5.80. Found: C, 46.93; H, 6.80.

Example 29

1-{1-(3-bromo-4-methoxyphenyl)-2-[4-(methylamino)piperidin-1-yl]ethyl}cyclohexanol dihydrochloride

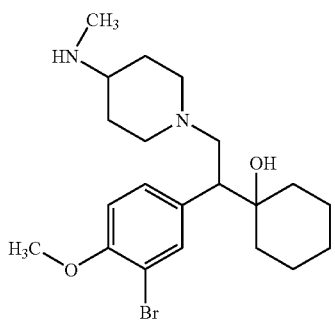

In an analogous manner to Example 1, step 1 tert-butyl {1-[(3-bromo-4-methoxyphenyl)(1-hydroxycyclohexyl)acetyl]piperidin-4-yl}carbamate was prepared from (3-bromo-4-methoxyphenyl)(1-hydroxycyclohexyl)acetic acid (Reference Example 1-l) and 4-N-boc-aminopiperidine. MS (ES) m/z 525.2 ([M+H]⁺); HRMS: calcd for $C_{25}H_{37}BrN_2O_5$, 524.1886; found (ESI), 525.1971.

In an analogous manner to Example 13, step 2 1-{1-(3-bromo-4-methoxyphenyl)-2-[4-(methylamino)piperidin-1-yl]ethyl}cyclohexanol dihydrochloride was prepared from tert-butyl {1-[(3-bromo-4-methoxyphenyl)(1-hydroxycyclohexyl)acetyl]piperidin-4-yl}carbamate. MS (ESI) m/z 425 ([M+H]⁺); HRMS: calcd for $C_{21}H_{33}BrN_2O_2.2.00$ HCl, 496.1259; found (ESI), 425.1793.

Example 30

1-{2-[4-(methylamino)piperidin-1-yl]-1-[3-(trifluoromethyl)phenyl]ethyl}cyclohexanol dihydrochloride

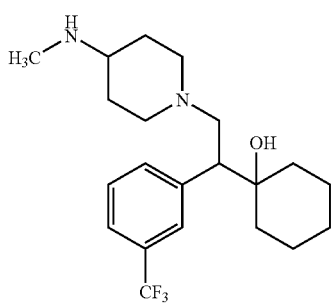

In an analogous manner to Example 1, step 1 tert-butyl (1-{(1-hydroxycyclohexyl)[3-(trifluoromethyl)phenyl]acetyl}piperidin-4-yl)carbamate was prepared from (1-hydroxycyclohexyl)[3-(trifluoromethyl)phenyl]acetic acid (Reference Example 1-m) and 4-N-boc-aminopiperidine. MS (ES) m/z 485.3 ([M+H]⁺); HRMS: calcd for $C_{25}H_{35}F_3N_2O_4$, 484.2549; found (ESI), 485.2612.

In an analogous manner to Example 13, step 2 1-{2-[4-(methylamino)piperidin-1-yl]-1-[3-(trifluoromethyl)phenyl]ethyl}cyclohexanol dihydrochloride was prepared from tert-butyl (1-{(1-hydroxycyclohexyl)[3-(trifluoromethyl)phenyl]acetyl}piperidin-4-yl)carbamate. MS m/z 385 ([M+H]⁺); HRMS: calcd for $C_{21}H_{31}F_3N_2O.2.00$ HCl, 456.1922; found (ESI), 385.2454.

Example 31

1-[1-(2-naphthyl)-2-(4-pyrrolidin-1-ylpiperidin-1-yl)ethyl]cyclohexanol dihydrochloride

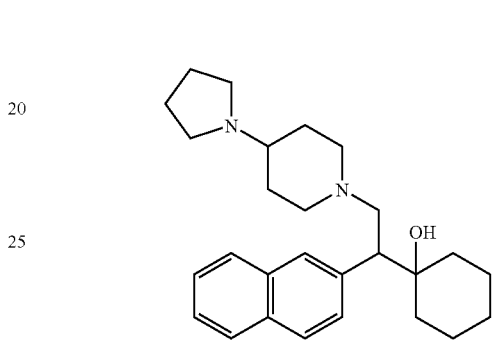

In an analogous manner to Example 1, step 1 1-[1-(2-naphthyl)-2-(4-pyrrolidin-1-ylpiperidin-1-yl)-2-oxoethyl]cyclohexanol was prepared from (1-hydroxycyclohexyl)(2-naphthyl)acetic acid (Reference Example 1-q) and 4-(1-pyrrolidinyl)piperidine.

In an analogous manner to Example 1, step 2 1-[1-(2-naphthyl)-2-(4-pyrrolidin-1-ylpiperidin-1-yl)ethyl]cyclohexanol dihydrochloride was prepared from 1-[1-(2-naphthyl)-2-(4-pyrrolidin-1-ylpiperidin-1-yl)-2-oxoethyl]cyclohexanol. MS m/z 407 ([M+H]⁺); HRMS: calcd for $C_{27}H_{38}N_2O.2.00$ HCl, 478.2518; found (ESI), 407.3055.

Example 32

1-[2-(4-aminopiperidin-1-yl)-1-(2-naphthyl)ethyl]cyclohexanol dihydrochloride

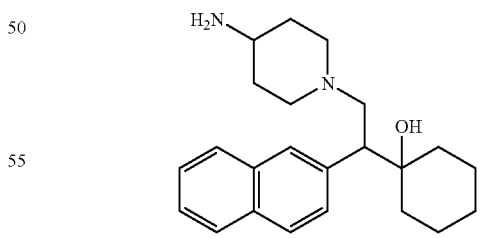

In an analogous manner to Example 1, step 1 tert-butyl {1-[(1-hydroxycyclohexyl)(2-naphthyl)acetyl]piperidin-4-yl}carbamate was prepared from (1-hydroxycyclohexyl)(2-naphthyl)acetic acid (Reference Example 1-q) and 4-N-boc-aminopiperidine. MS (ES) m/z 467.3 ([M+H]⁺); HRMS: calcd for $C_{28}H_{38}N_2O_4$, 466.2832; found (ESI), 467.2902.

In an analogous manner to Example 13, step 2 tert-butyl {1-[2-(1-hydroxycyclohexyl)-2-(2-naphthyl)ethyl]piperidin-4-yl}carbamate was prepared from tert-butyl {1-[(1-hydroxycyclohexyl)(2-naphthyl)acetyl]piperidin-4-yl}carbamate. MS (ES) m/z 453.4 ([M+H]$^+$); HRMS: calcd for $C_{28}H_{40}N_2O_3$, 452.3039; found (ESI), 453.3095.

In an analogous manner to Example 14, 1-[2-(4-aminopiperidin-1-yl)-1-(2-naphthyl)ethyl]cyclohexanol dihydrochloride was prepared from tert-butyl {1-[2-(1-hydroxycyclohexyl)-2-(2-naphthyl)ethyl]piperidin-4-yl}carbamate. MS m/z 353 ([M+H]$^+$); HRMS: calcd for $C_{23}H_{32}N_2O \cdot 2.00$ HCl, 424.2048; found (ESI), 353.2598.

Example 33

1-[2-[(3-chlorobenzyl)amino]-1-(2-naphthyl)ethyl]cyclohexanol hydrochloride

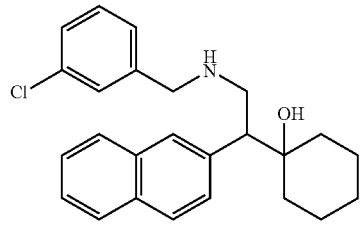

In an analogous manner to Example 1, step 1 N-(3-chlorobenzyl)-2-(1-hydroxycyclohexyl)-2-(2-naphthyl)acetamide was prepared from (1-hydroxycyclohexyl)(2-naphthyl)acetic acid (Reference Example 1-q) and 3-chlorobenzylamine. MS (ESI) m/z 408/410 ([M+H]$^+$).

In an analogous manner to Example 1, step 2 1-[2-[(3-chlorobenzyl)amino]-1-(2-naphthyl)ethyl]cyclohexanol hydrochloride was prepared from N-(3-chlorobenzyl)-2-(1-hydroxycyclohexyl)-2-(2-naphthyl)acetamide. MS m/z 394/396 ([M+H]$^+$); HRMS: calcd for $C_{25}H_{28}ClNO \cdot HCl$, 429.1626; found (ESI), 394.191.

Example 34

1-[1-(3-chlorophenyl)-2-pyrrolidin-1-ylethyl]cyclohexanol hydrochloride

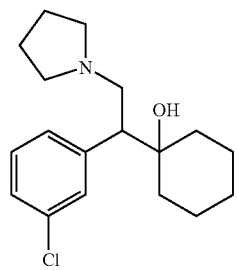

In an analogous manner to Example 1, step 1 1-[1-(3-chlorophenyl)-2-oxo-2-pyrrolidin-1-ylethyl]cyclohexanol was prepared from (3-chlorophenyl)(1-hydroxycyclohexyl)acetic acid (Reference Example 1-a) and pyrrolidine. MS (ESI) m/z 322/324 ([M+H]$^+$); HRMS: calcd for $C_{18}H_{24}ClNO_2$, 321.1496; found (ESI_FT), 322.15603.

In an analogous manner to Example 1, step 2 1-[1-(3-chlorophenyl)-2-pyrrolidin-1-ylethyl]cyclohexanol hydrochloride was prepared from 1-[1-(3-chlorophenyl)-2-oxo-2-pyrrolidin-1-ylethyl]cyclohexanol. HRMS: calcd for $C_{18}H_{26}ClNO \cdot HCl$, 343.1470; found (ESI_FT), 308.17736.

Example 35

1-[2-(4-aminopiperidin-1-yl)-1-(3-chlorophenyl)ethyl]cyclohexanol dihydrochloride

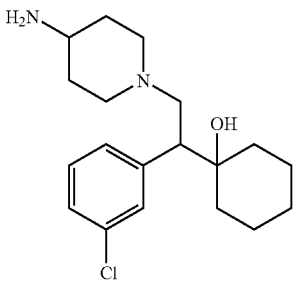

In an analogous manner to Example 1, step 1 tert-butyl {1-[(3-chlorophenyl)(1-hydroxycyclohexyl)acetyl]piperidin-4-yl}carbamate was prepared from (3-chlorophenyl)(1-hydroxycyclohexyl)acetic acid (Reference Example 1-a) and 4-N-boc-aminopiperidine. MS m/z 451/453 ([M+H]$^+$); HRMS: calcd for $C_{24}H_{35}ClN_2O_4$, 450.2285; found (ESI), 451.2353.

In an analogous manner to Example 13, step 2 1-[2-(4-aminopiperidin-1-yl)-1-(3-chlorophenyl)ethyl]cyclohexanol dihydrochloride was prepared from tert-butyl {1-[(3-chlorophenyl)(1-hydroxycyclohexyl)acetyl]piperidin-4-yl}carbamate. MS m/z 337/339 ([M+H]$^+$); HRMS: calcd for $C_{19}H_{29}ClN_2O \cdot 2.00$ HCl, 408.1502; found (ESI), 337.2022

Example 36

1-{1-(3-chlorophenyl)-2-[4-(dimethylamino)piperidin-1-yl]ethyl}cyclohexanol dihydrochloride

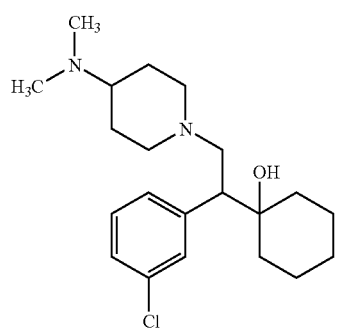

A solution of 1-[2-(4-aminopiperidin-1-yl)-1-(3-chlorophenyl)ethyl]cyclohexanol (50 mg, 0.15 mmol) (see Example 35), in formic acid (0.28 mL) was treated with an aqueous solution of formaldehyde (37% in water, 0.12 mL). The reaction was heated at 70° C. for 1 h, after which time the reaction was diluted with water (3 mL) and basified to pH=10 with a 2 N aqueous solution of sodium hydroxide. The product was extracted with ethyl acetate (4×5 mL), and the combined organic extracts were dried over magnesium sulfate and concentrated in vacuo. The resulting colorless oil was treated with methanolic hydrochloric acid and diethyl ether to yield 32 mg (53%) 1-{1-(3-chlorophenyl)-2-[4-(dimethylamino) piperidin-1-yl]ethyl}cyclohexanol dihydrochloride as a white solid. HRMS: calcd for $C_{21}H_{33}ClN_2O \cdot HCl$, 400.2048; found (ESI), 365.2349.

Example 37

4-[1-(3,4-dichlorophenyl)-2-piperazin-1-ylethyl]-1-methylpiperidin-4-ol trihydrochloride

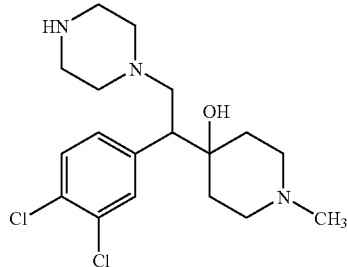

In an analogous manner to Example 1, step 1 tert-butyl 4-[(3,4-dichlorophenyl)(4-hydroxy-1-methylpiperidin-4-yl) acetyl]piperazine-1-carboxylate was prepared from (3,4-dichlorophenyl)(4-hydroxy-1-methylpiperidin-4-yl)acetic acid (Reference Example 1-i) and tert-butyl 1-piperazinecarboxylate. HRMS: calcd for $C_{23}H_{33}Cl_2N_3O_4$, 485.1848; found (ESI_FT), 486.19305.

In an analogous manner to Example 1, step 2 4-[1-(3,4-dichlorophenyl)-2-piperazin-1-ylethyl]-1-methylpiperidin-4-ol trihydrochloride was prepared from tert-butyl 4-[(3,4-dichlorophenyl)(4-hydroxy-1-methylpiperidin-4-yl)acetyl] piperazine-1-carboxylate. HRMS: calcd for $C_{18}H_{27}Cl_2N_3O \cdot 3.00\ HCl$, 479.0831; found (ESI_FT), 372.16065.

Example 38

1-[2-(benzylamino)-1-(3,4-dichlorophenyl)ethyl]cyclohexanol hydrochloride

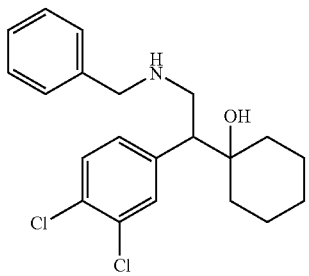

In an analogous manner to Example 1, step 1 N-benzyl-2-(3,4-dichlorophenyl)-2-(1-hydroxycyclohexyl)acetamide was prepared from 3,4-dichloro-alpha-(1-hydroxycyclohexyl)benzeneacetic acid (Reference Example 1-d) and benzylamine. HRMS: calcd for $C_{21}H_{23}Cl_2NO_2$, 391.1106; found (ESI_FT), 392.11598.

In an analogous manner to Example 1, step 2 4-[1-(3,4-dichlorophenyl)-2-piperazin-1-ylethyl]-1-methylpiperidin-4-ol hydrochloride was prepared from N-benzyl-2-(3,4-dichlorophenyl)-2-(1-hydroxycyclohexyl)acetamide. HRMS: calcd for $C_{21}H_{25}Cl_2NO \cdot HCl$, 413.1080; found (ESI_FT), 378.13864.

Example 39

1-{2-(4-aminopiperidin-1-yl)-1-[3-(trifluoromethyl) phenyl]ethyl}cyclohexanol dihydrochloride

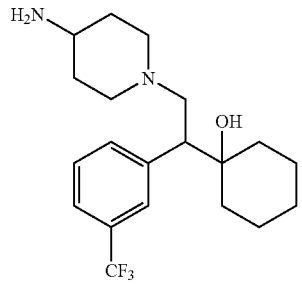

In an analogous manner to Example 1, step 1 tert-butyl (1-{(1-hydroxycyclohexyl)[3-(trifluoromethyl)phenyl] acetyl}piperidin-4-yl)carbamate was prepared from (1-hydroxycyclohexyl)[3-(trifluoromethyl)phenyl]acetic acid (Reference Example 1-m) and 4-N-boc-aminopiperidine. MS (ES) m/z 485.3 ([M+H]$^+$); HRMS: calcd for $C_{25}H_{35}F_3N_2O_4$, 484.2549; found (ESI), 485.2612.

In an analogous manner to Example 13, step 2 tert-butyl (1-{2-(1-hydroxycyclohexyl)-2-[3-(trifluoromethyl)phenyl] ethyl}piperidin-4-yl)carbamate was prepared from tert-butyl (1-{(1-hydroxycyclohexyl)[3-(trifluoromethyl)phenyl] acetyl}piperidin-4-yl)carbamate. MS (ES) m/z 471.4 ([M+H]$^+$); HRMS: calcd for $C_{25}H_{37}F_3N_2O_3$, 470.2756; found (ESI), 471.2852.

In an analogous manner to Example 14, 1-{2-(4-aminopiperidin-1-yl)-1-[3-(trifluoromethyl)phenyl] ethyl}cyclohexanol dihydrochloride was prepared from tert-butyl (1-{2-(1-hydroxycyclohexyl)-2-[3-(trifluoromethyl) phenyl]ethyl}piperidin-4-yl)carbamate. MS m/z 371 ([M+H]$^+$); HRMS: calcd for $C_{20}H_{29}F_3N_2O \cdot 2.00\ HCl$, 442.1766; found (ESI), 371.2309.

Example 40

1-[2-(benzylamino)-1-(3-bromophenyl)ethyl]cyclobutanol hydrochloride

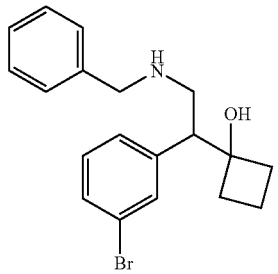

In an analogous manner to Example 1, step 1 N-benzyl-2-(3-bromophenyl)-2-(1-hydroxycyclobutyl)acetamide was prepared from (3-bromophenyl)(1-hydroxycyclobutyl)acetic acid (Reference Example 1-j) and benzylamine. HRMS: calcd for C$_{19}$H$_{20}$BrNO$_2$, 373.0677; found (ESI_FT), 374.07415.

In an analogous manner to Example 1, step 2 1-[2-(benzylamino)-1-(3-bromophenyl)ethyl]cyclobutanol hydrochloride was prepared from N-benzyl-2-(3-bromophenyl)-2-(1-hydroxycyclobutyl)acetamide. HRMS: calcd for C$_{19}$H$_{22}$BrNO.HCl, 395.0652; found (ESI_FT), 360.09546.

Example 41

1-[2-(benzylamino)-1-(3-chlorophenyl)ethyl]cyclohexanol hydrochloride

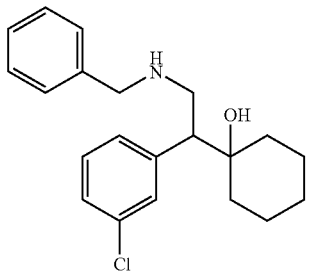

In an analogous manner to Example 1, step 1 N-benzyl-2-(3-chlorophenyl)-2-(1-hydroxycyclohexyl)acetamide was prepared from (3-chlorophenyl)(1-hydroxycyclohexyl)acetic acid (Reference Example 1-a) and benzylamine. HRMS: calcd for C$_{21}$H$_{24}$ClNO$_2$, 357.1496; found (ESI_FT), 358.15607.

In an analogous manner to Example 1, step 2 1-[2-(benzylamino)-1-(3-chlorophenyl)ethyl]cyclohexanol hydrochloride was prepared from N-benzyl-2-(3-chlorophenyl)-2-(1-hydroxycyclohexyl)acetamide. HRMS: calcd for C$_{21}$H$_{26}$ClNO.HCl, 379.1470; found (ESI_FT), 344.17761.

Example 42

1-[2-(cyclohexylamino)-1-(3,4-dichlorophenyl)ethyl]cyclohexanol hydrochloride

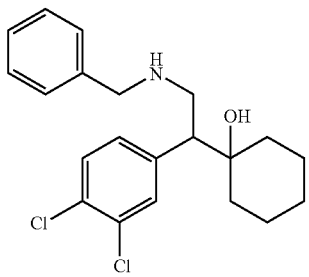

In an analogous manner to Example 1, step 1 N-cyclohexyl-2-(3,4-dichlorophenyl)-2-(1-hydroxycyclohexyl)acetamide was prepared from 3,4-dichloro-alpha-(1-hydroxycyclohexyl)benzeneacetic acid (Reference Example 1-d) and cyclohexylamine. MS (ESI) m/z 384/386/388 ([M+H]$^+$).

In an analogous manner to Example 1, step 2 1-[2-(cyclohexylamino)-1-(3,4-dichlorophenyl)ethyl]cyclohexanol hydrochloride was prepared from N-cyclohexyl-2-(3,4-dichlorophenyl)-2-(1-hydroxycyclohexyl)acetamide. MS (ESI) m/z [M+H]$^+$ (370/372/374); HRMS: calcd for C$_{20}$H$_{29}$Cl$_2$NO.HCl, 405.1393; found (ESI), 370.1687; Anal. Calcd for C$_{20}$H$_{29}$Cl$_2$NO.HCl: C, 59.05; H, 7.43; N, 3.44. Found: C, 59.00; H, 7.49; N, 3.37.

Example 43

1-[2-(4-aminopiperidin-1-yl)-1-(1-naphthyl)ethyl]cyclobutanol dihydrochloride

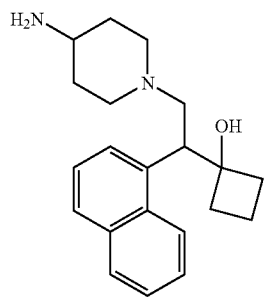

In an analogous manner to Example 1, step 1 tert-butyl {1-[(1-hydroxycyclobutyl)(1-naphthyl)acetyl]piperidin-4-yl}carbamate was prepared from (1-hydroxycyclobutyl)(1-naphthyl)acetic acid (Reference Example 1-o) and 4-N-boc-aminopiperidine. MS (ES) m/z 439.3 ([M+H]$^+$).

In an analogous manner to Example 1, step 2 1-[2-(4-aminopiperidin-1-yl)-1-(1-naphthyl)ethyl]cyclobutanol dihydrochloride was prepared from tert-butyl {1-[(1-hydroxycyclobutyl)(1-naphthyl)acetyl]piperidin-4-yl}carbamate. MS (ES) m/z 325.3 ([M+H]$^+$); HRMS: calcd for C$_{21}$H$_{28}$N$_2$O.2.00 HCl, 396.1735; found (ESI), 325.2272.

Example 44

4-[2-(benzylamino)-1-(3-bromophenyl)ethyl]-1-methylpiperidin-4-ol dihydrochloride

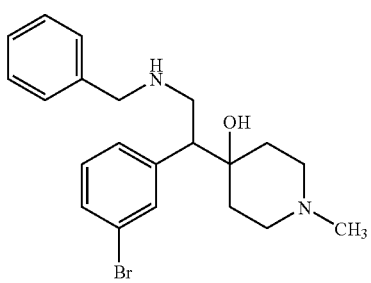

In an analogous manner to Example 1, step 1 N-benzyl-2-(3-bromophenyl)-2-(4-hydroxy-1-methylpiperidin-4-yl)acetamide was prepared from (3-bromophenyl)(4-hydroxy-1-methylpiperidin-4-yl)acetic acid (Reference Example 1-r) and benzylamine. HRMS: calcd for C$_{21}$H$_{25}$BrN$_2$O$_2$, 416.1099; found (ESI_FT), 417.11652.

In an analogous manner to Example 1, step 2 4-[2-(benzylamino)-1-(3-bromophenyl)ethyl]-1-methylpiperidin-4-ol dihydrochloride was prepared from N-benzyl-2-(3-bromophenyl)-2-(4-hydroxy-1-methylpiperidin-4-yl)acetamide. HRMS: calcd for C$_{21}$H$_{27}$BrN$_2$O.2.00 HCl, 474.0840; found (ESI_FT), 403.13802.

Example 45

1-[1-(1-naphthyl)-2-piperazin-1-ylethyl]cyclopentanol dihydrochloride

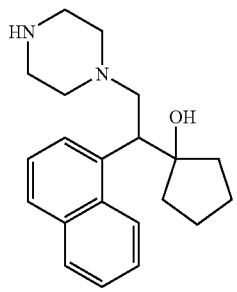

In an analogous manner to Example 1, step 1 tert-butyl 4-[(1-hydroxycyclopentyl)(1-naphthyl)acetyl]piperazine-1-carboxylate was prepared from (1-hydroxycyclopentyl)(1-naphthyl)acetic acid (Reference Example 1-s) and tert-butyl 1-piperazinecarboxylate. MS (ESI) m/z 439 ([M+H]$^+$); HRMS: calcd for $C_{26}H_{34}N_2O_4$, 438.2519; found (ESI), 439.2563.

In an analogous manner to Example 1, step 2 1-[1-(1-naphthyl)-2-piperazin-1-ylethyl]cyclopentanol dihydrochloride was prepared from tert-butyl 4-[(1-hydroxycyclopentyl)(1-naphthyl)acetyl]piperazine-1-carboxylate. MS (ESI) m/z 325 ([M+H]$^+$); HRMS: calcd for $C_{21}H_{28}N_2O.2.00$ HCl, 396.1735; found (ESI), 325.2267.

Example 46

1-{2-piperazin-1-yl-1-[3-(trifluoromethoxy)phenyl]ethyl}cyclobutanol dihydrochloride

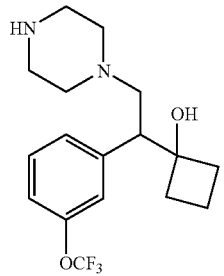

In an analogous manner to Example 1, step 1 tert-butyl 4-{(1-hydroxycyclobutyl)[3-(trifluoromethoxy)phenyl]acetyl}piperazine-1-carboxylate was prepared from (1-hydroxycyclobutyl)[3-(trifluoromethoxy)phenyl]acetic acid (Reference Example 1-k) and tert-butyl 1-piperazinecarboxylate. HRMS: calcd for $C_{22}H_{29}F_3N_2O_5$, 458.2029; found (ESI), 459.2118.

In an analogous manner to Example 1, step 2 1-{2-piperazin-1-yl-1-[3-(trifluoromethoxy)phenyl]ethyl}cyclobutanol dihydrochloride was prepared from tert-butyl 4-{(1-hydroxycyclobutyl)[3-(trifluoromethoxy) phenyl]acetyl}piperazine-1-carboxylate. HRMS: calcd for $C_{17}H_{23}F_3N_2O_2.2.00$ HCl, 416.1245; found (ESI), 345.1801.

Example 47

1-{2-[(4-fluorobenzyl)amino]-1-[3-(trifluoromethyl)phenyl]ethyl}cyclohexanol hydrochloride

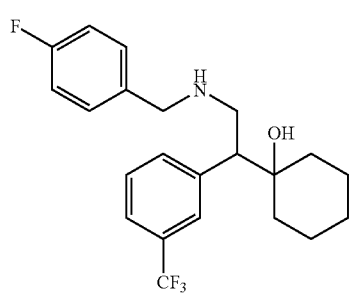

In an analogous manner to Example 1, step 1 N-(4-fluorobenzyl)-2-(1-hydroxycyclohexyl)-2-[3-(trifluoromethyl)phenyl]acetamide was prepared from (1-hydroxycyclohexyl)[3-(trifluoromethyl)phenyl]acetic acid (Reference Example 1-m) and 4-fluorobenzylamine. MS (ESI) m/z 410 ([M+H]$^+$).

In an analogous manner to Example 1, step 2 1-{2-[(4-fluorobenzyl)amino]-1-[3-(trifluoromethyl)phenyl]ethyl}cyclohexanol hydrochloride was prepared from N-(4-fluorobenzyl)-2-(1-hydroxycyclohexyl)-2-[3-(trifluoromethyl)phenyl]acetamide. MS (ESI) m/z 396 ([M+H]$^+$); HRMS: calcd for $C_{22}H_{25}F_4NO.HCl$, 431.1639; found (ESI), 396.1931.

Example 48

1-[1-(3-bromophenyl)-2-(cyclohexylamino)ethyl]cyclohexanol hydrochloride

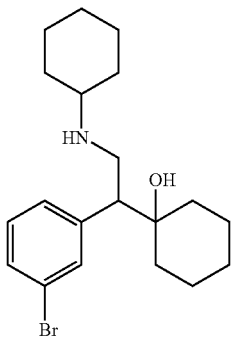

In an analogous manner to Example 1, step 1 2-(3-bromophenyl)-N-cyclohexyl-2-(1-hydroxycyclohexyl)acetamide was prepared from (3-bromophenyl)(1-hydroxycyclohexyl)acetic acid (Reference Example 1-b) and cyclohexylamine. MS (ESI) m/z 394/396 ([M+H]$^+$).

In an analogous manner to Example 1, step 2 1-[1-(3-bromophenyl)-2-(cyclohexylamino)ethyl]cyclohexanol hydrochloride was prepared from 2-(3-bromophenyl)-N-cyclohexyl-2-(1-hydroxycyclohexyl)acetamide. MS (ESI) m/z 380/382 ([M+H]$^+$); HRMS: calcd for $C_{20}H_{30}BrNO.HCl$, 415.1278; found (ESI), 380.1574.

Example 49

1-[2-[4-(methylamino)piperidin-1-yl]-1-(2-naphthyl)ethyl]cyclohexanol dihydrochloride

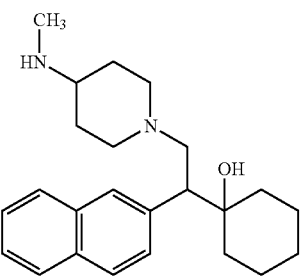

In an analogous manner to Example 1, step 1 tert-butyl {1-[(1-hydroxycyclohexyl)(2-naphthyl)acetyl]piperidin-4-yl}carbamate was prepared from (1-hydroxycyclohexyl)(2-naphthyl)acetic acid (Reference Example 1-c) and 4-N-boc-aminopiperidine. MS (ES) m/z 467.3 ([M+H]$^+$); HRMS: calcd for $C_{28}H_{38}N_2O_4$, 466.2832; found (ESI), 467.2902.

In an analogous manner to Example 13, step 2 1-[2-[4-(methylamino)piperidin-1-yl]-1-(2-naphthyl)ethyl]cyclohexanol dihydrochloride was prepared from tert-butyl {1-[(1-hydroxycyclohexyl)(2-naphthyl)acetyl]piperidin-4-yl}carbamate. MS m/z 367 ([M+H]$^+$); HRMS: calcd for $C_{24}H_{34}N_2O.2.00$ HCl, 438.2205; found (ESI), 367.2763.

Example 50

2-(3-bromophenyl)-3-ethyl-1-piperazin-1-ylpentan-3-ol dihydrochloride

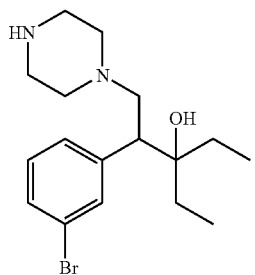

In an analogous manner to Example 1, step 1 tert-butyl 4-[2-(3-bromophenyl)-3-ethyl-3-hydroxypentanoyl]piperazine-1-carboxylate was prepared from 2-(3-bromophenyl)-3-ethyl-3-hydroxypentanoic acid (Reference Example 1-t) and tert-butyl 1-piperazinecarboxylate. MS (ESI) m/z 469/471 ([M+H]$^+$); HRMS: calcd for $C_{22}H_{33}BrN_2O_4$, 468.1624; found (ESI_FT), 469.17071.

In an analogous manner to Example 1, step 2 2-(3-bromophenyl)-3-ethyl-1-piperazin-1-ylpentan-3-ol dihydrochloride was prepared from tert-butyl 4-[2-(3-bromophenyl)-3-ethyl-3-hydroxypentanoyl]piperazine-1-carboxylate. MS (ESI) m/z 355/357 ([M+H]$^+$); HRMS: calcd for $C_{17}H_{27}BrN_2O.2.00$ HCl, 426.0840; found (ESI_FT), 355.13878.

Example 51

4-[1-(3-chlorophenyl)-2-piperazin-1-ylethyl]heptan-4-ol dihydrochloride

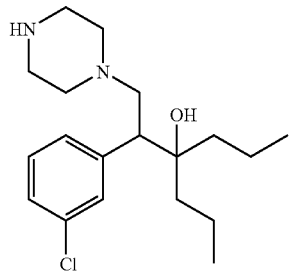

In an analogous manner to Example 1, step 1 tert-butyl 4-[2-(3-chlorophenyl)-3-hydroxy-3-propylhexanoyl]piperazine-1-carboxylate was prepared from 2-(3-chlorophenyl)-3-hydroxy-3-propylhexanoic acid (Reference Example 1-u) and tert-butyl 1-piperazinecarboxylate. MS (ESI) m/z 453/455 ([M+H]$^+$); HRMS: calcd for $C_{24}H_{37}ClN_2O_4$, 452.2442; found (ESI_FT), 453.25255.

In an analogous manner to Example 1, step 2 4-[1-(3-chlorophenyl)-2-piperazin-1-ylethyl]heptan-4-ol dihydrochloride was prepared from tert-butyl 4-[2-(3-chlorophenyl)-3-hydroxy-3-propylhexanoyl]piperazine-1-carboxylate. MS (ESI) m/z 339/341 ([M+H]$^+$); HRMS: calcd for $C_{19}H_{31}ClN_2O.2.00$ HCl, 410.1658; found (ESI_FT), 339.21916.

Example 52

2-(3-chlorophenyl)-3-ethyl-1-piperazin-1-ylpentan-3-ol dihydrochloride

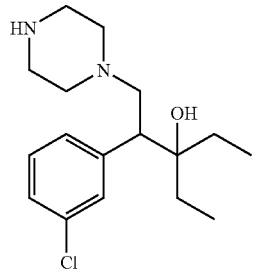

In an analogous manner to Example 1, step 1 tert-butyl 4-[2-(3-chlorophenyl)-3-ethyl-3-hydroxypentanoyl]piperazine-1-carboxylate was prepared from 2-(3-chlorophenyl)-3-ethyl-3-hydroxypentanoic acid (Reference Example 1-v) and tert-butyl 1-piperazinecarboxylate. MS (ESI) m/z 425/427 ([M+H]$^+$).

In an analogous manner to Example 1, step 2 2-(3-chlorophenyl)-3-ethyl-1-piperazin-1-ylpentan-3-ol dihydrochloride was prepared from tert-butyl 4-[2-(3-chlorophenyl)-3-ethyl-3-hydroxypentanoyl]piperazine-1-carboxylate. MS (ESI) m/z 311/313 ([M+H]⁺); HRMS: calcd for C₁₇H₂₇ClN₂O.HCl, 346.1579; found (ESI_FT), 311.18803.

Example 53

3-ethyl-2-(1-naphthyl)-1-piperazin-1-ylpentan-3-ol dihydrochloride

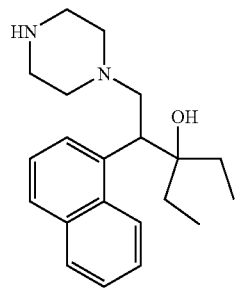

In an analogous manner to Example 1, step 1 tert-butyl 4-[2-(3-chlorophenyl)-3-ethyl-3-hydroxypentanoyl]piperazine-1-carboxylate was prepared from 3-ethyl-3-hydroxy-2-(1-naphthyl)pentanoic acid (Reference Example 1-w) and tert-butyl 1-piperazinecarboxylate. MS (ESI) m/z 441.2766 ([M+H]⁺); HRMS: calcd for C₂₆H₃₆N₂O₄, 440.2675; found (ESI), 441.2766.

In an analogous manner to Example 1, step 2 3-ethyl-2-(1-naphthyl)-1-piperazin-1-ylpentan-3-ol dihydrochloride was prepared from tert-butyl 4-[2-(3-chlorophenyl)-3-ethyl-3-hydroxypentanoyl]piperazine-1-carboxylate. MS (ESI) m/z 327 ([M+H]⁺); HRMS: calcd for C₂₁H₃₀N₂O.2.00 HCl, 398.1892; found (ESI), 327.2426.

Example 54

1-[2-(4-aminopiperidin-1-yl)-1-(1-naphthyl)ethyl]cyclohexanol dihydrochloride

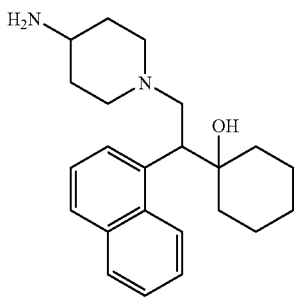

In an analogous manner to Example 1, step 1 tert-butyl {1-[(1-hydroxycyclohexyl)(1-naphthyl)acetyl]piperidin-4-yl}carbamate was prepared from (1-hydroxycyclohexyl)(1-naphthyl)acetic acid (Reference Example 1-e) and 4-N-boc-aminopiperidine. MS (ESI) m/z 467 ([M+H]⁺).

In an analogous manner to Example 1, step 2 1-[2-(4-aminopiperidin-1-yl)-1-(1-naphthyl)ethyl]cyclohexanol dihydrochloride was prepared from tert-butyl {1-[(1-hydroxycyclohexyl)(1-naphthyl)acetyl]piperidin-4-yl}carbamate. MS (ESI) m/z 353 ([M+H]⁺); HRMS: calcd for C₂₃H₃₂N₂O.2.00 HCl, 424.2048; found (ESI), 353.2583.

Example 55

1-[1-(3-bromophenyl)-2-(1,2,3,4-tetrahydronaphthalen-1-ylamino)ethyl]cyclohexanol hydrochloride

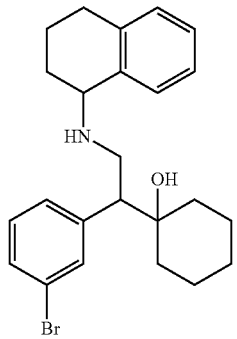

In an analogous manner to Example 1, step 1 2-(3-bromophenyl)-2-(1-hydroxycyclohexyl)-N-1,2,3,4-tetrahydronaphthalen-1-ylacetamide was prepared from (3-bromophenyl)(1-hydroxycyclohexyl)acetic acid (Reference Example 1-b) and 1,2,3,4-tetrahydro-1-napthylamine. MS (ESI) m/z 442/444 ([M+H]⁺).

In an analogous manner to Example 1, step 2 1-[1-(3-bromophenyl)-2-(1,2,3,4-tetrahydronaphthalen-1-ylamino)ethyl]cyclohexanol hydrochloride was prepared from 2-(3-bromophenyl)-2-(1-hydroxycyclohexyl)-N-1,2,3,4-tetrahydronaphthalen-1-ylacetamide. MS (ESI) m/z 428/430 ([M+H]⁺); HRMS: calcd for C₂₄H₃₀BrNO.HCl, 463.1278; found (ESI), 428.1593.

Example 56

1-[2-(4-methylpiperazin-1-yl)-1-(1-naphthyl)ethyl]cyclopentanol dihydrochloride

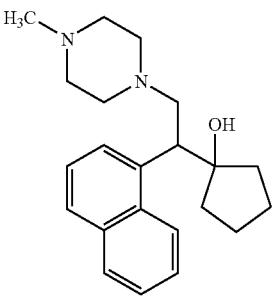

In an analogous manner to Example 1, step 1 1-[2-(4-methylpiperazin-1-yl)-1-(1-naphthyl)-2-oxoethyl]cyclopentanol was prepared from (1-hydroxycyclopentyl)(1-naphthyl)acetic acid (Reference Example 1-s) and N-methylpiperazine. MS (ESI) m/z 353 ([M+H]⁺).

In an analogous manner to Example 1, step 2 1-[2-(4-methylpiperazin-1-yl)-1-(1-naphthyl)ethyl]cyclopentanol dihydrochloride was prepared from 1-[2-(4-methylpiperazin-1-yl)-1-(1-naphthyl)-2-oxoethyl]cyclopentanol. MS m/z 339

([M+H]+); HRMS: calcd for $C_{22}H_{30}N_2O \cdot 2.00$ HCl, 410.1892; found (ESI), 339.2419.

Example 57

1-[1-(3-chlorophenyl)-2-morpholin-4-ylethyl]cyclohexanol hydrochloride

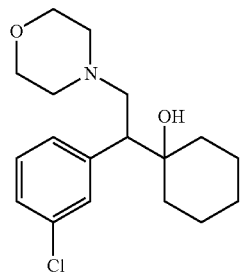

In an analogous manner to Example 1, step 1 1-[1-(3-chlorophenyl)-2-morpholin-4-yl-2-oxoethyl]cyclohexanol was prepared from (3-bromophenyl)(1-hydroxycyclohexyl)acetic acid (Reference Example 1-b) and morpholine. HRMS: calcd for $C_{18}H_{24}ClNO_3$, 337.1445; found (ESI_FT), 338.1521.

In an analogous manner to Example 1, step 2 1-[1-(3-chlorophenyl)-2-morpholin-4-ylethyl]cyclohexanol hydrochloride was prepared from 1-[1-(3-chlorophenyl)-2-morpholin-4-yl-2-oxoethyl]cyclohexanol. HRMS: calcd for $C_{18}H_{26}ClNO_2 \cdot HCl$, 359.1419; found (ESI_FT), 324.17137.

Example 58

4-[1-(3-bromophenyl)-2-piperazin-1-ylethyl]-1-methylpiperidin-4-ol dihydrochloride

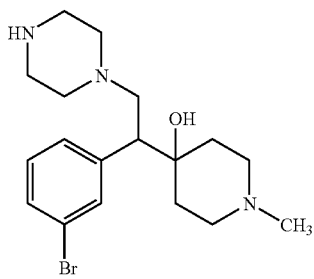

In an analogous manner to Example 1, step 1 tert-butyl 4-[(3-bromophenyl)(4-hydroxy-1-methylpiperidin-4-yl)acetyl]piperazine-1-carboxylate was prepared from (3-bromophenyl)(4-hydroxy-1-methylpiperidin-4-yl)acetic acid (Reference Example 1-r) and tert-butyl 1-piperazinecarboxylate. HRMS: calcd for $C_{23}H_{34}BrN_3O_4$, 495.1733; found (ESI_FT), 496.18082.

In an analogous manner to Example 1, step 2 4-[1-(3-bromophenyl)-2-piperazin-1-ylethyl]-1-methylpiperidin-4-ol dihydrochloride was prepared from tert-butyl 4-[(3-bromophenyl)(4-hydroxy-1-methylpiperidin-4-yl)acetyl]piperazine-1-carboxylate. HRMS: calcd for $C_{18}H_{28}BrN_3O \cdot 3.00$ HCl, 489.0716; found (ESI_FT), 382.14952.

Example 59

1-methyl-4-[1-(2-naphthyl)-2-piperazin-1-ylethyl]piperidin-4-ol dihydrochloride

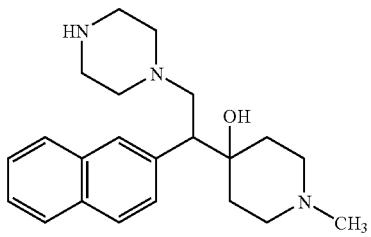

In an analogous manner to Example 1, step 1 tert-butyl 4-[(4-hydroxy-1-methylpiperidin-4-yl)(2-naphthyl)acetyl]piperazine-1-carboxylate was prepared from (4-hydroxy-1-methylpiperidin-4-yl)(2-naphthyl)acetic acid (Reference Example 1-x) and tert-butyl 1-piperazinecarboxylate. HRMS: calcd for $C_{27}H_{37}N_3O_4$, 467.2784; found (ESI_FT), 468.28561.

In an analogous manner to Example 1, step 2 1-methyl-4-[1-(2-naphthyl)-2-piperazin-1-ylethyl]piperidin-4-ol dihydrochloride was prepared from tert-butyl 4-[(4-hydroxy-1-methylpiperidin-4-yl)(2-naphthyl)acetyl]piperazine-1-carboxylate. HRMS: calcd for $C_{22}H_{31}N_3O \cdot 3.00$ HCl, 461.1767; found (ESI_FT), 354.25401.

Example 60

1-{1-(3-bromophenyl)-2-[(3-chlorobenzyl)amino]ethyl}cyclohexanol hydrochloride

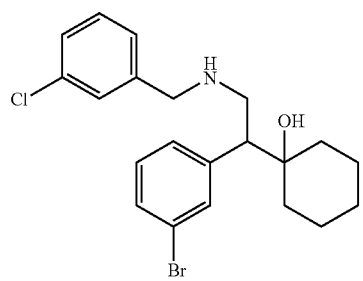

In an analogous manner to Example 1, step 1 2-(3-bromophenyl)-N-(3-chlorobenzyl)-2-(1-hydroxycyclohexyl)acetamide was prepared from (3-bromophenyl)(1-hydroxycyclohexyl)acetic acid (Reference Example 1-b) and 3-chlorobenzylamine. MS (ESI) m/z 43614381440 ([M+H]+).

In an analogous manner to Example 1, step 2 1-{1-(3-bromophenyl)-2-[(3-chlorobenzyl)amino]ethyl}cyclohexanol hydrochloride was prepared from 2-(3-bromophenyl)-N-(3-chlorobenzyl)-2-(1- hydroxycyclohexyl)acetamide. MS (ESI) m/z 422/424/426 ([M+H]+); HRMS: calcd for $C_{21}H_{25}BrClNO \cdot HCl$, 457.0575; found (ESI), 422.0873.

Example 61

1-[2-(benzylamino)-1-(3-bromophenyl)ethyl]cyclohexanol hydrochloride

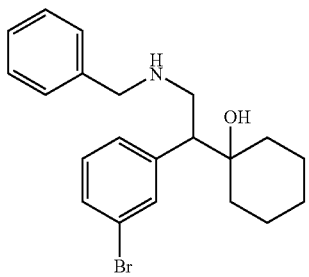

In an analogous manner to Example 1, step 1 N-benzyl-2-(3-bromophenyl)-2-(1-hydroxycyclohexyl)acetamide was prepared from (3-bromophenyl)(1-hydroxycyclohexyl)acetic acid (Reference Example 1-b) and benzylamine. HRMS: calcd for $C_{21}H_{24}BrNO_2$, 401.0990; found (ESI_FT), 402.10557.

In an analogous manner to Example 1, step 2 1-[2-(benzylamino)-1-(3-bromophenyl)ethyl]cyclohexanol hydrochloride was prepared from N-benzyl-2-(3-bromophenyl)-2-(1-hydroxycyclohexyl)acetamide. HRMS: calcd for $C_{21}H_{26}BrNO \cdot HCl$, 423.0965; found (ESI_FT), 388.12785.

Example 62

1-[2-(benzylamino)-1-(2-naphthyl)ethyl]cyclohexanol hydrochloride

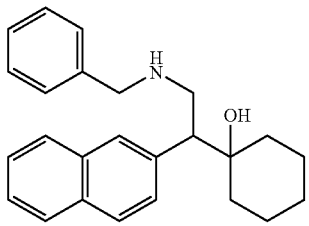

In an analogous manner to Example 1, step 1 N-benzyl-2-(1-hydroxycyclohexyl)-2-(2-naphthyl)acetamide was prepared from (1-hydroxycyclohexyl)(2-naphthyl)acetic acid (Reference Example 1-q) and benzylamine. HRMS: calcd for $C_{25}H_{27}NO_2$, 373.2042; found (ESI_FT), 374.21082.

In an analogous manner to Example 1, step 2 1-[2-(benzylamino)-1-(2-naphthyl)ethyl]cyclohexanol hydrochloride was prepared from N-benzyl-2-(1-hydroxycyclohexyl)-2-(2-naphthyl)acetamide. HRMS: calcd for $C_{25}H_{29}NO \cdot HCl$, 395.2016; found (ESI_FT), 360.23164.

Example 63

1-[1-(2-naphthyl)-2-piperazin-1-ylethyl]cyclohexanol dihydrochloride

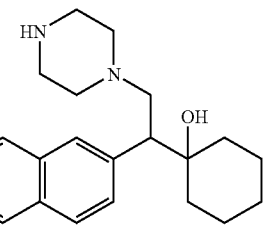

In an analogous manner to Example 1, step 1 tert-butyl 4[(1-hydroxycyclohexyl)(2-naphthyl)acetyl]piperazine-1-carboxylate was prepared from (1-hydroxycyclohexyl)(2-naphthyl)acetic acid (Reference Example 1-c) and tert-butyl 1-piperazinecarboxylate. MS (ESI) m/z 453 ([M+H]+).

In an analogous manner to Example 1, step 2 1-[1-(2-naphthyl)-2-piperazin-1-ylethyl]cyclohexanol dihydrochloride was prepared from tert-butyl 4-[(1-hydroxycyclohexyl)(2-naphthyl)acetyl]piperazine-1-carboxylate. MS (ESI) m/z 339 ([M+H]+); HRMS: calcd for $C_{22}H_{30}N_2O \cdot 2.00\ HCl$, 410.1892; found (ESI_FT), 339.2426.

Example 64

1-[2-(4-methylpiperazin-1-yl)-1-(2-naphthyl)ethyl]cyclohexanol dihydrochloride

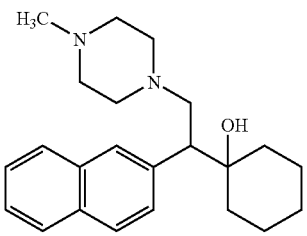

In an analogous manner to Example 24, 1-[2-(4-methylpiperazin-1-yl)-1-(2-naphthyl)ethyl]cyclohexanol dihydrochloride was prepared from 1-[1-(2-naphthyl)-2-piperazin-1-ylethyl]cyclohexanol (see Example 63). MS (ESI) m/z 353 ([M+H]+); HRMS: calcd for $C_{23}H_{32}N_2O \cdot 2.00\ HCl$, 424.2048; found (ESI_FT), 353.25994.

Example 65

2-(3-bromo-4-methoxyphenyl)-3-ethyl-1-piperazin-1-ylpentan-3-ol dihydrochloride

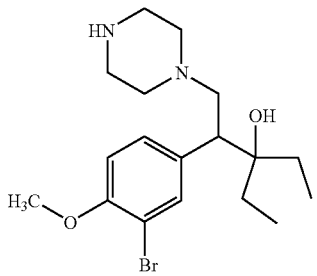

In an analogous manner to Example 1, step 1 tert-butyl 4-[2-(3-bromo-4-methoxyphenyl)-3-ethyl-3-hydroxypentanoyl]piperazine-1-carboxylate was prepared from 2-(3-bromo-4-methoxyphenyl)-3-ethyl-3-hydroxypentanoic acid (Reference Example 1-y) and tert-butyl 1-piperazinecarboxylate. MS (ESI) m/z 499/501 ([M+H]$^+$); HRMS: calcd for $C_{23}H_{35}BrN_2O_5$, 498.1729; found (ESI), 499.1793.

In an analogous manner to Example 1, step 2 2-(3-bromo-4-methoxyphenyl)-3-ethyl-1-(4-methylpiperazin-1-yl)pentan-3-ol dihydrochloride was prepared from tert-butyl 4-[2-(3-bromo-4-methoxyphenyl)-3-ethyl-3-hydroxypentanoyl]piperazine-1-carboxylate. MS m/z 385/387 ([M+H]$^+$); HRMS: calcd for $C_{18}H_{29}BrN_2O_2 \cdot 2.00$ HCl, 456.0946; found (ESI), 385.1494.

Example 66

2-(3-bromo-4-methoxyphenyl)-3-ethyl-1-(4-methylpiperazin-1-yl)pentan-3-ol dihydrochloride

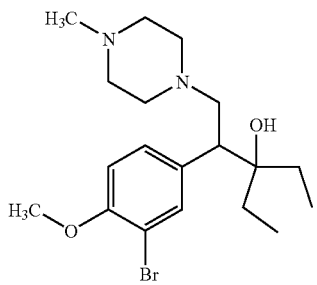

In an analogous manner to Example 24, 2-(3-bromo-4-methoxyphenyl)-3-ethyl-1-(4-methylpiperazin-1-yl)pentan-3-ol dihydrochloride was prepared from 2-(3-bromo-4-methoxyphenyl)-3-ethyl-1-(4-methylpiperazin-1-yl)pentan-3-ol (see Example 65). MS (ESI) m/z 399/401 ([M+H]$^+$); HRMS: calcd for $C_{19}H_{31}BrN_2O_2 \cdot 2.00$ HCl, 470.1102; found (ESI), 399.1632.

Example 67

1-[1-(3-chlorophenyl)-2-(cyclohexylamino)ethyl]cyclohexanol hydrochloride

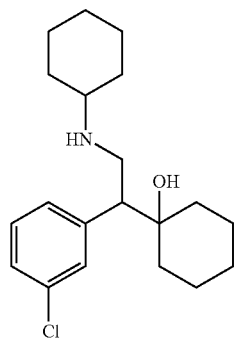

In an analogous manner to Example 1, step 1 2-(3-chlorophenyl)-N-cyclohexyl-2-(1-hydroxycyclohexyl)acetamide was prepared from (3-chlorophenyl)(1-hydroxycyclohexyl)acetic acid (Reference Example 1-a) and cyclohexylamine. MS (ESI) m/z 350/352 ([M+H]$^+$).

In an analogous manner to Example 1, step 2 1-[1-(3-chlorophenyl)-2-(cyclohexylamino)ethyl]cyclohexanol hydrochloride was prepared from 2-(3-chlorophenyl)-N-cyclohexyl-2-(1-hydroxycyclohexyl)acetamide. MS (ESI) m/z 336/338 ([M+H]$^+$); HRMS: calcd for $C_{20}H_{30}ClNO \cdot HCl$, 371.1783; found (ESI), 336.206.

Example 68

1-[1-(1-naphthyl)-2-piperazin-1-ylethyl]cyclobutanol dihydrochloride

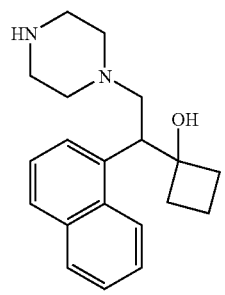

In an analogous manner to Example 1, step 1 tert-butyl 4-[(1-hydroxycyclobutyl)(1-naphthyl)acetyl]piperazine-1-carboxylate was prepared from (1-hydroxycyclobutyl)(1-naphthyl)acetic acid (Reference Example 1-o) and tert-butyl 1-piperazinecarboxylate. MS (ESI) m/z 425 ([M+H]$^+$).

In an analogous manner to Example 1, step 2 1-[1-(1-naphthyl)-2-piperazin-1-ylethyl]cyclobutanol dihydrochloride was prepared from tert-butyl 4-[(1-hydroxycyclobutyl)(1-naphthyl)acetyl]piperazine-1-carboxylate. MS (ESI) m/z 311 ([M+H]$^+$); HRMS: calcd for $C_{20}H_{26}N_2O \cdot 2.00$ HCl, 382.1579; found (ESI), 311.2127.

Example 69

1-[2-(4-methylpiperazin-1-yl)-1-(1-naphthyl)ethyl]cyclobutanol dihydrochloride

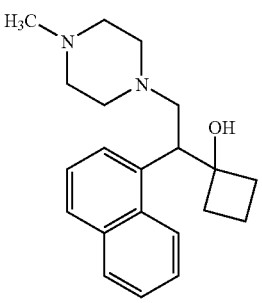

In an analogous manner to Example 24, 1-[2-(4-methylpiperazin-1-yl)-1-(1-naphthyl)ethyl]cyclobutanol dihydrochloride was prepared from 1-[1-(1-naphthyl)-2-piperazin-1-ylethyl]cyclobutanol (see Example 68). MS (ES) m/z 325.3

([M+H]+); HRMS: calcd for C21H28N2O.2.00 HCl, 396.1735; found (ESI), 325.2278.

Example 70

1-{1-[4-(benzyloxy)phenyl]-2-piperazin-1-ylethyl}cyclobutanol dihydrochloride

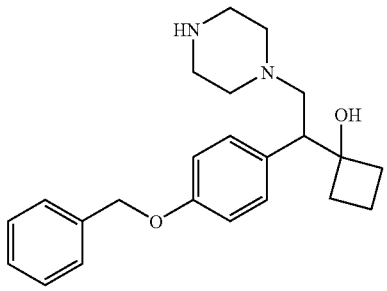

In an analogous manner to Example 1, step 1 tert-butyl 4-[[4-(benzyloxy)phenyl](1-hydroxycyclobutyl)acetyl]piperazine-1-carboxylate was prepared from (4-benzyloxyphenyl)(1-hydroxycyclobutyl)acetic acid (Reference Example 1-z) and tert-butyl 1-piperazinecarboxylate. MS (ESI) m/z 481 ([M+H]+); HRMS: calcd for C28H36N2O5, 480.2624; found (ESI), 481.2716.

In an analogous manner to Example 1, step 2 1-{1-[4-(benzyloxy)phenyl]-2-piperazin-1-ylethyl}cyclobutanol dihydrochloride was prepared from tert-butyl 4-[[4-(benzyloxy)phenyl](1-hydroxycyclobutyl)acetyl]piperazine-1-carboxylate. HRMS: calcd for C23H30N2O2.2.00 HCl, 438.1841; found (ESI), 367.2389.

Example 71

1-[1-[4-(benzyloxy)phenyl]-2-(4-methylpiperazin-1-yl)ethyl]cyclobutanol dihydrochloride

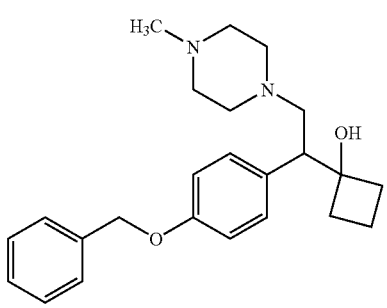

In an analogous manner to Example 24, 1-[1-[4-(benzyloxy)phenyl]-2-(4-methylpiperazin-1-yl)ethyl]cyclobutanol dihydrochloride was prepared from 1-{1-[4-(benzyloxy)phenyl]-2-piperazin-1-ylethyl}cyclobutanol (see Example 70). HRMS: calcd for C24H32N2O2.2.00 HCl, 452.1997; found (ESI), 381.2526.

Example 72

1-[1-(3-chlorophenyl)-2-piperazin-1-ylethyl]decahydronaphthalen-1-ol dihydrochloride

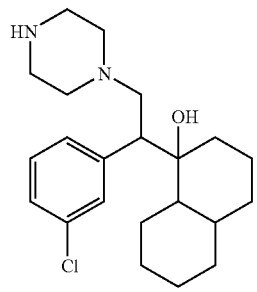

In an analogous manner to Example 1, step 1 tert-butyl 4-[1-(3-chlorophenylphenyl)(1-hydroxydecahydronapthyl)acetyl]piperazine-1-carboxylate was prepared from (3-chlorophenyl)(1-hydroxydecahydronapthyl)acetic acid (Reference Example 1-aa) and tert-butyl 1-piperazinecarboxylate. MS (ESI) m/z 4911493 ([M+H]+).

In an analogous manner to Example 1, step 2 1-[1-(3-chlorophenyl)-2-piperazin-1-ylethyl]decahydronaphthalen-1-ol dihydrochloride was prepared from tert-butyl 4-[1-(3-chlorophenylphenyl)(1-hydroxydecahydronapthyl)acetyl]piperazine-1-carboxylate. MS (ES) m/z 377.3 ([M+H]+); HRMS: calcd for C22H33ClN2O.2.00 HCl, 448.1815; found (ESI), 377.2351.

Example 73

1-[1-(3-bromo-4-methoxyphenyl)-2-(4-methylpiperazin-1-yl)ethyl]-4-tert-butylcyclohexanol dihydrochloride

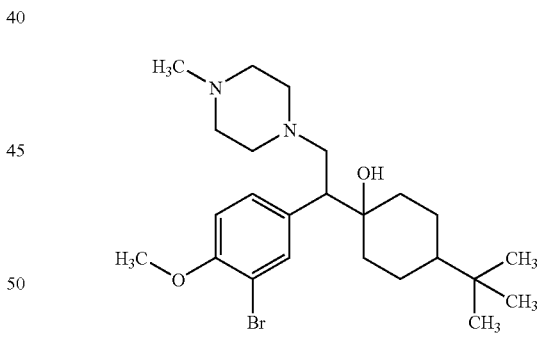

In an analogous manner to Example 1, step 1 1-[1-(3-bromo-4-methoxyphenyl)-2-(4-methylpiperazin-1-yl)-2-oxoethyl]-4-tert-butylcyclohexanol was prepared from (3-bromo-4-methoxyphenyl)(4-tert-butyl-1-hydroxycyclohexyl)acetic acid (Reference Example 1-bb) and N-methylpiperazine. MS (ESI) m/z 481/483 ([M+H]+).

In an analogous manner to Example 1, step 2 1-[1-(3-bromo-4-methoxyphenyl)-2-(4-methylpiperazin-1-yl)ethyl]-4-tert-butylcyclohexanol dihydrochloride was prepared from tert-butyl 1-[1-(3-bromo-4-methoxyphenyl)-2-(4-methylpiperazin-1-yl)-2-oxoethyl]-4-tert-butylcyclohexanol. MS (ESI) m/z 467/469 ([M+H]+); HRMS: calcd for C24H39BrN2O2.2.00 HCl, 538.1728; found (ESI), 467.2258.

Example 74

2-[1-(3-chlorophenyl)-2-piperazin-1-ylethyl]decahydronaphthalen-2-ol dihydrochloride

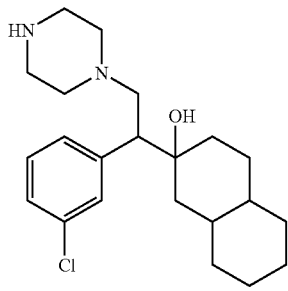

In an analogous manner to Example 1, step 1 tert-butyl 4-[1-(3-chlorophenylphenyl)(2-hydroxydecahydronapthyl)acetyl]piperazine-1-carboxylate was prepared from (3-chlorophenyl)(2-hydroxydecahydronapthyl)acetic acid (Reference Example 1-cc) and tert-butyl 1-piperazinecarboxylate. MS (ESI) m/z 491/493 ([M+H]$^+$).

In an analogous manner to Example 1, step 2 2-[1-(3-chlorophenyl)-2-piperazin-1-ylethyl]decahydronaphthalen-2-ol dihydrochloride was prepared from tert-butyl 4-[1-(3-chlorophenylphenyl)(2-hydroxydecahydronapthyl)acetyl]piperazine-1-carboxylate. MS (ESI) m/z 377 ([M+H]$^+$); HRMS: calcd for $C_{22}H_{33}ClN_2O.2.00$ HCl, 448.1815; found (ESI), 377.2346.

Example 75

1-(1-(3,4-dichlorophenyl)-2-{[4-(trifluoromethyl)benzyl]amino}ethyl)cyclohexanol hydrochloride

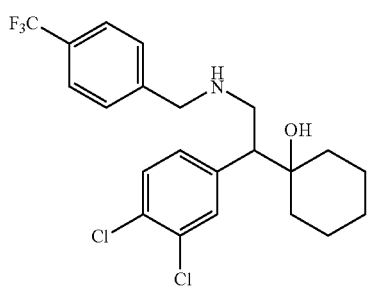

In an analogous manner to Example 1, step 1 2-(3,4-dichlorophenyl)-2-(1-hydroxycyclohexyl)-N-[4-(trifluoromethyl)benzyl]acetamide was prepared from 3,4-dichloro-alpha-(1-hydroxycyclohexyl)benzeneacetic acid (Reference Example 1-d) and 4-trifluoromethylbenzylamine. MS (ESI) m/z 460/462/464 ([M+H]$^+$).

In an analogous manner to Example 1, step 2 1-(1-(3,4-dichlorophenyl)-2-{[4-(trifluoromethyl)benzyl]amino}ethyl)cyclohexanol hydrochloride was prepared from 2-(3,4-dichlorophenyl)-2-(1-hydroxycyclohexyl)-N-[4-(trifluoromethyl)benzyl]acetamide. MS (ESI) m/z 446/448/450 ([M+H]$^+$); HRMS: calcd for $C_{22}H_{24}Cl_2F_3NO.HCl$, 481.0954; found (ESI), 446.1232; Anal. Calcd for $C_{22}H_{24}Cl_2F_3NO.HCl$: C, 54.73; H, 5.22; N, 2.90. Found: C, 54.69; H, 4.99; N, 2.78.

Example 76

4-tert-butyl-1-[1-(1-naphthyl)-2-piperazin-1-ylethyl]cyclohexanol dihydrochloride

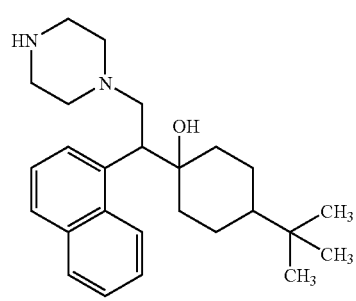

In an analogous manner to Example 1, step 1 tert-butyl 4-[(4-tert-butyl-1-hydroxycyclohexyl)(1-naphthyl)acetyl]piperazine-1-carboxylate was prepared from (4-tert-butyl-1-hydroxycyclohexyl)(1-naphthyl)acetic acid (Reference Example 1-dd) and tert-butyl 1-piperazinecarboxylate. MS (ESI) m/z 509 ([M+H]$^+$); HRMS: calcd for $C_{31}H_{44}N_2O_4$, 508.3301; found (ESI), 509.3354.

In an analogous manner to Example 1, step 2 4-tert-butyl-1-[1-(1-naphthyl)-2-piperazin-1-ylethyl]cyclohexanol dihydrochloride was prepared from tert-butyl 4-[(4-tert-butyl-1-hydroxycyclohexyl)(1-naphthyl)acetyl]piperazine-1-carboxylate. MS (ESI) m/z 395 ([M+H]$^+$); HRMS: calcd for $C_{26}H_{38}N_2O.2.00$ HCl, 466.2518; found (ESI), 395.3055.

Example 77

4-[1-(3-chlorophenyl)-2-piperazin-1-ylethyl]tetrahydro-2H-pyran-4-ol dihydrochloride

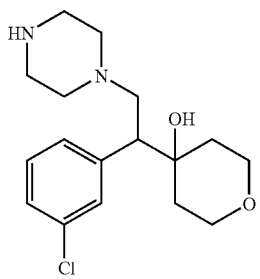

In an analogous manner to Example 1, step 1 tert-butyl 4-[(3-chlorophenyl)(4-hydroxytetrahydro-2H-pyran-4-yl)acetyl]piperazine-1-carboxylate was prepared from (3-chlorophenyl)(4-hydroxytetrahydro-2H-pyran-4-yl)acetic acid (Reference Example 1-ee) and tert-butyl 1-piperazinecarboxylate. MS (ESI) m/z 439/441 ([M+H]$^+$); HRMS: calcd for $C_{22}H_{31}ClN_2O_5$, 438.1921; found (ESI_FT), 439.19884.

In an analogous manner to Example 1, step 2 4-[1-(3-chlorophenyl)-2-piperazin-1-ylethyl]tetrahydro-2H-pyran-4-ol dihydrochloride was prepared from tert-butyl 4-[(3-chlorophenyl)(4-hydroxytetrahydro-2H-pyran-4-yl)acetyl]

Example 78

4-[1-(3-chlorophenyl)-2-(4-methylpiperazin-1-yl)ethyl]tetrahydro-2H-pyran-4-ol dihydrochloride

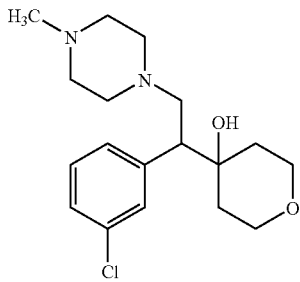

In an analogous manner to Example 24, 4-[1-(3-chlorophenyl)-2-(4-methylpiperazin-1-yl)ethyl]tetrahydro-2H-pyran-4-ol dihydrochloride was prepared from 4-[1-(3-chlorophenyl)-2-piperazin-1-ylethyl]tetrahydro-2H-pyran-4-ol (see Example 77). MS (ESI) m/z 339 ([M+H]$^+$); HRMS: calcd for $C_{18}H_{27}ClN_2O_2$.2.00 HCl, 410.1295; found (ESI), 339.1844.

Example 79

1-[1-(3-bromophenyl)-2-(4-methylpiperazin-1-yl)ethyl]-4-tert-butylcyclohexanol dihydrochloride

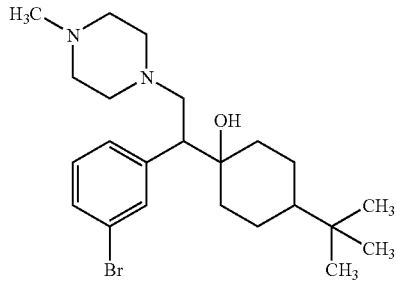

In an analogous manner to Example 1, step 1 1-[1-(3-bromophenyl)-2-(4-methylpiperazin-1-yl)-2-oxoethyl]-4-tert-butylcyclohexanol was prepared from (3-bromophenyl)(4-tert-butyl-1-hydroxycyclohexyl)acetic acid (Reference Example 1-ff) and N-methylpiperazine. MS (ESI) m/z 451/453 ([M+H]$^+$).

In an analogous manner to Example 1, step 2 1-[1-(3-bromophenyl)-2-(4-methylpiperazin-1-yl)ethyl]-4-tert-butylcyclohexanol dihydrochloride was prepared from 1-[1-(3-bromophenyl)-2-(4-methylpiperazin-1-yl)-2-oxoethyl]-4-tert-butylcyclohexanol. MS (ESI) m/z 437/439 ([M+H]$^+$); HRMS: calcd for $C_{23}H_{37}BrN_2O$.2.00 HCl, 508.1623; found (ESI), 437.2154.

Example 80

1-{1-(3,4-dichlorophenyl)-2-[(4-fluorobenzyl)amino]ethyl}cyclohexanol hydrochloride

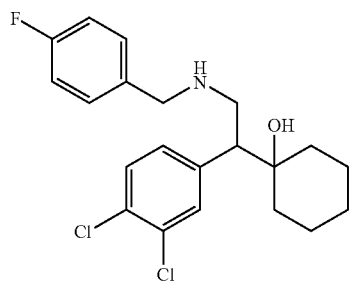

In an analogous manner to Example 1, step 1 2-(3,4-dichlorophenyl)-N-(4-fluorobenzyl)-2-(1-hydroxycyclohexyl)acetamide was prepared from 3,4-dichloro-alpha-(1-hydroxycyclohexyl)benzeneacetic acid (Reference Example 1-d) and 4-fluorobenzylamine. MS (ESI) m/z 410/412/414 ([M+H]$^+$).

In an analogous manner to Example 1, step 2 1-{1-(3,4-dichlorophenyl)-2-[(4-fluorobenzyl)amino]ethyl}cyclohexanol hydrochloride was prepared from 2-(3,4-dichlorophenyl)-N-(4-fluorobenzyl)-2-(1-hydroxycyclohexyl)acetamide. MS (ESI) m/z 396/398/400 ([M+H]$^+$); HRMS: calcd for $C_{21}H_{24}Cl_2FNO$.HCl, 431.0986; found (ESI), 396.1277.

Example 81

4-[1-(3-bromophenyl)-2-piperazin-1-ylethyl]heptan-4-ol dihydrochloride

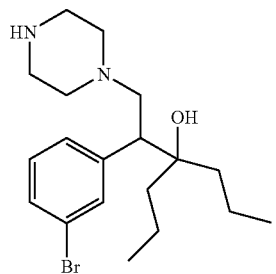

In an analogous manner to Example 1, step 1 tert-butyl 4-[2-(3-bromophenyl)-3-hydroxy-3-propylhexanoyl]piperazine-1-carboxylate was prepared from 2-(3-bromophenyl)-3-hydroxy-3-propylhexanoic acid (Reference Example 1-gg) and tert-butyl 1-piperazinecarboxylate. MS (ES) m/z 497.2 ([M+H]$^+$).

In an analogous manner to Example 1, step 2 4-[1-(3-bromophenyl)-2-piperazin-1-ylethyl]heptan-4-ol dihydrochloride was prepared from tert-butyl 4-[2-(3-bromophenyl)-3-hydroxy-3-propylhexanoyl]piperazine-1-carboxylate. MS (ES) m/z 383.2 ([M+H]$^+$); HRMS: calcd for $C_{19}H_{31}BrN_2O$.2.00 HCl, 454.1153; found (ESI), 383.1705.

Example 82

4-[1-(3-bromophenyl)-2-(4-methylpiperazin-1-yl)ethyl]heptan-4-ol dihydrochloride

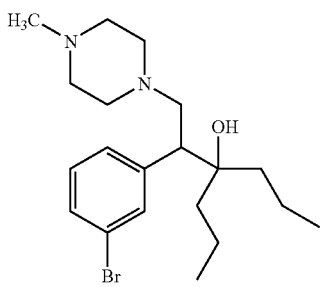

In an analogous manner to Example 24, 4-[1-(3-bromophenyl)-2-(4-methylpiperazin-1-yl)ethyl]heptan-4-ol dihydrochloride was prepared from 4-[1-(3-bromophenyl)-2-piperazin-1-ylethyl]heptan-4-ol (see Example 81). MS (ES) m/z 397.2 ([M+H]$^+$); HRMS: calcd for $C_{20}H_{33}BrN_2O$.2.00 HCl, 468.1310; found (ESI), 397.1865.

Example 83

1-[1-(3,4-dichlorophenyl)-2-morpholin-4-ylethyl]cyclobutanol hydrochloride

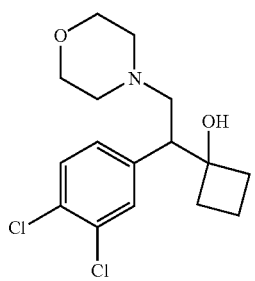

In an analogous manner to Example 1, step 1 1-[1-(3,4-dichlorophenyl)-2-morpholin-4-yl-2-oxoethyl]cyclobutanol was prepared from (3,4-dichlorophenyl)(1-hydroxycyclobutyl)acetic acid (Reference Example 1-p) and morpholine. HRMS: calcd for $C_{16}H_{19}Cl_2NO_3$, 343.0742; found (ESI_FT), 344.08102.

In an analogous manner to Example 1, step 2 1-[1-(3,4-dichlorophenyl)-2-morpholin-4-ylethyl]cyclobutanol hydrochloride was prepared from 1-[1-(3,4-dichlorophenyl)-2-morpholin-4-yl-2-oxoethyl]cyclobutanol. HRMS: calcd for $C_{16}H_{21}Cl_2NO_2$.HCl, 365.0716; found (ESI_FT), 330.10064.

Example 84

1-[1-(3-bromo-4-methoxyphenyl)-2-piperazin-1-ylethyl]-4-tert-butylcyclohexanol dihydrochloride

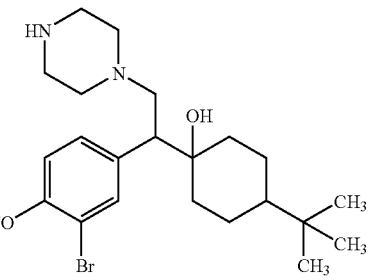

In an analogous manner to Example 1, step 1 tert-butyl 4-[(3-bromo-4-methoxyphenyl)(4-tert-butyl-1-hydroxycyclohexyl)acetyl]piperazine-1-carboxylate was prepared from (3-bromo-4-methoxyphenyl)(4-tert-butyl-1-hydroxycyclohexyl)acetic acid (Reference Example 1-bb) and tert-butyl 1-piperazinecarboxylate. MS (ESI) m/z 567/569 ([M+H]$^+$); HRMS: calcd for $C_{28}H_{43}BrN_2O_5$, 566.2355; found (ESI), 567.2435.

In an analogous manner to Example 1, step 2 1-[1-(3-bromo-4-methoxyphenyl)-2-piperazin-1-ylethyl]-4-tert-butylcyclohexanol dihydrochloride was prepared from tert-butyl 4-[(3-bromo-4-methoxyphenyl)(4-tert-butyl-1-hydroxycyclohexyl)acetyl]piperazine-1-carboxylate. MS (ESI) m/z 453/455 ([M+H]$^+$); HRMS: calcd for $C_{23}H_{37}BrN_2O_2$.2.00 HCl, 524.1572; found (ESI), 453.2119.

Example 85

1-[1-(3-chlorophenyl)-2-piperidin-1-ylethyl]cyclohexanol hydrochloride

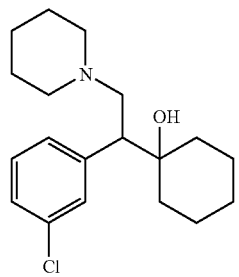

In an analogous manner to Example 1, step 1 1-[1-(3-chlorophenyl)-2-oxo-2-piperidin-1-ylethyl]cyclohexanol was prepared from (3-chlorophenyl)(1-hydroxycyclohexyl)acetic acid (Reference Example 1-a) and piperidine. HRMS: calcd for $C_{19}H_{26}ClNO_2$, 335.1652; found (ESI_FT), 336.17194.

In an analogous manner to Example 1, step 2 1-[1-(3-chlorophenyl)-2-piperidin-1-ylethyl]cyclohexanol hydrochloride was prepared from 1-[1-(3-chlorophenyl)-2-oxo-2-piperidin-1-ylethyl]cyclohexanol. HRMS: calcd for $C_{19}H_{28}ClNO$.HCl, 357.1626; found (ESI_FT), 322.19304.

Example 86

2-(3-chlorophenyl)-1,1-dicyclopropyl-3-(4-methylpiperazin-1-yl)propan-1-ol dihydrochloride

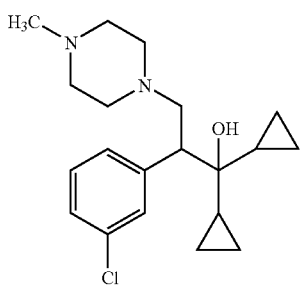

In an analogous manner to Example 1, step 1 tert-butyl 4-[2-(3-chlorophenyl)(3,3-dicyclopropyl-3-hydroxypropyl)acetyl]piperazine-1-carboxylate was prepared from 2-(3-chlorophenyl)-3,3-dicyclopropyl-3-hydroxypropanoic acid (Reference Example 1-hh) and N-methylpiperazine. MS (ESI) m/z 363 ([M+H]$^+$).

In an analogous manner to Example 1, step 2 2-(3-chlorophenyl)-1,1-dicyclopropyl-3-(4-methylpiperazin-1-yl)propan-1-ol dihydrochloride was prepared from tert-butyl 4-[2-(3-chlorophenyl) (3,3-dicyclopropyl-3-hydroxypropyl)acetyl]piperazine-1-carboxylate. MS (ESI) m/z 349.2037 ([M+H]$^+$); HRMS: calcd for $C_{20}H_{29}ClN_2O.2.00$ HCl, 420.1502; found (ESI), 349.2037.

Example 87

1-[1-(3-bromophenyl)-2-piperazin-1-ylethyl]-3,3,5,5-tetramethylcyclohexanol dihydrochloride

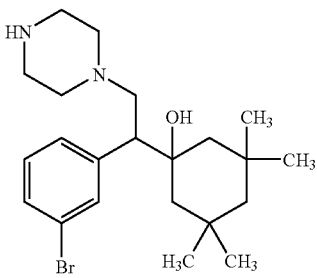

In an analogous manner to Example 1, step 1 tert-butyl 4-[(3-bromophenyl)(1-hydroxy-3,3,5,5-tetramethylcyclohexyl)acetyl]piperazine-1-carboxylate was prepared from (3-bromophenyl)(1-hydroxy-3,3,5,5-tetramethylcyclohexyl) acetic acid (Reference Example 1-ii) and tert-butyl 1-piperazinecarboxylate.

In an analogous manner to Example 1, step 2 1-[1-(3-bromophenyl)-2-piperazin-1-ylethyl]-3,3,5,5-tetramethylcyclohexanol dihydrochloride was prepared from tert-butyl 4-[(3-bromophenyl)(1-hydroxy-3,3,5,5-tetramethylcyclohexyl)acetyl]piperazine-1-carboxylate. MS (ES) m/z 423.2 ([M+H]$^+$); HRMS: calcd for $C_{22}H_{35}BrN_2O$, 422.1933; found (ESI), 423.2015.

Example 88

1-[1-(3-bromophenyl)-2-(4-methylpiperazin-1-yl)ethyl]-3,3,5,5-tetramethylcyclohexanol dihydrochloride

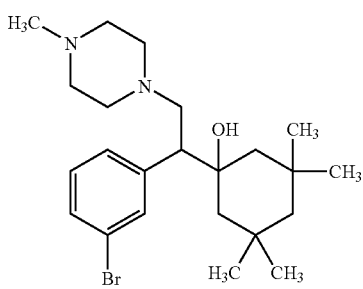

In an analogous manner to Example 24, 1-[1-(3-bromophenyl)-2-(4-methylpiperazin-1-yl)ethyl]-3,3,5,5-tetramethylcyclohexanol dihydrochloride was prepared from 1-[1-(3-bromophenyl)-2-piperazin-1-ylethyl]-3,3,5,5-tetramethylcyclohexanol (see Example 87). MS (ES) m/z 437.3 ([M+H]$^+$); HRMS: calcd for $C_{23}H_{37}BrN_2O.2.00$ HCl, 508.1623; found (ESI), 437.2162.

Example 89

3-ethyl-1-(4-methylpiperazin-1-yl)-2-(1-naphthyl)pentan-3-ol dihydrochloride

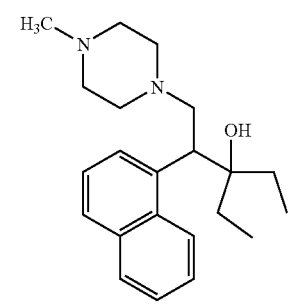

In an analogous manner to Example 24, 3-ethyl-1-(4-methylpiperazin-1-yl)-2-(1-naphthyl)pentan-3-ol dihydrochloride was prepared from 3-ethyl-2-(1-naphthyl)-1-piperazin-1-ylpentan-3-ol (see Example 53). MS (ESI) m/z 341 ([M+H]$^+$); HRMS: calcd for $C_{22}H_{32}N_2O.2.00$ HCl, 412.2048; found (ESI), 341.2583.

Example 90

1-(1-(3-bromophenyl)-2-{[4-(trifluoromethyl)benzyl]amino}ethyl)cyclohexanol hydrochloride

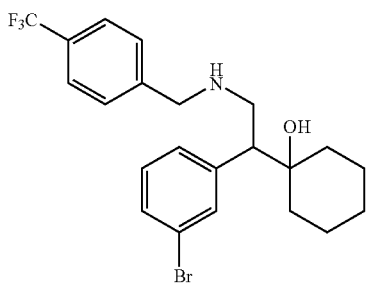

In an analogous manner to Example 1, step 1 2-(3-bromophenyl)-2-(1-hydroxycyclohexyl)-N-[4-(trifluoromethyl)benzyl]acetamide was prepared from (3-bromophenyl)(1-hydroxycyclohexyl)acetic acid (Reference Example 1-b) and 4-trifluoromethylbenzylamine. MS (ESI) m/z 470/472 ([M+H]$^+$).

In an analogous manner to Example 1, step 2 1-(1-(3-bromophenyl)-2-{[4-(trifluoromethyl)benzyl]amino}ethyl)cyclohexanol hydrochloride was prepared from 2-(3-bromophenyl)-2-(1-hydroxycyclohexyl)-N-[4-(trifluoromethyl)benzyl]acetamide. MS (ESI) m/z 456/458 ([M+H]$^+$); HRMS: calcd for $C_{22}H_{25}BrF_3NO·HCl$, 491.0838; found (ESI), 456.1147.

Example 91

4-ethyl-1-[1-(1-naphthyl)-2-piperazin-1-ylethyl]cyclohexanol dihydrochloride

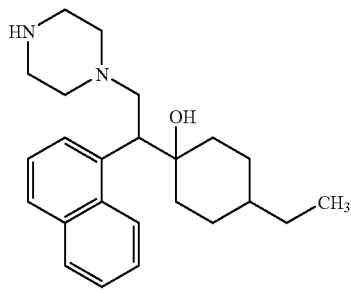

In an analogous manner to Example 1, step 1 tert-butyl 4-[1-(1-naphthyl)-(4-ethyl-1-hydroxycyclohexyl)acetyl]piperazine-1-carboxylate was prepared from (4-ethyl-1-hydroxycyclohexyl)-(1-naphthyl)acetic acid (Reference Example 1-jj) and tert-butyl 1-piperazinecarboxylate. MS (ESI) TT/z 481 ([M+H]$^+$);

In an analogous manner to Example 1, step 2 4-ethyl-1-[1-(1-naphthyl)-2-piperazin-1-ylethyl]cyclohexanol dihydrochloride was prepared from tert-butyl 4-[1-(1-naphthyl)-(4-ethyl-1-hydroxycyclohexyl)acetyl]piperazine-1-carboxylate. MS (ESI) m/z 367 ([M+H]$^+$); HRMS: calcd for $C_{24}H_{34}N_2O·2.00\ HCl$, 438.2205; found (ESI), 367.2749.

Example 92

1-{2-(4-methylpiperazin-1-yl)-1-[3-(trifluoromethoxy)phenyl]ethyl}cyclobutanol dihydrochloride

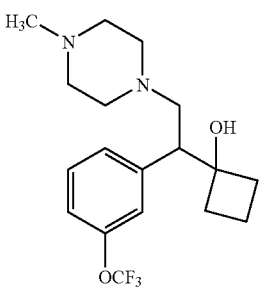

In an analogous manner to Example 24, 1-{2-(4-methylpiperazin-1-yl)-1-[3-(trifluoromethoxy)phenyl]ethyl}cyclobutanol dihydrochloride was prepared from 1-{2-piperazin-1-yl-1-[3-(trifluoromethoxy)phenyl]ethyl}cyclobutanol (see Example 46). HRMS: calcd for $C_{18}H_{25}F_3N_2O_2·2.00\ HCl$, 430.1402; found (ESI), 359.1965.

Example 93

4-tert-butyl-1-[1-(3-chlorophenyl)-2-piperazin-1-ylethyl]cyclohexanol dihydrochloride

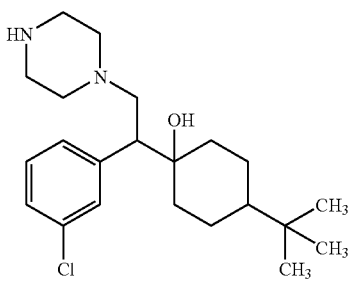

In an analogous manner to Example 1, step 1 tert-butyl 4-[(4-tert-butyl-1-hydroxycyclohexyl)(3-chlorophenyl)acetyl]piperazine-1-carboxylate was prepared from (3-chlorophenyl)(4-tert-butyl-1-hydroxycyclohexyl)acetic acid (Reference Example 1-kk) and tert-butyl 1-piperazinecarboxylate. MS (ES) m/z 493.4 ([M+H]$^+$).

In an analogous manner to Example 1, step 2 4-tert-butyl-1-[1-(3-chlorophenyl)-2-piperazin-1-ylethyl]cyclohexanol dihydrochloride was prepared from tert-butyl 4-[(4-tert-butyl-1-hydroxycyclohexyl)(3-chlorophenyl)acetyl]piperazine-1-carboxylate. MS (ESI) m/z 379 ([M+H]$^+$); HRMS: calcd for $C_{22}H_{35}ClN_2O$, 378.2438; found (ESI), 379.2513.

Example 94

2-(3-chlorophenyl)-3-ethyl-1-(4-methylpiperazin-1-yl)pentan-3-ol dihydrochloride

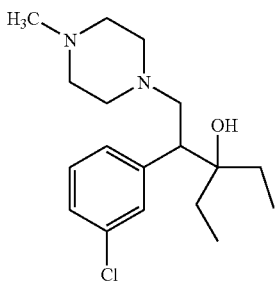

In an analogous manner to Example 24, 2-(3-chlorophenyl)-3-ethyl-1-(4-methylpiperazin-1-yl)pentan-3-ol dihydrochloride was prepared from 2-(3-chlorophenyl)-3-ethyl-1-piperazin-1-ylpentan-3-ol (see Example 52). (ESI) m/z 325/327 ([M+H]$^+$); HRMS: calcd for $C_{18}H_{29}ClN_2O.2.00$ HCl, 396.1502; found (ESI), 325.2032.

Example 95

1-[1-(3-bromophenyl)-2-morpholin-4-ylethyl]cyclobutanol hydrochloride

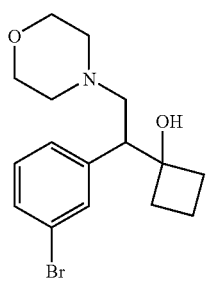

In an analogous manner to Example 1, step 1 1-[1-(3-bromophenyl)-2-morpholin-4-yl-2-oxoethyl]cyclobutanol was prepared from (3-bromophenyl)(1-hydroxycyclobutyl)acetic acid (Reference Example 1-j) and morpholine. HRMS: calcd for $C_{16}H_{20}BrNO_3$, 353.0627; found (ESI_FT), 354.06919.

In an analogous manner to Example 1, step 2 1-[1-(3-bromophenyl)-2-morpholin-4-ylethyl]cyclobutanol hydrochloride was prepared from tert-butyl 4-[(4-tert-butyl-1-hydroxycyclohexyl)(3-chlorophenyl)acetyl]piperazine-1-carboxylate. HRMS: calcd for $C_{16}H_{22}BrNO_2.HCl$, 375.0601; found (ESI_FT), 340.08898.

Example 96

1-[1-(3-bromophenyl)-2-piperazin-1-ylethyl]-4-tert-butylcyclohexanol dihydrochloride

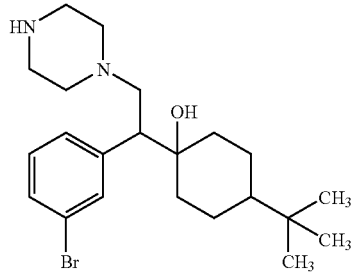

In an analogous manner to Example 1, step 1 tert-butyl 4-[(3-bromophenyl)(4-tert-butyl-1-hydroxycyclohexyl)acetyl]piperazine-1-carboxylate was prepared from (3-bromophenyl)(4-tert-butyl-1-hydroxycyclohexyl)acetic acid (Reference Example 1-ff) and tert-butyl 1-piperazinecarboxylate. MS (ESI) m/z 537/539 ([M+H]$^+$); HRMS: calcd for $C_{27}H_{41}BrN_2O_4$, 536.2250; found (ESI), 537.2324.

In an analogous manner to Example 1, step 2 1-[1-(3-bromophenyl)-2-piperazin-1-ylethyl]-4-tert-butylcyclohexanol dihydrochloride was prepared from tert-butyl 4-[(3-bromophenyl)(4-tert-butyl-1-hydroxycyclohexyl)acetyl]piperazine-1-carboxylate. MS (ESI) m/z 423/425 ([M+H]$^+$); HRMS: calcd for $C_{22}H_{35}BrN_2O.2.00$ HCl, 494.1466; found (ESI), 423.1994.

Example 97

4-methyl-1-[1-(1-naphthyl)-2-piperazin-1-ylethyl]cyclohexanol dihydrochloride

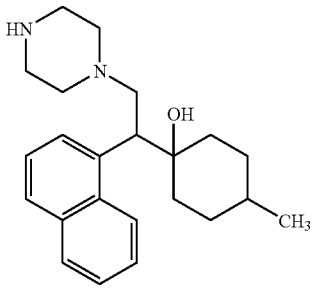

In an analogous manner to Example 1, step 1 tert-butyl 4-[1-(1-naphthyl)-(4-methyl-1-hydroxycyclohexyl)acetyl]piperazine-1-carboxylate was prepared from (4-methyl-1-hydroxycyclohexyl)-(1-naphthyl)acetic acid (Reference Example 1-ll) and tert-butyl 1-piperazinecarboxylate. MS (ESI) m/z 467 ([M+H]$^+$).

In an analogous manner to Example 1, step 2 4-methyl-1-[1-(1-naphthyl)-2-piperazin-1-ylethyl]cyclohexanol dihydrochloride was prepared from tert-butyl 4-[1-(1-naphthyl)-(4-methyl-1-hydroxycyclohexyl)acetyl]piperazine-1-carboxylate. MS (ESI) m/z 353 ([M+H]$^+$); HRMS: calcd for $C_{23}H_{32}N_2O.2.00$ HCl, 424.2048; found (ESI), 353.2599.

Example 98

1-{1-(3-bromophenyl)-2-[(4-fluorobenzyl)amino]ethyl}cyclohexanol hydrochloride

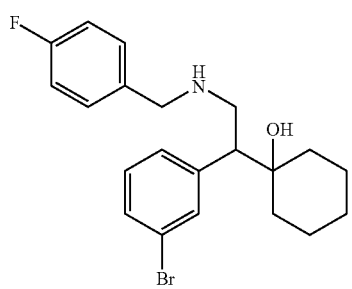

In an analogous manner to Example 1, step 1 2-(3-bromophenyl)-N-(4-fluorobenzyl)-2-(1-hydroxycyclohexyl)acetamide was prepared from (3-bromophenyl)(1-hydroxycyclohexyl)acetic acid (Reference Example 1-b) and 4-fluorobenzylamine. MS (ESI) m/z 420/422 ([M+H]$^+$).

In an analogous manner to Example 1, step 2 1-{1-(3-bromophenyl)-2-[(4-fluorobenzyl)amino]ethyl}cyclohexanol hydrochloride was prepared from 2-(3-bromophenyl)-N-(4-fluorobenzyl)-2-(1-hydroxycyclohexyl)acetamide. MS (ESI) m/z 406 ([M+H]$^+$); MS (ESI) m/z 408 ([M−H]$^-$); HRMS: calcd for $C_{21}H_{25}BrFNO \cdot HCl$, 441.0870; found (ESI), 406.1173.

Example 99

1-[1-(3-bromophenyl)-2-morpholin-4-ylethyl]cyclohexanol hydrochloride

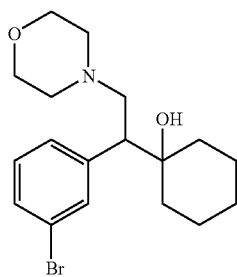

In an analogous manner to Example 1, step 1 1-[1-(3-bromophenyl)-2-morpholin-4-yl-2-oxoethyl]cyclohexanol was prepared from (3-bromophenyl)(1-hydroxycyclohexyl)acetic acid (Reference Example 1-b) and morpholine. HRMS: calcd for $C_{18}H_{24}BrNO_3$, 381.0940; found (ESI_FT), 382.10032.

In an analogous manner to Example 1, step 2 1-[1-(3-bromophenyl)-2-morpholin-4-ylethyl]cyclohexanol hydrochloride was prepared from 1-[1-(3-bromophenyl)-2-morpholin-4-yl-2-oxoethyl]cyclohexanol. HRMS: calcd for $C_{18}H_{26}BrNO_2 \cdot HCl$, 403.0914; found (ESI_FT), 368.12137.

Example 100

4-tert-butyl-1-[2-(4-methylpiperazin-1-yl)-1-(1-naphthyl)ethyl]cyclohexanol dihydrochloride

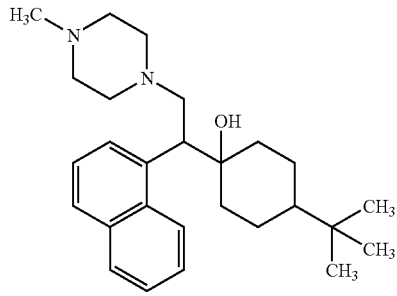

In an analogous manner to Example 24, 4-tert-butyl-1-[2-(4-methylpiperazin-1-yl)-1-(1-naphthyl)ethyl]cyclohexanol dihydrochloride was prepared from 4-tert-butyl-1-[1-(1-naphthyl)-2-piperazin-1-ylethyl]cyclohexanol (see Example 76). MS (ESI) m/z 409 ([M+H]$^+$); HRMS: calcd for $C_{27}H_{40}N_2O \cdot 2.00$ HCl, 480.2674; found (ESI), 409.3207.

Example 101

4-tert-butyl-1-[1-(3-chlorophenyl)-2-(4-methylpiperazin-1-yl)ethyl]cyclohexanol dihydrochloride

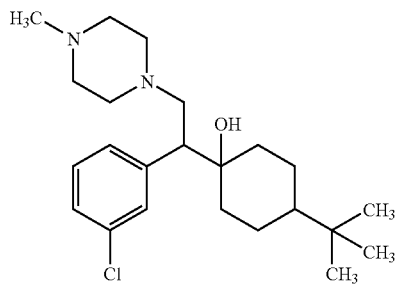

In an analogous manner to Example 24, 4-tert-butyl-1-[1-(3-chlorophenyl)-2-(4-methylpiperazin-1-yl)ethyl]cyclohexanol dihydrochloride was prepared from 4-tert-butyl-1-[1-(3-chlorophenyl)-2-piperazin-1-ylethyl]cyclohexanol (see Example 93). MS (ESI) m/z 393 ([M+H]$^+$); HRMS: calcd for $C_{23}H_{37}ClN_2O \cdot 2.00$ HCl, 464.2128; found (ESI), 393.2673.

Example 102

1-methyl-4-[2-morpholin-4-yl-1-(2-naphthyl)ethyl]piperidin-4-ol hydrochloride

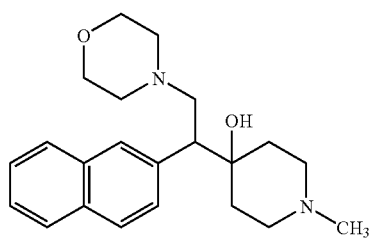

In an analogous manner to Example 1, step 1 1-methyl-4-[2-morpholin-4-yl-1-(2-naphthyl)-2-oxoethyl]piperidin-4-ol was prepared from (4-hydroxy-1-methylpiperidin-4-yl)(2-naphthyl)acetic acid (Reference Example 1-x) and morpholine HRMS: calcd for $C_{22}H_{28}N_2O_3$, 368.2100; found (ES-I_FT), 369.21652.

In an analogous manner to Example 1, step 2 1-methyl-4-[2-morpholin-4-yl-1-(2-naphthyl)ethyl]piperidin-4-ol hydrochloride was prepared from 1-methyl-4-[2-morpholin-4-yl-1-(2-naphthyl)-2-oxoethyl]piperidin-4-ol. HRMS: calcd for $C_{22}H_{30}N_2O_2 \cdot 2.00$ HCl, 426.1841; found (ESI_FT), 355.23761.

Example 103

4-[1-(3-bromophenyl)-2-piperazin-1-ylethyl]tetrahydro-2H-pyran-4-ol dihydrochloride

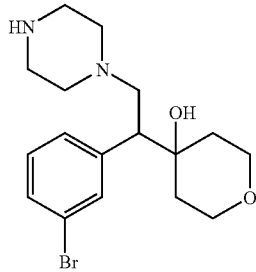

In an analogous manner to Example 1, step 1 tert-butyl 4-[(3-bromophenyl)(4-hydroxytetrahydro-2H-pyran-4-yl)acetyl]piperazine-1-carboxylate was prepared from (3-bromophenyl)(4-hydroxytetrahydro-2H-pyran-4-yl)acetic acid (Reference Example 1-mm) and tert-butyl 1-piperazinecarboxylate. MS (ESI) m/z 483/485 ([M+H]$^+$); HRMS: calcd for $C_{22}H_{31}BrN_2O_5$, 482.1416; found (ESI), 483.1508.

In an analogous manner to Example 1, step 2 4-[1-(3-bromophenyl)-2-piperazin-1-ylethyl]tetrahydro-2H-pyran-4-ol dihydrochloride was prepared from tert-butyl 4-[(3-bromophenyl)(4-hydroxytetrahydro-2H-pyran-4-yl)acetyl]piperazine-1-carboxylate. MS (ESI) m/z 369/371 ([M+H]$^+$); HRMS: calcd for $C_{17}H_{25}BrN_2O_2 \cdot 2.00$ HCl, 440.0633; found (ESI), 369.1166.

Example 104

1-{1-[3-(benzyloxy)phenyl]-2-piperazin-1-ylethyl}cyclohexanol dihydrochloride

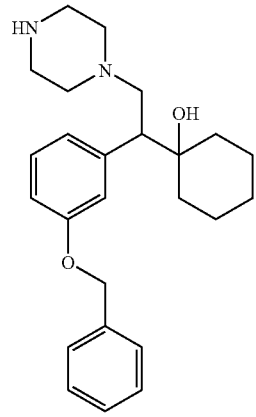

In an analogous manner to Example 1, step 1 tert-butyl 4-[[3-(benzyloxy)phenyl](1-hydroxycyclohexyl)acetyl]piperazine-1-carboxylate was prepared from (3-benzyloxyphenyl)(4-hydroxycyclohexyl)acetic acid (Reference Example 1-nn) and tert-butyl 1-piperazinecarboxylate. MS (ESI) m/z 509 ([M+H]$^+$); HRMS: calcd for $C_{30}H_{40}N_2O_5$, 508.2937; found (ESI), 509.2997.

In an analogous manner to Example 1, step 2 1-{1-[3-(benzyloxy)phenyl]-2-piperazin-1-ylethyl}cyclohexanol dihydrochloride was prepared from tert-butyl 4-[[3-(benzyloxy)phenyl](1-hydroxycyclohexyl)acetyl]piperazine-1-carboxylate. HRMS: calcd for $C_{25}H_{34}N_2O_2 \cdot 2.00$ HCl, 466.2154; found (ESI), 395.2676.

Example 105

1-(1-(3-chlorophenyl)-2-{[4-(trifluoromethyl)benzyl]amino}ethyl)cyclohexanol hydrochloride

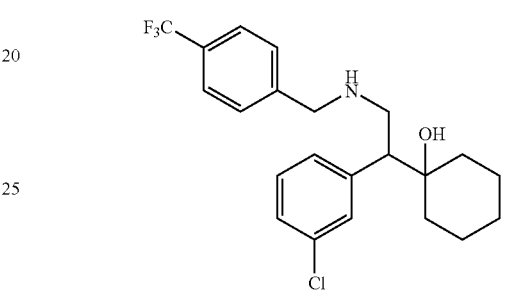

In an analogous manner to Example 1, step 1 2-(3-chlorophenyl)-2-(1-hydroxycyclohexyl)-N-[4-(trifluoromethyl)benzyl]acetamide was prepared from (3-chlorophenyl)(1-hydroxycyclohexyl)acetic acid (Reference Example 1-a) and 4-trifluoromethylbenzylamine. MS (ESI) m/z 426/428 ([M+H]$^+$).

In an analogous manner to Example 1, step 2 1-(1-(3-chlorophenyl)-2-{[4-(trifluoromethyl)benzyl]amino}ethyl)cyclohexanol hydrochloride was prepared from 2-(3-chlorophenyl)-2-(1-hydroxycyclohexyl)-N-[4-(trifluoromethyl)benzyl]acetamide. MS (ESI) m/z [M+H]+ (412/414).

Example 106

1-[2-morpholin-4-yl-1-(2-naphthyl)ethyl]cyclohexanol hydrochloride

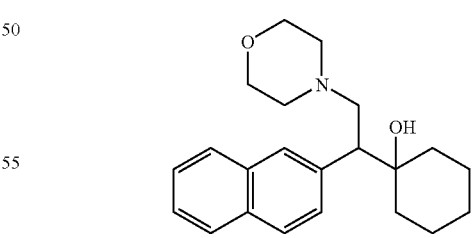

In an analogous manner to Example 1, step 1 1-[2-morpholin-4-yl-1-(2-naphthyl)-2-oxoethyl]cyclohexanol was prepared from (1-hydroxycyclohexyl)(2-naphthyl)acetic acid (Reference Example 1-q) and morpholine. HRMS: calcd for $C_{22}H_{27}NO_3$, 353.1991; found (ESI_FT), 354.20523.

In an analogous manner to Example 1, step 2 1-[2-morpholin-4-yl-1-(2-naphthyl)ethyl]cyclohexanol hydrochloride was prepared from 1-[2-morpholin-4-yl-1-(2-naphthyl)-2-

Example 107

2-[1-(3-bromophenyl)-2-piperazin-1-ylethyl]adamantan-2-ol dihydrochloride

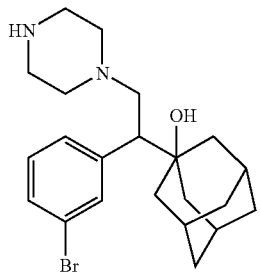

In an analogous manner to Example 1, step 1 tert-butyl 4-[(3-bromophenyl)(2-hydroxy-2-adamantyl)acetyl]piperazine-1-carboxylate was prepared from (3-bromophenyl)(2-hydroxy-2-adamantyl)acetic acid (Reference Example 1-oo) and tert-butyl 1-piperazinecarboxylate. MS (ESI) m/z 533/535 ([M+H]$^+$).

In an analogous manner to Example 1, step 2 2-[1-(3-bromophenyl)-2-piperazin-1-ylethyl]adamantan-2-ol dihydrochloride was prepared from tert-butyl 4-[(3-bromophenyl)(2-hydroxy-2-adamantyl)acetyl]piperazine-1-carboxylate. MS (ESI) m/z 419/421 ([M+H]$^+$); HRMS: calcd for $C_{22}H_{31}BrN_2O$.2.00 HCl, 490.1153; found (ESI), 419.1682.

Example 108

1-[1-[3-(benzyloxy)phenyl]-2-(4-methylpiperazin-1-yl)ethyl]cyclohexanol dihydrochloride

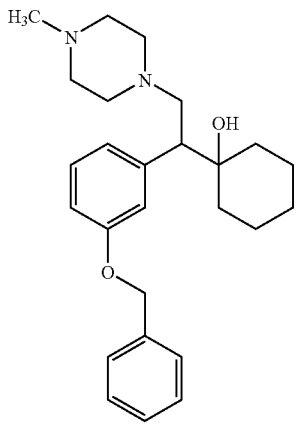

In an analogous manner to Example 24, 1-[1-[3-(benzyloxy)phenyl]-2-(4-methylpiperazin-1-yl)ethyl]cyclohexanol dihydrochloride was prepared from 1-{1-[3-(benzyloxy)phenyl]-2-piperazin-1-ylethyl}cyclohexanol (see Example 104). HRMS: calcd for $C_{26}H_{36}N_2O_2$.2.00 HCl, 480.2310; found (ESI), 409.2838.

Example 109

1-[2-morpholin-4-yl-1-(2-naphthyl)ethyl]cyclobutanol hydrochloride

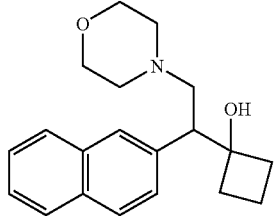

In an analogous manner to Example 1, step 1 1-[2-morpholin-4-yl-1-(2-naphthyl)-2-oxoethyl]cyclobutanol was prepared from (1-hydroxycyclobutyl)(2-naphthyl)acetic acid (Reference Example 1-c) and morpholine. HRMS: calcd for $C_{20}H_{23}NO_3$, 325.1678; found (ESI_FT), 326.17435.

In an analogous manner to Example 1, step 2 1-[2-morpholin-4-yl-1-(2-naphthyl)ethyl]cyclobutanol hydrochloride was prepared from 1-[2-morpholin-4-yl-1-(2-naphthyl)-2-oxoethyl]cyclobutanol. HRMS: calcd for $C_{20}H_{25}NO_2$.HCl, 347.1652; found (ESI_FT), 312.19602.

Example 110

4-[1-(3-bromo-4-methoxyphenyl)-2-piperazin-1-ylethyl]tetrahydro-2H-pyran-4-ol dihydrochloride

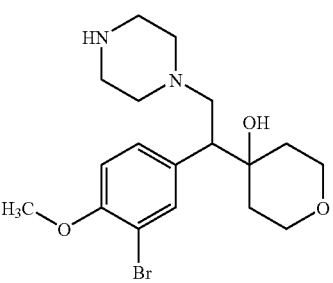

In an analogous manner to Example 1, step 1 tert-butyl 4-[(3-bromo-4-methoxyphenyl)(4-hydroxytetrahydro-2H-pyran-4-yl)acetyl]piperazine-1-carboxylate was prepared from (3-bromo-4-methoxyphenyl)(4-hydroxytetrahydro-2H-pyran-4-yl)acetic acid (Reference Example 1-pp) and tert-butyl 1-piperazinecarboxylate. MS (ESI) m/z 513/515 ([M+H]$^+$); HRMS: calcd for $C_{23}H_{33}BrN_2O_6$, 512.1522; found (ESI), 513.16.

In an analogous manner to Example 1, step 2 4-[1-(3-bromo-4-methoxyphenyl)-2-piperazin-1-ylethyl]tetrahydro-2H-pyran-4-ol dihydrochloride was prepared from tert-butyl 4-[(3-bromo-4-methoxyphenyl)(4-hydroxytetrahydro-2H-pyran-4-yl)acetyl]piperazine-1-carboxylate. MS (ESI) m/z 399/401 ([M+H]+); HRMS: calcd for C18H27BrN2O3.2.00 HCl, 470.0739; found (ESI), 399.1266.

Example 111

1-{1-[3-(benzyloxy)phenyl]-2-piperazin-1-ylethyl}cyclobutanol dihydrochloride

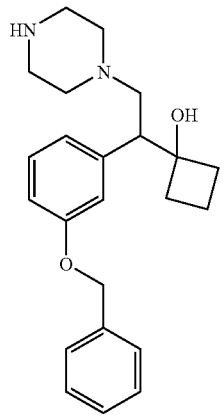

In an analogous manner to Example 1, step 1 tert-butyl 4-[[3-(benzyloxy)phenyl](1-hydroxycyclobutyl)acetyl]piperazine-1-carboxylate was prepared from (3-benzyloxyphenyl)(1-hydroxycyclohexyl)acetic acid (Reference Example 1-qq) and tert-butyl 1-piperazinecarboxylate. MS (ESI) m/z 481 ([M+H]+); HRMS: calcd for C28H36N2O5, 480.2624; found (ESI), 481.272.

In an analogous manner to Example 1, step 2 1-{1-[3-(benzyloxy)phenyl]-2-piperazin-1-ylethyl}cyclobutanol dihydrochloride was prepared from tert-butyl 4-[[3-(benzyloxy)phenyl](1-hydroxycyclobutyl)acetyl]piperazine-1-carboxylate. HRMS: calcd for C23H30N2O2.2.00 HCl, 438.1841; found (ESI), 367.2357.

Example 112

1-[1-(3,4-dichlorophenyl)-2-morpholin-4-ylethyl]cyclohexanol hydrochloride

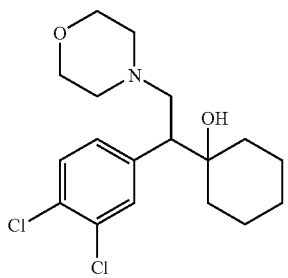

In an analogous manner to Example 1, step 1 1-[1-(3,4-dichlorophenyl)-2-morpholin-4-yl-2-oxoethyl]cyclohexanol was prepared from 3,4-dichloro-alpha-(1-hydroxycyclohexyl)benzeneacetic acid (Reference Example 1-d) and morpholine. HRMS: calcd for C18H23Cl2NO3, 371.1055; found (ESI_FT), 372.11122.

In an analogous manner to Example 1, step 2 1-[1-(3,4-dichlorophenyl)-2-morpholin-4-ylethyl]cyclohexanol hydrochloride was prepared from 1-[1-(3,4-dichlorophenyl)-2-morpholin-4-yl-2-oxoethyl]cyclohexanol. HRMS: calcd for C18H25Cl2NO2HCl, 393.1029; found (ESI_FT), 358.13358.

Example 113

1-[2-[(4-fluorobenzyl)amino]-1-(2-naphthyl)ethyl]cyclohexanol hydrochloride

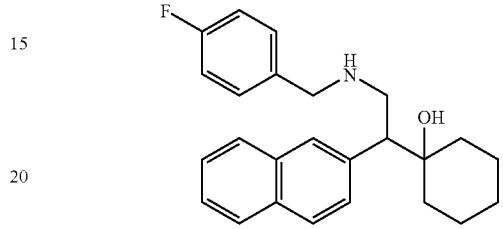

In an analogous manner to Example 1, step 1 N-(4-fluorobenzyl)-2-(1-hydroxycyclohexyl)-2-(2-naphthyl)acetamide was prepared from (1-hydroxycyclobutyl)(2-naphthyl)acetic acid (Reference Example 1-c) and 4-fluorolbenzylamine. MS (ESI) m/z 372 ([M+H–H2O]+).

In an analogous manner to Example 1, step 2 1-[2-[(4-fluorobenzyl)amino]-1-(2-naphthyl)ethyl]cyclohexanol hydrochloride was prepared from N-(4-fluorobenzyl)-2-(1-hydroxycyclohexyl)-2-(2-naphthyl)acetamide. MS m/z 378 ([M+H]+); HRMS: calcd for C25H28FNO.HCl, 413.1922; found (ESI), 378.2234.

Example 114

4-[1-(3,4-dichlorophenyl)-2-morpholin-4-ylethyl]-1-methylpiperidin-4-ol dihydrochloride

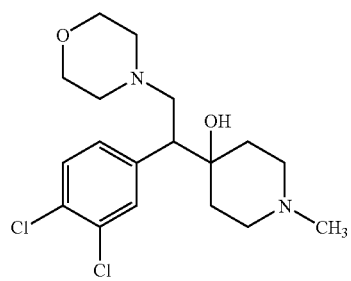

In an analogous manner to Example 1, step 1 4-[1-(3,4-dichlorophenyl)-2-morpholin-4-yl-2-oxoethyl]-1-methylpiperidin-4-ol was prepared from (3,4-dichlorophenyl)(4-hydroxy-1-methylpiperidin-4-yl)acetic acid (Reference Example 1-i) and morpholine. HRMS: calcd for C18H24Cl2N2O3, 386.1164; found (ESI_FT), 387.12304.

In an analogous manner to Example 1, step 2 4-[1-(3,4-dichlorophenyl)-2-morpholin-4-ylethyl]-1-methylpiperidin-4-ol dihydrochloride was prepared from 4-[1-(3,4-dichlorophenyl)-2-morpholin-4-yl-2-oxoethyl]-1- methylpiperidin-4-ol. HRMS: calcd for C$_{18}$H$_{26}$Cl$_2$N$_2$O$_2$.2.00 HCl, 444.0905; found (ESI_FT), 373.14421.

Example 115

1-[1-[3-(benzyloxy)phenyl]-2-(4-methylpiperazin-1-yl)ethyl]cyclobutanol dihydrochloride

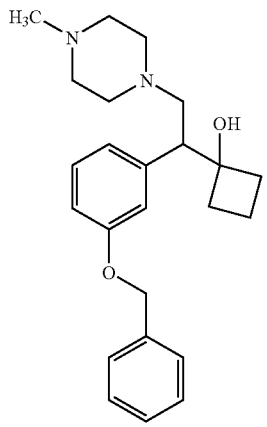

In an analogous manner to Example 24, 1-[1-[3-(benzyloxy)phenyl]-2-(4-methylpiperazin-1-yl)ethyl]cyclobutanol dihydrochloride was prepared from 1-{1-[3-(benzyloxy)phenyl]-2-piperazin-1-ylethyl}cyclobutanol (see Example 111). HRMS: calcd for C$_{24}$H$_{32}$N$_2$O$_2$.2.00 HCl, 452.1997; found (ESI), 381.2524.

Example 116

4-[1-(3-bromophenyl)-2-morpholin-4-ylethyl]-1-methylpiperidin-4-ol dihydrochloride

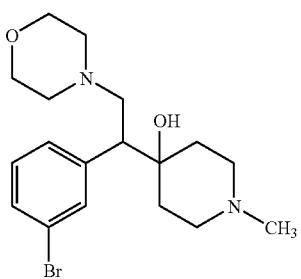

In an analogous manner to Example 1, step 1 4-[1-(3-bromophenyl)-2-morpholin-4-yl-2-oxoethyl]-1-methylpiperidin-4-ol was prepared from (3-bromophenyl)(4-hydroxy-1-methylpiperidin-4-yl)acetic acid (Reference Example 1-r) and morpholine. HRMS: calcd for C$_{18}$H$_{25}$BrN$_2$O$_3$, 396.1049; found (ESI_FT), 397.11148.

In an analogous manner to Example 1, step 2 4-[1-(3-bromophenyl)-2-morpholin-4-ylethyl]-1-methylpiperidin-4-ol dihydrochloride was prepared from 4-[1-(3-bromophenyl)-2-morpholin-4-yl-2-oxoethyl]-1-methylpiperidin-4-ol. HRMS: calcd for C$_{18}$H$_{27}$BrN$_2$O$_2$.HCl, 418.1023; found (ESI_FT), 383.13261.

Example 117

1-(1-(3-chlorophenyl)-2-{4-[(6-methoxy-2-naphthyl)methyl]piperazin-1-yl}ethyl)cyclohexanol dihydrochloride

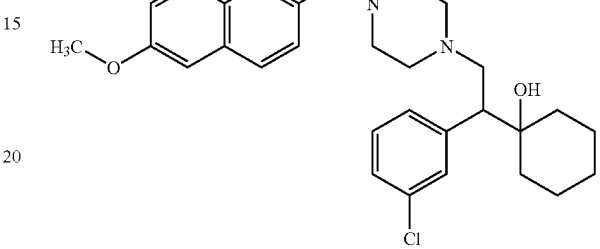

A solution of 1-[1-(3-chlorophenyl)-2-piperazin-1-ylethyl]cyclohexanol (see Example 1) (200 mg, 0.62 mmol) and 6-methoxy-2-napthaldehyde (173 mg, 0.93 mmol) in dichloroethane (4 mL) was treated with sodium trisacetoxyborohydride (195 mg, 0.92 mmol). The reaction was placed on a shaker and where it was stirred for 16 h. The reaction was then washed with a 2 N aqueous solution of hydrochloric acid (2×2 mL), and the organic layer was stored at 25° C. for 16 h. The resulting precipitate was collected, washed with diethyl ether and dried in vacuo to yield 194 mg (64%) 1-(1-(3-chlorophenyl)-2-{4-[(6-methoxy-2-naphthyl)methyl]-piperazin-1-yl}ethyl)cyclohexanol dihydrochloride as a white solid. MS (ESI) m/z 493/495 ([M+H]$^+$); HRMS: calcd for C$_{30}$H$_{37}$ClN$_2$O$_2$.2.00 HCl, 564.2077; found (ESI_FT), 493.2632.

Example 118

1-{1-(3-chlorophenyl)-2-[4-(cyclopropylmethyl)piperazin-1-yl]ethyl}cyclohexanol dihydrochloride

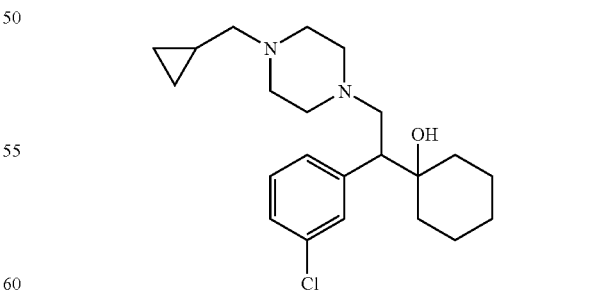

In an analogous manner to Example 117, 1-{1-(3-chlorophenyl)-2-[4-(cyclopropylmethyl)piperazin-1-yl]ethyl}cyclohexanol dihydrochloride was prepared from 1-[1-(3-chlorophenyl)-2-piperazin-1-ylethyl]cyclohexanol (see Example 1) and cyclopropanecarboxaldehyde. MS (ESI) m/z

[M+H]+ (377/379); HRMS: calcd for $C_{22}H_{33}ClN_2O \cdot 2.00$ HCl, 448.1815; found (ESI), 377.2347.

Example 119

1-{1-(3-chlorophenyl)-2-[4-(cyclohex-3-en-1-ylmethyl)piperazin-1-yl]ethyl}cyclohexanol dihydrochloride

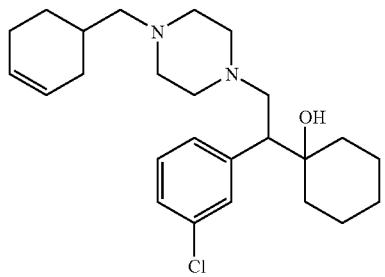

In an analogous manner to Example 117, 1-{1-(3-chlorophenyl)-2-[4-(cyclohex-3-en-1-ylmethyl)piperazin-1-yl]ethyl}cyclohexanol dihydrochloride was prepared from 1-[1-(3-chlorophenyl)-2-piperazin-1-ylethyl]cyclohexanol (see Example 1) and 3-cyclohexene-1-carboxaldehyde. MS (ESI) m/z [M+H]+ (417/419); HRMS: calcd for $C_{25}H_{37}ClN_2O \cdot 2.00$ HCl, 488.2128; found (ESI), 417.2655.

Example 120

6-({4-[2-(3-chlorophenyl)-2-(1-hydroxycyclohexyl)ethyl]piperazin-1-yl}methyl)tetrahydro-2H-pyran-2-ol dihydrochloride

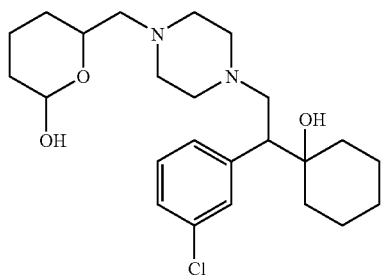

In an analogous manner to Example 117, 6-({4-[2-(3-chlorophenyl)-2-(1-hydroxycyclohexyl)ethyl]piperazin-1-yl}methyl)tetrahydro-2H-pyran-2-ol dihydrochloride was prepared from 1-[1-(3-chlorophenyl)-2-piperazin-1-ylethyl]cyclohexanol (see Example 1) and 3,4-dihydro-2H-pyran-2-carboxaldehyde. HRMS: calcd for $C_{24}H_{37}ClN_2O_3 \cdot 2.00$ HCl, 508.2026; found (ESI), 419.2455.

Example 121

1-{1-(3-chlorophenyl)-2-[4-(3-phenylbutyl)piperazin-1-yl]ethyl}cyclohexanol dihydrochloride

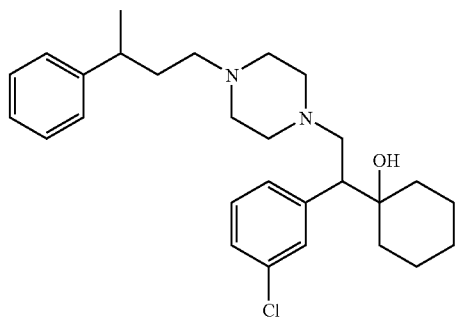

In an analogous manner to Example 117, 1-{1-(3-chlorophenyl)-2-[4-(3-phenylbutyl)piperazin-1-yl]ethyl}cyclohexanol dihydrochloride was prepared from 1-[1-(3-chlorophenyl)-2-piperazin-1-ylethyl]cyclohexanol (see Example 1) and 3-phenylbutyraldehyde. MS (ESI) m/z 455/457 ([M+H]+); HRMS: calcd for $C_{28}H_{39}ClN_2O \cdot 2.00$ HCl, 526.2284; found (ESI_FT), 455.28235.

Example 122

1-{1-(3-chlorophenyl)-2-[4-(2-phenylethyl)piperazin-1-yl]ethyl}cyclohexanol dihydrochloride

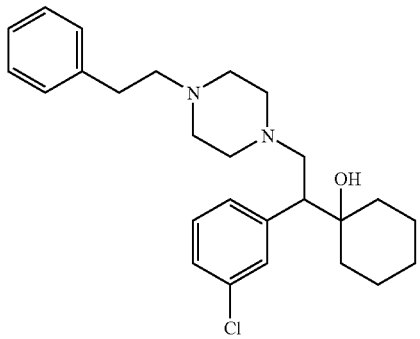

In an analogous manner to Example 117, 1-{1-(3-chlorophenyl)-2-[4-(2-phenylethyl)piperazin-1-yl]ethyl}cyclohexanol dihydrochloride was prepared from 1-[1-(3-chlorophenyl)-2-piperazin-1-ylethyl]cyclohexanol (see Example 1) and phenylacetaldehyde. MS (ESI) m/z 427/429 ([M+H]+); HRMS: calcd for $C_{26}H_{35}ClN_2O \cdot 2.00$ HCl, 498.1971; found (ESI), 427.2505.

Example 123

1-{1-(3-chlorophenyl)-2-[4-(3-phenoxybenzyl)piper-azin-1-yl]ethyl}cyclohexanol dihydrochloride

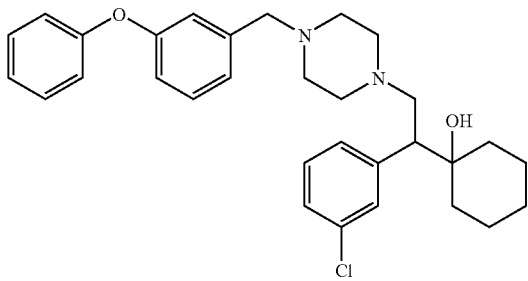

In an analogous manner to Example 117, 1-{1-(3-chlorophenyl)-2-[4-(3-phenoxybenzyl)piperazin-1-yl]-ethyl}cyclohexanol dihydrochloride was prepared from 1-[1-(3-chlorophenyl)-2-piperazin-1-ylethyl]cyclohexanol (see Example 1) and 3-phenoxybenzaldehyde. MS (ESI) m/z 505/507 ([M+H]$^+$); HRMS: calcd for $C_{31}H_{37}ClN_2O_2$.2.00 HCl, 576.2077; found (ESI_FT), 505.26266.

Example 124

1-{1-(3-chlorophenyl)-2-[4-(2-naphthylmethyl)piper-azin-1-yl]ethyl}cyclohexanol dihydrochloride

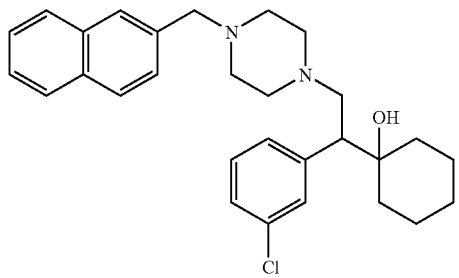

In an analogous manner to Example 117, 1-{1-(3-chlorophenyl)-2-[4-(2-naphthylmethyl)piperazin-1-yl]ethyl}cyclohexanol dihydrochloride was prepared from 1-[1-(3-chlorophenyl)-2-piperazin-1-ylethyl]cyclohexanol (see Example 1) and 2-napthaldehyde. MS (ESI) m/z 463/465 ([M+H]$^+$); HRMS: calcd for $C_{29}H_{35}ClN_2O$.2.00 HCl, 534.1971; found (ESI), 463.2499.

Example 125

1-{1-(3-chlorophenyl)-2-[4-(3-furylmethyl)piper-azin-1-yl]ethyl}cyclohexanol dihydrochloride

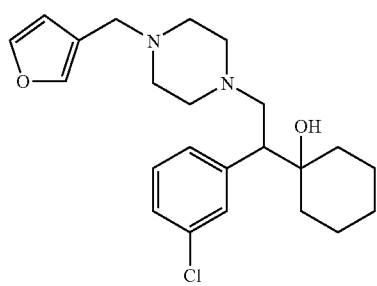

In an analogous manner to Example 117, 1-{1-(3-chlorophenyl)-2-[4-(3-furylmethyl)piperazin-1-yl]ethyl}cyclohexanol dihydrochloride was prepared from 1-[1-(3-chlorophenyl)-2-piperazin-1-ylethyl]cyclohexanol (see Example 1) and 3-furaldehyde. MS (ESI) m/z[M+H]+ (403/405); HRMS: calcd for $C_{23}H_{31}ClN_2O_2$.2.00 HCl, 474.1608; found (ESI), 403.2124.

Example 126

1-{1-(3-chlorophenyl)-2-[4-(cyclohexylmethyl)pip-erazin-1-yl]ethyl}cyclohexanol dihydrochloride

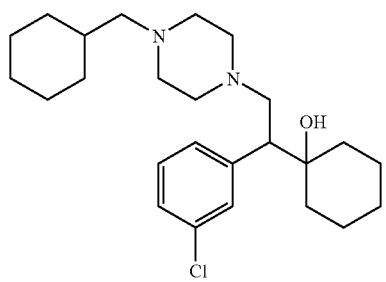

In an analogous manner to Example 117, 1-{1-(3-chlorophenyl)-2-[4-(cyclohexylmethyl)piperazin-1-yl]ethyl}cyclohexanol dihydrochloride was prepared from 1-[1-(3-chlorophenyl)-2-piperazin-1-ylethyl]cyclohexanol (see Example 1) and cyclohexanecarboxaldehyde. MS (ESI) m/z 419/421 ([M+H]$^+$); HRMS: calcd for $C_{25}H_{39}ClN_2O$.2.00 HCl, 490.2284; found (ESI), 419.2815.

Example 127

1-{1-(3-chlorophenyl)-2-[4-(quinolin-4-ylmethyl)piperazin-1-yl]ethyl}cyclohexanol dihydrochloride

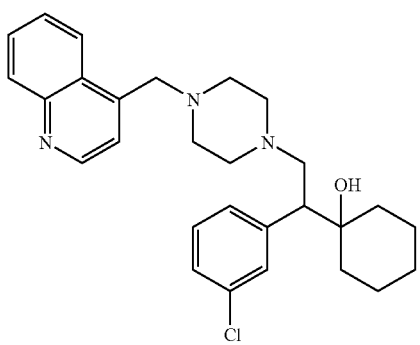

In an analogous manner to Example 117, 1-{1-(3-chlorophenyl)-2-[4-(quinolin-4-ylmethyl)piperazin-1-yl]ethyl}cyclohexanol dihydrochloride was prepared from 1-[1-(3-chlorophenyl)-2-piperazin-1-ylethyl]cyclohexanol (see Example 1) and 4-quinolinecarboxaldehyde. MS (ESI) m/z 464/466 ([M+H]$^+$); HRMS: calcd for $C_{28}H_{34}ClN_3O$.3.00 HCl, 571.1691; found (ESI_FT), 464.24693.

Example 128

1-(1-(3-chlorophenyl)-2-{4-[(5-ethyl-2-furyl)methyl]piperazin-1-yl}ethyl)cyclohexanol dihydrochloride

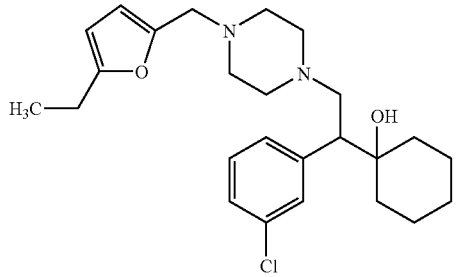

In an analogous manner to Example 117, 1-(1-(3-chlorophenyl)-2-{4-[(5-ethyl-2-furyl)methyl]piperazin-1-yl}ethyl)cyclohexanol dihydrochloride was prepared from 1-[1-(3-chlorophenyl)-2-piperazin-1-ylethyl]cyclohexanol (see Example 1) and 5-ethyl-2-furaldehyde. MS (ESI) m/z [M+H]+ (431/433); HRMS: calcd for $C_{25}H_{35}ClN_2O_2$.2.00 HCl, 502.1921; found (ESI), 431.2454.

Example 129

1-{1-(3-chlorophenyl)-2-[4-(2-phenylpropyl)piperazin-1-yl]ethyl}cyclohexanol dihydrochloride

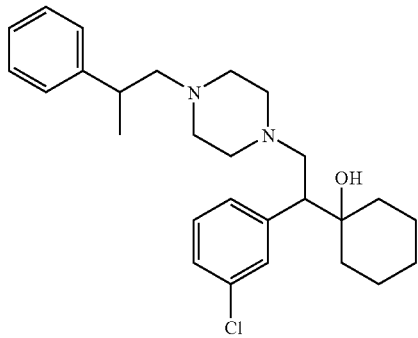

In an analogous manner to Example 117, 1-{1-(3-chlorophenyl)-2-[4-(2-phenylpropyl)piperazin-1-yl]ethyl}cyclohexanol dihydrochloride was prepared from 1-[1-(3-chlorophenyl)-2-piperazin-1-ylethyl]cyclohexanol (see Example 1) and 2-phenylpropionaldehyde. MS (ESI) m/z 441/443 ([M+H]+); HRMS: calcd for $C_{27}H_{37}ClN_2O$.2.00 HCl, 512.2128; found (ESI), 441.2662.

Example 130

1-[2-[4-(1-benzofuran-2-ylmethyl)piperazin-1-yl]-1-(3-chlorophenyl)ethyl]cyclohexanol dihydrochloride

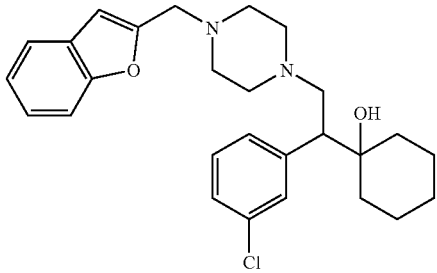

In an analogous manner to Example 117, 1-[2-[4-(1-benzofuran-2-ylmethyl)piperazin-1-yl]-1-(3-chlorophenyl)ethyl]cyclohexanol dihydrochloride was prepared from 1-[1-(3-chlorophenyl)-2-piperazin-1-ylethyl]cyclohexanol (see Example 1) and benzo[B]furan-2-carboxaldehyde. MS (ESI) m/z[M+H]+ (453/455); HRMS: calcd for $C_{27}H_{33}ClN_2O_2$.2.00 HCl, 524.1764; found (ESI), 453.2296.

Example 131

1-[2-{4-[4-(benzyloxy)benzyl]piperazin-1-yl}-1-(3-chlorophenyl)ethyl]cyclohexanol dihydrochloride

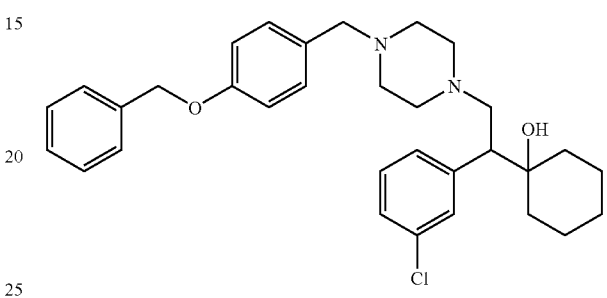

In an analogous manner to Example 117, 1-[2-{4-[4-(benzyloxy)benzyl]piperazin-1-yl}-1-(3-chlorophenyl)ethyl]cyclohexanol dihydrochloride was prepared from 1-[1-(3-chlorophenyl)-2-piperazin-1-ylethyl]cyclohexanol (see Example 1) and 4-benzyloxybenzaldehyde. MS (ESI) m/z 519/521 ([M+H]+); HRMS: calcd for $C_{32}H_{39}ClN_2O_2$.2.00 HCl, 590.2234; found (ESI_FT), 519.27544.

Example 132

1-{1-(3-chlorophenyl)-2-[4-(4-phenoxybenzyl)piperazin-1-yl]ethyl}cyclohexanol dihydrochloride

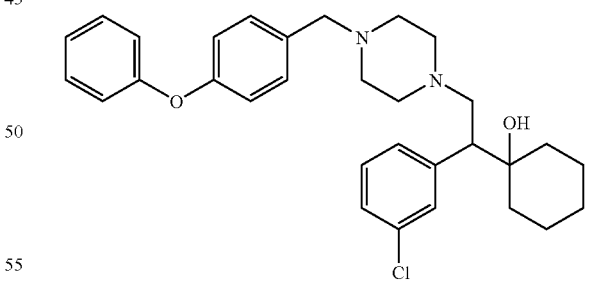

In an analogous manner to Example 117, 1-{1-(3-chlorophenyl)-2-[4-(4-Phenoxybenzyl)piperazin-1-yl]ethyl}cyclohexanol dihydrochloride was prepared from 1-[1-(3-chlorophenyl)-2-piperazin-1-ylethyl]cyclohexanol (see Example 1) and 4-phenoxybenzaldehyde. MS (ESI) m/z 5051507 ([M+H]+); HRMS: calcd for $C_{31}H_{37}ClN_2O_2$.2.00 HCl, 576.2077; found (ESI_FT), 505.26224.

Example 133

1-{1-(3-chlorophenyl)-2-[4-(pyridin-4-ylmethyl)piperazin-1-yl]ethyl}cyclohexanol dihydrochloride

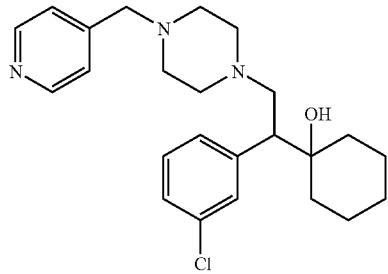

In an analogous manner to Example 117, 1-{1-(3-chlorophenyl)-2-[4-(pyridin-4-ylmethyl)piperazin-1-yl]ethyl}cyclohexanol dihydrochloride was prepared from 1-[1-(3-chlorophenyl)-2-piperazin-1-ylethyl]cyclohexanol (see Example 1) and 4-pyridinecarboxaldehyde. MS (ESI) m/z [M+H]+ (414/416); HRMS: calcd for $C_{24}H_{32}ClN_3O \cdot 2.00$ HCl, 485.1767; found (ESI), 414.2307.

Example 134

1-{1-(3-chlorophenyl)-2-[4-(pyridin-3-ylmethyl)piperazin-1-yl]ethyl}cyclohexanol dihydrochloride

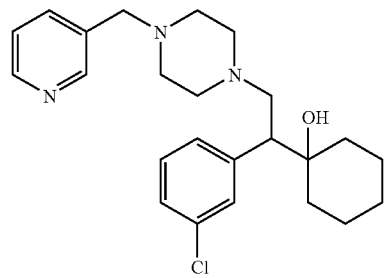

In an analogous manner to Example 117, 1-{1-(3-chlorophenyl)-2-[4-(pyridin-3-ylmethyl)piperazin-1-yl]ethyl}cyclohexanol dihydrochloride was prepared from 1-[1-(3-chlorophenyl)-2-piperazin-1-ylethyl]cyclohexanol (see Example 1) and 3-pyridinecarboxaldehyde. MS (ESI) m/z [M+H]+ (414/416); HRMS: calcd for $C_{24}H_{32}ClN_3O \cdot 2.00$ HCl, 485.1767; found (ESI), 414.2301.

Example 135

1-[1-(3',4'-dichloro-1,1'-biphenyl-3-yl)-2-piperazin-1-ylethyl]cyclohexanol dihydrochloride

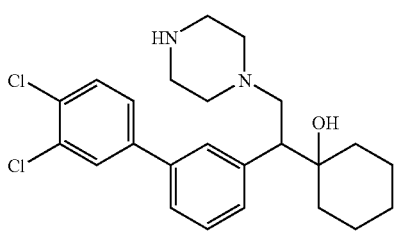

Step 1: In an analogous manner to Example 1, step 1 tert-butyl 4-[(3-bromophenyl)(1-hydroxycyclohexyl)acetyl]piperazine-1-carboxylate was prepared from (3-bromophenyl)(1-hydroxycyclohexyl)acetic acid (Reference Example 1-b) and tert-butyl 1-piperazinecarboxylate. HRMS: calcd for $C_{23}H_{33}BrN_2O_4$, 480.1624; found (ESI_FT), 481.16857.

Step 2: A solution of tert-butyl 4-[(3-bromophenyl)(1-hydroxycyclohexyl)acetyl]piperazine-1-carboxylate (2.12 g, 4.40 mmol) in dry tetrahydrofuran (10 mL) under nitrogen was treated dropwise with a solution of borane (1.0 M in tetrahydrofuran, 13.2 mL, 13.2 mmol). The resulting solution was heated at 70° C. for 2 h, after which time the reaction was cooled in an ice bath, treated dropwise with methanol (15 mL) and concentrated. The resulting viscous, colorless oil was re-dissolved in ethyl acetate (25 mL), washed with a saturated aqueous solution of sodium bicarbonate, water, brine, dried over sodium sulfate, filtered, and concentrated to give a white solid, which was purified via flash column chromatography (silica, gradient from 10% ethyl acetate/hexane to 20% ethyl acetate/hexane) to yield 2.02 g (98%) tert-butyl 4-[2-(3-bromophenyl)-2-(1-hydroxycyclohexyl)ethyl]piperazine-1-carboxylate as a white powder. MS (ESI) m/z 467/469 ([M+H]+); HRMS: calcd for $C_{23}H_{35}BrN_2O_3$, 466.1831; found (ESI), 467.1899; Anal. Calcd for $C_{23}H_{35}BrN_2O_3$: C, 59.10; H, 7.55; N, 5.99. Found: C, 59.14; H, 7.72; N, 5.77.

Step 3: A mixture of tert-butyl 4-[2-(3-bromophenyl)-2-(1-hydroxycyclohexyl)ethyl]piperazine-1-carboxylate (0.72 g, 1.55 mmol) and tetrakis(triphenylphosphine)palladium (37 mg, 0.032 mmol, 10 mol %) in 1,2-dimethoxyethane (30 mL) was stirred for 10 min at room temperature. To this mixture was added sequentially 3,4-dichlorophenyl boronic acid (0.44 g, 2.32 mmol) and a 2M aqueous solution of sodium carbonate (0.8 mL, 1.6 mmol, 5 equivalent), and the mixture was heated at reflux until all starting material was consumed and precipitation of black palladium occurred (3 h). After cooling, water was added and the reaction mixture was extracted with ethyl acetate (30 mL). The organic layer was washed with brine, dried over sodium sulfate, filtered and concentrated to give a crude solid, which was purified via flash column chromatography (silica, gradient from 0% ethyl acetate/hexane to 30% ethyl acetate/hexane) to yield 0.55 g (67%) of tert-butyl 4-[2-(3',4'-dichloro-biphenyl-3-yl)-2-(1-hydroxycyclohexyl)ethyl]piperazine-1-carboxylate as a foam, which was used as such in the next step.

Step 4: tert-butyl 4-[2-(3',4'-dichloro-biphenyl-3-yl)-2-(1-hydroxycyclohexyl)ethyl]piperazine-1-carboxylate (0.39 g 0.73 mmol) was dissolved in diethyl ether (15 mL) then a 2N ethereal solution of hydrochloric acid (10 mL) was added. Methanol (approximately 1 mL) was then added until the resulting precipitate dissolved, and the homogeneous solution was stirred for 18 h. The precipitated product was collected by filtration, washed with diethyl ether and dried in a vacuum oven at 50° C. to yield 0.28 g (81%) of 1-[1-(3',4'-dichloro-1,1'-biphenyl-3-yl)-2-piperazin-1-ylethyl]cyclohexanol dihydrochloride as a white solid. MS (ESI) m/z 433/435/437 ([M+H]+); HRMS: calcd for $C_{24}H_{30}N_2OCl_2 \cdot 2.00$ HCl, 433.1813; found (ESI), 433.1813

Example 136

1-[1-(1,1'-biphenyl-3-yl)-2-piperazin-1-ylethyl]cyclohexanol dihydrochloride

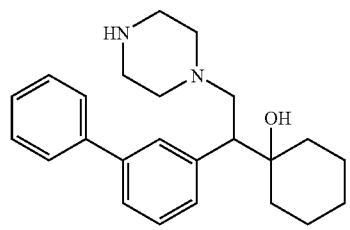

In an analogous manner to Example 135, step 3 tert-butyl 4-[2-(1,1'-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and phenyl boronic acid.

In an analogous manner to Example 135, step 4 1-[1-(1,1'-biphenyl-3-yl)-2-piperazin-1-ylethyl]cyclohexanol dihydrochloride was prepared from tert-butyl 4-[2-(1,1'-biphenyl-3-yl)-2-(1-hydroxycyclohexyl)ethyl]piperazine-1-carboxylate. MS (ESI) m/z [M+H]$^+$ (365); HRMS: calcd for $C_{24}H_{32}N_2O.2.00$ HCl, 436.2048; found (ESI), 365.2575

Example 137

1-[1-(4'-chloro-1,1'-biphenyl-3-yl)-2-piperazin-1-ylethyl]cyclohexanol dihydrochloride

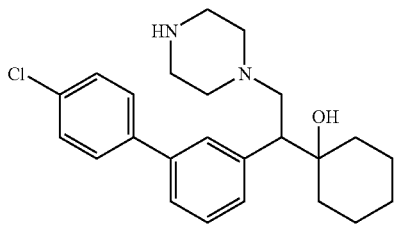

In an analogous manner to Example 135, step 3 tert-butyl 4-[2-(4'-chloro-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 4-chlorophenyl boronic acid.

In an analogous manner to Example 135, step 4 1-[1-(4'-chloro-1,1'-biphenyl-3-yl)-2-piperazin-1-ylethyl]cyclohexanol dihydrochloride was prepared from tert-butyl 4-[2-(4'-chloro-biphenyl-3-yl)-2-(1-hydroxycyclohexyl)ethyl]piperazine-1-carboxylate. MS (ESI) m/z 399/401 ([M+H]$^+$); HRMS: calcd for $C_{24}H_{31}ClN_2O.2.00$ HCl, 470.1658; found (ESI), 399.2203.

Example 138

1-[1-(3'-methoxy-1,1'-biphenyl-3-yl)-2-piperazin-1-ylethyl]cyclohexanol dihydrochloride

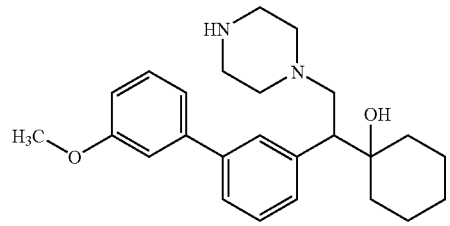

In an analogous manner to Example 135, step 3 tert-butyl 4-[2-(3'-methoxy-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 3-methoxyphenyl boronic acid.

In an analogous manner to Example 135, step 4 1-[1-(3'-methoxy-1,1'-biphenyl-3-yl)-2-piperazin-1-ylethyl]cyclohexanol dihydrochloride was prepared from tert-butyl 4-[2-(3'-methoxy-biphenyl-3-yl)-2-(1-hydroxycyclohexyl)ethyl]piperazine-1-carboxylate. MS (ESI) m/z 395 ([M+H]$^+$); HRMS: calcd for $C_{25}H_{34}N_2O_2.2.00$ HCl, 466.2154; found (ESI), 395.269.

Example 139

1-[1-(3'-chloro-1,1'-biphenyl-3-yl)-2-piperazin-1-ylethyl]cyclohexanol dihydrochloride

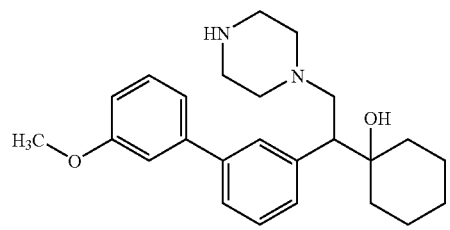

In an analogous manner to Example 135, step 3 tert-butyl 4-[2-(3'-chloro-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 3-chlorophenyl boronic acid.

In an analogous manner to Example 135, step 4 1-[1-(3'-chloro-1,1'-biphenyl-3-yl)-2-piperazin-1-ylethyl]cyclohexanol dihydrochloride was prepared from tert-butyl 4-[2-(3'-chloro-biphenyl-3-yl)-2-(1-hydroxycyclohexyl)ethyl]piperazine-1-carboxylate. MS (ESI) m/z 399/401 ([M+H]$^+$); HRMS: calcd for $C_{24}H_{31}ClN_2O.2.00$ HCl, 470.1658; found (ESI), 399.2183.

Example 140

1-[1-(2'-fluoro-1,1'-biphenyl-3-yl)-2-piperazin-1-ylethyl]cyclohexanol maleate

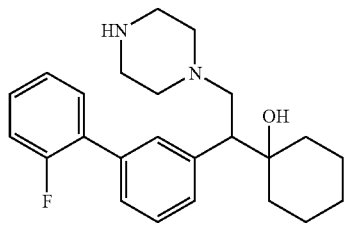

In an analogous manner to Example 135, step 3 tert-butyl 4-[2-(2'-fluoro-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 2-fluorophenyl boronic acid.

In an analogous manner to Example 135, step 4 1-[1-(2'-fluoro-1,1'-biphenyl-3-yl)-2-piperazin-1-ylethyl]cyclohexanol dihydrochloride was prepared from tert-butyl 4-[2-(2'-fluoro-biphenyl-3-yl)-2-(1-hydroxycyclohexyl)ethyl]piperazine-1-carboxylate. The compound was neutralized with 10% aqueous potassium carbonate, and the residue dissolved in methanol. One equivalent of maleic acid was then added and the solution was concentrated. The product was triturated with diethyl ether to yield 1-[1-(2'-fluoro-1,1'-biphenyl-3-yl)-2-piperazin-1-ylethyl]cyclohexanol maleate as a colorless solid. MS (ESI) m/z 383 ([M+H]+); Anal. Calcd for $C_{24}H_{31}FN_2O \cdot C_4H_4O_4 \cdot 0.50H_2O$: C, 66.25; H, 7.15; N, 5.52. Found: C, 66.03; H, 7.38; N, 5.31.

Example 141

1-[1-(2,5-dichlorothien-3-yl)-2-piperazine-1-ylethyl]cyclohexanol dihydrochloride

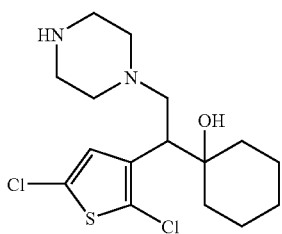

Step 1: A solution of 3-thiophene acetic acid (1.42 g, 10.0 mmol) in acetic acid (10 mL) was treated with N-chlorosuccinimide (3.1 g, 23 mmol, 2.3 equivalents), and the solution was stirred for 12 h at room temperature then concentrated in vacuo. The residue was diluted with water and stirred for 1 h whereupon the resulting solid was collected by filtration. The solid was dried in a vacuum oven at room temperature for 10 hours providing 1.51 g (72%) of (2,5-dichlorothien-3-yl)acetic acid as a brown solid, which was used as such in the next step. MS (ESI) m/z 209/211/213 ([M−H]−).

Step 2: In an analogous manner to Example 1, step 1 tert-butyl 4-[(2,5-dichlorothien-3-yl)acetyl]piperazine-1-carboxylate was prepared from 2,5-dichlorothiophene-3-acetic acid and tert-butyl 1-piperazinecarboxylate. The product was crystallized from ethyl acetate:hexane to yield a colorless solid.

Step 3: A solution of diisopropyl amine (0.80 mL, 5.6 mmol) in dry tetrahydrofuran (10 mL) under nitrogen was cooled to −78° C. and treated dropwise with a solution of n-butyllithium (1.6 M in hexanes, 3.5 mL, 5.6 mmol). To this reaction was added dropwise a solution of tert-butyl 4-[(2,5-dichlorothien-3-yl)acetyl]piperazine-1-carboxylate (1.7 g, 4.5 mmol) in tetrahydrofuran (10 mL). After the addition was complete, the solution was stirred for 0.5 hr at −78° C. whereupon cyclohexanone (0.57 mL, 5.6 mmol) was added via syringe. The solution was stirred for an additional 0.5 h. The reaction was quenched with a saturated aqueous solution of ammonium chloride and then warmed to room temperature. The solution was diluted with ethyl acetate; the organic phase was separated, and was washed with a 2N aqueous solution of hydrochloric acid (1×10 mL). The organic extract was dried over magnesium sulfate and concentrated. Chromatography of the residue via Biotage (FLASH 40 M, silica, 30% ethyl acetate/hexane) provided 1.2 g (58%) of 4-[(2,5-dichlorothien-3-yl)(1-hydroxycyclohexyl)acetyl]piperazine-1-carboxylate as a white foam. MS (ESI) m/z 477/479/481 ([M+H]), HRMS: calcd for $C_{21}H_{30}Cl_2N_2O_4S$, 476.1303; found (ESI), 477.1362.

Step 4: In an analogous manner to Example 135, Step 2 tert-butyl 4-[2-(2,5-dichlorothien-3-yl)-2-(1-hydroxycyclohexyl)ethyl]piperazine-1-carboxylate was prepared from tert-butyl 4-[(2,5-dichlorothien-3-yl)(1-hydroxycyclohexyl)acetyl]piperazine-1-carboxylate. MS (ESI) m/z 463/465/467 ([M+H]+), HRMS: calcd for $C_{21}H_{32}Cl_2N_2O_3S$, 462.1511; found (ESI), 463.1594.

Step 5: In an analogous manner to Example 135, step 4 1-[1-(2,5-dichlorothien-3-yl)-2-piperazine-1-ylethyl]cyclohexanol dihydrochloride was prepared from tert-butyl 4-[2-(2,5-dichlorothien-3-yl)-2-(1-hydroxycyclohexyl)ethyl]piperazine-1-carboxylate and isolated as a colorless powder. MS (ESI) m/z [M+H]+ (363/365/367); HRMS: calcd for $C_{16}H_{24}Cl_2N_2OS \cdot 2.00$ HCl, 434.0520; found (ESI), 363.1035.

Example 142

1-[1-(5-chlorothien-2-yl)-2-piperazin-1-ylethyl]cyclohexanol dihydrochloride

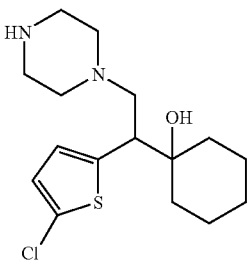

In an analogous manner to Example 141, step 1 (5-chlorothien-3-yl)acetic acid was prepared from 2-thiophene acetic acid and N-chlorosuccinimide. (This acid was used in Reference Example 1-rr) MS (ES) m/z 175.0 ([M−H]−)

In an analogous manner to Example 1, step 1 tert-butyl 4-[(5-chlorothien-2-yl)(1-hydroxycyclohexyl)acetyl]piperazine-1-carboxylate was prepared from (5-chlorothien-2-yl)

(1-hydroxycyclohexyl)acetic acid (Reference Example 1-rr) and tert-butyl 1-piperazinecarboxylate. MS (ESI) m/z 443/445 ([M+H]+)

In an analogous manner to Example 1, step 2 1-[1-(5-chlorothien-2-yl)-2-piperazin-1-ylethyl]cyclohexanol dihydrochloride product was prepared from tert-butyl 4-[(5-chlorothien-2-yl)(1-hydroxycyclohexyl)acetyl]piperazine-1-carboxylate. MS (ESI) m/z 329/331 ([M+H]$^+$); Anal. Calcd for $C_{16}H_{25}ClN_2OS.2.00$ HCl: C, 47.83; H, 6.77; N, 6.97. Found: C, 48.31; H, 7.40; N, 6.21

Example 143

1-[1-(5-bromothien-2-yl)-2-piperazin-1-ylethyl]cyclohexanol dihydrochloride

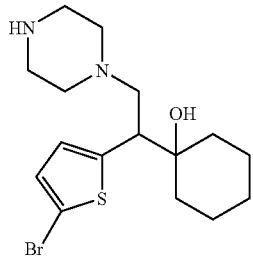

In an analogous manner to Example 141, step 1 (5-bromothien-3-yl)acetic acid was prepared from 2-thiophene acetic acid and N-bromosuccinimide. (This product was used in Reference Example 1-ss)

In an analogous manner to Example 1, step 1, tert-butyl 4-[(5-bromothien-2-yl)(1-hydroxycyclohexyl)acetyl]piperazine-1-carboxylate was prepared from (5-bromothien-2-yl)(1-hydroxycyclohexyl)acetic acid (Reference Example 1-ss) and tert-butyl 1-piperazinecarboxylate. MS (ESI) m/z 487/489 ([M+H]+

In an analogous manner to Example 1, step 2, 1-[1-(5-bromothien-2-yl)-2-piperazin-1-ylethyl]cyclohexanol dihydrochloride was prepared from tert-butyl 4-[(5-bromothien-2-yl)(1-hydroxycyclohexyl)acetyl]piperazine-1-carboxylate. MS (ESI) m/z 373/375 ([M+H]$^+$). Anal. Calcd for $C_{16}H_{25}BrN_2OS.2.00$ HCl: C, 43.06; H, 6.10; N, 6.28. Found: C, 43.76; H, 6.12; N, 5.60.

Example 144

1-[1-(5-chlorothien-3-yl)-2-piperazin-1-ylethyl]cyclohexanol dihydrochloride

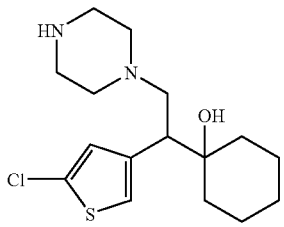

In an analogous manner to Example 1, step 1 tert-butyl 4-[(5-chlorothien-3-yl)acetyl]piperazine-1-carboxylate was prepared from 5-chlorothiophene-3-acetic acid[2] and tert-butyl 1-piperazinecarboxylate. MS (ES) m/z 289.0 ([M+H—C4H8]+); HRMS: calcd for C15H21ClN2O3S, 344.0961; found (ESI), 345.1018

[2] Monguzzi, R.; Ubassi, G.; Pinza, M.; Pifferi, G. Synthesis of new a-hydrazinoarylacetic acids and derivatives. Farnaco, Edizione Scientifica (1976), 31(8), 549-60

In an analogous manner to Example 141, step 3, tert-butyl 4-[2-(5-chlorothien-3-yl)-2-(1-hydroxycyclohexyl)ethyl]piperazine-1-carboxylate was prepared from tert-butyl 4-[(5-chlorothien-3-yl)acetyl]piperazine-1-carboxylate and cyclohexanone. MS (ESI) m/z 429 ([M+H]+); HRMS: calcd for $C_{21}H_{33}ClN_2O_3S$, 428.1900; found (ESI), 429.1973.

In an analogous manner to Example 135, step 2, tert-butyl 4-[2-(5-chlorothien-3-yl)-2-(1-hydroxycyclohexyl)ethyl]piperazine-1-carboxylate was prepared from tert-butyl 4-[2-(5-chlorothien-3-yl)-2-(1-hydroxycyclohexyl)ethyl]piperazine-1-carboxylate.

In an analogous manner to Example 135, step 4 1-[1-(5-chlorothien-3-yl)-2-piperazin-1-ylethyl]cyclohexanol dihydrochloride was prepared from tert-butyl 4-[2-(5-chlorothien-3-yl)-2-(1-hydroxycyclohexyl)ethyl]piperazine-1-carboxylate. MS (ES) m/z 329/331 ([M+H]$^+$); HRMS: calcd for $C_{16}H_{25}ClN_2OS.2.00$ HCl, 400.0910; found (ESI), 329.1444.

Example 145

1-[2-(4-aminopiperidin-1-yl)-1-(5-chlorothien-3-yl)ethyl]cyclohexanol dihydrochloride

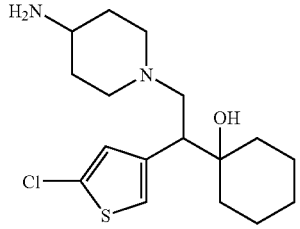

In an analogous manner to Example 1, step 1 tert-butyl{1-[2-(5-chloro-thiophen-3-yl)-acetyl]-piperidin-4-yl}-carbamate was prepared from 5-chlorothiophene-3-acetic acid and 4-N-boc-aminopiperidine.

In an analogous manner to Example 141, step 3, tert-butyl{1-[2-(5-chloro-thiophen-3-yl)(1-hydroxycyclohexyl)acetyl]-piperidin-4-yl}-carbamate was prepared from tert-butyl{1-[2-(5-Chloro-thiophen-3-yl)-acetyl]-piperidin-4-yl}-carbamate and cyclohexanone.

In an analogous manner to Example 135, step 2, tert-butyl{1-[2-(5-chloro-thiophen-3-yl)(1-hydroxycyclohexyl)ethyl]-piperidin-4-yl}-carbamate was prepared from tert-butyl{1-[2-(5-Chloro-thiophen-3-yl)(1-hydroxycyclohexyl)acetyl]-piperidin-4-yl}-carbamate.)

In an analogous manner to Example 135, step 4 1-[2-(4-aminopiperidin-1-yl)-1-(5-chlorothien-3-yl)ethyl]cyclohexanol dihydrochloride was prepared from tert-butyl{1-[2-(5-Chloro-thiophen-3-yl)(1-hydroxycyclohexyl)ethyl]- piperidin-4-yl}-carbamate. MS (ESI) m/z 343/345 ([M+H]⁺); HRMS: calcd for C₁₇H₂₇ClN₂OS 2.00 HCl, 414.1066; found (ESI), 343.1594.

Example 146

1-[1-(1-benzothien-3-yl)-2-piperazin-1-ylethyl]cyclohexanol dihydrochloride

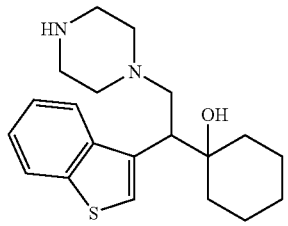

In an analogous manner to Example 1, step 1 t-butyl 4-[1-[1-(1-benzothien-3-yl)(1-hydroxycyclohexyl)acetyl]piperazine-1-carboxylate was prepared from 1-benzothien-3-yl(1-hydroxycyclohexyl)acetic acid (Reference Example 1-tt) and tert-butyl 1-piperazinecarboxylate. MS (ESI) m/z 487/489 ([M+H]+

In an analoguous manner to Example 1, step 2 1-[1-(1-benzothien-3-yl)-2-piperazin-1-ylethyl]cyclohexanol dihydrochloride was prepared from t-butyl 4-[1-[1-(1-benzothien-3-yl)(1-hydroxycyclohexyl)acetyl]piperazine-1-carboxylate. MS (ESI) m/z [M+H]⁺ (345); HRMS: calcd for C₂₀H₂₈N₂OS.2.00 HCl, 416.1456; found (ESI), 345.2024

Example 147

1-[1-(3',4'-difluoro-1,1'-biphenyl-3-yl)-2-piperazin-1-ylethyl]cyclohexanol dihydrochloride

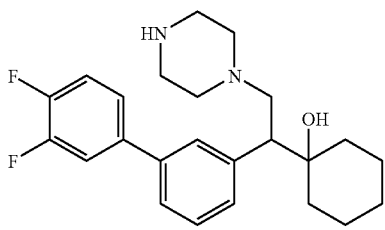

In an analogous manner to Example 135, step 3 tert-butyl 4-[2-(3',4'-difluoro-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 3,4-difluorophenyl boronic acid.

In an analogous manner to Example 135, step 4 1-[1-(3',4'-difluoro-1,1'-biphenyl-3-yl)-2-piperazin-1-ylethyl]cyclohexanol dihydrochloride was prepared from tert-butyl 4-[2-(3',4'-difluoro-biphenyl-3-yl)-2-(1-hydroxycyclohexyl) ethyl]piperazine-1-carboxylate. MS (ESI) m/z [M+H]⁺ (401); HRMS: calcd for C₂₄H₃₀F₂N₂O.2.00 HCl, 472.1860; found (ESI), 401.2378

Example 148

1-[1-(3',4'-dichloro-1,1'-biphenyl-2-yl)-2-piperazin-1-ylethyl]cyclohexanol dihydrochloride

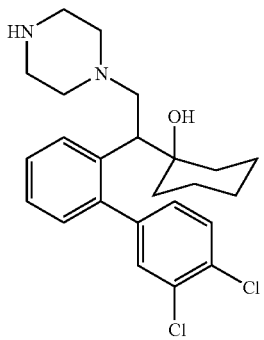

In an analogous manner to Example 1, step 1 tert-butyl 4-[(2-bromophenyl)(1-hydroxycyclohexyl)acetyl]piperazine-1-carboxylate was prepared from (2-bromophenyl)(1-hydroxycyclohexyl)acetic acid (Reference Example 1-uu) and tert-butyl 1-piperazinecarboxylate. MS (ESI) m/z 481/483 ([M+H]+); HRMS: calcd for C₂₃H₃₃BrN₂O₄, 480.1624; found (ESI), 481.1689

In an analoguous manner to Example 135, step 2, tert-butyl 4-[2-(2-bromophenyl)-2-(1-hydroxycyclohexyl)ethyl]piperazine-1-carboxylate was prepared from tert-butyl 4-[(2-bromophenyl)(1-hydroxycyclohexyl)acetyl]piperazine-1-carboxylate. MS (ESI) m/z 467/469 ([M+H]+); HRMS: calcd for C₂₃H₃₅BrN₂O₃, 466.1831; found (ESI), 467.1895;

In an analogous manner to Example 135, step 3 tert-butyl 4-[3'4'dichloro-1,1'-biphenyl-2-yl)-2-(1-hydroxycyclohexyl)ethyl]piperazine-1-carboxylate was prepared from tert-butyl 4-[2-(2-bromophenyl)-2-(1-hydroxycyclohexyl) ethyl]piperazine-1-carboxylate and 3,4-dichloro phenyl boronic acid.

In an analogous manner to Example 135, step 4 1-[1-(3',4'-dichloro-1,1'-biphenyl-2-yl)-2-piperazin-1-ylethyl]cyclohexanol dihydrochloride was prepared from tert-butyl 4-[3'4'dichloro-1,1'-biphenyl-2-yl)-2-(1-hydroxycyclohexyl)ethyl]piperazine-1-carboxylate. MS (ES) m/z 433.3 ([M+H]⁺); HRMS: calcd for C₂₄H₃₀Cl₂N₂O.2.00 HCl, 504.1269; found (ESI), 433.1797

Example 149

1-[1-(1,1'-biphenyl-2-yl)-2-piperazin-1-ylethyl]cyclohexanol dihydrochloride

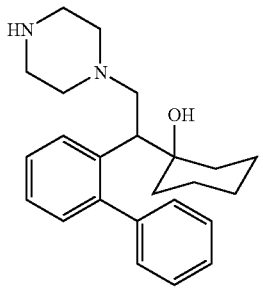

In an analogous manner to Example 135, step 3 tert-butyl 4-[1,1'-biphenyl-2-yl)-2-(1-hydroxycyclohexyl)ethyl]piperazine-1-carboxylate was prepared from tert-butyl 4-[2-(2-bromophenyl)-2-(1-hydroxycyclohexyl)ethyl]piperazine-1-carboxylate (see Example 148, step 2) and phenyl boronic acid.

In an analogous manner to Example 135, step 4 1-[1-(1,1'-biphenyl-2-yl)-2-piperazin-1-ylethyl]cyclohexanol dihydrochloride was prepared from tert-butyl 4-[1,1'-biphenyl-2-yl)-2-(1-hydroxycyclohexyl)ethyl]piperazine-1-carboxylate. MS (ES) m/z 365.4 ([M+H]$^+$); HRMS: calcd for $C_{24}H_{32}N_2O$.2.00 HCl, 436.2048; found (ESI), 365.2601

Example 150

1-[1-(3'-chloro-1,1'-biphenyl-2-yl)-2-piperazin-1-ylethyl]cyclohexanol dihydrochloride

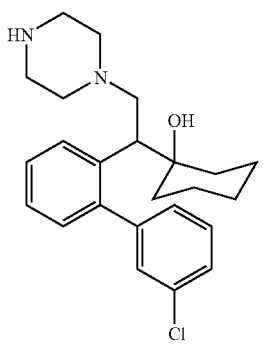

In an analogous manner to Example 135, step 3 tert-butyl 4-[3'-chloro-1,1'-biphenyl-2-yl)-2-(1-hydroxycyclohexyl)ethyl]piperazine-1-carboxylate was prepared from tert-butyl 4-[2-(2-bromophenyl)-2-(1-hydroxycyclohexyl)ethyl]piperazine-1-carboxylate (see Example 148, step 2) and 3-chloro phenyl boronic acid.

In an analogous manner to Example 135, step 4 1-[1-(3'-chloro-1,1'-biphenyl-2-yl)-2-piperazin-1-ylethyl]cyclohexanol dihydrochloride was prepared from tert-butyl 4-[3'-chloro-1,1'-biphenyl-2-yl)-2-(1-hydroxycyclohexyl)ethyl]piperazine-1-carboxylate. MS (ESI) m/z 561/563/565 ([M+H]$^+$); HRMS: calcd for $C_{24}H_{31}ClN_2O$.2.00 HCl, 470.1658; found (ESI), 399.2211

Example 151

1-{1-[2-(1,3-benzodioxol-5-yl)phenyl]-2-piperazin-1-ylethyl}cyclohexanol dihydrochloride

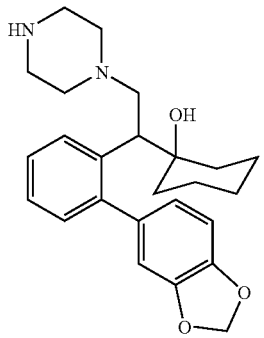

In an analogous manner to Example 135, step 3 tert-butyl 4-{1-(1,3-benzodioxol-5-ylphenyl)-2-(1-hydroxycyclohexyl)ethyl}piperazine-1-carboxylate was prepared from tert-butyl 4-[2-(2-bromophenyl)-2-(1-hydroxycyclohexyl)ethyl]piperazine-1-carboxylate (see Example 148, step 2) and 3,4-(methylenedioxy)phenyl boronic acid.

In an analogous manner to Example 135, step 4 1-{1-[2-(1,3-benzodioxol-5-yl)phenyl]-2-piperazin-1-ylethyl}cyclohexanol dihydrochloride was prepared from tert-butyl 4-[1-(1,3-benzodioxol-5-ylphenyl)-2-(1-hydroxycyclohexyl)ethyl]piperazine-1-carboxylate. MS (ES) m/z 409.3 ([M+H]$^+$); HRMS: calcd for $C_{25}H_{32}N_2O_3$.2.00 HCl, 480.1946; found (ESI), 409.2483.

Example 152

1-[2-(4-aminopiperidin-1-yl)-1-(3',4'-dichloro-1,1'-biphenyl-3-yl)ethyl]cyclohexanol dihydrochloride

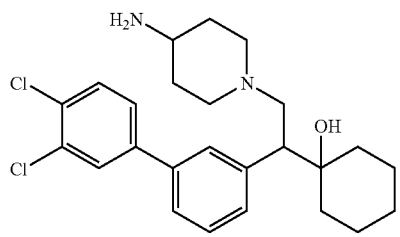

In an analogous manner to Example 135, step 3 tert-butyl {1-[(3',4'-dichloro-1,1'-biphenyl-3-yl)(1-hydroxycyclohexyl)acetyl]piperidin-4-yl}carbamate was prepared from tert-butyl {1-[(3-bromophenyl)(1-hydroxycyclohexyl)acetyl]piperidin-4-yl}carbamate (see Example 18, step 1) and 3,4-dichloro phenyl boronic acid. MS (ESI) m/z 561/563/565 ([M+H]+); HRMS: calcd for $C_{30}H_{38}Cl_2N_2O_4$, 560.2209; found (ESI), 561.2263

In an analogous manner to Example 135, step 2 tert-butyl {1-[2-(3',4'-dichloro-1,1'-biphenyl-3-yl)-2-(1-hydroxycyclohexyl)ethyl]piperidin-4-yl}carbamate was prepared from tert-butyl {1-[(3',4'-dichloro-1,1'-biphenyl-3-yl)(1-hydroxycyclohexyl)acetyl]piperidin-4-yl}carbamate. MS (ES) m/z 547.3 ([M+H]+); HRMS: calcd for $C_{30}H_{40}Cl_2N_2O_3$, 546.2416; found (ESI), 547.2473.

In an analogous manner to Example 135, step 3 1-[2-(4-aminopiperidin-1-yl)-1-(3',4'-dichloro-1,1'-biphenyl-3-yl)ethyl]cyclohexanol dihydrochloride was prepared from tert-butyl {1-[2-(3',4'-dichloro-1,1'-biphenyl-3-yl)-2-(1-hydroxycyclohexyl)ethyl]piperidin-4-yl}carbamate. MS (ES) m/z 447.2 ([M+H]$^+$); HRMS: calcd for $C_{25}H_{32}Cl_2N_2O$.2.00 HCl, 518.1425; found (ESI), 447.1962.

Example 153

1-[1-(3',4'-dichloro-1,1'-biphenyl-3-yl)-2-piperazin-1-ylethyl]cyclobutanol dihydrochloride

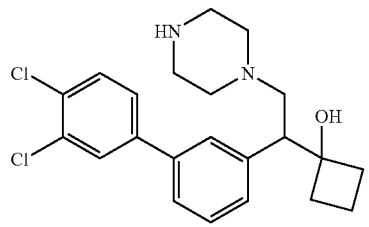

In an analogous manner to Example 1, step 1 tert-butyl 4-[(3-bromophenyl)(1-hydroxycyclobutyl)acetyl]piperazine-1-carboxylate was prepared (3-bromophenyl)(1-hydroxycyclobutyl)acetic acid (Reference Example 1-j) and tert-butyl 1-piperazinecarboxylate. HRMS: calcd for $C_{21}H_{29}BrN_2O_4$, 452.1311; found (ESI_FT), 453.13746.

In an analogous manner to Example 135, step 2 tert-butyl 4-[2-(3-bromophenyl)-2-(1-hydroxycyclobutyl)ethyl]piperazine-1-carboxylate was prepared from tert-butyl 4-[(3-bromophenyl)(1-hydroxycyclobutyl)acetyl]piperazine-1-carboxylate and 3,4-dichloro phenyl boronic acid.

In an analogous manner to Example 135, step 3 tert-butyl 4-[2-(3',4'-dichloro-biphenyl-3-yl)-2-(1-hydroxycyclobutyl)ethyl]piperazine-1-carboxylate was prepared from tert-butyl 4-[2-(3-bromophenyl)-2-(1-hydroxycyclobutyl)ethyl]piperazine-1-carboxylate and 3,4-dichloro phenyl boronic acid.

In an analogous manner to Example 135, step 4 1-[1-(3',4'-dichloro-1,1'-biphenyl-3-yl)-2-piperazin-1-ylethyl]cyclobutanol dihydrochloride was prepared from tert-butyl 4-[2-(3',4'-dichloro-biphenyl-3-yl)-2-(1-hydroxycyclobutyl)ethyl]piperazine-1-carboxylate. MS (ESI) m/z 405.1499 ([M+H]$^+$); HRMS: calcd for $C_{22}H_{26}Cl_2N_2O$.2.00 HCl, 476.0956; found (ESI), 405.1499.

Example 154

1-[1-(1-methyl-1H-indol-3-yl)-2-piperazin-1-ylethyl]cyclohexanol dihydrochloride

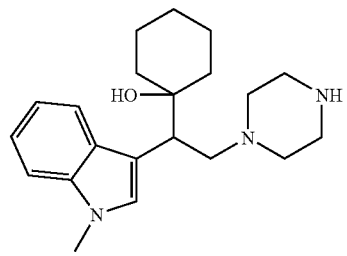

In an analogous manner to Example 1, step 1 tert-butyl 4-[(1-hydroxycyclohexyl)(1-methyl-1H-indol-3-ylacetyl]piperazine-1-carboxylate was prepared from (1-methyl-1H-indol-3-yl) (1-hydroxycylclohexyl)acetic acid (Reference Example 1-xx) and tert-butyl 1-piperazinecarboxylate. MS (ESI) m/z 456 ([M+H]+); HRMS: calcd for $C_{26}H_{37}N_3O_4$, 455.2784; found (ESI_FT), 456.28501.

In an analogous manner to Example 1, step 2 1-[1-(1-methyl-1H-indol-3-yl)-2-piperazin-1-ylethyl]cyclohexanol dihydrochloride was prepared from tert-butyl 4-[(1-hydroxycyclohexyl)(1-methyl-1H-indol-3-yl)acetyl]piperazine-1-carboxylate. MS (ESI) m/z 342 ([M+H]$^+$); HRMS: calcd for $C_{21}H_{31}N_3O$.2.00 HCl, 413.2001; found (ESI_FT), 342.25347

Example 155

1-[1-(1H-indol-3-yl)-2-piperazin-1-ylethyl]cyclohexanol dihydrochloride

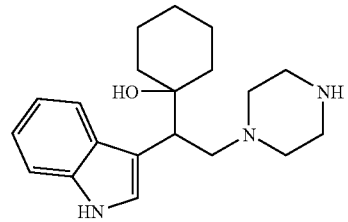

In an analogous manner to Example 1, step 1 tert-butyl 4-[(1-hydroxycyclohexyl)(1-(tert-butyl-dimethyl-silanyl)-1H-indol-3-yl)acetyl]piperazine-1-carboxylate was prepared from (1-(tert-Butyl-dimethyl-silanyl)-1H-indol-3-yl) (1-hydroxycylcohexyl)acetic acid (Reference Example 1-yy) and tert-butyl 1-piperazinecarboxylate.

In an analogous manner to Example 1, step 2 1-[1-(1H-indol-3-yl)-2-piperazin-1-ylethyl]cyclohexanol dihydrochloride was prepared from tert-butyl 4-[(1-hydroxycyclohexyl)(1-(tert-butyl-dimethyl-silanyl)-1H-indol-3-yl)acetyl]piperazine-1-carboxylate. MS (ESI) m/z 328 ([M+H]$^+$); HRMS: calcd for $C_{20}H_{29}N_3O$.2.00 HCl, 399.1844; found (ESI_FT), 328.23696

Example 156

1-[1-(2-chlorothien-3-yl)-2-piperazin-1-ylethyl]cyclohexanol dihydrochloride

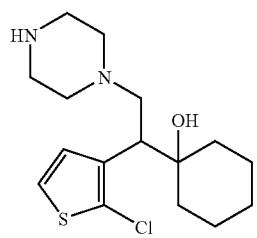

In an analogous manner to Example 141, step 1 (2-chlorothien-3-yl)acetic acid was prepared from 2-thiophene acetic acid and 1 equivalent of N-chlorosuccinimide. MS (ESI) m/z 175/177 ([M+H]+);

In an analogous manner to Example 1, step 1 tert-butyl 4-[(2-chlorothien-3-yl)acetyl]piperazine-1-carboxylate was prepared from (2-chlorothien-3-yl)acetic acid and tert-butyl 1-piperazinecarboxylate. MS (ES) m/z 289.0 ([M+H—C4H8]+); HRMS: calcd for $C_{15}H_{21}ClN_2O_3S$, 344.0961; found (ESI), 345.1057.

In an analogous manner to Example 141, step 3 tert-butyl 4-[(2-chlorothien-3-yl)(1-hydroxycyclohexyl)acetyl]piperazine-1-carboxylate was prepared from tert-butyl 4-[(2-chlorothien-3-yl)acetyl]piperazine-1-carboxylate and cyclohexanone.

In an analogous manner to Example 135, step 2 tert-butyl 4-[2-(2-chlorothien-3-yl)-2-(1-hydroxycyclohexyl)ethyl] piperazine-1-carboxylate was prepared from tert-butyl 4-[(2-chlorothien-3-yl)(1-hydroxycyclohexyl)acetyl]piperazine-1-carboxylate. MS (ESI) m/z 429/431 ([M+H]$^+$); HRMS: calcd for $C_{21}H_{33}ClN_2O_3S$, 428.1900; found (ESI), 429.1967

In an analogous manner to Example 135, step 4 1-[1-(2-chlorothien-3-yl)-2-piperazine-1-ylethyl]cyclohexanol dihydrochloride was prepared from tert-butyl 4-[2-(2-chlorothien-3-yl)-2-(1-hydroxycyclohexyl)ethyl]piperazine-1-carboxylate. MS (ESI) m/z 329/331 ([M+H]$^+$); HRMS: calcd for $C_{16}H_{25}ClN_2OS$ 2.00 HCl, 400.0910; found (ESI), 329.1442.

Example 157

1-[1-(1,1'-biphenyl-4-yl)-2-piperazin-1-ylethyl]cyclohexanol dihydrochloride

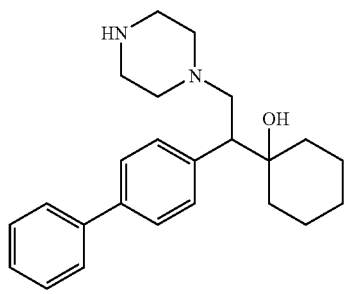

In an analogous manner to Example 1, step 1 tert-butyl 4-[1,1'-biphenyl-4-yl(1-hydroxycyclohexyl)acetyl]piperazine-1-carboxylate was prepared from (1-hydroxycyclohexyl)(1,1'-biphenyl-4-yl)acetic acid (Reference Example 1-zz) and tert-butyl 1-piperazinecarboxylate. MS (ESI) m/z 479 ([M+H]+); Anal. Calcd for $C_{29}H_{38}N_2O_4$: C, 72.77; H, 8.00; N, 5.85. Found: C, 72.69; H, 8.39; N, 5.80.

In an analogous manner to Example 13, step 2 1-[1-(1,1'-biphenyl-4-yl)-2-piperazin-1-ylethyl]cyclohexanol dihydrochloride was prepared from tert-butyl 4-[1,1'-biphenyl-4-yl (1-hydroxycyclohexyl)acetyl]piperazine-1-carboxylate. MS (ESI) m/z 365 ([M+H]+) HRMS: calcd for $C_{24}H_{32}N_2O$. HCl, 400.2281; found (ESI_FT), 365.25908.

Example 158

1-[1-(1,1'-biphenyl-4-yl)-2-(4-methylpiperazin-1-ylethyl]cyclohexanol dihydrochloride

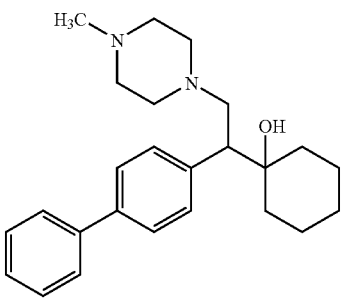

In an analogous manner to Example 24, 1-[1-(1,1'-biphenyl-4-yl)-2-(4-methylpiperazin-1-ylethyl]cyclohexanol dihydrochloride was prepared from 1-[1-(1,1'-biphenyl-4-yl)-2-piperazin-1-ylethyl]cyclohexanol (see Example 157). MS (ESI) m/z 379 ([M+H]$^+$); HRMS: calcd for $C_{25}H_{34}N_2O$.HCl, 414.2438; found (ESI_FT), 379.27468.

Example 159

1-[1-(5-chlorothien-3-yl)-2-(4-methylpiperazin-1-yl) ethyl]cyclohexanol dihydrochloride

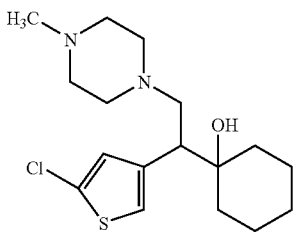

In an analogous manner to Example 24, 1-[1-(5-chlorothien-3-yl)-2-(4-methylpiperazin-1-yl)ethyl]cyclohexanol dihydrochloride was prepared from 1-[1-(5-chlorothien-3-yl)-2-piperazin-1-ylethyl]cyclohexanol (see Example 144). MS (ES) m/z 343.2 ([M+H]+); HRMS: calcd for $C_{17}H_{27}ClN_2OS$. 2.00 HCl, 414.1066; found (ESI), 343.1596.

Example 160

1-[1-(3-cyanophenyl)-2-piperazin-1-ylethyl]cyclohexanol dihydrochloride

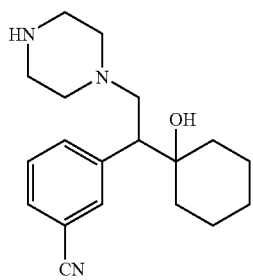

Step 1: A mixture of tert-butyl 4-[2-(3-bromophenyl)-2-(1-hydroxycyclohexyl)ethyl]piperazine-1-carboxylate (see Example 135, step 2) (467 mg, 1.00 mmol), zinc cyanide (141 mg, 1.20 mmol), tris(dibenzylideneacetone)dipalladium (46 mg, 0.0500 mmol), 1,1'-bis(diphenylphosphino)ferrocene (55 mg, 0.100 mmol), and zinc dust (16 mg, 0.25 mmol) in anhydrous N,N-dimethylformamide (5 mL) was heated at 125° C. under nitrogen until all starting material was consumed (5 h). After cooling to room temperature, water (10 mL) and a 2 N aqueous solution of ammonium hydroxide (5 mL) were added and the mixture was extracted with ethyl acetate (1×20 mL). The combined organic extracts were washed with brine (15 mL), dried over sodium sulfate, filtered, and concentrated to give a brown solid, which was purified via flash column chromatography (silica, gradient from 5% ethyl acetate/hexane to 30% ethyl acetate/hexane) to yield 345 mg (84%) tert-butyl 4-[2-(3-cyanophenyl)-2-(1-hydroxycyclohexyl)ethyl]piperazine-1-carboxylate as a yellow solid. MS (ESI) m/z 414 ([M+H]$^+$); HRMS: calcd for $C_{24}H_{35}N_3O_3$, 413.2678; found (ESI), 414.2745.

Step 2: In an analogous manner to Example 135, step 4, 1-[1-(3-cyanophenyl)-2-piperazin-1-ylethyl]cyclohexanol dihydrochloride was prepared from tert-butyl 4-[2-(3-cyanophenyl)-2-(1-hydroxycyclohexyl)ethyl]piperazine-1-carboxylate. MS (ESI) m/z 314 ([M+H]$^+$); HRMS: calcd for $C_{19}H_{27}N_3O.2.00$ HCl, 385.1688; found (ESI), 314.2225.

Example 161

1-[1-(3-cyanophenyl)-2-(4-methylpiperazin-1-yl)ethyl]cyclohexanol dihydrochloride

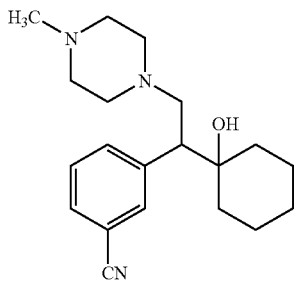

In an analogous manner to Example 24, 1-[1-(3-cyanophenyl)-2-(4-methylpiperazin-1-yl)ethyl]cyclohexanol dihydrochloride was prepared from 1-[1-(3-cyanophenyl)-2-piperazin-1-ylethyl]cyclohexanol (see Example 160). MS (ES) m/z 328.2 ([M+H]$^+$); HRMS: calcd for $C_{20}H_{29}N_3O.2.00$ HCl, 399.1844; found (ESI), 328.2383.

Example 162

1-[2-piperazin-1-yl-1-(3-vinylphenyl)ethyl]cyclohexanol dihydrochloride

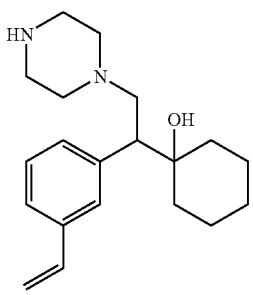

Step 1: A mixture of tert-butyl 4-[2-(3-bromophenyl)-2-(1-hydroxycyclohexyl)ethyl]piperazine-1-carboxylate (see Example 135, step 2) (141 mg, 0.300 mmol), tributyl(vinyl)tin (114 mg, 0.360 mmol, 1.2 equivalent), and tetrakis(triphenylphosphine)palladium (17 mg, 0.015 mmol, 5 mol %) in toluene (3 mL) was heated at reflux under nitrogen until all starting material was consumed and precipitation of black palladium occurred (1-2 h). Filtration through Celite® and purification via flash column chromatography (silica, gradient from 0% ethyl acetate/hexane to 10% ethyl acetate/hexane) yielded 111 mg (90%) tert-butyl 4-[2-(1-hydroxycyclohexyl)-2-(3-vinylphenyl)ethyl]piperazine-1-carboxylate as a viscous colorless oil. MS (ES) m/z 415.4 ([M+H]$^+$); HRMS: calcd for $C_{25}H_{38}N_2O_3$, 414.2882; found (ESI), 415.2966.

Step 2: In an analogous manner to Example 135, step 4, 1-[2-piperazin-1-yl-1-(3-vinylphenyl)ethyl]cyclohexanol dihydrochloride was prepared from tert-butyl 4-[2-(1-hydroxycyclohexyl)-2-(3-vinylphenyl)ethyl]piperazine-1-carboxylate. MS (ESI) m/z 315 ([M+H]$^+$); HRMS: calcd for $C_{20}H_{30}N_2O.2.00$ HCl, 386.1892; found (ESI), 315.242.

Example 163

1-[2-piperazin-1-yl-1-(4-vinylphenyl)ethyl]cyclohexanol dihydrochloride

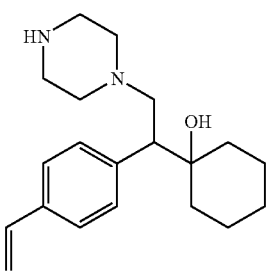

In an analogous manner to Example 1, step 1 tert-butyl 4-[(4-bromophenyl)(1-hydroxycyclohexyl)acetyl]piperazine-1-carboxylate was prepared from (4-bromophenyl)(1- hydroxycyclohexyl)acetic acid (Reference Example 1-h) and tert-butyl 1-piperazinecarboxylate. MS (ESI) m/z 481/483 ([M+H]$^+$); Anal. Calcd for $C_{23}H_{33}BrN_2O_4$: C, 57.38; H, 6.91; N, 5.82. Found: C, 57.06; H, 6.69; N, 5.73.

In an analogous manner to Example 135, step 2, tert-butyl 4-[2-(4-bromophenyl)-2-(1-hydroxycyclohexyl)ethyl]piperazine-1-carboxylate was prepared from tert-butyl 4-[(4-bromophenyl)(1-hydroxycyclohexyl)acetyl]piperazine-1-carboxylate. MS (ESI) m/z 467/469 ([M+H]$^+$).

In an analogous manner to Example 162, step 1, tert-butyl 4-[2-(1-hydroxycyclohexyl)-2-(4-vinylphenyl)ethyl]piperazine-1-carboxylate was prepared from tert-butyl 4-[2-(4-bromophenyl)-2-(1-hydroxycyclohexyl)ethyl]piperazine-1-carboxylate. MS (ES) m/z 415.4 ([M+H]$^+$); HRMS: calcd for $C_{25}H_{38}N_2O_3$, 414.2882; found (ESI), 415.2975.

In an analogous manner to Example 135, step 4, 1-[2-piperazin-1-yl-1-(4-vinylphenyl)ethyl]cyclohexanol dihydrochloride was prepared from tert-butyl 4-[2-(1-hydroxycyclohexyl)-2-(4-vinylphenyl)ethyl]piperazine-1-carboxylate. MS (ES) m/z 315.3 ([M+H]$^+$); HRMS: calcd for $C_{20}H_{30}N_2O.2.00$ HCl, 386.1892; found (ESI), 315.2424.

Example 164

1-[2-piperazin-1-yl-1-(4-prop-1-ynylphenyl)ethyl]cyclohexanol dihydrochloride

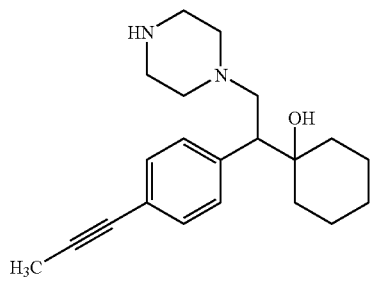

In an analogous manner to Example 162, step 1, tert-butyl 4-[2-(1-hydroxycyclohexyl-2-(4-prop-1-ynylphenyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using (1-propynyl)tributyltin. MS (ESI) m/z 427 ([M+H]$^+$); HRMS: calcd for $C_{26}H_{38}N_2O_3$, 426.2882; found (ESI), 427.2945.

In an analogous manner to Example 135, step 4, 1-[2-piperazin-1-yl-1-(4-prop-1-ynylphenyl)ethyl]cyclohexanol dihydrochloride was prepared from tert-butyl 4-[2-(1-hydroxycyclohexyl)-2-(4-prop-1-ynylphenyl)ethyl]piperazine-1-carboxylate. MS (ESI) m/z 327 ([M+H]$^+$); HRMS: calcd for $C_{21}H_{30}N_2O.2.00$ HCl, 398.1892; found (ESI), 327.2425.

Example 165

1-[1-(2'-chloro-1,1'-biphenyl-4-yl)-2-piperazin-1-ylethyl]cyclohexanol dihydrochloride

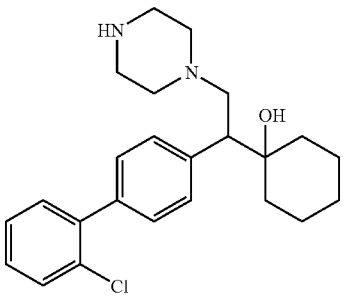

Step 1: In an analogous manner to Example 135, step 3, tert-butyl 4-[2-(2'-chloro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 2-chlorophenylboronic acid. MS (ESI) m/z 499 ([M+H]$^+$); HRMS: calcd for $C_{29}H_{39}ClN_2O_3$, 498.2649; found (ESI), 499.2745.

Step 2: In an analogous manner to Example 135, step 4, 1-[1-(2'-chloro-1,1'-biphenyl-4-yl)-2-piperazin-1-ylethyl]cyclohexanol dihydrochloride was prepared from tert-butyl 4-[2-(2'-chloro-1,1'-biphenyl-4-yl)-2-(1-hydroxycyclohexyl)ethyl]piperazine-1-carboxylate. MS (ESI) m/z 399 ([M+H]$^+$); HRMS: calcd for $C_{24}H_{31}ClN_2O.2.00$ HCl, 470.1658; found (ESI), 399.2200.

Example 166

1-[1-(3'-fluoro-1,1'-biphenyl-4-yl)-2-piperazin-1-ylethyl]cyclohexanol dihydrochloride

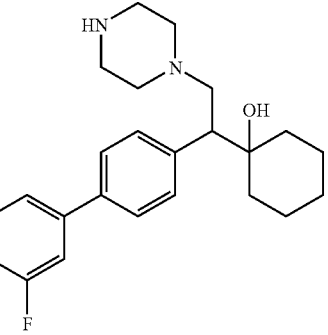

In an analogous manner to Example 135, step 3, tert-butyl 4-[2-(3'-fluoro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-fluorophenylboronic acid. MS (ESI) m/z 483 ([M+H]$^+$).

In an analogous manner to Example 135, step 4, 1-[1-(3'-fluoro-1,1'-biphenyl-4-yl)-2-piperazin-1-ylethyl]cyclohexanol dihydrochloride was prepared from tert-butyl 4-[2-(3'-fluoro-1,1'-biphenyl-4-yl)-2-(1-hydroxycyclohexyl)ethyl]

piperazine-1-carboxylate. MS (ES) m/z 383.3 ([M+H]⁺); HRMS: calcd for C₂₄H₃₁FN₂O.2.00 HCl, 454.1954; found (ESI), 383.2494.

Example 167

1-[1-(3'-chloro-1,1'-biphenyl-4-yl)-2-piperazin-1-ylethyl]cyclohexanol dihydrochloride

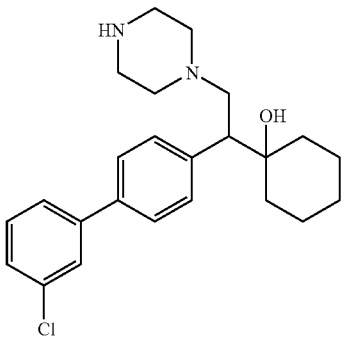

In an analogous manner to Example 135, step 3, tert-butyl 4-[2-(3'-chloro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-chlorophenylboronic acid. MS (ES) m/z 499.3 ([M+H]⁺); HRMS: calcd for C₂₉H₃₉ClN₂O₃, 498.2649; found (ESI), 499.2738.

In an analogous manner to Example 135, step 4, 1-[1-(3'-chloro-1,1'-biphenyl-4-yl)-2-piperazin-1-ylethyl]cyclohexanol dihydrochloride was prepared from tert-butyl 4-[2-(3'-chloro-1,1'-biphenyl-4-yl)-2-(1-hydroxycyclohexyl)ethyl]piperazine-1-carboxylate. MS (ESI) m/z 399/401 ([M+H]⁺); HRMS: calcd for C₂₄H₃₁ClN₂O.2.00 HCl, 470.1658; found (ESI), 399.2211.

Example 168

1-[1-(3'-cyano-1,1'-biphenyl-4-yl)-2-piperazin-1-ylethyl]cyclohexanol dihydrochloride

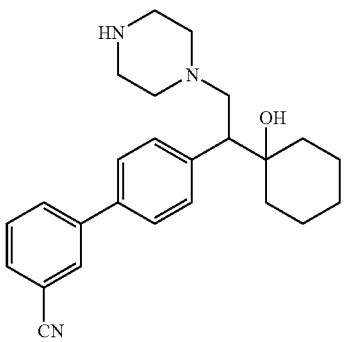

In an analogous manner to Example 135, step 3, tert-butyl 4-[2-(3'-cyano-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-cyanophenylboronic acid. MS (ESI) m/z 490 ([M+H]⁺).

In an analogous manner to Example 135, step 4, 1-[1-(3'-cyano-1,1'-biphenyl-4-yl)-2-piperazin-1-ylethyl]cyclohexanol dihydrochloride was prepared from tert-butyl 4-[2-(3'-cyano-1,1'-biphenyl-4-yl)-2-(1-hydroxycyclohexyl)ethyl]piperazine-1-carboxylate. MS (ES) m/z 390.3 ([M+H]⁺); HRMS: calcd for C₂₅H₃, N₃O.2.00 HCl, 461.2001; found (ESI), 390.2532.

Example 169

1-[1-(3'-nitro-1,1'-biphenyl-4-yl)-2-piperazin-1-yl-ethyl]cyclohexanol dihydrochloride

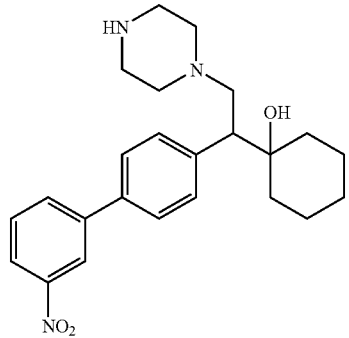

In an analogous manner to Example 135, step 3, tert-butyl 4-[2-(1-hydroxycyclohexyl)-2-(3'-nitro-1,1'-biphenyl-4-yl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-nitrophenylboronic acid. MS (ES) m/z 510.3 ([M+H]⁺).

In an analogous manner to Example 135, step 4, 1-[1-(3'-nitro-1,1'-biphenyl-4-yl)-2-piperazin-1-ylethyl]cyclohexanol dihydrochloride was prepared from tert-butyl 4-[2-(1-hydroxycyclohexyl)-2-(3'-nitro-1,1'-biphenyl-4-yl)ethyl]piperazine-1-carboxylate. MS (ES) m/z 410.3 ([M+H]⁺); HRMS: calcd for C₂₄H₃₁N₃O₃.2.00 HCl, 481.1899; found (ESI), 410.2452.

Example 170

1-[1-(3'-methoxy-1,1'-biphenyl-4-yl)-2-piperazin-1-ylethyl]cyclohexanol dihydrochloride

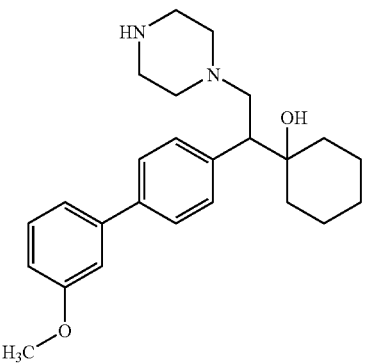

In an analogous manner to Example 135, step 3, tert-butyl 4-[2-(1-hydroxycyclohexyl)-2-(3'-methoxy-1,1'-biphenyl-4- yl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-methoxyphenylboronic acid. MS (ES) m/z 495.4 ([M+H]+).

In an analogous manner to Example 135, step 4, 1-[1-(3'-methoxy-1,1'-biphenyl-4-yl)-2-piperazin-1-ylethyl]cyclohexanol dihydrochloride was prepared from tert-butyl 4-[2-(1-hydroxycyclohexyl)-2-(3'-methoxy-1,1'-biphenyl-4-yl)ethyl]piperazine-1-carboxylate. MS (ES) m/z 395.4 ([M+H]+); HRMS: calcd for $C_{25}H_{34}N_2O_2$.2.00 HCl, 466.2154; found (ESI), 395.2697.

Example 171

1-{2-piperazin-1-yl-1-[3'-(trifluoromethoxy)-1,1'-biphenyl-4-yl]ethyl}cyclohexanol dihydrochloride

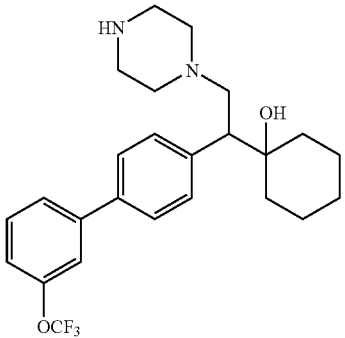

In an analogous manner to Example 135, step 3, tert-butyl 4-{2-(1-hydroxycyclohexyl)-2-[3'-(trifluoromethoxy-1,1'-biphenyl-4-yl]ethyl}piperazine-1-carboxylate was prepared tert-butyl 4-[2-(4-bromophenyl)-2-(1-hydroxycyclohexyl)ethyl]piperazine-1-carboxylate (see Example 163, step 2) using 3-trifluoromethoxy phenylboronic acid. MS (ES) m/z 549.4 ([M+H]+).

In an analogous manner to Example 135, step 4, 1-{2-piperazin-1-yl-1-[3'-(trifluoromethoxy)-1,1'-biphenyl-4-yl]ethyl}cyclohexanol dihydrochloride was prepared from tert-butyl 4-{2-(1-hydroxycyclohexyl)-2-[3'-(trifluoromethoxy)-1,1'-biphenyl-4-yl]ethyl}piperazine-1-carboxylate. MS (ES) m/z 449.3 ([M+H]+); HRMS: calcd for $C_{25}H_{31}F_3N_2O_2$.2.00 HCl, 520.1871; found (ESI), 449.2389.

Example 172

1-[1-(4'-chloro-1,1'-biphenyl-4-yl)-2-piperazin-1-ylethyl]cyclohexanol dihydrochloride

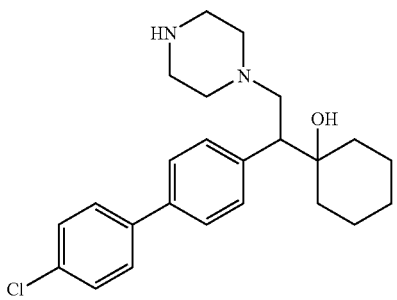

In an analogous manner to Example 135, step 3, tert-butyl 4-[2-(4'-chloro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 4-chlorophenylboronic acid. MS (ESI) m/z 499 ([M+H]+); HRMS: calcd for $C_{29}H_{39}ClN_2O_3$, 498.2649; found (ESI), 499.2718;

In an analogous manner to Example 135, step 4, 1-[1-(4'-chloro-1,1'-biphenyl-4-yl)-2-piperazin-1-ylethyl]cyclohexanol dihydrochloride was prepared from tert-butyl 4-[2-(4'-chloro-1,1'-biphenyl-4-yl)-2-(1-hydroxycyclohexyl)ethyl]piperazine-1-carboxylate. MS (ESI) m/z 399 ([M+H]+); HRMS: calcd for $C_{24}H_{31}ClN_2O$.2.00 HCl, 470.1658; found (ESI), 399.2209.

Example 173

1-[1-(3',4'-dichloro-1,1'-biphenyl-4-yl)-2-piperazin-1-ylethyl]cyclohexanol dihydrochloride

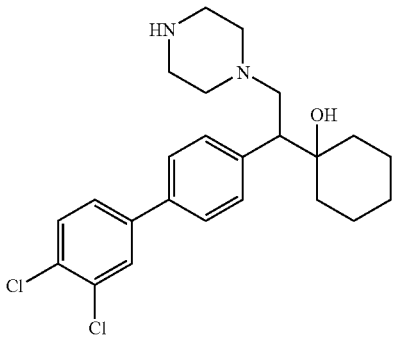

In an analogous manner to Example 135, step 3, tert-butyl 4-[2-(3',4'-dichloro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3,4-dichlorophenylboronic acid. MS m/z 533/535/537 ([M+H]+); HRMS: calcd for $C_{29}H_{38}Cl_2N_2O_3$, 532.2259; found (ESI), 533.2329.

In an analogous manner to Example 135, step 4, 1-[1-(3',4'-dichloro-111'-biphenyl-4-yl)-2-piperazin-1-ylethyl]cyclohexanol dihydrochloride was prepared from tert-butyl 4-[2-(3',4'-dichloro-1,1'-biphenyl-4-yl)-2-(1-hydroxycyclohexyl)ethyl]piperazine-1-carboxylate. MS (ESI) m/z 433 ([M+H]+); HRMS: calcd for $C_{24}H_{30}Cl_2N_2O$.2.00 HCl, 504.1269; found (ESI), 433.1793.

Example 174

1-[2-piperazin-1-yl-1-(4-thien-3-ylphenyl)ethyl]cyclohexanol dihydrochloride

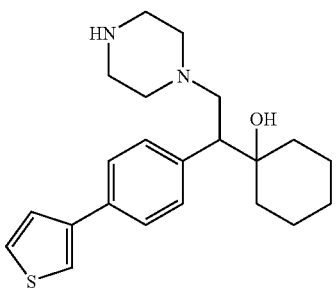

In an analogous manner to Example 135, step 3, tert-butyl 4-[2-(1-hydroxycyclohexyl)-2-(4-thien-3-ylphenyl)ethyl]piperazine-1-carboxylate was prepared from tert-butyl 4-[2-(4-bromophenyl)-2-(1-hydroxycyclohexyl)ethyl]piperazine-1-carboxylate (see Example 163, step 2) using 3-thiopheneboronic acid. MS (ES) m/z 471.3 ([M+H]$^+$); HRMS: calcd for $C_{27}H_{38}N_2O_3S$, 470.2603; found (ESI), 471.2678.

In an analogous manner to Example 135, step 4, 1-[2-piperazin-1-yl-1-(4-thien-3-ylphenyl)ethyl]cyclohexanol dihydrochloride was prepared from tert-butyl 4-[2-(1-hydroxycyclohexyl)-2-(4-thien-3-ylphenyl)ethyl]piperazine-1-carboxylate. MS m/z 371 ([M+H]$^+$); HRMS: calcd for $C_{22}H_{30}N_2OS \cdot 2.00$ HCl, 442.1612; found (ESI), 371.2144.

Example 175

1-[1-(2'-chloro-1,1'-biphenyl-4-yl)-2-(4-methylpiperazin-1-yl)ethyl]cyclohexanol dihydrochloride

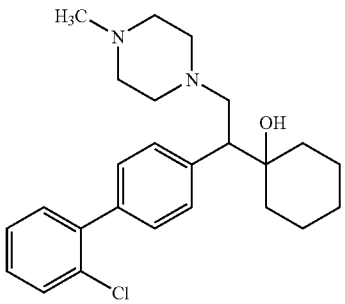

In an analogous manner to Example 24, 1-[1-(2'-chloro-1,1'-biphenyl-4-yl)-2-(4-methylpiperazin-1-yl)ethyl]cyclohexanol dihydrochloride was prepared from 1-[1-(2'-chloro-1,1'-biphenyl-4-yl)-2-piperazin-1-ylethyl]cyclohexanol (see Example 165). MS (ESI) m/z 413/415 ([M+H]$^+$); HRMS: calcd for $C_{25}H_{33}ClN_2O \cdot 2.00$ HCl, 484.1815; found (ESI), 413.2365.

Example 176

1-[1-(3'-chloro-1,1'-biphenyl-4-yl)-2-(4-methylpiperazin-1-yl)ethyl]cyclohexanol dihydrochloride

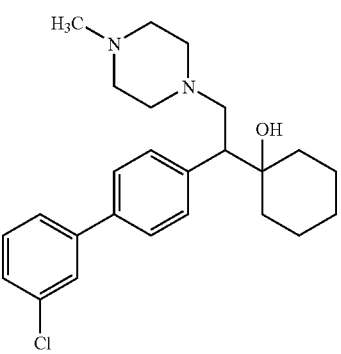

In an analogous manner to Example 24, 1-[1-(3'-chloro-1,1'-biphenyl-4-yl)-2-(4-methylpiperazin-1-yl)ethyl]cyclohexanol dihydrochloride was prepared from 1-[1-(3'-chloro-1,1'-biphenyl-4-yl)-2-piperazin-1-ylethyl]cyclohexanol (see Example 167). MS (ESI) m/z 413/415 ([M+H]$^+$); HRMS: calcd for $C_{25}H_{33}ClN_2O \cdot 2.00$ HCl, 484.1815; found (ESI), 413.2347.

Example 177

1-[1-(3'-cyano-1,1'-biphenyl-4-yl)-2-(4-methylpiperazin-1-yl)ethyl]cyclohexanol dihydrochloride

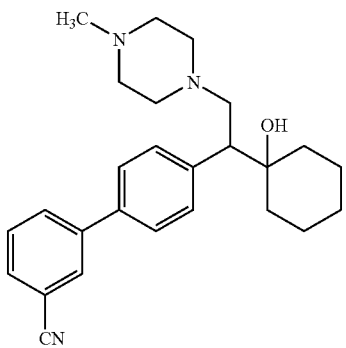

In an analogous manner to Example 24, 1-[1-(3'-cyano-1,1'-biphenyl-4-yl)-2-(4-methylpiperazin-1-yl)ethyl]cyclohexanol dihydrochloride was prepared from 1-[1-(3'-cyano-1,1'-biphenyl-4-yl)-2-piperazin-1-ylethyl]cyclohexanol (see Example 168). MS (ESI) m/z 404 ([M+H]$^+$); HRMS: calcd for $C_{26}H_{33}N_3O \cdot 2.00$ HCl, 475.2157; found (ESI), 404.2708.

Example 178

1-[2-(4-methylpiperazin-1-yl)-1-(3'-nitro-1,1'-biphenyl-4-yl)ethyl]cyclohexanol dihydrochloride

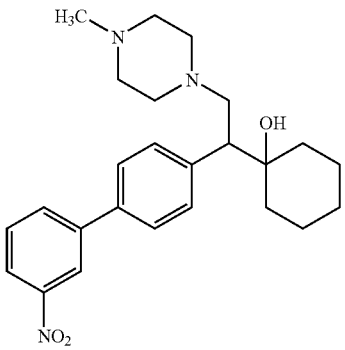

In an analogous manner to Example 24, 1-[2-(4-methylpiperazin-1-yl)-1-(3'-nitro-1,1'-biphenyl-4-yl)ethyl]cyclohexanol dihydrochloride was prepared from 1-[1-(3'-nitro-1,1'-biphenyl-4-yl)-2-piperazin-1-ylethyl]cyclohexanol (see Example 169). MS (ESI) m/z 424 ([M+H]$^+$); HRMS: calcd for $C_{25}H_{33}N_3O_3 \cdot 2.00$ HCl, 495.2055; found (ESI), 424.2603.

Example 179

1-[1-(3'-methoxy-1,1'-biphenyl-4-yl)-2-(4-methylpiperazin-1-yl)ethyl]cyclohexanol dihydrochloride

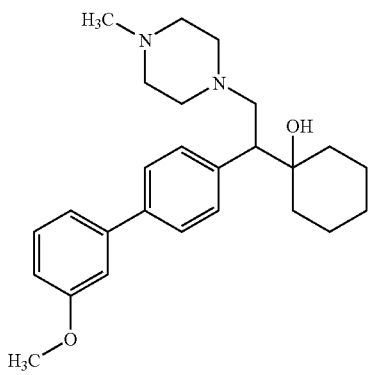

In an analogous manner to Example 24, 1-[1-(3'-methoxy-1,1'-biphenyl-4-yl)-2-(4-methylpiperazin-1-yl)ethyl]cyclohexanol dihydrochloride was prepared from 1-[1-(3'-methoxy-1,1'-biphenyl-4-yl)-2-piperazin-1-ylethyl]cyclohexanol (see Example 170). MS (ESI) m/z 409 ([M+H]$^+$); HRMS: calcd for $C_{26}H_{36}N_2O_2 \cdot 2.00$ HCl, 480.2310; found (ESI), 409.2844.

Example 180

1-[1-(4'-fluoro-1,1'-biphenyl-4-yl)-2-(4-methylpiperazin-1-yl)ethyl]cyclohexanol dihydrochloride

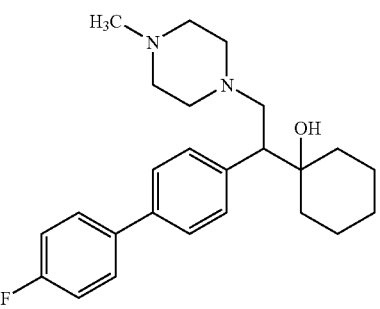

In an analogous manner to Example 1, step 2, 1-[1-(4-bromophenyl)-2-piperazin-1-ylethyl]cyclohexanol was prepared from tert-butyl 4-[(4-bromophenyl)(1-hydroxycyclohexyl)acetyl]piperazine-1-carboxylate (see Example 163, step 1). MS (ESI) m/z 367/369 ([M+H]$^+$); HRMS: calcd for $C_{18}H_{27}BrN_2O \cdot 2.00$ HCl, 438.0840; found (ESI), 367.1365.

In an analogous manner to Example 24, 1-[1-(4-bromophenyl)-2-(4-methylpiperazin-1-yl)ethyl]cyclohexanol was prepared from 1-[1-(4-bromophenyl)-2-piperazin-1-ylethyl]cyclohexanol. MS (ESI) m/z 381/383 ([M+H]$^+$); HRMS: calcd for $C_{19}H_{29}BrN_2O$, 380.1463; found (ESI), 381.1525.

In an analogous manner to Example 135, step 3, 1-[1-(4'-fluoro-1,1'-biphenyl-4-yl)-2-(4-methylpiperazin-1-yl)ethyl]cyclohexanol dihydrochloride was prepared from 1-[1-(4-bromophenyl)-2-(4-methylpiperazin-1-yl)ethyl]cyclohexanol using 4-fluorophenylboronic acid. Salt formation: A solution of 1-[1-(4'-fluoro-1,1'-biphenyl-4-yl)-2-(4-methylpiperazin-1-yl)ethyl]cyclohexanol, in diethyl ether (2 mL) was treated with a 4 N solution of hydrogen chloride in dioxane (1 mL) and stored in the refrigerator for 16 h. The resulting crystals were collected, washed with diethyl ether, and dried in vacuo to yield 1-[1-(4'-fluoro-1,1'-biphenyl-4-yl)-2-(4-methylpiperazin-1-yl)ethyl]cyclohexanol dihydrochloride. MS (ESI) m/z 397 ([M+H]$^+$); HRMS: calcd for $C_{25}H_{33}FN_2O \cdot 2.00$ HCl, 468.2110; found (ESI), 397.2639

Example 181

1-[1-(4'-methyl-1,1'-biphenyl-4-yl)-2-(4-methylpiperazin-1-yl)ethyl]cyclohexanol dihydrochloride

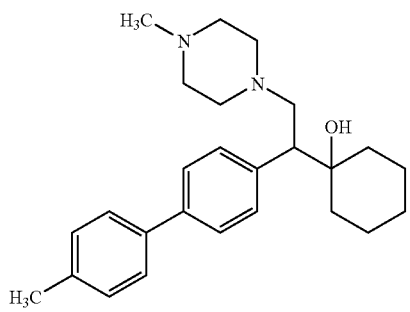

In an analogous manner to Example 135, step 3, 1-[1-(4'-methyl-1,1'-biphenyl-4-yl)-2-(4-methylpiperazin-1-yl)ethyl]cyclohexanol dihydrochloride was prepared from 1-(4-bromophenyl)-2-(4-methylpiperazin-1-yl)ethyl]cyclohexanol (see Example 180, step 3) using 4-tolylboronic acid. Salt formation: A solution of 1-[1-(4'-methyl-1,1'-biphenyl-4-yl)-2-(4-methylpiperazin-1-yl)ethyl]cyclohexanol, in diethyl ether (2 mL) was treated with a 4 N solution of hydrogen chloride in dioxane (1 mL) and stored in the refrigerator for 16 h. The resulting crystals were collected, washed with diethyl ether, and dried in vacuo to yield 1-[1-(4'-methyl-1,1'-biphenyl-4-yl)-2-(4-methylpiperazin-1-yl)ethyl]cyclohexanol dihydrochloride. MS (ESI) m/z 393 ([M+H]$^+$); HRMS: calcd for $C_{26}H_{36}N_2O.2.00$ HCl, 464.2361; found (ESI), 393.2913.

Example 182

1-[1-(3'-chloro-1,1'-biphenyl-4-yl)-2-piperazin-1-ylethyl]cyclobutanol dihydrochloride

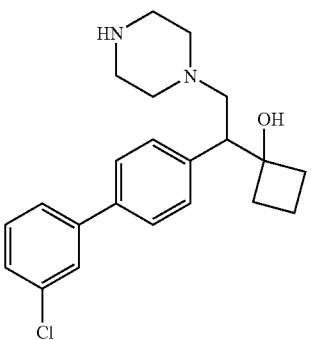

In an analogous manner to Example 1, step 1, tert-butyl 4-[(4-bromophenyl)(1-hydroxycyclobutyl)acetyl]piperazine-1-carboxylate was prepared from (4-bromophenyl)(1-hydroxycyclobutyl)acetic acid (Reference Example 1-ww) and tert-butyl 1-piperazinecarboxylate. MS (ESI) m/z 453/455 ([M+H]$^+$).

In an analogous manner to Example 135, step 2, tert-butyl 4-[2-(4-bromophenyl)-2-(1-hydroxycyclobutyl)ethyl]piperazine-1-carboxylate was prepared from tert-butyl 4-[(4-bromophenyl)(1-hydroxycyclobutyl)acetyl]piperazine-1-carboxylate. MS (ESI) m/z 439/441 ([M+H]$^+$).

In an analogous manner to Example 135, step 3, tert-butyl 4-[2-(3'-chloro-1,1'-biphenyl-4-yl)-2-(1-hydroxycyclobutyl)ethyl]piperazine-1-carboxylate was prepared from tert-butyl 4-[2-(4-bromophenyl)-2-(1-hydroxycyclobutyl)ethyl]piperazine-1-carboxylate using 3-chlorophenylboronic acid. MS (ES) m/z 471.3 ([M+H]$^+$); HRMS: calcd for $C_{27}H_{35}ClN_2O_3$, 470.2336; found (ESI), 471.2405.

In an analogous manner to Example 135, step 4, 1-[1-(3'-chloro-1,1'-biphenyl-4-yl)-2-piperazin-1-ylethyl]cyclobutanol dihydrochloride was prepared from tert-butyl 4-[2-(3'-chloro-1,1'-biphenyl-4-yl)-2-(1-hydroxycyclobutyl)ethyl]piperazine-1-carboxylate. MS (ES) m/z 371.3 ([M+H]$^+$); HRMS: calcd for $C_{22}H_{27}ClN_2O.2.00$ HCl, 442.1345; found (ESI), 371.1897.

Example 183

1-{2-piperazin-1-yl-1-[3'-(trifluoromethoxy)-1,1'-biphenyl-4-yl]ethyl}cyclobutanol dihydrochloride

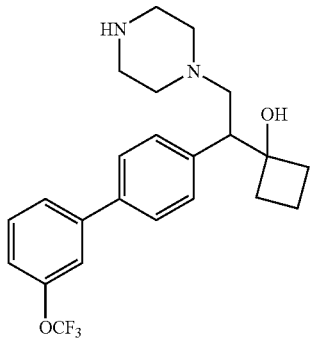

In an analogous manner to Example 135, step 3, tert-butyl 4-{2-(1-hydroxycyclobutyl)-2-[3'-(trifluoromethoxy)-1,1'-biphenyl-4-yl]ethyl}piperazine-1-carboxylate was prepared from tert-butyl 4-[2-(4-bromophenyl)-2-(1-hydroxycyclobutyl)ethyl]piperazine-1-carboxylate (see Example 182, step 2) using 3-trifluoromethoxyphenylboronic acid. MS (ES) m/z 521.4 ([M+H]$^+$); HRMS: calcd for $C_{28}H_{35}F_3N_2O_4$, 520.2549; found (ESI), 521.2639.

In an analogous manner to Example 135, step 4, 1-{2-piperazin-1-yl-1-[3'-(trifluoromethoxy)-1,1'-biphenyl-4-yl]ethyl}cyclobutanol dihydrochloride was prepared from tert-butyl 4-{2-(1-hydroxycyclobutyl)-2-[3'-(trifluoromethoxy)-1,1'-biphenyl-4-yl]ethyl}piperazine-1-carboxylate. MS (ES) m/z 421.3 ([M+H]$^+$); HRMS: calcd for $C_{23}H_{27}F_3N_2O_2.2.00$ HCl, 492.1558; found (ESI), 421.2097.

Example 184

1-[1-(3',4'-dichloro-1,1'-biphenyl-4-yl)-2-piperazin-1-ylethyl]cyclobutanol dihydrochloride

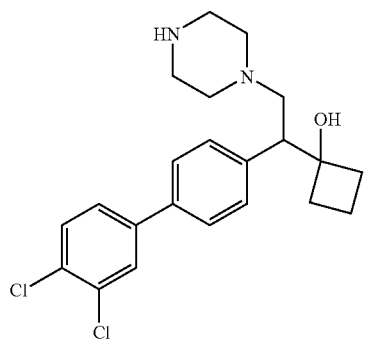

In an analogous manner to Example 135, step 3, tert-butyl 4-[2-(3',4'-dichloro-1,1'-biphenyl-4-yl)-2-(1-hydroxycyclobutyl)ethyl]piperazine-1-carboxylate was prepared from tert-butyl 4-[2-(4-bromophenyl)-2-(1-hydroxycyclobutyl)ethyl]piperazine-1-carboxylate (see Example 182, step 2) using 3,4-dichlorophenylboronic acid. MS (ES) m/z 505.3 ([M+H]$^+$); HRMS: calcd for $C_{27}H_{34}Cl_2N_2O_3$, 504.1946; found (ESI), 505.2036.

In an analogous manner to Example 135, step 4, 1-[1-(3',4'-dichloro-1,1'-biphenyl-4-yl)-2-piperazin-1-ylethyl]cyclobutanol dihydrochloride was prepared from tert-butyl 4-[2-(3',4'-dichloro-1,1'-biphenyl-4-yl)-2-(1-hydroxycyclobutyl)ethyl]piperazine-1-carboxylate. MS (ES) m/z 405.3 ([M+H]$^+$); HRMS: calcd for $C_{22}H_{26}Cl_2N_2O.2.00$ HCl, 476.0956; found (ESI), 405.1486.

Example 185

1-[1-(3',5'-dichloro-1,1'-biphenyl-4-yl)-2-piperazin-1-ylethyl]cyclobutanol dihydrochloride

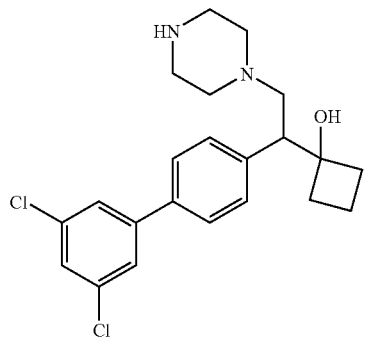

In an analogous manner to Example 135, step 3, tert-butyl 4-[2-(3',5'-dichloro-1,1'-biphenyl-4-yl)-2-(1-hydroxycyclobutyl)ethyl]piperazine-1-carboxylate was prepared from tert-butyl 4-[2-(4-bromophenyl)-2-(1-hydroxycyclobutyl)ethyl]piperazine-1-carboxylate (see Example 182, step 2) using 3,5-dichlorophenylboronic acid. MS (ES) m/z 505.2 ([M+H]$^+$); HRMS: calcd for $C_{27}H_{34}Cl_2N_2O_3$, 504.1946; found (ESI), 505.2007;

In an analogous manner to Example 135, step 4, 1-[1-(3',5'-dichloro-1,1'-biphenyl-4-yl)-2-piperazin-1-ylethyl]cyclobutanol dihydrochloride was prepared from tert-butyl 4-[2-(3',5'-dichloro-1,1'-biphenyl-4-yl)-2-(1-hydroxycyclobutyl)ethyl]piperazine-1-carboxylate. MS (ES) m/z 405.2 ([M+H]$^+$); HRMS: calcd for $C_{22}H_{26}Cl_2N_2O.2.00$ HCl, 476.0956; found (ESI), 405.151.

Example 186

1-{2-[(3R)-3-(methylamino)piperidin-1-yl]-1-[3-(trifluoromethoxy)phenyl]ethyl}cyclohexanol dihydrochloride

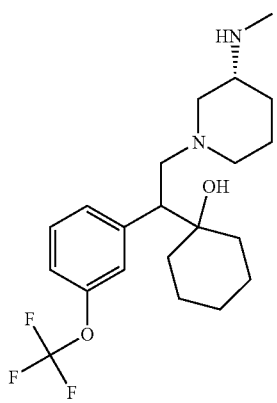

In an analogous manner to Example 1, step 1 tert-butyl ((3R)-1-{(1-hydroxycyclohexyl)[3-(trifluoromethoxy)phenyl]acetyl}piperidin-3-yl)carbamate was prepared from (1-hydroxycyclohexyl)[3-(trifluoromethoxy)phenyl]acetic acid (Reference Example 1-f) and (R)-(+)-3-t-butoxycarbonylaminopiperidine (Moon, S.; Lee, S., Synth. Commun. 1998, 28(21), 3919-3926.) MS (ES) m/z 501.1

In an analogous manner to Example 13, step 2 1-{2-[(3R)-3-(methylamino)piperidin-1-yl]-1-[3-(trifluoromethoxy)phenyl]ethyl}cyclohexanol dihydrochloride was prepared from tert-butyl ((3R)-1-{(1-hydroxycyclohexyl)[3-(trifluoromethoxy)phenyl]acetyl}piperidin-3-yl)carbamate. MS m/z 401; HRMS: calcd for $C_{21}H_{31}F_3N_2O_2$+H, 401.24159; found (ESI, [M+H]$^+$), 401.2406.

Example 187

1-{2-[(3R)-3-aminopiperidin-1-yl]-1-[3-(trifluoromethoxy)phenyl]ethyl}cyclohexanol dihydrochloride

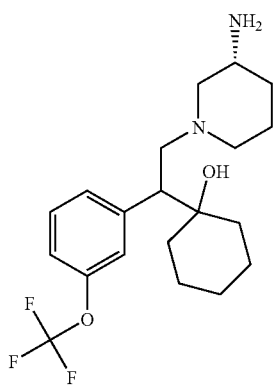

In an analogous manner to Example 1, step 1 tert-butyl ((3R)-1-{(1-hydroxycyclohexyl)[3-(trifluoromethoxy)phenyl]acetyl}piperidin-3-yl)carbamate was prepared from (1-hydroxycyclohexyl)[3-(trifluoromethoxy)phenyl]acetic acid (Reference Example 1-f) and (R)-(+)-3-t-butoxycarbonylaminopiperidine (Moon, S.; Lee, S., Synth. Commun. 1998, 28(21), 3919-3926.) MS (ES) m/z 501.1

In an analogous manner to Example 1, step 2 1-{2-[(3R)-3-aminopiperidin-1-yl]-1-[3-(trifluoromethoxy)phenyl]ethyl}cyclohexanol dihydrochloride was prepared from tert-butyl ((3R)-1-{(1-hydroxycyclohexyl)[3-(trifluoromethoxy)phenyl]acetyl}piperidin-3-yl)carbamate. HRMS: calcd for $C_{20}H_{29}F_3N_2O_2$+H, 387.22594; found (ESI, [M+H]+), 387.2248.

Example 188

1-{2-[(3R)-3-(dimethylamino)piperidin-1-yl]-1-[3-(trifluoromethoxy)phenyl]ethyl}cyclohexanol dihydrochloride

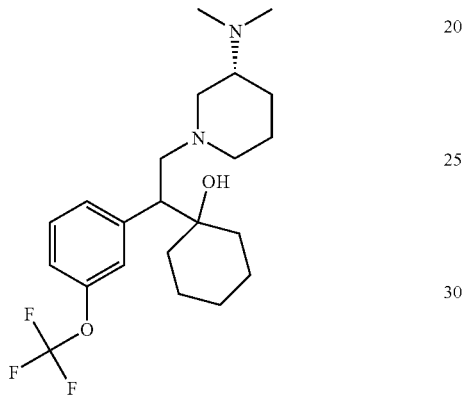

In an analogous manner to Example 36, 1-{2-[(3R)-3-(dimethylamino)piperidin-1-yl]-1-[3-(trifluoromethoxy)phenyl]ethyl}cyclohexanol dihydrochloride was prepared from 1-{2-[(3R)-3-aminopiperidin-1-yl]-1-[3-(trifluoromethoxy)phenyl]ethyl}cyclohexanol (See Example 187). MS (ESI) m/z 415; HRMS: calcd for $C_{22}H_{33}F_3N_2O_2$+H, 415.25724; found (ESI, [M+H]+), 415.2596.

Example 189

1-{2-[(3S)-3-(methylamino)piperidin-1-yl]-1-[3-(trifluoromethoxy)phenyl]ethyl}cyclohexanol dihydrochloride

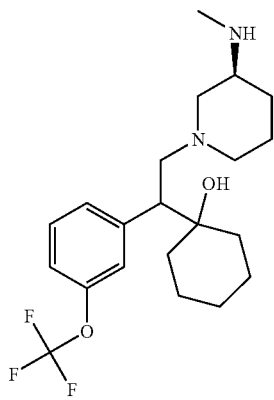

In an analogous manner to Example 1, step 1, tert-butyl ((3S)-1-{(1-hydroxycyclohexyl)[3-(trifluoromethoxy)phenyl]acetyl}piperidin-3-yl)carbamate was prepared from (1-hydroxycyclohexyl)[3-(trifluoromethoxy)phenyl]acetic acid (Reference Example 1-f) and (S)-(+)-3-t-butoxycarbonylaminopiperidine (Moon, S.; Lee, S., Synth. Commun. 1998, 28(21), 3919-3926.) MS (ES) m/z 501.1

In an analogous manner to Example 13, step 2, 1-{2-[(3S)-3-(methylamino)piperidin-1-yl]-1-[3-(trifluoromethoxy)phenyl]ethyl}cyclohexanol dihydrochloride was prepared from tert-butyl ((3S)-1-{(1-hydroxycyclohexyl)[3-(trifluoromethoxy)phenyl]acetyl}piperidin-3-yl)carbamate. MS m/z 401; HRMS: calcd for $C_{21}H_{31}F_3N_2O_2$+H, 401.24159; found (ESI, [M+H]+), 401.2419.

Example 190

1-{2-[(3S)-3-aminopiperidin-1-yl]-1-[3-(trifluoromethoxy)phenyl]ethyl}cyclohexanol dihydrochloride

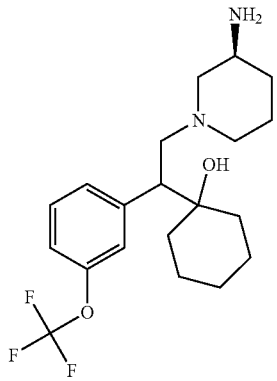

In an analogous manner to Example 1, step 1, tert-butyl ((3S)-1-{(1-hydroxycyclohexyl) [3-(trifluoromethoxy)phenyl]acetyl}piperidin-3-yl)carbamate was prepared from (1-hydroxycyclohexyl)[3-(trifluoromethoxy)phenyl]acetic acid (Reference Example 1-f) and (S)-(+)-3-t-butoxycarbonylaminopiperidine (Moon, S.; Lee, S., Synth. Commun. 1998, 28(21), 3919-3926.) MS (ES) m/z 501.1

In an analogous manner to Example 1, step 2, 1-{2-[(3S)-3-aminopiperidin-1-yl]-1-[3-(trifluoromethoxy)phenyl]ethyl}cyclohexanol dihydrochloride was prepared from tert-butyl ((3R)-1-{(1-hydroxycyclohexyl)[3-(trifluoromethoxy)phenyl]acetyl}piperidin-3-yl)carbamate. HRMS: calcd for $C_{20}H_{29}F_3N_2O_2$+H, 387.22594; found (ESI, [M+H]+), 387.2248.

Example 191

1-{2-[(3S)-3-(dimethylamino)piperidin-1-yl]-1-[3-(trifluoromethoxy)phenyl]ethyl}cyclohexanol dihydrochloride

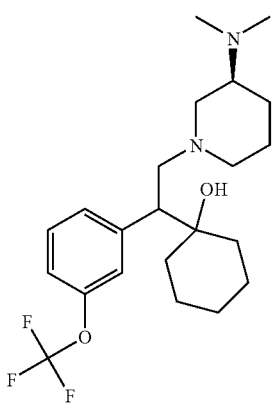

In an analogous manner to Example 36, 1-{2-[(3S)-3-(dimethylamino)piperidin-1-yl]-1-[3-(trifluoromethoxy)phenyl]ethyl}cyclohexanol dihydrochloride was prepared from 1-{2-[(3S)-3-aminopiperidin-1-yl]-1-[3-(trifluoromethoxy)phenyl]ethyl}cyclohexanol (See Example 190). MS (ESI) m/z 415; HRMS: calcd for $C_{22}H_{33}F_3N_2O_2+H$, 415.25724; found (ESI, [M+H]$^+$), 415.2549.

Example 192

1-{1-[4-(benzyloxy)-3-chlorophenyl]-2-[(3a)-3-(methylamino)piperidin-1-yl]ethyl}cyclohexanol dihydrochloride

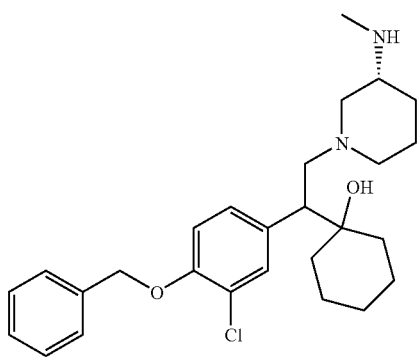

In an analogous manner to Example 1, step 1, tert-butyl {(3R)-1-[[4-(benzyloxy)-3-chlorophenyl](1-hydroxycyclohexyl)acetyl]piperidin-3-yl}carbamate was prepared from [4-(benzyloxy)-3-chlorophenyl](1-hydroxycyclohexyl)acetic acid (Reference Example 1-eee) and (R)-(+)-3-t-butoxycarbonylaminopiperidine (Moon, S.; Lee, S., Synth. Commun. 1998, 28(21), 3919-3926.) MS (ES) m/z 557.1

In an analogous manner to Example 13, step 2, 1-{1-[4-(benzyloxy)-3-chlorophenyl]-2-[(3R)-3-(methylamino)piperidin-1-yl]ethyl}cyclohexanol dihydrochloride was prepared from tert-butyl {(3R)-1-[[4-(benzyloxy)-3-chlorophenyl](1-hydroxycyclohexyl)acetyl]piperidin-3-yl}carbamate. MS m/z 457; HRMS: calcd for $C_{27}H_{37}ClN_2O_2+H$, 457.26218; found (ESI, [M+H]$^+$), 457.2622.

Example 193

1-{2-[(3R)-3-aminopiperidin-1-yl]-1-[4-(benzyloxy)-3-chlorophenyl]ethyl}cyclohexanol dihydrochloride

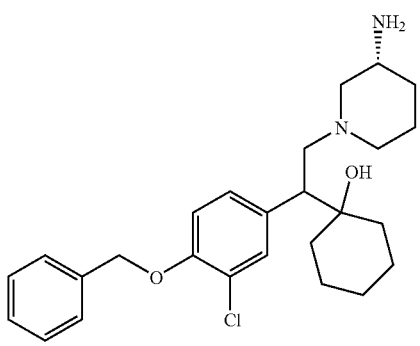

In an analogous manner to Example 1, step 1, tert-butyl {(3R)-1-[[4-(benzyloxy)-3-chlorophenyl](1-hydroxycyclohexyl)acetyl]piperidin-3-yl}carbamate was prepared from [4-(benzyloxy)-3-chlorophenyl](1-hydroxycyclohexyl)acetic acid (Reference Example 1-eee) and (R)-(+)-3-t-butoxycarbonylaminopiperidine (Moon, S.; Lee, S., Synth. Commun. 1998, 28(21), 3919-3926.) MS (ES) m/z 557.1

In an analogous manner to Example 1, step 2, 1-{2-[(3R)-3-aminopiperidin-1-yl]-1-[4-(benzyloxy)-3-chlorophenyl]ethyl}cyclohexanol dihydrochloride was prepared from tert-butyl {(3R)-1-[[4-(benzyloxy)-3-chlorophenyl](1-hydroxycyclohexyl)acetyl]piperidin-3-yl}carbamate. MS m/z 443; HRMS: calcd for $C_{26}H_{35}ClN_2O_2+H$, 443.24653; found (ESI, [M+H]$^+$), 443.2487.

Example 194

1-{1-[4-(benzyloxy)-3-chlorophenyl]-2-[(3R)-3-(dimethylamino)piperidin-1-yl]ethyl}cyclohexanol dihydrochloride

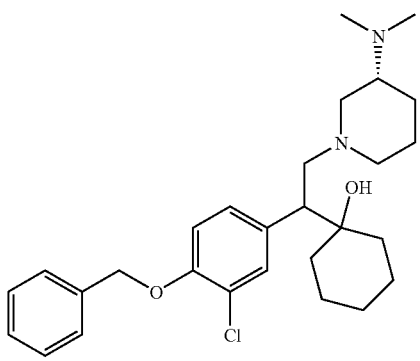

In an analogous manner to Example 36, 1-{1-[4-(benzyloxy)-3-chlorophenyl]-2-[(3R)-3-(dimethylamino)piperidin-1-yl]ethyl}cyclohexanol dihydrochloride was prepared from 1-{2-[(3R)-3-aminopiperidin-1-yl]-1-[4-(benzyloxy)-3-chlorophenyl]ethyl}cyclohexanol_(See Example 193). MS (ESI) m/z 415; HRMS: calcd for $C_{28}H_{39}ClN_2O_2$+H, 471.27783; found (ESI, [M+H]$^+$), 471.2767.

Example 195

1-{1-[4-(benzyloxy)-3-chlorophenyl]-2-[(3S)-3-(methylamino)piperidin-1-yl]ethyl}cyclohexanol dihydrochloride

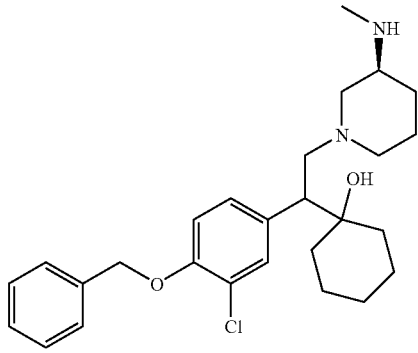

In an analogous manner to Example 1, step 1, tert-butyl {(3S)-1-[[4-(benzyloxy)-3-chlorophenyl](1-hydroxycyclohexyl)acetyl]piperidin-3-yl}carbamate was prepared from [4-(benzyloxy)-3-chlorophenyl](1-hydroxycyclohexyl)acetic acid (Reference Example 1-eee) and (S)-(+)-3-t-butoxycarbonylaminopiperidine (Moon, S.; Lee, S., Synth. Commun. 1998, 28(21), 3919-3926.) MS (ES) m/z 557.1

In an analogous manner to Example 13, step 2, 1-{1-[4-(benzyloxy)-3-chlorophenyl]-2-[(3S)-3-(methylamino)piperidin-1-yl]ethyl}cyclohexanol dihydrochloride was prepared from tert-butyl {(3S)-1-[[4-(benzyloxy)-3-chlorophenyl](1-hydroxycyclohexyl)acetyl]piperidin-3-yl}carbamate MS m/z 457; HRMS: calcd for $C_{27}H_{37}ClN_2O_2$+H, 457.26218; found (ESI, [M+H]$^+$), 457.2619

Example 196

1-{2-[(3S)-3-aminopiperidin-1-yl]-1-[4-(benzyloxy)-3-chlorophenyl]ethyl}cyclohexanol dihydrochloride

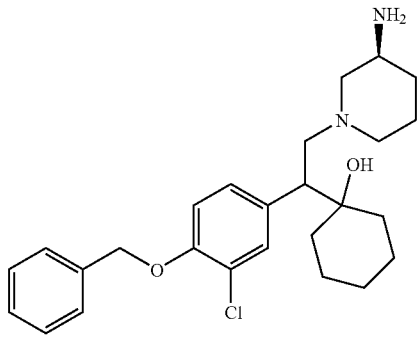

In an analogous manner to Example 1, step 1, tert-butyl {(3S)-1-[[4-(benzyloxy)-3-chlorophenyl](1-hydroxycyclohexyl)acetyl]piperidin-3-yl}carbamate was prepared from [4-(benzyloxy)-3-chlorophenyl](1-hydroxycyclohexyl)acetic acid (Reference Example 1-eee) and (S)-(+)-3-t-butoxycarbonylaminopiperidine (Moon, S.; Lee, S., Synth. Commun. 1998, 28(21), 3919-3926.) MS (ES) m/z 557.1

In an analogous manner to Example 1, step 2, 1-{2-[(3S)-3-aminopiperidin-1-yl]-1-[4-(benzyloxy)-3-chlorophenyl]ethyl}cyclohexanol dihydrochloride was prepared from tert-butyl {(3S)-1-[[4-(benzyloxy)-3-chlorophenyl](1-hydroxycyclohexyl)acetyl]piperidin-3-yl}carbamate. MS m/z 443; HRMS: calcd for $C_{26}H_{35}ClN_2O_2$+H, 443.24653; found (ESI, [M+H]$^+$), 443.2482.

Example 197

1-{1-[4-(benzyloxy)-3-chlorophenyl]-2-[(3S)-3-(dimethylamino)piperidin-1-yl]-ethyl}cyclohexanol dihydrochloride

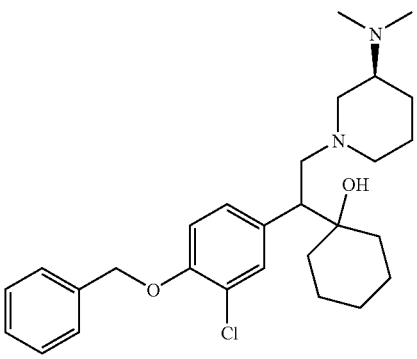

In an analogous manner to Example 36, 1-{1-[4-(benzyloxy)-3-chlorophenyl]-2-[(3S)-3-(dimethylamino)piperidin-1-yl]ethyl}cyclohexanol dihydrochloride was prepared from 1-{2-[(3S)-3-aminopiperidin-1-yl]-1-[4-(benzyloxy)-3-chlorophenyl]ethyl}cyclohexanol_(See Example 196). HRMS: calcd for $C_{28}H_{39}ClN_2O_2$+H, 471.27783; found (ESI, [M+H]$^+$), 471.2766.

Example 198

1-1-{1-(3-chlorophenyl)-2-[(3S)-3-(methylamino)pyrrolidin-1-yl]ethyl}cyclohexanol dihydrochloride

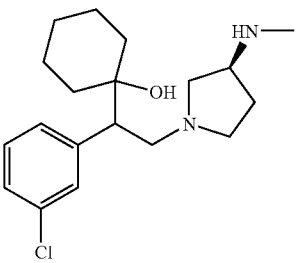

In an analogous manner to Example 1, step 1, tert-butyl {(3S)-1-[(3-chlorophenyl)(1-hydroxycyclohexyl)acetyl]pyrrolidin-3-yl}carbamate was prepared from (3-chlorophenyl)(1-hydroxycyclohexyl)acetic acid (Reference Example 1a) and (3S)-(−)-3-(tert-butoxycarbonylamino)pyrrolidine. MS (ES) m/z 437.0

In an analogous manner to Example 13, step 2, 1-{1-(3-chlorophenyl)-2-[(3S)-3-(methylamino)pyrrolidin-1-yl]ethyl}cyclohexanol dihydrochloride was prepared from tert-butyl {(3S)-1-[(3-chlorophenyl)(1-hydroxycyclohexyl)acetyl]pyrrolidin-3-yl}carbamate MS (ES) m/z 337.2; HRMS: calcd for $C_{19}H_{29}ClN_2O+H$, 337.20467; found (ESI, [M+H]$^+$), 337.2034.

Example 199

1-{1-(3-chlorophenyl)-2-[(3S)-3-(dimethylamino)pyrrolidin-1-yl]ethyl}cyclohexanol dihydrochloride

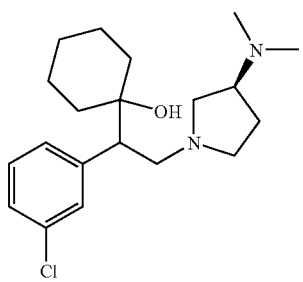

In an analogous manner to Example 36, 1-{1-(3-chlorophenyl)-2-[(3S)-3-(dimethylamino)pyrrolidin-1-yl]ethyl}cyclohexanol dihydrochloride was prepared from 1-{1-(3-chlorophenyl)-2-[(3S)-3-(methylamino)pyrrolidin-1-yl]ethyl}cyclohexanol (See Example 198). MS (ES) m/z 351.1; HRMS: calcd for $C_{20}H_{31}ClN_2O+H$, 351.22031; found (ESI, [M+H]$^+$), 351.2189.

Example 200

1-{1-(3-chlorophenyl)-2-[(3R)-3-(methylamino)pyrrolidin-1-yl]ethyl}cyclohexanol dihydrochloride

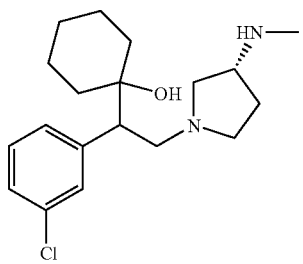

In an analogous manner to Example 1 step 1, tert-butyl {(3R)-1-[(3-chlorophenyl)(1-hydroxycyclohexyl)acetyl]pyrrolidin-3-yl}carbamate was prepared from (3-chlorophenyl)(1-hydroxycyclohexyl)acetic acid (Reference Example 1a) and (3R)-(−)-3-(tert-butoxycarbonylamino)pyrrolidine. MS m/z 437

In an analogous manner to Example 13, step 2, 1-{1-(3-chlorophenyl)-2-[(3R)-3-(methylamino)pyrrolidin-1-yl]ethyl}cyclohexanol dihydrochloride was prepared from tert-butyl {(3R)-1-[(3-chlorophenyl)(1-hydroxycyclohexyl)acetyl]pyrrolidin-3-yl}carbamate MS (ES) m/z 337.1; HRMS: calcd for $C_{19}H_{29}ClN_2O+H$, 337.20467; found (ESI, [M+H]$^+$), 337.2043.

Example 201

1-[2-[(3R)-3-aminopyrrolidin-1-yl]-1-(3-chlorophenyl)ethyl]cyclohexanol dihydrochloride

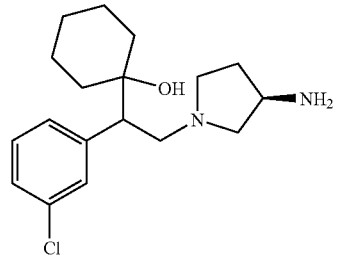

In an analogous manner to Example 1, step 1, tert-butyl {(3R)-1-[(3-chlorophenyl)(1-hydroxycyclohexyl)acetyl]pyrrolidin-3-yl}carbamate was prepared from (3-chlorophenyl)(1-hydroxycyclohexyl)acetic acid (Reference Example 1a) and (3R)-(−)-3-(tert-butoxycarbonylamino)pyrrolidine. MS m/z 437

In an analogous manner to Example 1, step 2, 1-[2-[(3R)-3-aminopyrrolidin-1-yl]-1-(3-chlorophenyl)ethyl]cyclohexanol dihydrochloride was prepared from tert-butyl {(3R)-1-[(3-chlorophenyl)(1-hydroxycyclohexyl)acetyl]pyrrolidin-3-yl}carbamate MS (ESI) m/z 323; HRMS: calcd for $C_{18}H_{27}ClN_2O+H$, 323.18901; found (ESI, [M+H]$^+$), 323.1895.

Example 202

1-{1-(3-chlorophenyl)-2-[(3R)-3-(dimethylamino)pyrrolidin-1-yl]ethyl}cyclohexanol dihydrochloride

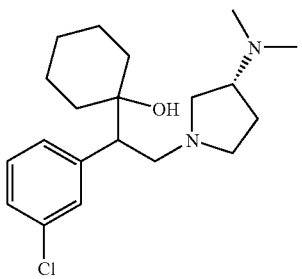

In an analogous manner to Example 36, 1-{1-(3-chlorophenyl)-2-[(3R)-3-(dimethylamino)pyrrolidin-1-yl]ethyl}cyclohexanol dihydrochloride was prepared from 1-[2-[(3R)-3-aminopyrrolidin-1-yl]-1-(3-chlorophenyl)ethyl]cyclohexanol (See Example 201). MS (ESI) m/z 351; HRMS: calcd for $C_{20}H_{31}ClN_2O+H$, 351.22031; found (ESI, [M+H]$^+$), 351.2193.

Example 203

1-[2-[(3S)-3-(methylamino)pyrrolidin-1-yl]-1-(2-naphthyl)ethyl]cyclohexanol dihydrochloride

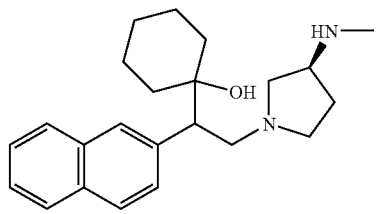

In an analogous manner to Example 1, step 1, tert-butyl {(3S)-1-[(1-hydroxycyclohexyl)(2-naphthyl)acetyl]pyrrolidin-3-yl}carbamate was prepared from (1-hydroxycyclohexyl)(2-naphthyl)acetic acid (Reference Example 1q) and (3S)-(−)-3-(tert-butoxycarbonylamino)pyrrolidine. MS m/z 437

In an analogous manner to Example 13, step 2, 1-[2-[(3S)-3-(methylamino)pyrrolidin-1-yl]-1-(2-naphthyl)ethyl]cyclohexanol dihydrochloride was prepared from tert-butyl {(3S)-1-[(1-hydroxycyclohexyl)(2-naphthyl)acetyl]pyrrolidin-3-yl}carbamate MS (ESI) m/z 353; HRMS: calcd for $C_{23}H_{32}N_2O+H$, 353.25929; found (ESI, [M+H]$^+$), 353.2582.

Example 204

1-[2-[(3S)-3-aminopyrrolidin-1-yl]-1-(2-naphthyl)ethyl]cyclohexanol dihydrochloride

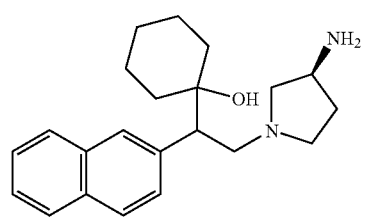

In an analogous manner to Example 1, step 1, tert-butyl {(3S)-1-[(1-hydroxycyclohexyl)(2-naphthyl)acetyl]pyrrolidin-3-yl}carbamate was prepared from (1-hydroxycyclohexyl)(2-naphthyl)acetic acid (Reference Example 1q) and (3S)-(−)-3-(tert-butoxycarbonylamino)pyrrolidine. MS m/z 437

In an analogous manner to Example 1, step 2, 1-[2-[(3S)-3-aminopyrrolidin-1-yl]-1-(2-naphthyl)ethyl]cyclohexanol dihydrochloride was prepared from tert-butyl {(3S)-1-[(1-hydroxycyclohexyl)(2-naphthyl)acetyl]pyrrolidin-3-yl}carbamate MS (ESI) m/z 339; HRMS: calcd for $C_{22}H_{30}N_2O+H$, 339.24364; found (ESI, [M+H]$^+$), 339.2441.

Example 205

1-[2-[(3S)-3-(dimethylamino)pyrrolidin-1-yl]-1-(2-naphthyl)ethyl]cyclohexanol dihydrochloride

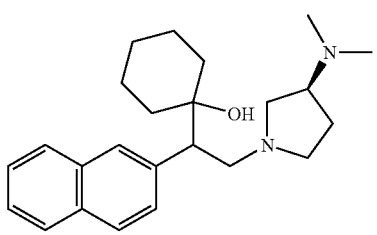

In an analogous manner to Example 36, 1-[2-[(3S)-3-(dimethylamino)pyrrolidin-1-yl]-1-(2-naphthyl)ethyl]cyclohexanol dihydrochloride was prepared from 1-[2-[(3S)-3-aminopyrrolidin-1-yl]-1-(2-naphthyl)ethyl]cyclohexanol (See Example 204). MS (ES) m/z 367.1; HRMS: calcd for $C_{24}H_{34}N_2O+H$, 367.27494; found (ESI, [M+H]$^+$), 367.2729.

Example 206

1-[2-[(3S)-3-(methylamino)pyrrolidin-1-yl]-1-(1-naphthyl)ethyl]cyclohexanol dihydrochloride

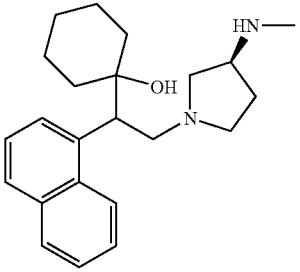

In an analogous manner to Example 1, step 1, tert-butyl {(3S)-1-[(1-hydroxycyclohexyl)(1-naphthyl)acetyl]pyrrolidin-3-yl}carbamate was prepared from (1-hydroxycyclohexyl)(1-naphthyl)acetic acid (Reference Example 1-e) and (3S)-(−)-3-(tert-butoxycarbonylamino)pyrrolidine. MS (ES) m/z 453.2

In an analogous manner to Example 13, step 2, 1-[2-[(3S)-3-(methylamino)pyrrolidin-1-yl]-1-(1-naphthyl)ethyl]cyclohexanol dihydrochloride was prepared from tert-butyl {(3S)-1-[(1-hydroxycyclohexyl)(1-naphthyl)acetyl]pyrrolidin-3-yl}carbamate MS (ESI) m/z 353; HRMS: calcd for $C_{23}H_{32}N_2O+H$, 353.25929; found (ESI, [M+H]$^+$), 353.2589.

Example 207

1-[2-[(3S)-3-aminopyrrolidin-1-yl]-1-(1-naphthyl)ethyl]cyclohexanol dihydrochloride

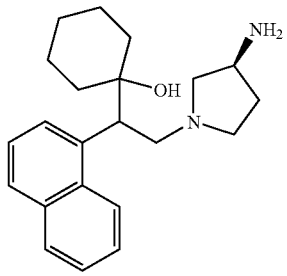

In an analogous manner to Example 1, step 1, tert-butyl {(3S)-1-[(1-hydroxycyclohexyl)(1-naphthyl)acetyl]pyrrolidin-3-yl}carbamate was prepared from (1-hydroxycyclohexyl)(1-naphthyl)acetic acid (Reference Example 1e) and (3S)-(−)-3-(tert-butoxycarbonylamino)pyrrolidine. MS (ES) m/z 453.2

In an analogous manner to Example 1, step 2, 1-[2-[(3S)-3-aminopyrrolidin-1-yl]-1-(1-naphthyl)ethyl]cyclohexanol dihydrochloride was prepared from tert-butyl {(3S)-1-[(1-hydroxycyclohexyl)(1-naphthyl)acetyl]pyrrolidin-3-yl}carbamate MS (ESI) m/z 339; HRMS: calcd for $C_{22}H_{30}N_2O+H$, 339.24364; found (ESI, [M+H]$^+$), 339.2421.

Example 208

1-[2-[(3S)-3-(dimethylamino)pyrrolidin-1-yl]-1-(1-naphthyl)ethyl]cyclohexanol dihydrochloride

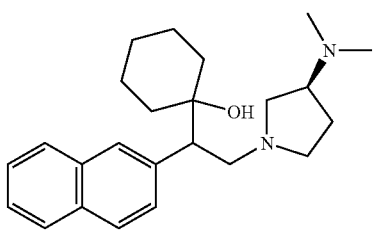

In an analogous manner to Example 36, 1-[2-[(3S)-3-(dimethylamino)pyrrolidin-1-yl]-1-(1-naphthyl)ethyl]cyclohexanol dihydrochloride was prepared from 1-[2-[(3S)-3-aminopyrrolidin-1-yl]-1-(1-naphthyl)ethyl]cyclohexanol (See Example 207). MS (ES) m/z 367.1; HRMS: calcd for $C_{24}H_{34}N_2O+H$, 367.27494; found (ESI, [M+H]$^+$), 367.275.

Example 209

1-{1-[4-(benzyloxy)-3-chlorophenyl]-2-[(3S)-3-(methylamino)pyrrolidin-1-yl]ethyl}cyclohexanol dihydrochloride

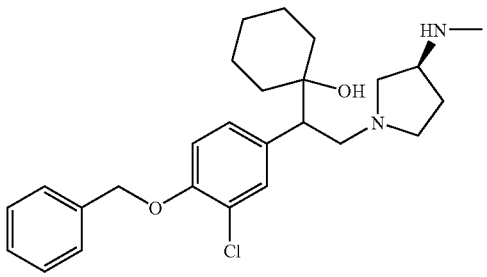

In an analogous manner to Example 1, step 1, tert-butyl {(3S)-1-[[4-(benzyloxy)-3-chlorophenyl](1-hydroxycyclohexyl)acetyl]pyrrolidin-3-yl}carbamate was prepared from [4-(benzyloxy)-3-chlorophenyl](1-hydroxycyclohexyl)acetic acid (Reference Example 1eee) and (3S)-(−)-3-(tert-butoxycarbonylamino)pyrrolidine. MS (ES) m/z 543.0

In an analogous manner to Example 13, step 2, 1-{1-[4-(benzyloxy)-3-chlorophenyl]-2-[(3S)-3-(methylamino)pyrrolidin-1-yl]ethyl}cyclohexanol dihydrochloride was prepared from tert-butyl {(3S)-1-[[4-(benzyloxy)-3-chlorophenyl](1-hydroxycyclohexyl)acetyl]pyrrolidin-3-yl}carbamate MS (ES) m/z 443.1; HRMS: calcd for $C_{26}H_{35}ClN_2O_2+H$, 443.24653; found (ESI, [M+H]$^+$), 443.2449.

Example 210

1-{2-[(3S)-3-aminopyrrolidin-1-yl]-1-[4-(benzyloxy)-3-chlorophenyl]ethyl}cyclohexanol dihydrochloride

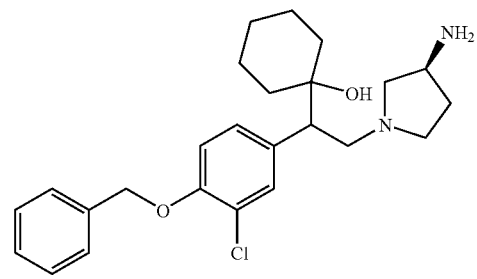

In an analogous manner to Example 1, step 1, tert-butyl {(3S)-1-[[4-(benzyloxy)-3-chlorophenyl](1-hydroxycyclohexyl)acetyl]pyrrolidin-3-yl}carbamate was prepared from [4-(benzyloxy)-3-chlorophenyl](1-hydroxycyclohexyl)acetic acid (Reference Example 1eee) and (3S)-(−)-3-(tert-butoxycarbonylamino)pyrrolidine. MS (ES) m/z 543.

In an analogous manner to Example 1, step 2, 1-{2-[(3S)-3-aminopyrrolidin-1-yl]-1-[4-(benzyloxy)-3-chlorophenyl]ethyl}cyclohexanol dihydrochloride was prepared from tert-butyl {(3S)-1-[[4-(benzyloxy)-3-chlorophenyl](1-hydroxycyclohexyl)acetyl]pyrrolidin-3-yl}carbamate MS (ES) m/z 429.0; HRMS: calcd for $C_{25}H_{33}ClN_2O_2+H$, 429.23088; found (ESI, [M+H]$^+$), 429.232.

Example 211

1-{1-[4-(benzyloxy)-3-chlorophenyl]-2-[(3S)-3-(dimethylamino)pyrrolidin-1-yl]ethyl}cyclohexanol dihydrochloride

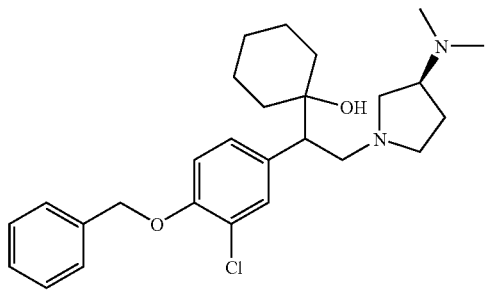

In an analogous manner to Example 36, 1-{1-[4-(benzyloxy)-3-chlorophenyl]-2-[(3S)-3-(dimethylamino)pyrrolidin-1-yl]ethyl}cyclohexanol dihydrochloride was prepared from, 1-{2-[(3S)-3-aminopyrrolidin-1-yl]-1-[4-(benzyloxy)-3-chlorophenyl]ethyl}cyclohexanol_(See Example 210). MS (ES) m/z 457.0; HRMS: calcd for $C_{27}H_{37}ClN_2O_2$+H, 457.26218; found (ESI, [M+H]$^+$), 457.2636.

Example 212

1-{1-[4-(benzyloxy)phenyl]-2-[(3S)-3-(methylamino)pyrrolidin-1-yl]ethyl}cyclohexanol dihydrochloride

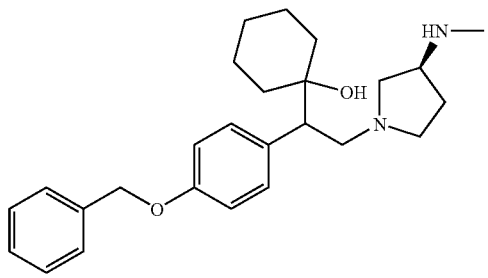

In an analogous manner to Example 1, step 1, tert-butyl {(3S)-1-[[4-(benzyloxy)phenyl](1-hydroxycyclohexyl)acetyl]pyrrolidin-3-yl}carbamate was prepared from (4-benzyloxyphenyl)(1-hydroxycyclohexyl)acetic (Reference Example 1n) and (3S)-(−)-3-(tert-butoxycarbonylamino)pyrrolidine. MS (ES) m/z 509.0

In an analogous manner to Example 13, step 2, 1-{1-[4-(benzyloxy)phenyl]-2-[(3S)-3-(methylamino)pyrrolidin-1-yl]ethyl}cyclohexanol dihydrochloride was prepared from tert-butyl {(3S)-1-[[4-(benzyloxy)phenyl](1-hydroxycyclohexyl)acetyl]pyrrolidin-3-yl}carbamate MS (ES) m/z 409.1; HRMS: calcd for $C_{26}H_{36}N_2O_2$+H, 409.28550; found (ESI, [M+H]$^+$), 409.2841

Example 213

1-{2-[(3S)-3-aminopyrrolidin-1-yl]-1-[4-(benzyloxy)phenyl]ethyl}cyclohexanol dihydrochloride

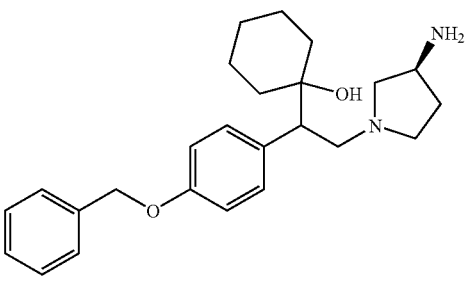

In an analogous manner to Example 1, step 1, tert-butyl {(3S)-1-[[4-(benzyloxy)phenyl](1-hydroxycyclohexyl)acetyl]pyrrolidin-3-yl}carbamate was prepared from (4-benzyloxyphenyl)(1-hydroxycyclohexyl)acetic-(Reference Example 1n) and (3S)-(−)-3-(tert-butoxycarbonylamino)pyrrolidine. MS (ES) m/z 509.0

In an analogous manner to Example 1, step 2, 1-{2-[(3S)-3-aminopyrrolidin-1-yl]-1-[4-(benzyloxy)phenyl]ethyl}cyclohexanol dihydrochloride was prepared from tert-butyl {(3S)-1-[[4-(benzyloxy)phenyl](1-hydroxycyclohexyl)acetyl]pyrrolidin-3-yl}carbamate MS (ES) m/z 395.1; HRMS: calcd for $C_{25}H_{34}N_2O_2$+H, 395.26985; found (ESI, [M+H]$^+$), 395.2696.

Example 214

1-{1-[4-(benzyloxy)phenyl]-2-[(3S)-3-(dimethylamino)pyrrolidin-1-yl]ethyl}cyclohexanol dihydrochloride

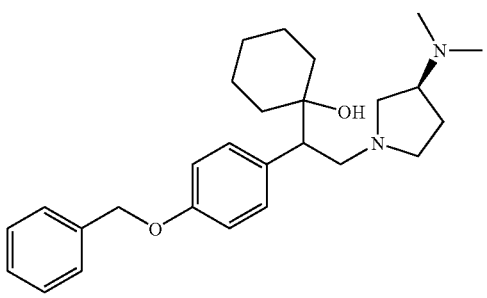

In an analogous manner to Example 36, 1-{1-[4-(benzyloxy)phenyl]-2-[(3S)-3-(dimethylamino)pyrrolidin-1-yl]ethyl}cyclohexanol dihydrochloride was prepared from, 1-{2-[(3S)-3-aminopyrrolidin-1-yl]-1-[4-(benzyloxy)phenyl]ethyl}cyclohexanol (See Example 213). MS (ES) m/z 423.1; HRMS: calcd for $C_{27}H_{38}N_2O_2$+H, 423.30115; found (ESI, [M+H]$^+$), 423.302

Example 215

1-{2-[(3S)-3-(methylamino)pyrrolidin-1-yl]-1-[3-(trifluoromethoxy)phenyl]ethyl}cyclohexanol dihydrochloride

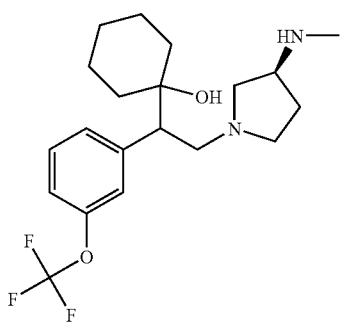

In an analogous manner to Example 1, step 1, tert-butyl ((3S)-1-{(1-hydroxycyclohexyl)[3-(trifluoromethoxy)phenyl]acetyl}pyrrolidin-3-yl)carbamate was prepared from (1-hydroxycyclohexyl)[3-(trifluoromethoxy)phenyl]acetic acid (Reference Example 1f) and (3S)-(−)-3-(tert-butoxycarbonylamino)pyrrolidine. MS (ES) m/z 487.0

In an analogous manner to Example 13, step 2, 1-{2-[(3S)-3-(methylamino)pyrrolidin-1-yl]-1-[3-(trifluoromethoxy)phenyl]ethyl}cyclohexanol dihydrochloride was prepared from tert-butyl ((3S)-1-{(1-hydroxycyclohexyl)[3-(trifluoromethoxy)phenyl]acetyl}pyrrolidin-3-yl)carbamate MS (ES) m/z 387.1; HRMS: calcd for $C_{20}H_{29}F_3N_2O_2$+H, 387.22594; found (ESI, [M+H]$^+$), 387.2255.

Example 216

1-{2-[(3S)-3-aminopyrrolidin-1-yl]-1-[3-(trifluoromethoxy)phenyl]ethyl}cyclohexanol dihydrochloride

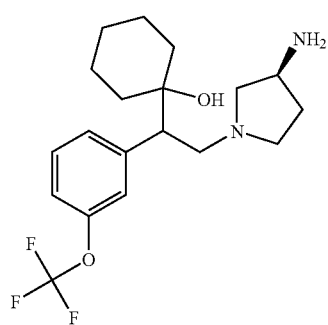

In an analogous manner to Example 1, step 1, tert-butyl ((3S)-1-{(1-hydroxycyclohexyl)[3-(trifluoromethoxy)phenyl]acetyl}pyrrolidin-3-yl)carbamate was prepared from (1-hydroxycyclohexyl)[3-(trifluoromethoxy)phenyl]acetic acid (Reference Example 1f) and (3S)-(−)-3-(tert-butoxycarbonylamino)pyrrolidine. MS (ES) m/z 487.0

In an analogous manner to Example 1, step 2, 1-{2-[(3S)-3-aminopyrrolidin-1-yl]-1-[3-(trifluoromethoxy)phenyl]ethyl}cyclohexanol dihydrochloride was prepared from tert-butyl ((3S)-1-{(1-hydroxycyclohexyl)[3-(trifluoromethoxy)phenyl]acetyl}pyrrolidin-3-yl)carbamate MS (ESI) m/z 373; HRMS: calcd for $C_{19}H_{27}F_3N_2O_2$+H, 373.21029; found (ESI, [M+H]$^+$), 373.2106.

Example 217

1-{2-[(3S)-3-(dimethylamino)pyrrolidin-1-yl]-1-[3-(trifluoromethoxy)phenyl]ethyl}cyclohexanol dihydrochloride

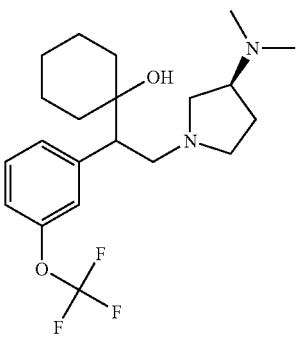

In an analogous manner to Example 36, 1-{2-[(3S)-3-(dimethylamino)pyrrolidin-1-yl]-1-[3-(trifluoromethoxy)phenyl]ethyl}cyclohexanol dihydrochloride was prepared from, 1-{2-[(3S)-3-aminopyrrolidin-1-yl]-1-[3-(trifluoromethoxy)phenyl]ethyl}cyclohexanol (See Example 216). MS (ESI) m/z 401; HRMS: calcd for $C_{21}H_{31}F_3N_2O_2$+H, 401.24159; found (ESI, [M+H]$^+$), 401.2413.

Example 218

1-{2-[(3R)-3-(methylamino)pyrrolidin-1-yl]-1-[3-(trifluoromethoxy)phenyl]ethyl}cyclohexanol dihydrochloride

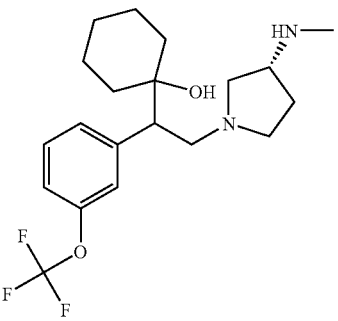

In an analogous manner to Example 1, step 1, tert-butyl ((3R)-1-{(1-hydroxycyclohexyl)[3-(trifluoromethoxy)phenyl]acetyl}pyrrolidin-3-yl)carbamate was prepared from (1-hydroxycyclohexyl)[3-(trifluoromethoxy)phenyl]acetic acid (Reference Example 1f) and (3R)-(−)-3-(tert-butoxycarbonylamino)pyrrolidine. MS (ES) m/z 487.0

In an analogous manner to Example 13, step 2, 1-{2-[(3R)-3-(methylamino)pyrrolidin-1-yl]-1-[3-(trifluoromethoxy)phenyl]ethyl}cyclohexanol dihydrochloride was prepared from tert-butyl ((3R)-1-{(1-hydroxycyclohexyl)[3-(trifluoromethoxy)phenyl]acetyl}pyrrolidin-3-yl)carbamate MS m/z 387; HRMS: calcd for $C_{20}H_{29}F_3N_2O_2$+H, 387.22594; found (ESI, [M+H]+), 387.225.

Example 219

1-{2-[(3R)-3-(dimethylamino)pyrrolidin-1-yl]-1-[3-(trifluoromethoxy)phenyl]ethyl}cyclohexanol dihydrochloride

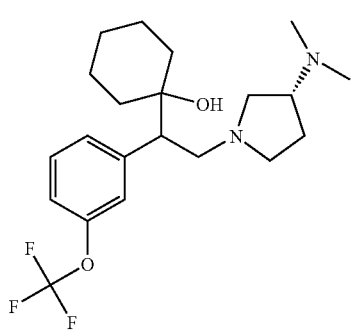

In an analogous manner to Example 36, 1-{2-[(3R)-3-(dimethylamino)pyrrolidin-1-yl]-1-[3-(trifluoromethoxy)phenyl]ethyl}cyclohexanol dihydrochloride was prepared from, 1-{2-[(3R)-3-(methylamino)pyrrolidin-1-yl]-1-[3(trifluoromethoxy)phenyl]ethyl}cyclohexanol (See Example 218). MS (ESI) m/z 401; HRMS: calcd for $C_{21}H_{31}F_3N_2O_2$+H, 401.24159; found (ESI, [M+H]+), 401.2397.

Example 220

1-{2-[(3S)-3-(methylamino)pyrrolidin-1-yl]-1-[3-(trifluoromethyl)phenyl]ethyl}cyclohexanol dihydrochloride

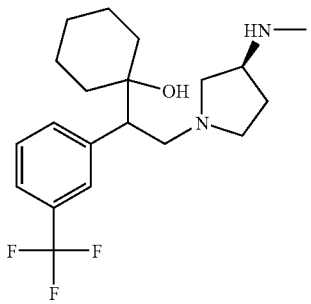

In an analogous manner to Example 1, step 1, tert-butyl ((3S)-1-{(1-hydroxycyclohexyl)[3-(trifluoromethyl)phenyl]acetyl}pyrrolidin-3-yl)carbamate was prepared from (1-hydroxycyclohexyl)[3-(trifluoromethyl)phenyl]acetic acid (Reference Example 1m) and (3S)-(−)-3-(tert-butoxycarbonylamino)pyrrolidine. MS (ES) m/z 471.1

In an analogous manner to Example 13, step 2, 1-{2-[(3S)-3-(methylamino)pyrrolidin-1-yl]-1-[3-(trifluoromethyl)phenyl]ethyl}cyclohexanol dihydrochloride was prepared from tert-butyl ((3S)-1-{(1-hydroxycyclohexyl)[3-(trifluoromethyl)phenyl]acetyl}pyrrolidin-3-yl)carbamate MS (ESI) m/z 371; HRMS: calcd for $C_{20}H_{29}F_3N_2O$+H, 371.23102; found (ESI, [M+H]+), 371.2293.

Example 221

1-{2-[(3S)-3-aminopyrrolidin-1-yl]-1-[3-(trifluoromethyl)phenyl]ethyl}cyclohexanol dihydrochloride

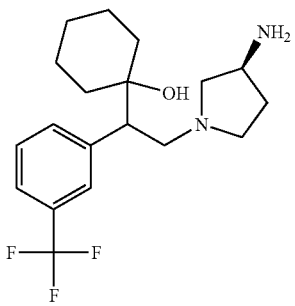

In an analogous manner to Example 1, step 1, tert-butyl ((3S)-1-{(1-hydroxycyclohexyl)-[3-(trifluoromethyl)phenyl]acetyl}pyrrolidin-3-yl)carbamate was prepared from (1-hydroxycyclohexyl)[3-(trifluoromethyl)phenyl]acetic acid (Reference Example 1m) and (3S)-(−)-3-(tert-butoxycarbonylamino)pyrrolidine. MS (ES) m/z 471.1

In an analogous manner to Example 1, step 2, 1-{2-[(3S)-3-aminopyrrolidin-1-yl]-1-[3-(trifluoromethyl)phenyl]ethyl}cyclohexanol dihydrochloride was prepared from tert-butyl ((3S)-1-{(1-hydroxycyclohexyl)[3-(trifluoromethyl)phenyl]acetyl}pyrrolidin-3-yl)carbamate MS (ESI) m/z 357; HRMS: calcd for $C_{19}H_{27}F_3N_2O$+H, 357.21537; found (ESI, [M+H]+), 357.2139.

Example 222

1-{2-[(3S)-3-(dimethylamino)pyrrolidin-1-yl]-1-[3-(trifluoromethyl)phenyl]ethyl}cyclohexanol dihydrochloride

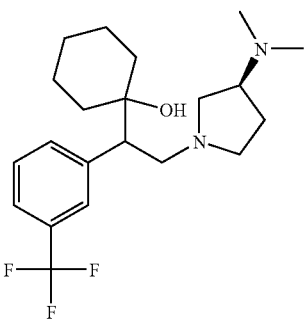

In an analogous manner to Example 36, 1-{2-[(3S)-3-(dimethylamino)pyrrolidin-1-yl]-1-[3-(trifluoromethyl)phenyl]ethyl}cyclohexanol dihydrochloride was prepared from, 1-{2-[(3S)-3-aminopyrrolidin-1-yl]-1-[3-(trifluoromethyl)

Example 223

1-{2-[(3R)-3-(methylamino)pyrrolidin-1-yl]-1-[3-(trifluoromethyl)phenyl]ethyl}cyclohexanol dihydrochloride

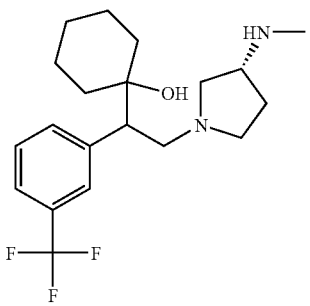

In an analogous manner to Example 1, step 1, tert-butyl ((3R)-1-{(1-hydroxycyclohexyl)[3-(trifluoromethyl)phenyl]acetyl}pyrrolidin-3-yl)carbamate was prepared from (1-hydroxycyclohexyl)[3-(trifluoromethyl)phenyl]acetic acid (Reference Example 1m) and (3R)-(−)-3-(tert-butoxycarbonylamino)pyrrolidine. MS (ES) m/z 471.0

In an analogous manner to Example 13, step 2, 1-{2-[(3R)-3-(methylamino)pyrrolidin-1-yl]-1-[3-(trifluoromethyl)phenyl]ethyl}cyclohexanol dihydrochloride was prepared from tert-butyl ((3R)-1-{(1-hydroxycyclohexyl)[3-(trifluoromethyl)phenyl]acetyl}pyrrolidin-3-yl)carbamate MS (ES) m/z 371.1; HRMS: calcd for $C_{20}H_{29}F_3N_2O$+H, 371.23102; found (ESI, [M+H]+), 371.2296.

Example 224

1-{2-[(3R)-3-aminopyrrolidin-1-yl]-1-[3-(trifluoromethyl)phenyl]ethyl}cyclohexanol dihydrochloride

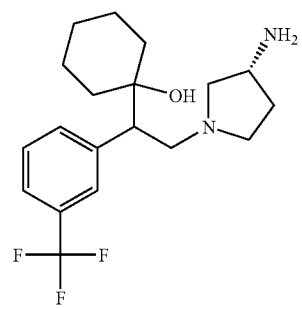

In an analogous manner to Example 1, step 1, tert-butyl ((3R)-1-{(1-hydroxycyclohexyl)[3-(trifluoromethyl)phenyl]acetyl}pyrrolidin-3-yl)carbamate was prepared from (1-hydroxycyclohexyl)[3-(trifluoromethyl)phenyl]acetic acid (Reference Example 1m) and (3R)-(−)-3-(tert-butoxycarbonylamino)pyrrolidine. MS (ES) m/z 471.0

In an analogous manner to Example 1, step 2, 1-{2-[(3R)-3-aminopyrrolidin-1-yl]-1-[3-(trifluoromethyl)phenyl]ethyl}cyclohexanol dihydrochloride was prepared from tert-butyl ((3R)-1-{(1-hydroxycyclohexyl)[3-(trifluoromethyl)phenyl]acetyl}pyrrolidin-3-yl)carbamate MS (ES) m/z 357.1; HRMS: calcd for $C_{19}H_{27}F_3N_2O$+H, 357.21537; found (ESI, [M+H]+), 357.2154.

Example 225

1-{2-[(3R)-3-(dimethylamino)pyrrolidin-1-yl]-1-[3-(trifluoromethyl)phenyl]ethyl}cyclohexanol dihydrochloride

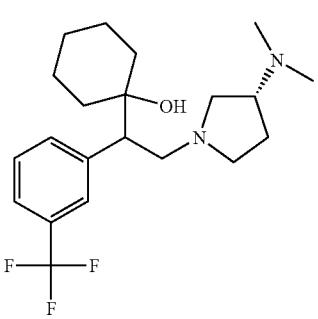

In an analogous manner to Example 36, 1-{2-[(3R)-3-(dimethylamino)pyrrolidin-1-yl]-1-[3-(trifluoromethyl)phenyl]ethyl}cyclohexanol dihydrochloride was prepared from, 1-{2-[(3R)-3-aminopyrrolidin-1-yl]-1-[3-(trifluoromethyl)phenyl]ethyl}cyclohexanol (See Example 224). MS (ESI) m/z 385; HRMS: calcd for $C_{21}H_{31}F_3N_2O$+H, 385.24667; found (ESI, [M+H]+), 385.2454.

Reference Example 2-a

Alkylation Reaction: Preparation of Acid Intermediates

A solution of diisopropylamine (1.80 mL, 12.9 mmol) in dry tetrahydrofuran (6 mL) under nitrogen was cooled to −78° C. and treated dropwise with a solution of n-butyllithium (2.4 M in hexanes, 5.4 mL, 12.9 mmol). The resulting solution was warmed to 0° C. and stirred for 15 min. The solution was re-cooled to −78° C. and treated, via cannula, with a solution of 3-chlorophenylacetic acid (1.0 g, 5.9 mmol) in tetrahydrofuran (6 mL). The reaction was then allowed to warm to 25° C. where it was stirred for 45 minutes and was then re-cooled to −78° C. Cyclopentyl bromide (0.76 mL, 7.1 mmol) was then added via syringe, and the resulting mixture was stirred at −78° C. for 1 hour. The reaction mixture was allowed to warm to room temperature and then stirred overnight. The reaction was then quenched by the addition of a saturated aqueous solution of ammonium chloride, and the tetrahydrofuran was removed in vacuo. The resulting residue was dissolved in a 2N aqueous solution of sodium hydroxide (30 mL) and washed with ethyl acetate (1×15 mL). The aqueous layer was then acidified to pH=1 with the addition of a 2 N aqueous solution of hydrochloric acid. The product was extracted with ethyl acetate (3×15 mL), and the combined organic extracts were dried over magnesium sulfate, concentrated in vacuo and the product was purified via Biotage Horizon (FLASH 25 M, silica, gradient from 0% EtOAc/hexane to 40% EtOAc/hexane) to yield 1.08 g (79%) (3-chlorophenyl)(cyclopentyl) acetic acid as a clear oil. HRMS: calcd for C13H15ClO2−H, 237.06823; found (ESI, [M−H]−), 237.0682 ss) In an analogous manner, (3-chlorophenyl)(cyclohexyl) acetic acid was prepared from 3-chlorophenylacetic acid and cyclohexylbromide. HRMS: calcd for $C_{14}H_{17}ClO_2-H$, 251.0817; found (ESI, [M−H]⁻), 251.0849.

tt) In an analogous manner, (3-chlorophenyl)(cycloheptyl) acetic acid was prepared from 3-chlorophenylacetic acid and cycloheptylbromide. HRMS: calcd for $C_{15}H_{19}ClO_2-H$, 265.0974; found (ESI, [M−H]⁻), 265.0985.

uu) In an analogous manner, (3-chlorophenyl)(2-hydroxycyclohexyl)acetic acid was prepared from 3-chlorophenylacetic acid and cyclohexene oxide. HRMS: calcd for $C_{14}H_{17}ClO_3-H$, 267.0766; found (ESI, [M−H]⁻), 267.0779

Example 226

1-[2-(3-chlorophenyl)-2-cyclopentylethyl]piperazine dihydrochloride

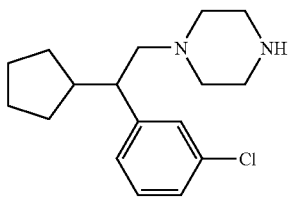

In an analogous manner to Example 1, step 1, tert-butyl 4-[(3-chlorophenyl)(cyclopentyl)acetyl]-piperazine-1-carboxylate was prepared from (3-chlorophenyl)(cyclopentyl) acetic acid (Reference Example 2-a) and tert-butyl 1-piperazinecarboxylate. HRMS: calcd for $C_{22}H_{31}ClN_2O_3+H$, 407.2123; found (ESI, [M+H]⁺), 407.2094.

In an analogous manner to Example 1, step 2, 1-[2-(3-chlorophenyl)-2-cyclopentylethyl]piperazine dihydrochloride was prepared from tert-butyl 4-[(3-chlorophenyl)(cyclopentyl)acetyl]piperazine-1-carboxylate HRMS: calcd for $C_{17}H_{25}ClN_2+H$, 293.17845; found (ESI, [M+H]⁺), 293.1776

Example 227

1-[2-(3-chlorophenyl)-2-cyclopentylethyl]-4-methylpiperazine dihydrochloride

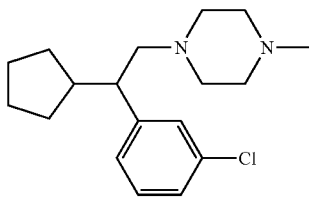

In an analogous manner to Example 24, 1-[2-(3-chlorophenyl)-2-cyclopentylethyl]-4-methylpiperazine dihydrochloride was prepared from, 1-[2-(3-chlorophenyl)-2-cyclopentylethyl]piperazine (See Example 226). MS (ES) m/z 307.2; HRMS: calcd for $C_{18}H_{27}ClN_2+H$, 307.19410; found (ESI, [M+H]⁺), 307.1935.

Example 228

1-[2-(3-chlorophenyl)-2-cyclopentylethyl]-N-methylpiperidin-4-amine dihydrochloride

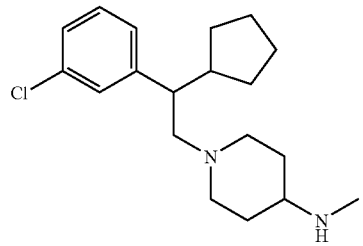

In an analogous manner to Example 1, step 1, tert-butyl {1-[(3-chlorophenyl)(cyclopentyl)acetyl]piperidin-4-yl}carbamate was prepared from (3-chlorophenyl)(cyclopentyl)acetic acid (Reference Example 2-a) and 4-N-Boc-aminopiperidine. HRMS: calcd for $C_{23}H_{33}ClN_2O_3+H$, 421.2280; found (ESI, [M+H]⁺), 421.2269.

In an analogous manner to Example 13, step 2, 1-[2-(3-chlorophenyl)-2-cyclopentylethyl]-N-methylpiperidin-4-amine dihydrochloride was prepared from tert-butyl {1-[(3-chlorophenyl)(cyclopentyl)acetyl]piperidin-4-yl}carbamate MS (ES) m/z 321.2; HRMS: calcd for $C_{19}H_{29}ClN_2+H$, 321.20975; found (ESI, [M+H]⁺), 321.2088.

Example 229

1-[2-(3-chlorophenyl)-2-cyclopentylethyl]-N,N-dimethylpiperidin-4-amine dihydrochloride

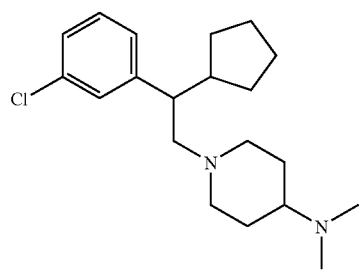

In an analogous manner to Example 36, 1-[2-(3-chlorophenyl)-2-cyclopentylethyl]-N,N-dimethylpiperidin-4-amine dihydrochloride was prepared from, 1-[2-(3-chlorophenyl)-2-cyclopentylethyl]-N-methylpiperidin-4-amine_(See Example 228). MS (ES) m/z 335.2;

HRMS: calcd for $C_{20}H_{31}ClN_2$+H, 335.22540; found (ESI, [M+H]$^+$), 335.2243.

Example 230

1-[2-(3-chlorophenyl)-2-cyclohexylethyl]piperazine dihydrochloride

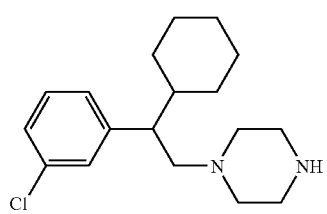

In an analogous manner to Example 1, step 1, tert-butyl 4-[(3-chlorophenyl)(cyclohexyl)acetyl]-piperazine-1-carboxylate was prepared from (3-chlorophenyl)(cyclohexyl) acetic acid (Reference Example 2-b) and tert-butyl 1-piperazinecarboxylate. HRMS: calcd for $C_{23}H_{33}ClN_2O_3$+H, 421.2280; found (ESI, [M+H]$^+$), 421.2261.

In an analogous manner to Example 1, step 2, 1-[2-(3-chlorophenyl)-2-cyclohexylethyl]piperazine dihydrochloride was prepared from tert-butyl 4-[(3-chlorophenyl)(cyclohexyl)acetyl]piperazine-1-carboxylate HRMS: calcd for $C_{18}H_{27}ClN_2$+H, 307.19410; found (ESI, [M+H]$^+$), 307.1943.

Example 231

1-[2-(3-chlorophenyl)-2-cyclohexylethyl]-4-methylpiperazine dihydrochloride

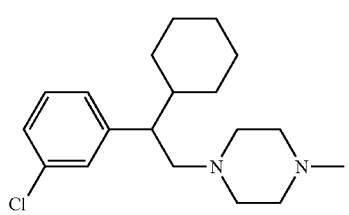

In an analogous manner to Example 24, 1-[2-(3-chlorophenyl)-2-cyclohexylethyl]-4-methylpiperazine dihydrochloride was prepared from, 1-[2-(3-chlorophenyl)-2-cyclohexylethyl]piperazine (See Example 230). MS (ES) m/z 321.2; HRMS: calcd for $C_{19}H_{29}ClN_2$+H, 321.20975; found (ESI, [M+H]$^+$), 321.2108.

Example 232

1-[2-(3-chlorophenyl)-2-cyclohexylethyl]-N-methylpiperidin-4-amine dihydrochloride

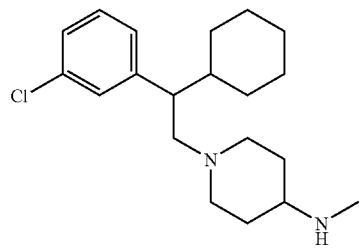

In an analogous manner to Example 1, step 1, tert-butyl {1-[(3-chlorophenyl)(cyclohexyl)acetyl]piperidin-4-yl}carbamate was prepared from (3-chlorophenyl)(cyclohexyl)acetic acid (Reference Example 2-b) and 4-N-Boc-aminopiperidine. HRMS: calcd for $C_{24}H_{35}ClN_2O_3$+H, 435.2436; found (ESI, [M+H]$^+$), 435.2422.

In an analogous manner to Example 13, step 2, 1-[2-(3-chlorophenyl)-2-cyclohexylethyl]-N-methylpiperidin-4-amine dihydrochloride was prepared from tert-butyl {1-[(3-chlorophenyl)(cyclohexyl)acetyl]piperidin-4-yl}carbamate MS (ES) m/z 335.3; HRMS: calcd for $C_{20}H_{31}ClN_2$+H, 335.22540; found (ESI, [M+H]$^+$), 335.2245.

Example 233

1-[2-(3-chlorophenyl)-2-cyclohexylethyl]-N,N-dimethylpiperidin-4-amine dihydrochloride

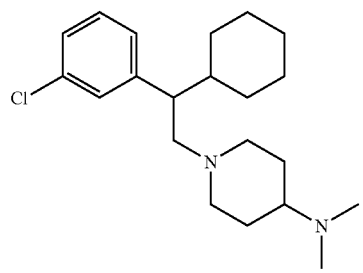

In an analogous manner to Example 36, 1-[2-(3-chlorophenyl)-2-cyclohexylethyl]-N,N-dimethylpiperidin-4-amine dihydrochloride was prepared from, 1-[2-(3-chlorophenyl)-2-cyclohexylethyl]-N-methylpiperidin-4-amine (See Example 232). HRMS: calcd for $C_{21}H_{33}ClN_2$+H, 349.24105; found (ESI, [M+H]$^+$), 349.2422.

Example 234

1-[2-(3-chlorophenyl)-2-cycloheptylethyl]piperazine dihydrochloride

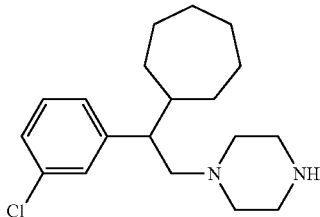

In an analogous manner to Example 1, step 1, tert-butyl 4-[(3-chlorophenyl)(cycloheptyl)acetyl]piperazine-1-carboxylate was prepared from (3-chlorophenyl)(cycloheptyl)acetic acid (Reference Example 2-c) and tert-butyl 1-piperazinecarboxylate. MS m/z 379

In an analogous manner to Example 1, step 2, 1-[2-(3-chlorophenyl)-2-cycloheptylethyl]piperazine dihydrochloride was prepared from tert-butyl 4-[(3-chlorophenyl)(cycloheptyl)acetyl]piperazine-1-carboxylate MS (ES) m/z 321.2; HRMS: calcd for $C_{19}H_{29}ClN_2$+H, 321.20975; found (ESI, [M+H]$^+$), 321.2105.

Example 235

1-[2-(3-chlorophenyl)-2-cycloheptylethyl]-4-methylpiperazine dihydrochloride

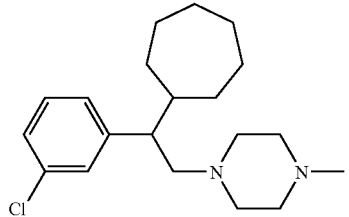

In an analogous manner to Example 24, 1-[2-(3-chlorophenyl)-2-cycloheptylethyl]-4-methylpiperazine dihydrochloride was prepared from, 1-[2-(3-chlorophenyl)-2-cycloheptylethyl]piperazine_(See Example 234). MS (ES) m/z 335.2; HRMS: calcd for $C_{20}H_{31}ClN_2$+H, 335.22540; found (ESI, [M+H]$^+$), 335.2253.

Example 236

1-[2-(3-chlorophenyl)-2-cycloheptylethyl]-N-methylpiperidin-4-amine dihydrochloride

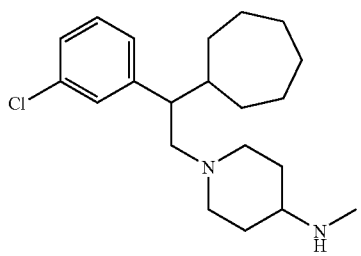

In an analogous manner to Example 1, step 1, tert-butyl {1-[(3-chlorophenyl)(cycloheptyl)acetyl]piperidin-4-yl}carbamate was prepared from (3-chlorophenyl)(cycloheptyl)acetic acid (Reference Example 2-c) and 4-N-Boc-aminopiperidine. MS m/z 449

In an analogous manner to Example 13, step 2, 1-[2-(3-chlorophenyl)-2-cycloheptylethyl]-N-methylpiperidin-4-amine dihydrochloride was prepared from tert-butyl {1-[(3-chlorophenyl)(cycloheptyl)acetyl]piperidin-4-yl}carbamate MS (ES) m/z 349.2; HRMS: calcd for $C_{21}H_{33}ClN_2$+H, 349.24105; found (ESI, [M+H]$^+$), 349.2412.

Example 237

1-[2-(3-chlorophenyl)-2-cycloheptylethyl]-N,N-dimethylpiperidin-4-amine dihydrochloride

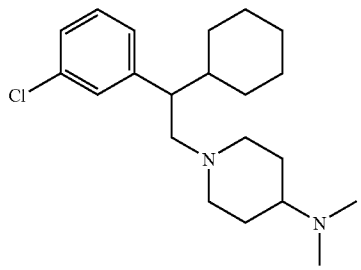

In an analogous manner to Example 36, 1-[2-(3-chlorophenyl)-2-cycloheptylethyl]-N,N-dimethylpiperidin-4-amine dihydrochloride was prepared from, 1-[2-(3-chlorophenyl)-2-cycloheptylethyl]-N-methylpiperidin-4-amine (See Example 236). MS (ES) m/z 363.3; HRMS: calcd for $C_{22}H_{35}ClN_2$+H, 363.25670; found (ESI, [M+H]$^+$), 363.2578.

Example 238

2-[1-(3-chlorophenyl)-2-piperazin-1-ylethyl]cyclohexanol dihydrochloride

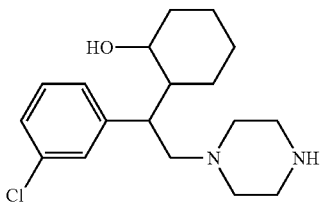

Step 1: A solution of (3-chlorophenyl)(2-hydroxycyclohexyl)acetic acid (Reference Example 2-d) (1.25 g, 4.66 mmol), benzotriazol-1-yloxytris(dimethylamino)phosphonium hexafluorophosphate (3.1 g, 7.0 mmol), and tert-butyl 1-piperazinecarboxylate (0.87 g, 4.66 mmol) in methylene chloride (12 mL) was treated with triethylamine (0.98 mL, 7.0 mmol). The reaction was stirred at 25° C. for 16 h, after which time the solvent was removed in vacuo and the product was purified via Biotage Horizon (FLASH 40 M, silica, gradient from 0% EtOAc/hexane to 25% EtOAc/hexane) to yield 0.97 g (83%) the lactone, 3-(3-chlorophenyl)hexahydro-1-benzofuran-2(3H)-one as a clear oil. HRMS: calcd for $C_{14}H_{15}ClO_2$+H, 251.0861; found (ESI, [M+H]$^+$), 251.0844.

Step 2: A solution of 3-(3-chlorophenyl)hexahydro-1-benzofuran-2(3H)-one (540 mg, 2.19 mmol) in dry tetrahydrofuran (7 mL) was cooled to −78° C. under nitrogen and was treated dropwise with a solution of DiBAL (1.0 M in toluene, 3.07 mL, 3.07 mmol). The resulting solution was stirred at −78° C. for 2 h, after which time the reaction was treated a 1 M aqueous solution of sulfuric acid to dissolve precipitated salts. The reaction mixture was allowed to warm to room temperature and was partitioned between diethyl ether and water. The organic layer was washed with a saturated aqueous solution of sodium bicarbonate, water, and brine and was dried over magnesium sulfate and concentrated in vacuo. The crude product was purified via Biotage Horizon (FLASH 25 M, silica, gradient from 0% EtOAc/hexane to 35% EtOAc/hexane) to yield 0.38 g (69%) the lactol, 3-(3-chlorophenyl) octahydro-1-benzofuran-2-ol as a white foam. HRMS: calcd for $C_{14}H_{17}ClO_2$−H, 251.0817; found (ESI, [M−H]$^-$), 251.0835.

Step 3: A solution of 3-(3-chlorophenyl)octahydro-1-benzofuran-2-ol (175 mg, 0.69 mmol) and tert-butyl 1-piperazinecarboxylate (128 mg, 0.69 mmol) in dichloroethane (3 mL) was treated with sodium trisacetoxyborohydride (220 mg, 1.04 mmol). The reaction was allowed to stir at room temperature for 16 h. The reaction was then diluted with methylene chloride and washed with a saturated aqueous solution of ammonium chloride (3 times). The organic layer was dried over magnesium sulfate and concentrated in vacuo and the product was purified via Biotage Horizon (FLASH 25 M, silica, gradient from 0% EtOAc/hexane to 30% EtOAc/hexane). This material was dissolved in methanol (0.5 mL) and treated with a saturated methanolic solution of hydrochloric acid (0.5 mL) followed by diethyl ether. After crystallizing in the refrigerator for 16 h, the resulting solid was collected, washed with diethyl ether and dried in vacuo to yield 250 mg (83%) 2-[1-(3-chlorophenyl)-2-piperazin-1-ylethyl]cyclohexanol dihydrochloride as a white solid. HRMS: calcd for $C_{18}H_{27}ClN_2O$+H, 323.18901; found (ESI, [M+H]$^+$), 323.1891.

Example 239

2-[2-(4-aminopiperidin-1-yl)-1-(3-chlorophenyl) ethyl]cyclohexanol dihydrochloride

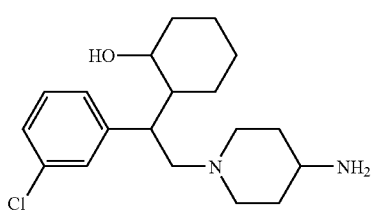

In an analogous manner to Example 238, step 3 2-[2-(4-aminopiperidin-1-yl)-1-(3-chlorophenyl)ethyl]cyclohexanol dihydrochloride was prepared from 3-(3-chlorophenyl)octahydro-1-benzofuran-2-ol (see Example 238, Step 2) and N-Boc-4-aminopiperidine. HRMS: calcd for $C_{19}H_{29}ClN_2O$+H, 337.20467; found (ESI, [M+H]$^+$), 337.2031.

Example 240

1-{2-(1-hydroxycyclohexyl)-2-[3-(trifluoromethoxy) phenyl]ethyl}piperidin-4-ol hydrochloride

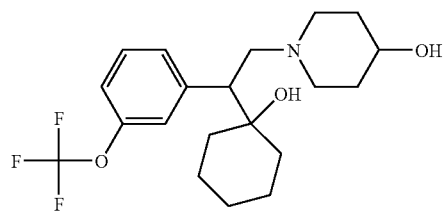

In an analogous manner to Example 1, step 1, 1-{(1-hydroxycyclohexyl)[3-(trifluoromethoxy)phenyl] acetyl}piperidin-4-ol was prepared from (1-hydroxycyclohexyl)[3-(trifluoromethoxy)phenyl]acetic acid (Reference Example 1-f) and 4-hydroxypiperidine. MS (ES) m/z 402.0

In an analogous manner to Example 1, step 2, 1-{2-(1-hydroxycyclohexyl)-2-[3-(trifluoromethoxy)phenyl] ethyl}piperidin-4-ol hydrochloride was prepared from 1-{(1-hydroxycyclohexyl)[3-(trifluoromethoxy)phenyl] acetyl}piperidin-4-ol MS (ES) m/z 388.0; HRMS: calcd for $C_{20}H_{28}F_3NO_3$+H, 388.20995; found (ESI, [M+H]$^+$), 388.2103.

Example 241

1-[2-[4-(benzyloxy)-3-chlorophenyl]-2-(1-hydroxycyclohexyl)ethyl]piperidin-4-ol hydrochloride

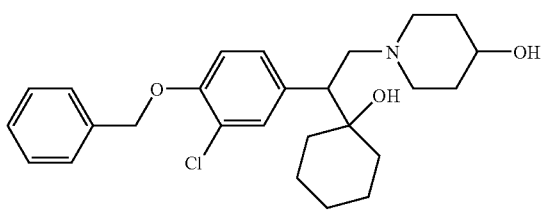

In an analogous manner to Example 1, step 1, 1-[[4-(benzyloxy)-3-chlorophenyl](1-hydroxycyclohexyl)acetyl]piperidin-4-ol was prepared from [4-(benzyloxy)-3-chlorophenyl](1-hydroxycyclohexyl)acetic acid_(Reference Example 1-eee) and 4-hydroxypiperidine. MS (ES) m/z 458.0

In an analogous manner to Example 1, step 2, 1-[2-[4-(benzyloxy)-3-chlorophenyl]-2-(1-hydroxycyclohexyl) ethyl]piperidin-4-ol hydrochloride was prepared from 1-[[4-(benzyloxy)-3-chlorophenyl](1-hydroxycyclohexyl)acetyl] piperidin-4-ol MS (ES) m/z 444.1; HRMS: calcd for $C_{26}H_{34}ClNO_3$+H, 444.23055; found (ESI, [M+H]$^+$), 444.2316.

Example 242

1-[1-[4-(benzyloxy)-3-chlorophenyl]-2-(4-methoxypiperidin-1-yl)ethyl]cyclohexanol hydrochloride

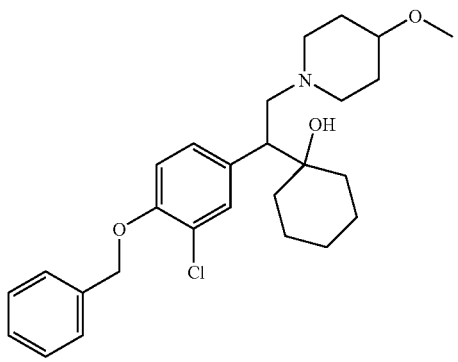

In an analogous manner to Example 1, step 1, 1-[1-[4-(benzyloxy)-3-chlorophenyl]-2-(4-methoxypiperidin-1-yl)-2-oxoethyl]cyclohexanol was prepared from [4-(benzyloxy)-3-chlorophenyl](1-hydroxycyclohexyl)acetic acid (Reference Example 1eee) and 4-methoxypiperidine (Baker, W. R.; Fung, A. K. I, Kleinhart, H. D et. Al. J. Med. Chem. 1992, 35 (10), 1722-1734.) MS m/z 379

In an analogous manner to Example 1, step 2, 1-[1-[4-(benzyloxy)-3-chlorophenyl]-2-(4-methoxypiperidin-1-yl) ethyl]cyclohexanol hydrochloride was prepared from 1-[1-[4-(benzyloxy)-3-chlorophenyl]-2-(4-methoxypiperidin-1-yl)-2-oxoethyl]cyclohexanol HRMS: calcd for $C_{27}H_{36}ClNO_3+H$, 458.24620; found (ESI, [M+H]$^+$), 458.2443.

Example 243

1-{(1S)-2-piperazin-1-yl-1-[3-(trifluoromethoxy) phenyl]ethyl}cyclohexanol dihydrochloride

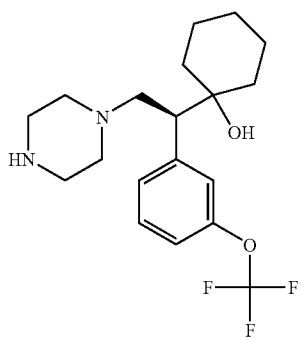

Racemic tert-butyl 4-{(1-hydroxycyclohexyl)[3-(trifluoromethoxy)phenyl]acetyl}piperazine-1-carboxylate (see Example 23, step 1) was dissolved in methanol at a concentration of approximately 50 mg/mL. The resulting solution was injected onto the Supercritical Fluid L.☐Chromatography instrument with an injection volume of 750 The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/min flow rate using Analytical Supercritical Fluid Chromatography (Berger Instruments, Inc. Newark, Del. USA).

| SFC Instrument: | Berger MultiGram PrepSFC (Berger Instruments, Inc. Newark, DE 19702. |
|---|---|
| Column: | Chiralpak AD-H; 5 u; 250 mm L × 20 mm ID (Chiral Technologies, Inc, Exton, PA, USA) |
| Column temperature: | 35° C. |
| SFC Modifier: | 10% EtOH |
| Flow rate: | 50 mL/min |
| Outlet Pressure: | 100 bar |
| Detector: | UV at 220 nm | tert-butyl 4-{(2R)-2-(1-hydroxycyclohexyl)-2-[3-(trifluoromethoxy)phenyl]acetyl}piperazine-1-carboxylate was isolated at peak 1. MS (ES) m/z 487.2; HRMS: calcd for $C_{24}H_{33}F_3N_2O_5+H$, 487.2442+H; found (ESI, [M+H]$^+$), 487.2428; $[\alpha]_D^{25}=+230$ (c=0.00116 G/ML, EtOH);

tert-butyl 4-{(2S)-2-(1-hydroxycyclohexyl)-2-[3-(trifluoromethoxy)phenyl]acetyl}piperazine-1-carboxylate was isolated at peak 2. MS (ESI) m/z 487; HRMS: calcd for $C_{24}H_{33}F_3N_2O_5+H$, 487.2442; found (ESI, [M+H]$^+$), $[\alpha]_D^{25}=-19°$ (c=0.0112 G/ML, MeOH).

In an analogous manner to Example 1, step 2 1-{(1S)-2-piperazin-1-yl-1-[3-(trifluoromethoxy)phenyl] ethyl}cyclohexanol dihydrochloride was prepared from tert-butyl 4-{(2R)-2-(1-hydroxycyclohexyl)-2-[3-(trifluoromethoxy)phenyl]acetyl}piperazine-1-carboxylate. MS (ES) m/z 373.2; HRMS: calcd for $C_{19}H_{27}F_3N_2O_2+H$, 373.21029; found (ESI, [M+H]$^+$), 373.2094; $[\alpha]_D^{25}=+2.20$ (c=0.0099 G/ML, MeOH).

Example 244

1-{(1R)-2-piperazin-1-yl-1-[3-(trifluoromethoxy) phenyl]ethyl}cyclohexanol dihydrochloride

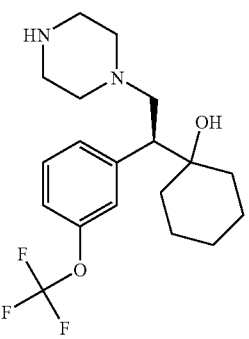

In an analogous manner to Example 1, step 2 1-{(1R)-2-piperazin-1-yl-1-[3-(trifluoromethoxy)phenyl] ethyl}cyclohexanol dihydrochloride was prepared from tert-butyl 4-{(2S)-2-(1-hydroxycyclohexyl)-2-[3-(trifluoromethoxy)phenyl]acetyl}piperazine-1-carboxylate (see Example 243). MS (ES) m/z 373.1; HRMS: calcd for $C_{19}H_{27}F_3N_2O_2$+H, 373.21029; found (ESI, [M+H]$^+$), 373.2102.

Example 245

1-{(1S)-2-(4-methylpiperazin-1-yl)-1-[3-(trifluoromethoxy)phenyl]ethyl}cyclohexanol dihydrochloride

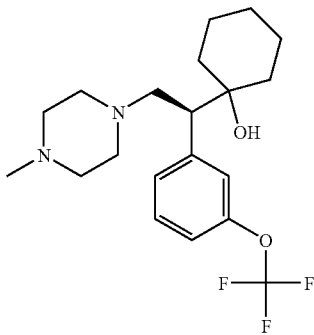

In an analogous manner to Example 24, 1-{(1S)-2-(4-methylpiperazin-1-yl)-1-[3-(trifluoromethoxy)phenyl]ethyl}cyclohexanol dihydrochloride was prepared from, 1-{(1S)-2-piperazin-1-yl-1-[3-(trifluoromethoxy)phenyl]ethyl}cyclohexanol_(See Example 243). MS (ES) m/z 387.2; HRMS: calcd for $C_{20}H_{29}F_3N_2O_2$+H, 387.22594; found (ESI, [M+H]$^+$), 387.2249.

Example 246

1-{(1R)-2-(4-methylpiperazin-1-yl)-1-[3-(trifluoromethoxy)phenyl]ethyl}cyclohexanol dihydrochloride

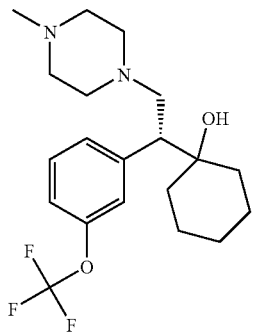

In an analogous manner to Example 24, 1-{(1R)-2-(4-methylpiperazin-1-yl)-1-[3-(trifluoromethoxy)phenyl]ethyl}cyclohexanol dihydrochloride was prepared from, 1-{(1R)-2-piperazin-1-yl-1-[3-(trifluoromethoxy)phenyl]ethyl}cyclohexanol (See Example 244). HRMS: calcd for $C_{20}H_{29}F_3N_2O_2$+H, 387.22594; found (ESI, [M+H]$^+$), 387.2269.

Example 247

1-[1-(3',4'-dichloro-1,1'-biphenyl-3-yl)-2-(4-methylpiperazin-1-yl)ethyl]cyclohexanol dihydrochloride

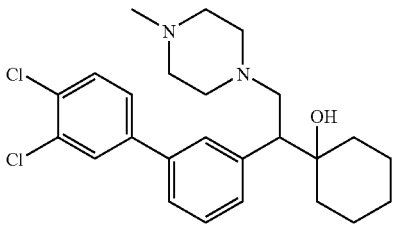

In an analogous manner to Example 24, 1-[1-(3',4'-dichloro-1,1'-biphenyl-3-yl)-2-(4-methylpiperazin-1-yl)ethyl]cyclohexanol dihydrochloride was prepared from 1-[1-(3',4'-dichloro-1,1'-biphenyl-3-yl)-2-piperazin-1-ylethyl]cyclohexanol (see Example 135). MS (ESI) m/z 447; HRMS: calcd for C25H32Cl2N2O+H, 447.19699; found (ESI, [M+H]$^+$), 447.1979.

Example 248

1-{2-piperazin-1-yl-1-[3'-(trifluoromethoxy)-1,1'-biphenyl-3-yl]ethyl}cyclohexanol dihydrochloride

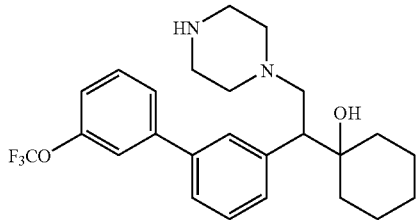

In an analogous manner to Example 135, step 3 tert-butyl 4-[2-(3'-trifluoromethoxy-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 3-trifluoromethoxy phenyl boronic acid.

In an analogous manner to Example 135, step 4 1-{2-piperazin-1-yl-1-[3'-(trifluoromethoxy)-1,1'-biphenyl-3-yl]ethyl}cyclohexanol dihydrochloride was prepared from tert-butyl 4-[2-(3'-trifluoromethoxy-biphenyl-3-yl)-2-(1-hydroxycyclohexyl)ethyl]piperazine-1-carboxylate. MS (ESI) m/z 449; HRMS: calcd for C25H31F3N2O2+H, 449.24159; found (ESI, [M+H]$^+$), 449.2434.

Example 249

1-{2-piperazin-1-yl-1-[4'-(trifluoromethyl)-1,1'-biphenyl-3-yl]ethyl}cyclohexanol dihydrochloride

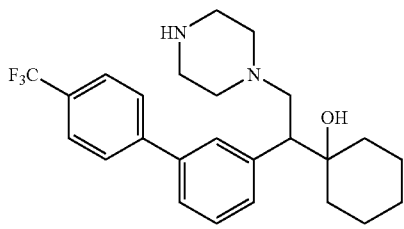

In an analogous manner to Example 135, step 3 tert-butyl 4-[2-(4'-trifluoromethyl-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 4-trifluoromethyl phenyl boronic acid.

In an analogous manner to Example 135, step 4 1-{2-piperazin-1-yl-1-[4'-(trifluoromethyl)-1,1'-biphenyl-3-yl]ethyl}cyclohexanol dihydrochloride was prepared from tert-butyl 4-[2-(4'-trifluoromethyl-biphenyl-3-yl)-2-(1-hydroxycyclohexyl)ethyl]piperazine-1-carboxylate. MS (ESI) m/z 433; HRMS: calcd for C25H31F3N2O+H, 433.24667; found (ESI, [M+H]$^+$), 433.2474.

Example 250

1-[1-(3',4'-dimethoxy-1,1'-biphenyl-3-yl)-2-piperazin-1-ylethyl]cyclohexanol dihydrochloride

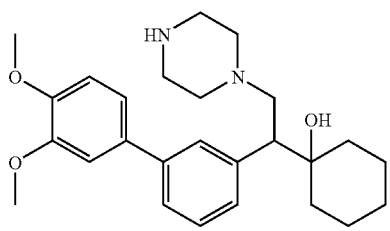

In an analogous manner to Example 135, step 3 tert-butyl 4-[2-(3',4'-dimethoxy-biphenyl-3-yl)-2-(1-hydroxycyclohexyl)ethyl]piperazine-1-carboxylate was prepared from tert-butyl 4-[2-(3-bromophenyl)-2-(1-hydroxycyclohexyl)ethyl]piperazine-1-carboxylate (see Example 135, step 2) and 3',4'-dimethoxy phenyl boronic acid.

In an analogous manner to Example 135, step 4 1-[1-(3',4'-dimethoxy-1,1'-biphenyl-3-yl)-2-piperazin-1-ylethyl]cyclohexanol dihydrochloride was prepared from tert-butyl 4-[2-(3',4'-dimethoxy-biphenyl-3-yl)-2-(1-hydroxycyclohexyl)ethyl]piperazine-1-carboxylate. MS (ESI) m/z 425; HRMS: calcd for C26H36N2O3+H, 425.28042; found (ESI, [M+H]$^+$), 425.2801.

Example 251

1-{1-[6-methoxy-3'-(trifluoromethoxy)-1,1'-biphenyl-3-yl]-2-piperazin-1-ylethyl}cyclohexanol dihydrochloride

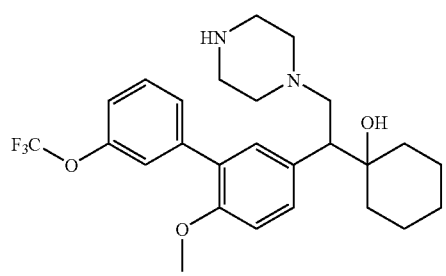

Step 1: In an analogous manner to Example 1, step 1 tert-butyl 4-[(3-bromo-4-methoxyphenyl) (1-hydroxycyclohexyl)acetyl]piperazine-1-carboxylate was prepared from (3-bromo-4-methoxyphenyl)(1-hydroxycyclohexyl)acetic acid (Reference Example 1-1) and tert-butyl 1-piperazinecarboxylate.

Step 2: In an analogous manner to Example 135, step 2 tert-butyl 4-[2-(3-bromo, 4-methyoxyphenyl)-2-(1-hydroxycyclohexyl)ethyl]piperazine-1-carboxylate was prepared from tert-butyl 4-[(3-bromo-4-methoxyphenyl)(1-hydroxycyclohexyl)acetyl]piperazine-1-carboxylate.

Step 3: In an analogous manner to Example 135, step 3 tert-butyl 4-[2-(1-Hydroxy-cyclohexyl)-2-(6-methoxy-3'-trifluoromethoxy-biphenyl-3-yl)-ethyl]-piperazine-1-carboxylate was prepared from tert-butyl 4-[2-(3-bromo,4-methoxyphenyl)-2-(1-hydroxycyclohexyl)ethyl]piperazine-1-carboxylate and 3-trifluoromethoxy phenyl boronic acid.

Step 4: In an analogous manner to Example 135, step 4 1-{1-[6-methoxy-3'-(trifluoromethoxy)-1,1'-biphenyl-3-yl]-2-piperazin-1-ylethyl}cyclohexanol dihydrochloride was prepared from tert-butyl 4-[2-(1-Hydroxy-cyclohexyl)-2-(6-methoxy-3'-trifluoromethoxy-biphenyl-3-yl)-ethyl]-piperazine-1-carboxylate.

MS (ESI) m/z 479; HRMS: calcd for C26H33F3N2O3+H, 479.25215; found (ESI, [M+H]+), 479.2529.

Example 252

1-[1-(3',4'-dichloro-6-methoxy-1,1'-biphenyl-3-yl)-2-piperazin-1-ylethyl]cyclohexanol dihydrochloride

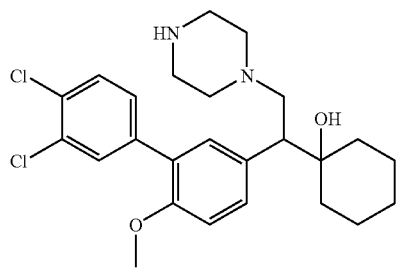

In an analogous manner to Example 135, step 3 tert-butyl 4-[2-(3',4'-dichloro-6-methoxy-1,1'-biphenyl-3-yl)-2-(1-hydroxycyclohexyl)ethyl]piperazine-1-carboxylate was prepared from tert-butyl-4-[2-(3-bromo,4-methoxyphenyl)-2-(1-hydroxycyclohexyl)ethyl]piperazine-1-carboxylate (see Example 251, step 2) and 3,4-dichlorophenyl boronic acid. MS m/z 563; HRMS: calcd for C30H40Cl2N2O4, 562.2365; found (ESI, [M+H]+), 563.2471.

In an analogous manner to Example 135, step 4 1-[1-(3',4'-dichloro-6-methoxy-1,1'-biphenyl-3-yl)-2-piperazin-1-ylethyl]cyclohexanol dihydrochloride was prepared from tert-butyl 4-[2-(3',4'-dichloro-6-methoxy-1,1'-biphenyl-3-yl)-2-(1-hydroxycyclohexyl)ethyl]piperazine-1-carboxylate. MS (ESI) m/z 463; HRMS: calcd for C25H32Cl2N2O2+H, 463.19191; found (ESI, [M+H]+), 463.1933.

Example 253

1-{1-[6-methoxy-4'-(trifluoromethyl)-1,1'-biphenyl-3-yl]-2-piperazin-1-ylethyl}cyclohexanol dihydrochloride

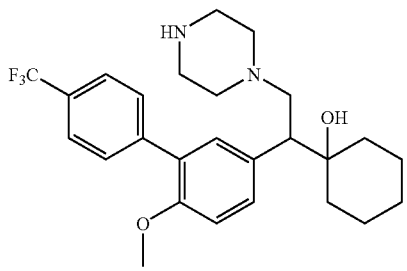

In an analogous manner to Example 135, step 3 tert-butyl 4-[2-(4'-trifluoromethyl-6-methoxy-1,1'-biphenyl-3-yl)-2-(1-hydroxycyclohexyl)ethyl]piperazine-1-carboxylate was prepared from tert-butyl-4-[2-(3-bromo,4-methoxyphenyl)-2-(1-hydroxycyclohexyl)ethyl]piperazine-1-carboxylate (see Example 251, step 2) and 4-trifluoromethyl phenyl boronic acid.

In an analogous manner to Example 135, step 4 1-{1-[6-methoxy-4'-(trifluoromethyl)-1,1'-biphenyl-3-yl]-2-piperazin-1-ylethyl}cyclohexanol dihydrochloride was prepared from tert-butyl 4-[2-(4'-trifluoromethyl-6-methoxy-1,1'-biphenyl-3-yl)-2-(1-hydroxycyclohexyl)ethyl]piperazine-1-carboxylate. MS (ESI) m/z 463; HRMS: calcd for C26H33F3N2O2+H, 463.25724; found (ESI, [M+H]+), 463.256.

Example 254

1-[1-(6-methoxy-1,1'-biphenyl-3-yl)-2-piperazin-1-ylethyl]cyclohexanol dihydrochloride

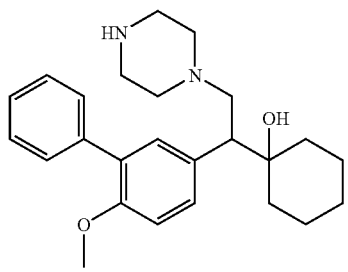

In an analogous manner to Example 135, step 3 tert-butyl 4-[2-(6-methoxy-1,1'-biphenyl-3-yl)-2-(1-hydroxycyclohexyl)ethyl]piperazine-1-carboxylate was prepared from tert-butyl-4-[2-(3-bromo,4-methoxyphenyl)-2-(1-hydroxycyclohexyl)ethyl]piperazine-1-carboxylate (see Example 251, step 2) and phenyl boronic acid.

In an analogous manner to Example 135, step 4 1-[1-(6-methoxy-1,1'-biphenyl-3-yl)-2-piperazin-1-ylethyl]cyclohexanol dihydrochloride was prepared from tert-butyl 4-[2-(6-methoxy-1,1'-biphenyl-3-yl)-2-(1-hydroxycyclohexyl)ethyl]piperazine-1-carboxylate. MS (ES) m/z 395.2; HRMS: calcd for C25H34N2O2+H, 395.2695; found (ESI, [M+H]+), 395.2693.

Example 255

1-[1-(3',4'-dichloro-6-methoxy-1,1'-biphenyl-3-yl)-2-(4-methylpiperazin-1-yl)ethyl]cyclohexanol dihydrochloride

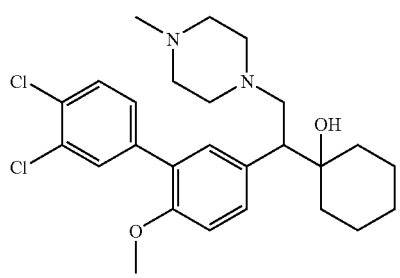

In an analogous manner to Example 24, 1-[1-(3',4'-dichloro-6-methoxy-1,1'-biphenyl-3-yl)-2-(4-methylpiperazin-1-yl)ethyl]cyclohexanol dihydrochloride was prepared from 1-[1-(3',4'-dichloro-6-methoxy-1,1'-biphenyl-3-yl)-2-piperazin-1-ylethyl]cyclohexanol (see Example 252). MS (ES) m/z 477.2; HRMS: calcd for C26H34Cl2N2O2+H, 477.20756; found (ESI, [M+H]+), 477.2064.

Example 256

1-[1-[6-methoxy-3'-(trifluoromethoxy)-1,1'-biphenyl-3-yl]-2-(4-methylpiperazin-1-yl)ethyl]cyclohexanol dihydrochloride

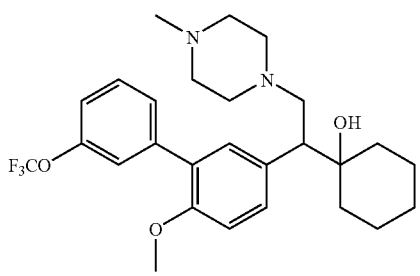

In an analogous manner to Example 24, 1-[1-[6-methoxy-3'-(trifluoromethoxy)-1,1'-biphenyl-3-yl]-2-(4-methylpiperazin-1-yl)ethyl]cyclohexanol dihydrochloride was prepared from 1-[1-(3'-trifluoromethoxy-6-methoxy-1,1'-biphenyl-3-yl)-2-piperazin-1-ylethyl]cyclohexanol (see Example 251). MS m/z 493; HRMS: calcd for C27H35F3N2O3+H, 493.26780; found (ESI, [M+H]+), 493.2692.

Example 257

1-[1-[6-methoxy-4'-(trifluoromethyl)-1,1'-biphenyl-3-yl]-2-(4-methylpiperazin-1-yl)ethyl]cyclohexanol dihydrochloride

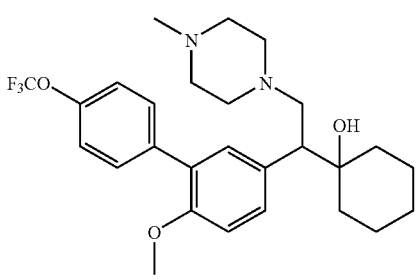

In an analogous manner to Example 24, 1-[1-[6-methoxy-4'-(trifluoromethyl)-1,1'-biphenyl-3-yl]-2-(4-methylpiperazin-1-yl)ethyl]cyclohexanol dihydrochloride was prepared from 1-[1-(6-methoxy-4'-(trifluormethyl)-1,1'-biphenyl-3-yl)-2-piperazin-1-ylethyl]cyclohexanol (see Example 253). MS m/z 477; HRMS: calcd for C27H35F3N2O2+H, 477.27289; found (ESI, [M+H]+), 477.2728.

Example 258

1-[(1R)-1-(5-chlorothien-3-yl)-2-(4-methylpiperazin-1-yl)ethyl]cyclohexanol dihydrochloride

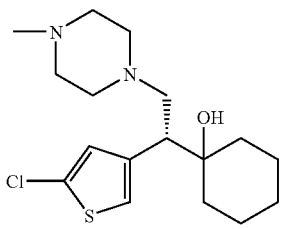

R-tert-butyl 4-[2-(5-chlorothien-3-yl)-2-(1-hydroxycyclohexyl)ethyl]piperazine-1-carboxylate was isolated from tert-butyl 4-[2-(5-chlorothien-3-yl)-2-(1-hydroxycyclohexyl)ethyl]piperazine-1-carboxylate (see Example 144) by chiral column chromatography (Chiral OD-H, 100% acetonitrile, 16 ml/min). Elution time=9.9 min, (−)-CD In an analogous manner to Example 24, 1-[(1R)-1-(5-chlorothien-3-yl)-2-(4-methylpiperazin-1-yl)ethyl]cyclohexanol dihydrochloride was prepared from the above isolated product. $[\alpha]_D^{25}$-150 (c=0.0092 G/ML, MeOH); MS (ESI) m/z 343.1627; HRMS: calcd for C17H27ClN2OS+H, 343.16108; found (ESI, [M+H]+), 343.1627.

Example 259

1-[(1S)-1-(5-chlorothien-3-yl)-2-(4-methylpiperazin-1-yl)ethyl]cyclohexanol dihydrochloride

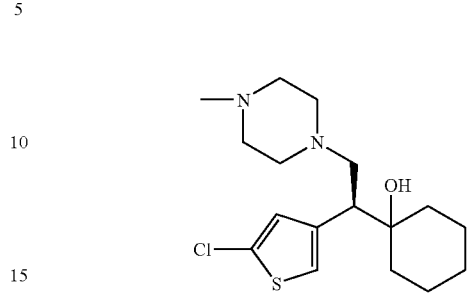

S-tert-butyl 4-[2-(5-chlorothien-3-yl)-2-(1-hydroxycyclohexyl)ethyl]piperazine-1-carboxylate was isolated from tert-butyl 4-[2-(5-chlorothien-3-yl)-2-(1-hydroxycyclohexyl)ethyl]piperazine-1-carboxylate (see Example 144) by chiral column chromatography (Chiral OD-H, 100% acetonitrile, 16 ml/min). Elution time=11.8 min, (+)-CD In an analogous manner to Example 24, 1-[(1S)-1-(5-chlorothien-3-yl)-2-(4-methylpiperazin-1-yl)ethyl]cyclohexanol dihydrochloride was prepared from the above isolated product. $[\alpha]_D^{25}$=+160 (c=0.0081 G/ML, MeOH); MS (ESI) m/z 343; HRMS: calcd for C17H27ClN2OS+H, 343.16108; found (ESI, [M+H]+), 343.1606.

Example 260

1-[1-(5-chloro-1-benzothien-3-yl)-2-piperazin-1-ylethyl]cyclohexanol dihydrochloride

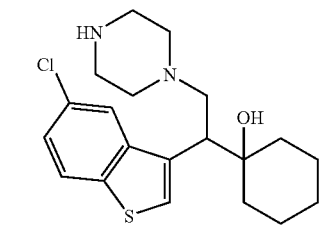

Step, 1: In an analogous manner to Example 1 step 1, tert-butyl 4-[(5-chloro-1-benzothien-3-yl)acetyl]piperazine-1-carboxylate was prepared from 5-chlorobenzothiophene-3-acetic acid and tert-butyl 1-piperazinecarboxylate. MS (ES) m/z 395.0; HRMS: calcd for C19H23ClN2O3S, 394.1118; found (ESI, [M+H]+), 395.1201.

Step 2: In an analogous manner to Example 141 step 3, tert-butyl 4-[(5-chloro-1-benzothien-3-yl)-2-(1-hydroxycyclohexyl)acetyl]piperazine-1-carboxylate was prepared from tert-butyl 4-[(5-chloro-1-benzothien-3-yl)acetyl]piperazine-1-carboxylate.

Step 3: In an analogous manner to Example 135 step 2, tert-butyl 4-[(5-chloro-1-benzothien-3-yl)-2-(1-hydroxycyclohexyl)ethyl]piperazine-1-carboxylate was prepared from tert-butyl 4-[(5-chloro-1-benzothien-3-yl)-2-(1-hydroxycyclohexyl)acetyl]piperazine-1-carboxylate.

Step 4: In an analogous manner to Example 135 step 4, 1-[1-(5-chloro-1-benzothien-3-yl)-2-piperazin-1-ylethyl]cyclohexanol dihydrochloride was prepared from tert-butyl 4-[(5-chloro-1-benzothien-3-yl)-2-(1-hydroxycyclohexyl)

ethyl]piperazine-1-carboxylate and isolated as a colorless powder. MS m/z 379; HRMS: calcd for C20H27ClN2OS+H, 379.16108; found (ESI, [M+H]+), 379.1607.

Example 261

1-[1-(1-benzothien-2-yl)-2-piperazin-1-ylethyl]cyclohexanoldihydrochloride

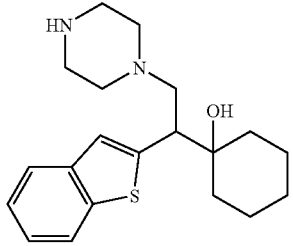

Step 1: A solution of benzo[b]thiophene-2-carbaldehyde (1.0 g, 6.17 mmol) and carbon tetrabromide (3.1 g, 9.25 mmol) in methylene chloride (50 mL) was cooled to 0° C. A solution of triphenylphosphine (4.86 g, 18.3 mmol) in methylene chloride (20 mL) was added dropwise. After ½ hour the solution was placed on a plug of silica gel and eluted with 20% ethyl acetate:hexane. Concentration of the eluent resulted in the isolation of 1.3 g (67%) of 2-(2,2-Dibromo-vinyl)-benzo[b]thiophene as a yellow oil, which was used as such in the next step.

Step 2: A 50 mL round bottom flask was charged with 2-(2,2-dibromo-vinyl)-benzo[b]thiophene (1.0 g, 3.17 mmol), tert-butyl 1-piperazinecarboxylate (0.09 g, 4.76 mmol) and potassium hydroxide (0.71 g, 12.5 mmol). A solution of tetrahydrofuran:water (4:1) was added and the solution was heated to 70° C. for 18 hours. At the end of this time the solution was concentrated and the residue was diluted with a 2N aqueous solution of hydrochloric acid and extracted 3 times with ethyl acetate. The ethyl acetate was dried and concentrated and the residue subjected chromatography via Biotage (FLASH 40 M, silica, 60% ethyl acetate/hexane) to yield 0.75 g (65%) of tert-butyl 4-[2-(1-benzothien-2-yl)-1-hydroxyethyl]piperazine-1-carboxylate as an off white solid. MS (ES) m/z 305.1; HRMS: calcd for C19H26N2O3S, 362.1664; found (ESI, [M+H]+), 361.1569.

Step 3: In an analogous manner to Example 141 step 3, tert-butyl 4-[(1-benzothien-2-yl)-2-(1-hydroxycyclohexyl)acetyl]piperazine-1-carboxylate was prepared from tert-butyl 4-[2-(1-benzothien-2-yl)-1-hydroxyethyl]piperazine-1-carboxylate and used as such in the next step.

Step 4: In an analogous manner to Example 135, Step 2, tert-butyl 4-[(1-benzothien-2-yl)-2-(1-hydroxycyclohexyl)ethyl]piperazine-1-carboxylate was prepared from tert-butyl 4-[(1-benzothien-2-yl)-2-(1-hydroxycyclohexyl)acetyl]piperazine-1-carboxylate.

Step 5: In an analogous manner to Example 135 step 4, 1-[1-(1-benzothien-2-yl)-2-piperazin-1-ylethyl]cyclohexanol dihydrochloride was prepared from tert-butyl 4-[(1-benzothien-2-yl)-2-(1-hydroxycyclohexyl)ethyl]piperazine-1-carboxylate. MS (ES) m/z 345.2; HRMS: calcd for C20H28N2OS+H, 345.20006; found (ESI, [M+H]+), 345.199.

Example 262

1-(2-piperazin-1-yl-1-quinolin-3-ylethyl)cyclohexanol dihydrochloride

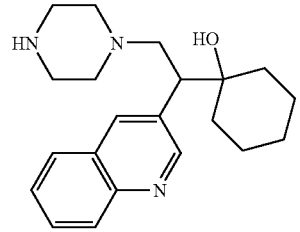

Step 1: In an analogous manner to Example 261 step 1, 3-(2,2-Dibromo-vinyl)-quinoline was prepared from quinoline-3-carboxaldehyde.

Step 2: In an analogous manner to Example 261 step 2, tert-butyl 4-(quinolin-3-ylacetyl)piperazine-1-carboxylate was prepared from 3-(2,2-Dibromo-vinyl)-quinoline. MS m/z 356; HRMS: calcd for C20H25N3O3, 355.1896; found (ESI, [M+H]+), 356.1963.

Step 3: In an analogous manner to Example 261 step 3, tert-butyl 4-[(2-quinoline-3-yl)-2-(1-hydroxycyclohexyl)acetyl]piperazine-1-carboxylate was prepared from tert-butyl 4-(quinolin-3-ylacetyl)piperazine-1-carboxylate.

Step 4: In an analogous manner to Example 261 step 4, tert-butyl 4-[(2-quinoline-3-yl)-2-(1-hydroxycyclohexyl)ethyl]piperazine-1-carboxylate was prepared from tert-butyl 4-[(2-quinoline-3-yl)-2-(1-hydroxycyclohexyl)acetyl]piperazine-1-carboxylate.

Step 5: In an analogous manner to Example 261 step 5, 1-(2-piperazin-1-yl-1-quinolin-3-ylethyl)cyclohexanol dihydrochloride was prepared from tert-butyl 4-[(2-quinoline-3-yl)-2-(1-hydroxycyclohexyl)ethyl]piperazine-1-carboxylate. MS m/z 340; HRMS: calcd for C21H29N3O+H, 340.23889; found (ESI, [M+H]+), 340.2402.

Example 263

1-{1-[4-(benzyloxy)-3-(trifluoromethyl)phenyl]-2-piperazin-1-ylethyl}cyclohexanol dihydrochloride

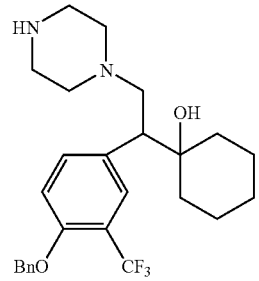

Step 1: A solution of 2-trifluoromethyl phenol (5.0 g, 30.86 mmol) and hexamethylenetetramine (8.64 g, 61.72 mmol) in trifluoracetic acid (50 mL) was heated at 65° C. for 18 h. At the end of this time the solution was concentrated and diluted with a 2N aqueous solution of hydrochloric acid. The acid phase was extracted twice with ethyl acetate and the combined organic extract dried over magnesium sulfate and concentrated. The residue was subjected to chromatography via Biotage (FLASH 40 M, silica, 20% ethyl acetate/hexane) to yield 2.1 g (36%) of 4-hydroxy-3-(trifluoromethyl)benzaldehyde. MS (ES) m/z 188.9; HRMS: calcd for C8H5F3O2, 190.0242; found (ESI, [M+H]+), 191.0324.

Step 2: A solution of 4-hydroxy-3-(trifluoromethyl)benzaldehyde (1.5 g, 8.0 mmol), benzyl bromide (1.51 g, 8.8 mmol) and potassium carbonate (1.66 g, 12.0 mmol) in dimethyl formamide (20 mL) was stirred water (100 mL) and extracted 3 times with ethyl acetate. The ethyl acetate extracts were combined and washed 2 times with water and dried over magnesium sulfate. Concentration in vacuo yielded 1.7 g of 4-benzyloxy-3-trifluoromethyl-benzaldehyde which was used as such in the next step.

Step 3: In an analogous manner to Example 261 step 1, 1-benzyloxy-4-(2,2-dibromo-vinyl)-2-trifluoromethyl-benzene was prepared from 4-benzyloxy-3-trifluoromethyl-benzaldehyde.

Step 4: In an analogous manner to Example 261, Step 2, tert-butyl 4-{[4-(benzyloxy)-3-trifluoromethylphenyl]acetyl}piperazine-1-carboxylate was prepared 1-benzyloxy-4-(2,2-dibromo-vinyl)-2-trifluoromethyl-benzene.

Step 5: In an analogous manner to Example 135 step 2, tert-butyl 4-[[4-(benzyloxy)-3-(trifluoromethyl)phenyl](1-hydroxycyclohexyl)acetyl]piperazine-1-carboxylate was prepared from tert-butyl 4-{[4-(benzyloxy)-3-trifluoromethylphenyl]acetyl}piperazine-1-carboxylate. MS (ESI) m/z 577; HRMS: calcd for C31H39F3N2O5, 576.2811; found (ESI, [M+H]⁺), 577.2901.

Step 6: In an analogous manner to Example 135 step 3, tert-butyl 4-[2-[4-(benzyloxy)-3-(trifluoromethyl)phenyl]-2-(1-hydroxycyclohexyl)ethyl]piperazine-1-carboxylate was prepared from tert-butyl 4-[[4-(benzyloxy)-3-(trifluoromethyl)phenyl](1-hydroxycyclohexyl)acetyl]piperazine-1-carboxylate. MS (ES) m/z 563.1; HRMS: calcd for C31H41F3N2O4, 562.3018; found (ESI, [M+H]+), 563.3096.

Step 7: In an analogous manner to Example 135 step 4, 1-{1-[4-(benzyloxy)-3-(trifluoromethyl)phenyl]-2-piperazin-1-ylethyl}cyclohexanol dihydrochloride was prepared from tert-butyl 4-[2-[4-(benzyloxy)-3-(trifluoromethyl)phenyl]-2-(1-hydroxycyclohexyl)ethyl]piperazine-1-carboxylate. MS (ES) m/z 463.0; HRMS: calcd for C26H33F3N2O2+H, 463.25724; found (ESI, [M+H]+), 463.2554.

Example 264

1-[1-[4-(benzyloxy)-3-(trifluoromethyl)phenyl]-2-(4-methylpiperazin-1-yl)ethyl]cyclohexanol dihydrochloride

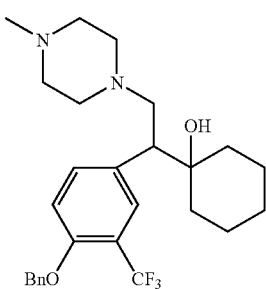

In an analogous manner to Example 24, 1-[1-[4-(benzyloxy)-3-(trifluoromethyl)phenyl]-2-(4-methylpiperazin-1-yl)ethyl]cyclohexanol dihydrochloride was prepared from tert-butyl 4-[2-[4-(benzyloxy)-3-(trifluoromethyl)phenyl]-2-(1-hydroxycyclohexyl)ethyl]piperazine-1-carboxylate. MS (ES) m/z 477.1; HRMS: calcd for C27H35F3N2O2+H, 477.27289; found (ESI, [M+H]+), 477.2711.

Example 265

1-[1-[4-(benzyloxy)-3-bromophenyl]-2-(4-methylpiperazin-1-yl)ethyl]cyclohexanol dihydrochloride

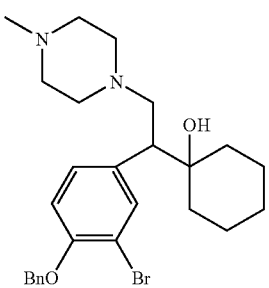

Step 1: In an analogous manner to Example 263 step 2, 4-benzyloxy-3-bromo-benzaldehyde was prepared from 3-bromo-4-hydroxy-benzaldehyde.

Step 2: In an analogous manner to Example 261 step 1, 1-benzyloxy-4-(2,2-dibromo-vinyl)-2-bromo-benzene was prepared from 4-benzyloxy-3-bromo-benzaldehyde.

Step 3: In an analogous manner to Example 261 step 2, tert-butyl 4-{[4-(benzyloxy)-3-bromophenyl]acetyl}piperazine-1-carboxylate was prepared from 1-benzyloxy-4-(2,2-dibromo-vinyl)-2-bromo-benzene. MS (ES) m/z 432.9; HRMS: calcd for C24H29BrN2O4, 488.1311; found (ESI, [M+H]+), 489.1394.

Step 4: In an analogous manner to Example 135 step 2, tert-butyl 4-[[4-(benzyloxy)-3-bromophenyl](1-hydroxycyclohexyl)acetyl]piperazine-1-carboxylate was prepared from, tert-butyl 4-{[4-(benzyloxy)-3-bromophenyl]acetyl}piperazine-1-carboxylate. MS (ES) m/z 587.0; HRMS: calcd for C30H39BrN2O5, 586.2042; found (ESI, [M+H]+), 587.2139.

Step 5: In an analogous manner to Example 135 step 3, tert-butyl 4-[[4-(benzyloxy)-3-bromophenyl](1-hydroxycyclohexyl)ethyl]piperazine-1-carboxylate was prepared from tert-butyl 4-[[4-(benzyloxy)-3-bromophenyl](1-hydroxycyclohexyl)acetyl]piperazine-1-carboxylate.

Step 6: In an analogous manner to Example 24, 1-[1-[4-(benzyloxy)-3-bromophenyl]-2-(4-methylpiperazin-1-yl)ethyl]cyclohexanol dihydrochloride was prepared from tert-butyl 4-[[4-(benzyloxy)-3-bromophenyl](1-hydroxycyclohexyl)ethyl]piperazine-1-carboxylate. MS (ES) m/z 487.0; HRMS: calcd for C26H35BrN2O2+H, 487.19601; found (ESI, [M+H]+), 487.1978.

Example 266

2-(benzyloxy)-5-[1-(1-hydroxycyclohexyl)-2-piperazin-1-ylethyl]benzonitrile dihydrochloride

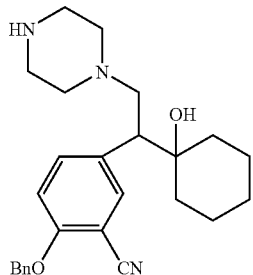

Step 1: In an analogous manner to Example 160, step 1, tert-butyl 4-[[4-(benzyloxy)-3-cyanophenyl](1-hydroxycyclohexyl)ethyl]piperazine-1-carboxylate was prepared from tert-butyl 4-[[4-(benzyloxy)-3-bromophenyl](1-hydroxycyclohexyl)ethyl]piperazine-1-carboxylate (See Example 265, step 5).

Step 2: In an analogous manner to Example 135, step 4, 2-(benzyloxy)-5-[1-(1-hydroxycyclohexyl)-2-piperazin-1-ylethyl]benzonitrile dihydrochloride was prepared from tert-butyl 4-[[4-(benzyloxy)-3-cyanophenyl](1-hydroxycyclohexyl)ethyl]piperazine-1-carboxylate. MS (ES) m/z 420.1; HRMS: calcd for C26H33N3O2+H, 420.26510; found (ESI, [M+H]+), 420.263.

Example 267

2-(benzyloxy)-5-[1-(1-hydroxycyclohexyl)-2-(4-methylpiperazin-1-yl)ethyl]benzonitrile dihydrochloride

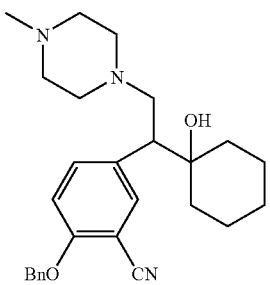

In an analogous manner to Example 24, 2-(benzyloxy)-5-[1-(1-hydroxycyclohexyl)-2-(4-methylpiperazin-1-yl)ethyl]benzonitrile dihydrochloride was prepared from 2-(benzyloxy)-5-[1-(1-hydroxycyclohexyl)-2-piperazin-1-ylethyl]benzonitrile dihydrochloride (See Example 267). MS m/z 434; HRMS: calcd for C27H35N3O2+H, 434.28075; found (ESI, [M+H]+), 434.2821.

Example 268

1-{1-[4-(benzyloxy)-3-(trifluoromethoxy)phenyl]-2-piperazin-1-ylethyl}cyclohexanol dihydrochloride

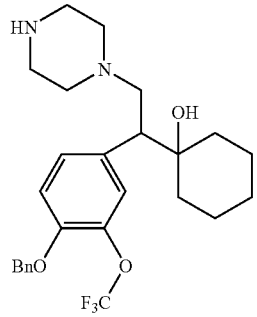

Step 1: In an analogous manner to Example 263 step 1 4-hydroxy-3-(trifluoromethoxy)benzaldehyde. was prepared from 2-trifluoromethoxy phenol. MS (ES) m/z 204.9; HRMS: calcd for C8H5F3O3, 206.0191; found (ESI, [M+H]+), 207.0279.

Step 2: In an analogous manner to Example 263 step 2, 4-benzyloxy-3-trifluoromethoxy-benzaldehyde was prepared from 4-hydroxy-3-(trifluoromethoxy)benzaldehyde.

Step 3: In an analogous manner to Example 261 step 1, 1-benzyloxy-4-(2,2-dibromo-vinyl)-2-(trifluoromethoxy)-benzene was prepared from 4-benzyloxy-3-trifluoromethoxy-benzaldehyde. HRMS: calcd for C16H11Br2F3O2, 449.9078; found (EI, M+.), 449.9079

Step 4: In an analogous manner to Example 261, Step 2, tert-butyl 4-{[4-(benzyloxy)-3-trifluoromethoxyphenyl]acetyl}piperazine-1-carboxylate was prepared 1-benzyloxy-4-(2,2-dibromo-vinyl)-2-(trifluoromethoxy)-benzene.

Step 5: In an analogous manner to Example 135 step 2, tert-butyl 4-[[4-(benzyloxy)-3-(trifluoromethoxy)phenyl](1-hydroxycyclohexyl)acetyl]piperazine-1-carboxylate was prepared from tert-butyl 4-{[4-(benzyloxy)-3-trifluoromethoxyphenyl]acetyl}piperazine-1-carboxylate.

Step 6: In an analogous manner to Example 135 step 3, tert-butyl 4-[2-[4-(benzyloxy)-3-(trifluoromethoxy)phenyl]-2-(1-hydroxycyclohexyl)ethyl]piperazine-1-carboxylate was prepared from tert-butyl 4-[[4-(benzyloxy)-3-(trifluoromethoxy)phenyl](1-hydroxycyclohexyl)acetyl]piperazine-1-carboxylate.

Step 7: In an analogous manner to Example 135 step 4, 1-{1-[4-(benzyloxy)-3-(trifluoromethoxy)phenyl]-2-piperazin-1-ylethyl}cyclohexanol dihydrochloride was prepared from tert-butyl 4-[2-[4-(benzyloxy)-3-(trifluoromethoxy)phenyl]-2-(1-hydroxycyclohexyl)ethyl]piperazine-1-carboxylate. MS (ES) m/z 479.0; HRMS: calcd for C26H33F3N2O3+H, 479.25215; found (ESI, [M+H]+), 479.2506.

Example 269

1-[1-(1-naphthyl)-2-piperazin-1-ylethyl]cyclooctanol dihydrochloride

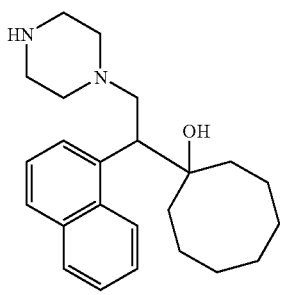

In an analogous manner to Example 1, step 1 tert-butyl 4-[(1-hydroxycyclooctyl)(1-naphthyl)acetyl]piperazine-1-carboxylate was prepared from (1-naphthyl)(1-hydroxycyclooctyl)acetic acid (Reference Example 1-ddd) and tert-butyl 1-piperazinecarboxylate. MS (ESI) m/z 481.

In an analogous manner to Example 1, step 2 1-[1-(1-naphthyl)-2-piperazin-1-ylethyl]cyclooctanol dihydrochloride was prepared from tert-butyl 4-[(1-hydroxycyclooctyl)(1-naphthyl)acetyl]piperazine-1-carboxylate. MS (ESI) m/z 367; HRMS: calcd for C24H34N2O+H, 367.27494; found (ESI, [M+H]+), 367.2732.

Example 270

1-[2-(4-methylpiperazin-1-yl)-1-(1-naphthyl)ethyl]cyclooctanol dihydrochloride

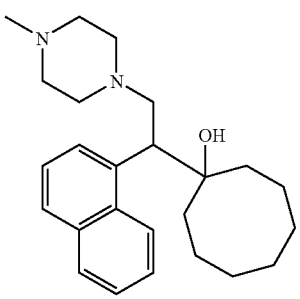

In an analogous manner to Example 24, 1-[2-(4-methylpiperazin-1-yl)-1-(1-naphthyl)ethyl]cyclooctanol dihydrochloride was prepared from 1-[1-(1-naphthyl)-2-piperazin-1-ylethyl]cyclooctanol dihydrochloride (See Example 269). MS (ESI) m/z 381; HRMS: calcd for C25H36N2O+H, 381.29059; found (ESI, [M+H]+), 381.2893.

Example 271

1-[1-(1-naphthyl)-2-piperazin-1-ylethyl]cycloheptanol dihydrochloride

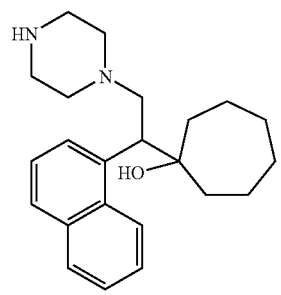

In an analogous manner to Example 1, step 1 tert-butyl 4-[(1-hydroxycycloheptyl)(1-naphthyl)acetyl]piperazine-1-carboxylate was prepared from (1-naphthyl)(1-hydroxycycloheptyl)acetic acid (Reference Example 1-fff) and tert-butyl 1-piperazinecarboxylate. MS (ESI) m/z 467.4.

In an analogous manner to Example 1, step 2 1-[1-(1-naphthyl)-2-piperazin-1-ylethyl]cycloheptanol dihydrochloride was prepared from tert-butyl 4-[(1-hydroxycycloheptyl)(1-naphthyl)acetyl]piperazine-1-carboxylate. MS (ES) m/z 353.3; HRMS: calcd for C23H32N2O+H, 353.25929; found (ESI, [M+H]+), 353.2609.

Example 272

1-[2-(4-methylpiperazin-1-yl)-1-(1-naphthyl)ethyl]cycloheptanol dihydrochloride

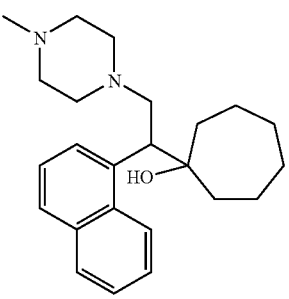

In an analogous manner to Example 24, 1-[2-(4-methylpiperazin-1-yl)-1-(1-naphthyl)ethyl]cycloheptanol dihydrochloride was prepared from 1-[1-(1-naphthyl)-2-piperazin-1-ylethyl]cycloheptanol dihydrochloride (see Example 271). MS (ES) m/z 367.3; HRMS: calcd for C24H34N2O+H, 367.27494; found (ESI, [M+H]+), 367.2733.

Example 273

4-(4-aminopiperidin-1-yl)-3-(3-chlorophenyl)-2-methylbutan-2-ol dihydrochloride

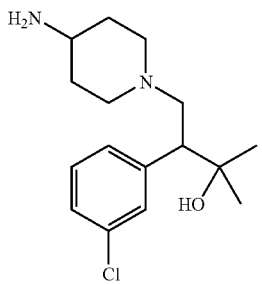

In an analogous manner to Example 1, step 1 tert-butyl {1-[2-(3-chlorophenyl)-3-hydroxy-3-methylbutanoyl]piperidin-4-yl}carbamate was prepared from 2-(3-chlorophenyl)-3-hydroxy-3-methylbutanoic acid (Reference Example 1-ggg) and 4-N-boc-aminopiperidine. MS (ESI) m/z 411.0.

In an analogous manner to Example 1, step 2 4-(4-aminopiperidin-1-yl)-3-(3-chlorophenyl)-2-methylbutan-2-ol dihydrochloride was prepared from tert-butyl {1-[2-(3-chlorophenyl)-3-hydroxy-3-methylbutanoyl]piperidin-4-yl}carbamate. MS (ESI) m/z 297; HRMS: calcd for $C_{16}H_{25}ClN_2O+H$, 297.17337; found (ESI, [M+H]+), 297.1734.

Example 274

3-(3-chlorophenyl)-4-[4-(dimethylamino)piperidin-1-yl]-2-methylbutan-2-ol dihydrochloride

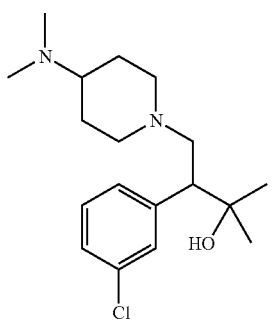

In an analogous manner to Example 24, 3-(3-chlorophenyl)-4-[4-(dimethylamino)piperidin-1-yl]-2-methylbutan-2-ol dihydrochloride was prepared from 4-(4-aminopiperidin-1-yl)-3-(3-chlorophenyl)-2-methylbutan-2-ol dihydrochloride (See Example 273). MS (ESI) m/z 325; HRMS: calcd for $C_{18}H_{29}ClN_2O+H$, 325.20467; found (ESI, [M+H]+), 325.2063.

Example 275

3-(3-chlorophenyl)-2-methyl-4-piperazin-1-ylbutan-2-ol dihydrochloride

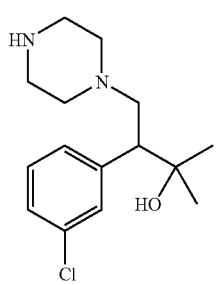

In an analogous manner to Example 1, step 1, tert-butyl 4-[2-(3-chlorophenyl)-3-hydroxy-3-methylbutanoyl]piperazine-1-carboxylate was prepared from 2-(3-chlorophenyl)-3-hydroxy-3-methylbutanoic acid (Reference Example 1-ggg) and tert-butyl 1-piperazinecarboxylate. MS (ESI) m/z 397.0.

In an analogous manner to Example 1, step 2, 3-(3-chlorophenyl)-2-methyl-4-piperazin-1-ylbutan-2-ol dihydrochloride was prepared from 1 tert-butyl 4-[2-(3-chlorophenyl)-3-hydroxy-3-methylbutanoyl]piperazine-1-carboxylate. MS (ES) m/z 283.0; HRMS: calcd for $C_{15}H_{23}ClN_2O+H$, 283.15772; found (ESI, [M+H]+), 283.1581.

Example 276

3-(3-chlorophenyl)-2-methyl-4-(4-methylpiperazin-1-yl)butan-2-ol dihydrochloride

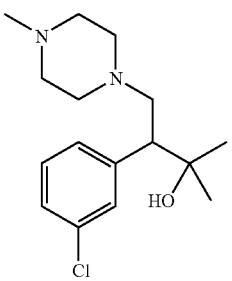

In an analogous manner to Example 24, 3-(3-chlorophenyl)-2-methyl-4-(4-methylpiperazin-1-yl)butan-2-ol dihydrochloride was prepared from 3-(3-chlorophenyl)-2-methyl-4-piperazin-1-ylbutan-2-ol dihydrochloride (See Example 275). MS (ES) m/z 297.0; HRMS: calcd for $C_{16}H_{25}ClN_2O+H$, 297.17337; found (ESI, [M+H]+), 297.1719.

Example 277

1-[1-(3-chlorophenyl)-2-piperazin-1-ylethyl]-3,3,5,5-tetramethylcyclohexanol dihydrochloride

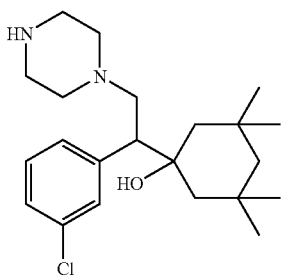

In an analogous manner to Example 1, step 1, tert-butyl 4-[(3-chlorophenyl)(1-hydroxy-3,3,5,5-tetramethylcyclohexyl)acetyl]piperazine-1-carboxylate was prepared from 3-chlorophenyl)(1-hydroxy-3,3,5,5-tetramethylcyclohexyl) acetic acid (Reference Example 1-hhh) and tert-butyl 1-piperazinecarboxylate.

In an analogous manner to Example 1, step 2, 1-[1-(3-chlorophenyl)-2-piperazin-1-ylethyl]-3,3,5,5-tetramethylcyclohexanol dihydrochloride was prepared from tert-butyl 4-[(3-chlorophenyl)(1-hydroxy-3,3,5,5-tetramethylcyclohexyl)acetyl]piperazine-1-carboxylate. MS (ES) m/z 379.3; HRMS: calcd for C22H35ClN2O+H, 379.25161; found (ESI, [M+H]+), 379.2527.

Example 278

1-[1-(3-chlorophenyl)-2-(4-methylpiperazin-1-yl)ethyl]-3,3,5,5-tetramethylcyclohexanol dihydrochloride

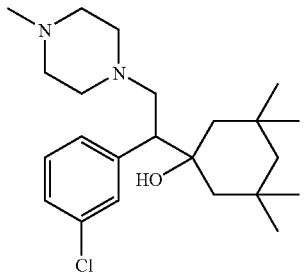

In an analogous manner to Example 24, 1-[1-(3-chlorophenyl)-2-(4-methylpiperazin-1-yl)ethyl]-3,3,5,5-tetramethylcyclohexanol dihydrochloride was prepared from 1-[1-(3-chlorophenyl)-2-piperazin-1-ylethyl]-3,3,5,5-tetramethylcyclohexanol dihydrochloride (See Example 277). MS (ESI) m/z 393; HRMS: calcd for C23H37ClN2O+H, 393.26727; found (ESI, [M+H]+), 393.2653.

Example 279

1-[1-(5-methoxy-1-benzothien-3-yl)-2-piperazin-1-ylethyl]cyclohexanol dihydrochloride

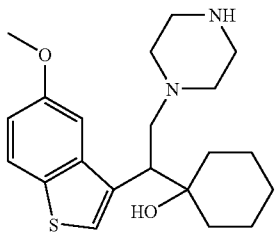

In an analogous manner to Example 1, step 1, tert-butyl 4-[(1-hydroxycyclohexyl)(5-methoxy-1-benzothien-3-yl)acetyl]piperazine-1-carboxylate was prepared from (1-hydroxy-cyclohexyl)-(5-methoxy-benzo[b]thiophen-3-yl)-acetic acid (Reference Example 1-iii) and tert-butyl 1-piperazinecarboxylate. MS (ES) m/z 489.0.

In an analogous manner to Example 1, step 2, 1-[1-(5-methoxy-1-benzothien-3-yl)-2-piperazin-1-ylethyl]cyclohexanol dihydrochloride was prepared tert-butyl 4-[(1-hydroxycyclohexyl)(5-methoxy-1-benzothien-3-yl)acetyl] piperazine-1-carboxylate. MS (ES) m/z 375.1; HRMS: calcd for $C_{21}H_{30}N_2O_2S+H$, 375.21062; found (ESI, [M+H]+), 375.2117.

Example 280

1-[2-(4-aminopiperidin-1-yl)-1-(5-methoxy-1-benzothien-3-yl)ethyl]cyclohexanol dihydrochloride

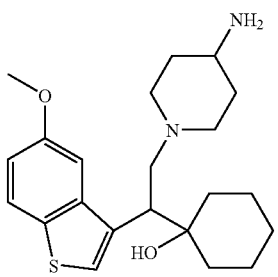

In an analogous manner to Example 1, step 1, tert-butyl 4-[(1-hydroxycyclohexyl)(5-methoxy-1-benzothien-3-yl)acetyl]-piperidine-4-yl carbamate was prepared from (1-hydroxy-cyclohexyl)-(5-methoxy-benzo[b]thiophen-3-yl)-acetic acid (Reference Example 1-iii) and 4-N-boc-aminopiperidine.

In an analogous manner to Example 1, step 2, 1-[2-(4-aminopiperidin-1-yl)-1-(5-methoxy-1-benzothien-3-yl)ethyl]cyclohexanol dihydrochloride was prepared from, tert-butyl 4-[(1-hydroxycyclohexyl) (5-methoxy-1-benzothien-3-yl)acetyl]piperidine-4-yl carbamate. MS (ES) m/z 389.0; HRMS: calcd for C22H32N2O2S+H, 389.22627; found (ESI, [M+H]+), 389.2262.

Example 281

1-[1-(4-bromothien-2-yl)-2-piperazin-1-ylethyl]cyclohexanol dihydrochloride

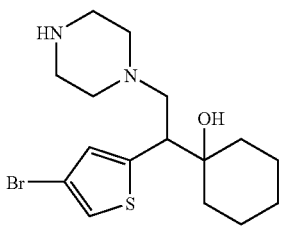

Step 1: In an analogous manner to Example 261 step 1, 4-bromo-2-(2,2-dibromovinyl)thiophene was prepared from 4-bromo-2-thiophenecarboxaldehyde.

Step 2: In an analogous manner to Example 261 step 2, tert-butyl 4-[(4-bromothien-2-yl)acetyl]piperazine-1-carboxylate was prepared from 4-bromo-2-(2,2-dibromovinyl)thiophene.

Step 3: In an analogous manner to Example 135 step 2, tert-butyl 4-[2-(4-Bromo-thiophen-2-yl)-2-(1-hydroxy-cyclohexyl)-acetyl]-piperazine-1-carboxylate was prepared from tert-butyl 4-[(4-bromothien-2-yl)acetyl]piperazine-1-carboxylate.

Step 4: In an analogous manner to Example 135 step 3, 4-[2-(4-Bromo-thiophen-2-yl)-2-(1-hydroxy-cyclohexyl)-ethyl]-piperazine-1-carboxylate was prepared from 4-[2-(4-Bromo-thiophen-2-yl)-2-(1-hydroxy-cyclohexyl)-acetyl]-piperazine-1-carboxylate.

Step 5: In an analogous manner to Example 135 step 4, 1-[1-(4-bromothien-2-yl)-2-piperazin-1-ylethyl]cyclohexanol dihydrochloride was prepared from 4-[2-(4-Bromo-thiophen-2-yl)-2-(1-hydroxy-cyclohexyl)-ethyl]-piperazine-1-carboxylate. MS (ES) m/z 372.9; HRMS: calcd for C16H25BrN2OS+H, 373.09492; found (ESI, [M+H]+), 373.0932.

Example 282

4-[2-(4-aminopiperidin-1-yl)-1-(3-chlorophenyl)ethyl]heptan-4-ol dihydrochloride

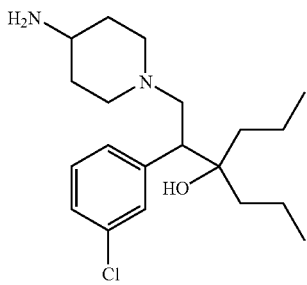

In an analogous manner to Example 1, step 1 tert-butyl {1-[2-(3-chlorophenyl)-3-hydroxy-3-propylhexanoyl]piperidin-4-yl}carbamate was prepared from 2-(3-chlorophenyl)-3-hydroxy-3-propylhexanoic acid (Reference Example 1-u) and 4-N-boc-aminopiperidine. MS (ESI) m/z 411.0.

In an analogous manner to Example 1, step 2 4-[2-(4-aminopiperidin-1-yl)-1-(3-chlorophenyl)ethyl]heptan-4-ol dihydrochloride was prepared from tert-butyl {1-[2-(3-chlorophenyl)-3-hydroxy-3-methylbutanoyl]piperidin-4-yl}carbamate. MS (ES) m/z 353.3; HRMS: calcd for C20H33ClN2O+H, 353.23597; found (ESI, [M+H]+), 353.237.

Example 283

1-{2-(4-methylpiperazin-1-yl)-1-[4-(trifluoromethoxy)phenyl]ethyl}cyclohexanol dihydrochloride

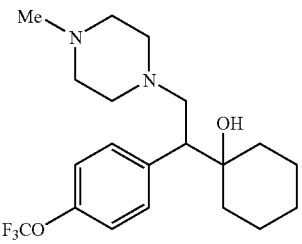

In an analogous manner to Example 1, step 1, 1-methyl-4-{(1-hydroxycyclohexyl) [4-trifluoromethoxy)phenyl]acetyl}piperazine was prepared from (1-hydroxycyclohexyl) [4-(trifluoromethoxy)phenyl]acetic acid (Reference Example 1-g) and 1-methylpiperazine. MS (ESI) m/z 401 ([M+H]+)

In an analogous manner Example 1 step 2 1-{2-(4-methylpiperazin-1-yl)-1-[4-(trifluoromethoxy)phenyl]ethyl}cyclohexanol dihydrochloride was prepared from 1-methyl-4-{(1-hydroxycyclohexyl) [4-trifluoromethoxy)phenyl]acetyl}piperazine. MS (ESI) m/z 387 ([M+H]+)

Example 284

1-{2-(1,4'-bipiperidin-1'-yl)-1-[4-(trifluoromethoxy)phenyl]ethyl}cyclohexanol dihydrochloride

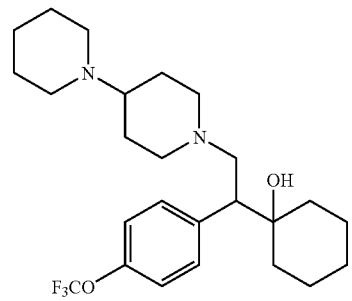

In an analogous manner to Example 1, step 1, 1-[2-(4-piperidin-1-ylpiperidin-1-yl)-1-[4-(trifluoromethoxy)phenyl]-2-oxoethyl]cyclohexanol was prepared from (1-hydroxycyclohexyl) [4-(trifluoromethoxy)phenyl]acetic acid (Reference Example 1-g) and 4-piperidinopiperidine. MS (ESI) m/z 469 ([M+H]+)

In an analogous manner Example 1, step 2 1-{2-(1,4'-bipiperidin-1'-yl)-1-[4-(trifluoromethoxy)phenyl]ethyl}cyclohexanol dihydrochloride was prepared from 1-{2-(4-piperidin-1-ylpiperidin-1-yl)-1-[4-(trifluoromethoxy)phenyl]-2-oxoethyl}cyclohexanol. MS (ESI) m/z 455 ([M+H]$^+$). Anal Calcd for $C_{25}H_{37}F_3N_2O_2$2HCl 0.1H$_2$O: C, 56.92; H, 7.45: N, 5.31. Found: C, 56.39; H, 7.64; N, 5.28

Example 285

1-{2-[4-(1,3-benzodioxol-5-ylmethyl)piperazin-1-yl]-1-[4-(trifluoromethoxy)phenyl]ethyl}cyclohexanol dihydrochloride

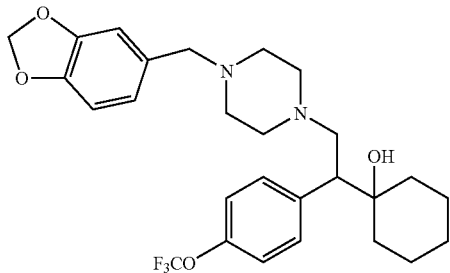

In an analogous manner to Example 1, step 1 1-{2-[4-(1,3-benzodioxol-5-ylmethyl)piperazin-1-yl]-1-[4-trifluoromethoxy)phenyl]-2-oxoethyl}cyclohexanol was prepared was prepared from (1-hydroxycyclohexyl) [4-(trifluoromethoxy)phenyl]acetic acid (Reference Example 1-g) and 1-piperonylpiperazine. MS (ESI) m/z 521 ([M+H]$^+$)

In an analogous manner Example 1, step 2 1-{2-[4-(1,3-benzoioxol-5-ylmethyl)piperazin-1-yl]-1-[4-(trifluoromethoxy)phenyl]ethyl}cyclohexanol dihydrochloride was prepared from 1-{2-[4-(1,3-benzodioxol-5-ylmethyl)piperazin-1-yl]-1-[4-trifluoromethoxy)phenyl]-2-oxoethyl}cyclohexanol. MS (ESI) m/z 507 ([M+H]$^+$). Anal Calcd for $C_{27}H_{33}F_3N_2O_4$2HCl 0.25H$_2$O: C, 55.53; H, 6.13: N, 4.80. Found: C, 55.29; H, 6.14; N, 4.74.

Example 286

1-{2-[4-(cyclohexylmethyl)piperazin-1-yl]-1-[4-(trifluoromethoxy)phenyl]ethyl}cyclohexanol dihydrochloride

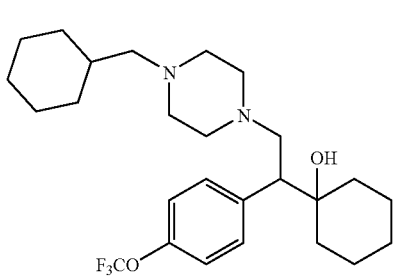

In an analogous manner to Example 1, step 1 1-{2-[4-(cyclohexylmethyl)piperazin-1-yl]-1-[4-(trifluoromethoxy)phenyl]2-oxoethyl}cyclohexanol was prepared from (1-hydroxycyclohexyl) [4-(trifluoromethoxy)phenyl]acetic acid (Reference Example 1-g) and 1-cyclohexylmethyl)piperazine. MS (ESI) m/z 483 ([M+H]$^+$)

In an analogous manner Example 1, step 2 1-{2-[4-(cyclohexylmethyl)piperazin-1-yl]-1-[4-(trifluoromethoxy)phenyl]ethyl}cyclohexanol dihydrochloride was prepared from 1-{2-[4-(cyclohexylmethyl)piperazin-1-yl]-1-[4-(trifluoromethoxy)phenyl]2-oxoethyl}cyclohexanol. MS (ESI) m/z 469 ([M+H]$^+$). Anal Calcd for $C_{26}H_{39}F_3N_2O_2$2HCl: C, 57.67; H, 7.63: N, 5.17. Found: C, 57.23; H, 7.64; N, 4.86

Example 287

1-{2-(4-ethylpiperazin-1-yl)-1-[4-(trifluoromethoxy)phenyl]ethyl}cyclohexanol dihydrochloride

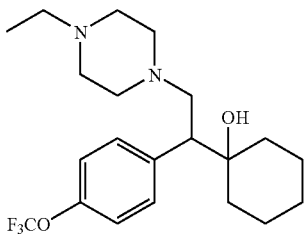

In an analogous manner to Example 1, step 1 1-{2-(4-ethylpiperazin-1-yl)-1-[4-(trifluoromethoxy)phenyl]-2-oxoethyl}cyclohexanol was prepared from (1-hydroxycyclohexyl) [4-(trifluoromethoxy)phenyl]acetic acid (Reference Example 1-g) and 1-ethylpiperazine. MS (ESI) m/z 415 ([M+H]$^+$ In an analogous manner to Example 1, step 2 1-{2-(4-ethylpiperazin-1-yl)-1-[4-(trifluoromethoxy)phenyl]ethyl}cyclohexanol dihydrochloride was prepared from 1-{2-(4-ethylpiperazin-1-yl)-1-[4-(trifluoromethoxy)phenyl]-2-oxoethyl}cyclohexanol. MS (ESI) m/z 401 ([M+H]$^+$). Anal Calcd for $C_{21}H_{31}F_3N_2O_2$2HCl 0.25H$_2$O: C, 52.78; H, 7.06; N, 5.86. Found: C, 52.48; H, 6.93; N, 5.81.

Example 288

1-{2-[cis-3,5-dimethylpiperazin-1-yl]-1-[4(trifluoromethoxy)phenyl]ethyl}cyclohexanol dihydrochloride

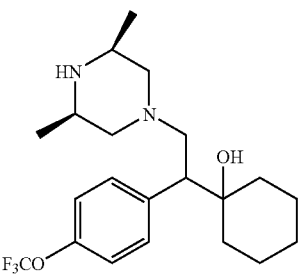

In an analogous manner to Example 1, step 1 1-{2-[cis-3,5-dimethylpiperazin-1-yl]-1-[4-(trifluoromethoxy)phenyl]-2-oxoethyl}cyclohexanol was prepared from (1-hydroxycyclohexyl) [4-(trifluoromethoxy)phenyl]acetic acid (Reference Example 1-g) and cis-2,6-dimethylpiperidine. MS (ESI) m/z 415 ([M+H]$^+$ In an analogous manner to Example 1, step 2 1-{2-[cis-3,5-dimethylpiperazin-1-yl]-1-[4-(trifluoromethoxy)phenyl]ethyl}cyclohexanol dihydrochloride was prepared from 1-{2-[cis-3,5-dimethylpiperazin-1-yl]-1-[4-(trifluoromethoxy)phenyl]-2-oxoethyl}cyclohexanol MS (ESI) m/z 401 ([M+H]⁺). Anal Calcd for C₂₁H₃₁F₃N₂O₂2HCl 0.33H₂O: C, 52.62; H, 7.08: N, 5.84. Found: C, 52.69; H, 6.97; N, 5.61.

Example 289

1-[1-(2'-fluoro-1,1'-biphenyl-4-yl)-2-piperazin-1-ylethyl]cyclohexanol dihydrochloride

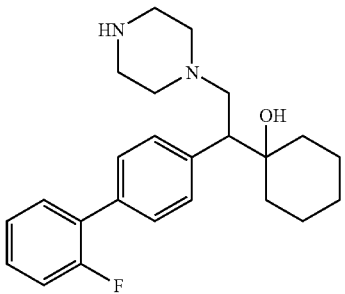

In an analogous manner to Example 135, step 3, tert-butyl 4-[2-(2'-fluoro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (Example 163, step 2) using 2-fluorophenylboronic acid. MS (ESI) m/z 483 ([M+H]⁺); HRMS: calcd for C₂₉H₃₉FN₂O₃+H, 483.3023; found (ESI, [M+H]⁺), 483.3006.

In an analogous manner to Example 135, step 4, 1-[1-(2'-fluoro-1,1'-biphenyl-4-yl)-2-piperazin-1-ylethyl]cyclohexanol dihydrochloride was prepared from tert-butyl 4-[2-(2'-fluoro-1,1'-biphenyl-4-yl)-2-(1-hydroxycyclohexyl)ethyl]piperazine-1-carboxylate. MS (ESI) m/z 383 ([M+H]⁺); HRMS: calcd for C₂₄H₃₁FN₂O+H, 383.2499; found (ESI, [M+H]⁺), 383.2499.

Example 290

4'-[1-(1-hydroxycyclohexyl)-2-piperazin-1-ylethyl]-1,1'-biphenyl-2-carbonitrile dihydrochloride

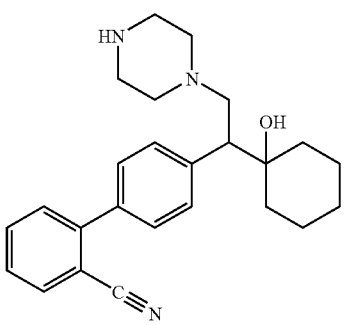

In an analogous manner to Example 135, step 3, tert-butyl 4-[2-(2'-cyano-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (Example 163, step 2) using 2-cyanophenylboronic acid. MS (ESI) m/z 490 ([M+H]⁺).

In an analogous manner to Example 135, step 4, 4'-[1-(1-hydroxycyclohexyl)-2-piperazin-1-ylethyl]-1,1'-biphenyl-2-carbonitrile dihydrochloride was prepared from tert-butyl 4-[2-(2'-cyano-1,1'-biphenyl-4-yl)-2-(1-hydroxycyclohexyl)ethyl]piperazine-1-carboxylate. MS (ESI) m/z 390 ([M+H]⁺); HRMS: calcd for C₂₅H₃₁N₃O+H, 390.2545; found (ESI, [M+H]⁺), 390.2532.

Example 291

1-[1-(2',5'-dichloro-1,1'-biphenyl-4-yl)-2-piperazin-1-ylethyl]cyclohexanol dihydrochloride

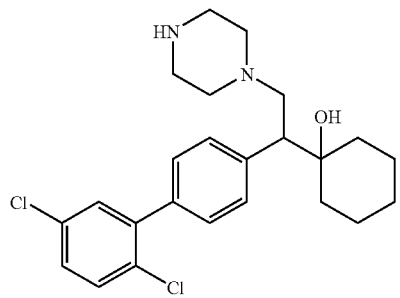

In an analogous manner to Example 135, step 3, tert-butyl 4-[2-(2',5'-dichloro-1,1'-biphenyl-4-yl)-2-(1-hydroxycyclohexyl)ethyl]piperazine-1-carboxylate was prepared from tert-butyl 4-[2-(4-bromophenyl)-2-(1-hydroxycyclohexyl)ethyl]piperazine-1-carboxylate (Example 163, step 2) using 2,5-dichlorophenylboronic acid. MS (ESI) m/z 533 ([M+H]⁺); HRMS: calcd for C₂₉H₃₈Cl₂N₂O₃+H, 533.2338; found (ESI, [M+H]⁺), 533.2332.

In an analogous manner to Example 135, step 4, 1-[1-(2',5'-dichloro-1,1'-biphenyl-4-yl)-2-piperazin-1-ylethyl]cyclohexanol dihydrochloride was prepared from tert-butyl 4-[2-(2',5'-dichloro-1,1'-biphenyl-4-yl)-2-(1-hydroxycyclohexyl)ethyl]piperazine-1-carboxylate. HRMS: calcd for C₂₄H₃₀Cl₂N₂O+H, 433.1813; found (ESI, [M+H]⁺), 433.1806.

Example 292

1-{1-[4-(benzyloxy)-3-chlorophenyl]-2-piperazin-1-ylethyl}cyclohexanol dihydrochloride

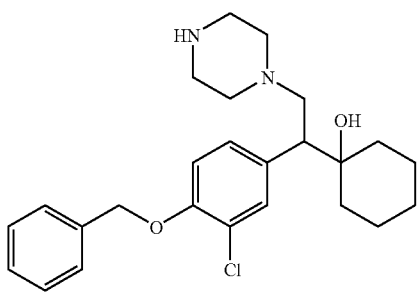

In an analogous manner to Example 1, step 1, tert-butyl 4-[[4-(benzyloxy)-3-chlorophenyl](1-hydroxycyclohexyl)acetyl]piperazine-1-carboxylate was prepared from [4-(benzyloxy)-3-chlorophenyl](1-hydroxycyclohexyl)acetic acid (reference Example 1eee) and tert-butyl 1-piperazinecarboxylate. MS (ESI) m/z 543 ([M+H]$^+$).

In an analogous manner to Example 135, step 2, tert-butyl 4-[2-(4-benzyloxy-3-chlorophenyl)-2-(1-hydroxycyclohexyl)ethyl]piperazine-1-carboxylate was prepared from tert-butyl 4-[[4-(benzyloxy)-3-chlorophenyl](1-hydroxycyclohexyl)acetyl]piperazine-1-carboxylate. MS (ESI) m/z 529/531 ([M+H]$^+$).

In an analogous manner to Example 135, step 4, 1-{1-[4-(benzyloxy)-3-chlorophenyl]-2-piperazin-1-ylethyl}cyclohexanol dihydrochloride was prepared from tert-butyl 4-[2-(4-benzyloxy-3-chlorophenyl)-2-(1-hydroxycyclohexyl)ethyl]piperazine-1-carboxylate. MS (ESI) m/z 429 ([M+H]$^+$); HRMS: calcd for $C_{25}H_{33}ClN_2O_2$+H, 429.2309; found (ESI, [M+H]$^+$), 429.2318.

Example 293

1-[1-[4-(benzyloxy)-3-chlorophenyl]-2-(4-methylpiperazin-1-yl)ethyl]cyclohexanol dihydrochloride

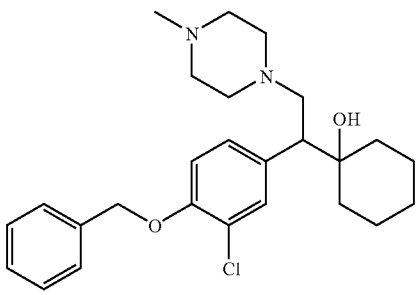

In an analogous manner to Example 24, 1-[1-[4-(benzyloxy)-3-chlorophenyl]-2-(4-methylpiperazin-1-yl)ethyl]cyclohexanol dihydrochloride was prepared from 1-{1-[4-(benzyloxy)-3-chlorophenyl]-2-piperazin-1-ylethyl}cyclohexanol (Example 292). MS (ESI) m/z 443 ([M+H]$^+$); HRMS: calcd for $C_{26}H_{35}ClN_2O_2$+H, 443.2465; found (ESI, [M+H]$^+$), 443.2459.

Example 294

1-[1-(3'-chloro-1,1'-biphenyl-4-yl)-2-(4-methylpiperazin-1-yl)ethyl]cyclobutanol dihydrochloride

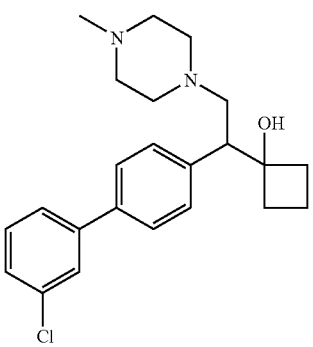

In an analogous manner to Example 24, 1-[1-(3'-chloro-1,1'-biphenyl-4-yl)-2-(4-methylpiperazin-1-yl)ethyl]cyclobutanol dihydrochloride was prepared from 1-[1-(3'-chloro-1,1'-biphenyl-4-yl)-2-piperazin-1-ylethyl]cyclobutanol (Example 182). MS (ESI) m/z 385 ([M+H]$^+$); HRMS: calcd for $C_{23}H_{29}ClN_2O$+H, 385.20467; found (ESI, [M+H]$^+$), 385.2054.

Example 295

1-{2-(4-methylpiperazin-1-yl)-1-[3'-(trifluoromethoxy)-1,1'-biphenyl-4-yl]ethyl}cyclobutanol dihydrochloride

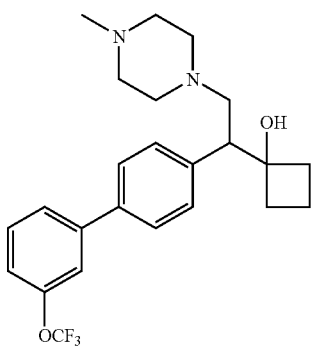

In an analogous manner to Example 24, 1-{2-(4-methylpiperazin-1-yl)-1-[3'-(trifluoromethoxy)-1,1'-biphenyl-4-yl]ethyl}cyclobutanol dihydrochloride was prepared from 1-{2-piperazin-1-yl-1-[3'-(trifluoromethoxy)-1,1'-biphenyl-4-yl]ethyl}cyclobutanol (Example 183). MS (ESI) m/z 435 ([M+H]$^+$); HRMS: calcd for $C_{24}H_{29}F_3N_2O_2$+H, 435.2259; found (ESI, [M+H]+), 435.2256.

Example 296

1-[1-(3',4'-dichloro-1,1'-biphenyl-4-yl)-2-(4-methylpiperazin-1-yl)ethyl]cyclobutanol dihydrochloride

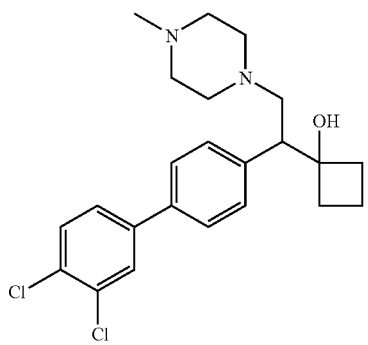

In an analogous manner to Example 24, 1-[1-(3',4'-dichloro-1,1'-biphenyl-4-yl)-2-(4-methylpiperazin-1-yl)ethyl]cyclobutanol dihydrochloride was prepared from 1-[1-(3',4'-dichloro-1,1'-biphenyl-4-yl)-2-piperazin-1-ylethyl]

cyclobutanol (Example 184). MS (ESI) m/z 419 ([M+H]+); HRMS: calcd for $C_{23}H_{28}Cl_2N_2O$+H, 419.1657; found (ESI, [M+H]+), 419.1667.

Example 297

1-[1-(3',5'-dichloro-1,1'-biphenyl-4-yl)-2-(4-methylpiperazin-1-yl)ethyl]cyclobutanol dihydrochloride

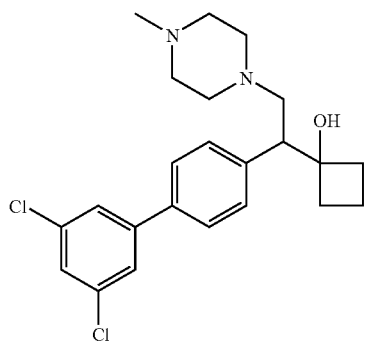

In an analogous manner to Example 24, 1-[1-(3',5'-dichloro-1,1'-biphenyl-4-yl)-2-(4-methylpiperazin-1-yl)ethyl]cyclobutanol dihydrochloride was prepared from 1-[1-(3',5'-dichloro-1,1'-biphenyl-4-yl)-2-piperazin-1-ylethyl]cyclobutanol (Example 185). MS (ESI) m/z 419 ([M+H]+); HRMS: calcd for $C_{23}H_{28}Cl_2N_2O$+H, 419.1657; found (ESI, [M+H]+), 419.1660.

Example 298

1-[1-(3-ethynylphenyl)-2-piperazin-1-ylethyl]cyclohexanol dihydrochloride

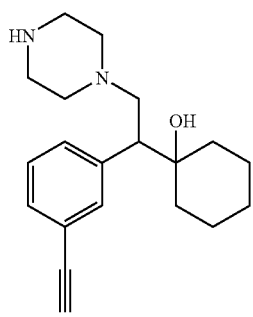

In an analogous manner to Example 162, step 1, tert-butyl 4-(2-(1-hydroxycyclohexyl)-2-{3-[(trimethylsilyl)ethynyl]phenyl}ethyl)piperazine-1-carboxylate was prepared from tert-butyl 4-[2-(3-bromophenyl)-2-(1-hydroxycyclohexyl)ethyl]piperazine-1-carboxylate (Example 135, step 2) using (trimethylsilylethynyl)tributyltin. MS (ESI) m/z 485 ([M+H]+); HRMS: calcd for $C_{28}H_{44}N_2O_3Si$+H, 485.3200; found (ESI, [M+H]+), 485.3202.

To a solution of tert-butyl 4-(2-(1-hydroxycyclohexyl)-2-{3-[(trimethylsilyl)ethynyl]phenyl}ethyl)piperazine-1-carboxylate (104 mg, 0.215 mmol) in methanol (3 mL) was added potassium carbonate (300 mg, 2.17 mmol) and the mixture was stirred for 30 min at room temperature. The reaction mixture was quenched with aqueous ammonium chloride (5 mL) and extracted with ethyl acetate. The organic layer was washed with water, brine, dried (sodium sulfate), filtered and concentrated to give a crude oil, which was purified via silica gel flash chromatography (gradient from 10% ethyl acetate/hexane to 30% ethyl acetate/hexane) to yield 70 mg (80%) tert-butyl 4-[2-(3-ethynylphenyl)-2-(1-hydroxycyclohexyl)ethyl]piperazine-1-carboxylate as a white solid. MS (ESI) m/z 413 ([M+H]+); HRMS: calcd for $C_{25}H_{36}N_2O_3$+H, 413.2804; found (ESI, [M+H]+), 413.2809.

In an analogous manner to Example 135, step 4, 1-[1-(3-ethynylphenyl)-2-piperazin-1-ylethyl]cyclohexanol dihydrochloride was prepared from tert-butyl 4-[2-(3-ethynylphenyl)-2-(1-hydroxycyclohexyl)ethyl]piperazine-1-carboxylate. MS (ESI) m/z 313 ([M+H]+); HRMS: calcd for $C_{20}H_{28}N_2O$+H, 313.2280; found (ESI, [M+H]+), 313.2280.

Example 299

1-[1-(3-ethynylphenyl)-2-(4-methylpiperazin-1-yl)ethyl]cyclohexanol dihydrochloride

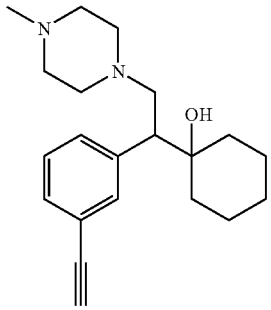

In an analogous manner to Example 24, 1-[1-(3-ethynylphenyl)-2-(4-methylpiperazin-1-yl)ethyl]cyclohexanol dihydrochloride was prepared from 1-[1-(3-ethynylphenyl)-2-piperazin-1-ylethyl]cyclohexanol (Example 298). MS (ESI) m/z 327 ([M+H]+); HRMS: calcd for $C_{21}H_{30}N_2O$+H, 327.2436; found (ESI, [M+H]+), 327.2425.

Example 300

1-[2-piperazin-1-yl-1-(3-prop-1-ynylphenyl)ethyl]cyclohexanol dihydrochloride

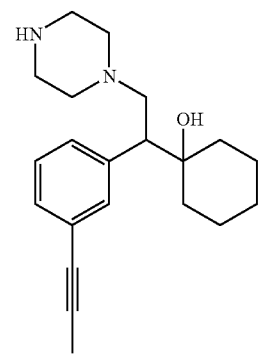

In an analogous manner to Example 162, step 1, tert-butyl 4-[2-(1-hydroxycyclohexyl)-2-(3-prop-1-ynylphenyl)ethyl]

piperazine-1-carboxylate was prepared from tert-butyl 4-[2-(3-bromophenyl)-2-(1-hydroxycyclohexyl)ethyl]piperazine-1-carboxylate (Example 135, step 2) using (1-propynyl)tributyltin. MS (ESI) m/z 427 ([M+H]$^+$); HRMS: calcd for $C_{26}H_{38}N_2O_3$+H, 427.2961; found (ESI, [M+H]$^+$), 427.2967.

In an analogous manner to Example 135, step 4, 1-[2-piperazin-1-yl-1-(3-prop-1-ynylphenyl)ethyl]cyclohexanol dihydrochloride was prepared from tert-butyl 4-[2-(1-hydroxycyclohexyl)-2-(3-prop-1-ynylphenyl)ethyl]piperazine-1-carboxylate. MS (ESI) m/z 327 ([M+H]$^+$); HRMS: calcd for $C_{21}H_{30}N_2O$+H, 327.2436; found (ESI, [M+H]$^+$), 327.2421.

Example 301

1-[2-(4-methylpiperazin-1-yl)-1-(3-prop-1-ynylphenyl)ethyl]cyclohexanol dihydrochloride

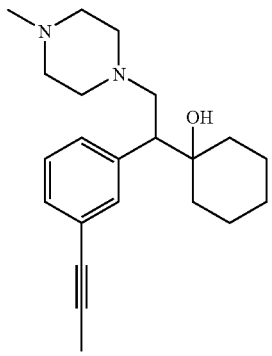

In an analogous manner to Example 24, 1-[2-(4-methylpiperazin-1-yl)-1-(3-prop-1-ynylphenyl)ethyl]cyclohexanol dihydrochloride was prepared from 1-[2-piperazin-1-yl-1-(3-prop-1-ynylphenyl)ethyl]cyclohexanol (Example 300). HRMS: calcd for $C_{22}H_{32}N_2O$+H, 341.2593; found (ESI, [M+H]$^+$), 341.2585.

Example 302

1-{2-(4-benzyl-1,4-diazepan-1-yl)-1-[4(trifluoromethoxy)phenyl]ethyl}cyclohexanol dihydrochloride

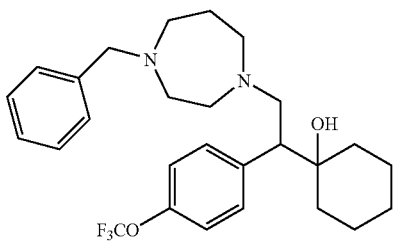

In an analogous manner to Example 1, step 1 1-{2-(4-benzyl-1,4-diazepan-1-yl)-1-[4-(trifluoromethoxy)phenyl]-2-oxoethyl}cyclohexanol was prepared from (1-hydroxycyclohexyl) [4-(trifluoromethoxy)phenyl]acetic acid (Reference Example 1-g) and 1-benzyl-homopiperazine. MS (ESI) m/z 491 ([M+H]$^+$ In an analogous manner to Example 1, step 2 1-{2-(4-benzyl-1,4-diazepan-1-yl)-1-[4-(trifluoromethoxy)phenyl]ethyl}cyclohexanol dihydrochloride was prepared from 1-{2-(4-benzyl-1,4-diazepan-1-yl)-1-[4-(trifluoromethoxy)phenyl]-2-oxoethyl}cyclohexanol.

MS (ESI) m/z 477 ([M+H]$^+$). Anal Calcd for $C_{27}H_{35}F_3N_2O_2$·2HCl 1H$_2$O: C, 57.14; H, 6.93: N, 4.94. Found: C, 57.02; H, 7.44; N, 4.98

Example 303

1-{2-(4-aminopiperidin-1-yl)-1-[4-(trifluoromethoxy)phenyl]ethyl}cyclohexanol dihydrochloride

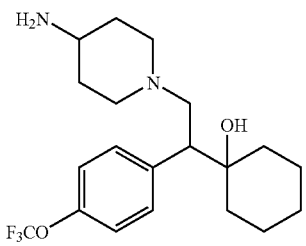

In an analogous manner to Example 1, step 1 tert-butyl (1-{(1-hydroxycyclohexyl) [4-(trifluoromethoxy)phenyl]acetyl}piperidin-4-yl)carbamate was prepared from (1-hydroxycyclohexyl) [4-(trifluoromethoxy)phenyl]acetic acid (Reference Example 1-g) and 4-N-BOC-aminopiperidine. MS (ESI) m/z 501 ([M+H]$^+$)

In an analogous manner to Example 1, step 2 1-{2-(4-aminopiperidin-1-yl)-1-[4-(trifluoromethoxy)phenyl]ethyl}cyclohexanol dihydrochloride was prepared from 1 tert-butyl (1-{(1-hydroxycyclohexyl)[4-(trifluoromethoxy)phenyl]acetyl}piperidin-4-yl)carbamate. MS (ESI) m/z 387 ([M+H]$^+$). Anal Calcd for $C_{20}H_{29}F_3N_2O_2$·2HCl: C, 52.29; H, 6.80: N, 6.10. Found: C, 52.22; H, 6.98; N, 5.98

Example 304

1-{2-piperazin-1-yl-1-[4-(trifluoromethoxy)phenyl]ethyl}cyclobutanol dihydrochloride

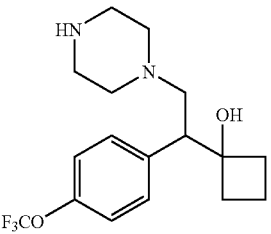

In an analogous manner to Example 1, step 1 tert-butyl 4-{(1-hydroxycyclobutyl)[4-(trifluoromethoxy)phenyl]acetyl}piperazine-carboxylate was prepared from (1-hydroxycyclobutyl)[4-trifluoromethoxy)phenyl]acetic acid (Reference Example 1-aaa) and tert-butyl 1-piperazincarboxylate. MS (ESI) m/z 459 ([M+H]$^+$).

In an analogous manner to Example 1, step 2 1-{2-piperazin-1-yl-1-[4-(trifluoromethoxy)phenyl]ethyl}cyclobutanol dihydrochloride was prepared from 1 tert-butyl 4-{(1-hydroxycyclobutyl)[4-(trifluoromethoxy)

phenyl]acetyl}piperazine-carboxylate. MS (ESI) m/z 345 ([M+H]$^+$). Anal Calcd for $C_{17}H_{23}F_3N_2O_2$2HCl 0.5H$_2$O: C, 47.90; H, 6.15: N, 6.57. Found: C, 47.81; H, 5.92; N, 6.43

Example 305

1-{2-(4-aminopiperidin-1-yl)-1-[4-(trifluoromethoxy)phenyl]ethyl}cyclobutanol dihydrochloride

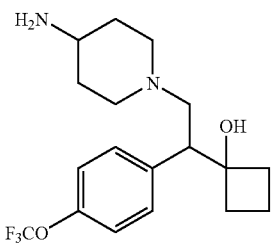

In an analogous manner to Example 1, step 1 tert-butyl (1-{(1-hydroxycyclobutyl)[4-(trifluoromethoxy)phenyl]acetyl}piperidin-4-yl)carbamate was prepared from (1-hydroxycyclobutyl)[4-trifluoromethoxy)phenyl]acetic acid (Reference Example 1-aaa) and 4-N-BOC-aminopiperidine. MS (ESI) m/z 473 ([M+H]$^+$).

In an analogous manner to Example 1, step 2 1-{2-(4-aminopiperidin-1-yl)-1-[4-(trifluoromethoxy)phenyl]ethyl}cyclobutanol dihydrochloride was prepared from tert-butyl (1-{(1-hydroxycyclobutyl)[4-(trifluoromethoxy)phenyl]acetyl}piperidin-4-yl)carbamate. MS (ESI) m/z 359 ([M+H]$^+$).

Example 306

1-{2-(4-methyl-1,4-diazepan-1-yl-1-[4-(trifluoromethoxy)phenyl]ethyl)cyclobutanol dihydrochloride

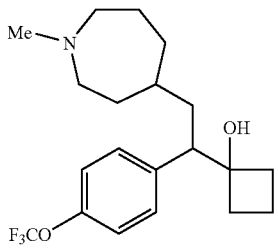

In an analogous manner to Example 1, step 1 1-{2-(4-methyl-1,4-diazepan-1-yl)-1-[4-(trifluoromethoxy)phenyl]-2-oxo-ethyl)cyclobutanol was prepared from (1-hydroxycyclobutyl)[4-trifluoromethoxy)phenyl]acetic acid (Reference Example 1-aaa) and 1-methylhomopiperazine. MS (ESI) m/z 387 ([M+H]$^+$).

In an analogous manner to Example 1, step 2 1-{2-(4-methyl-1,4-diazepan-1-yl)-1-[4-(trifluoromethoxy)phenyl]ethyl)cyclobutanol dihydrochloride was prepared from 1-{2-(4-methyl-1,4-diazepan-1-yl)-1-[4-(trifluoromethoxy)phenyl]-2-oxo-ethyl)cyclobutanol.

MS (ESI) m/z 373 ([M+H]$^+$). Anal Calcd for $C_{19}H_{27}F_3N_2O_2$2HCl 0.60H$_2$O: C, 50.03; H, 6.67: N, 6.10. Found: C, 49.88; H, 6.58; N, 6.02.

Example 307

1-[1-(4-phenoxyphenyl)-2-piperazin-1-ylethyl]cyclohexanol dihydrochloride

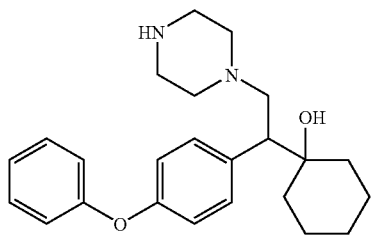

In an analogous manner to Example 1, step 1 tert-butyl 4-{(1-hydroxycyclohexyl)[4-(phenoxy)phenyl]acetyl}piperazine-carboxylate was prepared from (1-hydroxycyclohexyl)[4-phenoxyphenyl]acetic acid (Reference Example 1-bbb) and tert-butyl 1-piperazinecarboxylate. MS (ESI) m/z 495 ([M+H]$^+$).

In an analogous manner to Example 1, step 2 1-[1-(4-phenoxyphenyl)-2-piperazin-1-ylethyl]cyclohexanol dihydrochloride was prepared from tert-butyl 4-{(1-hydroxycyclohexyl)[4-(phenoxy)phenyl]acetyl}piperazine-carboxylate. MS (ESI) m/z 381 ([M+H]$^+$). Anal Calcd for $C_{24}H_{32}N_2O_2$2HCl 1H$_2$O: C, 61.14; H, 7.89; N, 5.94. Found: C, 60.96; H, 7.89; N, 5.96.

Example 308

1-[2-(4-methylpiperazin-1-yl)-1-(4-phenoxyphenyl)ethy]cyclohexanol dihydrochloride

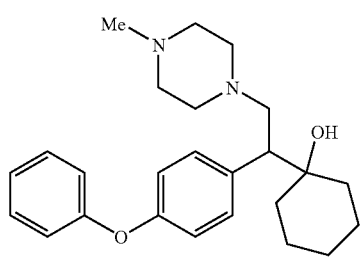

In an analogous manner to Example 1, step 1 1-[2-(4-methylpiperazin-1-yl)-1-(4-phenoxyphenyl)-2-oxoethy]cyclohexanol was prepared from (1-hydroxycyclohexyl)[4-phenoxyphenyl]acetic acid (Reference Example 1-bbb) and 1-methylpiperazine. MS (ESI) m/z 409 ([M+H]$^+$).

In an analogous manner to Example 1, step 2 1-[2-(4-methylpiperazin-1-yl)-1-(4-phenoxyphenyl)ethy]cyclohexanol dihydrochloride was prepared from 1-[2-(4-methylpiperazin-1-yl)-1-(4-phenoxyphenyl)-2-oxoethy]cyclohexanol. MS (ESI) m/z 395 ([M+H]$^+$). Anal Calcd for $C_{25}H_{34}N_2O_2$2HCl 0.9H$_2$O: C, 62.08; H, 7.88: N, 5.79. Found: C, 62.26; H, 8.11; N, 5.70.

Example 309

1-[2-[4-(cyclohexylmethyl)piperazin-1-yl]-1-(4-phenoxyphenyl)ethyl]cyclohexanol dihydrochloride

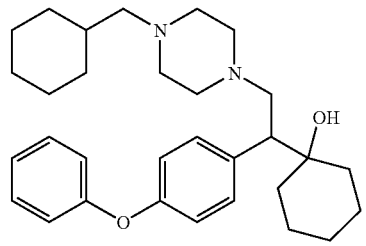

In an analogous manner to Example 1, step 1 1-[2-[4-(cyclohexylmethyl)piperazin-1-yl]-1-(4-phenoxyphenyl)-2-oxoethyl]cyclohexanol was prepared from (1-hydroxycyclohexyl)[4-phenoxyphenyl]acetic acid (Reference Example 1-bbb) and 1-(cyclohexylmethyl)piperazine. MS (ESI) m/z 491 ([M+H]$^+$).

In an analogous manner to Example 1, step 2 1-[2-[4-(cyclohexylmethyl)piperazin-1-yl]-1-(4-phenoxyphenyl)ethyl]cyclohexanol dihydrochloride was prepared from 1-[2-[4-(cyclohexylmethyl)piperazin-1-yl]-1-(4-phenoxyphenyl)-2-oxoethyl]cyclohexanol. MS (ESI) m/z 477 ([M+H]$^+$). Anal Calcd for $C_{31}H_{44}N_2O_2$ 2HCl 1H$_2$O: C, 65.59; H, 8.52: N, 4.94. Found: C, 65.55; H, 8.79; N, 4.90.

Example 310

1-{2-(4-aminopiperidin-1-yl)-1-(4-phenoxyphenyl)ethyl]cyclohexanol dihydrochloride

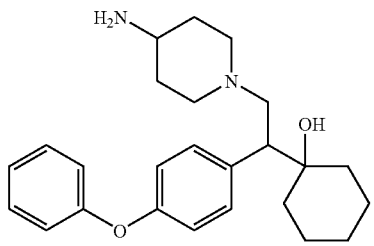

In an analogous manner to Example 1, step 1, tert-butyl (1-{(1-hydroxycyclohexyl)[4-(phenoxy)phenyl]acetyl}piperidin-4-yl)carbamate was prepared from (1-hydroxycyclohexyl)[4-phenoxyphenyl]acetic acid (Reference Example 1-bbb) and 4-N-BOC-aminopiperidine. MS (ESI) m/z 509 ([M+H]$^+$).

In an analogous manner to Example 1, step 2 1-{2-(4-aminopiperidin-1-yl)-1-(4-phenoxyphenyl)ethyl]cyclohexanol dihydrochloride was prepared from tert-butyl (1-{(1-hydroxycyclohexyl)[4-(phenoxy)phenyl]acetyl}piperidin-4-yl)carbamate. MS (ESI) m/z 395 ([M+H]$^+$).

Example 311

1-[1-(3-phenoxyphenyl)-2-piperazin-1-ylethyl]cyclohexanol dihydrochloride

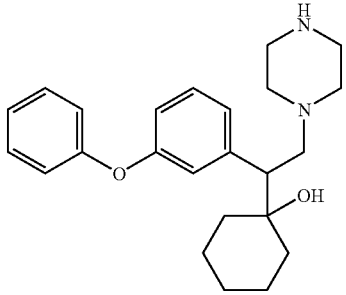

In an analogous manner to Example 1, step 1 tert-butyl 4-{(1-hydroxycyclohexyl)[3-(phenoxy)phenyl]acetyl}piperazine-carboxylate was prepared from (1-hydroxycyclohexyl)[3-phenoxyphenyl]acetic acid (Reference Example 1-ccc) and tert-butyl 1-piperazincarboxylate. MS (ESI) m/z 495 ([M+H]$^+$).

In an analogous manner to Example 1, step 2 1-[1-(3-phenoxyphenyl)-2-piperazin-1-ylethyl]cyclohexanol dihydrochloride was prepared from 1 tert-butyl 4-{(1-hydroxycyclohexyl)[3-(phenoxy)phenyl]acetyl}piperazine-carboxylate. MS (ESI) m/z 381 ([M+H]$^+$). Anal Calcd for $C_{24}H_{32}N_2O_2$ 2HCl 1.8H$_2$O: C, 59.33; H, 7.80: N, 5.77. Found: C, 59.09; H, 7.7.15; N, 5.48.

Example 312

1-[2-(4-methylpiperazin-1-yl)-1-(4-phenoxyphenyl)ethy]cyclohexanol dihydrochloride

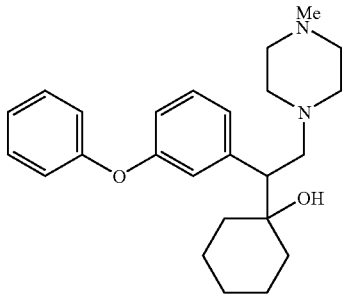

In an analogous manner to Example 1, step 1 1-[2-(4-methylpiperazin-1-yl)-1-(3-phenoxyphenyl)-2-oxoethy]cyclohexanol was prepared from (1-hydroxycyclohexyl)[3-phenoxyphenyl]acetic acid (Reference Example 1-ccc) and 1-methylpiperazine. MS (ESI) m/z 409 ([M+H]$^+$).

In an analogous manner to Example 1, step 2 1-[2-(4-methylpiperazin-1-yl)-1-(3-phenoxyphenyl)ethy]cyclohexanol dihydrochloride was prepared from 1-[2-(4-methylpiperazin-1-yl)-1-(4-phenoxyphenyl)-2-oxoethy]cyclohexanol. MS (ESI) m/z 395 ([M+H]$^+$). Anal Calcd for $C_{25}H_{34}N_2O_2$ 2HCl 0.9H$_2$O: C, 62.08; H, 7.88: N, 5.79. Found: C, 62.26; H, 8.11; N, 5.70.

Example 313

1-[2-[4-(cyclohexylmethyl)piperazin-1-yl]-1-(3-phenoxyphenyl)ethyl]cyclohexanol dihydrochloride

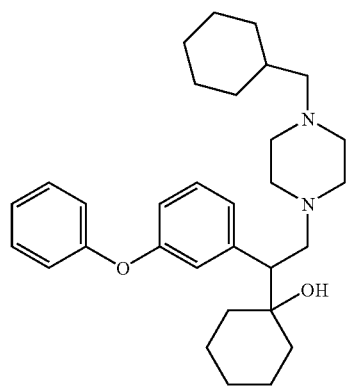

In an analogous manner to Example 1, step 1 1-[2-[4-(cyclohexylmethyl)piperazin-1-yl]-1-(3-phenoxyphenyl)-2-oxoethyl]cyclohexanol was prepared from (1-hydroxycyclohexyl)[3-phenoxyphenyl]acetic acid (Reference Example 1-ccc) and 1-(cyclohexylmethyl)piperazine. MS (ESI) m/z 491 ([M+H]$^+$).

In an analogous manner to Example 1, step 2 1-[2-[4-(cyclohexylmethyl)piperazin-1-yl]-1-(3-phenoxyphenyl)ethyl]cyclohexanol dihydrochloride was prepared from 1 1-[2-[4-(cyclohexylmethyl)piperazin-1-yl]-1-(3-phenoxyphenyl)-2-oxoethyl]cyclohexanol. MS (ESI) m/z 477 ([M+H]$^+$).

Example 314

1-[2-(1,4'-bipiperidin-1'-yl)-1-[3-(phenoxyphenyl)ethyl]cyclohexanol dihydrochloride

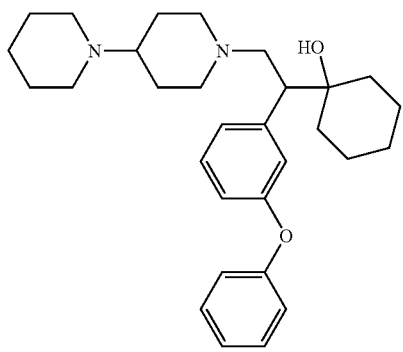

In an analogous manner to Example 1, step 1, 1-[2-(1,4'-bipiperidin-1'-yl)-1-[3-(phenoxyphenyl)-2-oxoethyl]cyclohexanol was prepared from (1-hydroxycyclohexyl)[3-phenoxyphenyl]acetic acid (Reference Example 1-ccc) and 4-piperidinopiperidine MS (ESI) m/z 477 ([M+H]$^+$)

In an analogous manner Example 1, step 2 1-[2-(1,4'-bipiperidin-1'-yl)-1-[3-(phenoxyphenyl)ethyl]cyclohexanol dihydrochloride was prepared from 1-[2-(1,4'-bipiperidin-1'-yl)-1-[3-(phenoxyphenyl)-2-oxoethyl]cyclohexanol MS (ESI) m/z 463 ([M+H]$^+$). Anal Calcd for C$_{30}$H$_{42}$N$_2$O$_2$2HCl 0.25H$_2$O: C, 66.72; H, 8.31: N, 5.18. Found: C, 66.96; H, 8.87; N, 4.32

Example 315

1-[2-(4-aminopiperidin-1-yl)-1-(3-phenoxyphenyl)ethyl]cyclohexanol dihydrochloride

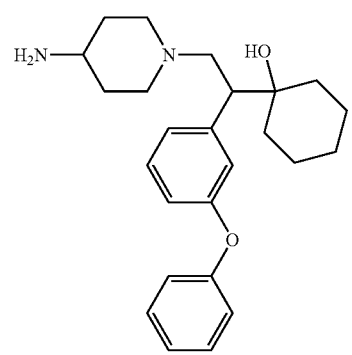

In an analogous manner to Example 1' step 1, tert-butyl (1-{(1-hydroxycyclohexyl)[3-(phenoxy)phenyl]acetyl}piperidin-4-yl)carbamate was prepared from (1-hydroxycyclohexyl)[3-phenoxyphenyl]acetic acid (Reference Example 1-ccc) and 4-N-BOC-aminopiperidine. MS (ESI) m/z 509 ([M+H]$^+$).

In an analogous manner to Example 1, step 2 1-{2-(4-aminopiperidin-1-yl)-1-(3-phenoxyphenyl)ethyl]cyclohexanol dihydrochloride was prepared from tert-butyl (1-{(1-hydroxycyclohexyl)[3-(phenoxy)phenyl]acetyl}piperidin-4-yl)carbamate. MS (ESI) m/z 395 ([M+H]$^+$).

Example 316

1-[1-(3-phenoxyphenyl)-2-(4-pyrrolidin-1-ylpiperidin-1-yl)ethyl]cyclohexanol dihydrochloride

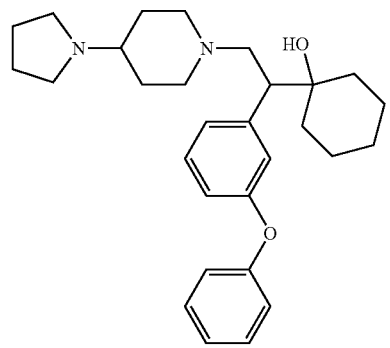

In an analogous manner to Example 1, step 1 1-[1-(3-phenoxyphenyl)-2-(4-pyrrolidin-1-ylpiperidin-1-yl)-2-oxoethyl]cyclohexanol was prepared from (1-hydroxycyclohexyl)[3-phenoxyphenyl]acetic acid (Reference Example 1-ccc) and 4-pyrrolidinylpiperidine. MS (ESI) m/z 463 ([M+H]$^+$).

In an analogous manner to Example 1, step 2 1-[1-(3-phenoxyphenyl)-2-(4-pyrrolidin-1-ylpiperidin-1-yl)ethyl]

Example 317

1-[2-[4-(dimethylamino)piperidin-1-yl]-1-(2-naphthyl)ethyl]cyclohexanol dihydrochloride

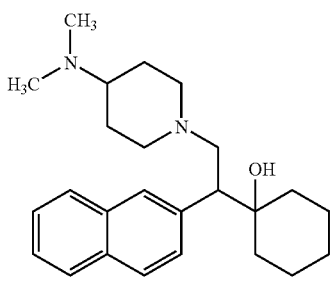

In an analogous manner to Example 36, 1-[2-[4-(dimethylamino)piperidin-1-yl]-1-(2-naphthyl)ethyl]cyclohexanol dihydrochloride was prepared from 1-[2-(4-aminopiperidin-1-yl)-1-(2-naphthyl)ethyl]cyclohexanol (see Example 32). HRMS: calcd for $C_{25}H_{36}N_2O+H$, 381.29059; found (ESI, [M+H]$^+$), 381.2887.

Example 318

1-{1-(3-bromo-4-methoxyphenyl)-2-[4-(dimethylamino)piperidin-1-yl]ethyl}cyclohexanol dihydrochloride

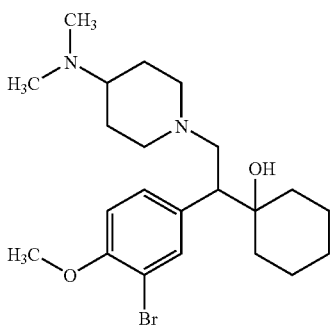

In an analogous manner to Example 36, 1-{1-(3-bromo-4-methoxyphenyl)-2-[4-(dimethylamino)piperidin-1-yl]ethyl}cyclohexanol dihydrochloride was prepared from 1-[2-(4-aminopiperidin-1-yl)-1-(3-bromo-4-methoxyphenyl)ethyl]cyclohexanol (see Example 25). HRMS: calcd for $C_{22}H_{35}BrN_2O_2+H$, 439.19601; found (ESI, [M+H]$^+$), 439.1938.

Example 319

1-{1-(3-bromophenyl)-2-[4-(dimethylamino)piperidin-1-yl]ethyl}cyclohexanol dihydrochloride

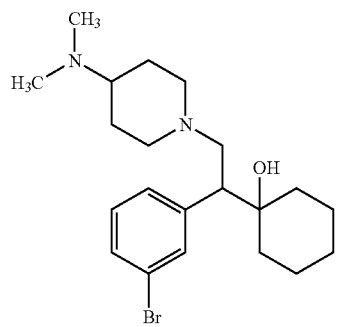

In an analogous manner to Example 36, 1-{1-(3-bromophenyl)-2-[4-(dimethylamino)piperidin-1-yl]ethyl}cyclohexanol dihydrochloride was prepared from 1-[2-(4-aminopiperidin-1-yl)-1-(3-bromophenyl)ethyl]cyclohexanol (see Example 18). HRMS: calcd for $C_{21}H_{33}BrN_2O+H$, 409.18545; found (ESI, [M+H]$^+$), 409.1841.

Example 320

1-{1-(3,4-dichlorophenyl)-2-[4-(dimethylamino)piperidin-1-yl]ethyl}cyclohexanol dihydrochloride

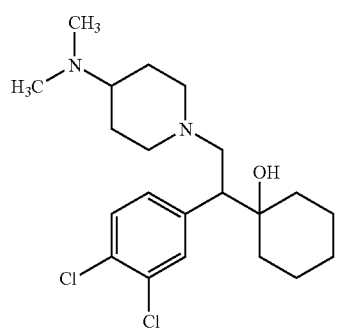

In an analogous manner to Example 36, 1-{1-(3,4-dichlorophenyl)-2-[4-(dimethylamino)piperidin-1-yl]ethyl}cyclohexanol dihydrochloride was prepared from 1-[2-(4-aminopiperidin-1-yl)-1-(3,4-dichlorophenyl)ethyl]cyclohexanol (see Example 14). HRMS: calcd for $C_{21}H_{32}Cl_2N_2O+H$, 399.19699; found (ESI, [M+H]$^+$), 399.197.

cyclohexanol dihydrochloride was prepared from 1-[1-(3-phenoxyphenyl)-2-(4-pyrrolidin-1-ylpiperidin-1-yl)-2-oxoethyl]cyclohexanol. MS (ESI) m/z 449 ([M+H]$^+$).

Example 321

1-{2-[4-(dimethylamino)piperidin-1-yl]-1-[3-(trifluoromethyl)phenyl]ethyl}cyclohexanol dihydrochloride

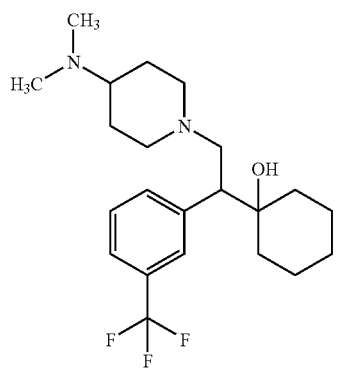

In an analogous manner to Example 36, 1-{2-[4-(dimethylamino)piperidin-1-yl]-1-[3-(trifluoromethyl)phenyl]ethyl}cyclohexanol dihydrochloride was prepared from 1-{2-(4-aminopiperidin-1-yl)-1-[3-(trifluoromethyl)phenyl]ethyl}cyclohexanol (see Example 39). HRMS: calcd for $C_{22}H_{33}F_3N_2O+H$, 399.26232; found (ESI, [M+H]$^+$), 399.2607.

Example 322

1-[2-(4-Methyl-1-piperazinyl)-1-[4-phenylmethoxy)phenyl]ethyl]cyclohexanol dihydrochloride

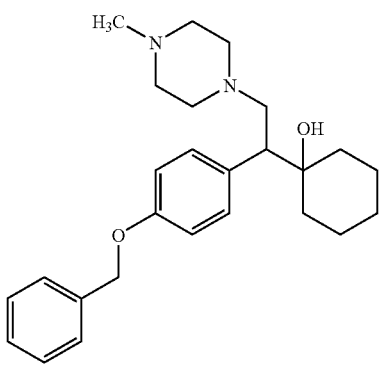

In an analogous manner to Example 24, 1-[2-(4-Methyl-1-piperazinyl)-1-[4-phenylmethoxy)phenyl]ethyl]cyclohexanol dihydrochloride was prepared from 1-{1-[4-(benzyloxy)phenyl]-2-piperazin-1-ylethyl}cyclohexanol (see Example 27). MS (ESI) m/z 409; HRMS: calcd for $C_{26}H_{36}N_2O_2+H$, 409.28550; found (ESI, [M+H]$^+$), 409.2831.

Example 323

1-{(1R)-1-[4-(benzyloxy)-3-chlorophenyl]-2-piperazin-1-ylethyl}cyclohexanol dihydrochloride

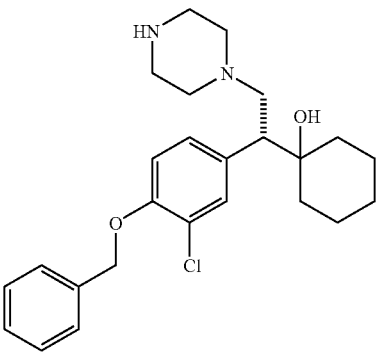

Racemic tert-butyl 4-[[4-(benzyloxy)-3-chlorophenyl](1-hydroxycyclohexyl)acetyl]piperazine-1-carboxylate (see Example 292, step 1) was dissolved in methanol at a concentration of approximately 50 mg/mL. The resulting solution was injected onto the Supercritical Fluid Chromatography instrument L.☐with an injection volume of 750 The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/min flow rate using Analytical Supercritical Fluid Chromatography (Berger Instruments, Inc. Newark, Del. USA).

| | |
|---|---|
| SFC Instrument: | Berger MultiGram PrepSFC (Berger Instruments, Inc. Newark, DE 19702. |
| Column: | Chiralcel OJ-H; 5 u; 250 mm L × 20 mm ID (Chiral Technologies, Inc, Exton, PA, USA) |
| Column temperature: | 35° C. |
| SFC Modifier: | 40% MeOH |
| Flow rate: | 60 mL/min |
| Outlet Pressure: | 100 bar |
| Detector: | UV at 220 nm | tert-butyl 4-[(2S)-2-[4-(benzyloxy)-3-chlorophenyl]-2-(1-hydroxycyclohexyl)acetyl]piperazine-1-carboxylate was isolated at peak 1. MS (ES) m/z 543.1; HRMS: calcd for $C_{30}H_{39}ClN_2O_5+H$, 543.26258; found (ESI, [M+H]$^+$), 543.262 tert-butyl 4-[(2R)-2-[4-(benzyloxy)-3-chlorophenyl]-2-(1-hydroxycyclohexyl)acetyl]piperazine-1-carboxylate was isolated at peak 2. MS (ESI) m/z 543; HRMS: calcd for $C_{30}H_{39}ClN_2O_5+H$, 543.26258; found (ESI, [M+H]$^+$), 543.263

In an analogous manner to Example 1, step 2 1-{(1R)-1-[4-(benzyloxy)-3-chlorophenyl]-2-piperazin-1-ylethyl}cyclohexanol dihydrochloride was prepared from tert-butyl 4-[(2S)-2-[4-(benzyloxy)-3-chlorophenyl]-2-(1-hydroxycyclohexyl)acetyl]piperazine-1-carboxylate. MS (ESI) m/z 429; HRMS: calcd for $C_{25}H_{33}ClN_2O_2+H$, 429.23088; found (ESI, [M+H]$^+$), 429.3206. CD=(−) @ 260-280 nm.

Example 324

1-{(1S)-1-[4-(benzyloxy)-3-chlorophenyl]-2-piperazin-1-ylethyl}cyclohexanol dihydrochloride

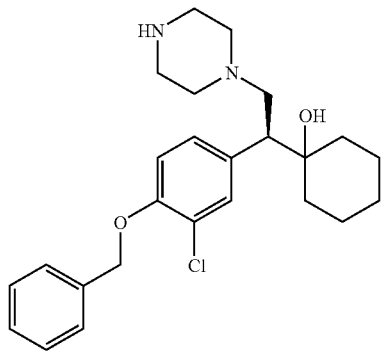

In an analogous manner to Example 1, step 2 1-{(1S)-1-[4-(benzyloxy)-3-chlorophenyl]-2-piperazin-1-ylethyl}cyclohexanol dihydrochloride was prepared from tert-butyl 4-[(2R)-2-[4-(benzyloxy)-3-chlorophenyl]-2-(1-hydroxycyclohexyl)acetyl]piperazine-1-carboxylate (see Example 323). MS (ES) m/z 429.0; HRMS: calcd for $C_{25}H_{33}ClN_2O_2$+H, 429.23088; found (ESI, [M+H]$^+$), 429.2319. CD=(+) @ 260-280 nm.

Example 325

1-[(1R)-1-[4-(benzyloxy)-3-chlorophenyl]-2-(4-methylpiperazin-1-yl)ethyl]cyclohexanol dihydrochloride

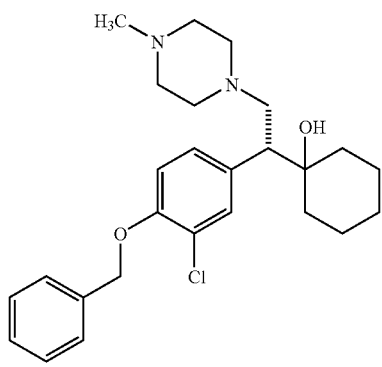

In an analogous manner to Example 24 1-[(1R)-1-[4-(benzyloxy)-3-chlorophenyl]-2-(4-methylpiperazin-1-yl)ethyl]cyclohexanol dihydrochloride was prepared from 1-{(1R)-1-[4-(benzyloxy)-3-chlorophenyl]-2-piperazin-1-ylethyl}cyclohexanol (see Example 323). MS (ESI) m/z 443; HRMS: calcd for $C_{26}H_{35}ClN_2O_2$+H, 443.24653; found (ESI, [M+H]$^+$), 443.2474. CD=(−) @ 260-280 nm.

Example 326

1-[(1S)-1-[4-(benzyloxy)-3-chlorophenyl]-2-(4-methylpiperazin-1-yl)ethyl]cyclohexanol dihydrochloride

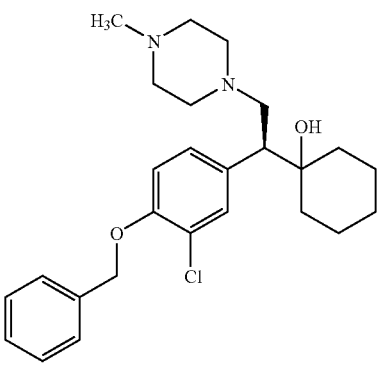

In an analogous manner to Example 24 1-[(1S)-1-[4-(benzyloxy)-3-chlorophenyl]-2-(4-methylpiperazin-1-yl)ethyl]cyclohexanol dihydrochloride was prepared from 1-{(1S)-1-[4-(benzyloxy)-3-chlorophenyl]-2-piperazin-1-ylethyl}cyclohexanol (see Example 324). MS (ES) m/z 443.1; HRMS: calcd for $C_{26}H_{35}ClN_2O_2$+H, 443.24653; found (ESI, [M+H]$^+$), 443.2473. CD=(+) @ 260-280 nm.

Example 327

2-[2-(4-aminopiperidin-1-yl)-1-(3-chlorophenyl)ethyl]decahydronaphthalen-2-ol dihydrochloride

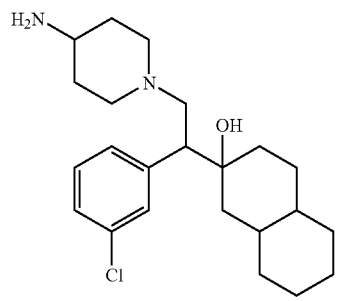

In an analogous manner to Example 1, step 1 tert-butyl {1-[(3-chlorophenyl)(2-hydroxydecahydronaphthalen-2-yl)acetyl]piperidin-4-yl}carbamate was prepared from (3-chlorophenyl)(2-hydroxydecahydronapthyl)acetic acid (Reference Example 1-cc) and 4-N-boc-aminopiperidine. MS (ES) m/z 505.3

In an analogous manner to Example 13, step 2 2-[2-(4-aminopiperidin-1-yl)-1-(3-chlorophenyl)ethyl]decahydronaphthalen-2-ol dihydrochloride was prepared from tert-butyl {1-[(3-chlorophenyl)(2-hydroxydecahydronaphthalen-2-yl)acetyl]piperidin-4-yl}carbamate. MS (ES) m/z 391.4; HRMS: calcd for $C_{23}H_{35}ClN_2O$+H, 391.25161; found (ESI, [M+H]$^+$), 391.2527

Example 328

4-ethyl-1-[2-(4-methylpiperazin-1-yl)-1-(1-naphthyl)ethyl]cyclohexanol dihydrochloride

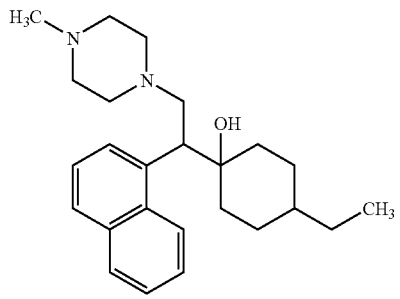

In an analogous manner to Example 24 4-ethyl-1-[2-(4-methylpiperazin-1-yl)-1-(1-naphthyl)ethyl]cyclohexanol dihydrochloride was prepared from 4-ethyl-1-[1-(1-naphthyl)-2-piperazin-1-ylethyl]cyclohexanol (see Example 91). MS (ESI) m/z 381; HRMS: calcd for $C_{25}H_{36}N_2O+H$, 381.29059; found (ESI, [M+H]$^+$), 381.2888

Example 329

2-[1-(1-naphthyl)-2-piperazin-1-ylethyl]decahydronaphthalen-2-ol dihydrochloride

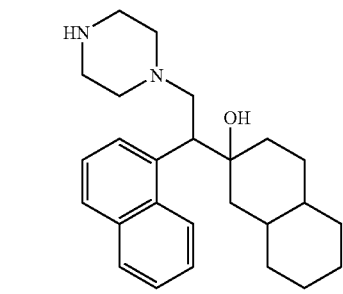

In an analogous manner to Example 1, step 1 tert-butyl 4-[(2-hydroxydecahydronaphthalen-2-yl)(1-naphthyl)acetyl]piperazine-1-carboxylate was prepared from (3-chlorophenyl)(2-hydroxydecahydronapthyl)acetic acid (Reference Example 1-jjj) and tert-butyl 1-piperazinecarboxylate. MS (ESI) m/z 507

In an analogous manner to Example 1, step 2 2-[1-(1-naphthyl)-2-piperazin-1-ylethyl]decahydronaphthalen-2-ol dihydrochloride was prepared from tert-butyl 4-[(2-hydroxydecahydronaphthalen-2-yl)(1-naphthyl)acetyl]piperazine-1-carboxylate. MS m/z 393; HRMS: calcd for $C_{26}H_{36}N_2O+H$, 393.29059; found (ESI, [M+H]$^+$), 393.2891

Example 330

1-[2-(4-aminopiperidin-1-yl)-1-(3-chlorophenyl)ethyl]-4-methylcyclohexanol dihydrochloride

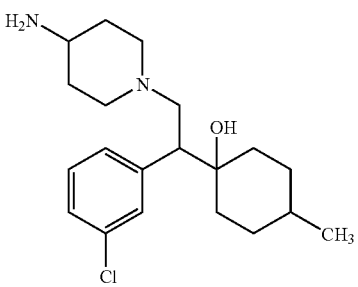

In an analogous manner to Example 1, step 1 tert-butyl {1-[(3-chlorophenyl)(1-hydroxy-4-methylcyclohexyl)acetyl]piperidin-4-yl}carbamate was prepared from (3-chlorophenyl)(2-hydroxydecahydronapthyl)acetic acid (Reference Example 1-kkk) and 4-N-boc-aminopiperidine. MS (ES) m/z 465.3

In an analogous manner to Example 1, step 2 1-[2-(4-aminopiperidin-1-yl)-1-(3-chlorophenyl)ethyl]-4-methylcyclohexanol dihydrochloride was prepared from tert-butyl {1-[(3-chlorophenyl)(1-hydroxy-4-methylcyclohexyl)acetyl]piperidin-4-yl}carbamate. MS m/z 351; HRMS: calcd for $C_{20}H_{31}ClN_2O+H$, 351.22031; found (ESI, [M+H]$^+$), 351.2219

Example 331

1-[1-(3-chlorophenyl)-2-(4-methylpiperazin-1-yl)ethyl]decahydronaphthalen-1-ol dihydrochloride

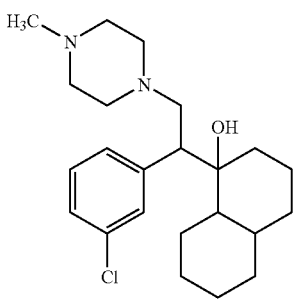

In an analogous manner to Example 24 1-[1-(3-chlorophenyl)-2-(4-methylpiperazin-1-yl)ethyl]decahydronaphthalen-1-ol dihydrochloride was prepared from 1-[1-(3-chlorophenyl)-2-piperazin-1-ylethyl]decahydronaphthalen-1-ol (see Example 72). MS (ES) m/z 391.3; RMS: calcd for $C_{23}H_{35}ClN_2O+H$, 391.25161; found (ESI, [M+H]$^+$), 391.2528

Example 332

2-[1-(3-chlorophenyl)-2-(4-methylpiperazin-1-yl)ethyl]decahydronaphthalen-2-ol dihydrochloride

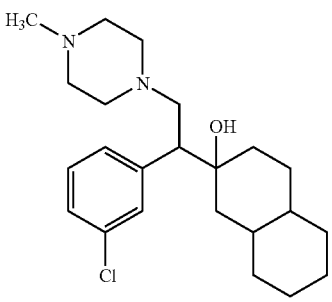

In an analogous manner to Example 24 2-[1-(3-chlorophenyl)-2-(4-methylpiperazin-1-yl)ethyl]decahydronaphthalen-2-ol dihydrochloride was prepared from 2-[1-(3-chlorophenyl)-2-piperazin-1-ylethyl]decahydronaphthalen-2-ol (see Example 74). MS m/z 391; HRMS: calcd for $C_{23}H_{35}ClN_2O+H$, 391.25161; found (ESI, [M+H]$^+$), 391.2522

Example 333

4-methyl-1-[2-(4-methylpiperazin-1-yl)-1-(1-naphthyl)ethyl]cyclohexanol dihydrochloride

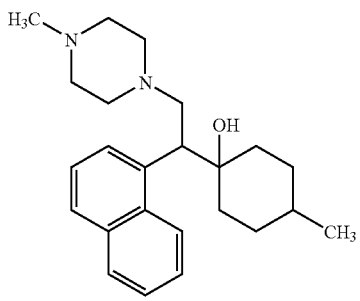

In an analogous manner to Example 24 4-methyl-1-[2-(4-methylpiperazin-1-yl)-1-(1-naphthyl)ethyl]cyclohexanol dihydrochloride was prepared from 4-methyl-1-[1-(1-naphthyl)-2-piperazin-1-ylethyl]cyclohexanol (see Example 97). MS m/z 367; HRMS: calcd for $C_{24}H_{34}N_2O+H$, 367.27494; found (ESI, [M+H]$^+$), 367.2738

Example 334

1-[1-(3-chlorophenyl)-2-piperazin-1-ylethyl]-4-methylcyclohexanol dihydrochloride

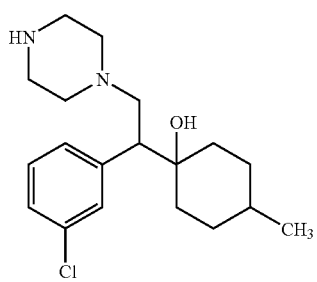

In an analogous manner to Example 1, step 1 tert-butyl {1-[(3-chlorophenyl)(1-hydroxy-4-methylcyclohexyl)acetyl]piperazine-1-carboxylate was prepared from (3-chlorophenyl)(4-methyl-1-hydroxycyclohexyl)acetic acid (Reference Example 1-kkk) and tert-butyl 1-piperazinecarboxylate. MS (ESI) m/z 451/453 ([M+H]$^+$).

In an analogous manner to Example 1, step 2 1-[1-(3-chlorophenyl)-2-piperazin-1-ylethyl]-4-methylcyclohexanol dihydrochloride was prepared from tert-butyl {1-[(3-chlorophenyl)(1-hydroxy-4-methylcyclohexyl)acetyl]piperazine-1-carboxylate. MS (ES) m/z 337.2; HRMS: calcd for $C_{19}H_{29}ClN_2O+H$, 337.20467; found (ESI, [M+H]$^+$), 337.20

Example 335

1-[1-(3-chlorophenyl)-2-(4-methylpiperazin-1-yl)ethyl]-4-methylcyclohexanol dihydrochloride

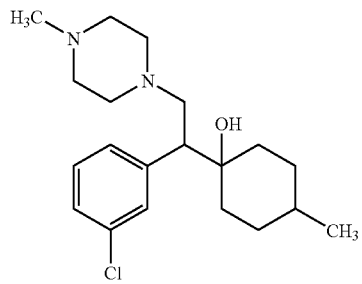

In an analogous manner to Example 24 1-[1-(3-chlorophenyl)-2-(4-methylpiperazin-1-yl)ethyl]-4-methylcyclohexanol dihydrochloride was prepared from 1-[1-(3-chlorophenyl)-2-piperazin-1-ylethyl]-4-methylcyclohexanol (see Example 335). MS (ES) m/z 351.3; HRMS: calcd for $C_{20}H_{31}ClN_2O+H$, 351.22031; found (ESI, [M+H]$^+$), 351.221

Example 336

1-[1-(3-chlorophenyl)-2-(4-methylpiperazin-1-yl)ethyl]-4-ethylcyclohexanol dihydrochloride

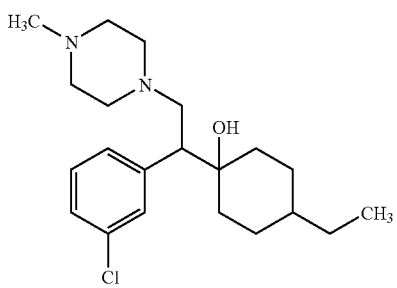

In an analogous manner to Example 1, step 1 tert-butyl {1-[(3-chlorophenyl)(1-hydroxy-4-ethylcyclohexyl)acetyl]piperazine-1-carboxylate was prepared from (3-chlorophenyl)(4-ethyl-1-hydroxycyclohexyl)acetic acid (Reference Example 1-lll) and tert-butyl 1-piperazinecarboxylate. MS (ESI) m/z 465/467 ([M+H]$^+$).

In an analogous manner to Example 1, step 2 1-[1-(3-chlorophenyl)-2-piperazin-1-ylethyl]-4-ethylcyclohexanol was prepared from tert-butyl {1-[(3-chlorophenyl)(1-hydroxy-4-ethylcyclohexyl)acetyl]piperazine-1-carboxylate.

MS (ESI) m/z 351; HRMS: calcd for $C_{20}H_{31}ClN_2O+H$, 351.22031; found (ESI, [M+H]$^+$), 351.2209

In an analogous manner to Example 24 1-[1-(3-chlorophenyl)-2-(4-methylpiperazin-1-yl)ethyl]-4-ethylcyclohexanol dihydrochloride was prepared from 1-[1-[(3-chlorophenyl)-2-piperazin-1-ylethyl]-4-ethylcyclohexanol. MS (ES) m/z 365.4; HRMS: calcd for $C_{21}H_{33}ClN_2O+H$, 365.23597; found (ESI, [M+H]$^+$), 365.236

Example 337

1-(2-piperazin-1-yl-1-pyridin-3-ylethyl)cyclohexanol trihydrochloride

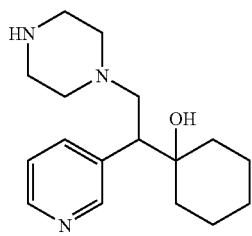

In an analogous manner to Example 1, step 1 tert-butyl 4-(2-Pyridin-3-yl-acetyl)-piperazine-1-carboxylate was prepared from pyridin-3-yl-acetic acid and tert-butyl 1-piperazinecarboxylate. MS (ES) m/z 306

In an analogous manner to Example 141, step 3 tert-butyl 4-[2-(1-hydroxycyclohexyl)-2-pyridin-3-ylacetyl]piperazine-1-carboxylate was prepared from tert-butyl 4-(2-Pyridin-3-yl-acetyl)-piperazine-1-carboxylate and cyclohexanone. MS (ES) m/z 404.3.

In an analogous manner to Example 1, step 2 1-(2-piperazin-1-yl-1-pyridin-3-ylethyl)cyclohexanol trihydrochloride was prepared from tert-butyl 4-[2-(1-hydroxycyclohexyl)-2-pyridin-3-ylacetyl]piperazine-1-carboxylate. MS m/z 290; HRMS: calcd for $C_{17}H_{27}N_3O+H$, 290.22324; found (ESI, [M+H]$^+$), 290.2221.

Example 338

1-(2-piperazin-1-yl-1-pyridin-3-ylethyl)cyclohexanol trihydrochloride

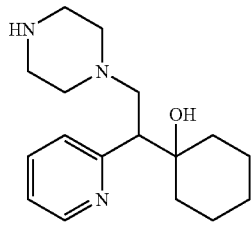

In an analogous manner to Example 1, step 1 tert-butyl 4-(2-Pyridin-2-yl-acetyl)-piperazine-1-carboxylate was prepared from pyridin-2-yl-acetic acid and tert-butyl 1-piperazinecarboxylate.

In an analogous manner to Example 1, step 2 tert-butyl 4-(2-Pyridin-2-yl-ethyl)-piperazine-1-carboxylate was prepared from tert-butyl 4-(2-Pyridin-2-yl-acetyl)-piperazine-1-carboxylate.

A solution of tert-butyl 4-(2-Pyridin-2-yl-ethyl)-piperazine-1-carboxylate (466 mg, 1.60 mmol) in dry tetrahydrofuran (6 mL) under nitrogen was cooled to −78° C. and treated dropwise with a solution of n-butyllithium (2.5 M in hexanes, 0.70 mL, 1.75 mmol). The resulting solution was stirred at −78° C. for 1 h. The reaction was then treated with a solution of cyclohexanone (174 mg, 1.77 mmol) in dry tetrahydrofuran (0.8 mL). The reaction was stirred at −78° C. for 45 min, after which time the reaction was then quenched by the addition of a saturated aqueous solution of sodium bicarbonate, and the tetrahydrofuran was removed in vacuo. The resulting residue was partitioned between water and ethyl acetate and the layers were separated. The aqueous layer was extracted with ethyl acetate (3×30 mL), and the combined organic extracts were dried over magnesium sulfate and concentrated in vacuo and the product was purified via Biotage Horizon (FLASH 25 M, silica, gradient from 0% methanol/EtOAc to 10% methanol/EtOAc) to yield 484 mg (78%) tert-butyl 4-[2-(1-hydroxy-cyclohexyl)-2-pyridin-2-yl-ethyl]-piperazine-1-carboxylate as a colorless oil.

In an analogous manner to 135, step 4 1-(2-piperazin-1-yl-1-pyridin-3-ylethyl)cyclohexanol trihydrochloride was prepared from tert-butyl 4-[2-(1-hydroxy-cyclohexyl)-2-pyridin-2-yl-ethyl]-piperazine-1-carboxylate. MS (ESI) m/z 290; HRMS: calcd for $C_{17}H_{27}N_3O+H$, 290.22324; found (ESI, [M+H]$^+$), 290.2232

Example 339

1-[1-[4-(benzyloxy)-3-chlorophenyl]-2-(4-methoxypiperidin-1-yl)ethyl]cyclohexanol hydrochloride

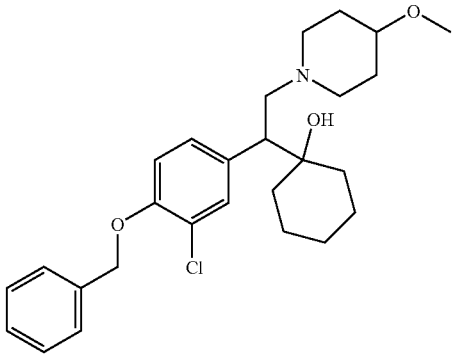

In an analogous manner to Example 1, step 1, 1-[1-[4-(benzyloxy)-3-chlorophenyl]-2-(4-methoxypiperidin-1-yl)-2-oxoethyl]cyclohexanol was prepared from [4-(benzyloxy)-3-chlorophenyl](1-hydroxycyclohexyl)acetic acid (Reference Example 1-eee) and 4-methoxypiperidine (Baker, W. R.; Fung, A. K. I, Kleinhart, H. D et. al. J. Med. Chem. 1992, 35 (10), 1722-1734.). MS (ES) m/z 472.0; HRMS: calcd for $C_{27}H_{34}ClNO_4$+H+, 472.22491; found (ESI, [M+H]$^+$), 472.2238.

In an analogous manner to Example 1, step 2, 1-[1-[4-(benzyloxy)-3-chlorophenyl]-2-(4-methoxypiperidin-1-yl)ethyl]cyclohexanol hydrochloride was prepared from 1-[1-[4-(benzyloxy)-3-chlorophenyl]-2-(4-methoxypiperidin-1- yl)-2-oxoethyl]cyclohexanol. HRMS: calcd for $C_{27}H_{36}ClNO_3$+H+, 458.24565; found (ESI, [M+H]+), 458.2443.

Example 340

1-[1-(6-methoxy-2-naphthyl)-2-piperazin-1-ylethyl]cyclohexanol dihydrochloride

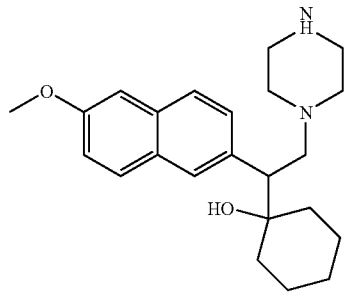

In an analogous manner to Example 1, step 1, tert-butyl 4-[(1-hydroxycyclohexyl)(6-methoxy-2-naphthyl)acetyl]piperazine-1-carboxylate was prepared from (1-hydroxycyclohexyl)(6-methoxy-2-naphthyl)acetic acid (Reference Example 1-sss) and tert-butyl 1-piperazinecarboxylate. HRMS: calcd for $C_{28}H_{38}N_2O_5$+H+, 483.28535; found (ESI, [M+H]+), 483.2834.

In an analogous manner to Example 1, step 2, 1-[1-(6-methoxy-2-naphthyl)-2-piperazin-1-ylethyl]cyclohexanol dihydrochloride was prepared from tert-butyl 4-[(1-hydroxycyclohexyl)(6-methoxy-2-naphthyl)acetyl]piperazine-1-carboxylate. HRMS: calcd for $C_{23}H_{32}N_2O_2$+H+, 369.25365; found (ESI, [M+H]+), 369.2525.

Example 341

1-[1-(6-methoxy-2-naphthyl)-2-(4-methylpiperazin-1-yl)ethyl]cyclohexanol dihydrochloride

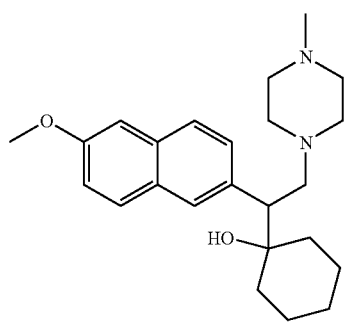

In an analogous manner to Example 24, 1-[1-(6-methoxy-2-naphthyl)-2-(4-methylpiperazin-1-yl)ethyl]cyclohexanol dihydrochloride was prepared from 1-[1-(6-methoxy-2-naphthyl)-2-piperazin-1-ylethyl]cyclohexanol (See Example 340). MS (ESI) m/z 383; HRMS: calcd for $C_{24}H_{34}N_2O_2$+H+, 383.26930; found (ESI, [M+H]+), 383.2682.

Example 342

1-[2-(4-aminopiperidin-1-yl)-1-(6-methoxy-2-naphthyl)ethyl]cyclohexanol dihydrochloride

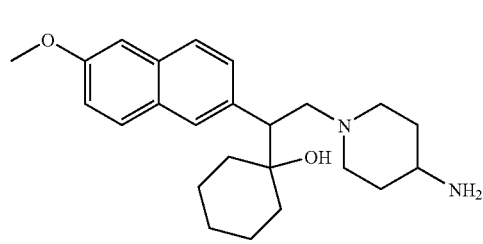

In an analogous manner to Example 1, step 1, tert-butyl {1-[(1-hydroxycyclohexyl)(6-methoxy-2-naphthyl)acetyl]piperidin-4-yl}carbamate was prepared from (1-hydroxycyclohexyl)(6-methoxy-2-naphthyl)acetic acid (Reference Example 1-sss) and 4-N-boc-aminopiperidine. HRMS: calcd for $C_{29}H_{40}N_2O_5$+H+, 497.30100; found (ESI, [M+H]+), 497.3034.

In an analogous manner to Example 1, step 2, 1-[2-(4-aminopiperidin-1-yl)-1-(6-methoxy-2-naphthyl)ethyl]cyclohexanol dihydrochloride was prepared from tert-butyl {1-[(1-hydroxycyclohexyl)(6-methoxy-2-naphthyl)acetyl]piperidin-4-yl}carbamate. HRMS: calcd for $C_{24}H_{34}N_2O_2$+H+, 383.26930; found (ESI, [M+H]+), 383.2704

Example 343

1-[2-[4-(dimethylamino)piperidin-1-yl]-1-(6-methoxy-2-naphthyl)ethyl]cyclohexanol dihydrochloride

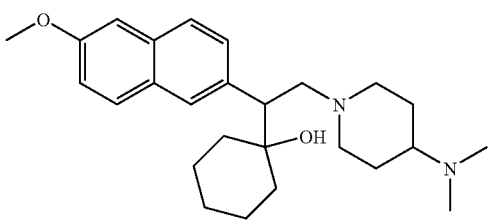

In an analogous manner to Example 36, 1-[2-[4-(dimethylamino)piperidin-1-yl]-1-(6-methoxy-2-naphthyl)ethyl]cyclohexanol dihydrochloride was prepared from 1-[2-(4-aminopiperidin-1-yl)-1-(6-methoxy-2-naphthyl)ethyl]cyclohexanol (See Example 342). MS (ES) m/z 411.2; HRMS: calcd for $C_{26}H_{38}N_2O_2$+H+, 411.30060; found (ESI, [M+H]+), 411.3002.

Example 344

1-{1-(6-methoxy-2-naphthyl)-2-[4-(methylamino)piperidin-1-yl]ethyl}cyclohexanol dihydrochloride

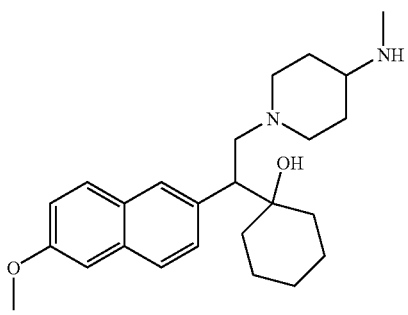

In an analogous manner to Example 1, step 1, tert-butyl {1-[(1-hydroxycyclohexyl)(6-methoxy-2-naphthyl)acetyl]piperidin-4-yl}carbamate was prepared from (1-hydroxycyclohexyl)(6-methoxy-2-naphthyl)acetic acid (Reference Example 1-sss) and 4-N-Boc-aminopiperidine. HRMS: calcd for $C_{29}H_{40}N_2O_5$+H+, 497.30100; found (ESI, [M+H]$^+$), 497.3034.

In an analogous manner to Example 13, step 2, 1-{1-(6-methoxy-2-naphthyl)-2-[4-(methylamino)piperidin-1-yl]ethyl}cyclohexanol dihydrochloride was prepared from tert-butyl {1-[(1-hydroxycyclohexyl)(6-methoxy-2-naphthyl)acetyl]piperidin-4-yl}carbamate. MS (ESI) m/z 397; HRMS: calcd for $C_{25}H_{36}N_2O_2$+H+, 397.28495; found (ESI, [M+H]$^+$), 397.2863.

Example 345

1-[1-(6-methoxy-2-naphthyl)-2-(4-pyrrolidin-1-ylpiperidin-1-yl)ethyl]cyclohexanol dihydrochloride

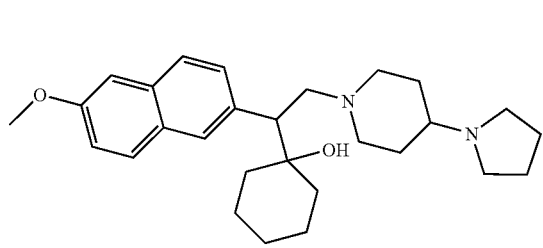

In an analogous manner to Example 1, step 1, 1-[1-(6-methoxy-2-naphthyl)-2-oxo-2-(4-pyrrolidin-1-ylpiperidin-1-yl)ethyl]cyclohexanol was prepared from (1-hydroxycyclohexyl)(6-methoxy-2-naphthyl)acetic acid (Reference Example 1-sss) and 4-(1-pyrrolidinyl)piperidine. MS (ES) m/z 451.2; HRMS: calcd for $C_{28}H_{38}N_2O_3$+H+, 451.29552; found (ESI, [M+H]$^+$), 451.2939.

In an analogous manner to Example 1, step 2, 1-[1-(6-methoxy-2-naphthyl)-2-(4-pyrrolidin-1-ylpiperidin-1-yl)ethyl]cyclohexanol dihydrochloride was prepared from 1-[1-(6-methoxy-2-naphthyl)-2-oxo-2-(4-pyrrolidin-1-ylpiperidin-1-yl)ethyl]cyclohexanol. HRMS: calcd for $C_{28}H_{40}N_2O_2$+H+, 437.31625; found (ESI, [M+H]$^+$), 437.3177.

Example 346

1-[2-(1,4'-bipiperidin-1'-yl)-1-(6-methoxy-2-naphthyl)ethyl]cyclohexanol dihydrochloride

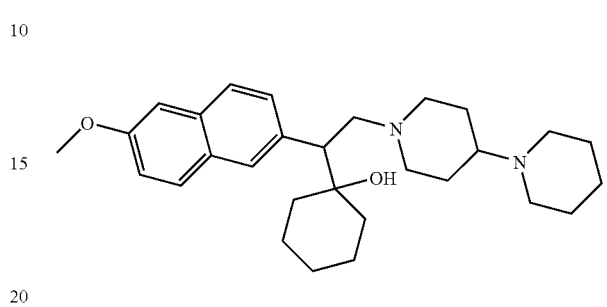

In an analogous manner to Example 1, step 1, 1-[2-(1,4'-bipiperidin-1'-yl)-1-(6-methoxy-2-naphthyl)-2-oxoethyl]cyclohexanol was prepared from (1-hydroxycyclohexyl)(6-methoxy-2-naphthyl)acetic acid (Reference Example 1-sss) and N-(4-piperidine)piperidine. MS (ES) m/z 465.2; HRMS: calcd for $C_{29}H_{40}N_2O_3$+H+, 465.31117; found (ESI, [M+H]$^+$), 465.3096.

In an analogous manner to Example 1, step 2, 1-[2-(1,4'-bipiperidin-1'-yl)-1-(6-methoxy-2-naphthyl)ethyl]cyclohexanol dihydrochloride was prepared from 1-[2-(1,4'-bipiperidin-1'-yl)-1-(6-methoxy-2-naphthyl)-2-oxoethyl]cyclohexanol. HRMS: calcd for $C_{29}H_{42}N_2O_2$+H+, 451.33190; found (ESI, [M+H]$^+$), 451.3325.

Example 347

1-{(1S)-2-[4-(3-phenylbutyl)piperazin-1-yl]-1-[3-(trifluoromethoxy)phenyl]ethyl}cyclohexanol dihydrochloride

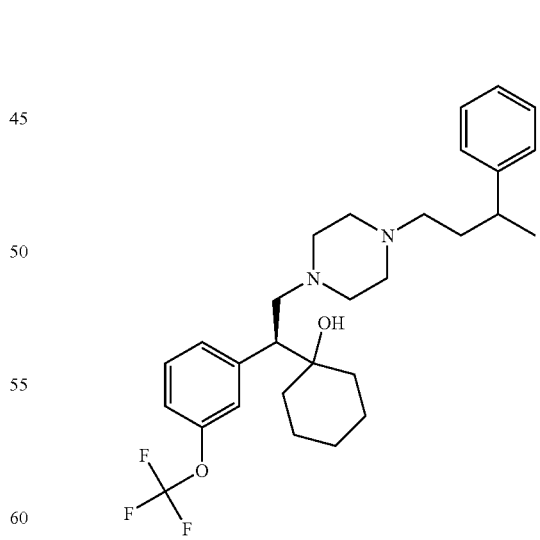

In an analogous manner to Example 117, 1-{(1S)-2-[4-(3-phenylbutyl)piperazin-1-yl]-1-[3-(trifluoromethoxy)phenyl]ethyl}cyclohexanol dihydrochloride was prepared from 3-phenylbutyraldehyde and 1-{(1S)-2-piperazin-1-yl-1-[3-(trifluoromethoxy)phenyl]ethyl}cyclohexanol (See Example 243). HRMS: calcd for $C_{29}H_{39}F_3N_2O_2$, 504.29636; found (ESI, [H+M]+), 505.3025. $[\alpha]_D^{25}$=−12 (c=0.0091 g/mL, MeOH); CD=+@9268 nm.

Example 348

1-{(1S)-2-[(3S)-3-methylpiperazin-1-yl]-1-[3-(trifluoromethoxy)phenyl]ethyl}cyclohexanol dihydrochloride

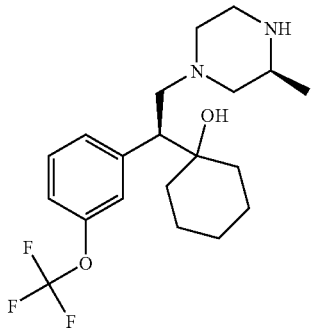

Step, 1: Racemic (1-hydroxycyclohexyl)[3-(trifluoromethoxy)phenyl]acetic acid (See Reference Example 1-f) was dissolved in methanol at a concentration of approximately 67 mg/mL. The resulting solution was injected onto the Supercritical Fluid Chromatography instrument with an injection volume of 1 mL. The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/min flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 10% MeOH |
| Flow rate: | 50 mL/min |
| Outlet Pressure: | 100 bar |
| Detector: | UV at 220 nm |

(2R)-(1-hydroxycyclohexyl)[3-(trifluoromethoxy)phenyl] acetic acid was isolated as peak 1; MS (ES) m/z 316.9; HRMS: calcd for $C_{15}H_{17}F_3O_4$+H+, 319.11517; found (ESI, [M+H]+), 319.1145; CD=+@281 nm; $[\alpha]_D^{25}$=+36° (c=0.0113 g/mL, MeOH).

Step 2: In an analogous manner to Example 1, step 1, 1-{(1R)-2-[(3S)-3-methylpiperazin-1-yl]-2-oxo-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and (S)-(+)-2-methylpiperazine. MS (ESI) m/z 401; HRMS: calcd for $C_{20}H_{27}F_3N_2O_3$+H+, 401.20465; found (ESI, [M+H]+), 401.2044.

Step 3: In an analogous manner to Example 1, step 2, 1-{(1S)-2-[(3S)-3-methylpiperazin-1-yl]-1-[3-(trifluoromethoxy)phenyl]ethyl}cyclohexanol dihydrochloride was prepared 1-{(1R)-2-[(3S)-3-methylpiperazin-1-yl]-2-oxo-1-[3-(trifluoromethoxy)phenyl]ethyl}cyclohexanol. MS (ESI) m/z 387; HRMS: calcd for $C_{20}H_{29}F_3N_2O_2$+H+, 387.22539; found (ESI, [M+H]+), 387.2241. $[\alpha]_D^{25}$=−2.30 (c=0.011 g/mL, MeOH); CD=+@267 nm.

Example 349

1-{(1S)-2-[(3S)-3,4-dimethylpiperazin-1-yl]-1-[3-(trifluoromethoxy)phenyl]ethyl}cyclohexanol dihydrochloride

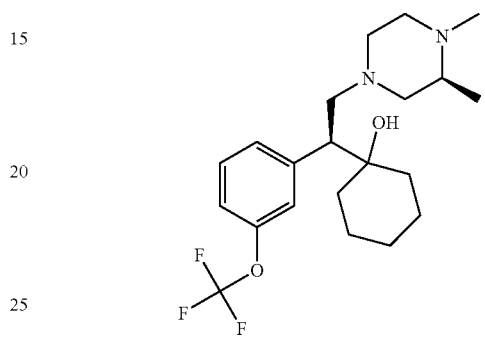

In an analogous manner to Example 24, 1-{(1S)-2-[(3S)-3,4-dimethylpiperazin-1-yl]-1-[3-(trifluoromethoxy)phenyl]ethyl}cyclohexanol dihydrochloride was prepared from 1-{(1S)-2-[(3S)-3-methylpiperazin-1-yl]-1-[3-(trifluoromethoxy)phenyl]ethyl}cyclohexanol (See Example 348 Step 3). MS (ESI) m/z 401; HRMS: calcd for $C_{21}H_{31}F_3N_2O_2$, 400.23376; found (ESI, [H+M]+), 400.2425. CD=+@&281 nm.

Example 350

1-{(1S)-2-(3-ethylpiperazin-1-yl)-1-[3-(trifluoromethoxy)phenyl]ethyl}cyclohexanol dihydrochloride

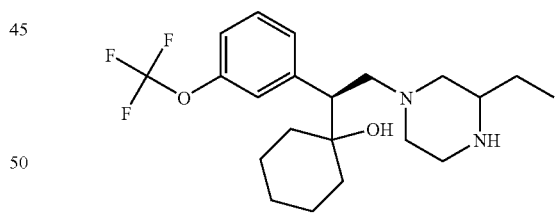

In an analogous manner to Example 1, step 1, 1-{(1R)-2-(3-ethylpiperazin-1-yl)-2-oxo-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and 2-ethylpiperazine. HRMS: calcd for $C_{21}H_{29}F_3N_2O_3$, 414.21303; found (ESI, [H+M]+), 415.2225. CD=+@281 nm.

In an analogous manner to Example 1, step 2, 1-{(1S)-2-(3-ethylpiperazin-1-yl)-1-[3-(trifluoromethoxy)phenyl]ethyl}cyclohexanol dihydrochloride was prepared from 1-{(1R)-2-(3-ethylpiperazin-1-yl)-2-oxo-1-[3-(trifluoromethoxy)phenyl]ethyl}cyclohexanol. MS (ES) m/z 401.2; HRMS: calcd for $C_{21}H_{31}F_3N_2O_2$+H+, 401.24104; found (ESI, [M+H]+), 401.2409.

Example 351

1-{(1S)-2-[(3S)-3-ethyl-4-methylpiperazin-1-yl]-1-[3-(trifluoromethoxy)phenyl]ethyl}cyclohexanol dihydrochloride

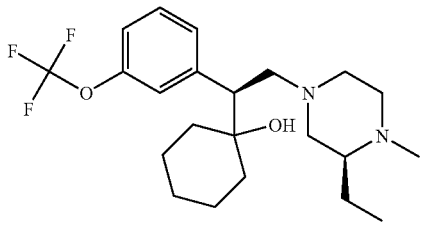

In an analogous manner to Example 24, 1-{(1S)-2-[(3S)-3-ethyl-4-methylpiperazin-1-yl]-1-[3-(trifluoromethoxy)phenyl]ethyl}cyclohexanol dihydrochloride was prepared from 1-{(1S)-2-(3-ethylpiperazin-1-yl)-1-[3-(trifluoromethoxy)phenyl]ethyl}cyclohexanol (See Example 350). MS (ES) m/z 415.2; HRMS: calcd for $C_{22}H_{33}F_3N_2O_2$+H+, 415.25669; found (ESI, [M+H]$^+$), 415.2561.

Example 352

1-{(1S)-2-[(3R)-3-ethyl-4-methylpiperazin-1-yl]-1-[3-(trifluoromethoxy)phenyl]ethyl}cyclohexanol dihydrochloride

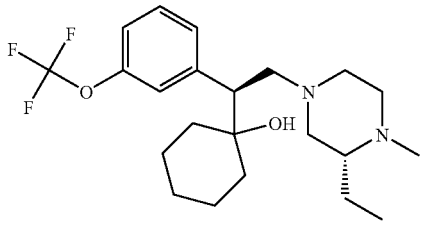

In an analogous manner to Example 24, 1-{(1S)-2-[(3R)-3-ethyl-4-methylpiperazin-1-yl]-1-[3-(trifluoromethoxy)phenyl]ethyl}cyclohexanol dihydrochloride was prepared from 1-{(1S)-2-(3-ethylpiperazin-1-yl)-1-[3-(trifluoromethoxy)phenyl]ethyl}cyclohexanol (See Example 350). HRMS: calcd for $C_{22}H_{33}F_3N_2O_2$+H+, 415.25669; found (ESI, [M+H]$^+$), 415.2563.

Example 353

1-[(1S)-2-(1,4'-bipiperidin-1'-yl)-1-(6-methoxy-2-naphthyl)ethyl]cyclohexanol dihydrochloride

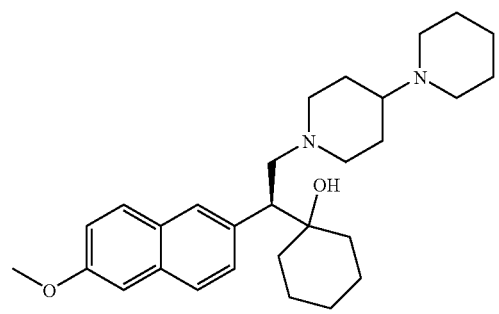

Racemic 1-[2-(1,4'-bipiperidin-1'-yl)-1-(6-methoxy-2-naphthyl)ethyl]cyclohexanol (see Example 346) was dissolved in methanol at a concentration of approximately 50 mg/mL. The resulting solution was injected onto the Supercritical Fluid Chromatography instrument. The baseline resolved enantiomers, using the conditions described below, were collected. The enantiomeric purity of each enantiomer was determined under the same Supercritical Fluid Chromatography conditions using a Chiralcel OJ-H 5u, 250 mm×4.6 mm ID column at 2.0 mL/min flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralcel OJ-H; 5 u; 250 mm L × 20 mm ID (Chiral Technologies, Inc, Exton, PA, USA) |
| Column temperature: | 35° C. |
| SFC Modifier: | 15% MeOH with 0.75% DEA |
| Flow rate: | 50 mL/min |
| Outlet Pressure: | 100 bar |
| Detector: | UV at 220 nm |

1-[(1S)-2-(1,4'-bipiperidin-1'-yl)-1-(6-methoxy-2-naphthyl)ethyl]cyclohexanol dihydrochloride was isolated as peak 1 after making the hydrochloride salt (In an analogous manner to Example 14). MS (ESI) m/z 451; HRMS: calcd for $C_{29}H_{42}N_2O_2$+H+, 451.33190; found (ESI, [M+H]$^+$), 451.3327; CD=+@281 nm; $[\alpha]_D^{25}$=+17.40 (c=0.009 G/ML, MeOH).

Example 354

1-[(1R)-2-(1,4'-bipiperidin-1'-yl)-1-(6-methoxy-2-naphthyl)ethyl]cyclohexanol dihydrochloride

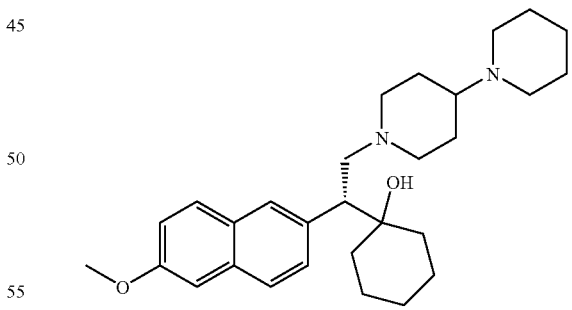

In an analogous manner to Example 353, 1-[(1R)-2-(1,4'-bipiperidin-1'-yl)-1-(6-methoxy-2-naphthyl)ethyl]cyclohexanol dihydrochloride was isolated as peak 2 after making the hydrochloride salt (In an analogous manner to Example 14). HRMS: calcd for $C_{29}H_{42}N_2O_2$+H+, 451.33190; found (ESI, [M+H]$^+$), 451.3322; CD=-@281 nm; $[\alpha]_D^{25}$=-29° (c=0.0088 G/ML, MeOH).

Example 355

1-[(2S)-2-(3-chlorophenyl)-2-cyclohexylethyl]-N-methylpiperidin-4-amine dihydrochloride

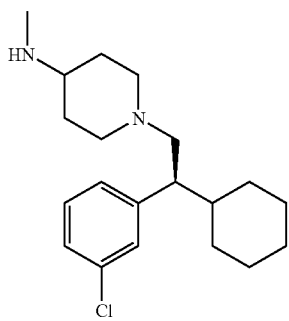

Racemic 1-[2-(3-chlorophenyl)-2-cyclohexylethyl]-N-methylpiperidin-4-amine (see Example 232) was dissolved in methanol at a concentration of approximately 50 mg/mL. The resulting solution was injected onto the Preparative High Performance Liquid Chromatography instrument. The baseline resolved enantiomers, using the conditions described below, were collected. The enantiomeric purity of each enantiomer was determined under the same HPLC conditions using a Chiralcel OD-H 5u, 250 mm×4.6 mm ID column at 1.0 mL/min flow rate using an HP 1100 HPLC (Agilent Technologies. Palo Alto, Calif., USA).

| | |
|---|---|
| HPLC Instrument: | 2 Dynamax SD-300 pumps, Varian Prostar 420 Autosampler, Varian Prostar 345 UV-Vis detector (Varian, Inc., Walnut Creek, CA 94598). |
| Column: | Chiralcel OD-H; 5 u; 250 mm L × 20 mm ID (Chiral Technologies, Inc, Exton, PA, USA) |
| Column temperature: | room temperature |
| HPLC Solvens: | 2% IPA/98% hexane (with 0.2% DEA) |
| Flow rate: | 20 mL/min |
| Detector: | UV at 268 nm |

1-[(2S)-2-(3-chlorophenyl)-2-cyclohexylethyl]-N-methylpiperidin-4-amine dihydrochloride was isolated as peak 1 after making the hydrochloride salt (In an analogous manner to Example 14). MS (ESI) m/z 335; HRMS: calcd for $C_{20}H_{31}ClN_2$+H+, 335.22485; found (ESI, [M+H]$^+$), 335.225; CD=+@9281 nm.

Example 356

1-[(2R)-2-(3-chlorophenyl)-2-cyclohexylethyl]-N-methylpiperidin-4-amine dihydrochloride

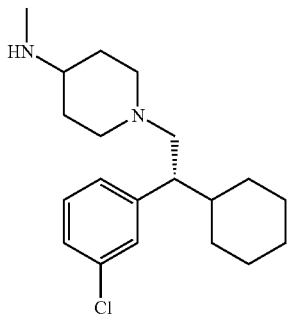

In an analogous manner to Example 355, 1-[(2R)-2-(3-chlorophenyl)-2-cyclohexylethyl]-N-methylpiperidin-4-amine dihydrochloride was isolated as peak 2 after making the hydrochloride salt (In an analogous manner to Example 14). HRMS: calcd for $C_{20}H_{31}ClN_2$+H+, 335.22485; found (ESI, [M+H]$^+$), 335.2244; CD=−@281 nm.

Example 357

1-[(1S)-1-(3-phenoxyphenyl)-2-piperazin-1-ylethyl]cyclohexanol dihydrochloride

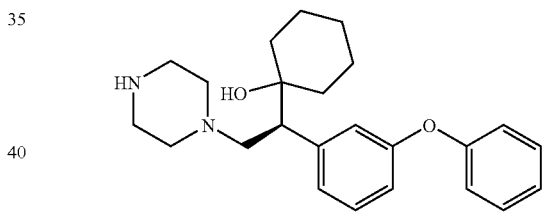

Racemic 1-[1-(3-phenoxyphenyl)-2-piperazin-1-ylethyl]cyclohexanol (see Example 311) was dissolved in methanol at a concentration of approximately 50 mg/mL. The resulting solution was injected onto the Preparative High Performance Liquid Chromatography instrument. The baseline resolved enantiomers, using the conditions described below, were collected. The enantiomeric purity of each enantiomer was determined under the same HPLC conditions using a Chiralcel OD-H 5u, 250 mm×4.6 mm ID column at 1.0 mL/min flow rate using an HP 1100 HPLC (Agilent Technologies. Palo Alto, Calif., USA).

| | |
|---|---|
| HPLC Instrument: | 2 Dynamax SD-300 pumps, Varian Prostar 420 Autosampler, Varian Prostar 345 UV-Vis detector (Varian, Inc., Walnut Creek, CA 94598). |
| Column: | Chiralcel OD-H; 5 u; 250 mm L × 20 mm ID (Chiral Technologies, Inc, Exton, PA, USA) |
| Column temperature: | room temperature |
| HPLC Solvent system: | 25% EtOH/75% hexane (with 0.15% DEA) |
| Flow rate: | 20 mL/min |
| Detector: | UV at 225 nm |

1-[(1S)-1-(3-phenoxyphenyl)-2-piperazin-1-ylethyl]cyclohexanol dihydrochloride was isolated as peak 1 after making the hydrochloride salt (In an analogous manner to Example 14). MS (ESI) m/z 381; HRMS: calcd for $C_{24}H_{32}N_2O_2$+H+, 381.25365; found (ESI, [M+H]+), 381.2552; CD=+@281 nm.

Example 358

1-[(1R)-1-(3-phenoxyphenyl)-2-piperazin-1-ylethyl] cyclohexanol dihydrochloride

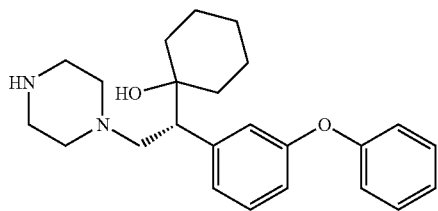

In an analogous manner to Example 357, 1-[(1R)-1-(3-phenoxyphenyl)-2-piperazin-1-ylethyl]cyclohexanol dihydrochloride was isolated as peak 2 after making the hydrochloride salt (In an analogous manner to Example 14). MS (ESI) m/z 381; HRMS: calcd for $C_{24}H_{32}N_2O_2$+H+, 381.25365; found (ESI, [M+H]+), 381.2538; CD=−@281 nm.

Example 359

1-{(1S)-2-[4-(methylamino)piperidin-1-yl]-1-[3-(trifluoromethoxy)phenyl]ethyl}cyclohexanol dihydrochloride

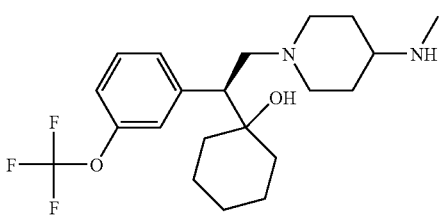

In an analogous manner to Example 1, step 1 tert-butyl (1-{(2R)-2-(1-hydroxycyclohexyl)-2-[3-(trifluoromethoxy)phenyl]acetyl}piperidin-4-yl)carbamate was prepared from (2R)-(1-hydroxycyclohexyl)[3-(trifluoromethoxy)phenyl] acetic acid (Example 348, Step 1) and 4-N-Boc-aminopiperidine. MS (ESI) m/z 501; HRMS: calcd for $C_{25}H_{35}F_3N_2O_5$+ H+, 501.25708; found (ESI, [M+H]+), 501.2589.

In an analogous manner to Example 13, step 2, 1-{(1S-2-[4-(methylamino)piperidin-1-yl]-1-[3-(trifluoromethoxy)phenyl]ethyl}cyclohexanol dihydrochloride was prepared from tert-butyl (1-{(2R)-2-(1-hydroxycyclohexyl)-2-[3-(trifluoromethoxy)phenyl]acetyl}piperidin-4-yl)carbamate MS (ESI) m/z 401; HRMS: calcd for $C_{21}H_{31}F_3N_2O_2$+H+, 401.24104; found (ESI, [M+H]+), 401.2433; CD=+@281 nm.

Example 360

1-{(1S)-2-[4-(dimethylamino)piperidin-1-yl]-1-[3-(trifluoromethoxy)phenyl]ethyl}cyclohexanol dihydrochloride

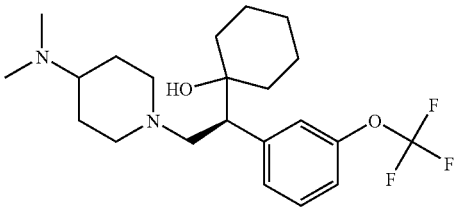

In an analogous manner to Example 36, 1-{(1S)-2-[4-(dimethylamino)piperidin-1-yl]-1-[3-(trifluoromethoxy) phenyl]ethyl}cyclohexanol dihydrochloride was prepared from 1-{(1S)-2-[4-(methylamino)piperidin-1-yl]-1-[3-(trifluoromethoxy)phenyl]ethyl}cyclohexanol (See Example 359). MS (ESI) m/z 415; HRMS: calcd for $C_{22}H_{33}F_3N_2O_2$+ H+, 415.25669; found (ESI, [M+H]+), 415.259; CD=+@281 nm.

Example 361

1-{2-(4-morpholin-4-ylpiperidin-1-yl)-1-[3-(trifluoromethoxy)phenyl]ethyl}cyclohexanol dihydrochloride

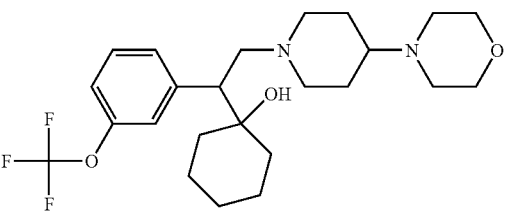

In an analogous manner to Example 1, step 1, 1-{2-(4-morpholin-4-ylpiperidin-1-yl)-2-oxo-1-[3-(trifluoromethoxy)phenyl]ethyl}cyclohexanol was prepared from (1-hydroxycyclohexyl)[3-(trifluoromethoxy)phenyl]acetic acid (Reference Example 1-f) and 4-Piperidin-4-yl-morpholine. MS (ES) m/z 471.1; HRMS: calcd for $C_{24}H_{33}F_3N_2O_4$+ H+, 471.24652; found (ESI, [M+H]+), 471.2455.

In an analogous manner to Example 1, step 2, 1-{2-(4-morpholin-4-ylpiperidin-1-yl)-1-[3-(trifluoromethoxy)phenyl]ethyl}cyclohexanol dihydrochloride was prepared from 1-{2-(4-morpholin-4-ylpiperidin-1-yl)-2-oxo-1-[3-(trifluoromethoxy)phenyl]ethyl}cyclohexanol. MS (ESI) m/z 457; HRMS: calcd for $C_{24}H_{35}F_3N_2O_3$+H+, 457.26725; found (ESI, [M+H]+), 457.2688.

Example 362

1-{2-(4-isopropylpiperazin-1-yl)-1-[3-(trifluoromethoxy)phenyl]ethyl}cyclohexanol dihydrochloride

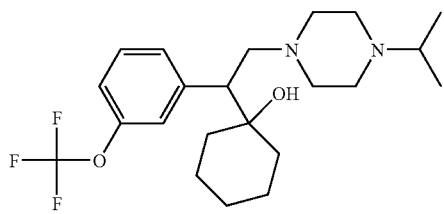

In an analogous manner to Example 1, step 1, 1-{2-(4-isopropylpiperazin-1-yl)-2-oxo-1-[3-(trifluoromethoxy)phenyl]ethyl}cyclohexanol was prepared from (1-hydroxycyclohexyl)[3-(trifluoromethoxy)phenyl]acetic acid (Reference Example 1-f) and 1-isopropyl-piperazine. HRMS: calcd for $C_{22}H_{31}F_3N_2O_3$+H+, 429.23595; found (ESI, [M+H]+), 429.2358.

In an analogous manner to Example 1, step 2, 1-{2-(4-isopropylpiperazin-1-yl)-1-[3-(trifluoromethoxy)phenyl]ethyl}cyclohexanol dihydrochloride was prepared from 1-{2-(4-isopropylpiperazin-1-yl)-2-oxo-1-[3-(trifluoromethoxy)phenyl]ethyl}cyclohexanol. MS (ES) m/z 415.1.

Example 363

1-{(1S)-2-{4-[(1S)-1-phenylethyl]piperazin-1-yl}-1-[3-(trifluoromethoxy)phenyl]ethyl}cyclohexanol dihydrochloride

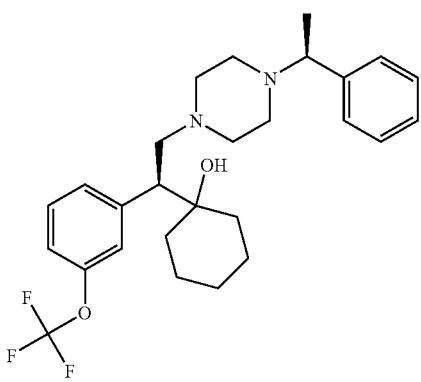

In an analogous manner to Example 1, step 1, 1-{(1R)-2-oxo-2-{4-[(1S)-1-phenylethyl]piperazin-1-yl}-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and 1-(1(S)-phenylethyl)piperazine (Ley, S. V.; Bolli, M. H.; Hinzen, B.; Gervois, A.; Hall, B. J.; J. Chem. Soc. Perkin Trans. 1; 15; 1998; 2239-2242.) MS (ES) m/z 492.2; HRMS: calcd for $C_{27}H_{33}F_3N_2O_3$+H+, 491.25160; found (ESI, [M+H]+), 491.2514.

In an analogous manner to Example 1, step 2, 1-{(1S)-2-{4-[(1S)-1-phenylethyl]piperazin-1-yl}-1-[3-(trifluoromethoxy)phenyl]ethyl}cyclohexanol dihydrochloride was prepared from 1-{(1R)-2-oxo-2-{4-[(1S)-1-phenylethyl]piperazin-1-yl}-1-[3-(trifluoromethoxy)phenyl]ethyl}cyclohexanol. MS (ESI) m/z 477; HRMS: calcd for $C_{27}H_{35}F_3N_2O_2$+H+, 477.27234; found (ESI, [M+H]+), 477.2718. CD=+@267 nm.

Example 364

1-{(1S)-2-{4-[(1R)-1-phenylethyl]piperazin-1-yl}-1-[3-(trifluoromethoxy)phenyl]ethyl}cyclohexanol dihydrochloride

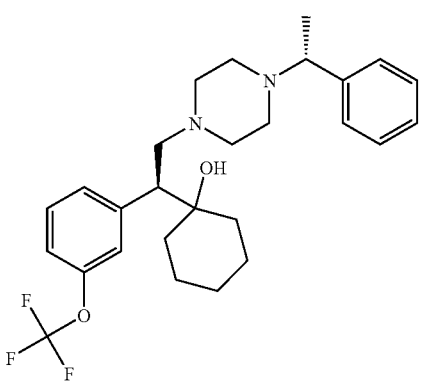

In an analogous manner to Example 1, step 1, 1-{(1R)-2-oxo-2-{4-[(1R)-1-phenylethyl]piperazin-1-yl}-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and 1-(1(R)-phenylethyl)piperazine Ley, S. V.; Bolli, M. H.; Hinzen, B.; Gervois, A.; Hall, B. J.; J. Chem. Soc. Perkin Trans. 1; 15; 1998; 2239-2242.) MS (ES) m/z 491.2; HRMS: calcd for $C_{27}H_{33}F_3N_2O_3$+H+, 491.25160; found (ESI, [M+H]+), 491.2537.

In an analogous manner to Example 1, step 2, 1-{(1S)-2-{4-[(1R)-1-phenylethyl]piperazin-1-yl}-1-[3-(trifluoromethoxy)phenyl]ethyl}cyclohexanol dihydrochloride was prepared from 1-{(1R)-2-oxo-2-{4-[(1R)-1-phenylethyl]piperazin-1-yl}-1-[3-(trifluoromethoxy)phenyl]ethyl}cyclohexanol. MS (ESI) m/z 477; HRMS: calcd for $C_{27}H_{36}F_3N_2O_2$+H+, 477.2729; found (ESI, [M+H]+), 477.2720. CD=+@270 nm.

Example 365

1-{(1S)-2-(4-pyrrolidin-1-ylpiperidin-1-yl)-1-[3-(trifluoromethoxy)phenyl]ethyl}cyclohexanol dihydrochloride

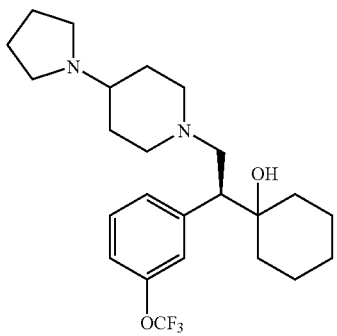

In an analogous manner to Example 1, step 1, 1-{(1R)-2-oxo-2-(4-pyrrolidin-1-ylpiperidin-1-yl)-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and 4-(1-pyrrolidinyl)piperidine. MS (ESI) m/z 455; HRMS: calcd for $C_{24}H_{33}F_3N_2O_3$+H+, 455.25160; found (ESI, [M+H]+), 455.252.

In an analogous manner to Example 1, step 2, 1-{(1S)-2-(4-pyrrolidin-1-ylpiperidin-1-yl)-1-[3-(trifluoromethoxy) phenyl]ethyl}cyclohexanol dihydrochloride was prepared from 1-{(1R)-2-oxo-2-(4-pyrrolidin-1-ylpiperidin-1-yl)-1-[3-(trifluoromethoxy)phenyl]ethyl}cyclohexanol. MS (ESI) m/z 441; HRMS: calcd for $C_{24}H_{35}F_3N_2O_2$+H+, 441.27234; found (ESI, [M+H]+), 441.2716. $[\alpha]_D^{25}$=–16° (c=0.01 g/mL, MeOH); CD=+@267 nm.

Example 366

1-{(1S)-2-(1,4'-bipiperidin-1'-yl)-1-[3-(trifluoromethoxy)phenyl]ethyl}cyclohexanol dihydrochloride

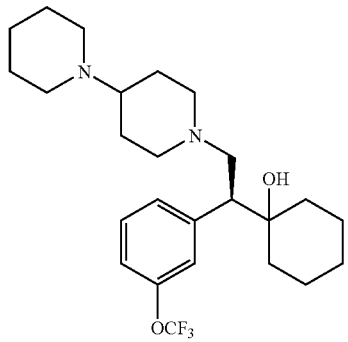

In an analogous manner to Example 1, step 1, 1-{(1R)-2-(1,4'-bipiperidin-1'-yl)-2-oxo-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and N-(4-piperidine)piperidine. MS (ESI) m/z 469; HRMS: calcd for $C_{25}H_{35}F_3N_2O_3$+H+, 469.26725; found (ESI, [M+H]+), 469.2656.

In an analogous manner to Example 1, step 2, 1-{(1S)-2-(1,4'-bipiperidin-1'-yl)-1-[3-(trifluoromethoxy)phenyl] ethyl}cyclohexanol dihydrochloride was prepared from 1-{ (1R)-2-(1,4'-bipiperidin-1'-yl)-2-oxo-1-[3-(trifluoromethoxy)phenyl]ethyl}cyclohexanol. MS (ESI) m/z 455; HRMS: calcd for $C_{25}H_{37}F_3N_2O_2$+H+, 455.28799; found (ESI-FTMS, [M+H]$^{1+}$), 455.28826. $[\alpha]_D^{25}$=–170 (c=0.01 g/mL, MeOH); CD=+@265 nm.

Example 367

1-{(1S)-2-[(3R,5S)-3,5-dimethylpiperazin-1-yl]-1-[3-(trifluoromethoxy)phenyl]ethyl}cyclohexanol dihydrochloride

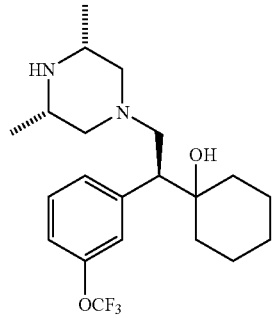

In an analogous manner to Example 1, step 1, 1-[(1R)-2-{(3R,5S)-3,5-dimethylpiperazin-1-yl]-2-oxo-1-[3-(trifluoromethoxy)phenyl]ethyl}cyclohexanol was prepared from (2R)-(1-hydroxycyclohexyl)[3-(trifluoromethoxy)phenyl] acetic acid (Example 348, Step 1) and 2 (S),6(R)-dimethylpiperazine. MS (ESI) m/z 415; HRMS: calcd for $C_{21}H_{29}F_3N_2O_3$+H+, 415.22030; found (ESI, [M+H]+), 415.2202.

In an analogous manner to Example 1, step 2, 1-{(1S)-2-[(3R,5S)-3,5-dimethylpiperazin-1-yl]-1-[3-(trifluoromethoxy)phenyl]ethyl}cyclohexanol dihydrochloride was prepared from 1-{(1R)-2-[(3R,5S)-3,5-dimethylpiperazin-1-yl]-2-oxo-1-[3-(trifluoromethoxy)phenyl] ethyl}cyclohexanol. MS (ESI) m/z 401; HRMS: calcd for $C_{21}H_{31}F_3N_2O_2$+H+, 401.24104; found (ESI, [M+H]+), 401.2418. $[\alpha]_D^{25}$=–100 (c=0.01 g/mL, MeOH); CD=+@268 nm.

Example 368

1-{(1S)-1-[3-(trifluoromethoxy)phenyl]-2-[(3R,5S)-3,4,5-trimethylpiperazin-1-yl]ethyl}cyclohexanol dihydrochloride

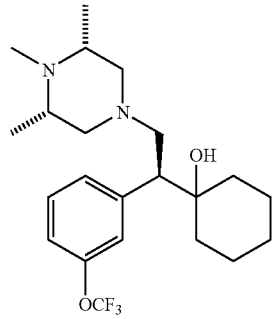

In an analogous manner to Example 24, 1-{(1S)-1-[3-(trifluoromethoxy)phenyl]-2-[(3R,5S)-3,4,5-trimethylpiperazin-1-yl]ethyl}cyclohexanol dihydrochloride was prepared from 1-{(1S)-2-[(3R,5S)-3,5-dimethylpiperazin-1-yl]-1-[3-(trifluoromethoxy)phenyl]ethyl}cyclohexanol (See Example 367). MS (ESI) m/z 415; HRMS: calcd for $C_{22}H_{33}F_3N_2O_2$+H+, 415.25669; found (ESI, [M+H]+), 415.2589. $[\alpha]_D^{25}$=–6° (c=0.009 g/mL, MeOH); CD=+@268 nm.

Example 369

1-{(1S)-2-[(3R)-3-methylpiperazin-1-yl]-1-[3-(trifluoromethoxy)phenyl]ethyl}cyclohexanol dihydrochloride

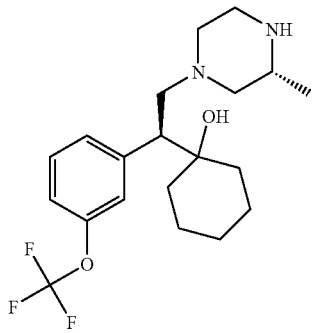

In an analogous manner to Example 1, step 1, 1-{(1R)-2-[(3R)-3-methylpiperazin-1-yl]-2-oxo-1-[3-(trifluoromethoxy)phenyl]ethyl}cyclohexanol was prepared from (2R)-(1-hydroxycyclohexyl)[3-(trifluoromethoxy)phenyl] acetic acid (Example 348, Step 1) and 2(R)-methylpiperazine. MS (ESI) m/z 401; HRMS: calcd for $C_{20}H_{27}F_3N_2O_3$+H+, 401.20465; found (ESI, [M+H]+), 401.2039.

In an analogous manner to Example 1, step 2, 1-{(1S)-2-[(3R)-3-methylpiperazin-1-yl]-1-[3-(trifluoromethoxy)phenyl]ethyl}cyclohexanol dihydrochloride was prepared from 1-{(1R)-2-[(3R)-3-methylpiperazin-1-yl]-2-oxo-1-[3-(trifluoromethoxy)phenyl]ethyl}cyclohexanol. MS (ESI) m/z 387; HRMS: calcd for $C_{20}H_{29}F_3N_2O_2$+H+, 387.22539; found (ESI, [M+H]+), 387.2243. $[\alpha]_D^{25}$=-160 (c=0.0094 g/mL, MeOH); CD=+@268 nm.

Example 370

1-{(1S)-2-[(3R)-3,4-dimethylpiperazin-1-yl]-1-[3-(trifluoromethoxy)phenyl]ethyl}cyclohexanol dihydrochloride

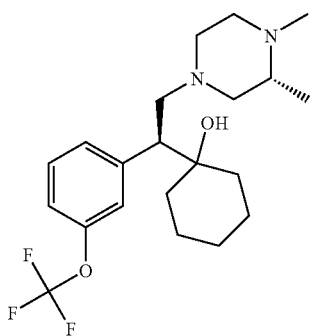

In an analogous manner to Example 24, 1-[(1S)-2-{(3R)-3,4-dimethylpiperazin-1-yl]-1-[3-(trifluoromethoxy)phenyl]ethyl}cyclohexanol dihydrochloride was prepared from 1-{(1S)-2-[(3R)-3-methylpiperazin-1-yl]-1-[3-(trifluoromethoxy)phenyl]ethyl}cyclohexanol (See Example 369). MS (ESI) m/z 401; HRMS: calcd for $C_{21}H_{31}F_3N_2O_2$+H+, 401.24104; found (ESI, [M+H]+), 401.241. $[\alpha]_D^{25}$=-13° (c=0.0085 g/mL, MeOH); CD=+@281 nm.

Example 371

1-{(1S)-2-(octahydro-2H-pyrido[1,2-a]pyrazin-2-yl)-1-[3-(trifluoromethoxy)phenyl]ethyl}cyclohexanol dihydrochloride

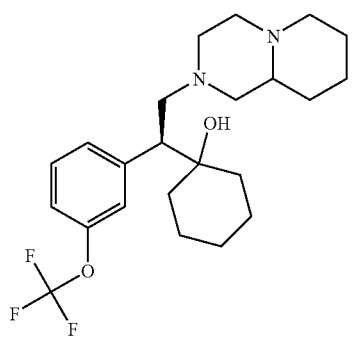

In an analogous manner to Example 1, step 1, 1-{(1R)-2-(octahydro-2H-pyrido[1,2-a]pyrazin-2-yl)-2-oxo-1-[3-(trifluoromethoxy)phenyl]ethyl}cyclohexanol was prepared from (2R)-(1-hydroxycyclohexyl)[3-(trifluoromethoxy)phenyl]acetic acid (Example 348, Step 1) and octahydro-pyrido[1,2-a]pyrazine. MS (ESI) m/z 441; HRMS: calcd for $C_{23}H_{31}F_3N_2O_3$+H+, 441.23595; found (ESI, [M+H]+), 441.2369.

In an analogous manner to Example 1, step 2, 1-{(1S)-2-(octahydro-2H-pyrido[1,2-a]pyrazin-2-yl)-1-[3-(trifluoromethoxy)phenyl]ethyl}cyclohexanol dihydrochloride was prepared from 1-{(1R)-2-(octahydro-2H-pyrido[1,2-a]pyrazin-2-yl)-2-oxo-1-[3-(trifluoromethoxy)phenyl]ethyl}cyclohexanol. MS (ESI) m/z 427; HRMS: calcd for $C_{23}H_{33}F_3N_2O_2$+H+, 427.25669; found (ESI, [M+H]+), 427.258. $[\alpha]_D^{25}$=-10° (c=0.01 g/mL, MeOH); CD=+@268 nm.

Example 372

1-{2-[4-(2-hydroxy-2-methylpropyl)piperazin-1-yl]-1-[3-(trifluoromethoxy)phenyl]ethyl}cyclohexanol dihydrochloride

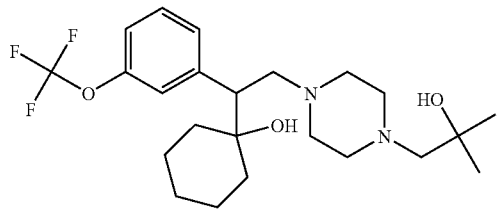

Step 1: A solution of 1-{2-piperazin-1-yl-1-[3-(trifluoromethoxy)phenyl]ethyl}cyclohexanol (see Example 23) (0.15 g, 0.403 mmol) and 2,2-dimethyloxirane (0.2 mL, 2.25 mmol), in ethyl alcohol (1.5 mL) was heated to 75° C. for 2 h. After this time, the solvent was removed in vacuo and the product was purified via HPLC. Crude compound was dissolved in acetonitrile and water at a concentration of approximately 42 mg/mL was injected onto the Preparative High Performance Liquid Chromatography instrument with an injection volume of 200 µL. The baseline resolved components, using the conditions described below, were collected. The purity of each component was determined under the same Chromatography conditions using a Xterra MS C18, 5u; 150 mm L×3.0 mm ID column at 0.5 mL/min flow rate using an HP 1100 HPLC (Agilent Technologies. Palo Alto, Calif., USA).

| | |
|---|---|
| HPLC Instrument: | 2 Dynamax SD-1 pumps, Dynamax UV-1 UV-Vis detector (Varian, Inc., Walnut Creek, CA 94598). |
| Column: | Xterra MS C18 prep, 5 u; 150 mm L × 19 mm ID (Waters Corp., Milford, Massachusetts 01757) |
| Column temperature: | room temperature |
| HPLC Solvent system: | 70% ACN/30% water with 0.05% NH$_4$OH |
| Flow rate: | 20 mL/min |
| Detector: | UV at 210 nm | to yield (1-{2-[4-(2-hydroxy-2-methylpropyl)piperazin-1-yl]-1-[3-(trifluoromethoxy)phenyl]ethyl}cyclohexanol as peak 1 and as a clear oil.

Step 2: (1-{2-[4-(2-hydroxy-2-methylpropyl)piperazin-1-yl]-1-[3-(trifluoromethoxy)phenyl]ethyl}cyclohexanol (30 mg) was dissolved in methanol (0.5 mL) and treated with a saturated methanolic solution of hydrochloric acid (0.5 mL) followed by diethyl ether. After crystallizing in the refrigerator for 16 h, the resulting solid was collected, washed with diethyl ether and dried in vacuo to yield 16 mg (54%) (1-{2-[4-(2-hydroxy-2-methylpropyl)piperazin-1-yl]-1-[3-(trifluoromethoxy)phenyl]ethyl}cyclohexanol dihydrochloride as a white solid. MS m/z 445; HRMS: calcd for $C_{23}H_{35}F_3N_2O_3$+H+, 445.26725; found (ESI, [M+H]+), 445.268.

Example 373

1-{2-[4-(2-hydroxy-1,1-dimethylethyl)piperazin-1-yl]-1-[3-(trifluoromethoxy)phenyl]ethyl}cyclohexanol dihydrochloride

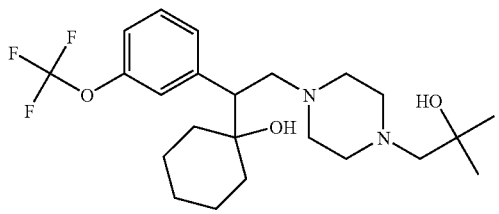

In an analogous manner to Example 372, Step 1 1-{2-[4-(2-hydroxy-1,1-dimethylethyl)piperazin-1-yl]-1-[3-(trifluoromethoxy)phenyl]ethyl}cyclohexanol dihydrochloride was isolated as peak 2 after making the hydrochloride salt (In an analogous manner to Example 372, Step 2). HRMS: calcd for $C_{23}H_{35}F_3N_2O_3$+H+, 445.26725; found (ESI, [M+H]+), 445.2687

Example 374

1-[2-[(3R)-3-aminopyrrolidin-1-yl]-1-(2-naphthyl)ethyl]cyclohexanol dihydrochloride

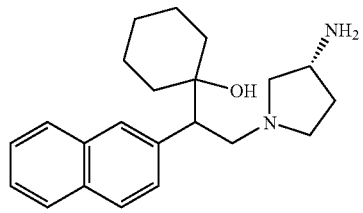

In an analogous manner to Example 1, step 1, tert-butyl {(3R)-1-[(1-hydroxycyclohexyl)(2-naphthyl)acetyl]pyrrolidin-3-yl}carbamate was prepared from (1-hydroxycyclohexyl)(2-naphthyl)acetic acid (Reference Example 1-q) and (3R)-(−)-3-(tert-butoxycarbonylamino)pyrrolidine. MS (ES) m/z 453.1; HRMS: calcd for $C_{27}H_{36}N_2O_4$+H+, 453.27478; found (ESI, [M+H]+), 453.2732.

In an analogous manner to Example 1, step 2, 1-[2-[(3R)-3-aminopyrrolidin-1-yl]-1-(2-naphthyl)ethyl]cyclohexanol dihydrochloride was prepared from tert-butyl {(3R)-1-[(1-hydroxycyclohexyl)(2-naphthyl)acetyl]pyrrolidin-3-yl}carbamate. MS (ESI) m/z 339; HRMS: calcd for $C_{22}H_{30}N_2O$+H+, 339.24309; found (ESI, [M+H]+), 339.243.

Example 375

1-[2-[(3R)-3-(dimethylamino)pyrrolidin-1-yl]-1-(2-naphthyl)ethyl]cyclohexanol dihydrochloride

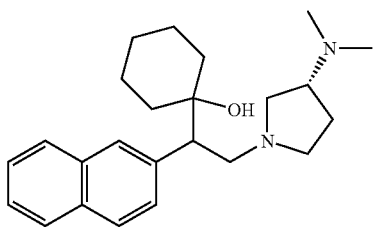

In an analogous manner to Example 36, 1-[2-[(3R)-3-(dimethylamino)pyrrolidin-1-yl]-1-(2-naphthyl)ethyl]cyclohexanol dihydrochloride was prepared from 1-[2-[(3R)-3-aminopyrrolidin-1-yl]-1-(2-naphthyl)ethyl]cyclohexanol (See Example 374). MS (ES) m/z 367.1; HRMS: calcd for $C_{24}H_{34}N_2O$+H+, 367.27439; found (ESI, [M+H]+), 367.275.

Example 376

1-[2-[(3R)-3-(methylamino)pyrrolidin-1-yl]-1-(2-naphthyl)ethyl]cyclohexanol dihydrochloride

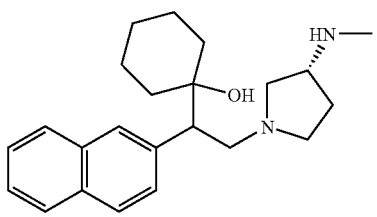

In an analogous manner to Example 1, step 1, tert-butyl {(3R)-1-[(1-hydroxycyclohexyl)(2-naphthyl)acetyl]pyrrolidin-3-yl}carbamate was prepared from (1-hydroxycyclohexyl)(2-naphthyl)acetic acid (Reference Example 1-q) and (3R)-(−)-3-(tert-butoxycarbonylamino)pyrrolidine. MS (ES) m/z 453.1; HRMS: calcd for $C_{27}H_{36}N_2O_4$+H+, 453.27478; found (ESI, [M+H]+), 453.2732.

In an analogous manner to Example 13, step 2, 1-[2-[(3R)-3-(methylamino)pyrrolidin-1-yl]-1-(2-naphthyl)ethyl]cyclohexanol dihydrochloride was prepared from tert-butyl {(3R)-1-[(1-hydroxycyclohexyl)(2-naphthyl)acetyl]pyrrolidin-3-yl}carbamate. MS m/z 353; HRMS: calcd for $C_{23}H_{32}N_2O$+H+, 353.25874; found (ESI, [M+H]+), 353.2583.

Example 377

1-[2-[(3R)-3-aminopyrrolidin-1-yl]-1-(1-naphthyl)ethyl]cyclohexanol dihydrochloride

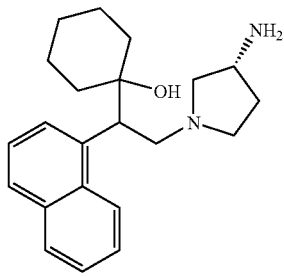

In an analogous manner to Example 1, step 1, tert-butyl {(3R)-1-[(1-hydroxycyclohexyl)(1-naphthyl)acetyl]pyrrolidin-3-yl}carbamate was prepared from (1-hydroxycyclohexyl)(1-naphthyl)acetic acid (Reference Example 1-e) and (3R)-(–)-3-(tert-butoxycarbonylamino)pyrrolidine. MS (ES) m/z 453.1; HRMS: calcd for $C_{27}H_{36}N_2O_4$+H+, 453.27478; found (ESI, [M+H]+), 453.2735.

In an analogous manner to Example 1, step 2, 1-[2-[(3R)-3-aminopyrrolidin-1-yl]-1-(1-naphthyl)ethyl]cyclohexanol dihydrochloride was prepared from tert-butyl {(3R)-1-[(1-hydroxycyclohexyl)(1-naphthyl)acetyl]pyrrolidin-3-yl}carbamate. MS (ESI) m/z 339; HRMS: calcd for $C_{22}H_{30}N_2O$+H+, 339.24309; found (ESI, [M+H]+), 339.2409.

Example 378

1-[2-[(3R)-3-(dimethylamino)pyrrolidin-1-yl]-1-(1-naphthyl)ethyl]cyclohexanol dihydrochloride

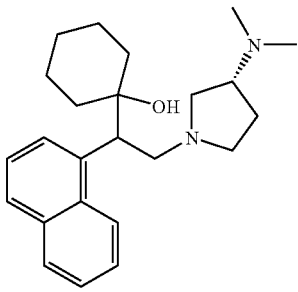

In an analogous manner to Example 36, 1-[2-[(3R)-3-(dimethylamino)pyrrolidin-1-yl]-1-(1-naphthyl)ethyl]cyclohexanol dihydrochloride was prepared from 1-[2-[(3R)-3-aminopyrrolidin-1-yl]-1-(1-naphthyl)ethyl]cyclohexanol (See Example 377). MS (ES) m/z 367.2; HRMS: calcd for $C_{24}H_{34}N_2O$+H+, 367.27439; found (ESI, [M+H]+), 367.2735

Example 379

1-[2-[(3R)-3-(methylamino)pyrrolidin-1-yl]-1-(1-naphthyl)ethyl]cyclohexanol dihydrochloride

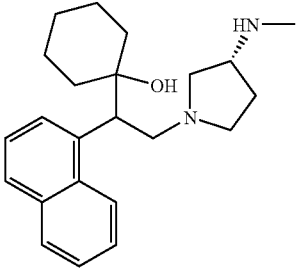

In an analogous manner to Example 1, step 1, tert-butyl {(30)-1-[(1-hydroxycyclohexyl)(1-naphthyl)acetyl]pyrrolidin-3-yl}carbamate was prepared from (1-hydroxycyclohexyl)(1-naphthyl)acetic acid (Reference Example 1-e) and (3R)-(–)-3-(tert-butoxycarbonylamino)pyrrolidine. MS (ES) m/z 453.1; HRMS: calcd for $C_{27}H_{36}N_2O_4$+H+, 453.27478; found (ESI, [M+H]+), 453.2735.

In an analogous manner to Example 13, step 2, 1-[2-[(3R)-3-(methylamino)pyrrolidin-1-yl]-1-(1-naphthyl)ethyl]cyclohexanol dihydrochloride was prepared from tert-butyl {(3R)-1-[(1-hydroxycyclohexyl)(1-naphthyl)acetyl]pyrrolidin-3-yl}carbamate. MS m/z 353; HRMS: calcd for $C_{23}H_{32}N_2O$+H+, 353.25874; found (ESI, [M+H]+), 353.2578.

Example 380

1-{2-[(3R)-3-aminopyrrolidin-1-yl]-1-[4-(benzyloxy)phenyl]ethyl}cyclohexanol dihydrochloride

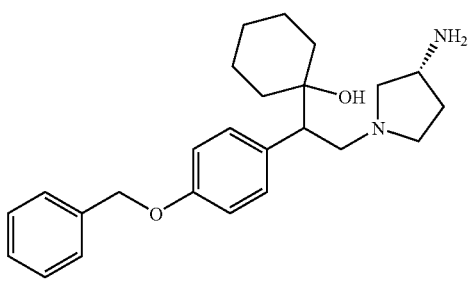

In an analogous manner to Example 1 step 1, tert-butyl {(3R)-1-[[4-(benzyloxy)phenyl](1-hydroxycyclohexyl)acetyl]pyrrolidin-3-yl}carbamate was prepared from [4-(benzyloxy)phenyl](1-hydroxycyclohexyl)acetic acid (Reference Example 1-n) and (3R)-(–)-3-(tert-butoxycarbonylamino)pyrrolidine. MS (ES) m/z 509.1; HRMS: calcd for $C_{30}H_{40}N_2O_5$+H+, 509.30100; found (ESI, [M+H]+), 509.2988.

In an analogous manner to Example 1, step 2, 1-{2-[(3R)-3-aminopyrrolidin-1-yl]-1-[4-(benzyloxy)phenyl]ethyl}cyclohexanol dihydrochloride was prepared from tert-butyl {(3R)-1-[[4-(benzyloxy)phenyl](1-hydroxycyclohexyl)acetyl]pyrrolidin-3-yl}carbamate. MS (ESI) m/z 395; HRMS: calcd for $C_{25}H_{34}N_2O_2$+H+, 395.26930; found (ESI, [M+H]+), 395.2684

Example 381

1-{1-[4-(benzyloxy)phenyl]-2-[(3R)-3-(dimethylamino)pyrrolidin-1-yl]ethyl}cyclohexanol dihydrochloride

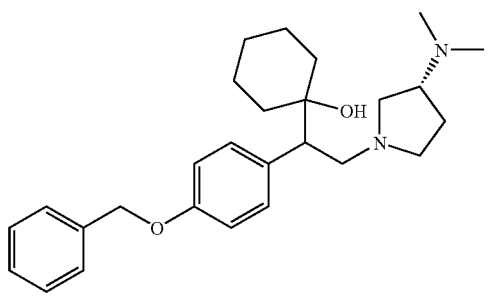

In an analogous manner to Example 36, 1-{1-[4-(benzyloxy)phenyl]-2-[(3R)-3-(dimethylamino)pyrrolidin-1-yl]ethyl}cyclohexanol dihydrochloride was prepared from 1-{2-[(3R)-3-aminopyrrolidin-1-yl]-1-[4-(benzyloxy)phenyl]ethyl}cyclohexanol (See Example 380). MS (ES) m/z 423.1; HRMS: calcd for $C_{27}H_{38}N_2O_2$+H+, 423.30060; found (ESI, [M+H]+), 423.3002.

Example 382

1-{1-[4-(benzyloxy)phenyl]-2-[(3R)-3-(methylamino)pyrrolidin-1-yl]ethyl}cyclohexanol dihydrochloride

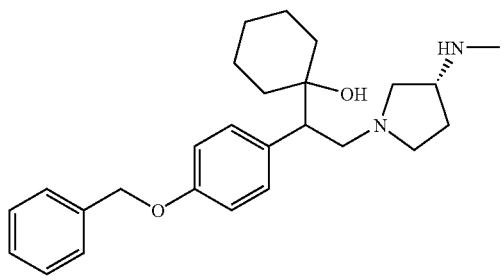

In an analogous manner to Example 1, step 1, tert-butyl {(3R)-1-[[4-(benzyloxy)phenyl](1-hydroxycyclohexyl)acetyl]pyrrolidin-3-yl}carbamate was prepared from [4-(benzyloxy)phenyl](1-hydroxycyclohexyl)acetic acid (Reference Example 1-n, and (3R)-(−)-3-(tert-butoxycarbonylamino)pyrrolidine. MS (ES) m/z 509.1; HRMS: calcd for $C_{30}H_{40}N_2O_5$+H+, 509.30100; found (ESI, [M+H]+), 509.2988.

In an analogous manner to Example 13, step 2, 1-{1-[4-(benzyloxy)phenyl]-2-[(3R)-3-(methylamino)pyrrolidin-1-yl]ethyl}cyclohexanol dihydrochloride was prepared from tert-butyl {(3R)-1-[[4-(benzyloxy)phenyl](1-hydroxycyclohexyl)acetyl]pyrrolidin-3-yl}carbamate. MS m/z 409; HRMS: calcd for $C_{26}H_{36}N_2O_2$+H+, 409.28495; found (ESI, [M+H]+), 409.2876.

Example 383

1-{2-[(3R)-3-aminopyrrolidin-1-yl]-1-[4-(benzyloxy)-3-chlorophenyl]ethyl}cyclohexanol dihydrochloride

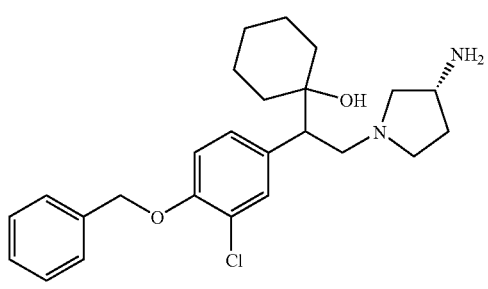

In an analogous manner to Example 1, step 1 tert-butyl {(3R)-1-[[4-(benzyloxy)-3-chlorophenyl](1-hydroxycyclohexyl)acetyl]pyrrolidin-3-yl}carbamate was prepared from [4-(benzyloxy)-3-chlorophenyl](1-hydroxycyclohexyl)acetic acid (Reference Example 1-eee) and (3R)-(−)-3-(tert-butoxycarbonylamino)pyrrolidine. MS (ES) m/z 543.0; HRMS: calcd for $C_{30}H_{39}ClN_2O_5$+H+, 543.26203; found (ESI, [M+H]+), 543.2637.

In an analogous manner to Example 1, step 2, 1-{2-[(3R)-3-aminopyrrolidin-1-yl]-1-[4-(benzyloxy)-3-chlorophenyl]ethyl}cyclohexanol dihydrochloride was prepared from tert-butyl {(3R)-1-[[4-(benzyloxy)-3-chlorophenyl](1-hydroxycyclohexyl)acetyl]pyrrolidin-3-yl}carbamate. MS (ES) m/z 429.1; HRMS: calcd for $C_{25}H_{33}ClN_2O_2$+H+, 429.23033; found (ESI, [M+H]+), 429.2306

Example 384

1-{1-[4-(benzyloxy)-3-chlorophenyl]-2-[(3R)-3-(dimethylamino)pyrrolidin-1-yl]ethyl}cyclohexanol dihydrochloride

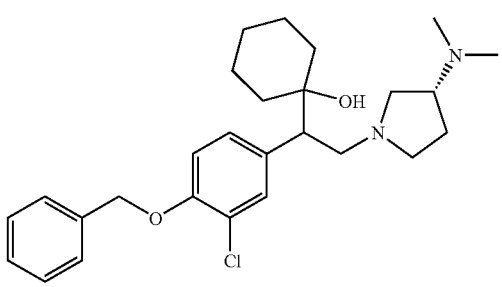

In an analogous manner to Example 36, 1-{1-[4-(benzyloxy)-3-chlorophenyl]-2-[(3R)-3-(dimethylamino)pyrrolidin-1-yl]ethyl}cyclohexanol dihydrochloride was prepared from 1-{2-[(3R)-3-aminopyrrolidin-1-yl]-1-[4-(benzyloxy)-3-chlorophenyl]ethyl}cyclohexanol (See Example 383). MS (ES) m/z 457.1; HRMS: calcd for $C_{27}H_{37}ClN_2O_2$+H+, 457.26163; found (ESI, [M+H]+), 457.2608.

Example 385

1-{1-[4-(benzyloxy)-3-chlorophenyl]-2-[(3R)-3-(methylamino)pyrrolidin-1-yl]ethyl}cyclohexanol dihydrochloride

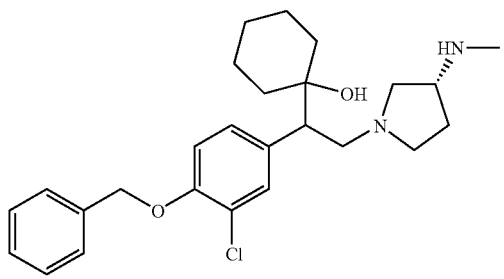

In an analogous manner to Example 1, step 1, tert-butyl {(3R)-1-[[4-(benzyloxy)-3-chlorophenyl](1-hydroxycyclohexyl)acetyl]pyrrolidin-3-yl}carbamate was prepared from [4-(benzyloxy)-3-chlorophenyl](1-hydroxycyclohexyl)acetic acid (Reference Example 1-eee) and (3R)-(–)-3-(tert-butoxycarbonylamino)pyrrolidine. MS (ES) m/z 543.0; HRMS: calcd for $C_{30}H_{39}ClN_2O_5+H+$, 543.26203; found (ESI, [M+H]$^+$), 543.2637.

In an analogous manner to Example 13, step 2, 1-{1-[4-(benzyloxy)-3-chlorophenyl]-2-[(3R)-3-(methylamino)pyrrolidin-1-yl]ethyl}cyclohexanol dihydrochloride was prepared from tert-butyl {(3R)-1-[[4-(benzyloxy)-3-chlorophenyl](1-hydroxycyclohexyl)acetyl]pyrrolidin-3-yl}carbamate. MS m/z 443; HRMS: calcd for $C_{26}H_{35}ClN_2O_2+H+$, 443.24598; found (ESI, [M+H]$^+$), 443.2482.

Example 386

1-{2-[(3R)-3-aminopyrrolidin-1-yl]-1-[3-(trifluoromethoxy)phenyl]ethyl}cyclohexanol dihydrochloride

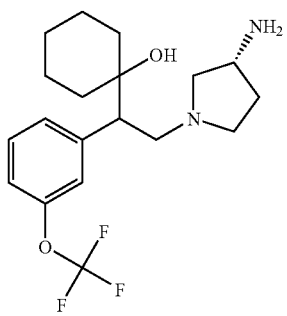

In an analogous manner to Example 1, step 1, tert-butyl ((3R)-1-{(1-hydroxycyclohexyl) [3-(trifluoromethoxy)phenyl]acetyl}pyrrolidin-3-yl)carbamate was prepared from (1-hydroxycyclohexyl)[3-(trifluoromethoxy)phenyl]acetic acid (Reference Example 1-f) and (3R)-(–)-3-(tert-butoxycarbonylamino)pyrrolidine. MS (ES) m/z 487.0; HRMS: calcd for $C_{24}H_{33}F_3N_2O_5+H+$, 487.24143; found (ESI, [M+H]$^+$), 487.2421.

In an analogous manner to Example 1, step 2, 1-{2-[(3R)-3-aminopyrrolidin-1-yl]-1-[3-(trifluoromethoxy)phenyl]ethyl}cyclohexanol dihydrochloride was prepared from tert-butyl ((3R)-1-{(1-hydroxycyclohexyl)[3-(trifluoromethoxy)phenyl]acetyl}pyrrolidin-3-yl)carbamate. MS (ESI) m/z 373; HRMS: calcd for $C_{19}H_{27}F_3N_2O_2+H+$, 373.20974; found (ESI, [M+H]$^+$), 373.2097.

Example 387

1-[(1S)-2-[(3S)-3-aminopyrrolidin-1-yl]-1-(3-chlorophenyl)ethyl]cyclohexanol dihydrochloride

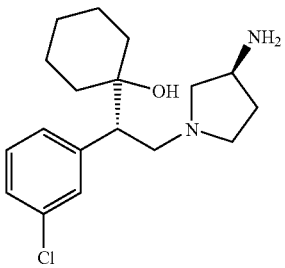

Racemic 1-[2-[(3S)-3-aminopyrrolidin-1-yl]-1-(3-chlorophenyl)ethyl]cyclohexanol (Reference Example 16) was dissolved in ethanol at a concentration of approximately 100 mg/mL. The resulting solution was injected onto the Supercritical Fluid Chromatography instrument with an injection volume of 200 μL. The baseline resolved enantiomers, using the conditions described below, were collected. The enantiomeric purity of each enantiomer was determined under the same Supercritical Fluid Chromatography conditions using a Chiralpak AD-H 5u, 250 mm×4.6 mm ID column at 2.0 mL/min flow rate using Analytical Supercritical Fluid Chromatography (Berger Instruments, Inc. Newark, Del. USA).

| | |
|---|---|
| SFC Instrument: | Berger MultiGram Prep SFC (Berger Instruments, Inc. Newark, DE 19702. |
| Column: | Chiralpak AD-H; 5 u; 250 mm L × 20 mm ID (Chiral Technologies, Inc, Exton, PA, USA) |
| Column temperature: | 35° C. |
| SFC Modifier: | 20% EtOH |
| Flow rate: | 50 mL/min |
| Outlet Pressure: | 100 bar |
| Detector: | UV at 220 nm |

A) tert-butyl {(3S)-1-[(2R)-2-(3-chlorophenyl)-2-(1-hydroxycyclohexyl)acetyl]pyrrolidin-3-yl}carbamate was isolated at peak 1. MS (ES) m/z 437.2; HRMS: calcd for $C_{24}H_{33}F_3N_2O_5+H$, 487.2442+H; found (ESI, [M+H]$^+$), 487.2428; $[\alpha]_D^{25}$=+9° (c=0.010 G/ML, MeOH); CD=+@281 nm.

B) tert-butyl {(3S)-1-[(2S)-2-(3-chlorophenyl)-2-(1-hydroxycyclohexyl)acetyl]pyrrolidin-3-yl}carbamate was isolated at peak 2. MS (ES) m/z 437.2; HRMS: calcd for $C_{24}H_{33}F_3N_2O_5+H$, 487.2442; found (ESI, [M+H]$^+$), $[\alpha]_D^{25}$=–400 (c=0.0095 G/ML, MeOH); CD=–@281 nm.

In an analogous manner to Example 1, step 2, 1-[(1S)-2-[(3S)-3-aminopyrrolidin-1-yl]-1-(3-chlorophenyl)ethyl]cyclohexanol dihydrochloride was prepared from tert-butyl {(3S)-1-[(2R)-2-(3-chlorophenyl)-2-(1-hydroxycyclohexyl)acetyl]pyrrolidin-3-yl}carbamate (Reference Example 387A). MS (ESI) m/z 323; HRMS: calcd for $C_{18}H_{27}ClN_2O+$ H+, 323.18847; found (ESI, [M+H]$^+$), 323.1883; $[\alpha]_D^{25}=-16°$ (c=0.011 g/mL, MeOH); CD=+@281 nm.

Example 388

1-[(1R)-2-[(3S)-3-aminopyrrolidin-1-yl]-1-(3-chlorophenyl)ethyl]cyclohexanol dihydrochloride

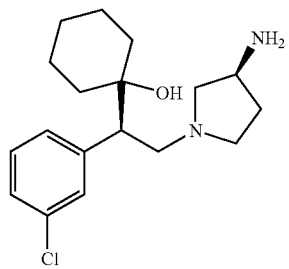

In an analogous manner to Example 1, step 2, 1-[(1R)-2-[(3S)-3-aminopyrrolidin-1-yl]-1-(3-chlorophenyl)ethyl]cyclohexanol dihydrochloride was prepared from tert-butyl {(3S)-1-[(2S)-2-(3-chlorophenyl)-2-(1-hydroxycyclohexyl) acetyl]pyrrolidin-3-yl}carbamate (see Example 387B). MS (ES) m/z 323.1; HRMS: calcd for $C_{18}H_{27}ClN_2O+H+$, 323.18847; found (ESI, [M+H]$^+$), 323.188; $[\alpha]_D^{25}=+240$ (c=0.0105 g/mL, MeOH); CD=-@281 nm.

Example 389

1-{1-[4-(1-naphthyloxy)phenyl]-2-piperazin-1-ylethyl}cyclohexanol dihydrochloride

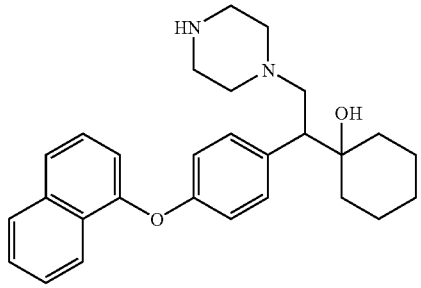

In an analogous manner to Example 400, step 1 tert-butyl 4-[(1-hydroxycyclohexyl)(4-hydroxyphenyl)acetyl]piperazine-1-carboxylate was prepared from tert-butyl 4-[(1-hydroxycyclohexyl)(4-benzyloxyphenyl)acetyl]piperazine-1-carboxylate (see Example 27). MS (ES) m/z 417.1.

In an analogous manner to Example 135, step 2 tert-butyl 4-[2-(1-hydroxycyclohexyl)-2-(4-hydroxyphenyl)ethyl]piperazine-1-carboxylate was prepared from tert-butyl 4-[(1-hydroxycyclohexyl)(4-hydroxyphenyl)acetyl]piperazine-1-carboxylate. MS (ESI) m/z 405; MS (ESI) m/z 403; HRMS: calcd for $C_{23}H_{36}N_2O_4+H+$, 405.27478; found (ESI, [M+H]$^+$), 405.2736.

To a stirred solution of tert-butyl 4-[2-(1-hydroxycyclohexyl)-2-(4-hydroxyphenyl)ethyl]piperazine-1-carboxylate (120 mg, 0.30 mmol), naphthalene-1-boronic acid (54 mg, 0.31 mmol) in dry dichloromethane (2 mL) was added copper (II) L, 0.51 mmol), and☐acetate (19 mg, 0.10 mmol), triethylamine (71 powdered 4 Å sieves (100 mg) was stirred at room temperature for 16 h, after which time the reaction was filtered through a pad of Celite®, which was washed with dichloromethane (20 mL), and concentrated in vacuo. The product was purified via Biotage Horizon (FLASH 25 S, silica, gradient from 10% EtOAc/hexane to 60% EtOAc/hexane) to yield tert-butyl 4-{2-(1-hydroxycyclohexyl)-2-[4-(1-naphthyloxy)phenyl]ethyl}piperazine-1-carboxylate as a colorless oil. MS (ESI) m/z 531; HRMS: calcd for $C_{33}H_{42}N_2O_4^+H+$, 531.32173; found (ESI, [M+H]$^+$), 531.3203.

In an analogous manner to Example 135, step 4 1-{1-[4-(1-naphthyloxy)phenyl]-2-piperazin-1-ylethyl}cyclohexanol dihydrochloride was prepared from tert-butyl 4-{2-(1-hydroxycyclohexyl)-2-[4-(1-naphthyloxy)phenyl]ethyl}piperazine-1-carboxylate. MS (ESI) m/z 431; HRMS: calcd for $C_{28}H_{34}N_2O_2+H+$, 431.26930; found (ESI, [M+H]$^+$), 431.2717.

Example 390

1-{1-[4-(benzyloxy)-3-bromo-5-methoxyphenyl]-2-piperazin-1-ylethyl}cyclohexanol dihydrochloride

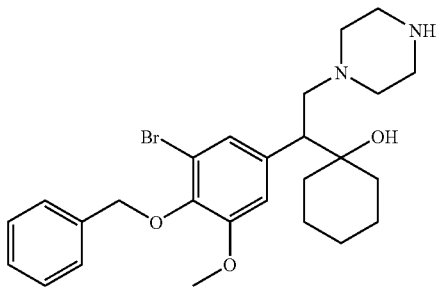

In an analogous manner to Example 261, step 1, 1-Bromo-5-(2,2-dibromo-vinyl)-2-benzyloxy-3-methoxy-benzene was prepared from 4-Benzyloxy-3-bromo-5-methoxy-benzaldehyde.

In an analogous manner to Example 261, step 2, 4-[2-(4-Benzyloxy-3-bromo-5-methoxy-phenyl)-acetyl]-piperazine-1-carboxylic acid tert-butyl ester was prepared from 1-Bromo-5-(2,2-dibromo-vinyl)-2-benzyloxy-3-methoxy-benzene and tert-butyl 1-piperazinecarboxylate.

In an analogous manner to Example 141, step 3, 4-[2-(4-Benzyloxy-3-bromo-5-methoxy-phenyl)-2-(1-hydroxy-cyclohexyl)-acetyl]-piperazine-1-carboxylic acid tert-butyl ester was prepared from 4-[2-(4-Benzyloxy-3-bromo-5-methoxy-phenyl)-acetyl]-piperazine-1-carboxylic acid tert-butyl ester.

In an analogous manner to Example 1, step 2, 1-{1-[4-(benzyloxy)-3-bromo-5-methoxyphenyl]-2-piperazin-1-ylethyl}cyclohexanol dihydrochloride was prepared from 4-[2-(4-Benzyloxy-3-bromo-5-methoxy-phenyl)-2-(1-hydroxy-cyclohexyl)-acetyl]-piperazine-1-carboxylic acid tert-butyl ester. MS (ESI) m/z 503; HRMS: calcd for $C_{26}H_{35}BrN_2O_3+H+$, 503.19038; found (ESI, [M+H]$^+$), 503.1892.

Example 391

1-[1-[4-(benzyloxy)-3-bromo-5-methoxyphenyl]-2-(4-methylpiperazin-1-yl)ethyl]cyclohexanol dihydrochloride

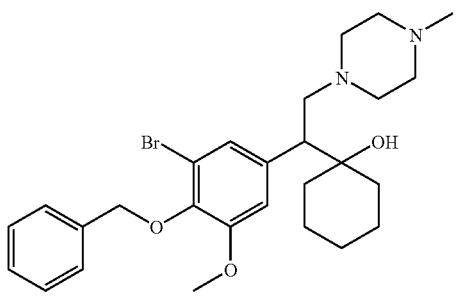

In an analogous manner to Example 24, 1-[1-[4-(benzyloxy)-3-bromo-5-methoxyphenyl]-2-(4-methylpiperazin-1-yl)ethyl]cyclohexanol dihydrochloride was prepared from 1-{1-[4-(benzyloxy)-3-bromo-5-methoxyphenyl]-2-piperazin-1-ylethyl}cyclohexanol (See Example 390). MS (ES) m/z 517.0; HRMS: calcd for $C_{27}H_{37}BrN_2O_3$+H+, 517.20603; found (ESI, [M+H]$^+$), 517.2069

Example 392

1-{1-[4-(benzyloxy)-3,5-dibromophenyl]-2-piperazin-1-ylethyl}cyclohexanol dihydrochloride

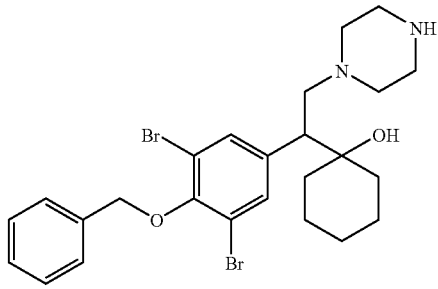

In an analogous manner to Example 261, step 1, 1,3-Dibromo-5-(2,2-dibromo-vinyl)-2-benzyloxy-benzene was prepared from 4-benzyloxy-3,5-dibromo-benzaldehyde.

In an analogous manner to Example 261, step 2, 4-[2-(4-Benzyloxy-3,5-dibromo-phenyl)-acetyl]-piperazine-1-carboxylic acid tert-butyl ester was prepared from 1,3-Dibromo-5-(2,2-dibromo-vinyl)-2-benzyloxy-benzene and tert-butyl 1-piperazinecarboxylate.

In an analogous manner to Example 141, step 3, 4-[2-(4-Benzyloxy-3,5-dibromo-phenyl)-2-(1-hydroxy-cyclohexyl)-acetyl]-piperazine-1-carboxylic acid tert-butyl ester was prepared from 4-[2-(4-Benzyloxy-3,5-dibromo-phenyl)-acetyl]-piperazine-1-carboxylic acid tert-butyl ester.

In an analogous manner to Example 1, step 2, 1-{1-[4-(benzyloxy)-3,5-dibromophenyl]-2-piperazin-1-ylethyl}cyclohexanol dihydrochloride was prepared from 4-[2-(4-Benzyloxy-3,5-dibromo-phenyl)-2-(1-hydroxy-cyclohexyl)-acetyl]-piperazine-1-carboxylic acid tert-butyl ester. MS (ES) m/z 551.0; HRMS: calcd for $C_{25}H_{32}Br_2N_2O_2$+H+, 551.09033; found (ESI, [M+H]$^+$), 551.0882.

Example 393

1-[1-[4-(benzyloxy)-3,5-dibromophenyl]-2-(4-methylpiperazin-1-yl)ethyl]cyclohexanol dihydrochloride

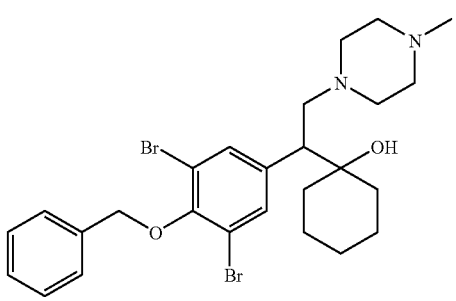

In an analogous manner to Example 24, 1-[1-[4-(benzyloxy)-3,5-dibromophenyl]-2-(4-methylpiperazin-1-yl)ethyl]cyclohexanol dihydrochloride was prepared from 1-{1-[4-(benzyloxy)-3,5-dibromophenyl]-2-piperazin-1-ylethyl}cyclohexanol (See Example 392). MS (ESI) m/z 565; HRMS: calcd for $C_{26}H_{34}Br_2N_2O_2$+H+, 565.10598; found (ESI, [M+H]$^+$), 565.1088.

Example 394

(3R)-3-methyl-1-{2-piperazin-1-yl-1-[3-(trifluoromethoxy)phenyl]ethyl}cyclopentanol dihydrochloride

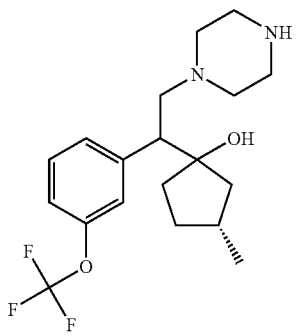

In an analogous manner to Example 1, step 1, tert-butyl 4-{[(3R)-1-hydroxy-3-methylcyclopentyl][3-(trifluoromethoxy)phenyl]acetyl}piperazine-1-carboxylate was prepared from [(3R)-1-hydroxy-3-methylcyclopentyl][3-(trifluoromethoxy)phenyl]acetic acid (Reference Example 1-qqq) and tert-butyl 1-piperazinecarboxylate.

In an analogous manner to Example 1, step 2, (3R)-3-methyl-1-{2-piperazin-1-yl-1-[3-(trifluoromethoxy)phenyl]ethyl}cyclopentanol dihydrochloride was prepared from tert-butyl 4-{[(3R)-1-hydroxy-3-methylcyclopentyl][3-(trifluoromethoxy)phenyl]acetyl}piperazine-1-carboxylate.

Example 395

(3R)-3-methyl-1-{2-(4-methylpiperazin-1-yl)-1-[3-(trifluoromethoxy)phenyl]ethyl}cyclopentanol dihydrochloride

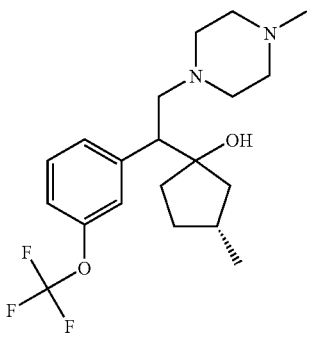

In an analogous manner to Example 24, (3R)-3-methyl-1-{2-(4-methylpiperazin-1-yl)-1-[3-(trifluoromethoxy)phenyl]ethyl}cyclopentanol dihydrochloride was prepared from (3R)-3-methyl-1-{2-piperazin-1-yl-1-[3-(trifluoromethoxy)phenyl]ethyl}cyclopentanol (See Example 394). MS (ESI) m/z 387; HRMS: calcd for $C_{20}H_{29}F_3N_2O_2$+H+, 387.22539; found (ESI, [M+H]$^+$), 387.2275.

Example 396

2,2-dimethyl-1-{2-piperazin-1-yl-1-[3-(trifluoromethoxy)phenyl]ethyl}cyclopentanol dihydrochloride

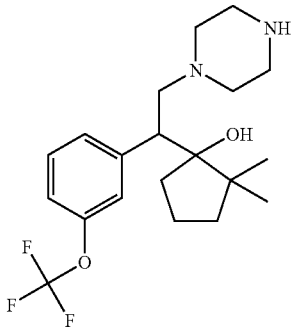

In an analogous manner to Example 1, step 1, 4-[2-(1-hydroxy-2,2-dimethyl-cyclopentyl)-2-(3-trifluoromethoxy-phenyl)-acetyl]-piperazine-1-carboxylic acid tert-butyl ester was prepared from (1-Hydroxy-2,2-dimethyl-cyclopentyl)-(3-trifluoromethoxy-phenyl)-acetic acid (Reference Example 1-rrr) and tert-butyl 1-piperazinecarboxylate.

In an analogous manner to Example 1, step 2, 2,2-dimethyl-1-{2-piperazin-1-yl-1-[3-(trifluoromethoxy)phenyl]ethyl}cyclopentanol dihydrochloride was prepared from 4-[2-(1-Hydroxy-2,2-dimethyl-cyclopentyl)-2-(3-trifluoromethoxy-phenyl)-acetyl]-piperazine-1-carboxylic acid tert-butyl ester. MS (ESI) m/z 387; HRMS: calcd for $C_{20}H_{29}F_3N_2O_2$+H+, 387.22539; found (ESI, [M+H]$^+$), 387.2275.

Example 397

2,2-dimethyl-1-{2-(4-methylpiperazin-1-yl)-1-[3-(trifluoromethoxy)phenyl]ethyl}cyclopentanol dihydrochloride

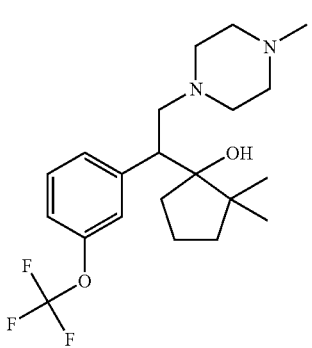

In an analogous manner to Example 24, 2,2-dimethyl-1-{2-(4-methylpiperazin-1-yl)-1-[3-(trifluoromethoxy)phenyl]ethyl}cyclopentanol dihydrochloride was prepared from 2,2-dimethyl-1-{2-piperazin-1-yl-1-[3-(trifluoromethoxy)phenyl]ethyl}cyclopentanol (See Example 396). MS (ES) m/z 401.2; HRMS: calcd for $C_{21}H_{32}F_3N_2O_2$+H+, 401.2416; found (ESI, [M+H]$^+$), 401.2403.

Example 398

(3R)-1-{2-(1,4'-bipiperidin-1'-yl)-1-[3-(trifluoromethoxy)phenyl]ethyl}-3-methylcyclopentanol dihydrochloride

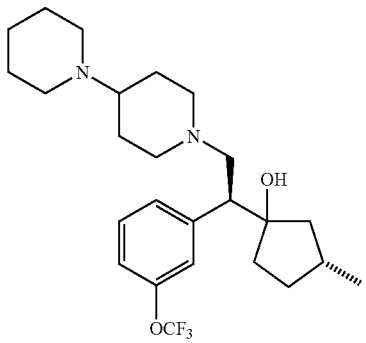

In an analogous manner to Example 1, step 1, (3R)-1-{2-(1,4'-bipiperidin-1'-yl)-2-oxo-1-[3-(trifluoromethoxy)phenyl]ethyl}-3-methylcyclopentanol was prepared from [(3R)-1-hydroxy-3-methylcyclopentyl][3-(trifluoromethoxy)phenyl]acetic acid (Reference Example 1-qqq) and N-(4-piperidine)piperidine.

In an analogous manner to Example 1, step 2, (3R)-1-{2-(1,4'-bipiperidin-1'-yl)-1-[3-(trifluoromethoxy)phenyl]ethyl}-3-methylcyclopentanol dihydrochloride was prepared from (3R)-1-{2-(1,4'-bipiperidin-1'-yl)-2-oxo-1-[3-(trifluoromethoxy)phenyl]ethyl}-3-methylcyclopentanol. MS (ESI)

m/z 455; HRMS: calcd for $C_{25}H_{37}F_3N_2O_2$+H+, 455.28799; found (ESI, [M+H]$^+$), 455.2901.

Example 399

1-{2-(4-methylpiperazin-1-yl)-1-[4-(1-naphthyloxy)phenyl]ethyl}cyclohexanol dihydrochloride

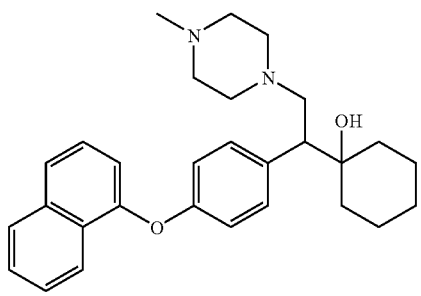

In an analogous manner to Example 24, 1-{2-(4-methylpiperazin-1-yl)-1-[4-(1-naphthyloxy)phenyl]ethyl}cyclohexanol dihydrochloride was prepared from 1-{1-[4-(1-naphthyloxy)phenyl]-2-piperazin-1-ylethyl}cyclohexanol (see Example 389). MS (ESI) m/z 445; HRMS: calcd for $C_{29}H_{36}N_2O_2$+H+, 445.28495; found (ESI, [M+H]$^+$), 445.2848.

Example 400

4-[1-(1-hydroxycyclohexyl)-2-piperazin-1-ylethyl]-2-(trifluoromethoxy)phenol dihydrochloride

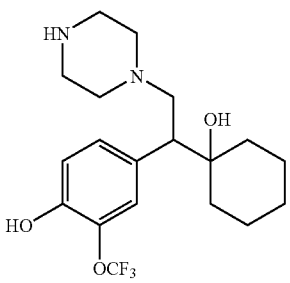

Step 1: A mixture of tert-Butyl 4-[[4-(benzyloxy)-3-(trifluoromethoxy)phenyl](1-hydroxycyclohexyl)acetyl]piperazine-1-carboxylate (1.7 g, 2.87 mmol) (See Example 268, Step 5), ammonium formate (0.95 g, 15.0 mmol), and a catalytic amount of palladium on carbon was heated at 50° C. for 1 hr in methanol (25 mL). At the end of this time the solution was concentrated and the residue taken up in ethyl acetate and filtered through a plug of silica gel eluting with 30% ethyl acetate:hexane. The filtrate was concentrated to afford 1.02 g of tert-butyl 4-{(1-hydroxycyclohexyl)[4-hydroxy-3-(trifluoromethoxy)phenyl]acetyl}piperazine-1-carboxylate. MS (ESI) m/z 503; HRMS: calcd for C24H33F3N2O6+H+, 503.23635; found (ESI, [M+H]+), 503.2343.

Step 2: In an analogous manner to Example 135 step 3 tert-butyl 4-[2-[4-(hydroxy)-3-(trifluoromethoxy)phenyl]-2-(1-hydroxycyclohexyl)ethyl]piperazine-1-carboxylate was prepared from tert-butyl 4-{(1-hydroxycyclohexyl)[4-hydroxy-3-(trifluoromethoxy)phenyl]acetyl}piperazine-1-carboxylate.

Step 3: In an analogous manner to Example 135 step 4, 4-[1-(1-hydroxycyclohexyl)-2-piperazin-1-ylethyl]-2-(trifluoromethoxy)phenol dihydrochloride was prepared from tert-butyl 4-[2-[4-(hydroxy)-3-(trifluoromethoxy)phenyl]-2-(1-hydroxycyclohexyl)ethyl]piperazine-1-carboxylate. MS (ESI) m/z 389; HRMS: calcd for $C_{19}H_{27}F_3N_2O_3$+H+, 389.20465; found (ESI, [M+H]$^+$), 389.2066.

Example 401

4-[1-(1-hydroxycyclohexyl)-2-(4-methylpiperazin-1-yl)ethyl]-2-(trifluoromethoxy)phenol dihydrochloride

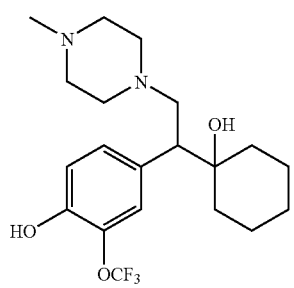

In an analogous manner to Example 24, 4-[1-(1-hydroxycyclohexyl)-2-(4-methylpiperazin-1-yl)ethyl]-2-(trifluoromethoxy)phenol dihydrochloride was prepared from 4-[1-(1-hydroxycyclohexyl)-2-piperazin-1-ylethyl]-2-(trifluoromethoxy)phenol dihydrochloride (see Example 400). MS (ESI) m/z 403; HRMS: calcd for $C_{20}H_{29}F_3N_2O_3$+H+, 403.22030; found (ESI, [M+H]$^+$), 403.2201

Example 402

1-{1-[4-methoxy-3-(trifluoromethoxy)phenyl]-2-piperazin-1-ylethyl}cyclohexanol dihydrochloride

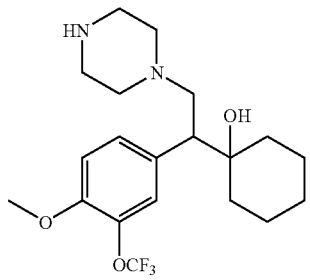

Step 1: A solution of tert-butyl 4-{(1-hydroxycyclohexyl)[4-hydroxy-3-(trifluoromethoxy)phenyl]acetyl}piperazine-1-carboxylate (0.35 g 0.72 mmol) (See Example 400, step 1) and iodomethane (0.16 g, 1.08 mmol) in N-N'-dimethylformamide (5 mL) was treated with potassium carbonate (0.12 g, 0.86 mmol), and the solution was stirred at room temperature for 16 hours. The reaction was then poured into water and extracted 3 times with ethyl acetate. The combined extracts were washed twice with water, then dried over magnesium sulfate and concentrated to afford 0.31 g of tert-butyl 4-{(1-hydroxycyclohexyl)[4-methoxy-3-(trifluoromethoxy)phenyl]acetyl}piperazine-1-carboxylate). The product was used in the next step without further purification.

Step 2: In an analogous manner to Example 135, step 3 tert-butyl 4-[2-[4-(methoxy)-3-(trifluoromethoxy)phenyl]-2-(1-hydroxycyclohexyl)ethyl]piperazine-1-carboxylate was prepared from tert-butyl 4-{(1-hydroxycyclohexyl)[4-methoxy-3-(trifluoromethoxy)phenyl]acetyl}piperazine-1-carboxylate).

Step 3: In an analogous manner to Example 135, step 4, 1-{1-[4-methoxy-3-(trifluoromethoxy)phenyl]-2-piperazin-1-ylethyl}cyclohexanol dihydrochloride was prepared from tert-butyl 4-[2-[4-(methoxy)-3-(trifluoromethoxy)phenyl]-2-(1-hydroxycyclohexyl)ethyl]piperazine-1-carboxylate. MS (ESI) m/z 403; HRMS: calcd for $C_{20}H_{29}F_3N_2O_3$+H+, 403.22030; found (ESI, [M+H]+), 403.2197.

Step 2: In an analogous manner to Example 135, step 3 tert-butyl 4-[2-[4-(ethoxy)-3-(trifluoromethoxy)phenyl]-2-(1-hydroxycyclohexyl)ethyl]piperazine-1-carboxylate was prepared from tert-butyl 4-{(1-hydroxycyclohexyl)[4-ethoxy-3-(trifluoromethoxy)phenyl]acetyl}piperazine-1-carboxylate).

Step 3: In an analogous manner to Example 135, step 4 1-{1-[4-ethoxy-3-(trifluoromethoxy)phenyl]-2-piperazin-1-ylethyl}cyclohexanol dihydrochloride was prepared from tert-butyl 4-[2-[4-(ethoxy)-3-(trifluoromethoxy)phenyl]-2-(1-hydroxycyclohexyl)ethyl]piperazine-1-carboxylate. MS (ES) m/z 417.1; HRMS: calcd for $C_{21}H_{31}F_3N_2O_3$+H+, 417.23595; found (ESI, [M+H]+), 417.2354.

Example 403

1-[1-[4-methoxy-3-(trifluoromethoxy)phenyl]-2-(4-methylpiperazin-1-yl)ethyl]cyclohexanol dihydrochloride

Example 405

1-[1-[4-ethoxy-3-(trifluoromethoxy)phenyl]-2-(4-methylpiperazin-1-yl)ethyl]cyclohexanol dihydrochloride

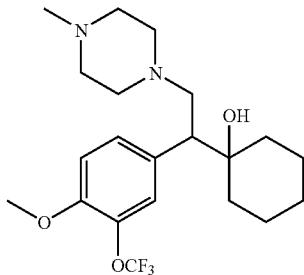

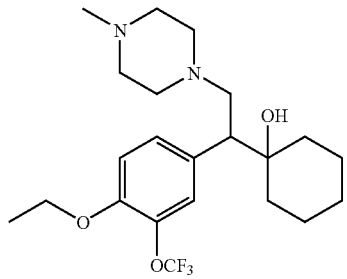

In an analogous manner to Example 24, 1-[1-[4-methoxy-3-(trifluoromethoxy)phenyl]-2-(4-methylpiperazin-1-yl)ethyl]cyclohexanol dihydrochloride was prepared from 1-{1-[4-methoxy-3-(trifluoromethoxy)phenyl]-2-piperazin-1-ylethyl}cyclohexanol dihydrochloride (see Example 402). MS (ESI) m/z 403; HRMS: calcd for $C_{20}H_{29}F_3N_2O_3$+H+, 403.22030; found (ESI, [M+H]+), 403.2201

In an analogous manner to Example 24, 1-[1-[4-ethoxy-3-(trifluoromethoxy)phenyl]-2-(4-methylpiperazin-1-yl)ethyl]cyclohexanol dihydrochloride was prepared from 1-{1-[4-ethoxy-3-(trifluoromethoxy)phenyl]-2-piperazin-1-ylethyl}cyclohexanol dihydrochloride (see Example 404). HRMS: calcd for $C_{22}H_{33}F_3N_2O_3$+H+, 431.25160; found (ESI, [M+H]+), 431.25.

Example 404

1-{1-[4-ethoxy-3-(trifluoromethoxy)phenyl]-2-piperazin-1-ylethyl}cyclohexanol dihydrochloride

Example 406

1-{1-[4-isobutoxy-3-(trifluoromethoxy)phenyl]-2-piperazin-1-ylethyl}cyclohexanol dihydrochloride

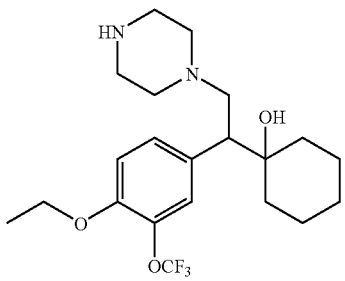

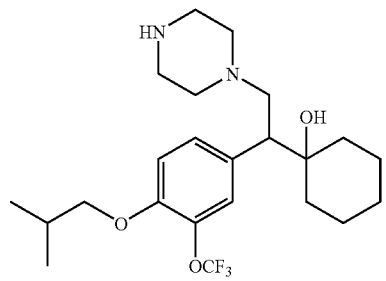

Step 1: In an analogous manner to Example 402, step 1, tert-butyl 4-{(1-hydroxycyclohexyl)[4-ethoxy-3-(trifluoromethoxy)phenyl]acetyl}piperazine-1-carboxylate was prepared from tert-butyl 4-{(1-hydroxycyclohexyl)[4-hydroxy-3-(trifluoromethoxy)phenyl]acetyl}piperazine-1-carboxylate (See Example 400, step 1) and bromoethane.

Step 1: In an analogous manner to Example 402, step 1, tert-butyl 4-{(1-hydroxycyclohexyl)[4-isobutoxy-3-(trifluoromethoxy)phenyl]acetyl}piperazine-1-carboxylate was prepared from tert-butyl 4-{(1-hydroxycyclohexyl)[4-hydroxy-3-(trifluoromethoxy)phenyl]acetyl}piperazine-1-carboxylate (See Example 400, step 1) and isobutyl bromide.

Step 2: In an analogous manner to Example 135, step 3 tert-butyl 4-[2-[4-(isobutoxy)-3-(trifluoromethoxy)phenyl]-2-(1-hydroxycyclohexyl)ethyl]piperazine-1-carboxylate was prepared from tert-butyl 4-{(1-hydroxycyclohexyl)[4-isobutoxy-3-(trifluoromethoxy)phenyl]acetyl}piperazine-1-carboxylate).

Step 3: In an analogous manner to Example 135, step 4, 1-{1-[4-isobutoxy-3-(trifluoromethoxy)phenyl]-2-piperazin-1-ylethyl}cyclohexanol dihydrochloride was prepared from tert-butyl 4-[2-[4-(isobutoxy)-3-(trifluoromethoxy)phenyl]-2-(1-hydroxycyclohexyl)ethyl]piperazine-1-carboxylate. MS (ESI) m/z 445; HRMS: calcd for $C_{23}H_{35}F_3N_2O_3+H+$, 445.26725; found (ESI, $[M+H]^+$), 445.267.

Example 407

1-[1-[4-isobutoxy-3-(trifluoromethoxy)phenyl]-2-(4-methylpiperazin-1-yl)ethyl]cyclohexanol dihydrochloride

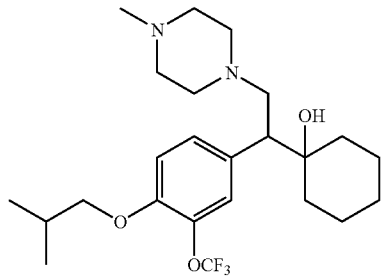

In an analogous manner to Example 24, 1-[1-[4-isobutoxy-3-(trifluoromethoxy)phenyl]-2-(4-methylpiperazin-1-yl)ethyl]cyclohexanol dihydrochloride was prepared from 1-{1-[4-isobutoxy-3-(trifluoromethoxy)phenyl]-2-piperazin-1-ylethyl}cyclohexanol dihydrochloride (see Example 406). HRMS: calcd for $C_{24}H_{37}F_3N_2O_3+H+$, 459.28290; found (ESI, $[M+H]^+$), 459.2813.

Example 408

1-[1-[4-(benzyloxy)-3-(trifluoromethoxy)phenyl]-2-(4-methylpiperazin-1-yl)ethyl]cyclohexanol dihydrochloride

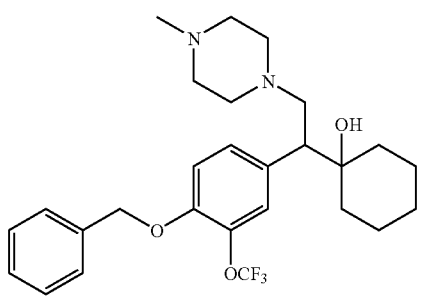

In an analogous manner to Example 24, 1-[1-[4-(benzyloxy)-3-(trifluoromethoxy)phenyl]-2-(4-methylpiperazin-1-yl)ethyl]cyclohexanol dihydrochloride was prepared from 1-{1-[4-(benzyloxy)-3-(trifluoromethoxy)phenyl]-2-piperazin-1-ylethyl}cyclohexanol dihydrochloride (see Example 268). MS (ES) m/z 493.3; HRMS: calcd for $C_{27}H_{35}F_3N_2O_3+H+$, 493.26725; found (ESI, $[M+H]^+$), 493.2689.

Example 409

1-{1-[4-(2-phenylethyl)phenyl]-2-piperazin-1-ylethyl}cyclohexanol dihydrochloride

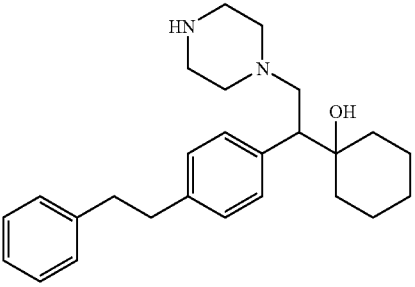

In an analogous manner to Example 1, step 1 tert-butyl 4-[(1-hydroxycyclohexyl)(2-phenylethyl phenyl)acetyl]piperazine-1-carboxylate was prepared from (1-hydroxycyclohexyl)[4-(2-phenylethyl)phenyl]acetic acid (Reference Example I-lll) and tert-butyl 1-piperazinecarboxylate.

In an analogous manner to Example 135, step 3 tert-butyl 4-[(1-hydroxycyclohexyl)(2-phenylethyl Phenyl)ethyl]piperazine-1-carboxylate was prepared from tert-butyl 4-[(1-hydroxycyclohexyl)(2-phenylethyl phenyl)acetyl]piperazine-1-carboxylate.

In an analogous manner to Example 135, step 4 1-{1-[4-(2-phenylethyl)phenyl]-2-piperazin-1-ylethyl}cyclohexanol dihydrochloride was prepared from tert-butyl 4-[(1-hydroxycyclohexyl)(2-phenylethyl phenyl)ethyl]piperazine-1-carboxylate. MS (ESI) m/z 393; HRMS: calcd for C26H36N2O+H+, 393.29004; found (ESI, $[M+H]^+$), 393.2904.

Example 410

1-[1-[4-(benzyloxy)-3-(trifluoromethoxy)phenyl]-2-(4-methylpiperazin-1-yl)ethyl]cyclohexanol dihydrochloride

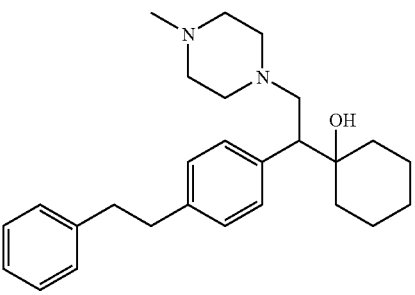

In an analogous manner to Example 24, 1-{2-(4-methylpiperazin-1-yl)-1-[4-(2-phenylethyl)phenyl]ethyl}cyclohexanol dihydrochloride was prepared from 1-{1-[4-(2-phenylethyl)phenyl]-2-piperazin-1-ylethyl}cyclohexanol dihydrochloride (see Example 409).

MS (ESI) m/z 407; HRMS: calcd for C27H38N2O+H+, 407.30569; found (ESI, [M+H]+), 407.3062;

Example 411

1-[(2S)-1-[4-(benzyloxy)phenyl]-2-(4-methylpiperazin-1-yl)ethyl]cyclohexanol dihydrochloride

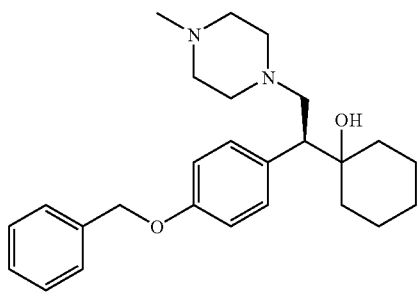

In an analogous manner to Example 135, step 3 tert-butyl 4-[2-[4-(benzyloxy)phenyl]-2-(1-hydroxycyclohexyl)ethyl]piperazine-1-carboxylate was prepared from tert-butyl 4-[[4-(benzyloxy)phenyl](1-hydroxycyclohexyl)acetyl]piperazine-1-carboxylate (See Example 27).

tert-Butyl 4-[(2S)-2-[4-(benzyloxy)phenyl]-2-(1-hydroxycyclohexyl)ethyl]piperazine-1-carboxylate was isolated from tert-butyl 4-[2-[4-(benzyloxy)phenyl]-2-(1-hydroxycyclohexyl)ethyl]piperazine-1-carboxylate by chiral column chromatography (Chiral OD-H, 100% acetonitrile, 16 ml/min) $[\alpha]_D^{25}$=+29° (c=0.0097 g/mL, MeOH); HRMS: calcd for C30H42N2O4+H+, 495.32173; found (ESI, [M+H]+), 495.3203.

In an analogous manner to Example 24, 1-[(2S)-1-[4-(benzyloxy)phenyl]-2-(4-methylpiperazin-1-yl)ethyl]cyclohexanol dihydrochloride was prepared from the above isolated product. $[\alpha]_D^{25}$=+36° (c=0.0094 g/mL, MeOH); MS (ESI) m/z 409; HRMS: calcd for C26H36N2O2+H+, 409.28495; found (ESI, [M+H]+), 409.2857.

Example 412

1-[(2R)-1-[4-(benzyloxy)phenyl]-2-(4-methylpiperazin-1-yl)ethyl]cyclohexanol dihydrochloride

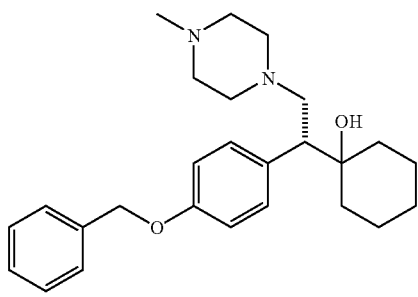

tert-Butyl 4-[(2R)-2-[4-(benzyloxy)phenyl]-2-(1-hydroxycyclohexyl)ethyl]piperazine-1-carboxylate was isolated from tert-butyl 4-[[4-(benzyloxy)phenyl]-2-(1-hydroxycyclohexyl)ethyl]piperazine-1-carboxylate (see Example 411) by chiral column chromatography (Chiral OD-H, 100% acetonitrile, 16 ml/min). $[\alpha]_D^{25}$=−27° (c=0.0097 g/mL, MeOH); MS (ESI) m/z 495.

In an analogous manner to Example 24, 1-[(2R)-1-[4-(benzyloxy)phenyl]-2-(4-methylpiperazin-1-yl)ethyl]cyclohexanol dihydrochloride was prepared from the above isolated product. MS (ESI) m/z 409; HRMS: calcd for C26H36N2O2+H+, 409.28495; found (ESI, [M+H]+), 409.2873.

Example 413

1-{1-[4-(benzyloxy)-3-fluorophenyl]-2-piperazin-1-ylethyl}cyclohexanol dihydrochloride

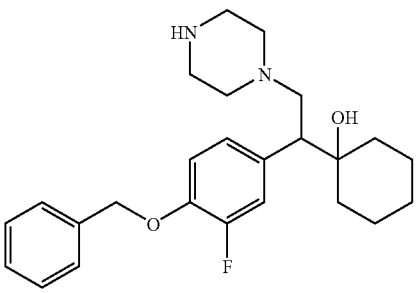

In an analogous manner to Example 1, step 1 tert-butyl 4-[[4-(benzyloxy)-3-fluorophenyl](1-hydroxycyclohexyl)acetyl]piperazine-1-carboxylate was prepared from [4-(benzyloxy)-3-fluorophenyl](1-hydroxycyclohexyl)acetic acid (Reference Example I-mmm) and tert-butyl 1-piperazinecarboxylate. MS (ESI) m/z 527.

In an analogous manner to Example 1, step 2, 1-{1-[4-(benzyloxy)-3-fluorophenyl]-2-piperazin-1-ylethyl}cyclohexanol dihydrochloride was prepared from tert-butyl 4-[[4-(benzyloxy)-3-fluorophenyl](1-hydroxycyclohexyl)acetyl]piperazine-1-carboxylate. MS (ESI) m/z 413; HRMS: calcd for C25H33FN2O2+H+, 413.25988; found (ESI, [M+H]+), 413.2593.

Example 414

1-{1-[4-(benzyloxy)-3-fluorophenyl]-2-(4-methylpiperazin-1-yl)ethyl}cyclohexanol dihydrochloride

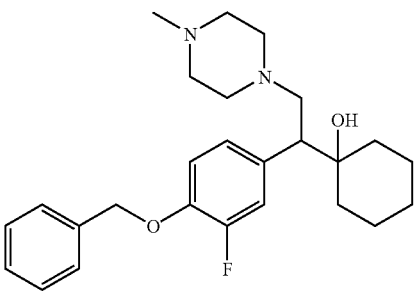

In an analogous manner to Example 24, 1-[1-[4-(benzyloxy)-3-fluorophenyl]-2-(4-methylpiperazin-1-yl)ethyl]cyclohexanol dihydrochloride was prepared from 1-{1-[4-(benzyloxy)-3-fluorophenyl]-2-piperazin-1-ylethyl}cyclohexanol dihydrochloride (See Example 413).

MS (ES) m/z 427.1; HRMS: calcd for C26H35FN2O2+H+, 427.27553; found (ESI, [M+H]+), 427.2756.

Example 415

1-[1-(3-fluoro-4-{[4-(trifluoromethyl)benzyl]oxy}phenyl)-2-piperazin-1-ylethyl]cyclohexanol dihydrochloride

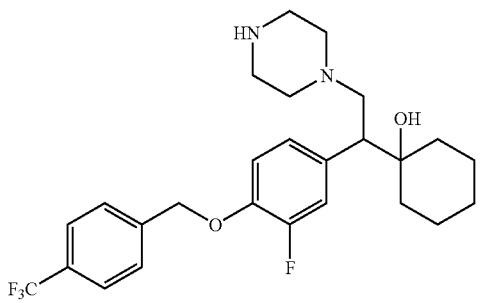

Step 1: In an analogous manner to Example 400, step 1 tert-butyl 4-[(3-fluoro-4-hydroxyphenyl)(1-hydroxycyclohexyl)acetyl]piperazine-1-carboxylate was prepared from tert-butyl 4-[[4-(benzyloxy)-3-fluorophenyl](1-hydroxycyclohexyl)acetyl]piperazine-1-carboxylate (See Example 413). MS (ESI) m/z 437; MS (ESI) m/z 435.

Step 2: In an analogous manner to Example 402, step 1 tert-butyl 4-[(3-fluoro-4-{[4-(trifluoromethyl)benzyl]oxy}phenyl)(1-hydroxycyclohexyl)acetyl]piperazine-1-carboxylate was prepared from tert-butyl 4-[(3-fluoro-4-hydroxyphenyl)(1-hydroxycyclohexyl)acetyl]piperazine-1-carboxylate and 4-trifluoromethyl benzyl bromide. MS (ES) m/z 595.

Step 3: In an analogous manner to Example 1, step 2 1-[1-(3-fluoro-4-{[4-(trifluoromethyl)benzyl]oxy}phenyl)-2-piperazin-1-ylethyl]cyclohexanol dihydrochloride was prepared from tert-butyl 4-[(3-fluoro-4-{[4-(trifluoromethyl)benzyl]oxy}phenyl)(1-hydroxycyclohexyl)acetyl]piperazine-1-carboxylate. MS (ESI) m/z 481; HRMS: calcd for C26H32F4N2O2+H+, 481.24727; found (ESI, [M+H]+), 481.2492.

Example 416

1-[1-(3-fluoro-4-{[4-(trifluoromethyl)benzyl]oxy}phenyl)-2-(4-methylpiperazin-1-yl)ethyl]cyclohexanol dihydrochloride

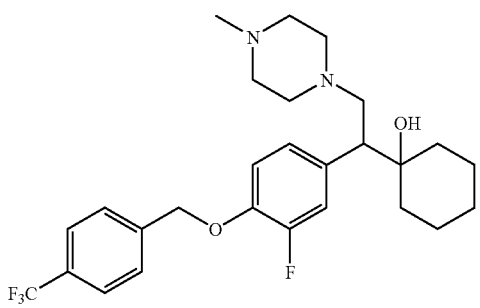

In an analogous manner to Example 24, 1-[1-(3-fluoro-4-{[4-(trifluoromethyl)benzyl]oxy}phenyl)-2-(4-methylpiperazin-1-yl)ethyl]cyclohexanol dihydrochloride was prepared from 1-[1-(3-fluoro-4-{[4-(trifluoromethyl)benzyl]oxy}phenyl)-2-piperazin-1-ylethyl]cyclohexanol dihydrochloride (See Example 415). MS (ESI) m/z 495; HRMS: calcd for C27H34F4N2O2+H+, 495.26292; found (ESI, [M+H]+), 495.2659.

Example 417

1-(1-{3-fluoro-4-[(4-methylbenzyl)oxy]phenyl}-2-piperazin-1-ylethyl)cyclohexanol dihydrochloride

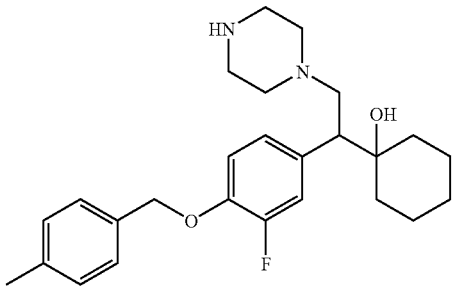

In an analogous manner to Example 402, step 1 tert-butyl 4-[(3-fluoro-4-{[4-(methyl)benzyl]oxy}phenyl)(1-hydroxycyclohexyl)acetyl]piperazine-1-carboxylate was prepared from tert-butyl 4-[(3-fluoro-4-hydroxyphenyl) (1-hydroxycyclohexyl)acetyl]piperazine-1-carboxylate (see Example 415, step 1) and 4-methylbenzyl bromide. MS (ES) m/z 541.2.

In an analogous manner to Example 1, step 2 1-[1-(3-fluoro-4-{[4-(trifluoromethyl)benzyl]oxy}phenyl)-2-(4-methylpiperazin-1-yl)ethyl]cyclohexanol dihydrochloride was prepared from tert-butyl 4-[(3-fluoro-4-{[4-(methyl)benzyl]oxy}phenyl)(1-hydroxycyclohexyl)acetyl]piperazine-1-carboxylate. MS (ESI) m/z 427; HRMS: calcd for C26H35FN2O2+H+, 427.27553; found (ESI, [M+H]+), 427.2776.

Example 418

1-[1-(3-fluoro-4-{[4-(methyl)benzyl]oxy}phenyl)-2-(4-methylpiperazin-1-yl)ethyl]cyclohexanol dihydrochloride

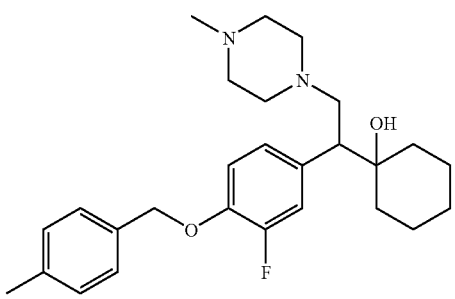

In an analogous manner to Example 24, 1-[1-(3-fluoro-4-{[4-(methyl)benzyl]oxy}phenyl)-2-(4-methylpiperazin-1-yl)ethyl]cyclohexanol dihydrochloride was prepared from 1-[1-(3-fluoro-4-{[4-(methyl)benzyl]oxy}phenyl)-2-piperazin-1-ylethyl]cyclohexanol dihydrochloride (See Example 417). MS (ESI) m/z 441; HRMS: calcd for C27H37FN2O2+ H+, 441.29118; found (ESI, [M+H]+), 441.2941.

Example 419

1-[1-(3-chloro-4-{[4-(trifluoromethyl)benzyl]oxy}phenyl)-2-piperazin-1-ylethyl]cyclohexanol dihydrochloride

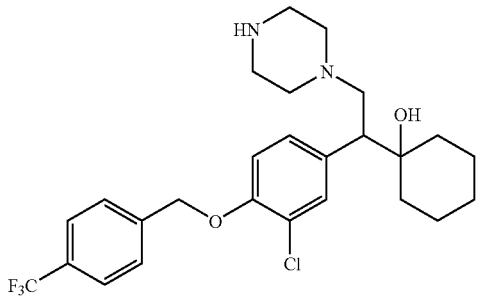

In an analogous manner to Example 400, step 1 tert-butyl 4-[(3-chloro-4-hydroxyphenyl)(1-hydroxycyclohexyl)acetyl]piperazine-1-carboxylate was prepared from tert-butyl 4-[[4-(benzyloxy)-3-chlorophenyl](1-hydroxycyclohexyl)acetyl]piperazine-1-carboxylate (See Example 292, step 1).

In an analogous manner to Example 402, step 1 tert-butyl 4-[(3-chloro-4-{[4-(trifluoromethyl)benzyl]oxy}phenyl)(1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate and 4-trifluoromethylbenzyl bromide. MS m/z 611.

In an analogous manner to Example 1, step 2 1-[1-(3-chloro-4-{[4-(trifluoromethyl)benzyl]oxy}phenyl)-2-piperazin-1-ylethyl]cyclohexanol dihydrochloride was prepared from tert-butyl 4-[(3-chloro-4-{[4-(trifluoromethyl)benzyl]oxy}phenyl)(1-hydroxycyclohexyl)acetyl]piperazine-1-carboxylate. MS (ESI) m/z 497; HRMS: calcd for C26H32ClF3N2O2+H+, 497.21771; found (ESI, [M+H]+), 497.2176.

Example 420

1-[1-(3-chloro-4-{[4-(trifluoromethyl)benzyl]oxy}phenyl)-2-(4-methylpiperazin-1-yl)ethyl]cyclohexanol dihydrochloride

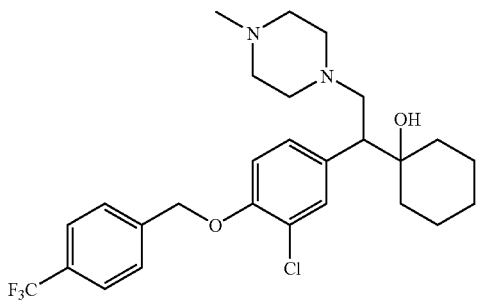

In an analogous manner to Example 24, 1-[1-(3-chloro-4-{[4-(trifluoromethyl)benzyl]oxy}phenyl)-2-(4-methylpiperazin-1-yl)ethyl]cyclohexanol dihydrochloride was prepared from 1-[1-(3-chloro-4-{[4-(trifluoromethyl)benzyl]oxy}phenyl)-2-piperazin-1-ylethyl]cyclohexanol dihydrochloride (See Example 419). MS (ESI) m/z 511.

Example 421

1-[1-(3-chloro-4-{[2-(trifluoromethyl)benzyl]oxy}phenyl)-2-piperazin-1-ylethyl]cyclohexanol dihydrochloride

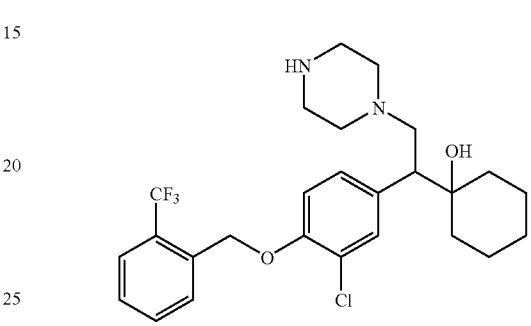

In an analogous manner to Example 402, step 1 tert-butyl 4-[(3-chloro-4-{[2-(trifluoromethyl)benzyl]oxy}phenyl)(1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate (See Example 419) and 2-trifluoromethylbenzyl bromide. MS (ESI) m/z 611.

In an analogous manner to Example 1, step 2 1-[1-(3-chloro-4-{[2-(trifluoromethyl)benzyl]oxy}phenyl)-2-piperazin-1-ylethyl]cyclohexanol dihydrochloride was prepared from tert-butyl 4-[(3-chloro-4-{[2-(trifluoromethyl)benzyl]oxy}phenyl)(1-hydroxycyclohexyl)acetyl]piperazine-1-carboxylate. MS (ESI) m/z 497; HRMS: calcd for C26H32ClF3N2O2+H+, 497.21771; found (ESI, [M+H]+), 497.22.

Example 422

1-[1-(3-chloro-4-{[2-(trifluoromethyl)benzyl]oxy}phenyl)-2-(4-methylpiperazin-1-yl)ethyl]cyclohexanol dihydrochloride

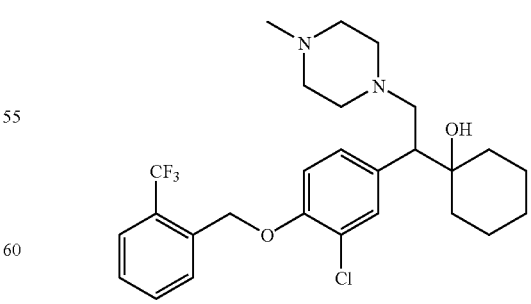

In an analogous manner to Example 24, 1-[1-(3-chloro-4-{[2-(trifluoromethyl)benzyl]oxy}phenyl)-2-(4-methylpiperazin-1-yl)ethyl]cyclohexanol dihydrochloride was prepared from 1-[1-(3-chloro-4-{[2-(trifluoromethyl)benzyl]

oxy}phenyl)-2-piperazin-1-ylethyl]cyclohexanol dihydrochloride (See Example 421). MS (ESI) m/z 511; HRMS: calcd for C27H34ClF3N2O2+H+, 511.23336; found (ESI, [M+H]+), 511.2314.

Example 423

1-[1-(3-chloro-4-{[3-(trifluoromethyl)benzyl]oxy}phenyl)-2-piperazin-1-ylethyl]cyclohexanol dihydrochloride

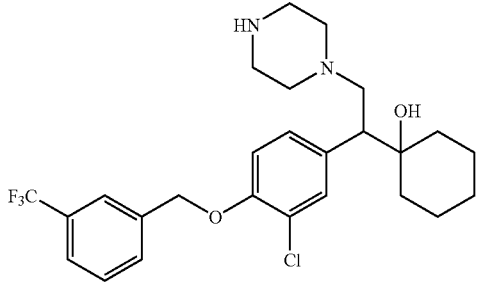

In an analogous manner to Example 402, step 1 tert-butyl 4-[(3-chloro-4-{[3-(trifluoromethyl)benzyl]oxy}phenyl)(1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate (See Example 419) and 3-trifluoromethylbenzyl bromide.

In an analogous manner to Example 1, step 2 1-[1-(3-chloro-4-{[3-(trifluoromethyl)benzyl]oxy}phenyl)-2-piperazin-1-ylethyl]cyclohexanol dihydrochloride was prepared from tert-butyl 4-[(3-chloro-4-{[3-(trifluoromethyl)benzyl]oxy}phenyl)(1-hydroxycyclohexyl)acetyl]piperazine-1-carboxylate. HRMS: calcd for C26H32ClF3N2O2+H+, 497.21771; found (ESI, [M+H]+), 497.2203.

Example 424

1-[1-(3-chloro-4-{[3-(trifluoromethyl)benzyl]oxy}phenyl)-2-(4-methylpiperazin-1-yl)ethyl]cyclohexanol dihydrochloride

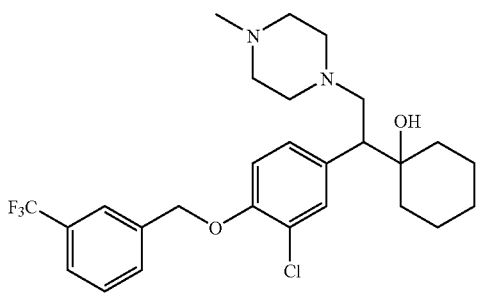

In an analogous manner to Example 24, 1-[1-(3-chloro-4-{[3-(trifluoromethyl)benzyl]oxy}phenyl)-2-(4-methylpiperazin-1-yl)ethyl]cyclohexanol dihydrochloride was prepared from 1-[1-(3-chloro-4-{[3-(trifluoromethyl)benzyl]oxy}phenyl)-2-piperazin-1-ylethyl]cyclohexanol dihydrochloride (See Example 423). MS (ESI) m/z 511; HRMS: calcd for C27H34ClF3N2O2+H+, 511.23336; found (ESI, [M+H]+), 511.231.

Example 425

1-(1-{4-[(4-bromo-2-fluorobenzyl)oxy]-3-chlorophenyl}-2-piperazin-1-ylethyl)cyclohexanol dihydrochloride

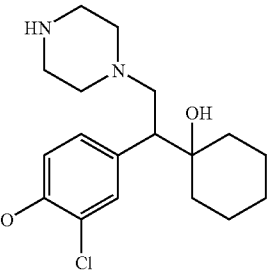

In an analogous manner to Example 402, step 1 tert-butyl 4-{[4-[(4-bromo-2-fluorobenzyl)oxy]-3-chlorophenyl}(1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate (See Example 419) and 4-bromo-2-fluorobenzyl bromide. MS (ESI) m/z 639.

In an analogous manner to Example 1, step 2 1-(1-{4-[(4-bromo-2-fluorobenzyl)oxy]-3-chlorophenyl}-2-piperazin-1-ylethyl)cyclohexanol dihydrochloride was prepared from tert-butyl 4-{{4-[(4-bromo-2-fluorobenzyl)oxy]-3-chlorophenyl}(1-hydroxycyclohexyl)acetyl]piperazine-1-carboxylate. MS (ESI) m/z 525; HRMS: calcd for C25H31BrClFN2O2+H+, 525.13142; found (ESI, [M+H]+), 525.1335.

Example 426

1-[1-{4-[(4-bromo-2-fluorobenzyl)oxy]-3-chlorophenyl}-2-(4-methylpiperazin-1-yl)ethyl]cyclohexanol dihydrochloride

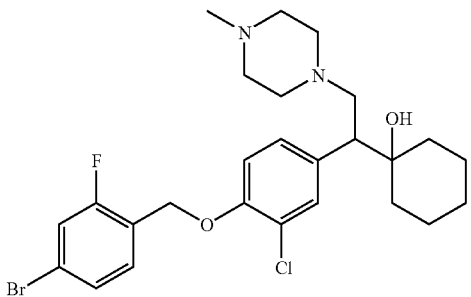

In an analogous manner to Example 24, 1-[1-{4-[(4-bromo-2-fluorobenzyl)oxy]-3-chlorophenyl}-2-(4-methylpiperazin-1-yl)ethyl]cyclohexanol was prepared from 1-(1-{4-[(4-bromo-2-fluorobenzyl)oxy]-3-chlorophenyl}-2-piperazin-1-ylethyl)cyclohexanol dihydrochloride (See Example 421). MS (ESI) m/z 539; HRMS: calcd for C26H33BrClFN2O2+H+, 539.14707; found (ESI, [M+H]+), 539.1453.

Example 427

1-{1-[3-chloro-4-(2-naphthylmethoxy)phenyl]-2-piperazin-1-ylethyl}cyclohexanol dihydrochloride

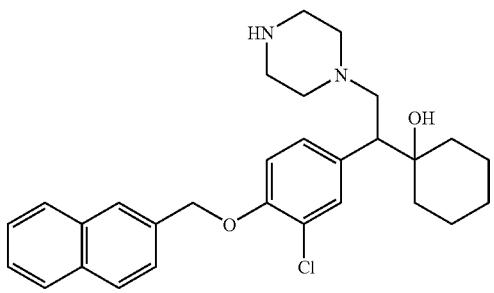

In an analogous manner to Example 402, step 1 tert-butyl {1-[[3-chloro-4-(2-naphthylmethoxy)phenyl](1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate (See Example 419) and 2-chloromethylnaphthalene. MS (ESI) m/z 639.

In an analogous manner to Example 1, step 2 1-{1-[3-chloro-4-(2-naphthylmethoxy)phenyl]-2-piperazin-1-ylethyl}cyclohexanol dihydrochloride was prepared from tert-butyl {1-[[3-chloro-4-(2-naphthylmethoxy)phenyl](1-hydroxycyclohexyl)acetyl]piperazine-1-carboxylate. MS (ESI) m/z 479; HRMS: calcd for C29H35ClN2O2+H+, 479.24598; found (ESI, [M+H]+), 479.2481.

Example 428

1-{2-(4-aminopiperidin-1-yl)-1-[4-(benzyloxy)-3-chlorophenyl]ethyl}cyclohexanol dihydrochloride

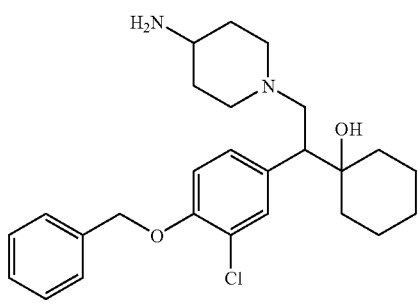

In an analogous manner to Example 1, step 1 tert-butyl {1-[[4-(benzyloxy)-3-chlorophenyl](1-hydroxycyclohexyl)acetyl]piperidin-4-yl}carbamate was prepared from [4-(benzyloxy)-3-chlorophenyl](1-hydroxycyclohexyl)acetic acid (Reference Example eee) and 4-N-boc-aminopiperidine. MS m/z 557; HRMS: calcd for C31H41ClN2O5+H+, 557.27768; found (ESI, [M+H]+), 557.2805.

In an analogous manner to Example 1, step 2 {2-(4-aminopiperidin-1-yl)-1-[4-(benzyloxy)-3-chlorophenyl]ethyl}cyclohexanol dihydrochloride was prepared from tert-butyl {1-[[4-(benzyloxy)-3-chlorophenyl](1-hydroxycyclohexyl)acetyl]piperidin-4-yl}carbamate. MS (ESI) m/z 443; HRMS: calcd for C26H35ClN2O2+H+, 443.24598; found (ESI, [M+H]+), 443.2461.

Example 429

1-{1-[4-(benzyloxy)-3-chlorophenyl]-2-[4-(dimethylamino)piperidin-1-yl]ethyl}cyclohexanol

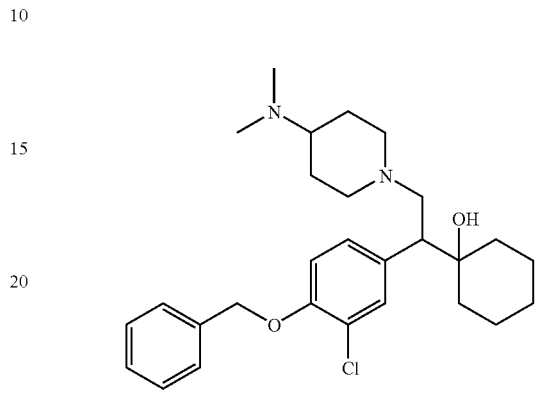

In an analogous manner to Example 361-{1-[4-(benzyloxy)-3-chlorophenyl]-2-[4-(dimethylamino)piperidin-1-yl]ethyl}cyclohexanol dihydrochloride was prepared from {2-(4-aminopiperidin-1-yl)-1-[4-(benzyloxy)-3-chlorophenyl]ethyl}cyclohexanol dihydrochloride (See Example 428). MS (ESI) m/z 471; HRMS: calcd for C28H39ClN2O2+H+, 471.27728; found (ESI, [M+H]+), 471.2786.

Example 430

1-{2-(4-aminopiperidin-1-yl)-1-[3-chloro-4-(2-naphthylmethoxy)phenyl]-ethyl}cyclohexanol dihydrochloride

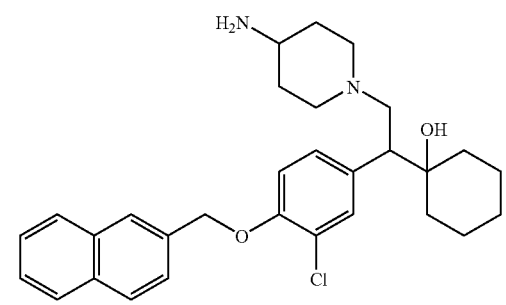

In an analogous manner to Example 400, step 1 tert-butyl {1-[(3-chloro-4-hydroxyphenyl)(1-hydroxycyclohexyl)acetyl]piperidin-4-yl}carbamate was prepared from tert-butyl {1-[[4-(benzyloxy)-3-chlorophenyl](1-hydroxycyclohexyl)acetyl]piperidin-4-yl}carbamate. (see Example 428). MS (ESI) m/z 467; MS (ESI) m/z 465.

In an analogous manner to Example 402, step 1 tert-butyl {1-[[3-chloro-4-(2-naphthylmethoxy)phenyl](1-hydroxycyclohexyl)acetyl]piperidin-4-yl}carbamate was prepared from tert-butyl {1-[(3-chloro-4-hydroxyphenyl)(1-hydroxycyclohexyl)acetyl]piperidin-4-yl}carbamate and 2-chloromethylnaphthalene. MS (ES) m/z 607.1.

In an analogous manner to Example 1, step 2 1-{2-(4-aminopiperidin-1-yl)-1-[3-chloro-4-(2-naphthylmethoxy)

phenyl]ethyl}cyclohexanol dihydrochloride was prepared from tert-butyl {1-[[3-chloro-4-(2-naphthylmethoxy)phenyl](1-hydroxycyclohexyl)acetyl]piperidin-4-yl}carbamate. MS (ESI) m/z 493; HRMS: calcd for C30H37ClN2O2+H+, 493.26163; found (ESI, [M+H]+), 493.2599.

Example 431

1-{1-[3-chloro-4-(2-naphthylmethoxy)phenyl]-2-[4-(dimethylamino)piperidin-1-yl]ethyl}cyclohexanol dihydrochloride

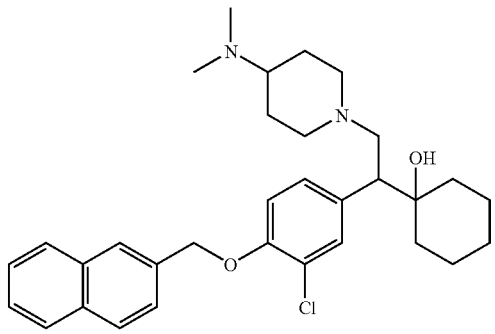

In an analogous manner to Example 36, 1-{1-[3-chloro-4-(2-naphthylmethoxy)phenyl]-2-[4-(dimethylamino)piperidin-1-yl]ethyl}cyclohexanol dihydrochloride was prepared from 1-{2-(4-aminopiperidin-1-yl)-1-[3-chloro-4-(2-naphthylmethoxy)phenyl]ethyl}cyclohexanol dihydrochloride (See Example 430). MS (ESI) m/z 521; HRMS: calcd for C32H41ClN2O2+H+, 521.29293; found (ESI, [M+H]+), 521.2932.

Example 432

1-{1-[4-(2-naphthylmethoxy)phenyl]-2-piperazin-1-ylethyl}cyclohexanol

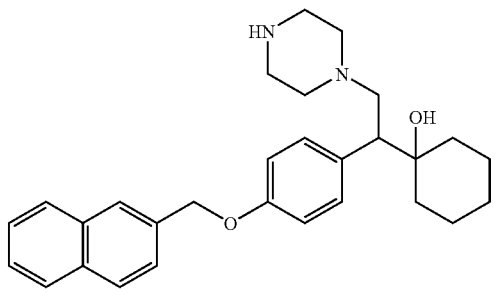

In an analogous manner to Example 400, step 1 tert-butyl 4-[(1-hydroxycyclohexyl)(4-hydroxyphenyl)acetyl]-piperazine-1-carboxylate was prepared from tert-butyl 4-[(1-hydroxycyclohexyl)(4-benzyloxyphenyl)acetyl]piperazine-1-carboxylate (see Example 27). MS (ES) m/z 417.1.

In an analogous manner to Example 402, step 1 tert-butyl 4-{(1-hydroxycyclohexyl)[4-(2-naphthylmethoxy)phenyl]acetyl}piperazine-1-carboxylate was prepared from tert-butyl 4-[(1-hydroxycyclohexyl)(4-hydroxyphenyl)acetyl]piperazine-1-carboxylate and 2-bromomethylnaphthalene. MS m/z 559.

In an analogous manner to Example 1, step 2, 1-{1-[4-(2-naphthylmethoxy)phenyl]-2-piperazin-1-ylethyl}cyclohexanol was prepared from tert-butyl 4-{(1-hydroxycyclohexyl)[4-(2-naphthylmethoxy)phenyl]acetyl}piperazine-1-carboxylate. MS (ES) m/z 445.1; HRMS: calcd for C29H36N2O2+H+, 445.28495; found (ESI, [M+H]+), 445.2838.

Example 433

1-{2-(4-methylpiperazin-1-yl)-1-[4-(2-naphthylmethoxy)phenyl]ethyl}cyclohexanol

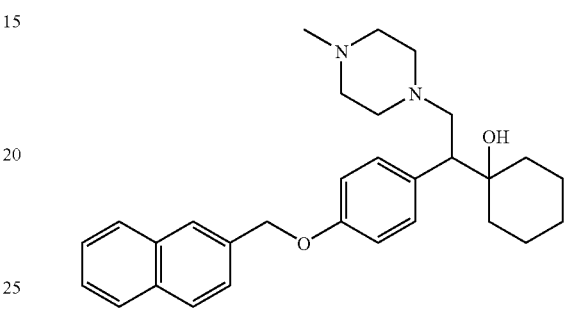

In an analogous manner to Example 24, 1-{2-(4-methylpiperazin-1-yl)-1-[4-(2-naphthylmethoxy)phenyl]ethyl}cyclohexanol was prepared from 1-{1-[4-(2-naphthylmethoxy)phenyl]-2-piperazin-1-ylethyl}cyclohexanol (see Example 432). MS (ES) m/z 459.1; HRMS: calcd for C30H38N2O2+H+, 459.30060; found (ESI, [M+H]+), 459.2996.

Example 434

1-(1-{4-[(4-bromo-2-fluorobenzyl)oxy]phenyl}-2-piperazin-1-ylethyl)cyclohexanol

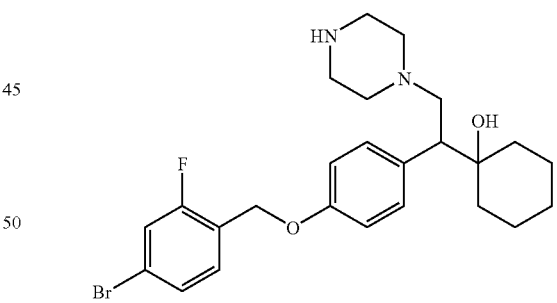

In an analogous manner to Example 402, step 1, tert-butyl 4-[{4-[(4-bromo-2-fluorobenzyl)oxy]phenyl}(1-hydroxycyclohexyl)acetyl]piperazine-1-carboxylate was prepared from tert-butyl 4-[(1-hydroxycyclohexyl)(4-hydroxyphenyl)acetyl]piperazine-1-carboxylate (see Example 432) and 4-bromo-2-fluorobenzyl bromide. MS (ES) m/z 605.0.

In an analogous manner to Example 1, step 2, 1-(1-{4-[(4-bromo-2-fluorobenzyl)oxy]phenyl}-2-piperazin-1-ylethyl)cyclohexanol was prepared from tert-butyl 4-[{4-[(4-bromo-2-fluorobenzyl)oxy]phenyl}(1-hydroxycyclohexyl)acetyl]piperazine-1-carboxylate. MS (ESI) m/z 491; HRMS: calcd for C25H32BrFN2O2+H+, 491.17039; found (ESI, [M+H]+), 491.1695.

Example 435

1-[1-{4-[(4-bromo-2-fluorobenzyl)oxy]phenyl}-2-(4-methylpiperazin-1-yl)ethyl]cyclohexanol dihydrochloride

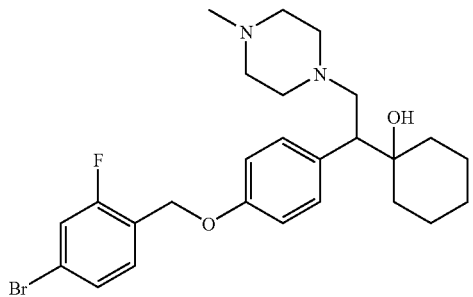

In an analogous manner to Example 24, 1-[1-{4-[(4-bromo-2-fluorobenzyl)oxy]phenyl}-2-(4-methylpiperazin-1-yl)ethyl]cyclohexanol dihydrochloride was prepared from 1-(1-{4-[(4-bromo-2-fluorobenzyl)oxy]phenyl}-2-piperazin-1-ylethyl)cyclohexanol (see Example 434). MS (ES) m/z 505.0; HRMS: calcd for $C_{26}H_{34}BrFN_2O_2$+H+, 505.18604; found (ESI, [M+H]$^+$), 505.1839.

Example 436

1-[2-piperazin-1-yl-1-(4-{[4-(trifluoromethyl)benzyl]oxy}phenyl)ethyl]cyclohexanol dihydrochloride

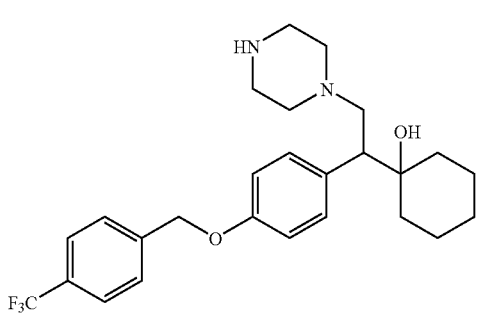

In an analogous manner to Example 402, step 1 tert-butyl 4-[(1-hydroxycyclohexyl)(4-{[4-(trifluoromethyl)benzyl]oxy}phenyl)acetyl]piperazine-1-carboxylate was prepared from tert-butyl 4-[(1-hydroxycyclohexyl)(4-hydroxyphenyl)acetyl]piperazine-1-carboxylate (see Example 432) and 4-trifluoromethylbenzyl bromide. MS (ES) m/z 577.0.

In an analogous manner to Example 1, step 2, 1-[2-piperazin-1-yl-1-(4-{[4-(trifluoromethyl)benzyl]oxy}phenyl)ethyl]cyclohexanol dihydrochloride was prepared from tert-butyl 4-[(1-hydroxycyclohexyl)(4-{[4-(trifluoromethyl)benzyl]oxy}phenyl)acetyl]piperazine-1-carboxylate. MS (ESI) m/z 463.

Example 437

1-[2-(4-methylpiperazin-1-yl)-1-(4-{[4-(trifluoromethyl)benzyl]oxy}phenyl)ethyl]cyclohexanol dihydrochloride

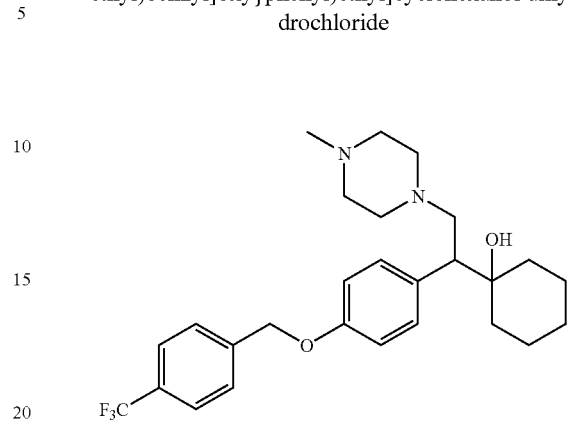

In an analogous manner to Example 24, 1-[2-(4-methylpiperazin-1-yl)-1-(4-{[4-(trifluoromethyl)benzyl]oxy}phenyl)ethyl]cyclohexanol dihydrochloride was prepared from 1-[2-piperazin-1-yl-1-(4-{[4-(trifluoromethyl)benzyl]oxy}phenyl)ethyl]cyclohexanol (see Example 436). MS (ESI) m/z 477; HRMS: calcd for $C_{27}H_{35}F_3N_2O_2$+H+, 477.27234; found (ESI, [M+H]$^+$), 477.2702.

Example 438

1-[2-piperazin-1-yl-1-(4-{[3-(trifluoromethyl)benzyl]oxy}phenyl)ethyl]cyclohexanol dihydrochloride

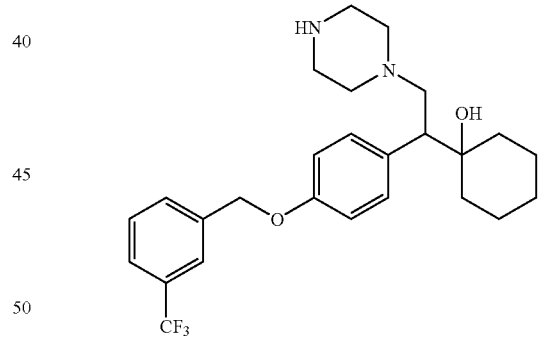

In an analogous manner to Example 402, step 1, tert-butyl 4-[(1-hydroxycyclohexyl)(4-{[3-(trifluoromethyl)benzyl]oxy}phenyl)acetyl]piperazine-1-carboxylate was prepared from tert-butyl 4-[(1-hydroxycyclohexyl)(4-hydroxyphenyl)acetyl]piperazine-1-carboxylate (see Example 432) and 4-trifluoromethylbenzyl bromide. MS (ESI) m/z 577.

In an analogous manner to Example 1, step 2 1-[2-piperazin-1-yl-1-(4-{[3-(trifluoromethyl)benzyl]oxy}phenyl)ethyl]cyclohexanol dihydrochloride was prepared from tert-butyl 4-[(1-hydroxycyclohexyl)(4-{[3-(trifluoromethyl)benzyl]oxy}phenyl)acetyl]piperazine-1-carboxylate. MS (ESI) m/z 463; HRMS: calcd for $C_{26}H_{33}F_3N_2O_2$+H+, 463.25669; found (ESI, [M+H]$^+$), 463.2576.

Example 439

1-[2-(4-methylpiperazin-1-yl)-1-(4-{[3-(trifluoromethyl)benzyl]oxy}phenyl)ethyl]cyclohexanol dihydrochloride

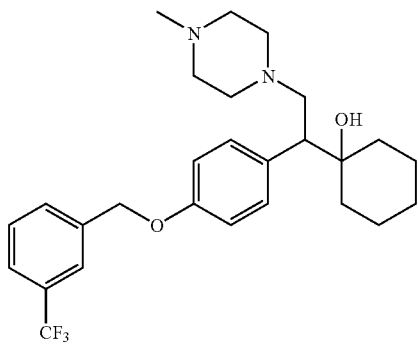

In an analogous manner to Example 24, 1-[2-(4-methylpiperazin-1-yl)-1-(4-{[3-(trifluoromethyl)benzyl]oxy}phenyl)ethyl]cyclohexanol dihydrochloride was prepared from 1-[2-piperazin-1-yl-1-(4-{[3-(trifluoromethyl)benzyl]oxy}phenyl)ethyl]cyclohexanol (see Example 438). MS (ESI) m/z 477; HRMS: calcd for $C_{27}H_{35}F_3N_2O_2$+H+, 477.27234; found (ESI, [M+H]$^+$), 477.2708.

Example 440

1-[2-piperazin-1-yl-1-(4-{[2-(trifluoromethyl)benzyl]oxy}phenyl)ethyl]cyclohexanol dihydrochloride

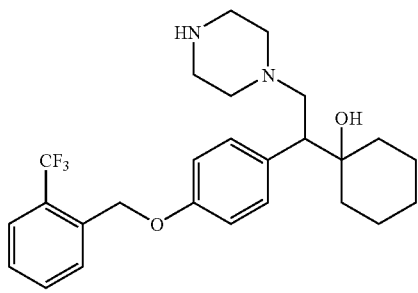

In an analogous manner to Example 402, step 1, tert-butyl 4-[(1-hydroxycyclohexyl)(4-{[2-(trifluoromethyl)benzyl]oxy}phenyl)acetyl]piperazine-1-carboxylate was prepared from tert-butyl 4-[(1-hydroxycyclohexyl)(4-hydroxyphenyl)acetyl]piperazine-1-carboxylate (see Example 432) and 1-bromomethyl-2-trifluoromethyl-benzene. MS (ESI) m/z 577.

In an analogous manner to Example 1, step 2, 1-[2-piperazin-1-yl-1-(4-{[2-(trifluoromethyl)benzyl]oxy}phenyl)ethyl]cyclohexanol dihydrochloride was prepared from tert-butyl 4-[(1-hydroxycyclohexyl)(4-{[2-(trifluoromethyl)benzyl]oxy}phenyl)acetyl]piperazine-1-carboxylate. MS (ES) m/z 463.3; HRMS: calcd for $C_{26}H_{33}F_3N_2O_2$+H+, 463.25669; found (ESI-FT/MS, [M+H]$^{1+}$), 463.2574.

Example 441

1-[2-(4-methylpiperazin-1-yl)-1-(4-{[2-(trifluoromethyl)benzyl]oxy}phenyl)ethyl]cyclohexanol dihydrochloride

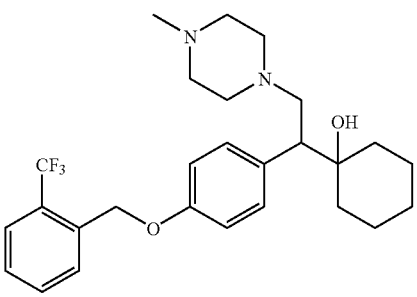

In an analogous manner to Example 24, 1-[2-(4-methylpiperazin-1-yl)-1-(4-{[2-(trifluoromethyl)benzyl]oxy}phenyl)ethyl]cyclohexanol dihydrochloride was prepared from 1-[2-piperazin-1-yl-1-(4-{[2-(trifluoromethyl)benzyl]oxy}phenyl)ethyl]cyclohexanol (see Example 440). MS (ESI) m/z 477; HRMS: calcd for $C_{27}H_{35}F_3N_2O_2$+H+, 477.27234; found (ESI, [M+H]$^+$), 477.2738.

Example 442

1-{1-[4-(benzyloxy)-3-methoxyphenyl]-2-piperazin-1-ylethyl}cyclohexanol dihydrochloride

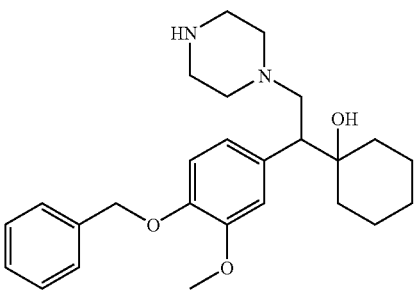

In an analogous manner to Example 1, step 1 tert-butyl 4-[[4-(benzyloxy)-3-methoxyphenyl](1-hydroxycyclohexyl)acetyl]piperazine-1-carboxylate was prepared from [4-(benzyloxy)-3-methoxyphenyl](1-hydroxycyclohexyl)acetic acid (Reference Example I-nnn) and tert-butyl 1-piperazinecarboxylate. MS (ES) m/z 539.1.

In an analogous manner to Example 1, step 2 1-{1-[4-(benzyloxy)-3-methoxyphenyl]-2-piperazin-1-ylethyl}cyclohexanol dihydrochloride was prepared from tert-butyl 4-[[4-(benzyloxy)-3-methoxyphenyl](1-hydroxycyclohexyl)acetyl]piperazine-1-carboxylate. MS (ES) m/z 425.2; HRMS: calcd for C26H36N2O3+H+, 425.27987; found (ESI, [M+H]+), 425.2805.

Example 443

1-[1-[4-(benzyloxy)-3-methoxyphenyl]-2-(4-methylpiperazin-1-yl)ethyl]cyclohexanol dihydrochloride

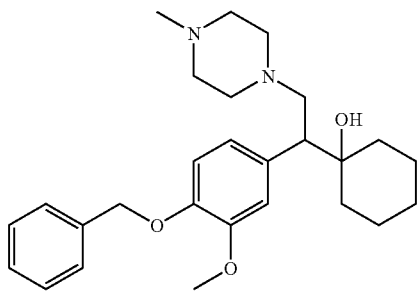

In an analogous manner to Example 24, 1-[1-[4-(benzyloxy)-3-methoxyphenyl]-2-(4-methylpiperazin-1-yl)ethyl]cyclohexanol dihydrochloride was prepared from 1-{1-[4-(benzyloxy)-3-methoxyphenyl]-2-piperazin-1-ylethyl}cyclohexanol (see Example 442). MS (ES) m/z 439.2; HRMS: calcd for C27H38N2O3+H+, 439.29552; found (ESI, [M+H]+), 439.2944.

Example 444

1-{1-[3-methoxy-4-(2-naphthylmethoxy)phenyl]-2-piperazin-1-ylethyl}cyclohexanol dihydrochloride

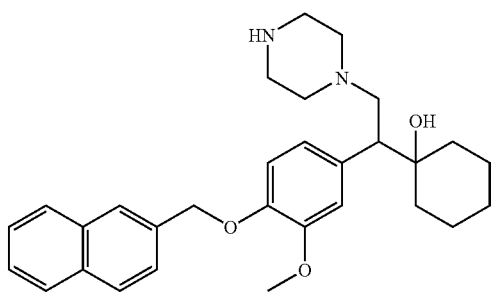

In an analogous manner to Example 400, step 1 tert-butyl 4-[(1-hydroxycyclohexyl)(4-hydroxy-3-methoxyphenyl)acetyl]piperazine-1-carboxylate was prepared from tert-butyl 4-[[4-(benzyloxy)-3-methoxyphenyl](1-hydroxycyclohexyl)acetyl]piperazine-1-carboxylate (see Example 442). MS (ES) m/z 447.0.

In an analogous manner to Example 402, step 1 tert-butyl 4-{(1-hydroxycyclohexyl)[3-methoxy-4-(2-naphthylmethoxy)phenyl]acetyl}piperazine-1-carboxylate was prepared tert-butyl 4-[(1-hydroxycyclohexyl)(4-hydroxy-3-methoxyphenyl)acetyl]piperazine-1-carboxylate and 2-bromomethylnaphthalene. MS (ES) m/z 589.1.

In an analogous manner to Example 1, step 2 1-{1-[3-methoxy-4-(2-naphthylmethoxy)phenyl]-2-piperazin-1-ylethyl}cyclohexanol dihydrochloride was prepared from tert-butyl 4-{(1-hydroxycyclohexyl)[3-methoxy-4-(2-naphthylmethoxy)phenyl]acetyl}piperazine-1-carboxylate. MS (ESI) m/z 475; HRMS: calcd for $C_{30}H_{38}N_2O_3$+H+, 475.29552; found (ESI, [M+H]$^+$), 475.2938.

Example 445

1-[1-[3-methoxy-4-(2-naphthylmethoxy)phenyl]-2-(4-methylpiperazin-1-yl)ethyl]cyclohexanol dihydrochloride

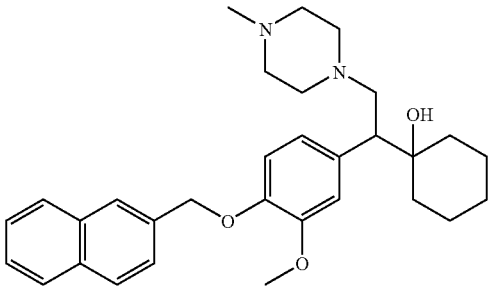

In an analogous manner to Example 24, 1-[1-[3-methoxy-4-(2-naphthylmethoxy)phenyl]-2-(4-methylpiperazin-1-yl)ethyl]cyclohexanol dihydrochloride was prepared from 1-{1-[3-methoxy-4-(2-naphthylmethoxy)phenyl]-2-piperazin-1-ylethyl}cyclohexanol (see Example 444). MS (ESI) m/z 489; HRMS: calcd for $C_{31}H_{40}N_2O_3$+H+, 489.31117; found (ESI, [M+H]$^+$), 489.3126.

Example 446

1-(1-{4-[(4-bromo-2-fluorobenzyl)oxy]-3-methoxyphenyl}-2-piperazin-1-ylethyl)cyclohexanol

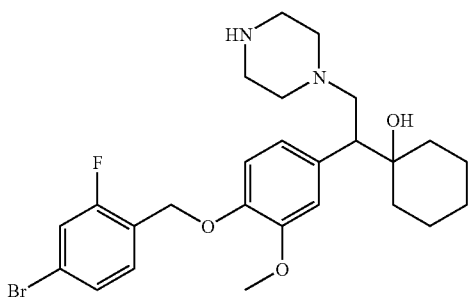

In an analogous manner to Example 402, step 1 tert-butyl 4-[{4-[(4-bromo-2-fluorobenzyl)oxy]-3-methoxyphenyl}(1-hydroxycyclohexyl)acetyl]piperazine-1-carboxylate was prepared tert-butyl 4-[(1-hydroxycyclohexyl)(4-hydroxy-3-methoxyphenyl)acetyl]piperazine-1-carboxylate (see Example 444) and 4-bromo-2-fluorobenzyl bromide. MS (ESI) m/z 635.

In an analogous manner to Example 1, step 2 1-(1-{4-[(4-bromo-2-fluorobenzyl)oxy]-3-methoxyphenyl}-2-piperazin-1-ylethyl)cyclohexanol was prepared from tert-butyl 4-[{4-[(4-bromo-2-fluorobenzyl)oxy]-3-methoxyphenyl}(1-hydroxycyclohexyl)acetyl]piperazine-1-carboxylate. MS (ES) m/z 521.0; HRMS: calcd for $C_{26}H_{34}BrFN_2O_3$+H+, 521.18096; found (ESI, [M+H]+), 521.1846.

Example 447

1-[1-{4-[(4-bromo-2-fluorobenzyl)oxy]-3-methoxyphenyl}-2-(4-methylpiperazin-1-yl)ethyl]cyclohexanol

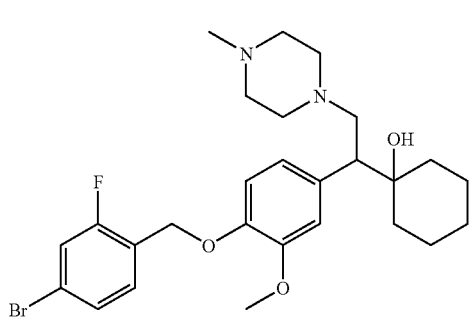

In an analogous manner to Example 24, 1-[1-{4-[(4-bromo-2-fluorobenzyl)oxy]-3-methoxyphenyl}-2-(4-methylpiperazin-1-yl)ethyl]cyclohexanol was prepared from 1-(1-{4-[(4-bromo-2-fluorobenzyl)oxy]-3-methoxyphenyl}-2-piperazin-1-ylethyl)cyclohexanol (see Example 446). MS (ES) m/z 534.9; HRMS: calcd for $C_{27}H_{36}BrFN_2O_3$+H+, 535.19661; found (ESI, [M+H]+), 535.196.

Example 448

1-[1-(3-methoxy-4-{[4-(trifluoromethyl)benzyl]oxy}phenyl)-2-piperazin-1-ylethyl]cyclohexanol dihydrochloride

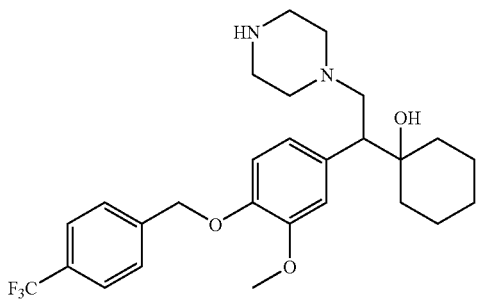

In an analogous manner to Example 402, step 1 tert-butyl 4-[(1-hydroxycyclohexyl)(3-methoxy-4-{[4-(trifluoromethyl)benzyl]oxy}phenyl)acetyl]piperazine-1-carboxylate was prepared tert-butyl 4-[(1-hydroxycyclohexyl)(4-hydroxy-3-methoxyphenyl)acetyl]piperazine-1-carboxylate (see Example 444) and 4-trifluoromethylbenzyl bromide. MS (ES) m/z 607.0.

In an analogous manner to Example 1, step 2 1-[1-(3-methoxy-4-{[4-(trifluoromethyl)benzyl]oxy}phenyl)-2-piperazin-1-ylethyl]cyclohexanol dihydrochloride was prepared from tert-butyl 4-[(1-hydroxycyclohexyl)(3-methoxy-4-{[4-(trifluoromethyl)benzyl]oxy}phenyl)acetyl]piperazine-1-carboxylate. MS (ESI) m/z 493; HRMS: calcd for $C_{27}H_{35}F_3N_2O_3$+H+, 493.26725; found (ESI, [M+H]+), 493.2701.

Example 449

1-[1-(3-methoxy-4-{[4-(trifluoromethyl)benzyl]oxy}phenyl)-2-(4-methylpiperazin-1-yl)ethyl]cyclohexanol dihydrochloride

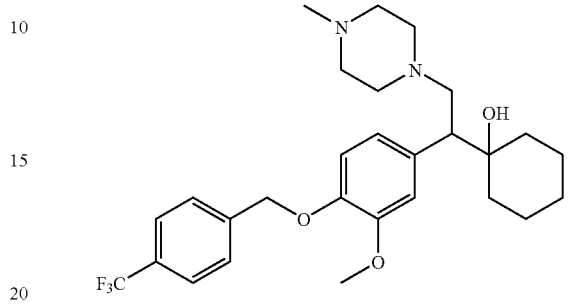

In an analogous manner to Example 24, 1-[1-(3-methoxy-4-{[4-(trifluoromethyl)benzyl]oxy}phenyl)-2-(4-methylpiperazin-1-yl)ethyl]cyclohexanol dihydrochloride was prepared from 1-[1-(3-methoxy-4-{[4-(trifluoromethyl)benzyl]oxy}phenyl)-2-piperazin-1-ylethyl]cyclohexanol (see Example 448). MS (ESI) m/z 507; HRMS: calcd for $C_{28}H_{37}F_3N_2O_3$+H+, 507.28290; found (ESI, [M+H]+), 507.2808.

Example 450

1-{2-(4-aminopiperidin-1-yl)-1-[4-(benzyloxy)-3-methoxyphenyl]ethyl}cyclohexanol dihydrochloride

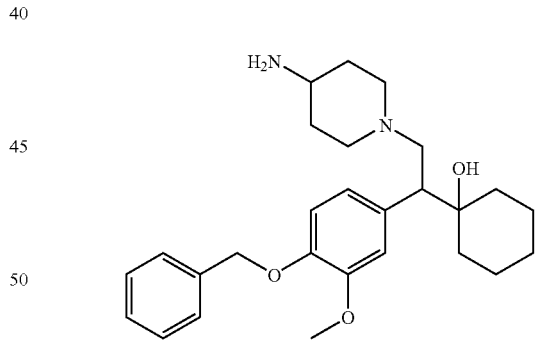

In an analogous manner to Example 1, step 1 tert-butyl {1-[2-(4-benzyloxy-3-methoxyphenyl)-2-(1-hydroxycyclohexyl)acetyl]piperidin-4-yl}carbamate was prepared from [4-(benzyloxy)-3-methoxyphenyl](1-hydroxycyclohexyl)acetic acid (Reference Example nnn) and 4-N-boc-aminopiperidine. MS (ES) m/z 553.2.

In an analogous manner to Example 1, step 2 1-{2-(4-aminopiperidin-1-yl)-1-[4-(benzyloxy)-3-methoxyphenyl]ethyl}cyclohexanol dihydrochloride was prepared from {1-[2-(4-Benzyloxy-3-methoxy-phenyl)-2-(1-hydroxycyclohexyl)-acetyl]-piperidin-4-yl}-carbamic acid tert-butyl ester. MS (ES) m/z 439.2.

Example 451

1-{1-[4-(benzyloxy)-3-methoxyphenyl]-2-[4-(dimethylamino)piperidin-1-yl]ethyl}cyclohexanol dihydrochloride

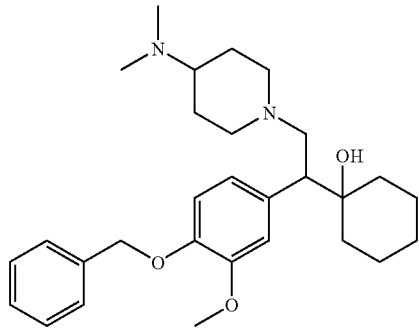

In an analogous manner to Example 36, 1-{1-[4-(benzyloxy)-3-methoxyphenyl]-2-[4-(dimethylamino)piperidin-1-yl]ethyl}cyclohexanol dihydrochloride was prepared from 1-{2-(4-aminopiperidin-1-yl)-1-[4-(benzyloxy)-3-methoxyphenyl]ethyl}cyclohexanol (see Example 450). MS (ES) m/z 467.1.

Example 452

1-{1-[3-chloro-4-(2-phenylethoxy)phenyl]-2-piperazin-1-ylethyl}cyclohexanol dihydrochloride

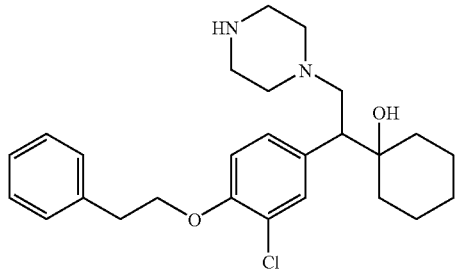

In an analogous manner to Example 402, step tert-butyl 4-[[3-chloro-4-(2-phenylethoxy)phenyl](1-hydroxycyclohexyl)acetyl]piperazine-1-carboxylate was prepared from tert-butyl 4-[(3-chloro-4-hydroxyphenyl)(1-hydroxycyclohexyl)acetyl]piperazine-1-carboxylate (See Example 419) and 2-phenylethyl bromide. MS (ESI) m/z 557.

In an analogous manner to Example 1 step 2 1-{1-[3-chloro-4-(2-phenylethoxy)phenyl]-2-piperazin-1-ylethyl}cyclohexanol dihydrochloride was prepared from tert-butyl 4-[[3-chloro-4-(2-phenylethoxy)phenyl](1-hydroxycyclohexyl)acetyl]piperazine-1-carboxylate. MS (ESI) m/z 443; HRMS: calcd for $C_{26}H_{35}ClN_2O_2$, 442.23870; found (ESI, $[H+M]^+$), 443.2483.

Example 453

1-[1-[3-chloro-4-(2-phenylethoxy)phenyl]-2-(4-methylpiperazin-1-yl)ethyl]cyclohexanol dihydrochloride

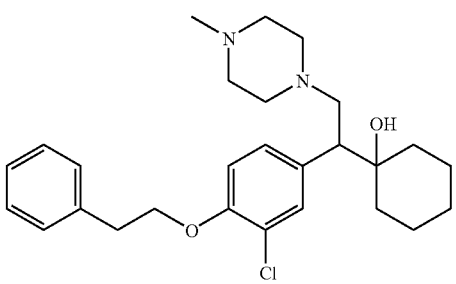

In an analogous manner to Example 24, 1-[1-[3-chloro-4-(2-phenylethoxy)phenyl]-2-(4-methylpiperazin-1-yl)ethyl]cyclohexanol dihydrochloride was prepared from 1-{1-[3-chloro-4-(2-phenylethoxy)phenyl]-2-piperazin-1-ylethyl}cyclohexanol (see Example 451). HRMS: calcd for $C_{27}H_{37}ClN_2O_2$, 456.25435; found (ESI, $[H+M]^+$), 457.2629.

Example 454

1-(1-{3-chloro-4-[(3-methoxybenzyl)oxy]phenyl}-2-piperazin-1-ylethyl)cyclohexanol dihydrochloride

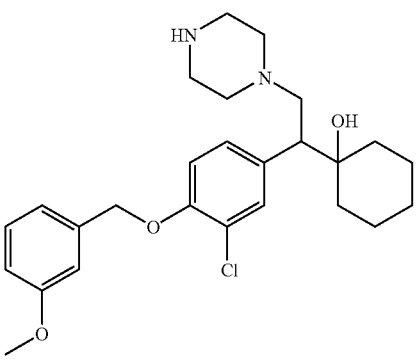

In an analogous manner to Example 1, step 1, tert-butyl 4-{[3-chloro-4-[(3-methoxybenzyl)oxy]phenyl](1-hydroxycyclohexyl)acetyl]piperazine-1-carboxylate was prepared from [3-chloro-4-(3-methoxy-benzyloxy)-phenyl]-(1-hydroxy-cyclohexyl)-acetic acid (Reference Example I-ooo) and tert-butyl 1-piperazinecarboxylate. MS (ESI) m/z 573.

In an analogous manner to Example 1, step 2 1-(1-{3-chloro-4-[(3-methoxybenzyl)oxy]phenyl}-2-piperazin-1-ylethyl)cyclohexanol dihydrochloride was prepared from tert-butyl 4-[{3-chloro-4-[(3-methoxybenzyl)oxy]phenyl}(1-hydroxycyclohexyl)acetyl]piperazine-1-carboxylate. MS (ESI) m/z 459.

Example 455

1-[1-{3-chloro-4-[(3-methoxybenzyl)oxy]phenyl}-2-(4-methylpiperazin-1-yl)ethyl]cyclohexanol dihydrochloride

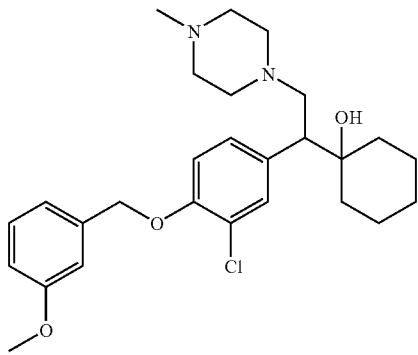

In an analogous manner to Example 24, 1-[1-{3-chloro-4-[(3-methoxybenzyl)oxy]phenyl}-2-(4-methylpiperazin-1-yl)ethyl]cyclohexanol dihydrochloride was prepared from 1-(1-{3-chloro-4-[(3-methoxybenzyl)oxy]phenyl}-2-piperazin-1-ylethyl)cyclohexanol (see Example 454). MS (ESI) m/z 473; HRMS: calcd for $C_{27}H_{37}ClN_2O_3$+H+, 473.25655; found (ESI, [M+H]+), 473.259.

Example 456

1-(1-{3-chloro-4-[(2-methoxybenzyl)oxy]phenyl}-2-piperazin-1-ylethyl)cyclohexanol dihydrochloride

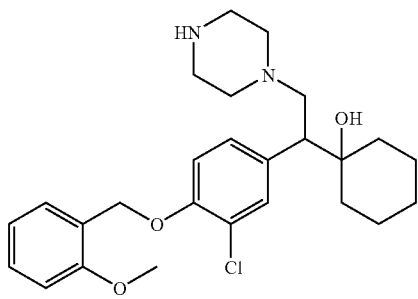

In an analogous manner to Example 1, step 1 tert-butyl 4-{[3-chloro-4-[(2-methoxybenzyl)oxy]phenyl}(1-hydroxycyclohexyl)acetyl]piperazine-1-carboxylate was prepared from [3-Chloro-4-(2-methoxy-benzyloxy)-phenyl]-(1-hydroxy-cyclohexyl)-acetic acid (see Reference Example 1-ppp) and tert-butyl 1-piperazinecarboxylate. MS (ESI) m/z 573.

In an analogous manner to Example 1, step 2 1-(1-{3-chloro-4-[(2-methoxybenzyl)oxy]phenyl}-2-piperazin-1-ylethyl)cyclohexanol dihydrochloride was prepared from tert-butyl 4-{[3-chloro-4-[(2-methoxybenzyl)oxy]phenyl}(1-hydroxycyclohexyl)acetyl]piperazine-1-carboxylate. MS (ESI) m/z 459; HRMS: calcd for $C_{26}H_{35}ClN_2O_3$+H+, 459.24090; found (ESI, [M+H]+), 459.2444.

Example 457

1-[1-{3-chloro-4-[(2-methoxybenzyl)oxy]phenyl}-2-(4-methylpiperazin-1-yl)ethyl]cyclohexanol dihydrochloride

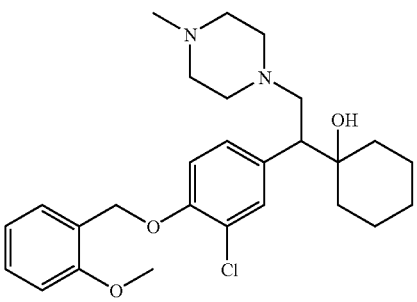

In an analogous manner to Example 24, 1-[1-{3-chloro-4-[(2-methoxybenzyl)oxy]phenyl}-2-(4-methylpiperazin-1-yl)ethyl]cyclohexanol dihydrochloride was prepared from 1-(1-{3-chloro-4-[(2-methoxybenzyl)oxy]phenyl}-2-piperazin-1-ylethyl)cyclohexanol (see Example 456). MS (ES) m/z 473.3; HRMS: calcd for $C_{27}H_{37}ClN_2O_3$+H+, 473.25655; found (ESI, [M+H]+), 473.2582.

Example 458

1-[2-(1,4'-bipiperidin-1'-yl)-1-(3-chloro-4-methoxyphenyl)ethyl]cyclohexanol dihydrochloride

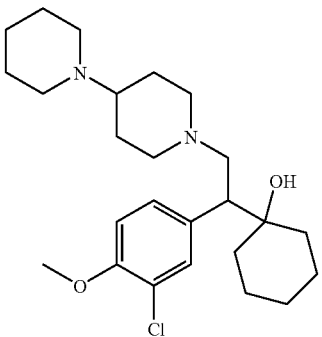

In an analogous manner to Example 1, step 1 1-[2-(1,4'-bipiperidin-1'-yl)-1-(3-chloro-4-methoxyphenyl)-2-oxoethyl]cyclohexanol was prepared from (3-chloro-4-methoxyphenyl)-1(1-hydroxycyclohexyl)acetic acid (Reference Example 1-ttt) and 4-piperidinopiperidine. MS (ESI) m/z 449 ([M+H]+).

In an analogous manner to Example 1, step 2 1-[2-(1,4'-bipiperidin-1'-yl)-1-(3-chloro-4-methoxyphenyl)ethyl]cyclohexanol dihydrochloride was prepared from 1-[1,4']bipiperidinyl-1'-yl-2-(3-chloro-4-methoxyphenyl)-2-(1-

Example 459

1-{1-[4-(2-phenylethoxy)phenyl]-2-piperazin-1-ylethyl}cyclohexanol dihydrochloride

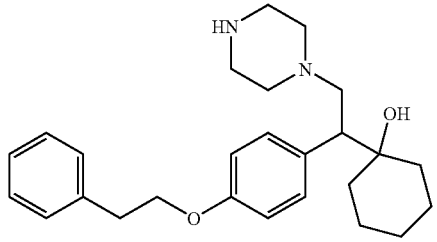

In an analogous manner to Example 1, step 1 tert-butyl 4-[(1-hydroxycyclohexyl)(4-(2-phenylethoxy)phenyl)acetyl]piperazine-1-carboxylate was prepared from 1-hydroxycyclohexyl)-(4-phenethyloxyphenyl)acetic acid (Reference Example 1-uuu) and tert-butyl 1-piperazinecarboxylate. MS (ESI) m/z 523 ([M+H]$^+$).

In an analogous manner to Example 1, step 2 1-{1-[4-(2-phenylethoxy)phenyl]-2-piperazin-1-ylethyl}cyclohexanol dihydrochloride was prepared from tert-butyl 4-[(1-hydroxycyclohexyl)(4-(2-phenylethoxy)phenyl)acetyl]piperazine-1-carboxylate.

Example 460

1-{2-(4-methylpiperazin-1-yl)-1-[4-(2-phenylethoxy)phenyl]ethyl}cyclohexanol dihydrochloride

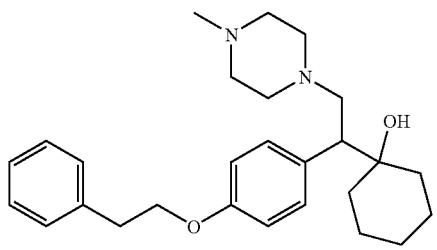

In an analogous manner to Example 24, 1-{2-(4-methylpiperazin-1-yl)-1-[4-(2-phenylethoxy)phenyl]ethyl}cyclohexanol dihydrochloride was prepared from 1-{1-[4-(2-phenylethoxy)phenyl]-2-piperazin-1-ylethyl}cyclohexanol (see Example 459). MS (APCI) m/z 423.

Example 461

1-{2-(1,4'-bipiperidin-1'-yl)-1-[4-(2-phenylethoxy)phenyl]ethyl}cyclohexanol dihydrochloride

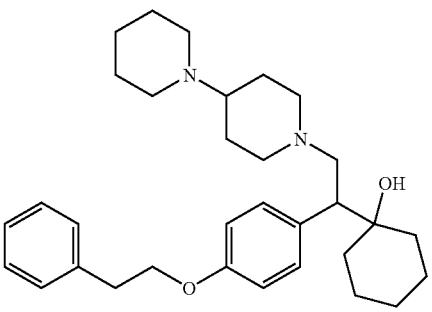

In an analogous manner to Example 1, step 1 1-[2-(1,4'-bipiperidin-1'-yl)-1-[4-(2-phenylethoxy)phenyl]-2-oxoethyl]cyclohexanol was prepared from 1-hydroxycyclohexyl)-(4-phenethyloxyphenyl)acetic acid (Reference Example 1-uuu) and 4-piperidinopiperidine. MS (ESI) m/z 505 ([M+H]$^+$).

In an analogous manner to Example 1, step 2 1-{2-(1,4'-bipiperidin-1'-yl)-1-[4-(2-phenylethoxy)phenyl]ethyl}cyclohexanol dihydrochloride was prepared from 1-{2-(1,4'-bipiperidin-1'-yl)-1-[4-(2-phenylethoxy)phenyl]-2-oxoethyl}cyclohexanol. MS (ESI) m/z 491.

Example 462

1-(1-{4-[2-(4-fluorophenyl)ethoxy]phenyl}-2-piperazin-1-ylethyl)cyclohexanol dihydrochloride

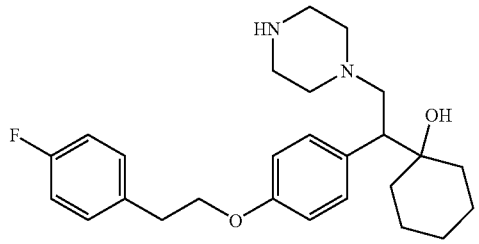

In an analogous manner to Example 1, step 1 tert-butyl 4-[(1-hydroxycyclohexyl{4-[2-(4-fluorophenyl)ethoxy]phenyl}acetyl]piperazine-1-carboxylate was prepared from {4-[2-(4-Fluoro-phenyl)-ethoxy]-phenyl}-(1-hydroxy-cyclohexyl)-acetic acid (Reference Example 1-vvv) and tert-butyl 1-piperazinecarboxylate. MS (ESI) m/z 541 ([M+H]$^+$).

In an analogous manner to Example 1, step 2 1-(1-{4-[2-(4-fluorophenyl)ethoxy]phenyl}-2-piperazin-1-ylethyl)cyclohexanol dihydrochloride was prepared from tert-butyl 4-[(1-hydroxycyclohexyl{4-[2-(4-fluorophenyl)ethoxy]phenyl}acetyl]piperazine-1-carboxylate. MS (ES) m/z 427.2.

Example 463

1-[1-{4-[2-(4-fluorophenyl)ethoxy]phenyl}-2-(4-methylpiperazin-1-yl)ethyl]cyclohexanol dihydrochloride

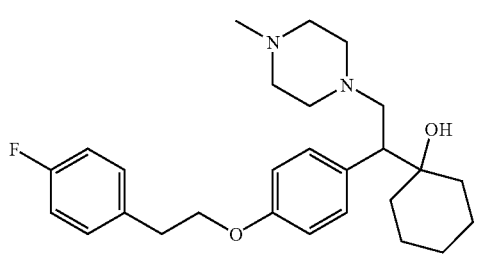

In an analogous manner to Example 24, 1-[1-{4-[2-(4-fluorophenyl)ethoxy]phenyl}-2-(4-methylpiperazin-1-yl)ethyl]cyclohexanol dihydrochloride was prepared from 1-(1-{4-[2-(4-fluorophenyl)ethoxy]phenyl}-2-piperazin-1-ylethyl)cyclohexanol (see Example 462). MS (ESI) m/z 441.

Example 464

1-(1-{4-[2-(1-naphthyl)ethoxy]phenyl}-2-piperazin-1-ylethyl)cyclohexanol dihydrochloride

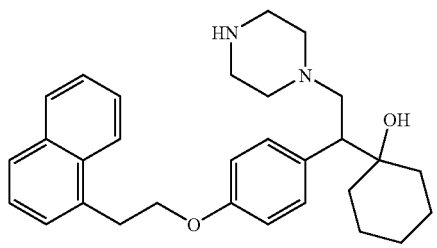

In an analogous manner to Example 1, step 1 tert-butyl 4-[(1-hydroxycyclohexyl{4-[2-(1-napthyl)ethoxy]phenyl}acetyl]piperazine-1-carboxylate was prepared from (1-hydroxy-cyclohexyl)-[4-(2-naphthalen-1-yl-ethoxy)-phenyl]-acetic acid (Reference Example 1-www) and tert-butyl 1-piperazinecarboxylate. MS (ESI) m/z 573 ([M+H]$^+$).

In an analogous manner to Example 1 step 2 1-(1-{4-[2-(1-naphthyl)ethoxy]phenyl}-2-piperazin-1-ylethyl)cyclohexanol dihydrochloride was prepared from 1 tert-butyl 4-[(1-hydroxycyclohexyl{4-[2-(1-nathyl)ethoxy]phenyl}acetyl]piperazine-1-carboxylate. MS (ESI) m/z 458 ([M+H]$^+$).

Example 465

1-(2-(4-methylpiperazin-1-yl)-1-{4-[2-(1-naphthyl)ethoxy]phenyl}ethyl)cyclohexanol dihydrochloride

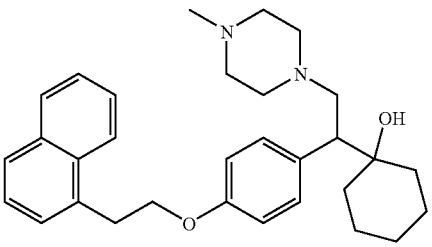

In an analogous manner to Example 24, 1-(2-(4-methylpiperazin-1-yl)-1-{4-[2-(1-naphthyl)ethoxy]phenyl}ethyl)cyclohexanol dihydrochloride was prepared from 1-(1-{4-[2-(1-naphthyl)ethoxy]phenyl}-2-piperazin-1-ylethyl)cyclohexanol (see Example 464). MS (ESI) m/z 473 ([M+H]$^+$).

Example 466

1-[1-{{4-[2-(4-methoxyphenyl)ethoxy]phenyl}-2-(4-methylpiperazin-1-yl)ethyl]cyclohexanol dihydrochloride

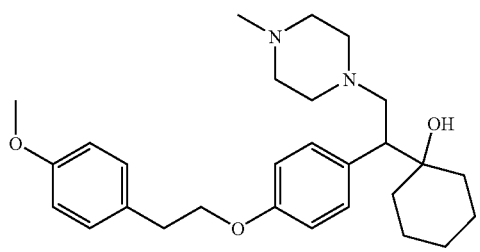

In an analogous manner to Example 1, step 1 1-[1-{{4-[2-(4-methoxyphenyl)ethoxy]phenyl}-2-(4-methylpiperazin-1-yl)acetyl]cyclohexanol was prepared from (1-hydroxy-cyclohexyl)-{4-[2-(4-methoxy-phenyl)-ethoxy]-phenyl}-acetic acid (Reference Example 1-xxx) and 1-methyl piperazine. MS (ESI) m/z 467 ([M+H]$^+$).

In an analogous manner to Example 1, step 2 1-[1-{{4-[2-(4-methoxyphenyl)ethoxy]phenyl}-2-(4-methylpiperazin-1-yl)ethyl]cyclohexanol dihydrochloride was prepared from 1-[1-{{4-[2-(4-methoxyphenyl)ethoxy]phenyl}-2-(4-methylpiperazin-1-yl)acetyl]cyclohexanol. MS (ESI) m/z 453 ([M+H]$^+$).

Example 467

1-(2-(1,4'-bipiperidin-1'-yl)-1-{4-[2-(4-methoxyphenyl)ethoxy]phenyl}ethyl)cyclohexanol dihydrochloride

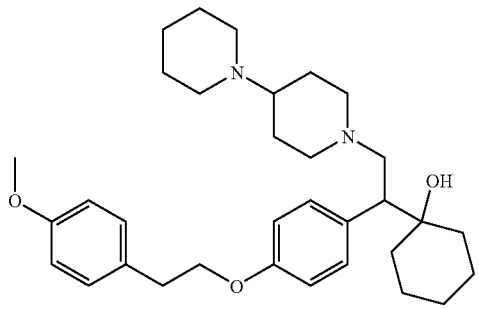

In an analogous manner to Example 1, step 1 1-(2-(1,4'-bipiperidin-1'-yl)-1-{4-[2-(4-methoxyphenyl)ethoxy]phenyl}-2-oxoethyl)cyclohexanol was prepared from (1-hydroxy-cyclohexyl)-{4-[2-(4-methoxy-phenyl)-ethoxy]-phenyl}-acetic acid (Reference Example 1-xxx) and 4-piperidinopiperidine. MS (ESI) m/z 535 ([M+H]$^+$).

In an analogous manner to Example 1, step 2 1-(2-(1,4'-bipiperidin-1'-yl)-1-{4-[2-(4-methoxyphenyl)ethoxy]phenyl}ethyl)cyclohexanol dihydrochloride was prepared from 1-(2-(1,4'-bipiperidin-1'-yl)-1-{4-[2-(4-methoxyphenyl)ethoxy]phenyl}-2-oxoethyl)cyclohexanol. MS (ESI) m/z 521 ([M+H]$^+$).

Example 468

1-[1-[4-(cyclohexylmethoxy)phenyl]-2-(4-methylpiperazin-1-yl)ethyl]cyclohexanol dihydrochloride

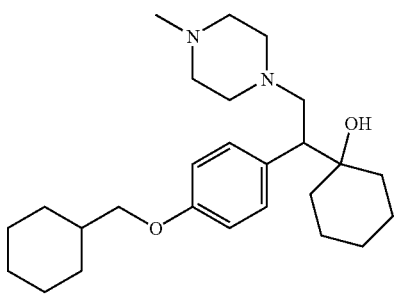

In an analogous manner to Example 1, step 1, 1-[1-[4-(cyclohexylmethoxy)phenyl]-2-(4-methylpiperazin-1-yl)acetyl]cyclohexanol was prepared from (4-cyclohexylmethoxy-phenyl)-(1-hydroxy-cyclohexyl)-acetic acid (Reference Example 1-yyy) and 1-methylpiperazine. MS (ESI) m/z 429 ([M+H]$^+$).

In an analogous manner to Example 1, step 2 1-[1-[4-(cyclohexylmethoxy)phenyl]-2-(4-methylpiperazin-1-yl)ethyl]cyclohexanol dihydrochloride was prepared from 1-[1-[4-(cyclohexylmethoxy)phenyl]-2-(4-methylpiperazin-1-yl)acetyl]cyclohexanol. MS (ESI) m/z 415 ([M+H]$^+$).

Example 469

1-(2-(4-methylpiperazin-1-yl)-1-{4-[(1R)-1-phenylethoxy]phenyl}ethyl)cyclohexanol dihydrochloride

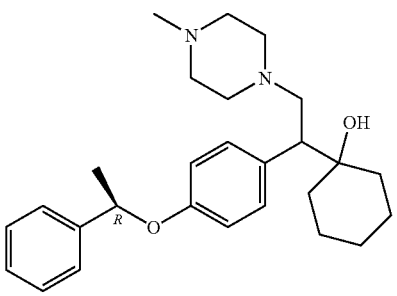

In an analogous manner to Example 1, step 1 1-(2-(4-methylpiperazin-1-yl)-1-{4-[(1R)-1-phenylethoxy]phenyl}acetyl)cyclohexanol was prepared from (1-hydroxy-cyclohexyl)-[4-((1R)-1-phenylethoxyphenyl)acetic acid (Reference Example 1-zzz) and 1-methylpiperazine. MS (ESI) m/z 437 ([M+H]$^+$).

In an analogous manner to Example 1, step 2 1-(2-(4-methylpiperazin-1-yl)-1-{4-[(1R)-1-phenylethoxy]phenyl}ethyl)cyclohexanol dihydrochloride was prepared from 1-(2-(4-methylpiperazin-1-yl)-1-{4-[(1R)-1-phenylethoxy]phenyl}acetyl)cyclohexanol dihydrochloride. MS (ESI) m/z 423 ([M+H]$^+$).

Example 470

1-(2-(4-methylpiperazin-1-yl)-1-{4-[(1S)-1-phenylethoxy]phenyl}ethyl)cyclohexanol dihydrochloride

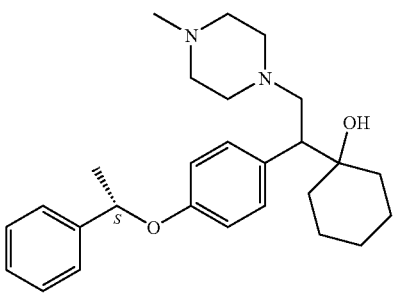

In an analogous manner to Example 1, step 1 1-(2-(4-methylpiperazin-1-yl)-1-{4-[(1S)-1-phenylethoxy]phenyl}acetyl)cyclohexanol was prepared from (1-hydroxy-cyclohexyl)-[4-((1S)-1-phenylethoxyphenyl)acetic acid (Reference Example 1-aaaa) and 1-methylpiperazine. MS (ESI) m/z 437 ([M+H]$^+$).

In an analogous manner to Example 1, step 2 1-(2-(4-methylpiperazin-1-yl)-1-{4-[(1S)-1-phenylethoxy]phenyl}ethyl)cyclohexanol dihydrochloride was prepared from 1-(2-(4-methylpiperazin-1-yl)-1-{4-[(1S)-1-phenylethoxy]phenyl}acetyl)cyclohexanol. MS (ESI) m/z 423 ([M+H]+).

Cell Lines, Culture Reagents, and Assays

MDCK-Net6 cells, stably transfected with human hNET (Pacholczyk, T., R. D. Blakely, and S. G. Amara, *Nature*, 1991, 350(6316): p. 350-4) were cultured in growth medium containing high glucose DMEM (Gibco, Cat. No. 11995), 10% FBS (dialyzed, heat-inactivated, US Bio-Technologies, Lot FBD1129HI) and 500 µg/ml G418 (Gibco, Cat. No. 10131). Cells were plated at 300,000/T75 flask and cells were split twice weekly. The JAR cell line (human placental choriocarcinoma) was purchased from ATCC (Cat. No. HTB-144). The cells were cultured in growth medium containing RPMI 1640 (Gibco, Cat. No. 72400), 10% FBS (Irvine, Cat. No. 3000), 1% sodium pyruvate (Gibco, Cat. No. 1136) and 0.25% glucose. Cells were plated at 250,000 cells/T75 flask and split twice weekly. For all assays, cells were plated in Wallac 96-well sterile plates (PerkinElmer, Cat. No. 3983498).

Norepinephrine (NE) Uptake Assay

On day 1, cells were plated at 3,000 cells/well in growth medium and maintained in a cell incubator (37° C., 5% $CO_2$). On day 2, growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. Plates containing cells with 200 µl of assay buffer were equilibrated for 10 minutes at 37° C. prior to addition of compounds. A stock solution of desipramine was prepared in DMSO (10 mM) and delivered to triplicate wells containing cells for a final test concentration of 1 µM. Data from these wells were used to define non-specific NE uptake (minimum NE uptake). Test compounds were prepared in DMSO (10 mM) and diluted in assay buffer according to test range (1 to 10,000 nM). Twenty-five microliters of assay buffer (maximum NE uptake) or test compound were added directly to triplicate wells containing cells in 200 µl of assay buffer. The cells in assay buffer with test compounds were incubated for 20 minutes at 37° C. To initiate the NE uptake, [$^3$H]NE diluted in assay buffer (120 nM final assay concentration) was delivered in 25 µl aliquots to each well and the plates were incubated for 5 minutes (37° C.). The reaction was terminated by decanting the supernatant from the plate. The plates containing cells were washed twice with 200 µl assay buffer (37° C.) to remove free radioligand. The plates were then inverted, left to dry for 2 minutes, then reinverted and air-dried for an additional 10 minutes. The cells were lysed in 25 µl of 0.25 N NaOH solution (4° C.), placed on a shake table and vigorously shaken for 5 minutes. After cell lysis, 75 µl of scintillation cocktail was added to each well and the plates were sealed with film tape. The plates were returned to the shake table and vigorously shaken for a minimum of 10 minutes to ensure adequate partitioning of organic and aqueous solutions. The plates were counted in a Wallac Microbeta counter (PerkinElmer) to collect the raw cpm data.

Serotonin (5-HT) Uptake Assay

The methods for 5-HT functional reuptake using the JAR cell line were modified using a previous literature report (Prasad, et al., *Placenta*, 1996. 17(4): 201-7). On day 1, cells were plated at 15,000 cells/well in 96-well plates containing growth medium (RPMI 1640 with 10% FBS) and maintained in a cell incubator (37° C., 5% $CO_2$). On day 2, cells were stimulated with staurosporine (40 nM) to increase the expression of the 5-HT transporter [17]. On day 3, cells were removed from the cell incubator two hours prior to assay and maintained at room temperature to equilibrate the growth medium to ambient oxygen concentration. Subsequently, the growth medium was replaced with 200 µl of assay buffer (25 mM HEPES; 120 mM NaCl; 5 mM KCl; 2.5 mM $CaCl_2$; 1.2 mM $MgSO_4$; 2 mg/ml glucose (pH 7.4, 37° C.)) containing 0.2 mg/ml ascorbic acid and 10 µM pargyline. A stock solution of paroxetine (AHR-4389-1) was prepared in DMSO (10 mM) and delivered to triplicate wells containing cells for a final test concentration of 1 µM. Data from these wells were used to define non-specific 5-HT uptake (minimum 5-HT uptake). Test compounds were prepared in DMSO (10 mM) and diluted in assay buffer according to test range (1 to 1,000 nM). Twenty-five microliters of assay buffer (maximum 5-HT uptake) or test compound were added directly to triplicate wells containing cells in 200 µl of assay buffer. The cells were incubated with the compound for 10 minutes (37° C.). To initiate the reaction, [$^3$H]hydroxytryptamine creatinine sulfate diluted in assay buffer was delivered in 25 µl aliquots to each well for a final test concentration of 15 nM. The cells were incubated with the reaction mixture for 5 minutes at 37-C. The 5-HT uptake reaction was terminated by decanting the assay buffer. The cells were washed twice with 200 µl assay buffer (37° C.) to remove free radioligand. The plates were inverted and left to dry for 2 minutes, then reinverted and air-dried for an additional 10 minutes. Subsequently, the cells were lysed in 25 µl of 0.25 N NaOH (4° C.) then placed on a shaker table and shaken vigorously for 5 minutes. After cell lysis, 75 µl of scintillation cocktail was added to the wells, the plates were sealed with film tape and replaced on the shake table for a minimum of 10 minutes. The plates were counted in a Wallac Microbeta counter (PerkinElmer) to collect the raw cpm data.

Evaluation of Results

For each experiment, a data stream of cpm values collected from the Wallac Microbeta counter was downloaded to a Microsoft Excel statistical application program. Calculations of $EC_{50}$ values were made using the transformed-both-sides logistic dose response program written by Wyeth Biometrics Department. The statistical program uses mean cpm values from wells representing maximum binding or uptake (assay buffer) and mean cpm values from wells representing minimum binding or uptake ((1 µM desipramine (hNET) or 1 µM paroxetine (hSERT)). Estimation of the $EC_{50}$ value was completed on a log scale and the line was fit between the maximum and minimum binding or uptake values. All graphic data representation was generated by normalizing each data point to a mean percent based on the maximum and minimum binding or uptake values. The $EC_{50}$ values reported from multiple experiments were calculated by pooling the raw data from each experiment and analyzing the pooled data as one experiment.

The results are reported in Table 1.

TABLE 1

| Example | % Inhibition @ 1 µM (hNET) | hNET $EC_{50}$ (nM) |
|---|---|---|
| 1 | 93 | 18 |
| 23 | 85 | 350 |
| 24 | 85 | 150 |
| 27 | 82 | 470 |
| 28 | 80 | |
| 46 | 44 | |
| 70 | 8 | |
| 71 | 25 | |
| 92 | 13 | |

TABLE 1-continued

| Example | % Inhibition @ 1 μM (hNET) | hNET EC$_{50}$ (nM) |
|---|---|---|
| 104 | 3 | |
| 108 | 0 | |
| 111 | −3 | |
| 115 | −10 | |
| 135 | 65 | 635 |
| 136 | 62 | 1000 |
| 137 | 41 | |
| 138 | 44 | |
| 139 | 45 | |
| 140 | 52 | 870 |
| 147 | 13 | |
| 148 | 32 | |
| 149 | 31 | |
| 150 | 18 | |
| 151 | 12 | |
| 152 | 1 | |
| 153 | 2 | |
| 157 | 54 | |
| 158 | 57 | |
| 160 | 50 | |
| 161 | 70 | 220 |
| 162 | 78 | 410 |
| 163 | 17 | |
| 164 | 56 | |
| 165 | 13 | |
| 166 | 48 | |
| 167 | 25 | |
| 168 | 66 | 180 |
| 169 | 69 | 850 |
| 170 | 19 | |
| 171 | 32 | |
| 172 | 55 | |
| 173 | 35 | |
| 174 | 2 | |
| 175 | 20 | |
| 176 | 28 | |
| 177 | 54 | |
| 178 | 33 | |
| 179 | 27 | |
| 180 | 47 | |
| 181 | 31 | |
| 182 | 43 | |
| 183 | 16 | |
| 184 | 40 | |
| 185 | 27 | |
| 243 | 91 | |
| 244 | 15.6 | |
| 245 | 88 | |
| 246 | 7.4 | |
| 247 | 49 | |
| 248 | 7 | |
| 249 | 32 | |
| 250 | 15 | |
| 251 | 47 | |
| 252 | 35 | |
| 253 | 19 | |
| 254 | 29 | |
| 255 | 70.7% @ 10 μM | |
| 256 | 72.8% @ 10 μM | |
| 257 | 17 | |
| 263 | 31 | |
| 264 | 89 | |
| 265 | 44 | |
| 266 | 91 | |
| 267 | 89 | |
| 268 | 84 | |
| 283 | 70.7 | |
| 285 | 20 | |
| 286 | 78.6 | |
| 287 | 60.8 | |
| 288 | 77.6 | |
| 289 | 34 | |
| 290 | 36 | |
| 291 | 40 | |
| 292 | 89 | |
| 293 | 96 | |
| 294 | 27.2% @ 10 μM | |
| 295 | 2.0% @ 10 μM | |
| 296 | 13 | |
| 297 | 4 | |
| 298 | 91 | |
| 299 | 95 | |
| 300 | 38 | |
| 301 | 23 | |
| 302 | 50 | |
| 304 | 41 | |
| 306 | 47.5 | |
| 307 | 44.5% @ 10 μM | |
| 308 | 35.9% @ 10 μM | |
| 309 | 19.7 | |
| 311 | 86.2 | |
| 312 | 57.3 | |
| 313 | 57.3 | |
| 322 | 97.2 | |
| 323 | 95.8 | |
| 324 | 98.4 | |
| 325 | 93.9 | |
| 326 | 99.7 | |
| 347 | 92 | |
| 348 | 91 | |
| 349 | 82 | |
| 350 | 79 | |
| 351 | 61 | |
| 352 | 68 | |
| 357 | 87 | |
| 358 | 73 | |
| 362 | 51 | |
| 363 | 42 | |
| 364 | | |
| 367 | 94 | |
| 368 | 93 | |
| 369 | 90 | |
| 370 | 79 | |
| 371 | 78 | |
| 372 | 37 | |
| 373 | 90 | |
| 389 | 16 | |
| 390 | 6 | |
| 391 | 30 | |
| 392 | 68 | |
| 393 | 59 | |
| 394 | 35 | |
| 395 | 92 | |
| 396 | 33 | |
| 397 | | |
| 399 | 17 | |
| 400 | 38 | |
| 401 | 25 | |
| 402 | 42 | |
| 403 | 48 | |
| 404 | 42 | |
| 405 | 27 | |
| 406 | 22 | |
| 407 | 12 | |
| 408 | | 398 |
| 409 | 62 | |
| 410 | 51 | |
| 411 | | 483 |
| 412 | | 138 |
| 413 | 76 | |
| 414 | 96 | |
| 415 | 84 | |
| 416 | 91 | |
| 417 | 78 | |
| 418 | 71 | |
| 419 | 46 | |
| 420 | 68 | |
| 421 | 59 | |
| 422 | 20 | |
| 423 | 79 | |
| 424 | 75 | |
| 425 | 80 | |

TABLE 1-continued

| Example | % Inhibition @ 1 μM (hNET) | hNET EC$_{50}$ (nM) |
|---|---|---|
| 426 | 84 | |
| 427 | 33 | |
| 432 | 64 | |
| 433 | 49 | |
| 434 | 34 | |
| 435 | 85 | |
| 436 | 63 | |
| 437 | 38 | |
| 438 | 69 | |
| 439 | 79 | |
| 440 | 28 | |
| 441 | 33 | |
| 442 | 57 | |
| 443 | 90 | |
| 444 | 98 | |
| 445 | 22 | |
| 446 | 69 | |
| 447 | 97 | |
| 448 | 78 | |
| 449 | 88 | |
| 452 | 35 | |
| 453 | 82 | |
| 454 | 99 | |
| 455 | 99 | |
| 456 | 90 | |
| 457 | 77 | |
| 459 | 58 | |
| 460 | 82 | |
| 462 | 47 | |
| 463 | 69 | |
| 464 | 33 | |
| 465 | | |
| 466 | 20 | |
| 468 | 0 | |
| 469 | 12 | |
| 470 | 14 | |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

The invention claimed is:
1. A compound of formula I:

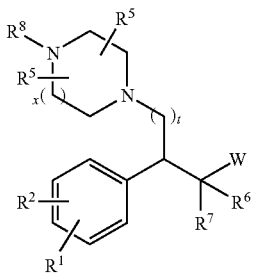

or a pharmaceutical salt thereof;

wherein:
W is H or OR$^9$;
R$^1$ is phenyl, naphthyl, heteroaryl, benzyloxy, phenoxy, naphthyloxy, phenylethoxy, phenoxyethoxy, naphthylmethoxy, naphthylethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino;
where said phenyl, naphthyl, heteroaryl, benzyloxy, phenoxy, naphthyloxy, phenylethoxy, phenoxyethoxy, naphthylmethoxy, naphthylethoxy, phenylcarbonylamino, and phenylaminocarbonyl are optionally substituted with one or more R$^2$;
R$^2$ is R$^1$, H, or one to two substituents independently selected from OH, alkyl, alkoxy, halo, trifluoromethyl, alkanoyloxy, trifluoromethoxy, nitrile, nitro, alkenyl, alkynyl, sulfonyl, or sulfonamido;
or two R$^2$ together form methylenedioxy;
R$^5$ is H, (C$_1$-C$_6$)alkyl, or trifluoromethyl;
R$^6$ and R$^7$ are, independently, (C$_1$-C$_6$)alkyl or (C$_3$-C$_6$)cycloalkyl;
or R$^6$ and R$^7$ can together form a ring of 4 to 8 carbon atoms;
where any carbon atom of said R$^6$ and R$^7$ may be optionally replaced with N, S, or O;
where R$^6$ and R$^7$ may be optionally substituted with R$^5$ or OH;
where R$^6$ and R$^7$ can form a ring with 4 to 8 carbons fused onto a cycloalkyl ring of 4 to 6 carbon atoms;
R$^8$ is H, (C$_1$-C$_6$)alkyl, hydroxy(C$_1$-C$_6$)alkyl, benzyl optionally substituted with benzyloxy or phenyloxy, naphthylmethyl optionally substituted with one or more R$^1$, phenyl(C$_2$-C$_6$)alkyl optionally substituted with one or more R$^1$, heteroarylmethyl optionally substituted with R$^1$, cycloalkyl, cycloalkenyl, cycloalkylmethyl where any carbon atom can be optionally replaced with N, S, or O and where said cycloalkylmethyl can be optionally substituted with OH, CF$_3$, halo, alkoxy, alkyl, benzyloxy, or alkanoyloxy, cycloalkenylmethyl where any carbon atom can be optionally replaced with N, S, or O and where said cycloalkenylmethyl can be optionally substituted with OH, CF$_3$, halo, alkoxy, alkyl, benzyloxy, or alkanoyloxy;
or R$^5$ and R$^8$, together with the nitrogen atom to which R$^8$ is attached, form a ring optionally substituted with R$^5$;
R$^9$ is H, (C$_1$-C$_4$)alkyl, or (C$_1$-C$_4$)alkyl-C(=O);
t is 1, 2, or 3;
and x is 2.

2. A compound according to claim 1, wherein R$^6$ and R$^7$ together with the carbon to which they are attached form a 4, 5 or 6 carbon ring.

3. A compound of formula I according to claim 1, wherein R$^6$ and R$^7$ together with the carbon to which they are attached form a cyclohexyl ring.

4. A compound of formula I according to claim 1, wherein R$^1$ is selected from trifluoromethoxy; thienyl; phenoxy; phenylethoxy; naphthyloxy; naphthylmethoxy; naphthylethoxy; alkenyl of 2 to 6 carbon atoms; alkynyl of 2 to 6 carbon atoms; phenyl optionally substituted by one to three substituents selected from halo, methylenedioxy, nitrile, nitro, alkoxy of 1 to 6 carbon atoms, alkyl of 1 to 6 carbon atoms, alkenyl of 2 to 6 carbon atoms, alkynyl of 2 to 6 carbon atoms trifluoromethoxy and trifluoromethyl; and benzyloxy optionally substituted by one to two substituents selected from halo, alkoxy of 1 to 6 carbon atoms, alkyl of 1 to 6 carbon atoms and trifluoromethyl.

5. A compound of formula I according to claim 1, wherein $R^2$ is hydrogen, halo, alkoxy of 1 to 6 carbon atoms, or hydroxy.

6. A compound of formula I according to claim 1, wherein $R^8$ is H, alkyl of 1 to 6 carbon atoms, hydroxy($C_1$-$C_6$)alkyl, benzyl, phenyl($C_2$-$C_6$)alkyl and cycloalkylmethyl.

7. A compound of formula I according to claim 1, wherein W is OH.

8. A compound of formula I according to claim 1, wherein each $R^5$ is selected independently from H and alkyl of 1 to 6 carbon atoms.

9. A compound of formula I according to claim 1, wherein t is 1.

10. A compound of according to claim 1, wherein:
W is H or $OR^9$;
$R^1$ is phenyl, naphthyl, heteroaryl, benzyloxy, phenoxy, naphthyloxy, phenylethoxy, phenoxyethoxy, naphthylmethoxy, naphthylethoxy, phenylcarbonylamino, phenylaminocarbonyl, trifluoromethoxy, nitrile, alkenyl, alkynyl, sulfonyl, sulfonamido, alkanoyl, alkoxycarbonyl, alkylaminocarbonyl, or amino;
where said phenyl, naphthyl, heteroaryl, benzyloxy, phenoxy, naphthyloxy, phenylethoxy, phenoxyethoxy, naphthylmethoxy, naphthylethoxy, phenylcarbonylamino, and phenylaminocarbonyl are optionally substituted with one or more $R^2$;
$R^2$ is $R^1$, H, OH, alkyl, alkoxy, halo, trifluoromethyl, alkanoyloxy, trifluoromethoxy, nitrile, nitro, alkenyl, alkynyl, sulfonyl, or sulfonamido;
or two $R^2$ together form methylenedioxy;
$R^5$ is H, ($C_1$-$C_6$)alkyl or trifluoromethyl;
$R^6$ and $R^7$ together form a ring of 4 to 8 carbon atoms;
$R^8$ is H, ($C_1$-$C_6$)alkyl, hydroxy($C_1$-$C_6$)alkyl, benzyl optionally substituted with benzyloxy or phenyloxy, naphthylmethyl optionally substituted with one or more $R^1$, phenyl($C_2$-$C_6$)alkyl optionally substituted with one or more $R^1$, heteroarylmethyl optionally substituted with $R^1$, cycloalkyl, cycloalkenyl, cycloalkylmethyl where any carbon atom can be optionally replaced with N, S, or O and where said cycloalkylmethyl can be optionally substituted with OH, $CF_3$, halo, alkoxy, alkyl, benzyloxy, or alkanoyloxy, cycloalkenylmethyl where any carbon atom can be optionally replaced with N, S, or O and where said cycloalkenylmethyl can be optionally substituted with OH, $CF_3$, halo, alkoxy, alkyl, benzyloxy, or alkanoyloxy;
or $R^5$ and $R^8$, together with the nitrogen atom to which $R^8$ is attached, form a ring optionally substituted with $R^5$;
$R^9$ is H;
t is 1, or 2;
and x is 2.

11. A compound according to claim 1, wherein said compound is one of the following:
1-{2-(4-benzyl-1,4-diazepan-1-yl)-1-[4-(trifluoromethoxy)-phenyl]ethyl)cyclohexanol;
1-{2-(4-methyl-1,4-diazepan-1-yl)-1-[4-(trifluoromethoxy)phenyl]ethyl)cyclobutanol;
or a pharmaceutically acceptable salt thereof.

12. A composition, comprising:
a. at least one compound according to claim 1;
and b. at least one pharmaceutically acceptable carrier.

* * * * *

UNITED STATES PATENT AND TRADEMARK OFFICE
CERTIFICATE OF CORRECTION

PATENT NO. : 7,550,456 B2
APPLICATION NO. : 12/031187
DATED : June 23, 2009
INVENTOR(S) : Eugene John Trybulski et al.

Page 1 of 1

It is certified that error appears in the above-identified patent and that said Letters Patent is hereby corrected as shown below:

1). Column 291, line 14 please add "formula I" after "of".

Signed and Sealed this

Fifteenth Day of December, 2009

David J. Kappos
*Director of the United States Patent and Trademark Office*